US011466046B2

(12) United States Patent
Myers et al.

(10) Patent No.: US 11,466,046 B2
(45) Date of Patent: *Oct. 11, 2022

(54) 14-MEMBERED KETOLIDES AND METHODS OF THEIR PREPARATION AND USE

(71) Applicant: President and Fellows of Harvard College, Cambridge, MA (US)

(72) Inventors: Andrew G. Myers, Boston, MA (US); Ian Bass Seiple, San Francisco, CA (US); Ziyang Zhang, San Francisco, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,259

(22) Filed: Apr. 8, 2020

(65) Prior Publication Data

US 2020/0361980 A1 Nov. 19, 2020

Related U.S. Application Data

(63) Continuation of application No. 15/517,843, filed as application No. PCT/US2015/054700 on Oct. 8, 2015, now Pat. No. 10,633,407.

(60) Provisional application No. 62/061,571, filed on Oct. 8, 2014.

(51) Int. Cl.
*C07H 17/08* (2006.01)
*C07D 498/04* (2006.01)
*A61K 31/7048* (2006.01)

(52) U.S. Cl.
CPC ......... *C07H 17/08* (2013.01); *A61K 31/7048* (2013.01); *C07D 498/04* (2013.01)

(58) Field of Classification Search
CPC ............................ C07H 17/08; A61K 31/7048
See application file for complete search history.

(56) References Cited

U.S. PATENT DOCUMENTS

| | | |
|---|---|---|
| 5,656,607 A | 8/1997 | Roussel et al. |
| 6,262,030 B1 | 7/2001 | Wu et al. |
| 6,399,582 B1 | 6/2002 | Hlasta et al. |
| 6,777,543 B2 | 8/2004 | Wu et al. |
| 6,939,861 B2 | 9/2005 | Gary et al. |
| 7,601,695 B2 | 10/2009 | Liang et al. |
| 7,767,797 B1 | 8/2010 | Gutke et al. |
| 8,012,943 B2 | 9/2011 | Liang et al. |
| 8,063,021 B2 | 11/2011 | Li et al. |
| 8,343,936 B2 | 1/2013 | Duffield et al. |
| 8,759,500 B2 | 6/2014 | Pereira et al. |
| 8,791,080 B2 | 7/2014 | Fernandes |
| 8,796,232 B2 | 8/2014 | Fernandes et al. |
| 8,796,474 B1 | 8/2014 | Williams et al. |
| 9,982,005 B2 | 5/2018 | Myers et al. |
| 10,633,407 B2 | 4/2020 | Myers et al. |
| 10,640,528 B2 | 5/2020 | Myers et al. |
| 10,913,764 B2 | 2/2021 | Myers et al. |
| 2002/0013281 A1 | 1/2002 | Agouridas et al. |
| 2002/0128212 A1 | 9/2002 | Or et al. |
| 2003/0199458 A1 | 10/2003 | Kosan et al. |
| 2005/0090461 A1 | 4/2005 | Leadlay et al. |
| 2006/0096158 A1 | 5/2006 | Robinson |
| 2006/0100164 A1 | 5/2006 | Liang et al. |
| 2006/0141589 A1 | 6/2006 | Okuda et al. |
| 2008/0021226 A1 | 1/2008 | Kanada et al. |
| 2008/0287376 A1 | 11/2008 | Das et al. |
| 2009/0170790 A1 | 7/2009 | Das et al. |
| 2009/0209547 A1 | 8/2009 | Kim et al. |
| 2010/0035832 A1 | 2/2010 | Heggelund et al. |
| 2010/0216731 A1 | 8/2010 | Pereira et al. |
| 2011/0195920 A1 | 8/2011 | Fernandes |
| 2011/0201566 A1 | 8/2011 | Fernandes et al. |
| 2011/0237534 A1* | 9/2011 | Fernandes ............... A61P 31/00 514/29 |
| 2012/0058963 A1 | 3/2012 | Alihoszic et al. |
| 2012/0172323 A1 | 7/2012 | Fernandes |
| 2013/0018008 A1 | 1/2013 | Pereira et al. |
| 2013/0045937 A1 | 2/2013 | Fernandes |
| 2013/0066056 A1 | 3/2013 | Pereira et al. |
| 2013/0172280 A1 | 7/2013 | Pereira et al. |
| 2013/0178429 A1 | 7/2013 | Liu et al. |
| 2013/0345410 A1 | 12/2013 | Liang et al. |
| 2014/0213515 A1 | 7/2014 | Liu et al. |

(Continued)

FOREIGN PATENT DOCUMENTS

| | | |
|---|---|---|
| CN | 1259955 A | 7/2000 |
| CN | 1333782 A | 1/2002 |

(Continued)

OTHER PUBLICATIONS

±U.S. Appl. No. 14/781,719, filed Oct. 1, 2015, Myers et al.
±U.S. Appl. No. 15/946,658, filed Apr. 5, 2018, Myers et al.
±U.S. Appl. No. 15/517,843, filed Apr. 7, 2017, Myers et al.
±U.S. Appl. No. 15/558,896, filed Mar. 8, 2018, Myers et al.
±U.S. Appl. No. 16/843,017, filed Apr. 8, 2020, Myers et al.
EP 14779590.0, Oct. 26, 2016, Partial Supplementary European Search Report.
EP14779590.0, Feb. 6, 2017, Extended European Search Report.
EP14779590.0, Jul. 18, 2020, European Office Action.

(Continued)

*Primary Examiner* — Leigh C Maier
(74) *Attorney, Agent, or Firm* — Wolf, Greenfield & Sacks, P.C.

(57) ABSTRACT

Provided herein are methods of preparing new 14-membered ketolides via coupling of an eastern and western half moiety, followed by macrocyclization, and optional functionalization. Intermediates in the synthesis of these ketolides including the eastern and western halves are also provided. Pharmaceutical compositions and methods of treating infectious diseases and inflammatory conditions using these ketolides are also provided.

22 Claims, 2 Drawing Sheets

(56) References Cited

U.S. PATENT DOCUMENTS

| | | |
|---|---|---|
| 2015/0105339 A1 | 4/2015 | Fernandes et al. |
| 2016/0052951 A1 | 2/2016 | Myers et al. |
| 2017/0305953 A1 | 10/2017 | Myers et al. |
| 2018/0066008 A1 | 3/2018 | Myers et al. |
| 2018/0111956 A1 | 4/2018 | Myers et al. |
| 2018/0298048 A1 | 10/2018 | Myers et al. |
| 2020/0377542 A1 | 12/2020 | Myers et al. |

FOREIGN PATENT DOCUMENTS

| | | |
|---|---|---|
| CN | 1984918 A | 6/2007 |
| CN | 101103039 A | 1/2008 |
| CN | 101142225 A | 3/2008 |
| CN | 101631795 A | 1/2010 |
| CN | 102245022 A | 11/2011 |
| CN | 102690297 A | 9/2012 |
| EP | 1 985 620 A1 | 10/2008 |
| EP | 2988597 A2 | 3/2016 |
| JP | S61-152663 A | 7/1986 |
| JP | H08-198832 A | 8/1996 |
| JP | 2001-247595 A | 9/2001 |
| JP | 2002-542254 A | 12/2002 |
| JP | 2003-507487 A | 2/2003 |
| JP | 2005-511752 A | 4/2005 |
| JP | 2008-526808 A | 7/2008 |
| JP | 2012-506872 A | 3/2012 |
| JP | 2013-501757 A | 1/2013 |
| KR | 10-2009-0105309 A | 10/2009 |
| WO | WO 98/56801 A1 | 12/1998 |
| WO | WO 1999/00125 A1 | 1/1999 |
| WO | WO 99/21866 A1 | 5/1999 |
| WO | WO 2001/10879 | 2/2001 |
| WO | WO 2001/55158 A1 | 8/2001 |
| WO | WO 02/32918 A2 | 4/2002 |
| WO | WO 2003/050132 A1 | 6/2003 |
| WO | WO 2004/065346 A1 | 8/2004 |
| WO | WO 2004/080391 A2 | 9/2004 |
| WO | WO 2004/101591 A1 | 11/2004 |
| WO | WO 2005/030227 A1 | 4/2005 |
| WO | WO 2006/074962 A2 | 7/2006 |
| WO | WO 2006/087644 A2 | 8/2006 |
| WO | WO 2006/120541 A1 | 11/2006 |
| WO | WO 2007/012464 A1 | 2/2007 |
| WO | WO 2007/091393 A1 | 8/2007 |
| WO | WO 2008/110918 A2 | 9/2008 |
| WO | WO 2009/055557 A1 | 4/2009 |
| WO | WO 2010/015703 A2 | 2/2010 |
| WO | WO 2010/048599 A1 | 4/2010 |
| WO | WO 2010/048600 A1 | 4/2010 |
| WO | WO 2010/048601 A1 | 4/2010 |
| WO | WO 2011/018510 A1 | 2/2011 |
| WO | WO 2011/032052 A1 | 3/2011 |
| WO | WO 2011/119604 A1 | 9/2011 |
| WO | WO 2011/131749 A1 | 10/2011 |
| WO | WO 2012/001089 A1 | 1/2012 |
| WO | WO 2012/034058 A1 | 3/2012 |
| WO | WO 2012/051126 A2 | 4/2012 |
| WO | WO 2012/127351 A1 | 9/2012 |
| WO | WO 2013/148891 A1 | 10/2013 |
| WO | WO 2014/145210 A1 | 9/2014 |
| WO | WO 2014/152326 A1 | 9/2014 |
| WO | WO 2014/165792 A2 | 10/2014 |
| WO | WO 2016/154591 A1 | 9/2016 |

OTHER PUBLICATIONS

PCT/US2014/033025, Aug. 14, 2014, Invitation to Pay Additional Fees.
PCT/US2014/033025, Oct. 28, 2014, International Search Report and Written Opinion.
PCT/US2014/033025, Oct. 15, 2015, International Preliminary Report on Patentability.
EP 15848340.4, Jun. 22, 2018, Partial Supplementary European Search Report.
EP 15848340.4, Sep. 26, 2018, Extended European Search Report.
PCT/US2015/054700, Jan. 11, 2016, International Search Report and Written Opinion.
PCT/US2015/054700, Apr. 20, 2017, International Preliminary Report on Patentability.
16769811.7, Jul. 17, 2018, Partial Supplementary European Search Report.
EP 16769811.7, Oct. 24, 2018, Extended European Search Report.
EP 16769811.7, Apr. 9, 2020, European Office Action.
PCT/US2016/024333, May 18, 2016, Invitation to Pay Additional Fees.
PCT/US2016/024333, Aug. 5, 2016, International Search Report and Written Opinion.
PCT/US2018/030002, Sep. 25, 2018, Invitation to Pay Additional Fees.
PCT/US2019/062030, Feb. 26, 2020, International Search Report and Written Opinion.
PCT/US2019/062045, Mar. 9, 2020, International Search Report and Written Opinion.
U.S. Appl. No. 17/112,743, filed Dec. 4, 2020, Myers et al.
U.S. Appl. No. 16/609,120, filed Oct. 28, 2019, Myers et al.
Partial Supplementary European Search Report for Application No. EP 14779590.0, dated Oct. 26, 2016.
Extended European Search Report for EP14779590, dated Feb. 6, 2017.
European Office Action in connection with Application No. EP 14779590.0, dated Jul. 16, 2020).
Invitation to Pay Additional Fees for PCT/US2014/033025, dated Aug. 14, 2014.
International Search Report and Written Opinion for PCT/US2014/033025, dated Oct. 28, 2014.
International Preliminary Report on Patentability for PCT/US2014/033025, dated Oct. 15, 2015.
Partial Supplementary European Search Report for Application No. EP 15848340.4 dated Jun. 22, 2018.
Extended European Search Report for EP 15848340, dated Sep. 26, 2018.
International Search Report and Written Opinion for PCT/US2015/054700, dated Jan. 11, 2016.
International Preliminary Report on Patentability for PCT/US2015/054700, dated Apr. 20, 2017.
Partial Supplementary European Search Report for Application No. EP 16769811.7, dated Jul. 17, 2018.
Extended European Search Report for Application No. EP 16769811.7, dated Oct. 24, 2018).
European Office Action in connection with Application No. EP 16769811.7 dated Apr. 9, 2020.
Invitation to Pay Additional Fees for PCT/US2016/024333, dated May 18, 2016.
International Search Report and Written Opinion for PCT/US2016/024333, dated Aug. 5, 2016.
Invitation to Pay Additional Fees for PCT/US2018/030002, dated Sep. 25, 2018.
International Search Report and Written Opinion for PCT/US2019/062030 dated Feb. 26, 2020.
International Search Report and Written Opinion for PCT/US2019/062045 dated Mar. 9, 2020.
[No Author Listed] 2005 Caplus entry for AN 2005:124660 (Romero).
[No Author Listed] 2016 Caplus entry for AN 2016:590903 (Myers).
[No Author Listed] 2005 CAS Registry No. 849407-75-6.
[No Author Listed] PubChem Substance Summary for CID 10839468. Deposit date Oct. 26, 2006.
[No Author Listed] STN Registry: CAS Registrtion No. 1631076 to 29-3. 2014.
Alihodzic et al., Synthesis and antibacterial activity of isomeric 15-membered azalides. J Antibiot (Tokyo). Dec. 2006;59(12):753-69.
Amsden, Anti-inflammatory effects of macrolides—an underappreciated benefit in the treatment of community-acquired respiratory tract infections and chronic inflammatory pulmonary conditions? Journal of Antimicrobial Chemotherapy. 2005;55:10-21.

(56) References Cited

OTHER PUBLICATIONS

Asaka et al., Recent developments in macrolide antimicrobial research. Curr Top Med Chem (Sharjah, United Arab Emirates). 2003;961-989.

Baer et al., A Stereospecific Synthesis of L-Desosamine. Canadian Journal of Chemistry. 1974;52(1):122-4.

Baer et al., Reactions of nitro sugars. V. Some reactions with methyl 3-deoxy-3-nitro-a, d-hexopyranoside. Canadian J Chem. 1967;45:983-990.

Bertrand et al., Molecular characterization of off-target activities of telithromycin: a potential role for nicotinic acetylcholine receptors. Antimicrob Agents Chemother. Dec. 2010;54(12):5399-402. doi: 10.1128/AAC.00840-10. Epub Sep. 20, 2010.

Boeckman et al., A new, highly efficient, selective methodology for formation of medium-ring and macrocyclic lactones via intramolecular ketene trapping: an application to a convergent synthesis of (−)-kromycin. J Am Chem Soc. 1989;111:8286-8288.

Breton et al., Total synthesis of erythromycin B. Tetrahedron. Jan. 25, 2007;63(26):5709-29.

Bright et al., Synthesis, in vitro and in vivo activity of novel 9-deoxo-9a-AZA-9a-homoerythromycin A derivatives; a new class of macrolide antibiotics, the azalides. J Antibiot. 1988;41:1029-1047.

Bryskier, Ketolides-telithromycin, an example of a new class of antibacterial agents. Clin Microbiol Infect. Dec. 2000;6(12):661-9.

Bulkley et al., Revisiting the structures of several antibiotics bound to the bacterial ribosome. Proc Natl Acad Sci U.S.A. 2010;107:17158-17163.

Bulman et al., Synthesis of enantiomerically pure tertiary 1,2-aminoalcohols by the highly diastereoselective reductive ring opening of oxazolidines. Tetrahedron. Nov. 2007;63(45):10991-10999.

Burger et al., Synthesis and antibacterial activity of novel C12 ethyl ketolides. Bioorg Med Chem. Aug. 15, 2006;14(16):5592-604. Epub May 11, 2006.

Chen et al., Synthesis and antibacterial activity of novel modified 5-O-desosamine ketolides. Bioorg Med Chem Lett. Dec. 15, 2012;22(24):7402-5. Doi: 10.1016/j.bmcl.2012.10.064. Epub Oct. 23, 2012.

Clark et al., Synthesis and antibacterial activity of novel 6-O-substituted erythromycin A derivatives. Bioorganic & Medicinal Chemistry Letters. 2000;10:815-819.

Cossy et al., Formal total synthesis of methynolide. Tetrahedron. 2002;58:5909-5922.

Davidson et al., Stereoselective synthesis of d-desosamine and related glycals via tungsten-catalyzed alkynol cycloisomerization. Org Lett. May 13, 2004;6(10):1601-3.

Denis et al., Synthesis of 6-O-methyl-azithromycin and its ketolide analogue via Beckmann rearrangement of 9€-6-O-methyl-erythromycin oxime. Bioorg Med Chem Lett. Sep. 22, 1998;8(18):2427-32.

Djokic et al., Erythromycin series. XII. Antibacterial in vitro evaluation of 10-dihydro-10-deoxo-11-azaerythromycin A: synthesis and structure-activity relationship of its acyl derivatives. J Antibiot. 1987;40:1006-1015.

Douthwaite et al., Macrolide-ketolide inhibition of MLS-resistant ribosomes is improved by alternative drug interaction with domain II of 23S rRNA. Mol Microbiol. 2000;36:183-192.

Dunkle et al., Structures of the *Escherichia coli* ribosome with antibiotics bound near the peptidyl transferase center explain spectra of drug action. Proc Natl Acad Sci U.S.A. 2010;107: 17152-17157.

Fajdetic et al., Synthesis and structural properties of novel tricyclic 15-membered azilides. Croatia Chemica Acta. 2009;82(4):715-23.

Falzari et al., In vitro and in vivo activities of macrolide derivatives against Mycobacterium tuberculosis. Antimicrob Agents Chemother. Apr. 2005;49(4):1447-54.

Farrell et al., The in vitro evaluation of solithromycin (CEM-101) against pathogens isolated in the United States and Europe (2009). J Infect. Dec. 2010;61(6):476-83. doi: 10.1016/j.jinf.2010.08.010. Epub Sep. 8, 2010.

Giguere et al., Enantioselective de novo synthesis of 4-deoxy-D-hexopyranoses via hetero-Diels-Alder cycloadditions: total synthesis of ezoaminuroic acid and neosidomycin. J Org Chem. Dec. 2, 2011;76(23):9687-98. Doi: 10.1021/jo201673w. Epub Nov. 10, 2011.

Girard et al., Pharmacokinetic and in vivo studies with azithromycin (CP-62,993), a new macrolide with an extended half-life and excellent tissue distribution. Antimicrob Agents Chemother. 1987;31:1948-1954.

Griesgraber et al., Anhydrolide macrolides. 2. Synthesis and antibacterial activity of 2,3-anhydro-6-O-methyl 11,12-carbazate erythromycin A analogues. J Med Chem. May 7, 1998;41(10):1660-70.

Gunnes et al., Chemoselective synthesis of erythromycin A ketolides substituted in the C10-methyl group. Bioorganic & Medicinal Chemistry Jan. 2007;15(1):119-129.

Hansen et al., Structures of five antibiotics bound at the peptidyl transferase center of the large ribosomal subunit. J Mol Biol. 2003;330:1061-1075.

Hansen et al., The macrolide-ketolide antibiotic binding site is formed by structures in domains II and V of 23S ribosomal RNA. Mol Microbiol. 1999;31:623-631.

Hansen et al., The structures of four macrolide antibiotics bound to the large ribosomal subunit. Mol Cell. 2002;10:117-128.

He et al., Formation of unusual sugars: mechanistic studies and biosynthetic applications. Annu Rev Biochem. 2002;71:701-54. Epub Nov. 9, 2001.

Hoye et al., Dual macrolactonization/pyran-hemiketal formation via acylketenes: applications to the synthesis of (−)-callipeltoside A and a lyngbyaloside B model system. Angew Chem Int Ed Engl. 2008;47(50):9743-6. doi: 10.1002/anie.200804049.

Hoye et al., Total synthesis of (−)-callipeltoside A. J Org Chem. Nov. 5, 2010;75(21):7052-60. doi: 10.1021/jo101598y.

Jakopovic et al., Novel desosamine-modified 14- and 15-membered macrolides without antibacterial activity. Bioorg Med Chem Lett. May 15, 2012;22(10):3527-30. Doi: 10.1016/j.bmcl.2012.03.076. Epub Mar. 29, 2012.

Jones et al., New macrolide antibiotics. Synthesis of a 14-membered azalide. J Org Chem. 1992;57:4361-4367.

Kanemasa et al., Asymmetric anti-Selective Aldol Reactions of Titanium Z-Enolates Derived from N-Alkylideneglycinamides Bearing a 2,2-Dimethyloxazolidine Chiral Controller. Tetrahedron Letts. Dec. 1993;34(51):8293-96.

Kim et al., Total synthesis of azithromycin. Angew Chem Int Ed Engl. 2009;48(10):1827-9. doi: 10.1002/anie.200805334.

Knapp et al., Synthesis of the Ezomycin Nucleoside Disaccharide. Org. Lett. 2000;2(10):1391-1393.

Kummer et al., Stereocontrolled Alkylative Construction of Quaternary Carbon Centers. J Am Chem Soc. Sep. 13, 2008;130(40):13231-13233.

Kurath et al., Acid degradation of erythromycin A and erythromycin B. Experientia. 1971;27:362.

Leclercq et al., Bacterial resistance to macrolide, lincosamide, and streptogramin antibiotics by target modification. Antimicrob Agents Chemother. 1991;35:1267-1272.

Leclercq et al., Intrinsic and unusual resistance to macrolide, lincosamide, and streptogramin antibiotics in bacteria. Antimicrob Agents Chemother. 1991;35:1273-1276.

Lee et al., Chemistry and biology of macrolide antiparasitic agents. J Med Chem. 2011;54:2792-2804.

Letorneau et al., Synthesis and antibacterial activity of desosamine-modified macrolide derivatives. Bioorg Med Chem Lett. Jul. 15, 2012;22(14):4575-8. Doi: 10.1016/j.bmcl.2012.05.110. Epub Jun. 6, 2012.

Liang et al., Synthesis and biological activity of new 5-O-sugar modified ketolide and 2-fluoro-ketolide antibiotics. Bioorg Med Chem Lett. 2005;15:1307-1310.

Llano-Sotelo et al., Binding and action of CEM-101, a new fluoroketolide antibiotic that inhibits protein synthesis. Antimicrob Agents Chemother. 2010;54:4961-4970.

Ma et al., Regioselective Synthesis of Bifunctional Macrolides for Probing Ribosomal Binding. Org. Lett. 2002;4(6):987-990.

(56) References Cited

OTHER PUBLICATIONS

Ma et al., Significant breakthroughs in search for anti-infectious agents derived from erythromycin A. Curr Med Chem. 2011; 18:1993-2015.
Ma et al., Various novel erthyromycin derivatives obtained by different modifications: recent advance in macrolide antibiotics. Mini-Rev Med Chem. 2010;10:272-286.
Mankin, Macrolide myths. Curr Opin Microbiol. 2008;11:414-421.
Martins et al., Antimicrobial activity of chitosan derivatives containing N-quaternized moieties in its backbone: a review. Int J Mol Sci. Nov. 13, 2014;15(11):20800-32. Doi: 10.3390/ijms151120800.
Marusic et al., Novel 9a, 11-bridged azalides: One-pot synthesis of N'-substituted 2-imino-1,3-oxazolidines condensed to an azalide aglycome. Bioorg Med Chem. 2011;19:556-66.
Marusic et al., Novel 9a-carbamoyl-and9a-thiocarbamoyl-3-decladinosyl-6-hydroxy and 6-methoxy derivatives of 15-membered macrolides. Bioorg Med Chem. 2007;15:4498-4510.
Masataka et al. , Chiral synthesis of polyketide-derived natural products. 27. Stereoselective synthesis of erythronolide A via an extremely efficient macrolactonization by the modified Yamaguchi method. J. Org. Chem., Jan. 1990;55(1):7-9.
Morales et al., Pseudoephenamine: a practical chiral auxiliary for asymmetric synthesis. Angew Chem Int Ed Engl. May 7, 2012;51(19):4568-71. doi: 10.1002/anie.201200370. Epub Mar. 27, 2012.
Morimoto et al., Chemical modification of erythromycins. I. Synthesis and antibacterial activity of 6-O-methylerythromycins A. J Antibiot (Tokyo). Feb. 1984;37(2):187-9.
Morimoto et al., Chemical modification of erythromycins. II. Synthesis and antibacterial activity of O-alkyl derivatives of erythromycin A. J Antibiot (Tokyo). 1990;43:286-294.
Mutak, Azalides from azithromycin to new azalide derivatives. J Antibiot. 2007;60:85-122.
Myers et al., Greatly Simplified Procedures for the Synthesis of α-Amino Acids by the Direct Alkylation of Pseudoephedrine Glycinamide Hydrate. J Org Chem. Apr. 16, 1999;64(9):3322-27.
Myers et al., Practical Syntheses of Enantiomerically Enriched γ-Lactones and γ-Hydroxy Ketones by the Alkylation of Pseudoephedrine Amides with Epoxides and Their Derivatives. J Org Chem. Apr. 5, 1996;61(7):2428-2420.
Myers et al., Pseudoephedrine as a Practical Chiral Auxiliary for the Synthesis of Highly Enantiomerically Enriched Carboxylic Acids, Alcohols, Aldehydes, and Ketones. J Am Chem Soc. Jul. 16, 1997;119(28):6496-6511.
Myers et al., Synthesis of tertiary alkyl fluoride centers by asymmetric C☐C(F) bond formation. Tetrahedron Letts. Oct. 6, 1997;38(40):7037-40.
Myers et al., Use of Pseudoephedrine as a Practical Chiral Auxiliary for Asymmetric Synthesis. J Am Chem Soc. Oct. 1994; 116(20):9361-62.
Nakasutka et al., Total synthesis of FK506 and an FKBP probe reagent, [C(8),C(9)-13C2]-FK506. J Am Chem Soc. 1990;112:5583-5601.
Nakata et al., Total synthesis of 6-deoxyerythronolide B. J Am Chem Soc. 1981; 103:1568.
Newman, Degradation and Synthesis of Desosamine. J Org Chem. 1964;29(6):1461-8.
Oh et al., Total synthesis of methymycin. Org. Biomol Chem. 2009;7:4458-4463.
Paterson et al., Total Synthesis of Denticulatins A and B Using Efficient Methods of Acyclic Stereocontrol. Tetrahedron. 1996;52:1811-1834.
Paterson, Tetrahedron report No. 190: Recent developments in the total synthesis of macrolide antibiotics. Tetrahedron. 1985;41:3569-3624.
Pavlovic et al., Novel hybrids of 15-membered 8a- and 9a-azahomoerythromycin A ketolides and quinolones as potent antibacterials. Bioorg Med Chem. 2010;18:8566-8582.

Pereira et al. , Synthesis and antibacterial activity of novel 4-aryl-[1,2,3]-triazole containing macrolides. Bioorg Med Chem Lett. Jan. 1, 2011;21(1):510-3. doi: 10.1016/j.bmcl.2010.10.091. Epub Oct. 25, 2010.
Phan et al., Synthesis and antibacterial activity of a novel class of 4'-substituted 16-membered ring macrolides derived from tylosin. J Med Chem. Jun. 3, 2004;47(12):2965-8.
Prunier et al., Clinical isolates of *Staphylococcus aureus* with ribosomal mutations conferring resistance to macrolides. Antimicrob Agents Chemother. 2002;46:3054-3056.
Putnam et al., Antimicrobial characterisation of solithromycin (CEM-101), a novel fluoroketolide: activity against staphylococci and enterococci. Int J Antimicrob Agents. Jan. 2011;37(1):39-45. doi: 10.1016/j.ijantimicag.2010.08.021.
Retsema et al., Spectrum and mode of action of azithromycin (CP-62,993), a new 15-membered-ring macrolide with improved potency against gram-negative organisms. Antimicrob Agents Chemother. 1987;31:1939-1947.
Richardson, A stereospecific synthesis of desosamine hydrochloride. Proceedings of the Chemical Society. 1963:131.
Romero et al., An efficient entry to new sugar modified ketolide antibiotics. Tetrahedron Lett. 2005;46:1483-1487.
Rück, Asymmetric Alkylation of Amide Enolates with Pseudoephedrine and Ephedrine as Chiral Auxiliaries—Unexpected Influence of Additives? Angewandte Chemie. International Edition. Mar. 7, 1995;34(4):433-35.
Seiple et al., A platform for the discovery of new macrolide antibiotics. Nature. May 18, 2016;533(7603):338-45. doi: 10.1038/nature17967.
Shvekhgeimer et al., Aliphatic nitro alcohols. Synthesis, chemical transformations and applications. Russian Chemical Reviews. 1998;67(1):35-68.
Song et al., Protein Phosphatase 2A-SUR-6/B55 Regulates Centriole Duplication in C. elegans by Controlling the Levels of Centriole Assembly Factors. Dev Cell. Apr. 19, 2011; 20(4): 563-571. doi: [10.1016/j.devcel.2011.03.007].
Sutcliffe et al., *Streptococcus pneumoniae* and *Streptococcus pyogenes* resistant to macrolides but sensitive to clindamycin: a common resistance pattern mediated by an efflux system. Antimicrob Agents Chemother. 1996;40:1817-1824.
Tu et al., Structures of MLSBK antibiotics bound to mutated large ribosomal subunits provide a structural explanation for resistance. Cell. 2005;121:257-270.
Van Summeren et al., New approaches towards the synthesis of the side-chain of mycolactones A and B. J Org Biomol Chem. 2005;3:2524-2533.
Velvadapu et al., Concise syntheses of D-desosamine, 2-thiopyrimidinyl desosamine donors, and methyl desosaminide analogues from D-glucose. Carbohydr Res. 2008;343:145-150.
Velvadupu et al., Total synthesis of (−)-4,8,10-tridesmethyl telithromycin. J Org Chem. Sep. 16, 2011;76(18):7516-27. doi: 10.1021/jo201319b. Epub Aug. 24, 2011.
Vester et al., Macrolide resistance conferred by base substitutions in 23S rRNA. Antimicrob Agents Chemother. 2001;45:1-12.
Vicario et al., Asymmetric aldol reactions using (S,S)-(+)-pseudoephedrine-based amides: stereoselective synthesis of alpha-methyl-beta-hydroxy acids, esters, ketones, and 1,3-Syn and 1,3-anti diols. J Org Chem. Jun. 16, 2000;65(12):3754-60.
Wagh et al., Desmethyl Macrolides: Synthesis and Evaluation of 4,8-Didesmethyl Telithromycin. ACS Med Chem Lett. Dec. 12, 2012;3(12): 1013-1018.
Wang et al., Synthesis of novel 6,11-O-bridged bicyclic ketolides via a palladium-catalyzed bis-allylation. Org Lett. Nov. 25, 2004;6(24):4455-8.
Washington et al., Erythromycin: a microbial and clinical perspective after 30 years of clinical use (1). Mayo Clin Proc. 1985;60:189-203.
Washington et al., Erythromycin: a microbial and clinical perspective after 30 years of clinical use (2). Mayo Clin Proc. 1985;60:271-278.
Watanabe et al., Chemical modification of erythromycins. IX. Selective methylation at the C-6 hydroxyl group of erythromycin A

(56) References Cited

OTHER PUBLICATIONS oxime derivatives and preparation of clarithromycin. J Antibiot (Tokyo). Apr. 1993;46(4):647-60.

Watanabe et al., Chemical modification of erythromycins. XII. A facile synthesis of clarithromycin (6-O-methylerythromycin A) via 2'-silylethers of erythromycin A derivatives. J Antibiot (Tokyo). Jul. 1993;46(7): 1163-7.

Watanabe et al., Tetronothiodin, a novel cholecystokinin type-B receptor antagonist produced by *Streptomyces* sp. NR0489. I. Taxonomy, yield improvement and fermentation. J Antibiot (Tokyo). Jan. 1993;46(1):1-10.

Weisblum, Erythromycin resistance by ribosome modification. Antimicrob Agents Chemother. 1995;39:577-585.

Wilkening et al., The synthesis of novel 8a-AZA-8a-homoerythromycin derivatives via the Beckman rearrangement of (9z)-erythrromycin a oxime. Bioorg Med Chem. 1993;3(6): 1287-92.

Wondrack et al., Clinical strain of *Staphylococcus aureus* inactivates and causes efflux of macrolides. Antimicrob Agents Chemother. 1996;40:992-998.

Woodward et al., Asymmetric total synthesis of erythromcin. 1. Synthesis of an erythronolide A secoacid derivative via asymmetric induction. J Am Chem Soc. 1981;103(11):3210-3213.

Woodward et al., Asymmetric total synthesis of erythromycin. 2. Synthesis of an erythronolide A lactone system. J Am Chem Soc. 1981; 103(11):3213-3215.

Woodward et al., Asymmetric total synthesis of erythromycin. 3. Total synthesis of erythromycin. J Am Chem Soc. 1981;103(11):3215-3217.

Worch et al., Unexpected formation of complex bridged tetrazoles via intramolecular 1,3-dipolar cycloaddition of 1,2-O-cyanoalkylidene derivatives of 3-azido-3-deoxy-D-allose. Carbohydr Res. Aug. 11, 2008;343(12):2118-29. Epub Nov. 6, 2007.

Wright, Molecular mechanisms of antibiotic resistance. Chem Commun. 2011;47:4055-4061.

Wu et al., Recent developments on ketolides and macrolides. Curr Med Chem. Dec. 2001;8(14):1727-58.

Wu, Highlights of semi-synthetic developments from erythromycin A. Curr Pharm Des. 2000;6:181-223.

Zhanel et al., The ketolides: a critical review. Drugs. 2002;62(12):1771-804.

Zhang et al., Synthesis of D-Desosamine and Analogs by Rapid Assembly of 3-Amino Sugars. Angewandte Chemie Int Ed. Jan. 11, 2016;55(2):523-7. Epub Nov. 27, 2015.

Zjndel et al., Synthesis of 3-(trans-2'-Nitrocyclopropyl)alanine, a Constituent of the Natural Peptide-Lactone Hormaomycin. J. Org. Chem. 1995;60(10):2968-73.

Boulard et al., Synthesis of the C1-C13 fragment of (+)-callipeltoside A, Synlett. 2007; 9:1461-1463.

Marinier et al., Synthesis and transannular Diels-Alder reaction of a cis-trans-trans and a trans-cis-cis 13-membered macrocyclic trienone. Canadian Journal of Chemistry. 1989;.67(10):1609-1617.

Singer et al., Catalytic, Enantioselective Dienolate Additions to Aldehydes: Preparation of Optically Active Acetoacetate Aldol Adducts. Journal of the American Chemical Society. 1995;117(49): 12360-12361.

Sugita et al., Use of 1,3-dioxin-4-ones and related compounds in synthesis. Part 39. Enantioselective synthesis of 1,3-dioxin-4-ones having 2,3-dihydroxy- or 2,3,4-trihydroxyalkyl groups at the 6-position: versatile building blocks of polyhydroxylated 4-7 carbon backbones. J Chem Soc Perkin Trans. 1992; 21: 2855-2861.

Venkatraman et al., Total synthesis of narbonolide and biotransformation to pikromycin. J Org Chem. Dec. 22, 2006;71(26):9853-6. doi: 10.1021/jo062047u.

\* cited by examiner

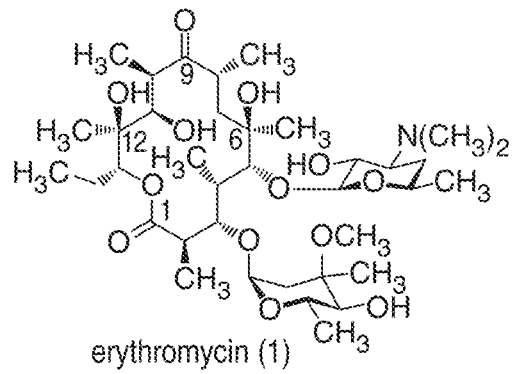
Preparation:
US FDA Approval:
erythromycin (1)
14-membered macrolide
fermentation from *S. erythraea*
1952
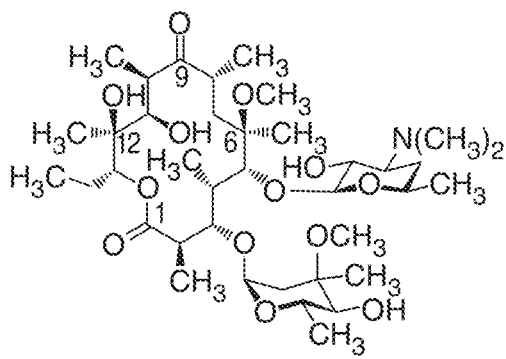
clarithromycin (2)
14-membered macrolide
semi-synthesis: 6 steps
from erythromycin
1991
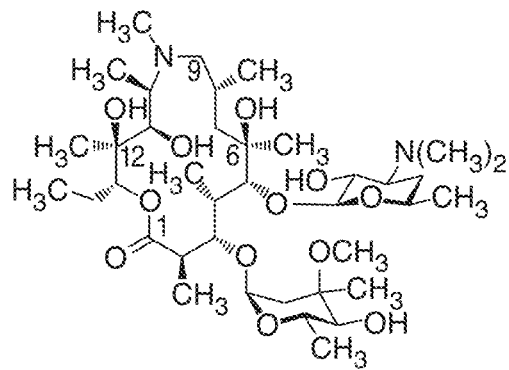
azithromycin (3)
15-membered azalide
semi-synthesis: 4 steps
from erythromycin
1991
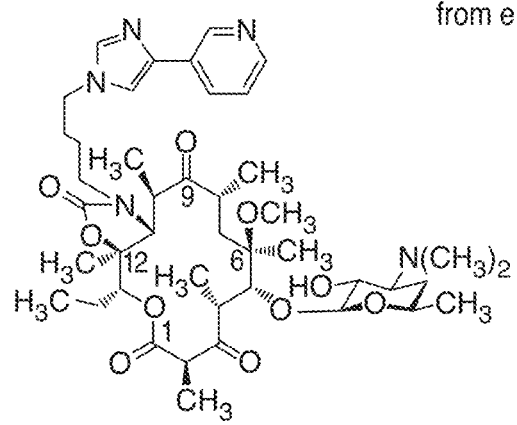
telithromycin (4)
14-membered ketolide
semi-synthesis: 12 steps from erythromycin
2004

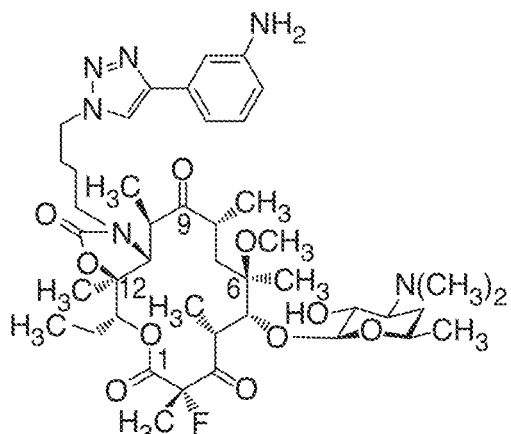
solithromycin (5)
14-membered ketolide
semi-synthesis: 16 steps from erythromycin
(Clinic Phase II)
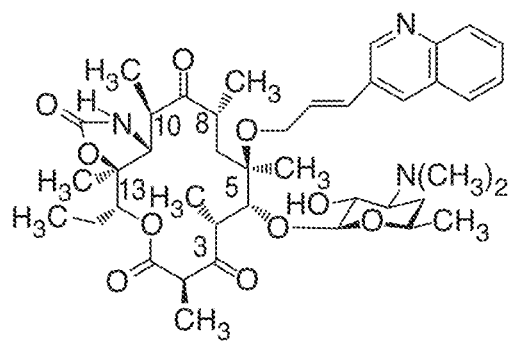
cethromycin (7)
14-membered ketolide
(Clinic Phase III)
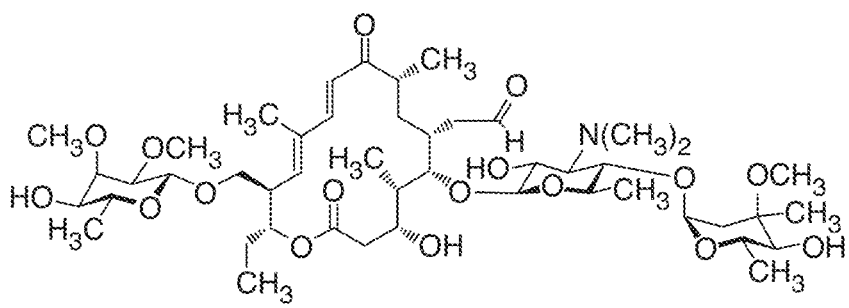
tylosin (6)
16-membered macrolide
fermentation from *S. fradiae*
(veterinary medicine)
(continued)

14-MEMBERED KETOLIDES AND METHODS OF THEIR PREPARATION AND USE

RELATED APPLICATIONS

The present application is a continuation of and claims priority under 35 U.S.C. § 120 to U.S. patent application Ser. No. 15/517,843, filed Apr. 7, 2017, which is a national stage filing under 35 U.S.C. § 371 of international PCT application, PCT/US2015/054700, filed Oct. 8, 2015, which claims priority under 35 U.S.C. § 119(e) to U.S. provisional patent application, U.S. Ser. No. 62/061,571, filed Oct. 8, 2014, each of which is incorporated herein by reference.

BACKGROUND OF THE INVENTION

Emerging resistance to existing antibiotics is rapidly developing as a crisis of global proportions, especially for *Staphylococcus aureus*, *Streptococcus pyogenes*, and *Streptococcus pneumonia* infections. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. This year, >99,000 people will die in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 122:160-166. The current crisis is exacerbated by the fact that most major pharmaceutical companies have essentially abandoned research in the development of new antibiotics. See, e.g., Projan *Curr. Opin. Microbiol.* (2003) 6: 427-430. The current rate of introduction of new antibiotics does not adequately address growing resistance, and with the ease of international travel and increasing population densities, the need for innovation in the field has never been higher.

The macrolides are one of the few major clinically important classes of antibiotics for which the only practical access has been through semi-synthesis, or chemical manipulation of structurally complex fermentation products, in routes as long as 16 steps. See, e.g., Paterson, *Tetrahedron* (1985) 41:3569-3624; Omura, Ed., *Macrolide Antibiotics: Chemistry, Biology, and Practice, Second Edition*; Academic Press, 2002. The macrolide class of antibiotics has proven safe and effective in the battle against pathogenic bacteria since the discovery of erythromycin over 60 years ago. See, e.g., Wu et al., *Curr. Med. Chem.* (2001) 8, 1727-1758. Erythromycin displays a spectrum of antibacterial activity against Gram-positive bacteria similar to that of penicillin but has a lesser propensity to induce allergic interactions, and has been routinely prescribed for upper and lower respiratory tract infections and urogenital infections. See, e.g., Washington et al., *Mayo. Clin. Proc.* (1985) 60:189-203; Washington et al., *Mayo. Clin. Proc.* (1985) 60:271-278. However, erythromycin is known to undergo acid-promoted internal ketalization (cyclization of the C6 and C12 hydroxyl groups onto the C9 ketone) in the gut, which leads to adverse gastrointestinal events. See, e.g., Kurath et al., *Experientia* (1971) 27:362. Second-generation macrolide antibiotics clarithromycin and azithromycin addressed issues of acid instability and were prepared semi-synthetically in 4-6 steps from erythromycin, which is readily available through large-scale fermentation. See, e.g., Ma et al., *Curr. Med. Chem.* (2011) 18:1993-2015; Wu et al., *Curr. Pharm. Des.* (2000) 6:181-223; Ma et al., *Mini-Rev. Med. Chem.* (2010) 10:272-286; Asaka et al., *Curr. Top. Med. Chem.* (*Sharjah, United Arab Emirates*) (2003) 3:961-989; Morimoto et al., *J. Antibiot.* (1990) 43:286-294; Morimoto et al., *J. Antibiot.* (1984) 37:187-189; Watanabe et al., *J. Antibiot.* (1993) 46: 1163-1167; Watanabe et al., *J. Antibiot.* (1993) 46:647-660; Bright et al., *J. Antibiot.* (1988) 41: 1029-1047; Djokic et al., *J. Antibiot.* (1987) 40:1006-1015; Mutak et al., *J. Antibiot.* (2007) 60: 85-122; and Retsema et al., *Antimicrob. Agents Chemother.* (1987) 31:1939-1947. Azithromycin has been shown to exhibit markedly improved efficacy against Gram-negative organisms, and has a longer half-life and higher tissue distribution than the other macrolide antibiotics, thought to correlate with its 15-membered ring containing a tertiary amine. See, e.g., Ferwerda et al., *J. Antimicrob. Chemother.* (2001) 47:441-446; Girard et al., *Antimicrob. Agents Chemother.* (1987) 31:1948-1954. The natural product tylosin, a 16-membered macrolide used in veterinary medicine, has been shown by X-ray crystallography to occupy the same binding pocket as erythromycin and azithromycin, suggesting that there is a high tolerance for variability in ring size and composition of the macrocycle.

The three primary causes of resistance to macrolides in bacterial organisms are ribosome methylation encoded by erm genes, mutations in ribosomal RNA or peptides, and cell efflux mediated by mef and msr genes. See, e.g., Leclercq et al., *Antimicrob. Agents Chemother.* (1991) 35:1273-1276; Leclercq et al., *Antimicrob. Agents Chemother.* (1991) 35:1267-1272; Weisblum, *Antimicrob. Agents Chemother.* (1995) 39:577-585; Vester et al., *Antimicrob. Agents Chemother.* (2001) 45:1-12; Prunier et al., *Antimicrob. Agents Chemother.* (2002) 46:3054-3056; Li et al., *J. Antimicrob. Chemother.* (2011) 66:1983-1986; Sutcliffe et al., *Antimicrob. Agents Chemother.* (1996) 40:1817-1824; Wondrack et al., *Antimicrob. Agents Chemother.* (1996) 40: 992-998. Ketolides such as telithromycin and solithromycin defeat the efflux mechanism of resistance by replacement of the C3 cladinose sugar with a carbonyl group (hence the name "ketolides"), and are thought to exhibit greatly increased binding by virtue of favorable interactions between the novel aryl-alkyl sidechain and the ribosome. See, e.g., Ma et al., *Curr. Med. Chem.* (2011) 18:1993-2015; Ma et al., *Mini-Rev. Med. Chem.* (2010) 10:272-286. Despite greatly improved ribosomal binding, ketolides such as telithromycin and solithromycin have not addressed several of the newest forms of macrolide resistance that have evolved in nosocomial settings, especially ribosome methylation and RNA point mutations.

SUMMARY OF THE INVENTION

Described herein are methods and intermediates for making ketolides. This synthetic approach to macrolides, particularly 14-membered ketolides, includes the coupling of two components, a western half (A-i) or (A-ii) with an eastern half (B-i) or (B-ii), as depicted in Scheme 1, to provide a compound of Formula (N-1):

Scheme 1.

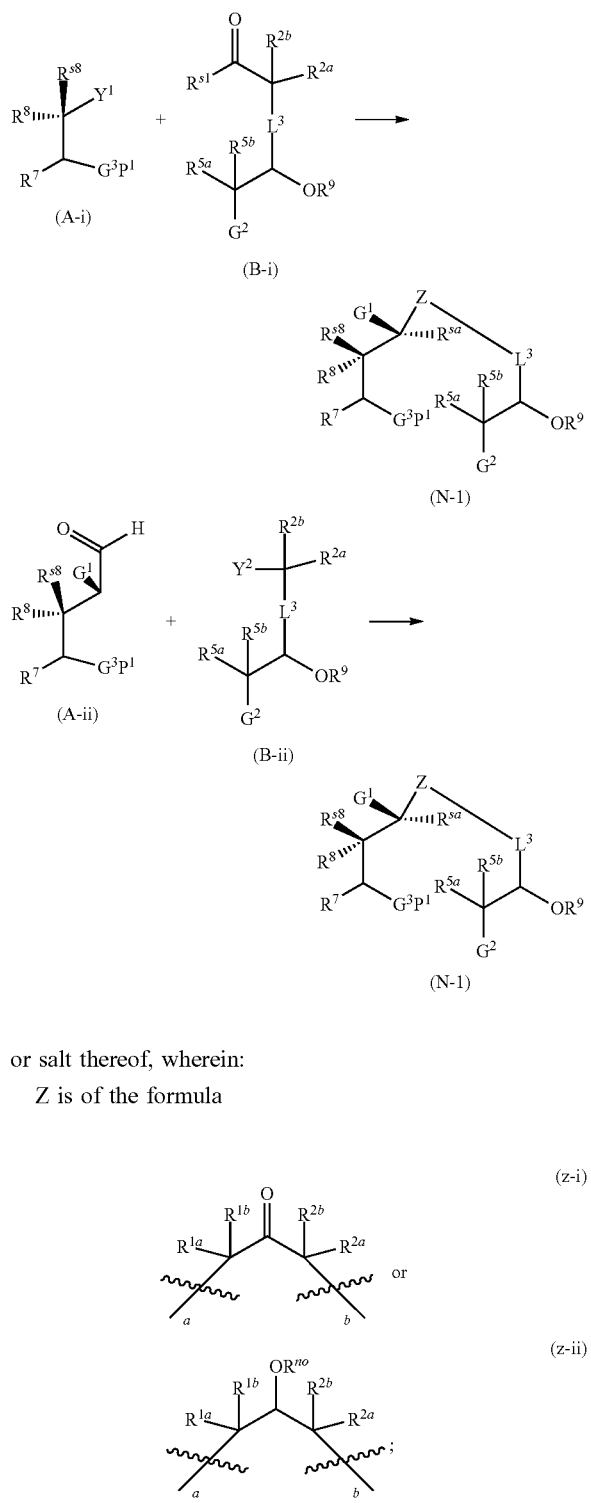

or salt thereof, wherein:

Z is of the formula

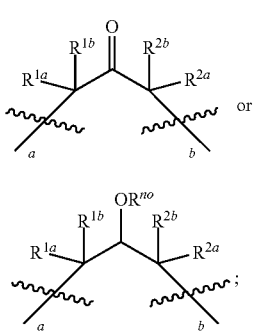

each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl, or wherein $R^{1a}$ and $R^{1b}$ or $R^{2a}$ and $R^{2b}$ are taken together to form

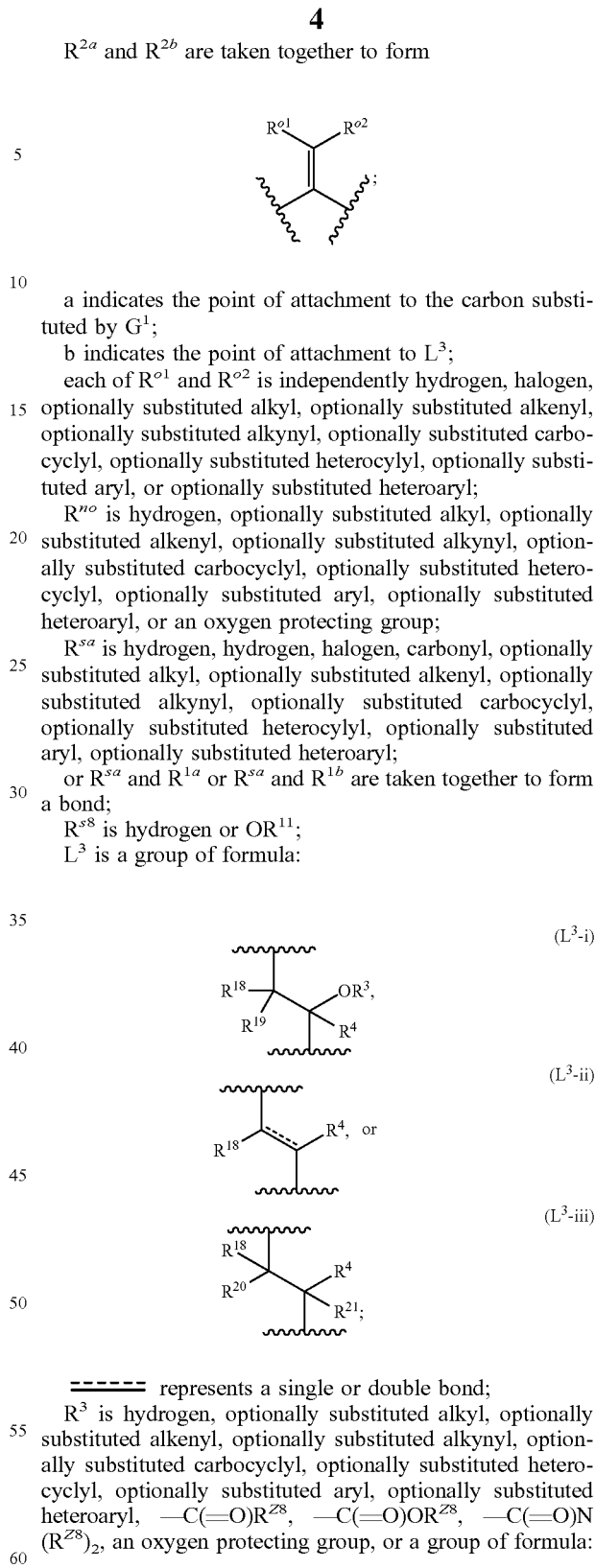

a indicates the point of attachment to the carbon substituted by $G^1$;

b indicates the point of attachment to $L^3$;

each of $R^{o1}$ and $R^{o2}$ is independently hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;

$R^{no}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{sa}$ is hydrogen, hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl;

or $R^{sa}$ and $R^{1a}$ or $R^{sa}$ and $R^{1b}$ are taken together to form a bond;

$R^{s8}$ is hydrogen or $OR^{11}$;

$L^3$ is a group of formula:

------ represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{Z8}$, —C(=O)OR$^{Z8}$, —C(=O)N(R$^{Z8}$)$_2$, an oxygen protecting group, or a group of formula:

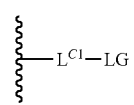

-continued

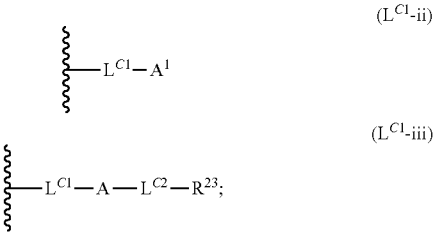

R[4] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of R[18] and R[19] independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of R[20] and R[21] is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, carbonyl, or R[20] and R[21] are joined to form an optionally substituted cyclopropyl or an oxiranyl ring;

each instance of R[5] and R[5b] is independently hydrogen, halogen, silyl, optionally substituted alkyl, optionally substituted carbocyclyl, or optionally substituted heterocyclyl;

R[Y1] is —OR[17] and R[Y2] is hydrogen, or R[Y1] is halogen and R[Y2] is hydrogen, or R[Y1] is halogen and R[Y2] is halogen, or R[Y1] and R[Y2] are joined to form an oxo (=O) group;

R[6] is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen;

R[7] and R[8] are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R[9] and R[17] are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R[Z8], —C(=O)OR[Z8], —C(=O)N(R[Z8])$_2$, an oxygen protecting group, or a carbohydrate;

R[10] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, carbonyl, silyl, and halogen;

G[3] is —O—, —S—, or —N(R[G1])—, wherein R[G1] is hydrogen, optionally substituted alkyl, or a nitrogen protecting group;

G[1] is hydrogen, —OR[12] or —NR[13]R[14];

provided when G[1] is —OR[12], then R[11] and R[12] are joined as a group of formula —C(=O)— to provide a cyclic carbonate, or R[11] and R[12] are not joined, and R[11] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and R[12] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

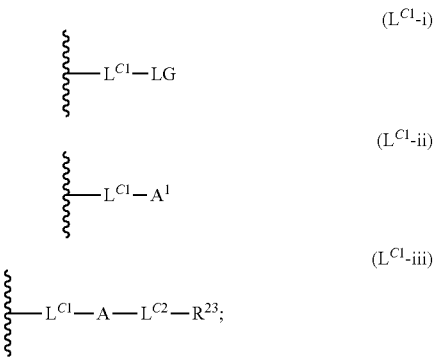

or provided when G[1] is —NR[13]R[14], then R[11] and R[13] are joined as a group of formula —C(=O)— to provide a cyclic carbamate, or R[11] and R[13] are not joined, R[11] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, R[13] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R[14] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)R[Z8], or —C(=O)OR[Z8], or a group of formula:

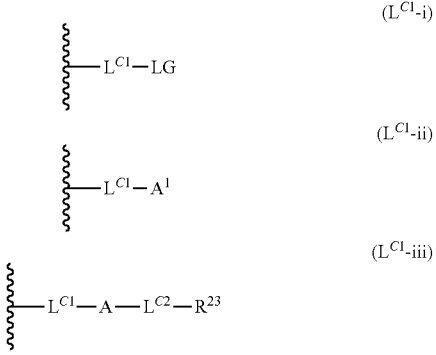

or R[13] and R[14] are joined to form an optionally substituted heterocyclyl or optionally substituted heteroaryl;

each instance of $L^{C1}$ and $L^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, optionally substituted carbocyclylene, optionally substituted heterocyclylene, and combinations thereof;

each instance of $A^1$ is independently a leaving group (LG), —SH, —OH, —NH$_2$, —NH—NH$_2$, —N$_3$, —O—NH$_2$,

—C(=O)R$^{X1}$,

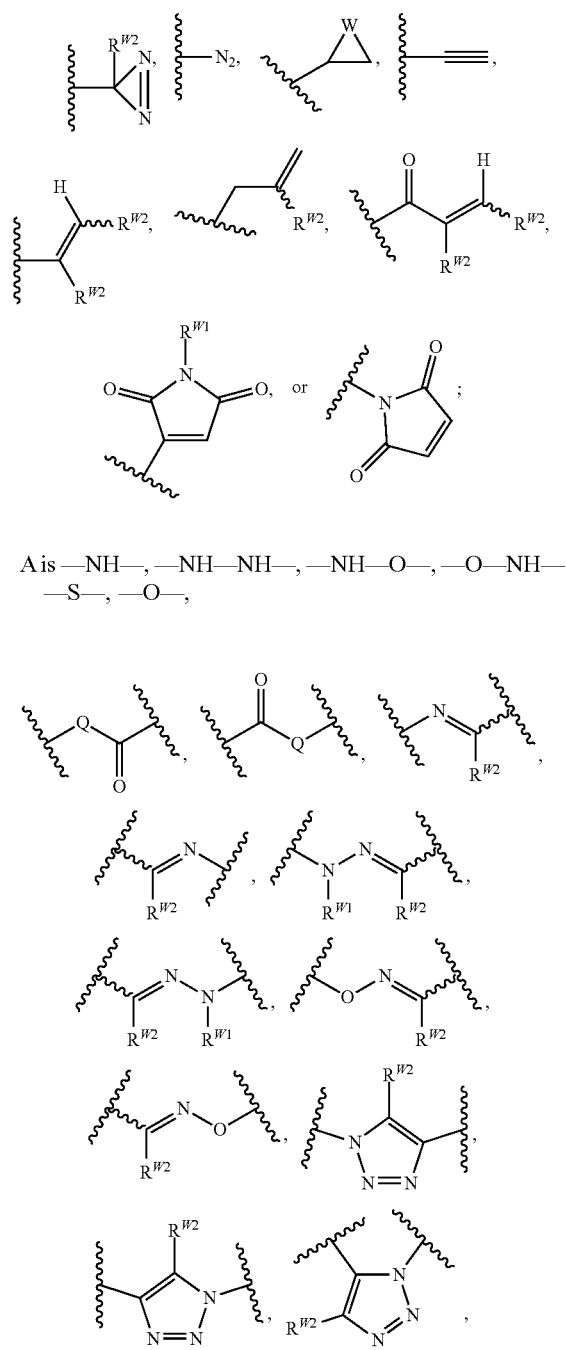

A is —NH—, —NH—NH—, —NH—O—, —O—NH—, —S—, —O—,

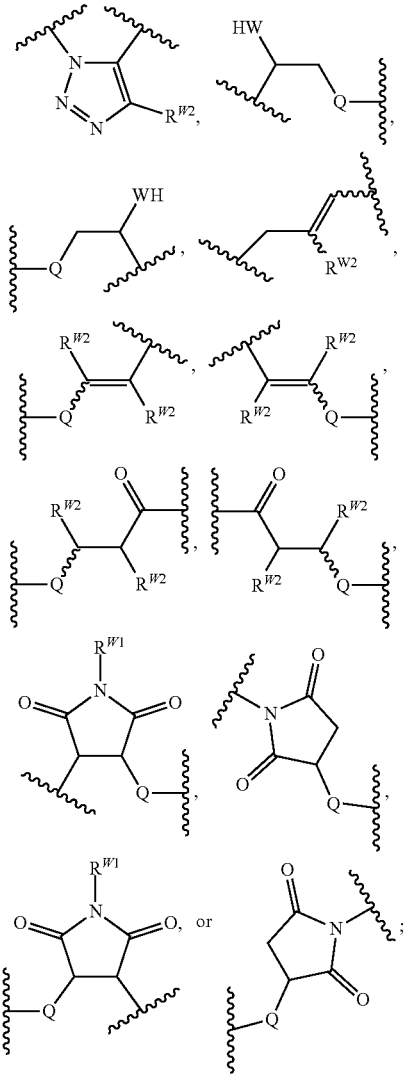

Q is —NH—, —NH—NH—, —O—NH—, —NH—O—, —S—, —O—;

W is O, S, or NR$^{W1}$;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form an optionally substituted cyclic moiety;

R$^{X1}$ is hydrogen, halogen, or —OR$^{X2}$, wherein R$^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

R$^{23}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of $R^{Z8}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl, or two $R^{Z8}$ groups are joined to form an optionally substituted heterocylyl or optionally substituted heteroaryl ring;

or A is a cyclic moiety selected from the group consisting of optionally substituted carbocyclyl, optionally substituted heterocyclyl, optionally substituted aryl, and optionally substituted heteroaryl;

$R^{s1}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$G^2$ is a group of formula:

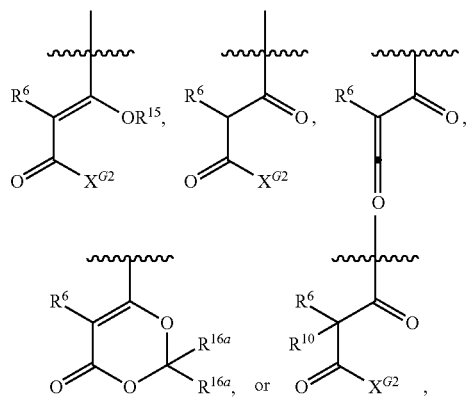

wherein $R^6$, $R^{10}$, $R^{15}$, $R^{16a}$, and $X^{G2}$ are as defined herein;

$P^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$Y^1$ is

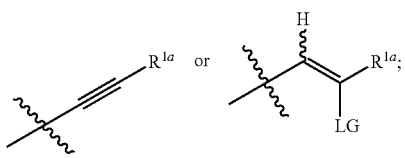

LG is a leaving group;

$Y^2$ is —C(=O)—CH=P($R^{P1}$)($R^{P2}$)($R^{P3}$) or —C(=O)—CH$_2$—P(O)(O$R^{P3}$);

wherein the leaving group (LG), $R^{P1}$, $R^{P2}$, and $R^{P3}$ are as defined herein, to provide various linkages of formula Z, as defined herein.

As demonstrated herein, macrolides which incorporate rigidifying motifs (e.g., unsaturated or cyclic motifs) into the $L^{C1}$ or $L^{C2}$ linker show improved potencies compared with solithromycin (See, e.g., Tables B1-B13). Therefore, in certain embodiments, one or both of $L^{C1}$ and $L^{C2}$ is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, and combinations thereof, provided the linker comprises a optionally substituted alkenylene, optionally substituted alkynylene, or optionally substituted carbocyclylene group therein, thereby rigidifying the linker moiety. In certain embodiments, $L^{C1}$ is a rigidified linker, as described herein, and $L^{C2}$ is a bond.

In certain embodiments, one or both of $L^{C1}$ and $L^{C2}$ is independently selected from one of the following formulae:

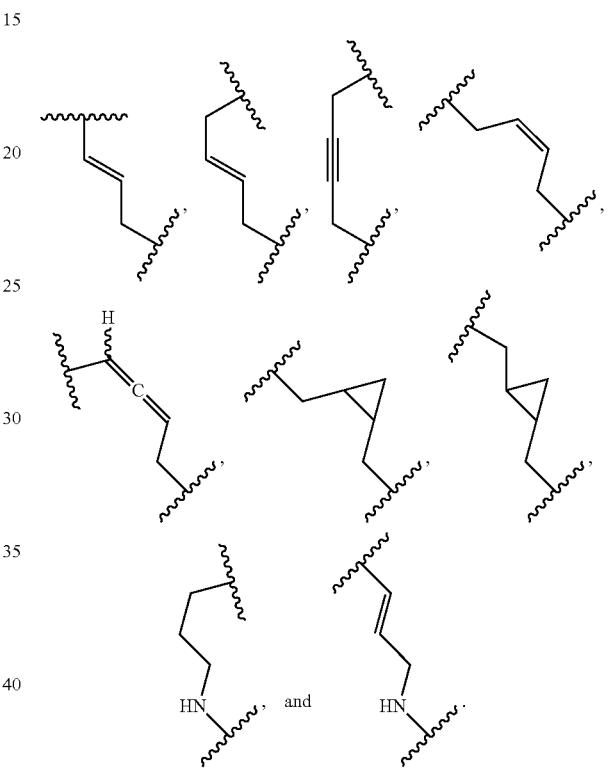

Furthermore, macrolides which comprising a non-hydrogen $R^{1a}$ and/or $R^{1b}$ group, such as a —CH$_3$ group, are found to be more potent than analogs without such substitution. The combination of a rigidified linker in addition to a non-hydrogen $R^{1a}$ and/or $R^{1b}$ group is thus envisioned as providing even more potent analogs.

Furthermore, as described herein, ketolides comprising heteroaryl $R^{23}$ groups have been found to be more potent than solithromycin and analogs thereof. The combination of a rigidified $L^{C1}$ and/or $L^{C2}$ linker, a non-hydrogen $R^{1a}$ and/or $R^{1b}$ group, and a heteroaryl $R^{23}$ group is thus envisioned as providing even more potent analogs. Therefore, in certain embodiments, $R^{23}$ is of the formula:

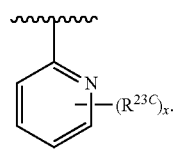

In specific embodiments, $R^{23}$ is of the formula:

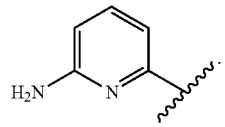

In certain embodiments, Z is

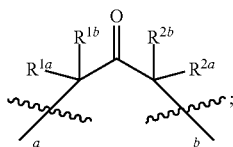

(z-i)

and $R^{1a}$, $R^{1b}$, $R^{2a}$, and $R^{2b}$ are as defined herein. In certain embodiments, $R^{1a}$ and $R^{1b}$ are hydrogen; and each of $R^{2a}$ and $R^{2b}$ is independently hydrogen or optionally substituted alkyl. In certain embodiments, $R^{1a}$ is hydrogen; $R^{1b}$ is optionally substituted alkyl; and each of $R^{2a}$ and $R^{2b}$ is independently hydrogen or optionally substituted alkyl. In some embodiments, $R^{1a}$ and $R^{1b}$ or $R^{2a}$ and $R^{2b}$ are taken together to form

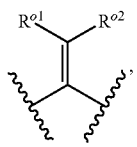

wherein $R^{o1}$ and $R^{o2}$ are as defined herein. In certain embodiments, $L^{C1}$ is a rigidified linker, as described herein, and $L^{C2}$ is a bond.

In certain embodiments, Z is

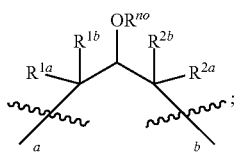

(z-ii)

$R^{no}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{1a}$, $R^{1b}$, $R^{2a}$, and $R^{2b}$ are as defined herein. In certain embodiments, $R^{no}$, $R^{1a}$ and $R^{1b}$ are hydrogen and each of $R^{2a}$ and $R^{2b}$ is independently hydrogen or optionally substituted alkyl. In certain embodiments, $R^{no}$ and $R^{1a}$ are hydrogen; $R^{1b}$ is optionally substituted alkyl; and each of $R^{2a}$ and $R^{2b}$ is independently hydrogen or optionally substituted alkyl. In some embodiments, $R^{1a}$ and $R^{1b}$ or $R^{2a}$ and $R^{2b}$ are taken together to form

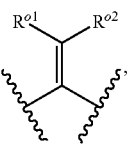

wherein $R^{o1}$ and $R^{o2}$ are as defined herein. In certain embodiments, $L^{C1}$ is a rigidified linker, as described herein, and $L^{C2}$ is a bond.

Furthermore, various macrolides may be accessed from the coupled product of Formula (N-i), depending upon the nature of the group $G^2$, upon macrocyclization, e.g., via thermally induced macrocylization. As depicted in Scheme 2, when $G^2$ is a group of formula:

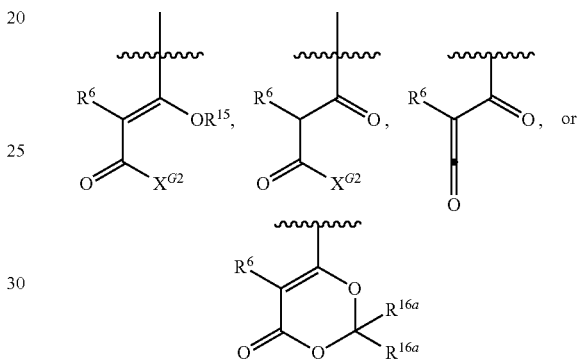

$P^1$ is hydrogen, and $R^6$ is a hydrogen or non-hydrogen group, macrocyclization of the compound of Formula (N-1) provides a macrolide of Formula (N-2). Enolization of the macrolide of Formula (N-2) in the presence of a base, followed by addition of a non-hydrogen group $R^{10}$, provides a macrolide of Formula (N-3).

Scheme 2.

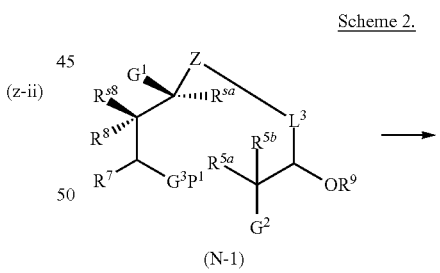

(N-1)

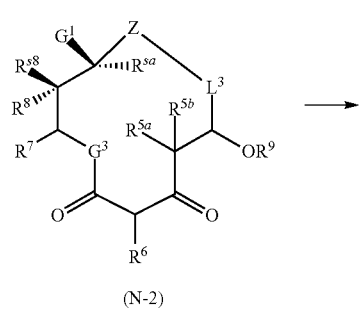

(N-2)

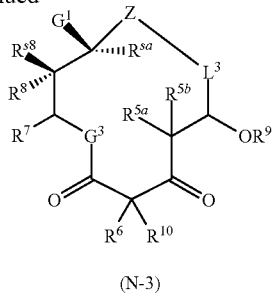

(N-3)

Alternatively, as depicted in Scheme 3, when $G^2$ is a group of formula:

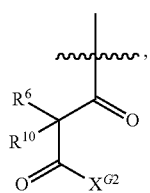

wherein $P^1$ is hydrogen, and each of $R^6$ and $R^{10}$ is independently a hydrogen or non-hydrogen group, macrocyclization of the compound of Formula (N-1) provides a macrolide of Formula (N-3).

Scheme 3.

(N-1)

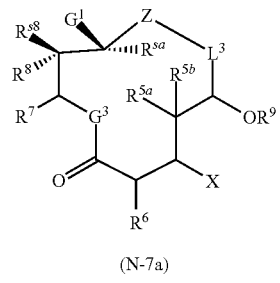

(N-3)

Additional functionalization of the macrolide is also contemplated. For example, as depicted in Schemes 4 and 5, reduction of the C3 ketone of macrolides (N-2) and (N-3) to a hydroxyl group, optionally followed by protection or other modification, provides macrolides (N-4) and (N-5), respectively, wherein $R^{17}$ is as defined herein. Dihalogenation of the C3 ketone of macrolides (N-2) and (N-3), or monohalogenation of macrolides (N-4) and (N-5), providing the products, (N6a/b) and (N7a/b), is further contemplated, wherein X is halogen, e.g., fluoro.

Scheme 4.

(N-7a)

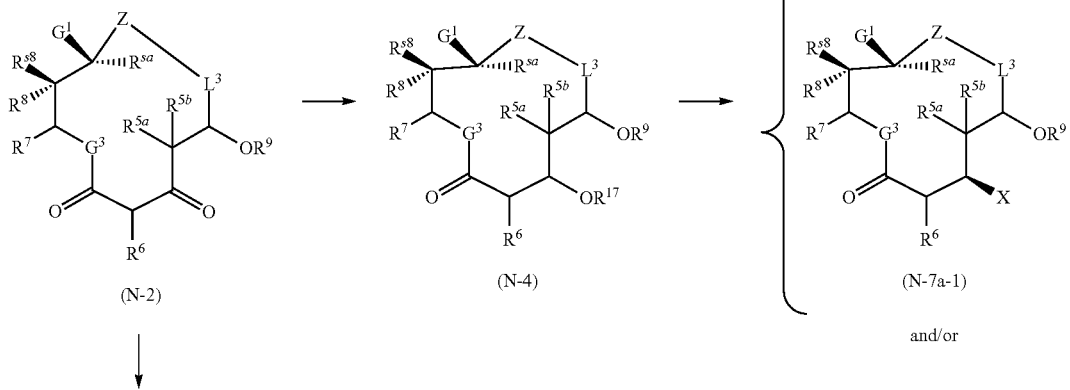

(N-2)　　(N-4)　　and/or (N-7a-1)

and/or

-continued

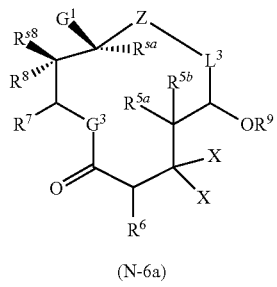

(N-6a)

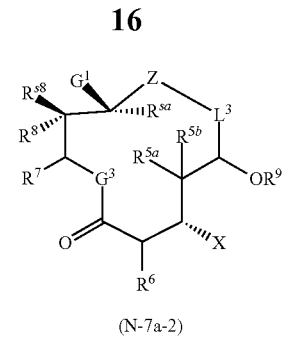

(N-7a-2)

Scheme 5.

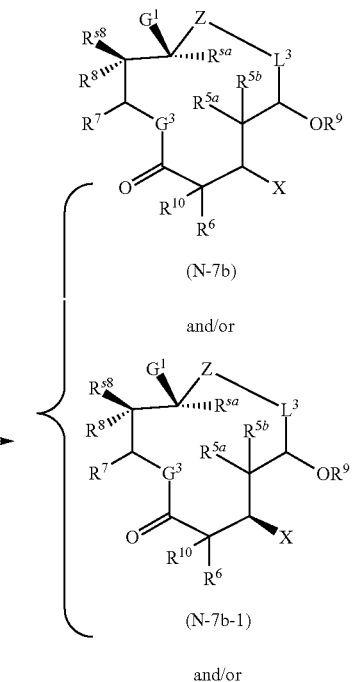

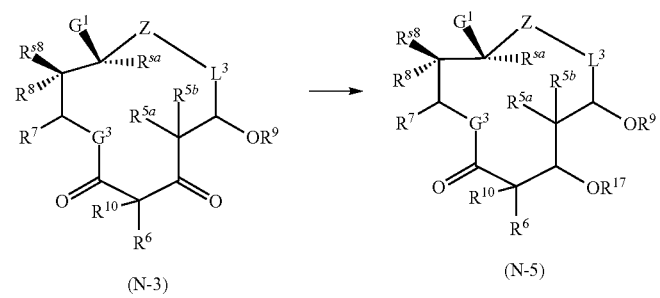

(N-3)    (N-5)    (N-7b-1)

and/or

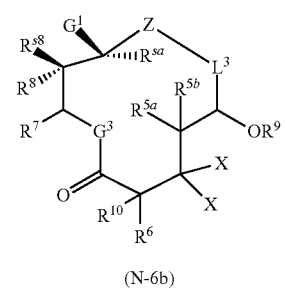

(N-6b)

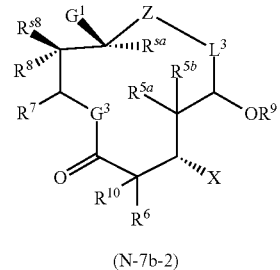

(N-7b-2)

Formula (N-6) and subgenera thereof as described herein are intended to encompass compounds of Formulae (N-2), (N-4), (N-6a), and (N-7a) and subgenera thereof, wherein $R^{Y1}$ is —$OR^{17}$, and $R^{Y2}$ is hydrogen; or $R^{Y1}$ is halogen, and $R^{Y2}$ is hydrogen; or $R^{Y1}$ is halogen, and $R^{Y2}$ is halogen.

Likewise, Formula (N-7) and subgenera thereof are intended to encompass compounds of Formula (N-3), (N-5), (N-6b), and (N-7b), wherein $R^{Y1}$ is —$OR^{17}$, and $R^{Y2}$ is hydrogen; or $R^{Y1}$ is halogen and $R^{Y2}$ is hydrogen; or $R^{Y1}$ is halogen, and $R^{Y2}$ is halogen; or $R^{Y1}$ and $R^{Y2}$ are joined to form an oxo (=O) group.

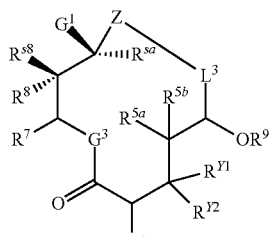

(N-6)

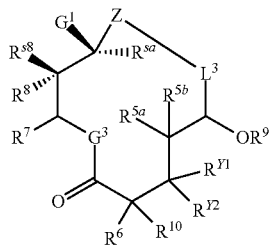

(N-7)

Additional functionalization of the coupled product (N-1) and the macrolides (N-2), (N-3), (N-4), (N-5), (N-6), and (N-7), for example, by addition and synthetic manipulation of a tethered moiety on the eastern and/or western portion of the molecule, and construction of the eastern and western halves, is also described herein.

It is generally understood that the synthetic methodologies described herein are both useful in the synthesis of known macrolides, such as those depicted in FIG. 1, and in the synthesis and development of new macrolides (e.g., 14-membered ketolides) as described herein. New macrolides synthesized using the inventive methodology, and pharmaceutical compositions thereof, are contemplated to be useful in the treatment of various conditions such as, for example, the treatment and/or prevention of infectious diseases, such as bacterial and parasitic infections, and the treatment and/or prevention of inflammatory conditions.

The details of certain embodiments of the invention are set forth in the Detailed Description of Certain Embodiments, as described below. Other features, objects, and advantages of the invention will be apparent from the Definitions, Examples, FIGURES, and Claims.

BRIEF DESCRIPTION OF THE DRAWINGS

FIG. 1 depicts exemplary 14-, 15-, and 16-membered macrolide antibiotics used in the United States.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75' Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds and macrolides described herein can comprise one or more asymmetric centers, and thus can exist in various stereoisomeric forms, e.g., enantiomers and/or diastereomers. For example, the compounds and macrolides described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds and macrolides as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl (C). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-7}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{1-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl (C), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-6}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydro-thieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety. An exemplary aralkyl group is —CH$_2$-phenyl (benzyl, Bz), wherein the phenyl moiety may be substituted or unsubstituted.

As used herein, "heteroaryl" refers to a radical of a 5-14 membered monocyclic or polycyclic (e.g., bicyclic, tricyclic) 4n+2 aromatic ring system (e.g., having 6, 10, or 14 πelectrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)(R$^{aa}$)$_2$, —OP(=O)(R$^{aa}$)$_2$, —OP(=O)(OR$^{cc}$)$_2$, —NR$^{bb}$P(=O)(OR$^{cc}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

In certain embodiments, the carbon substituents are selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, $C_{1-10}$ alkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-14}$ carbocyclyl, 3-14 membered heterocyclyl, $C_{6-14}$ aryl, and 5-14 membered heteroaryl; or two geminal hydrogens on a carbon atom are replaced with the group =O, =S, or =NR$^{bb}$.

In certain embodiments, the carbon substituents are selected from the group consisting of halogen, —CN, —NO$_2$, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —C(=O)N(R$^{bb}$)$_2$, —OC(=O)N(R$^{bb}$)$_2$, —NR$^{bb}$C(=O)R$^{aa}$, —SO$_2$N(R$^{bb}$)$_2$, —SO$_2$R$^{aa}$, $C_{1-6}$ alkyl, $C_{1-6}$ perhaloalkyl, $C_{2-6}$ alkenyl, $C_{2-6}$ alkynyl, $C_{3-6}$ carbocyclyl, 3-6 membered heterocyclyl, $C_6$ aryl, and 5-6 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxy," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(=O)(R$^{aa}$)$_2$, and —OP(=O)(OR$^{cc}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, and —NHP(=O)(OR$^{cc}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, and —NR$^{bb}$P(=O)(OR$^{cc}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

As used herein, the term "alkoxyalkyl" refers to an alkyl group as defined herein substituted by a group of formula —OR$^{aa}$ wherein R$^{aa}$ is as defined herein, wherein the point of attachment is on the alkyl group.

As used herein, the term "aminoalkyl" refers to an alkyl group as defined herein substituted by an amino or substituted amino group, as defined herein, wherein the point of attachment is on the alkyl group.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{CC}$, —P(=O)(R$^{AA}$)$_2$, $C_{1-10}$ ALKYL, $C_{1-10}$ PERHALOALKYL, $C_{2-10}$ ALKENYL, $C_{2-10}$ ALKYNYL, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, nitrogen substituents are selected from the group consisting of hydrogen, —OH, —$OR^{aa}$, —$N(R^{cc})_2$, —C(=O)$R^{aa}$, —C(=O)N($R^{cc})_2$, —$CO_2R^{aa}$, —$SO_2R^{aa}$, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —C(=O)$R^{aa}$, —C(=O)N($R^{cc})_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc})_2$, —$SO_2N(R^{cc})_2$, —$SO_2R^{cc}$, —$SO_2OR^{cc}$, —$SOR^{aa}$, —C(=S)N($R^{cc})_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, and —$P(=O)(R^{aa})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —$OR^{aa}$ (when the 0 atom is attached to a carbonyl group, wherein $R^{aa}$ is as defined herein), —O(C=O)$R^{LG}$, or —O(SO)$_2R^{LG}$ (e.g., tosyl, mesyl, besyl), wherein $R^{LG}$ is optionally substituted alkyl, optionally substituted aryl, or optionally substituted heteroaryl. In some cases, the leaving group is a halogen. In some embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

A "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers.

As used herein, a nucleophile refers to a chemical species that donates an electron pair to an electrophile to form a chemical bond in relation to a reaction. All molecules or ions with a free pair of electrons or at least one pi bond can act as nucleophiles. The nucleophile can be a compound or an atom. In certain embodiments, a nucleophile is of formula $X^{a1}$—$R^{23}$, M-$R^{23}$ or $M_s(X^{n2})_t$, wherein M is a metal (e.g., Li, Na, or K), or a metal complex (e.g. metal halide such as $CuX^n$, or $MgX^{n2}$); $X^{n1}$ is —$OR^{xn}$, —$SR^{xn}$, or —$N(R^{xn})_2$; $X^{n2}$ is a halogen, CN, N$_3$, —$OR^{xn}$, —$SR^{xn}$, —$N(R^{xn})_2$; each instance of $R^{xn}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; $R^{23}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl; s is 1, 2, 3, or 4; and t is 1, 2, 3, or 4. As used herein, a metal complex refers to a metal chelated with ligands such as organic compounds, anions such as halides, hydroxyls, or carboxylates. In certain embodiments, the nucleophile is $X^{n1}$—$R^{23}$ (e.g. $R^{23}$—OH; $R^{23}$—SH, $R^{23}$—NH$_2$ (e.g., NH$_3$)). In certain embodiments, nucleophile is M-$R^{23}$ (e.g., Li-alkyl). In certain embodiments, nucleophile is $M_s(X^{n2})_t$ (e.g. NaCN, NaN$_3$, NaNH$_2$, LiOR$^{xn}$, NaOR$^{xn}$).

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the macrolides of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds as described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrates, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2H$_2$O) and hexahydrates (R·6H$_2$O)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds as described herein which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds as described herein may be preferred in certain instances.

The term "isotopes" refers to variants of a particular chemical element such that, while all isotopes of a given element share the same number of protons in each atom of the element, those isotopes differ in the number of neutrons.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

"Disease," "disorder," and "condition" are used interchangeably herein.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

Detailed Description of Certain Embodiments of the Invention

As generally understood from the present disclosure, the present invention is, in part, directed to ketolides of the formulae below, constructed from the coupling of an eastern half and a western half, followed by macrocyclization and optionally further synthetic manipulation:

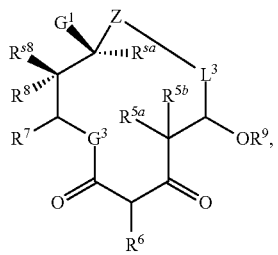
(N-2)

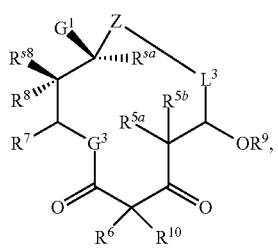
(N-3)

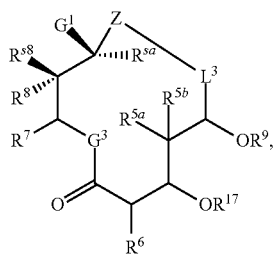
(N-4)

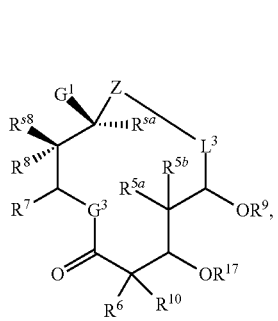
(N-5)

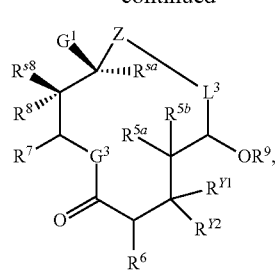
(N-6)

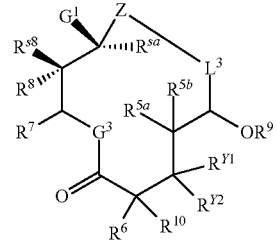
(N-7)

or a salt thereof,
Z is of the formula

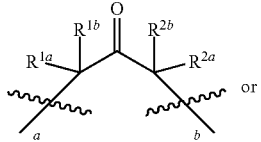
(z-i)

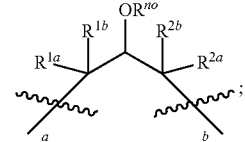
(z-ii)

each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl, or wherein $R^{1a}$ and $R^{1b}$ or $R^{2a}$ and $R^{2b}$ are taken together to form

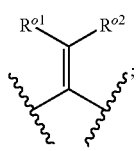

a indicates the point of attachment to the carbon substituted by G1;
b indicates the point of attachment to $L^3$;
each of $R^{o1}$ and $R^{o2}$ is independently hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;
$R^{no}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{sa}$ is hydrogen, hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl;

or $R^{sa}$ and $R^{1a}$ or $R^{sa}$ and $R^{1b}$ are taken together to form a bond;

$R^{s8}$ is hydrogen or $OR^{11}$;

$L^3$ is a group of formula:

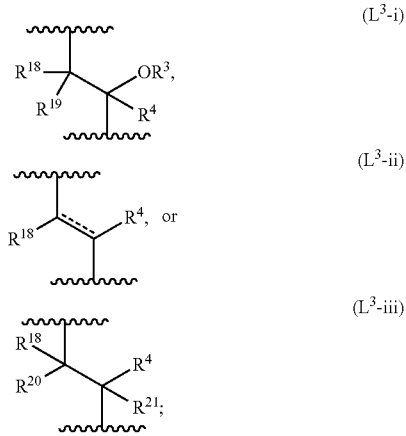

$\text{------}$ represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a group of formula:

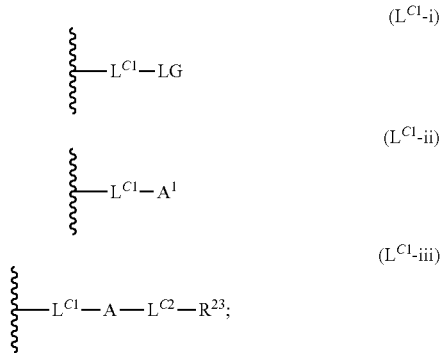

$R^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of $R^{18}$ and $R^{19}$ independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{20}$ and $R^{21}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, carbonyl, or $R^{20}$ and $R^{21}$ are joined to form an optionally substituted cyclopropyl or an oxiranyl ring;

each instance of $R^5$ and $R^{5b}$ is independently hydrogen, halogen, silyl, optionally substituted alkyl, optionally substituted carbocyclyl, or optionally substituted heterocyclyl;

$R^{Y1}$ is —$OR^{17}$ and $R^{Y2}$ is hydrogen, or $R^{Y1}$ is halogen and $R^{Y2}$ is hydrogen, or R is halogen and $R^{Y2}$ is halogen, or $R^{Y1}$ and $R^{Y2}$ are joined to form an oxo (=O) group;

$R^6$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ and $R^{17}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a carbohydrate;

$R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, carbonyl, silyl, and halogen;

$G^3$ is —O—, —S—, or —N($R^{G1}$)—, wherein $R^{G1}$ is hydrogen, optionally substituted alkyl, or a nitrogen protecting group;

$G^1$ is hydrogen, —$OR^{12}$ or —$NR^{13}R^{14}$;

provided when $G^1$ is —$OR^{12}$, then $R^{11}$ and $R^{12}$ are joined as a group of formula —C(=O)— to provide a cyclic carbonate, or $R^{11}$ and $R^{12}$ are not joined, and $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

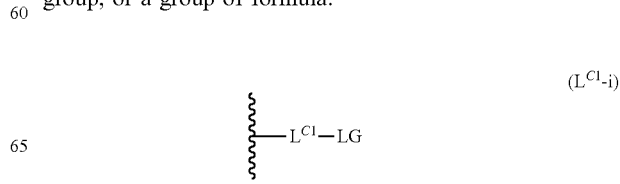

-continued

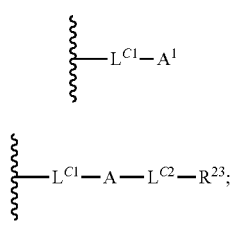
(L^{C1}-ii)

$$-L^{C1}-A^1$$

(L^{C1}-iii)

$$-L^{C1}-A-L^{C2}-R^{23};$$

or provided when $G^1$ is —NR$^{13}$R$^{14}$, then R$^{11}$ and R$^{13}$ are joined as a group of formula —C(=O)— to provide a cyclic carbamate, or R$^{11}$ and R$^{13}$ are not joined, R$^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, R$^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R$^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)R$^{Z8}$, or —C(=O)OR$^{Z8}$, or a group of formula:

(L^{C1}-i)

$$-L^{C1}-LG$$

(L^{C1}-ii)

$$-L^{C1}-A^1$$

(L^{C1}-iii)

$$-L^{C1}-A-L^{C2}-R^{23}$$

or R$^{13}$ and R$^{14}$ are joined to form an optionally substituted heterocyclyl or optionally substituted heteroaryl;

each instance of L$^{C1}$ and L$^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, optionally substituted carbocyclylene, optionally substituted heterocyclylene, and combinations thereof;

each instance of A is independently a leaving group (LG), —SH, —OH, —NH$_2$, —NH—NH$_2$, —N$_3$, —O—NH$_2$, —C(=O)R$^{X1}$,

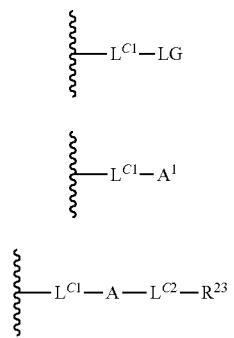

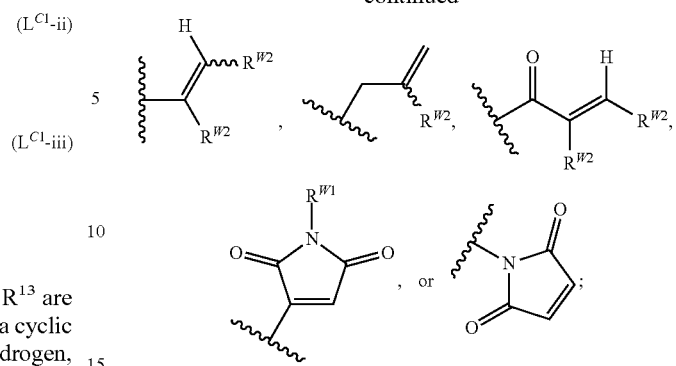

A is —NH—, —NH—NH—, —NH—O—, —O—NH—, —S—, —O—,

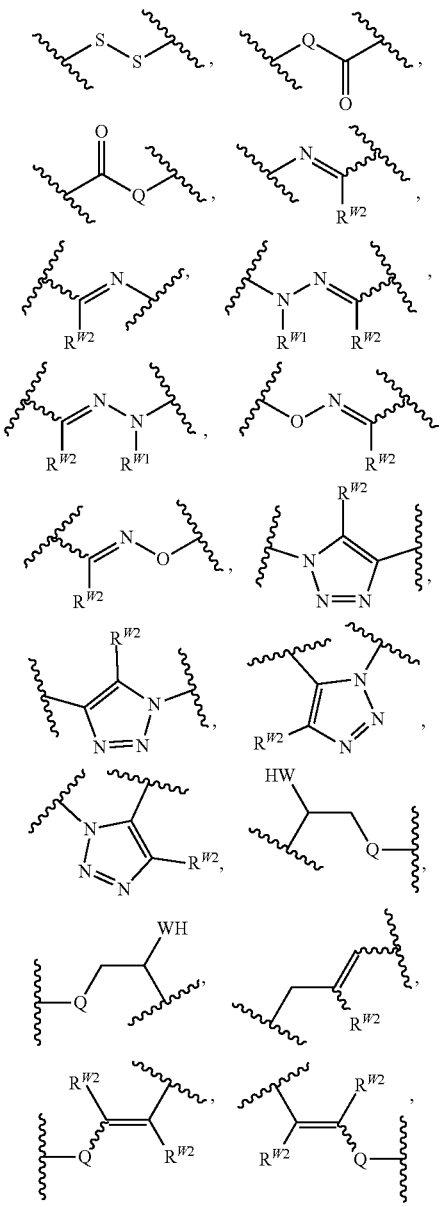

-continued

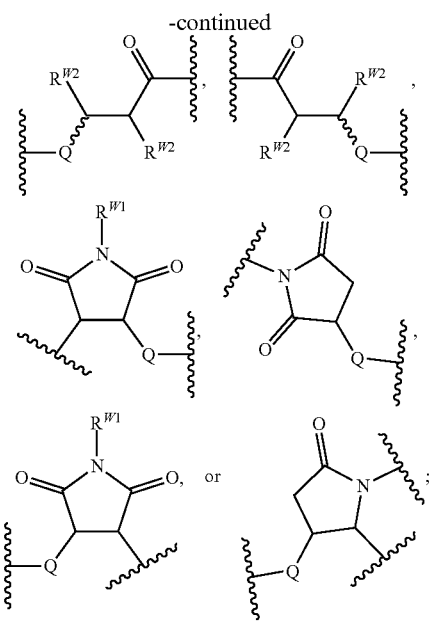

Q is —NH—, —NH—NH—, —O—NH—, —NH—O—, —S—, —O—;
W is O, S, or NR$^{W1}$;
R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;
R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form an optionally substituted cyclic moiety;
R$^{X1}$ is hydrogen, halogen, or —OR$^{X2}$, wherein R$^{X2}$ is hydrogen; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;
R$^{Z3}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and
each instance of R$^{Z8}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl, or two R$^{Z8}$ groups are joined to form an optionally substituted heterocylyl or optionally substituted heteroaryl ring;
or A is a cyclic moiety selected from the group consisting of optionally substituted carbocyclyl, optionally substituted heterocyclyl, optionally substituted aryl, and optionally substituted heteroaryl;
R$^{s1}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^{s1}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

Y$^1$ is 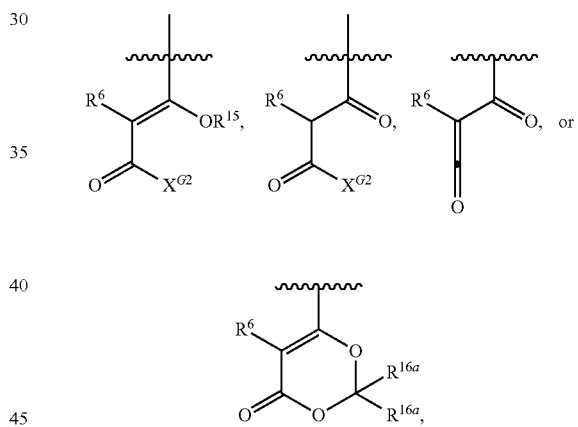

Y$^2$ is —C(=O)—CH=P(R$^{P1}$)(R$^{P2}$)(R$^{P3}$) or —C(=O)—CH$_2$—P(O(OR$^{P2}$)(OR$^{P3}$);
each of R$^{P1}$, R$^{P2}$, and R$^{P3}$ is independently optionally substituted alkyl, optionally substituted alkenyl, optionally substituted alkynyl, optionally substituted carbocycyl, optionally substituted heterocyclyl, optionally substituted aryl, or optionally substituted heteroaryl;
P$^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group; and
G$^2$ is a group of formula:

wherein:
each instance of X$^{G2}$ is —OR$^{15}$, —SR$^{15}$, or —N(R$^{15}$)$_2$;
each instance of R$^{15}$ is independently silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^{15}$ groups are taken together to form an optionally substituted heteroaryl or heterocyclic ring; and
each instance of R$^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Unless otherwise stated, any formulae as described herein are also meant to include a salt, solvate, hydrate, polymorph, co-crystal, tautomer, stereoisomer, isotopically labeled derivative, and prodrug thereof. In certain embodiments, the provided macrolide is a salt of any of the formulae as described herein. In certain embodiments, the provided compound is a pharmaceutically acceptable salt of any of the formulae as described herein. In certain embodiments, the provided compound is a solvate of any of the formulae as described herein. In certain embodiments, the provided compound is a hydrate of any of the formulae as described herein. In certain embodiments, the provided compound is a polymorph of any of the formulae as described herein. In certain embodiments, the provided compound is a co-crystal of any of the formulae as described herein. In certain embodiments, the provided compound is a tautomer of any of the formulae as described herein. In certain embodiments, the provided compound is a stereoisomer of any of the formulae as described herein. In certain embodiments, the provided compound is of an isotopically labeled form of any of the formulae as described herein. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. In certain embodiments, the provided compound is of a deuterated labeled form of any of the formulae as described herein. In certain embodiments, the provided compound is a prodrug of any of the formulae as described herein.

In certain embodiments, the macrolide is prepared from macrocyclization (e.g., thermally induced macrocyclization) of the coupled precursor of the formula below, optionally followed by further synthetic manipulation, as described herein:

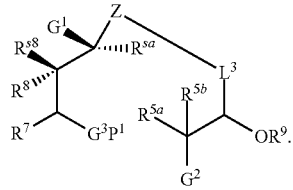

Coupling and Macrocyclization

As generally described herein, macrolides of the present invention are prepared by coupling of a western half (A-i) or (A-ii) with an eastern half (B-i) or (B-ii) to provide a compound of Formula (N-1), as depicted in Scheme 1. Scheme 8a and 8b depict certain specific embodiments of this coupling and macrocyclization steps to provide compounds falling with the scope of Formula (N-1).

As shown in Scheme 8a, when $Y^1$ is

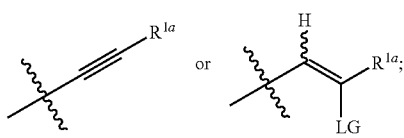

$R^{1a}$ is as defined herein, $R^{S1}$ is hydrogen, and LG is a leaving group; coupling of a compound of Formula (N-1b) and Formula (N-1a) via hydromagnesiation provides a compound of Formula (N-1c).

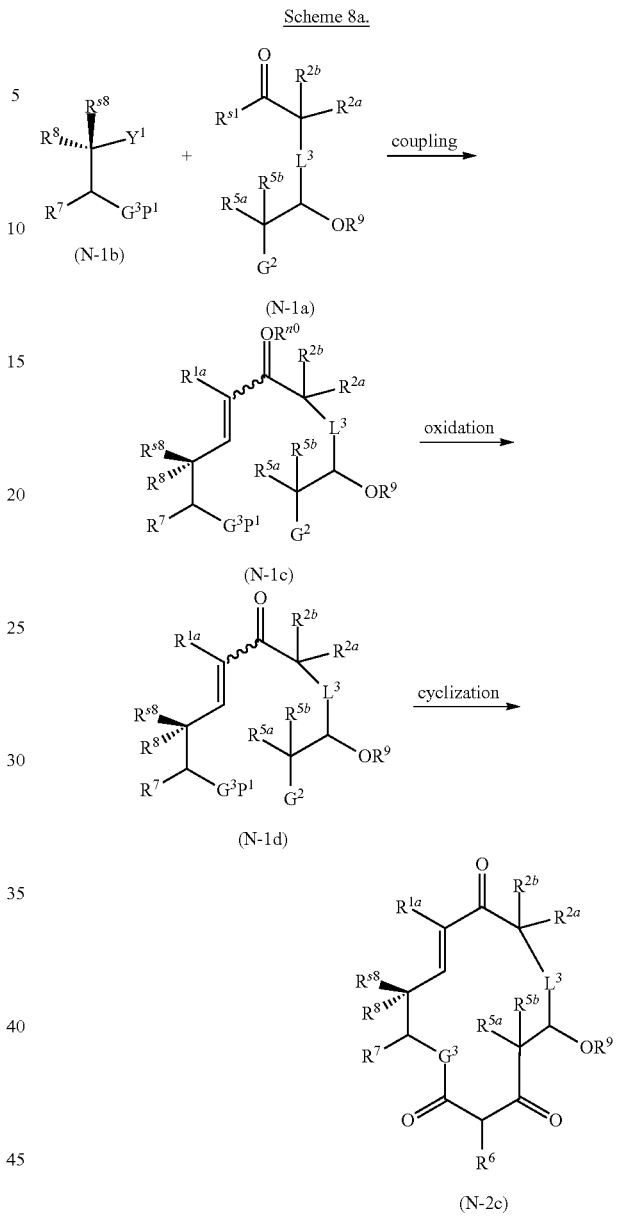

In certain embodiments, the hydromagnesiation reaction is carried out in the presence of an organic base such as a Grignard reagent. In certain embodiments, more than one Grignard reagents are present. In certain embodiments, the Grignard reagent is of the formula $R^{gr}$—Mg—$X^{gr}$, wherein $X^{gr}$ is halogen; and $R^{gr}$ is optionally substituted alkyl, optionally substituted alkyl, optionally substituted alkenyl, optionally substituted alkynyl, optionally substituted carbocyclyl, optionally substituted heterocylyl, optionally substituted aryl, or optionally substituted heteroaryl. In certain embodiments, $R^{gr}$ is optionally substituted alkyl or optionally substituted carbocyclyl. In certain embodiments, $R^{gr}$ is optionally substituted alkyl. In certain embodiments, $R^{gr}$ is branched alkyl (e.g., iso-propyl, iso-butyl, or tert-butyl). In certain embodiments, $R^{gr}$ is optionally substituted carbocyclyl (e.g., cyclcopentyl). In certain embodiments, the Grignard reagent is iso-butyl-MgCl.

In certain embodiments, the hydromagnesiation reaction is carried out in the presence of a catalyst. In certain embodiments, the catalyst is a Ti catalyst. In certain embodiments, the Ti catalyst is $Cp_2TiCl_2$.

In certain embodiments, the hydromagnesiation yields a compound of Formula (N-1), wherein Z is of the formula:

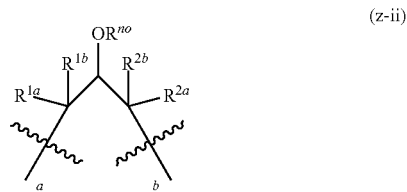

(z-ii)

wherein $R^{sa}$ and $R^{1a}$ or $R^{sa}$ and $R^{1b}$ are joined to form a bond; and $R^{no}$, $R^{2b}$, and $R^{2a}$ are as defined herein.

As generally defined herein, LG is a leaving group capable of being displaced by a nucleophile as defined herein. In certain embodiments, the LG is a halide. In certain embodiments, the LG is I. In certain embodiments, the LG is a Br.

As shown in Scheme 8b, when $Y^2$ is —C(=O)—CH=P($R^{P1}$)($R^{P2}$)($R^{P3}$) or —C(=O)—CH$_2$—P(O)(O$R^{P2}$)(O$R^{P3}$), coupling of Formula (N-1n) and Formula (N-1m) via a Wittig or Horner-Emmons reaction forms the moiety —CH=CH—C(=O)—, and provides a compound of Formula (N-1d).

As generally defined herein, $R^{P1}$ is independently optionally substituted alkyl, optionally substituted alkenyl, optionally substituted alkynyl, optionally substituted carbocycyl, optionally substituted heterocyclyl, optionally substituted aryl, or optionally substituted heteroaryl. In certain embodiments, $R^{P2}$ is optionally substituted alkyl. In certain embodiments, $R^{P2}$ is unsubstituted alkyl.

As generally defined herein, $R^{P2}$ is independently optionally substituted alkyl, optionally substituted alkenyl, optionally substituted alkynyl, optionally substituted carbocycyl, optionally substituted heterocyclyl, optionally substituted aryl, or optionally substituted heteroaryl. In certain embodiments, $R^{P2}$ is optionally substituted alkyl. In certain embodiments, $R^{P2}$ is unsubstituted alkyl.

As generally defined herein, $R^{P3}$ is independently optionally substituted alkyl, optionally substituted alkenyl, optionally substituted alkynyl, optionally substituted carbocycyl, optionally substituted heterocyclyl, optionally substituted aryl, or optionally substituted heteroaryl. In certain embodiments, $R^{P3}$ is optionally substituted alkyl. In certain embodiments, $R^{P3}$ is unsubstituted alkyl.

In certain embodiments, the double bond of the above recited formula such as Formula (N-1-b) is in the cis-configuration. In certain embodiments, the double bond of the above recited formula such as Formula (N-1-b) is in the trans-configuration.

Various macrolides may be accessed from these coupled products of Formula (N-1), depending upon the nature of the group $G^2$, upon macrocyclization. For example, as depicted in Scheme 9, when $G^2$ is a group of formula:

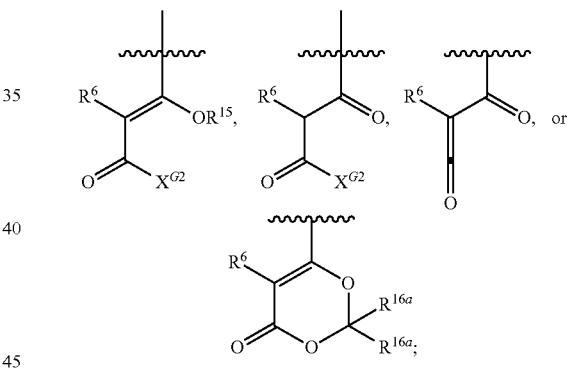

and $R^6$ is a hydrogen or non-hydrogen group, macrocyclization of the compound of Formula (N-1), e.g., wherein $P^1$ is hydrogen, provides a macrolide of Formula (N-2). Enolization of the macrolide of Formula (N-2), followed by addition of a non-hydrogen group $R^{10}$ (e.g., with a base and an $R^{10}$ alkylating agent, e.g., $R^{10}$-LG, or with a halogenating agent if $R^{10}$ is halogen), provides a macrolide of Formula (N-3).

Scheme 8b.

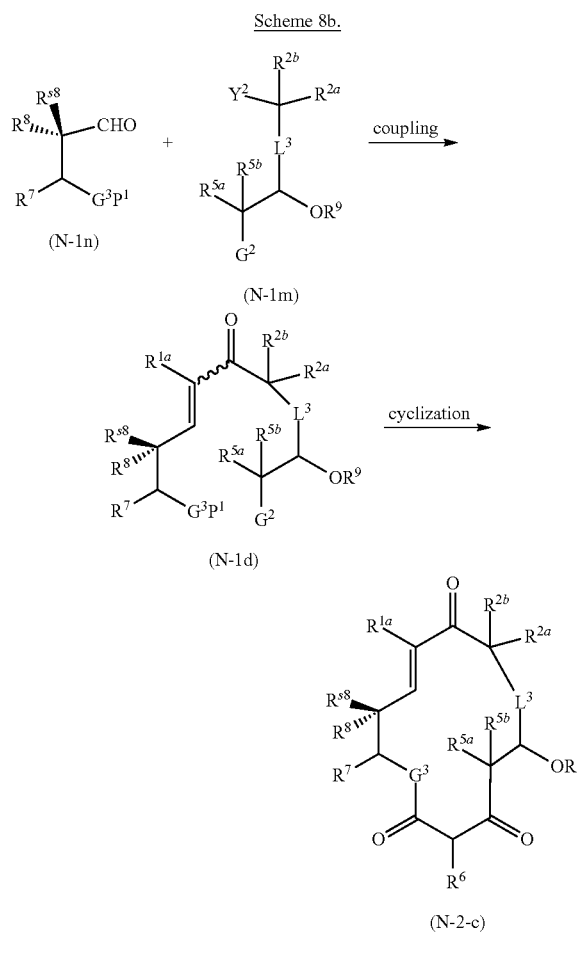

Scheme 9.

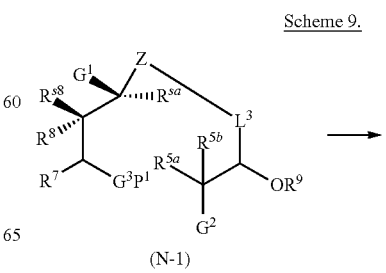

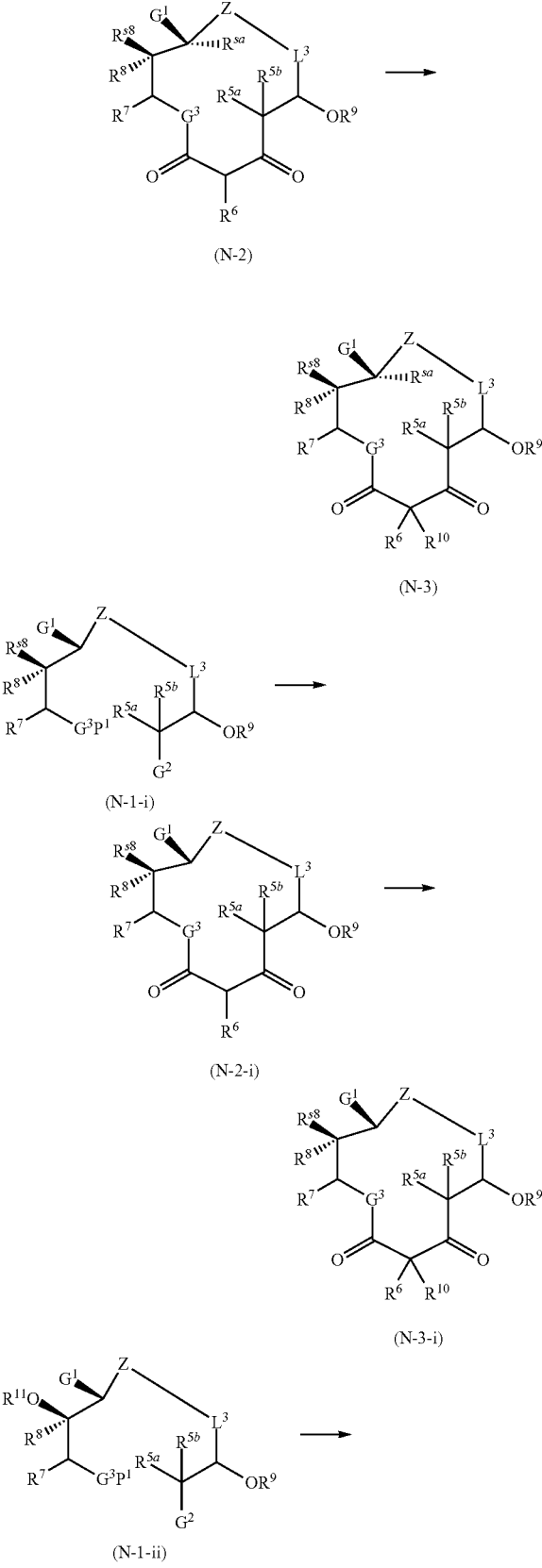
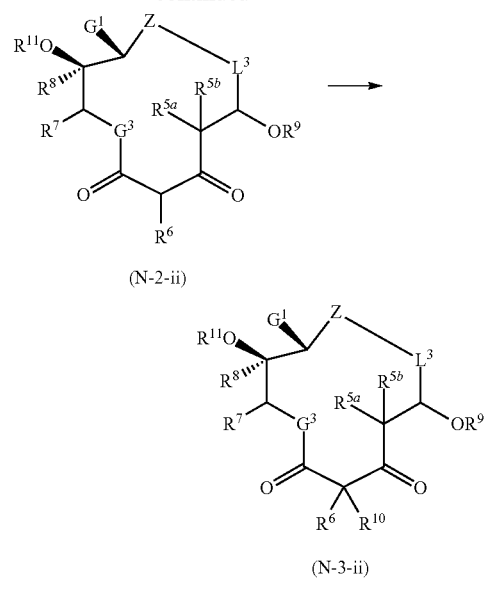
Alternatively, as depicted in Scheme 10, when G² is a group of formula:
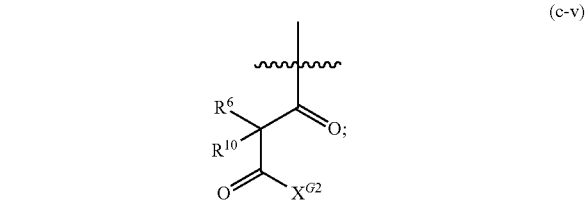
(c-v)
wherein each of R⁶ and R¹⁰ is hydrogen or a non-hydrogen group, macrocyclization of the compound of Formula (N-1), e.g., wherein P¹ is hydrogen, provides a macrolide of Formula (N-3).
Scheme 10.
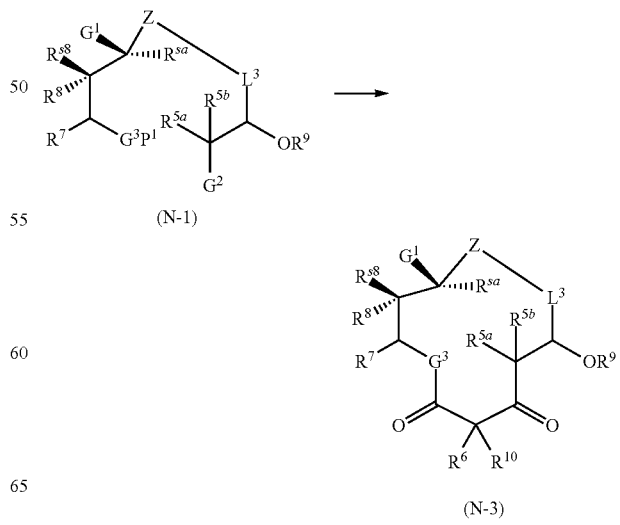

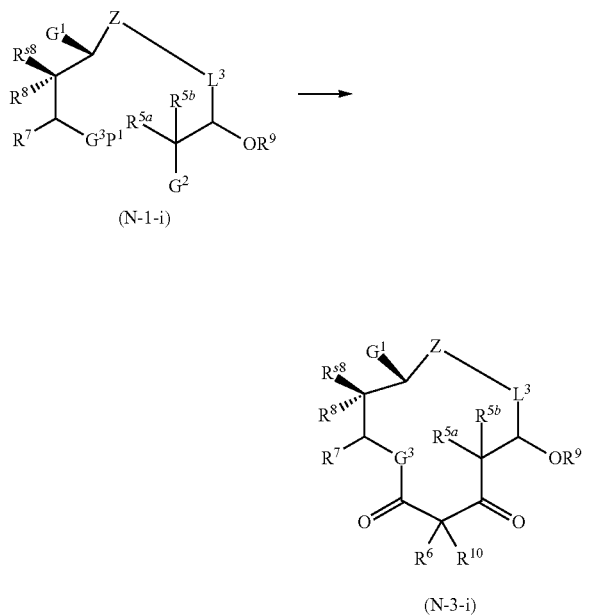

(N-1-i)

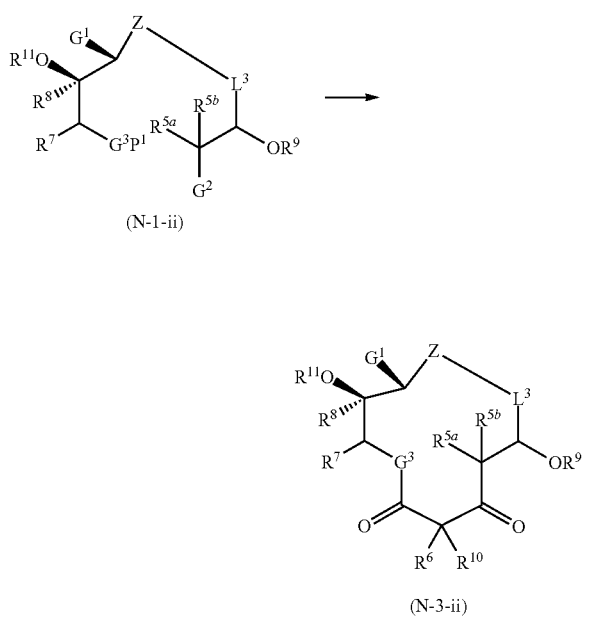

(N-1-ii)

Further functionalization of the macrolide is also contemplated herein. For example, as depicted in Schemes 11 and 12, reduction of the C3 ketone of macrolides (N-2) and (N-3) to a hydroxyl group, optionally followed by protection, provides macrolides (N-4) and (N-5), respectively. Alternatively, the hydroxyl group at C3 can be modified through O-alkylation or acylation as depicted in Schemes 13A-13B, where LG is a leaving group as defined herein. In certain embodiments, $R^{17}$ is —C(=O)$R^{Z8}$, wherein $R^{Z8}$ is optionally substituted alkyl (e.g., optionally substituted aralkyl or optionally substituted heteroaralkyl).

The ability to readily alter the oxidation state of the oxygen substituent at C3 enables the protection of this position as a carbonyl group while other free hydroxy groups are modified (e.g., by O-alkylation). Therefore, oxidation or reduction of this position at various points along the specific synthetic sequence is contemplated herein.

Scheme 11.

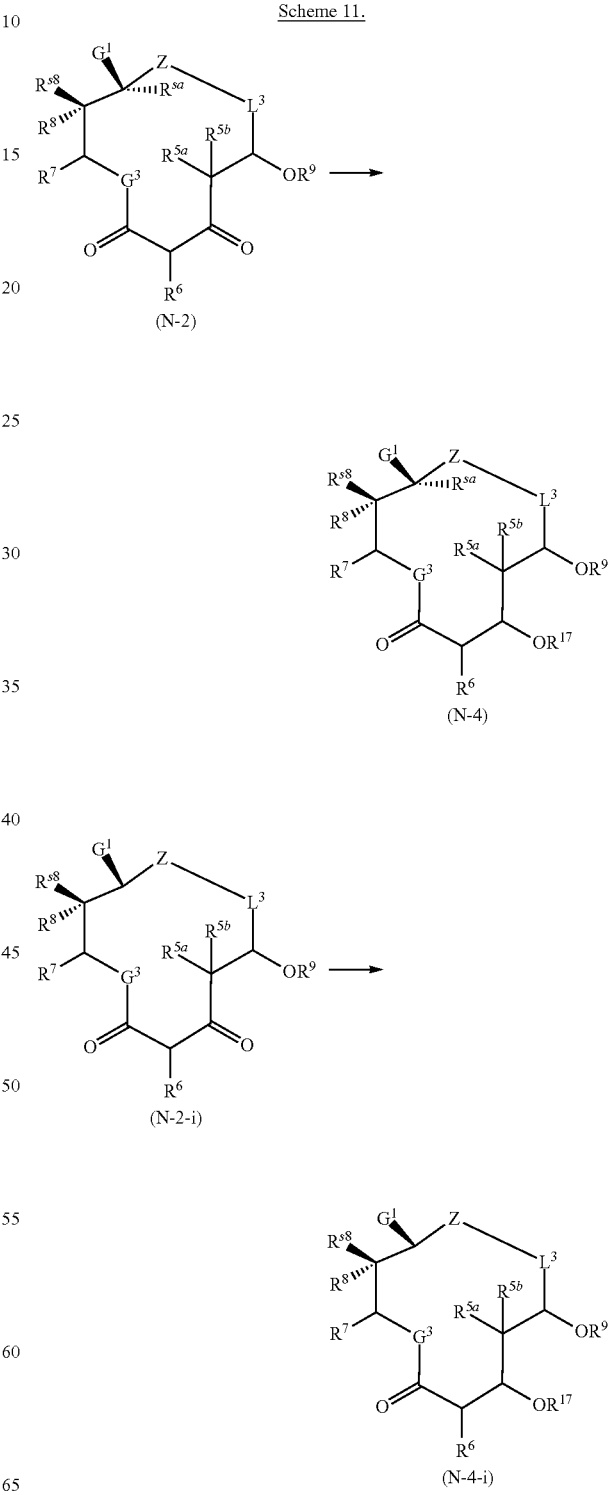

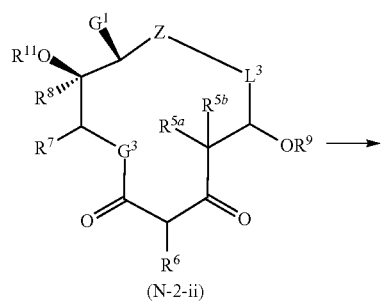
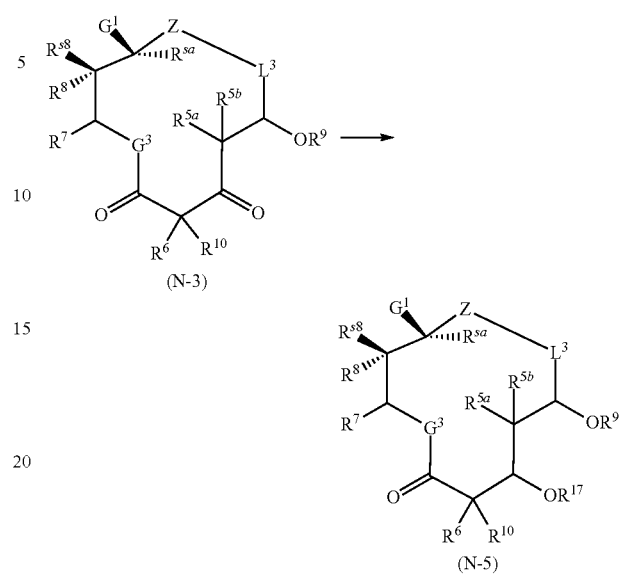
Scheme 12.
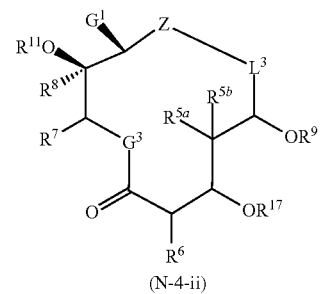
Scheme 13A.
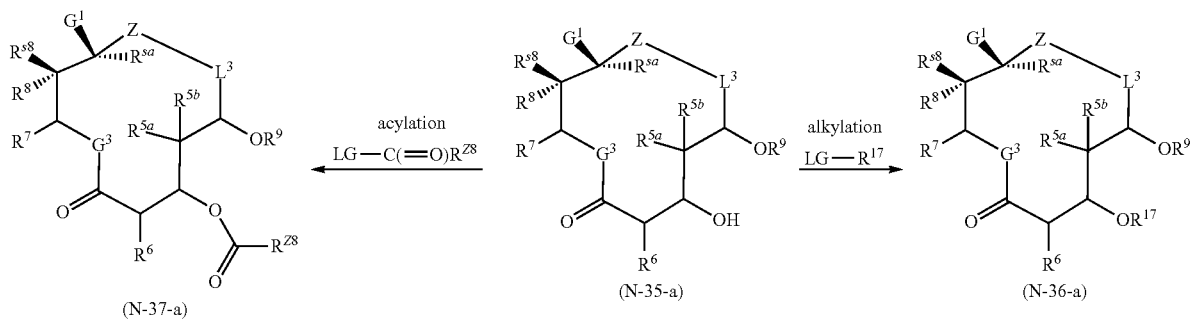
Scheme 13B.
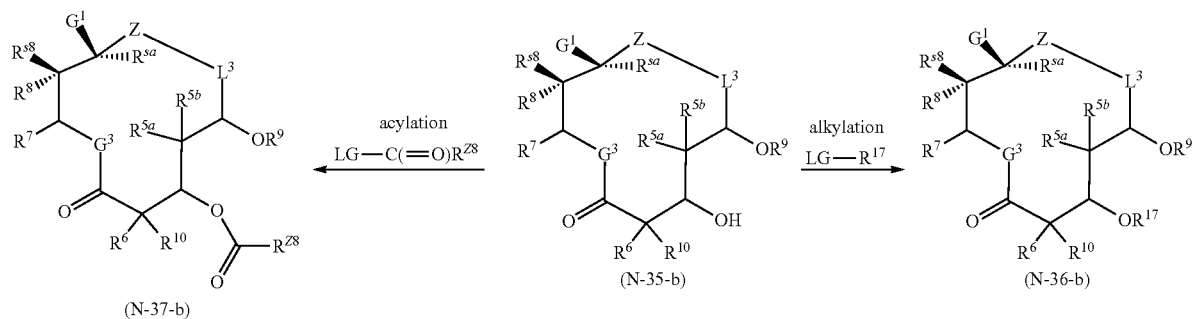

Further modification of the ketone or reduced macrolide is also contemplated herein. For example, as depicted in Schemes 14A-14B and 15A-15B, the C3 ketone of Formula (N-2) or (N-3), or (N-4) or (N-5) (e.g., hydroxyl at C3, wherein $R^{17}$ is hydrogen), can be halogenated with an electrophilic halogenating agent (e.g., Deoxo-Fluor) to give geminal dihalides such as Formula (N-6), or monohalides such as Formula (N-7), respectively, wherein each instance of X is independently a halogen (e.g., fluorine, bromine, iodine).

Scheme 14A.

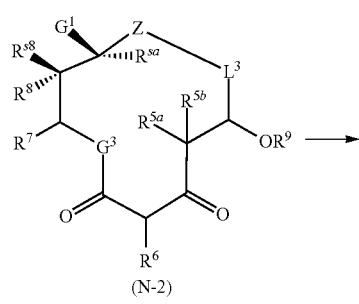
(N-2)

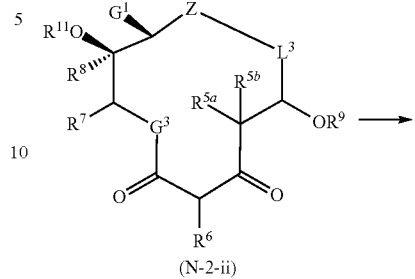
(N-2-ii)

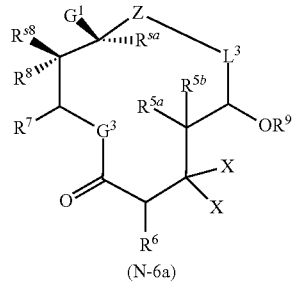
(N-6a)

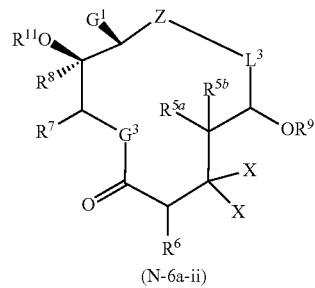
(N-6a-ii)

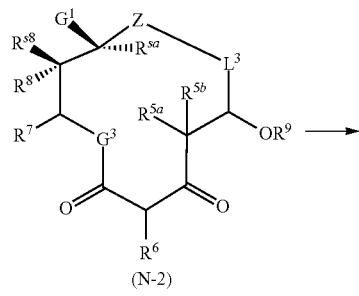
(N-2-i)

Scheme 14B.

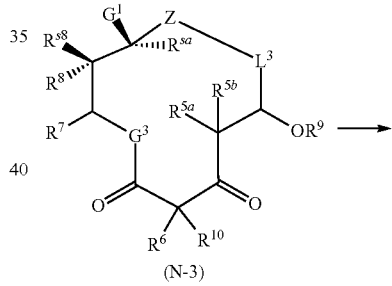
(N-3)

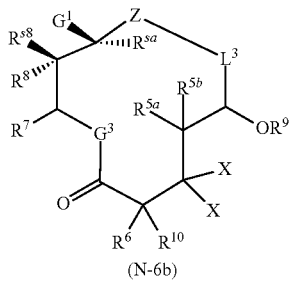
(N-6b)

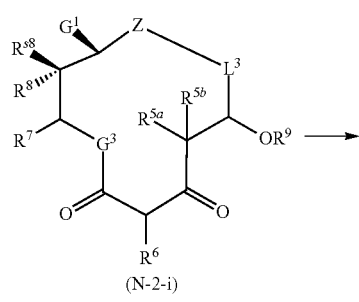
(N-6a-i)

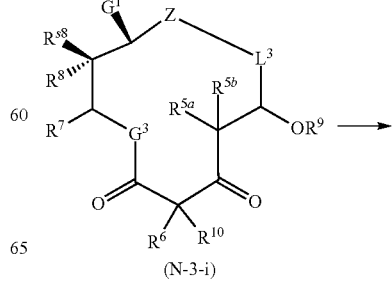
(N-3-i)

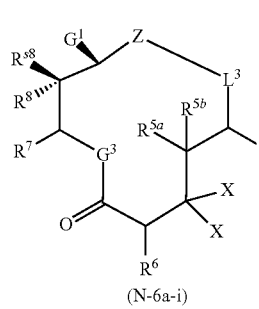

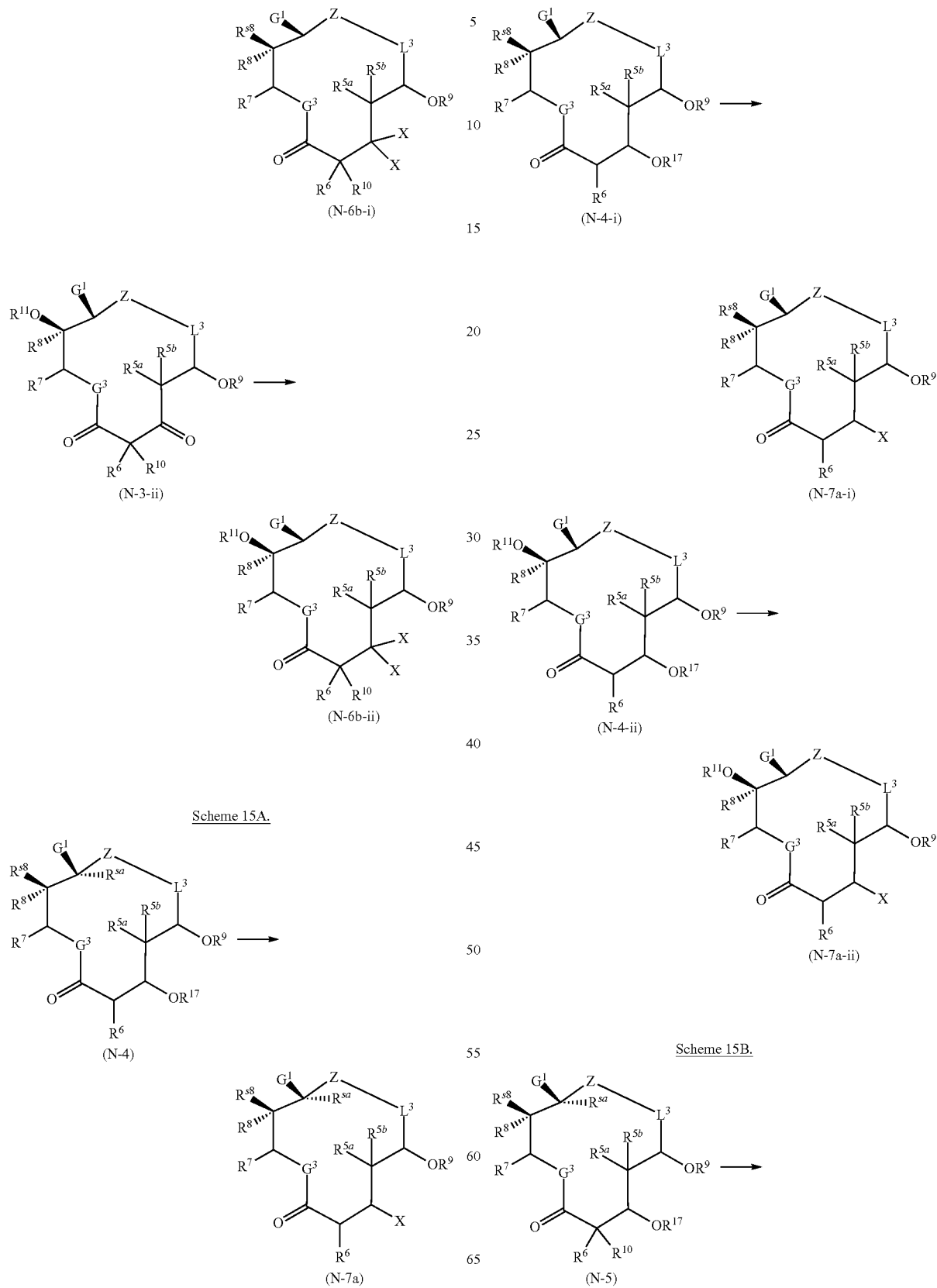

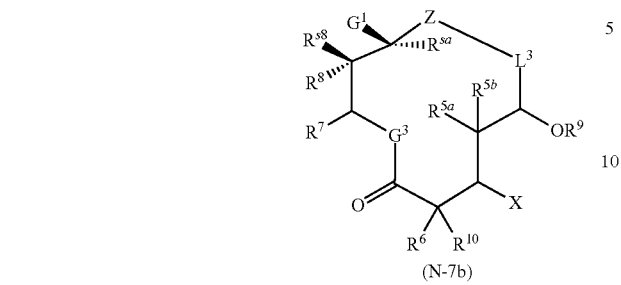

(N-7b)

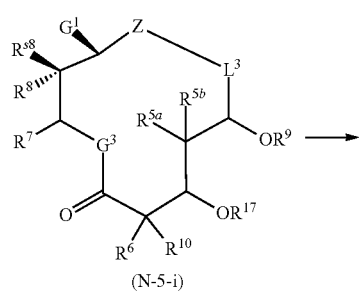

(N-5-i)

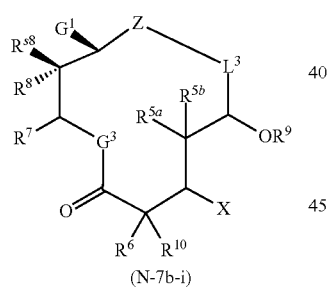

(N-7b-i)

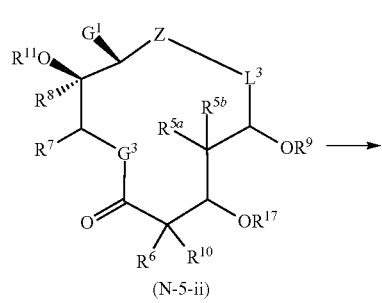

(N-5-ii)

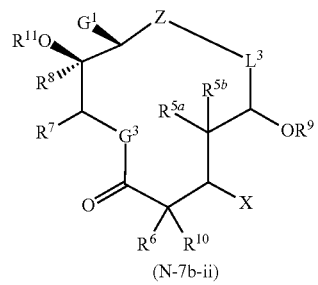

(N-7b-ii)

Instances wherein either $R^3$ or $R^4$ is allyl enable derivitization into novel macrolides as demonstrated in Schemes 16A-16B and 17A-17B. A variety of groups, such as heteroaryl or aryl moieties, may be introduced through a transition metal catalyzed cross coupling (e.g., Heck reaction) or through an olefin metathesis reaction (e.g., cross methathesis using a Grubbs or Schrock metal carbene catalyst) leading to derivatives such as derivatives of Formula (N-9) or (N-15). Subsequent manipulation of the olefin (e.g. hydrogenation) can be used to access further structural diversity (e.g. N-10a-b, N-16a-b). Alternatively, the olefin functionality can be oxidatively cleaved to produce a carbonyl functionality (N-11a-b or N-17a-b) that may be further modified by transformations such as reduction, nucleophilic additions (N-13a-b or N-19a-b), or reductive amination (N-12a-b or N-18a-b), wherein $R^{23}$ is as defined herein; each instance of $R^{22}$ is independently hydrogen or optionally substituted alkyl and $R^{24}$ is hydrogen, optionally substituted alkyl, or optionally substituted aryl. In certain embodiments, $R^{22}$ is —$CH_2C(=O)OH$. In certain embodiments, $R^{22}$ is

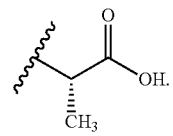

In certain embodiments, $R^{22}$ is

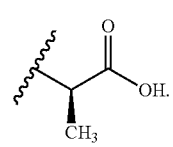

Scheme 16A.
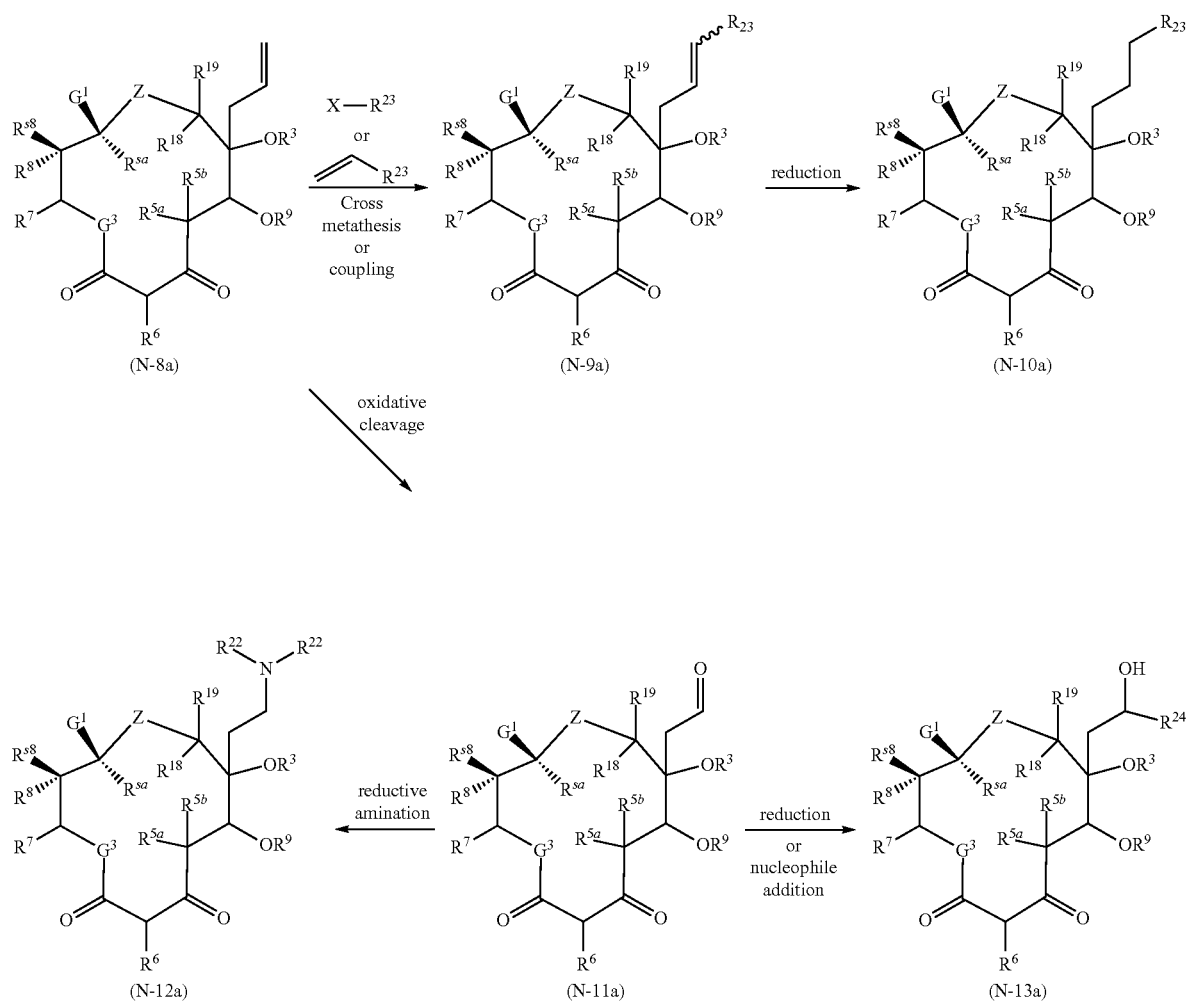
Scheme 16B.
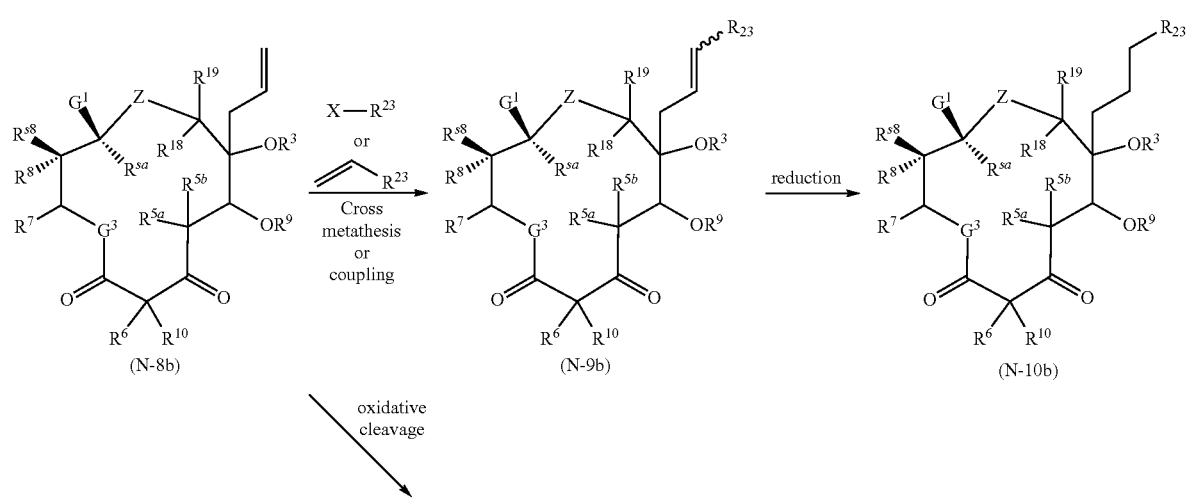

-continued
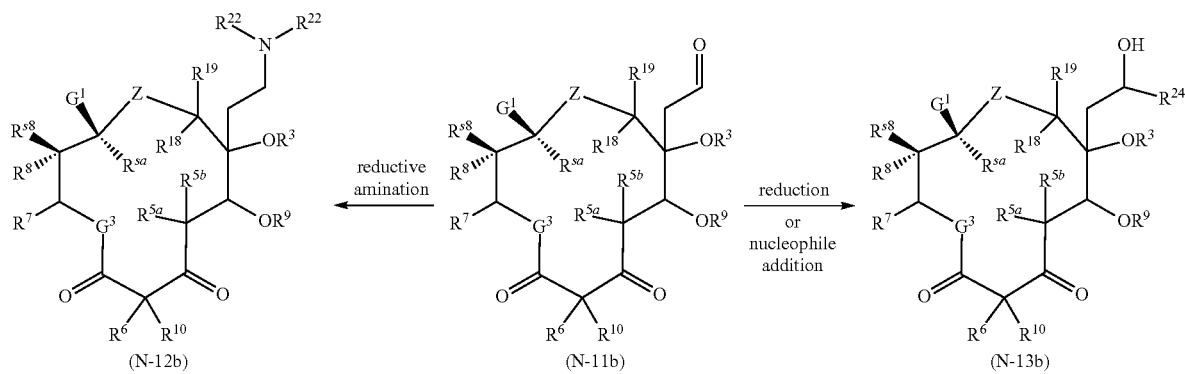
Scheme 17A.
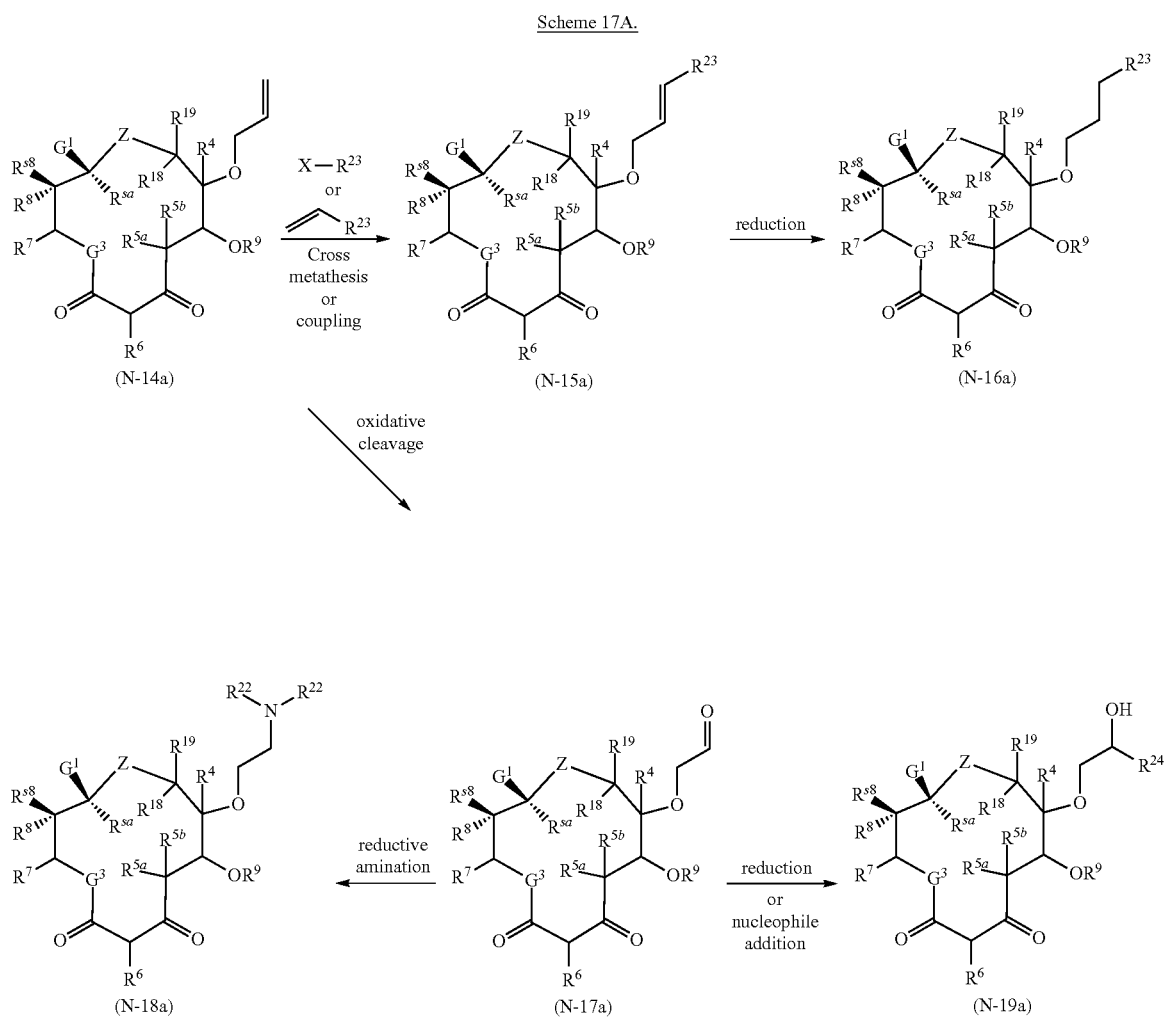

Scheme 17B.

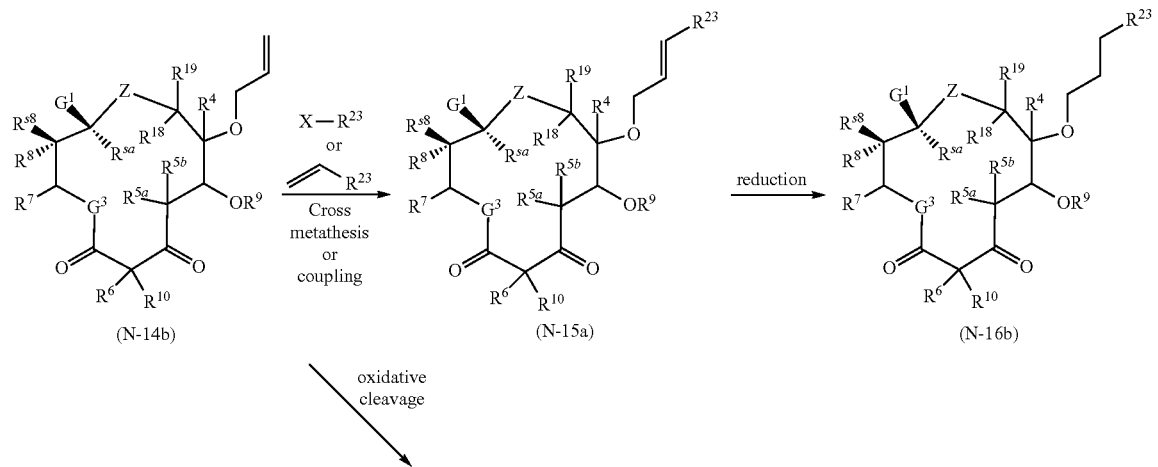

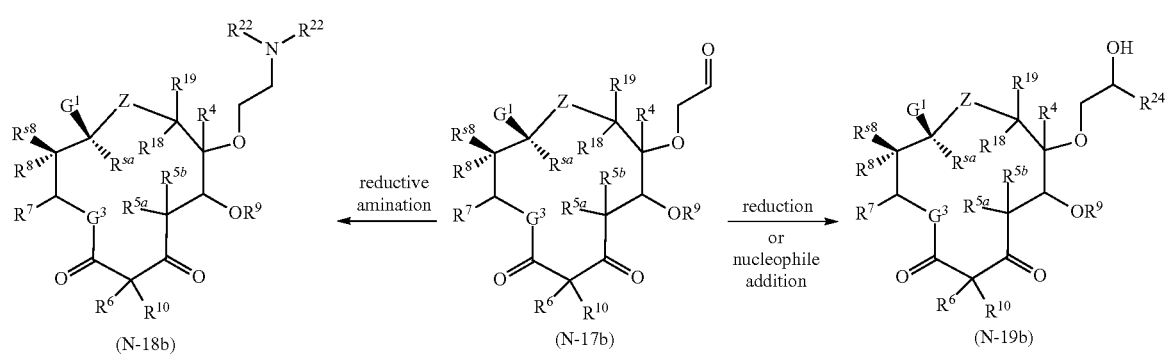

Further derivatization may be carried out using the transformations described herein pre- or post-macrocyclization wherein any of $R^{1a}$, $R^{1b}$, $R^{2a}$, or $R^{2b}$ is allyl. While only depicted for macrocycles of Formulae (N-20a)-(N-20b) in Scheme 18A-B, such modifications are contemplated for any macrocycle, wherein at least one of $R^{1a}$, $R^{1b}$, $R^{2a}$, or $R^{2b}$ is allyl. Derivatives wherein a —$CH_2$— moiety in the chain has been removed may be prepared using the precursor wherein any of $R^{1a}$, $R^{1b}$, $R^{2a}$, or $R^{2b}$ is vinyl (Scheme 19A-19B). In certain embodiments, $R^{22}$ is —$CH_2C(=O)$OH. In certain embodiments, $R^{22}$ is

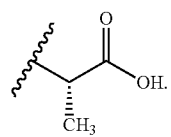

In certain embodiments, $R^{22}$ is

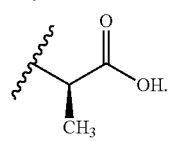

Scheme 18A.
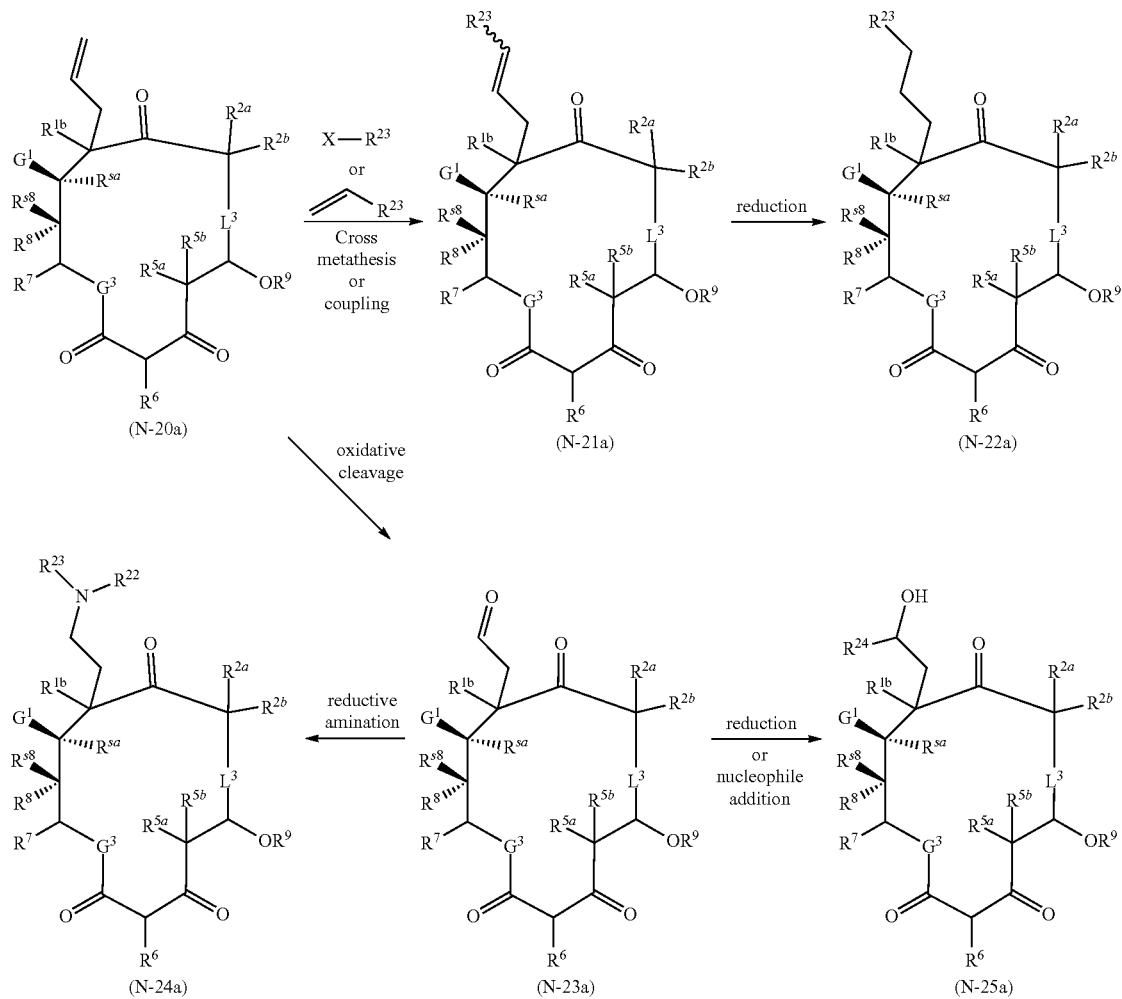
Scheme 18B.
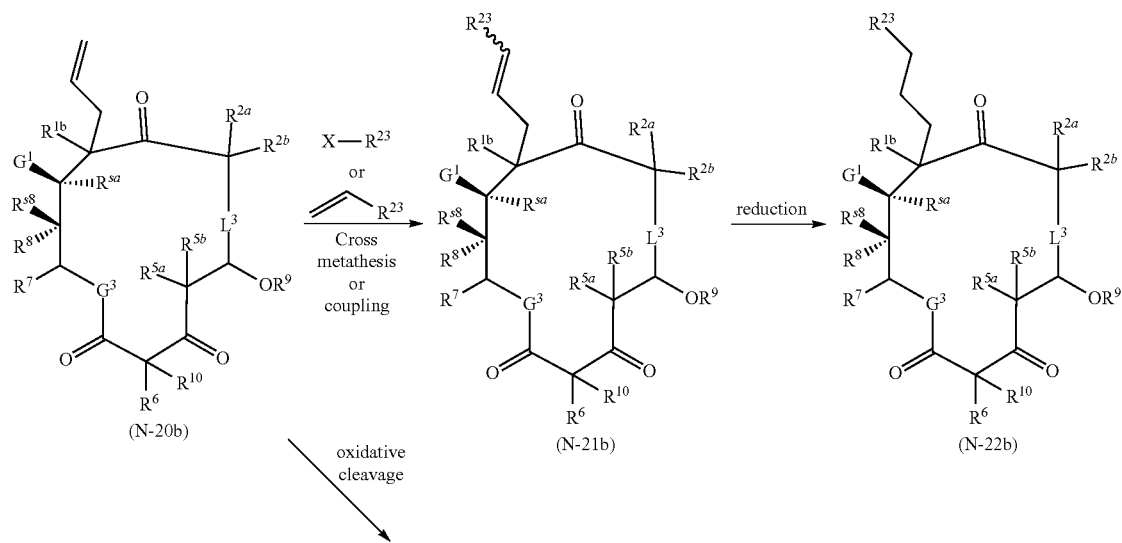

-continued
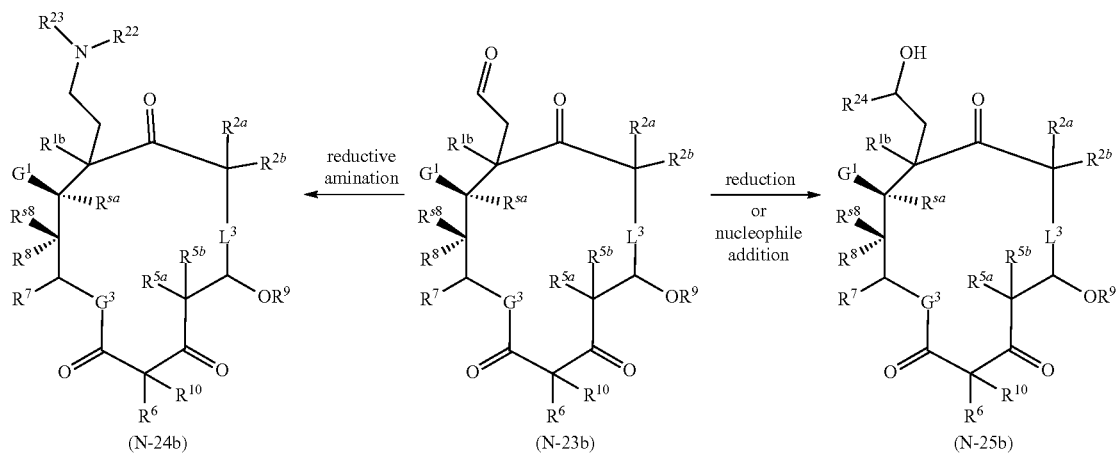
Scheme 19A.
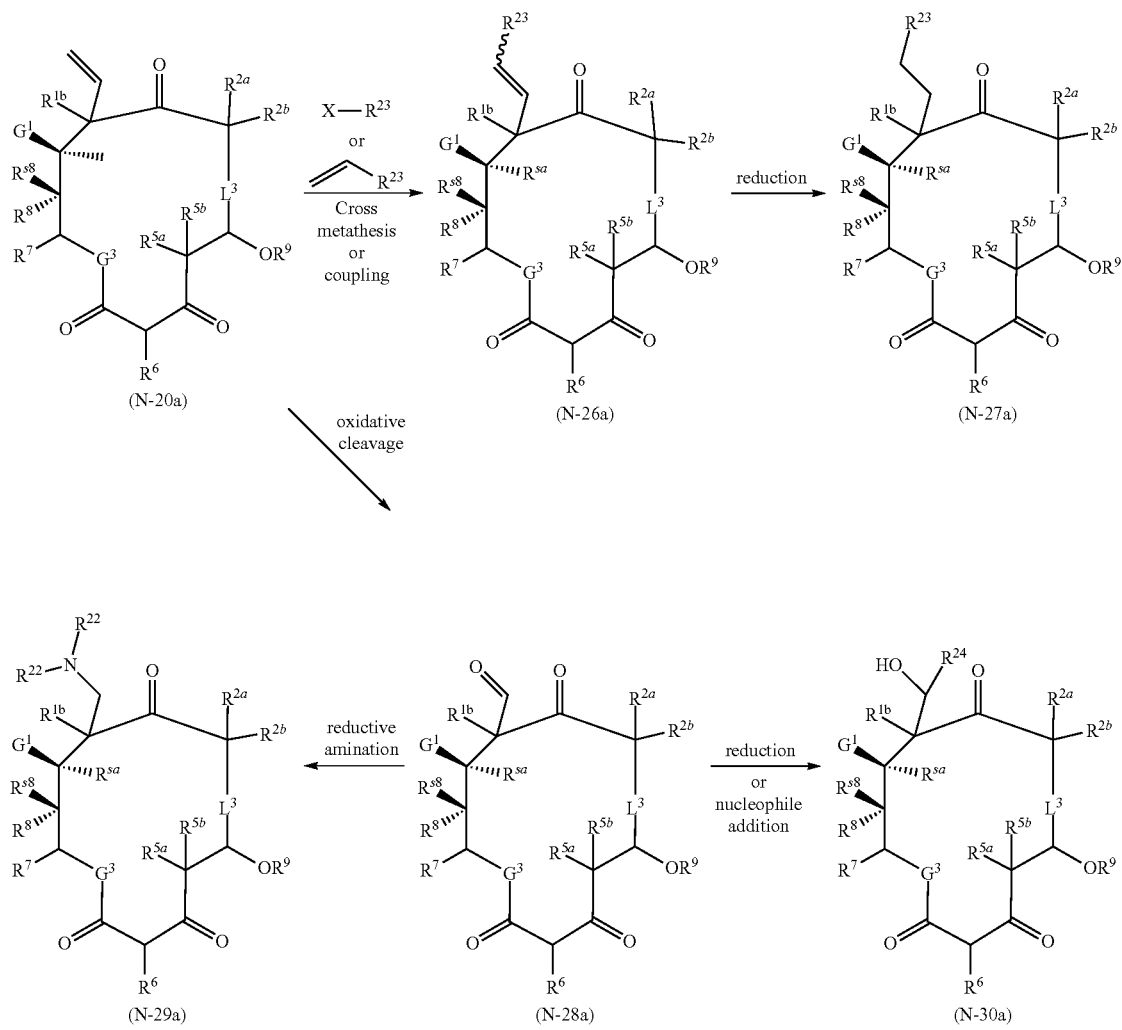

Scheme 19B.

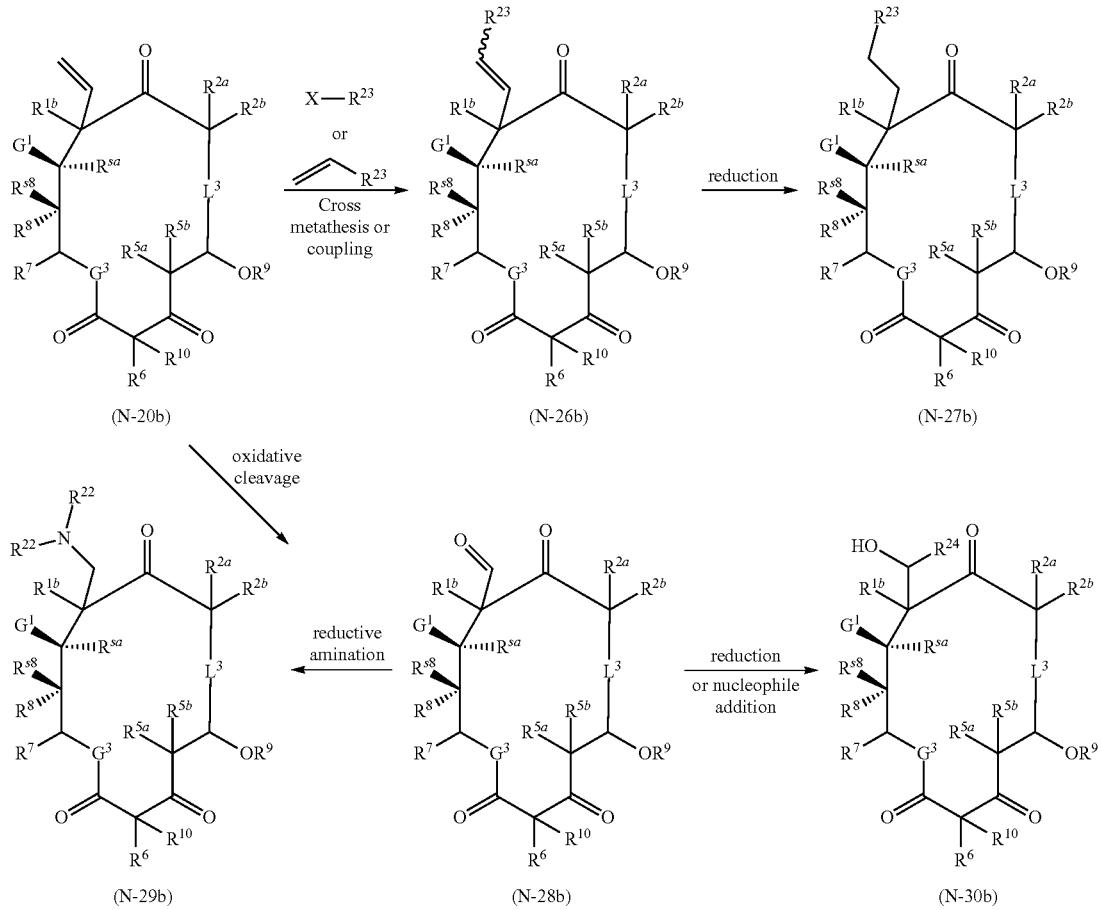

Further derivatization may be carried out using the transformations described herein pre- or post-macrocyclization when $R^{1a}$ and $R^{1b}$ or $R^{2a}$ and $R^{2b}$ are taken together to form

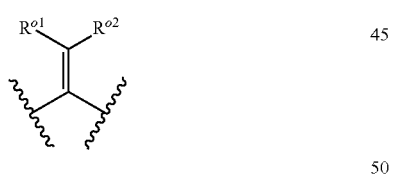

alpha to an oxo (=O) moiety, wherein $R^{o1}$ and $R^{o2}$ are as defined herein, and Z is of Formula (z-i-a). Exemplary transformations of Formula (z-i-a) include, but are not limited to, cross-coupling or nucleophilic addition (e.g. conjugated addition).

Scheme 20A.

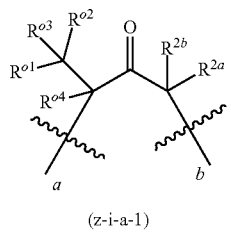

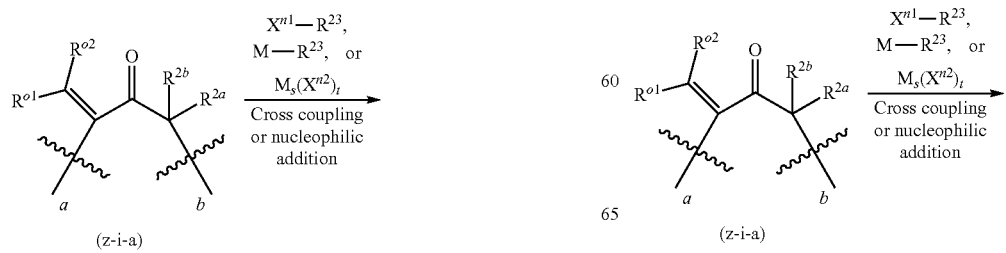

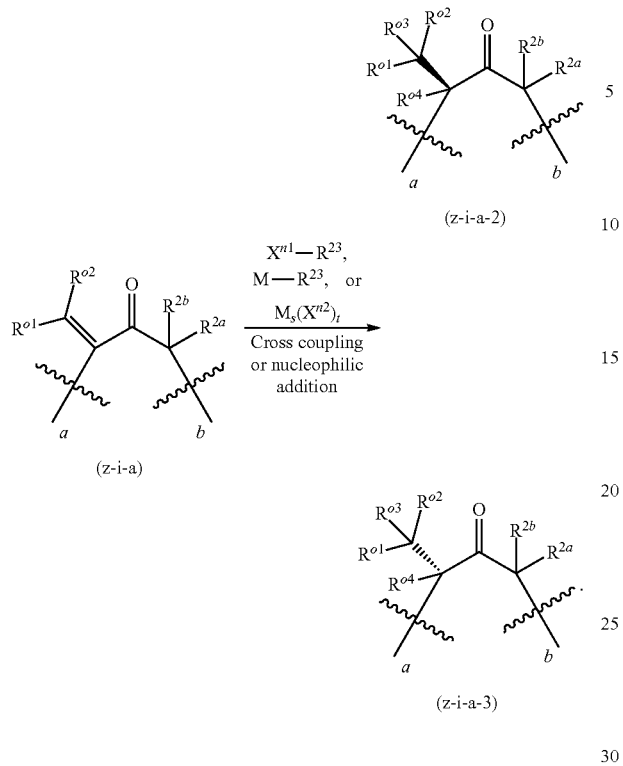

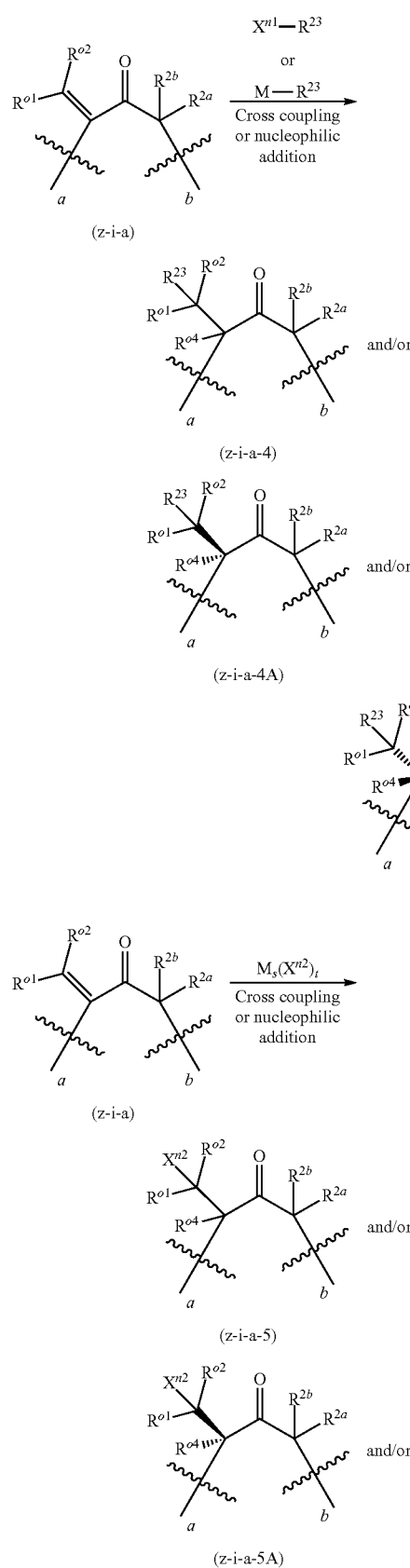

Conjugate addition reactions using a nucleophile such as an $R^{23}$ species provide compounds of formula (N-42a) or (N-42b). As used herein, nucleophilic $R^{23}$ species include, but are not limited to $X^{a1}$—$R^{23}$, M-$R^{23}$, or $M_s(X^{n2})_t$, wherein each instance of M is independently a metal (e.g., Li, Na, K), or metal complex (e.g. $CuX^{n2}$, or $MgX^{n2}$); $X^{n1}$ is —$OR^{xn}$, —$SR^{xn}$, or —$N(R^{xn})_2$; each instance of $X^{n2}$ is independently halogen, CN, $N_3$, —$OR^{xn}$, —$SR^{xn}$, —$N(R^{xn})_2$; each instance of $R^{xn}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl; $R^{23}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl; s is 1, 2, 3, or 4; and t is 1, 2, 3, or 4. As used herein, a metal complex refers to a metal coordination complex having a central metal atom having one or more bound ligands (e.g. ion such as halide; or molecule (functional group) such as carboxylate) to form a coordination complex. The bonding between metal and ligand generally involves formal donation of one or more of the ligand's electron pairs. The nature of the metal-ligand bonding can range from covalent to ionic. Furthermore, the metal-ligand bond order can range from one to three. In certain embodiments, the nucleophile is $X^{n1}$—$R^{23}$ (e.g. $R^{23}$—OH; $R^{23}$—SH, $R^{23}$—$NH_2$ (e.g. $NH_3$)). In certain embodiments, the nucleophile is M-$R^{23}$ (e.g. Li-alkyl). In certain embodiments, the nucleophile is $M_s(X^{n2})_t$ (e.g. NaCN, $NaN_3$, $NaNH_2$, $LiOR^{xn}$, $NaOR^{xn}$).

In certain embodiments, $R^{o3}$ is $R^{23}$, wherein $R^{23}$ is as defined herein. In certain embodiments, $R^{o3}$ is $X^{n2}$, wherein $X^{n2}$ is as defined herein.

-continued
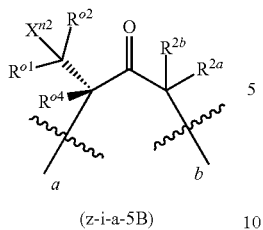
(z-i-a-5B)
In certain embodiments, exemplified conjugated additions are carried out on Formulae (N-41a) and (N-41b) as shown in Schemes 20C-N.
Scheme 20C.
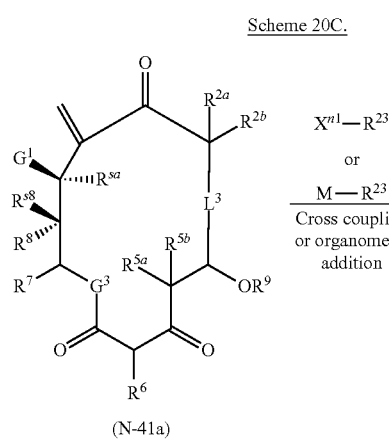
(N-41a)
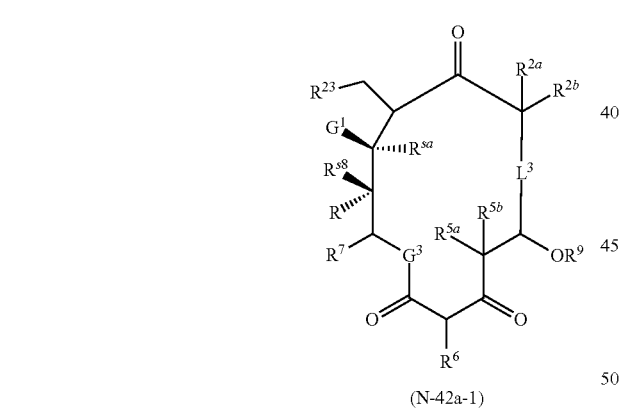
(N-42a-1)
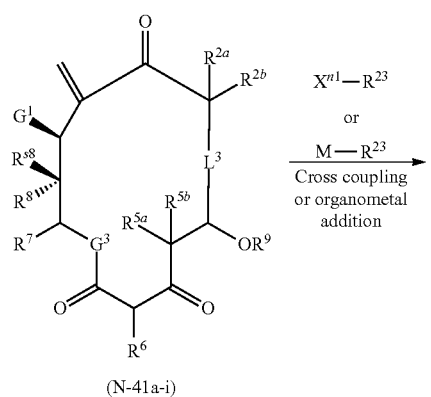
(N-41a-i)
-continued
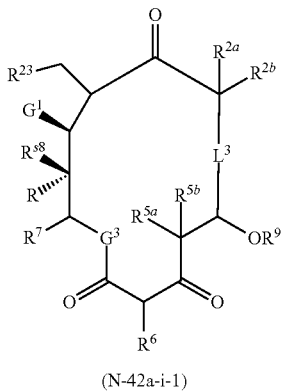
(N-42a-i-1)
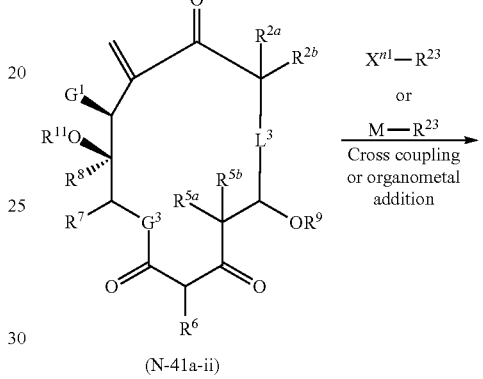
(N-41a-ii)
(N-42a-ii-1)
Scheme 20D.
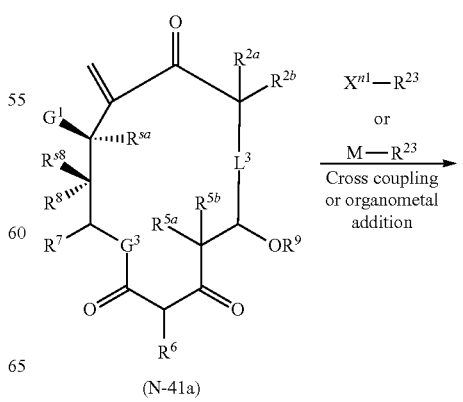
(N-41a)

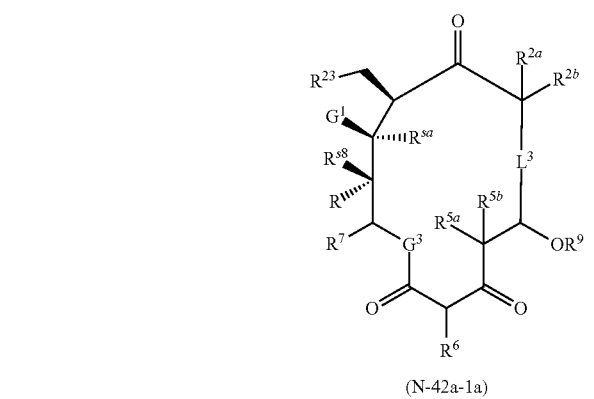
(N-42a-1a)
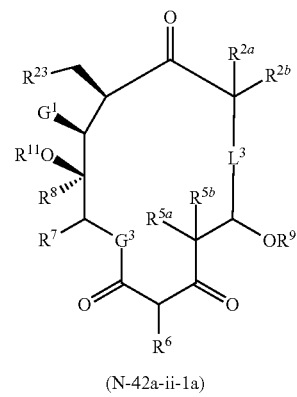
(N-42a-ii-1a)
Scheme 20E.
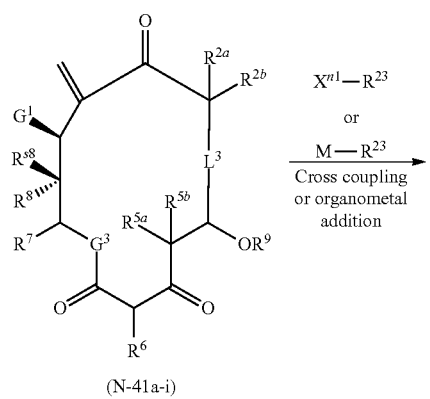
(N-41a-i)
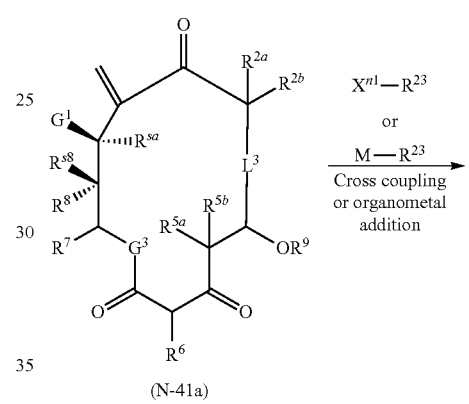
(N-41a)
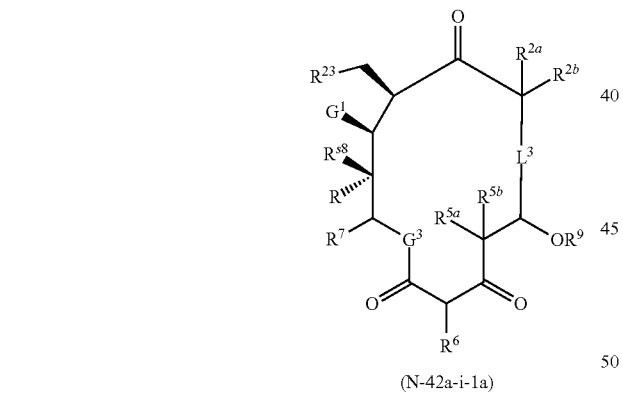
(N-42a-i-1a)
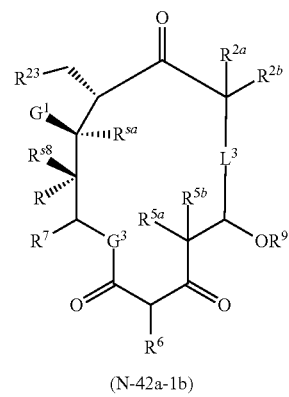
(N-42a-1b)
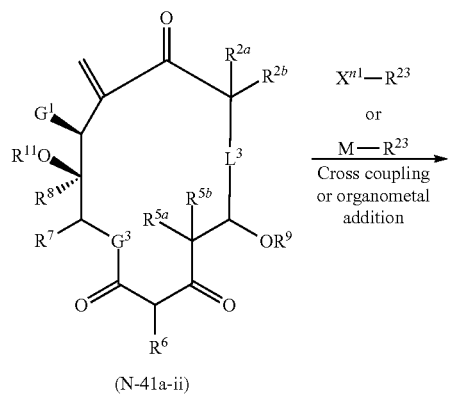
(N-41a-ii)
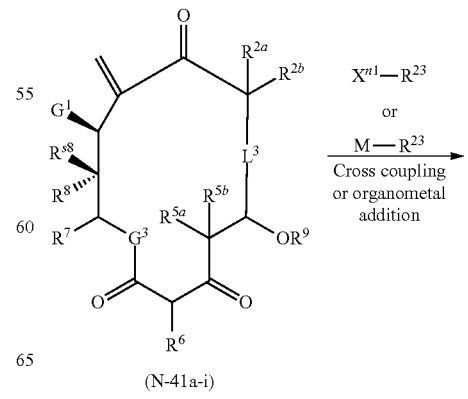
(N-41a-i)

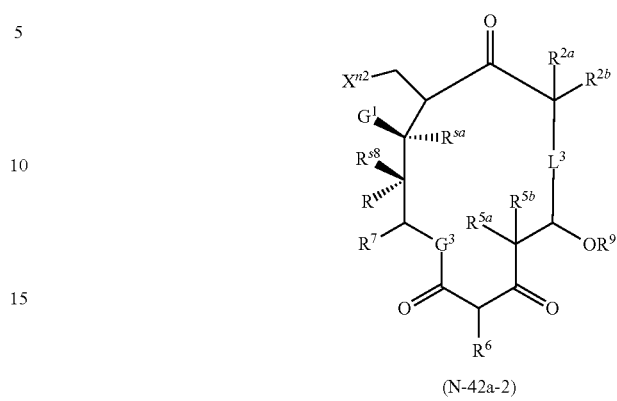
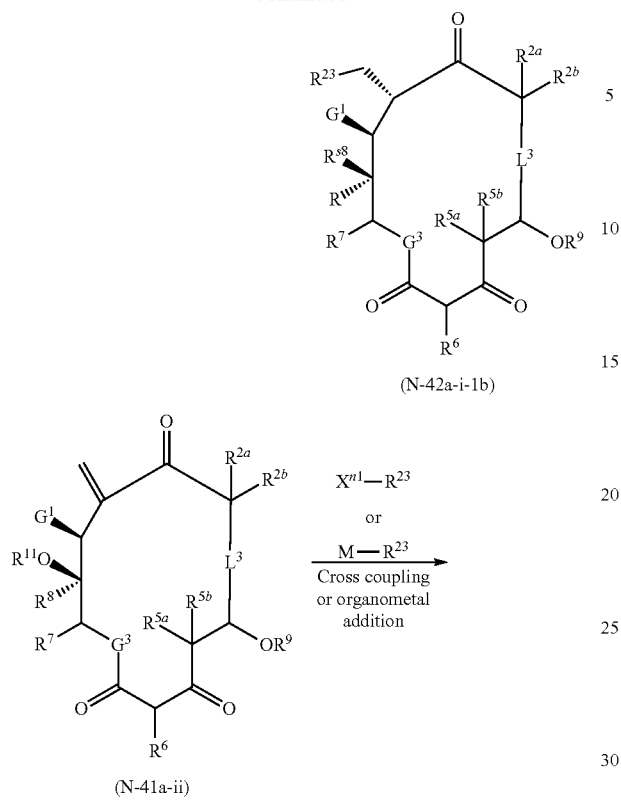
Scheme 20F.
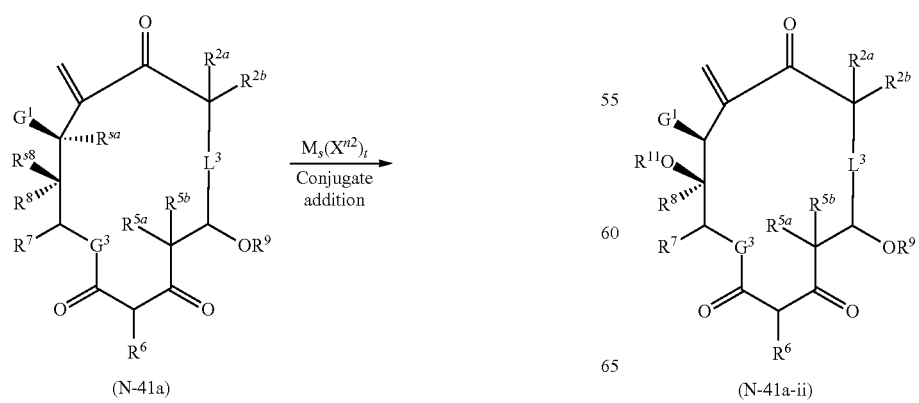

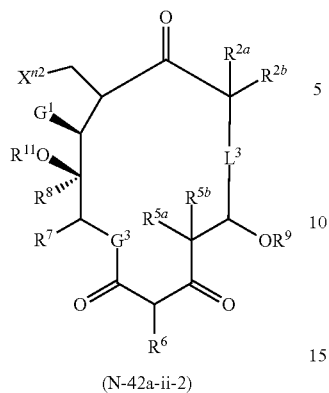
(N-42a-ii-2)
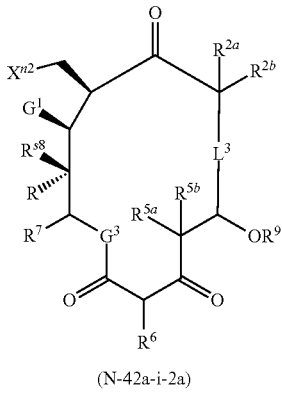
(N-42a-i-2a)
Scheme 20G.
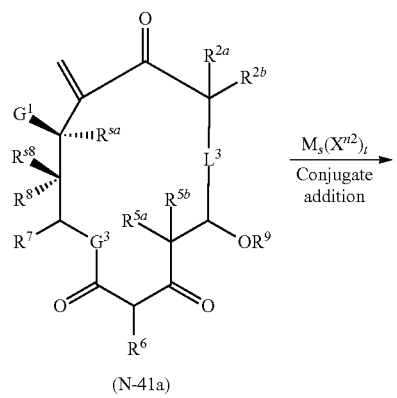
(N-41a)
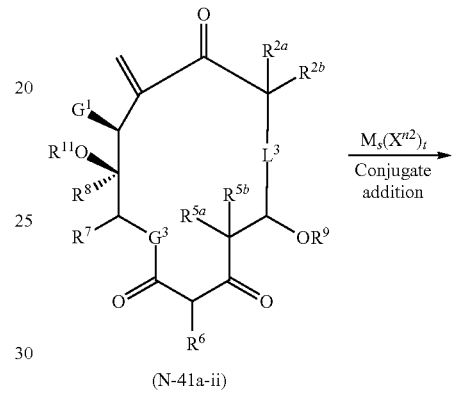
(N-41a-ii)
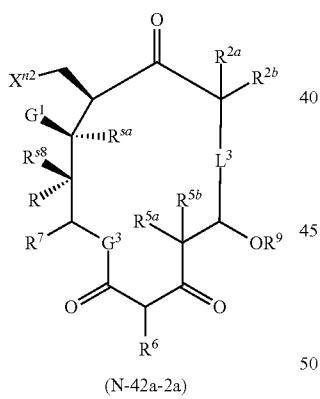
(N-42a-2a)
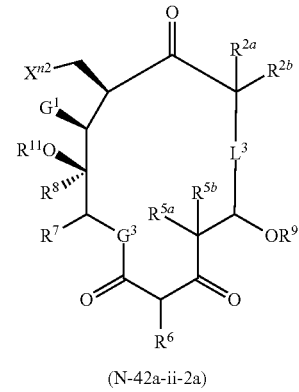
(N-42a-ii-2a)
Scheme 20H.
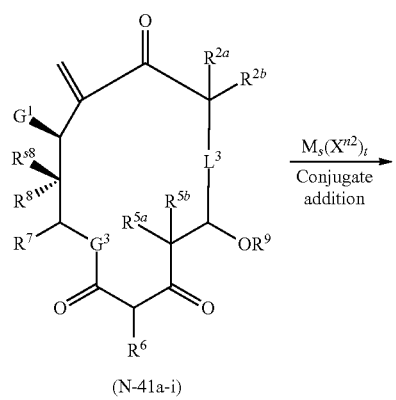
(N-41a-i)
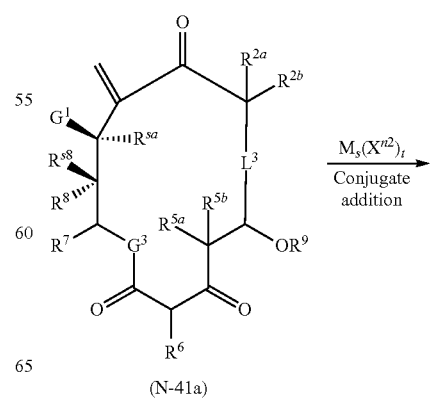
(N-41a)

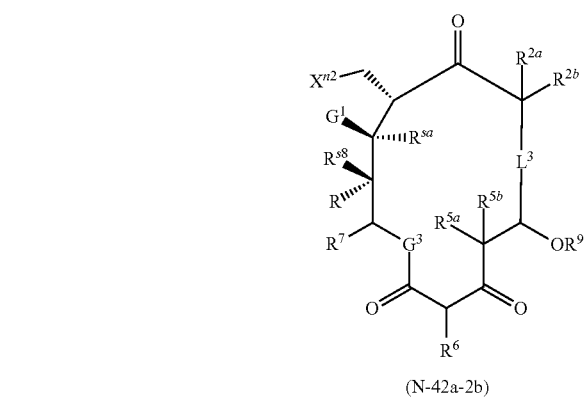
(N-42a-2b)
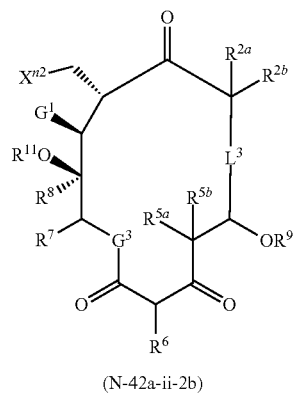
(N-42a-ii-2b)
Scheme 20I.
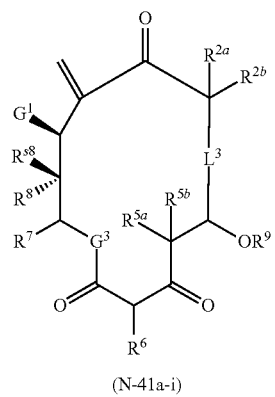
(N-41a-i)
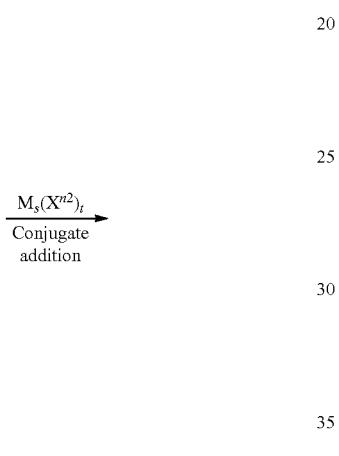
(N-41b)
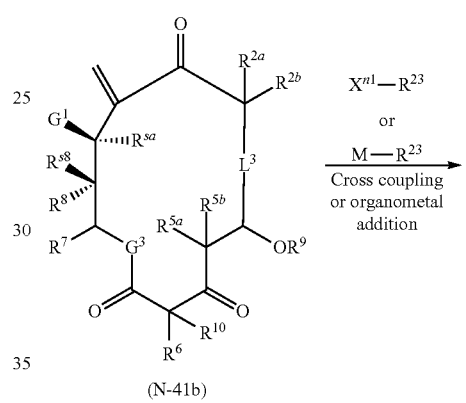
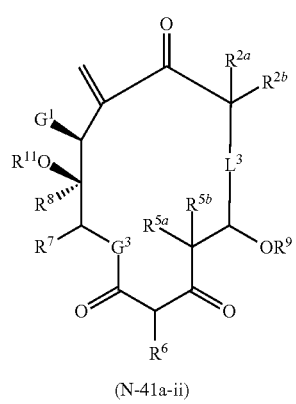
(N-42a-i-2b)
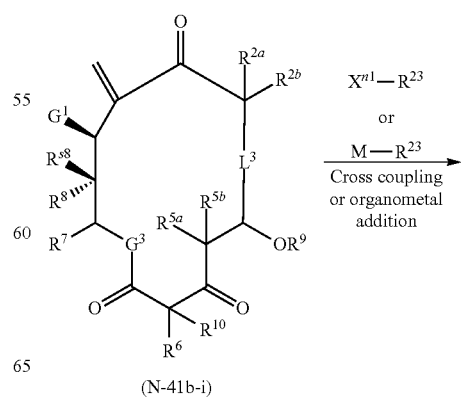
(N-42b-1)
(N-41a-ii)
(N-41b-i)

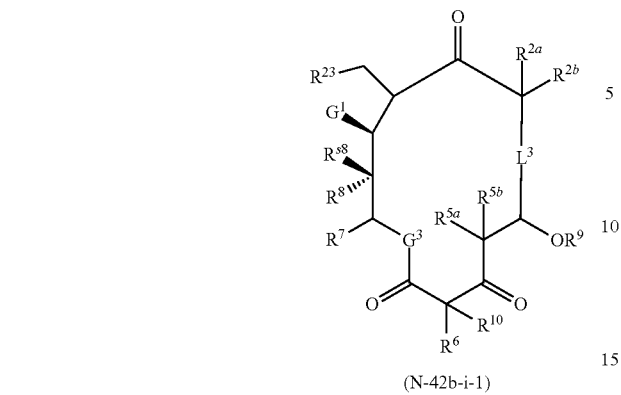
(N-42b-i-1)
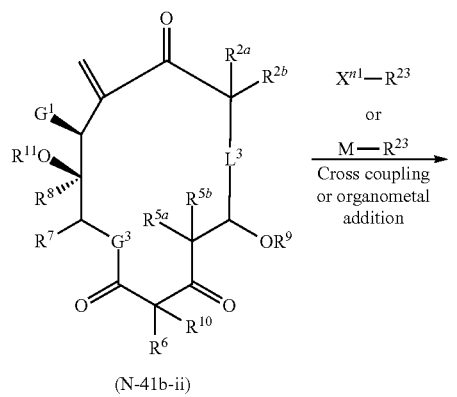
(N-41b-ii)
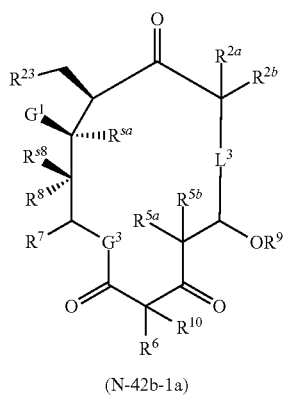
(N-42b-ii-1)
Scheme 20J.
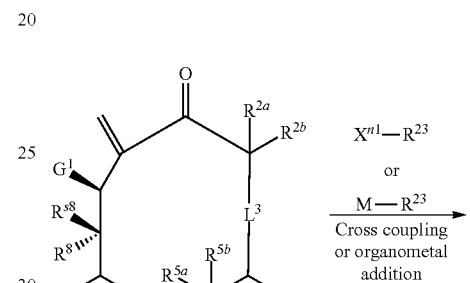
(N-41b-i)
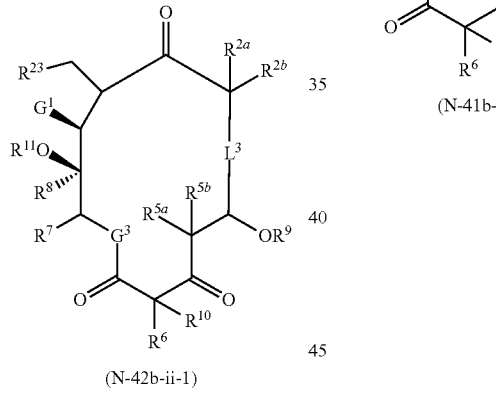
(N-42b-1a)
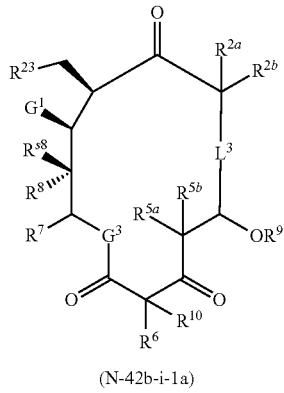
(N-42b-i-1a)
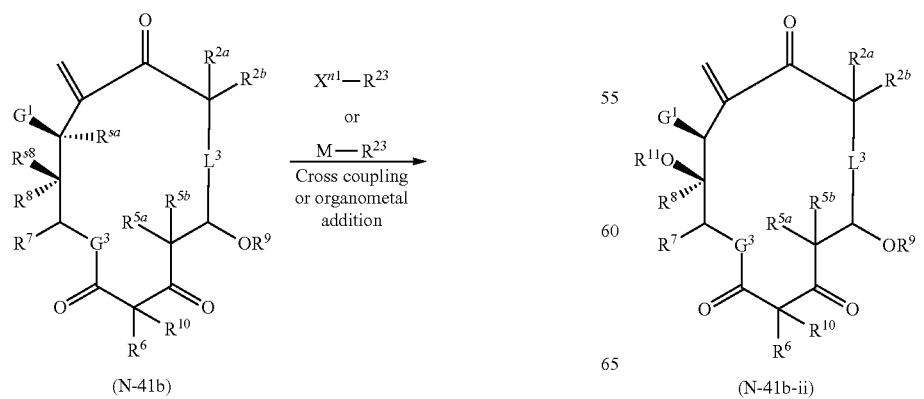
(N-41b)          (N-41b-ii)

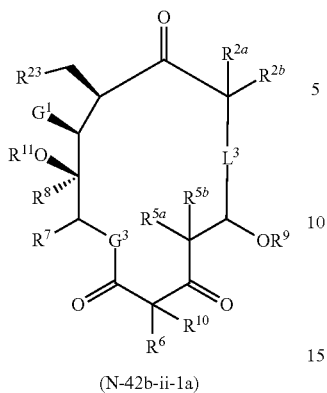
(N-42b-ii-1a)
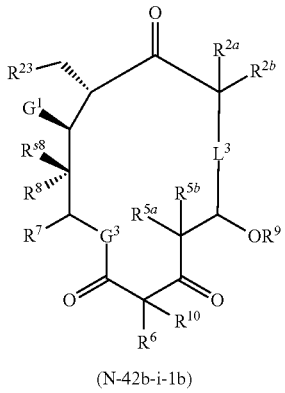
(N-42b-i-1b)
Scheme 20K.
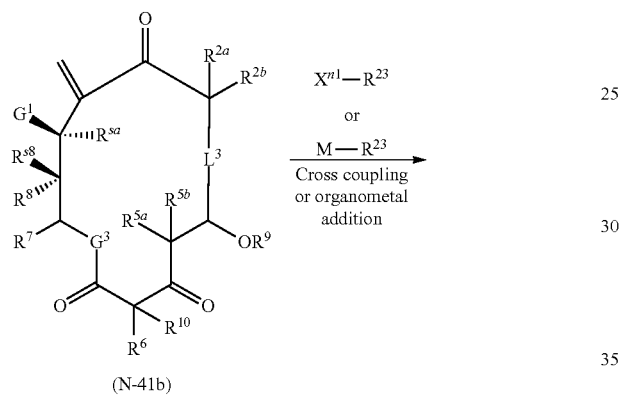
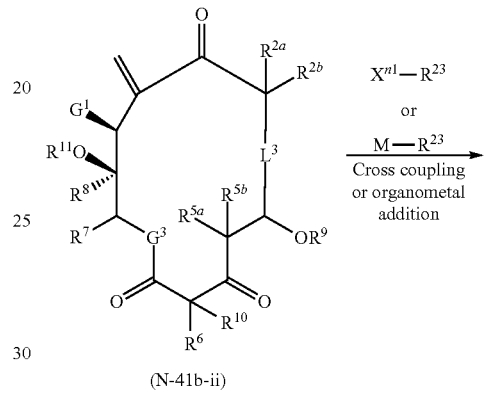
(N-41b-ii)
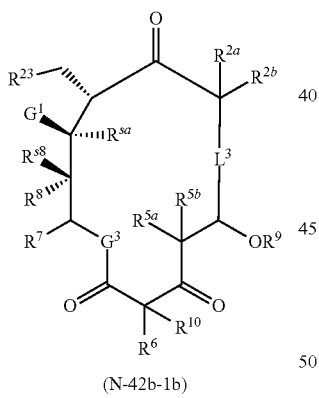
(N-42b-1b)
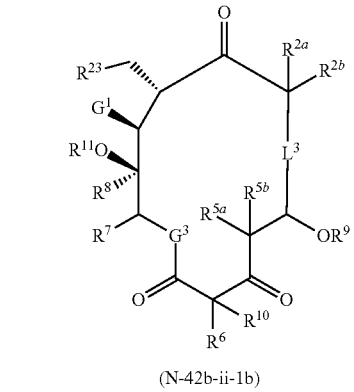
(N-42b-ii-1b)
Scheme 20L.
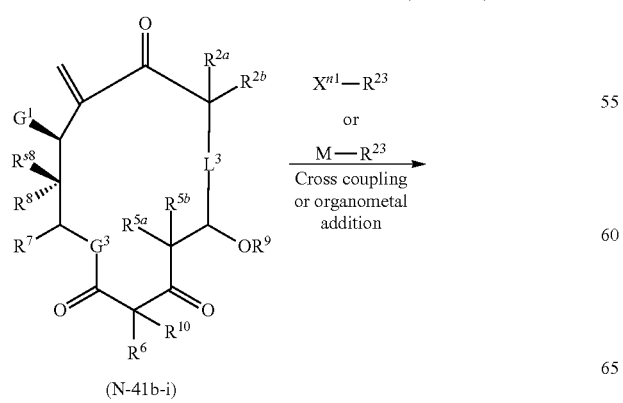
(N-41b-i)
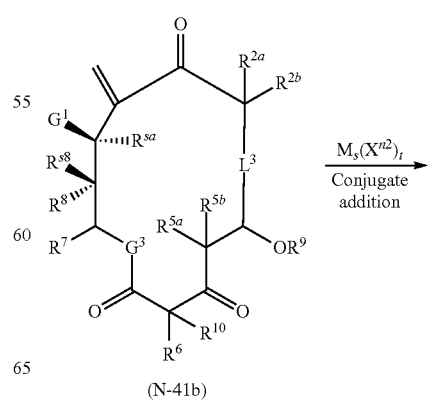
(N-41b)

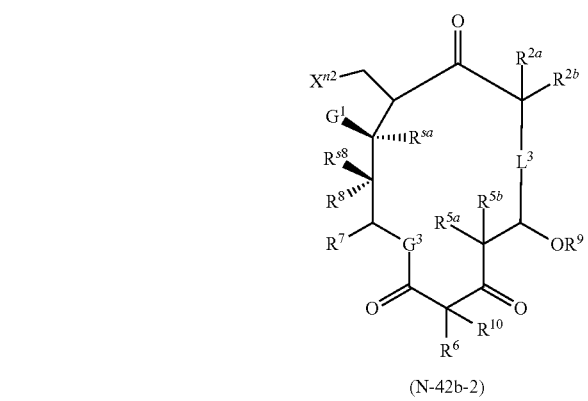
(N-42b-2)
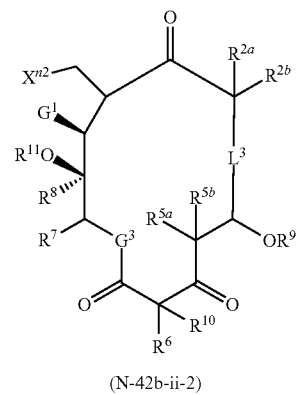
(N-42b-ii-2)
Scheme 20M.
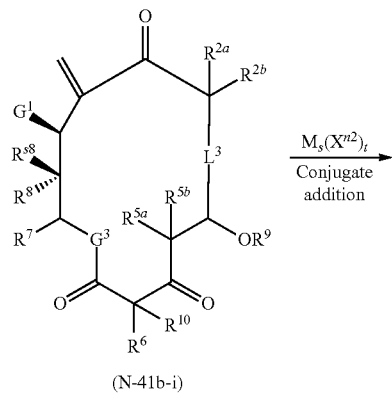
(N-41b-i)
$\xrightarrow{M_s(X^{n2})_t}$
Conjugate addition
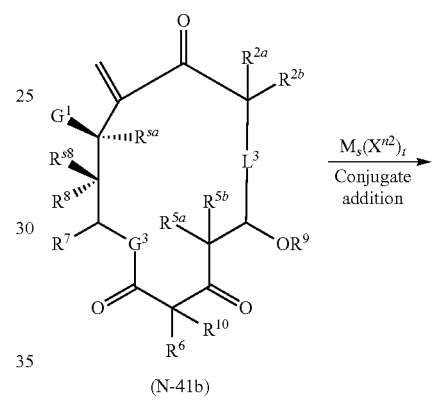
(N-41b)
$\xrightarrow{M_s(X^{n2})_t}$
Conjugate addition
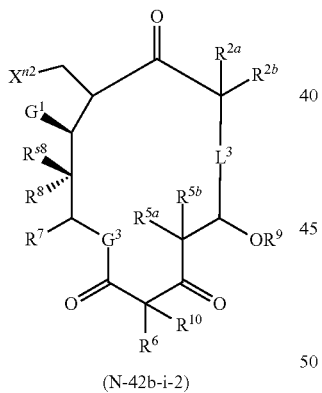
(N-42b-i-2)
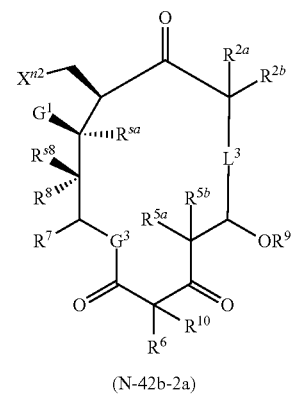
(N-42b-2a)
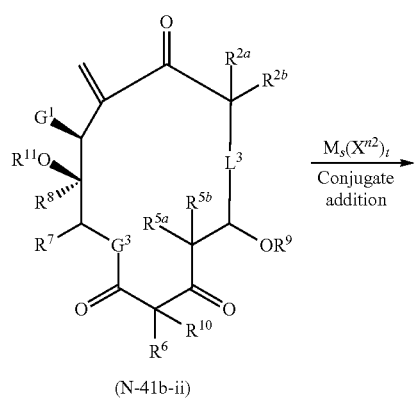
(N-41b-ii)
$\xrightarrow{M_s(X^{n2})_t}$
Conjugate addition
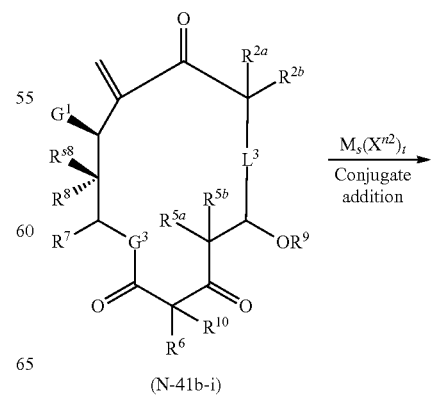
(N-41b-i)
$\xrightarrow{M_s(X^{n2})_t}$
Conjugate addition

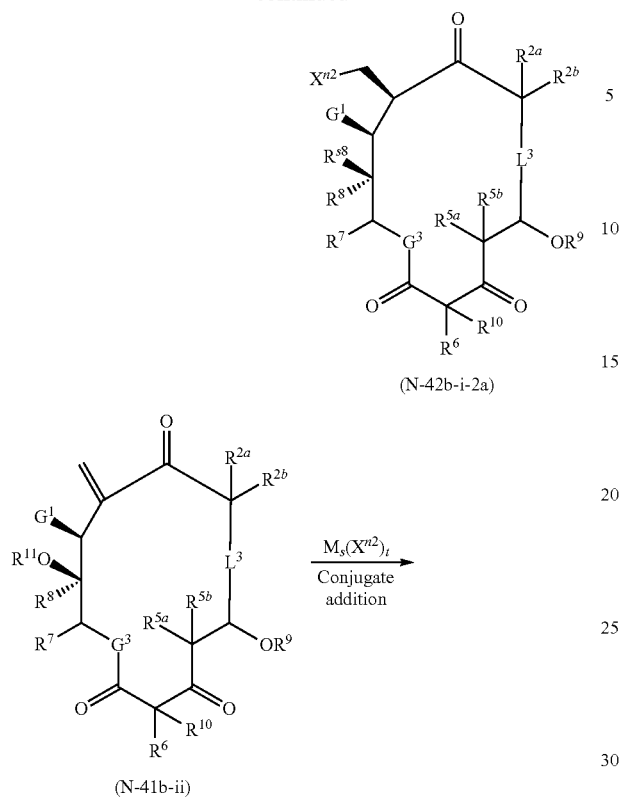
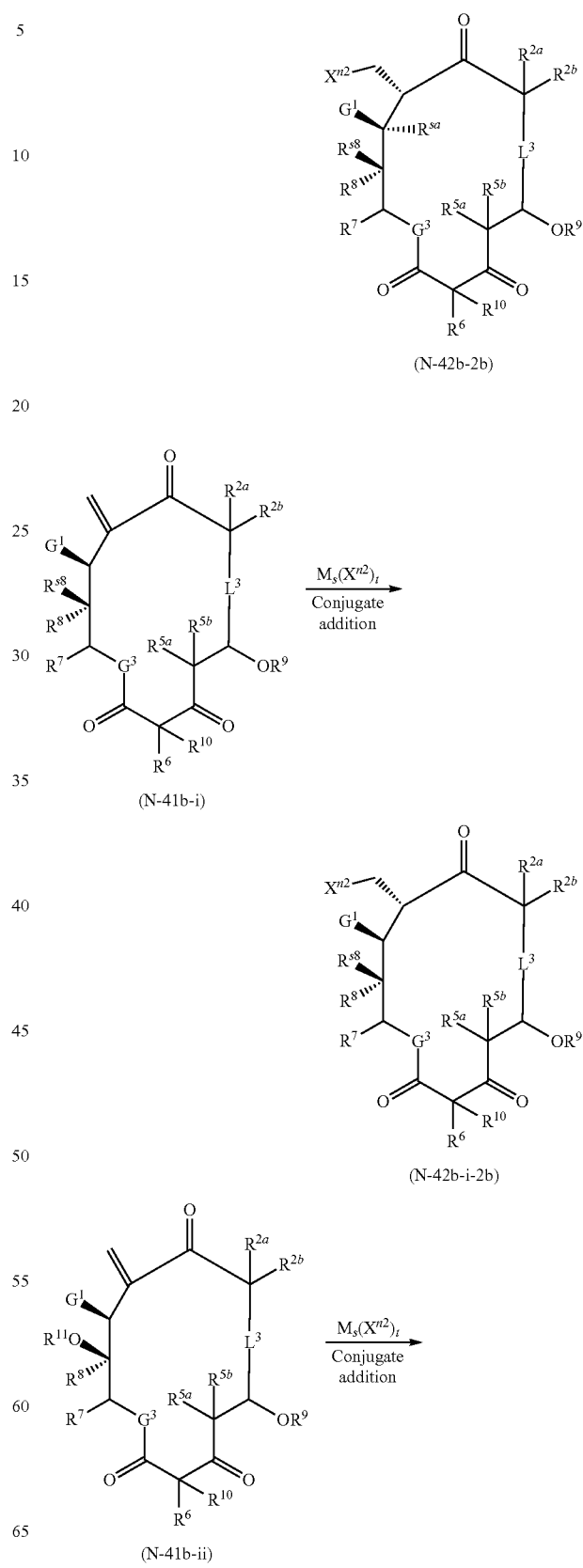
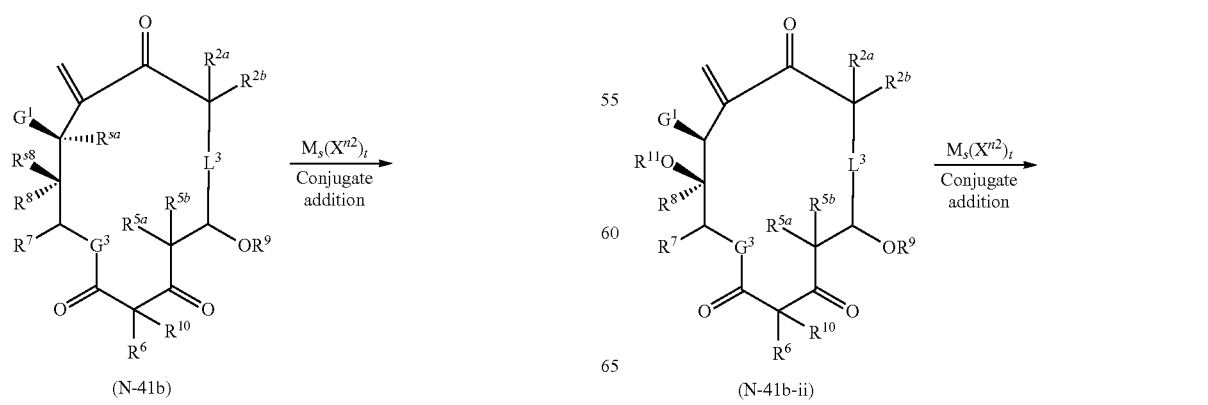
Scheme 20N.

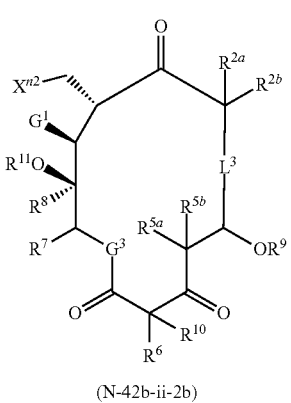

(N-42b-ii-2b)

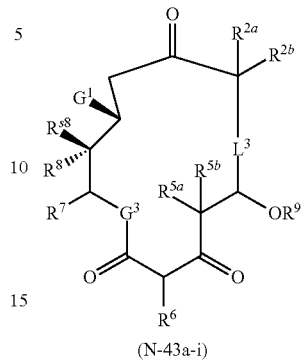

(N-43a-i)

Further derivatization may be carried out using the transformations described herein pre- or post-macrocyclization when any of $R^{1a}$, $R^{1b}$, $R^{2a}$, and $R^{2b}$ is hydrogen, attached alpha to an oxo (=O) moiety. Base-mediated deprotonation and nucleophilic addition of the enolate to leaving group conjugates of $R^{1a}$, wherein LG is a leaving group as defined herein and $R^{1a}$ is a non-hydrogen group, provide alpha-functionalized ketolides of Formula (N-44a) or Formula (44-b).

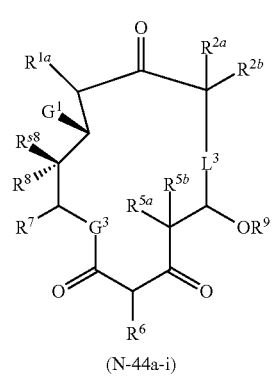

(N-44a-i)

Scheme 21A.

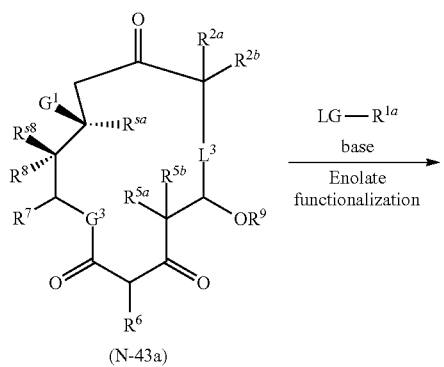

(N-43a)

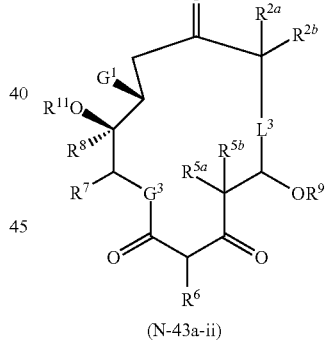

(N-43a-ii)

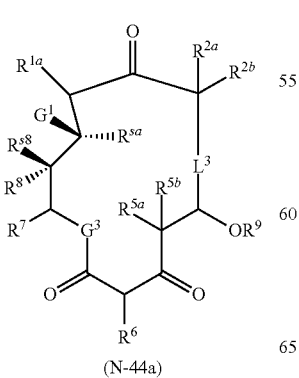

(N-44a)

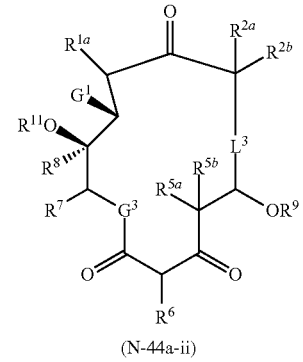

(N-44a-ii)

Scheme 21B.

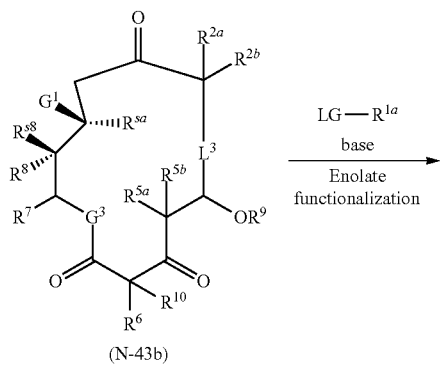

(N-43b)

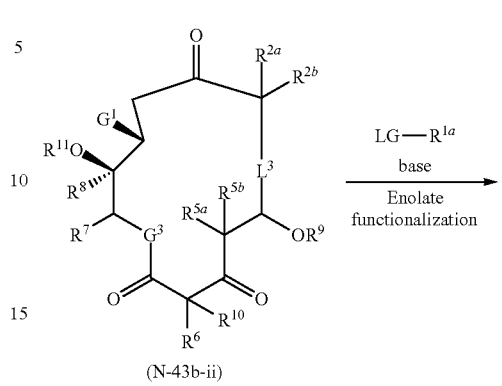

(N-43b-ii)

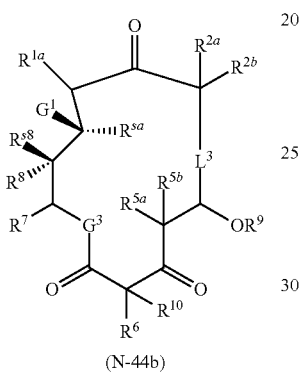

(N-44b)

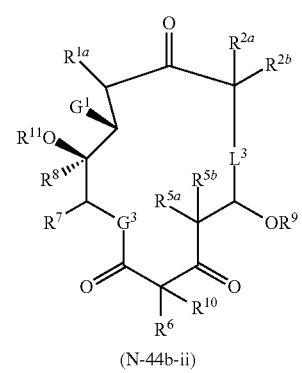

(N-44b-ii)

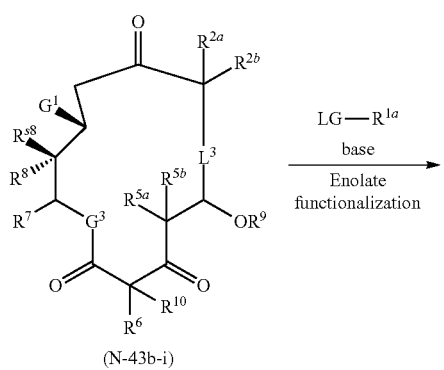

(N-43b-i)

Furthermore, as depicted in Schemes 23-26, wherein $G^1$ is —$NHR^{13}$, installation of a group of Formula ($L^{C1}$-i) by reaction of the alcohol with a compound of formula LG-$L^{C1}$-LG, followed by displacement of the second leaving group with a nucleophilic group $A^1$ to provide a group of Formula ($L^{C1}$-ii), followed by reaction of the group $A^1$ and with a compound of formula $A^2$-$L^{C2}$-$R^{23}$ to install a group of Formula ($L^{C1}$-iii), is contemplated herein.

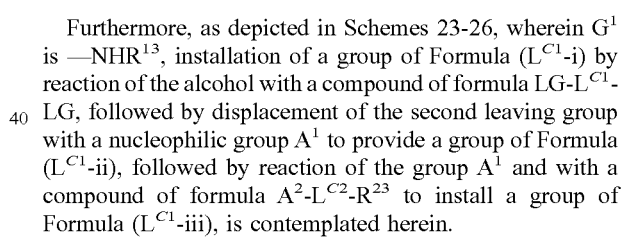

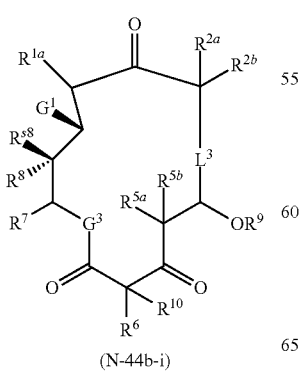

(N-44b-i)

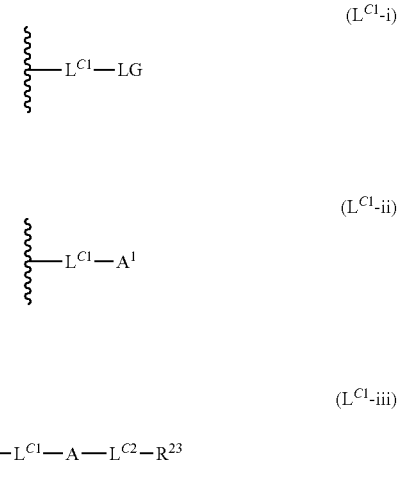

Scheme 23.
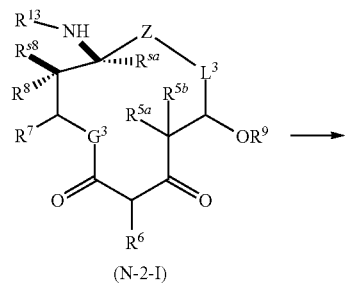
(N-2-I)
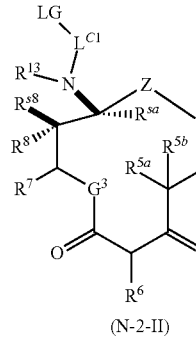
(N-2-II)
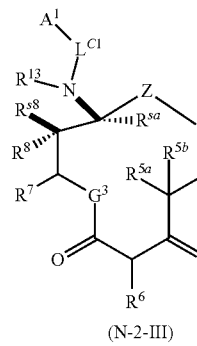
(N-2-III)
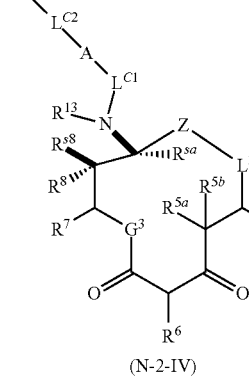
(N-2-IV)
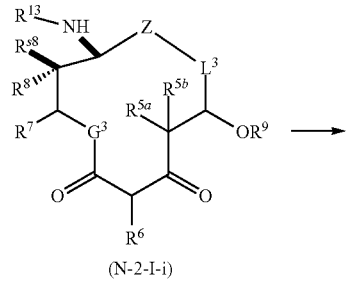
(N-2-I-i)
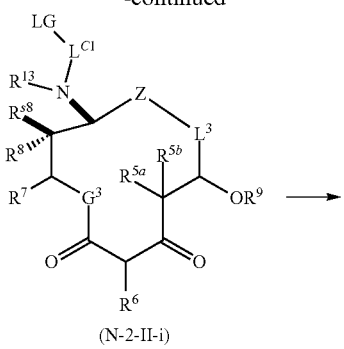
(N-2-II-i)
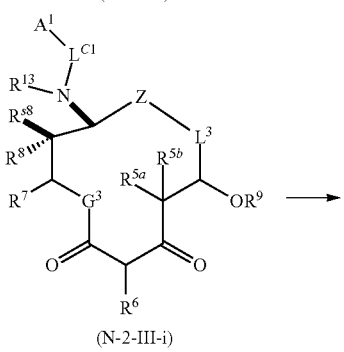
(N-2-III-i)
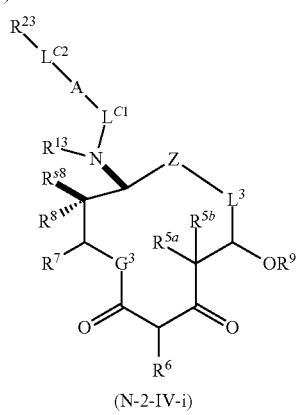
(N-2-IV-i)
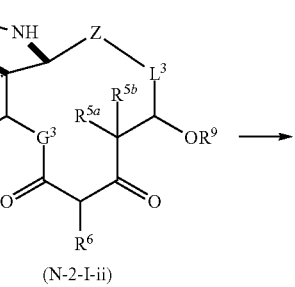
(N-2-I-ii)
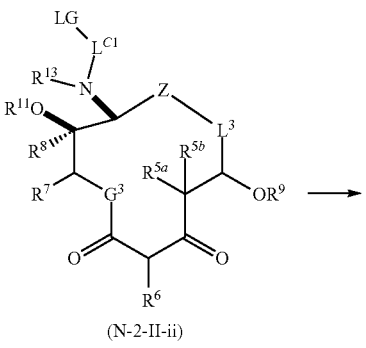
(N-2-II-ii)

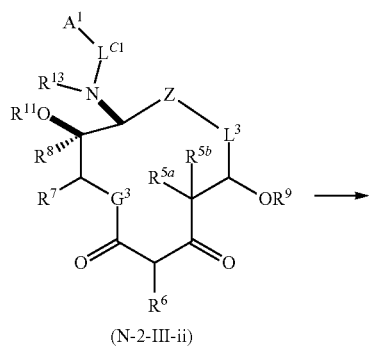
(N-2-III-ii)
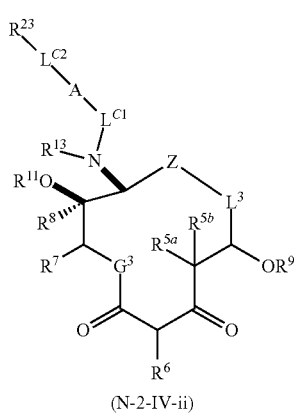
(N-2-IV-ii)
Scheme 24.
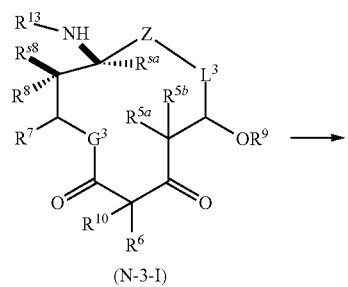
(N-3-I)
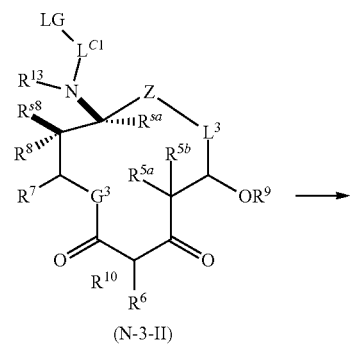
(N-3-II)
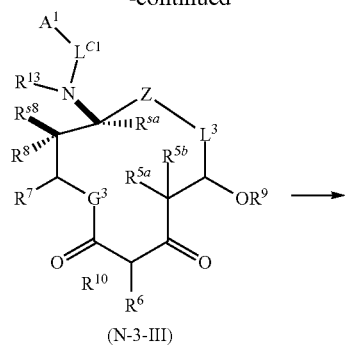
(N-3-III)
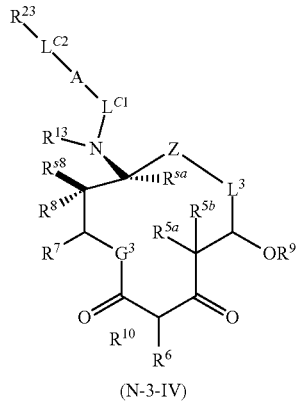
(N-3-IV)
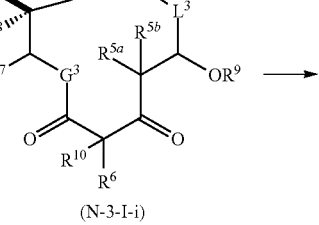
(N-3-I-i)
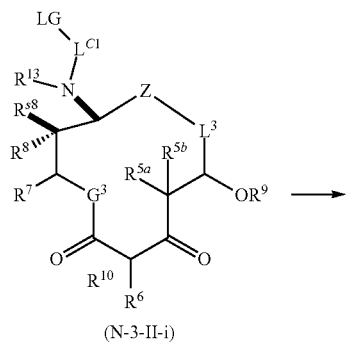
(N-3-II-i)
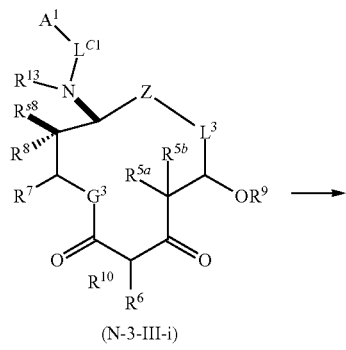
(N-3-III-i)

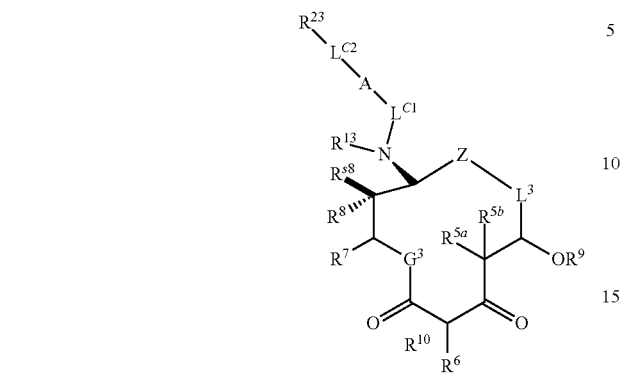
(N-3-IV-i)
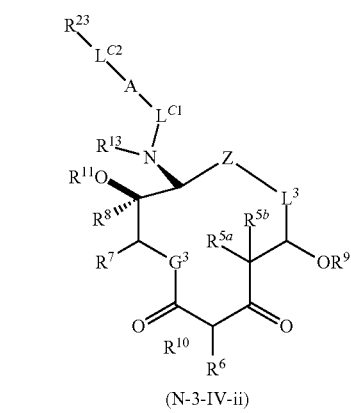
(N-3-IV-ii)
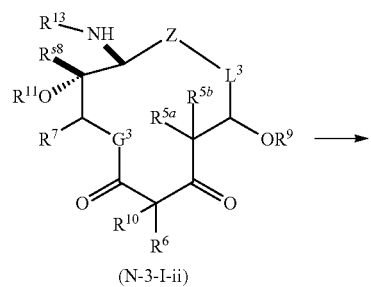
(N-3-I-ii)
Scheme 25.
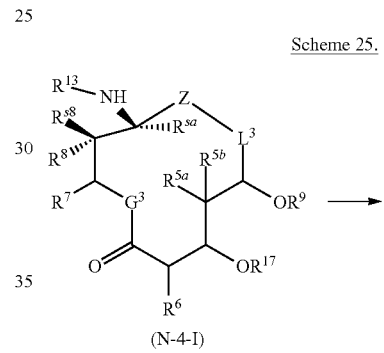
(N-4-I)
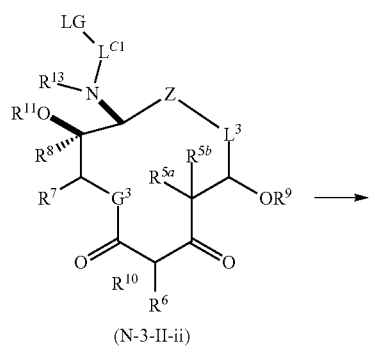
(N-3-II-ii)
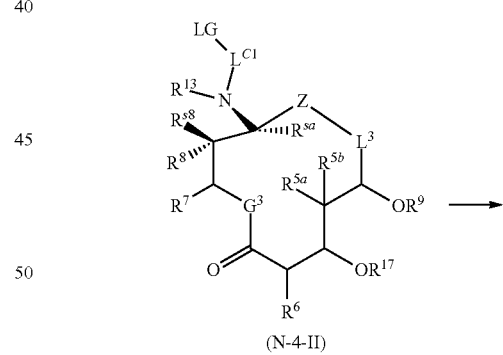
(N-4-II)
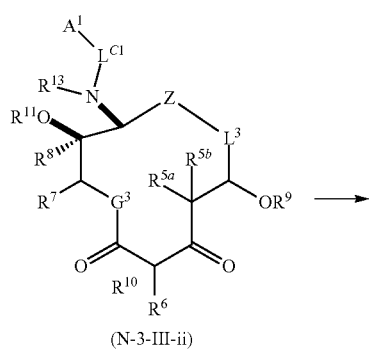
(N-3-III-ii)
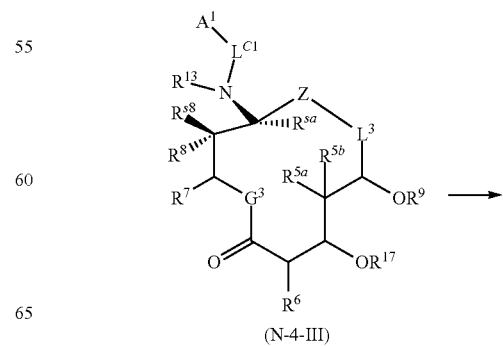
(N-4-III)

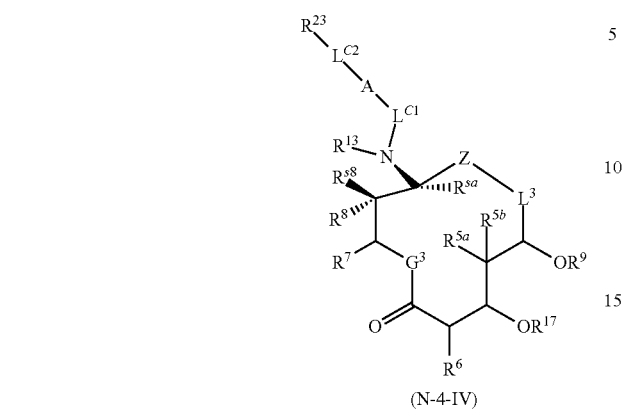
(N-4-IV)
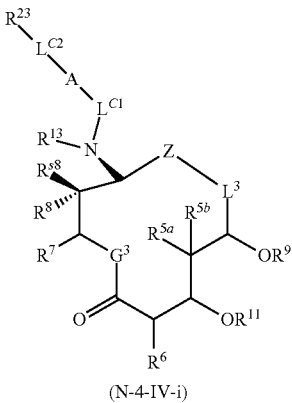
(N-4-IV-i)
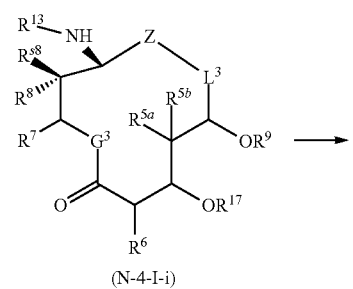
(N-4-I-i)
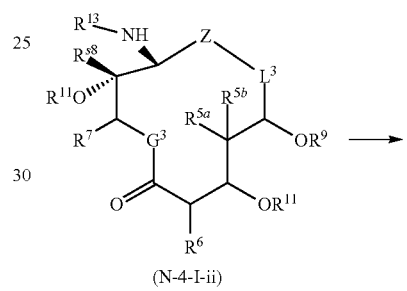
(N-4-I-ii)
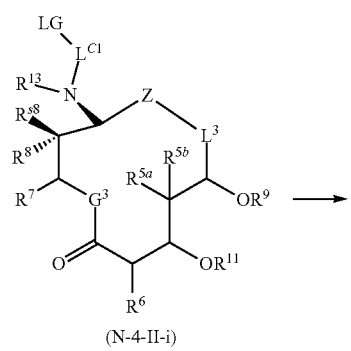
(N-4-II-i)
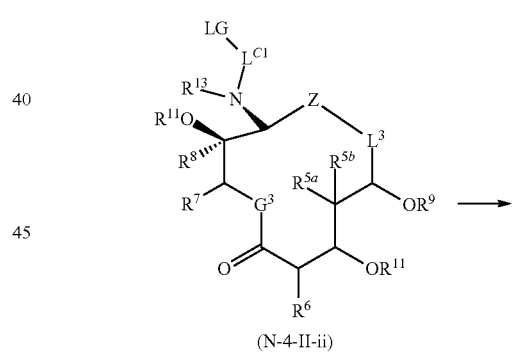
(N-4-II-ii)
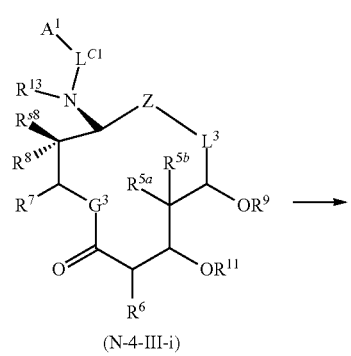
(N-4-III-i)
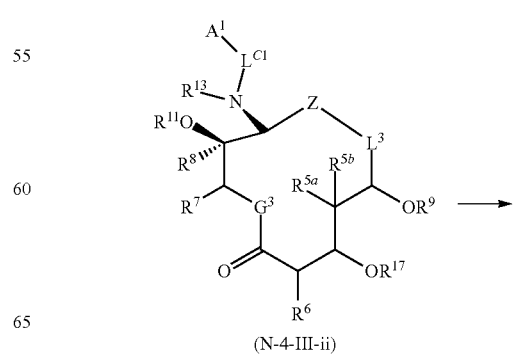
(N-4-III-ii)

107
-continued
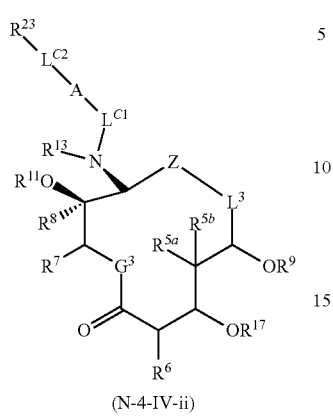
(N-4-IV-ii)
108
-continued
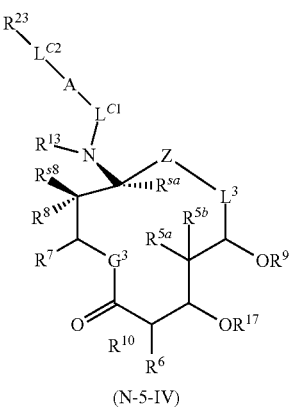
(N-5-IV)
Scheme 26.
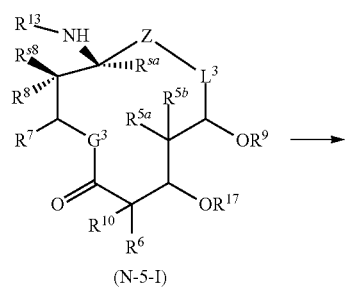
(N-5-I)
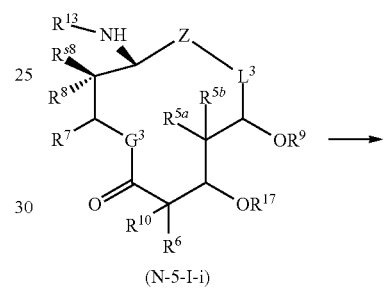
(N-5-I-i)
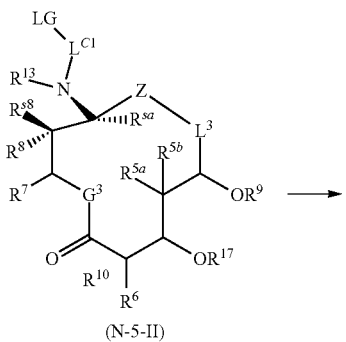
(N-5-II)
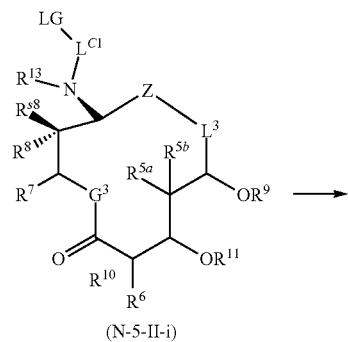
(N-5-II-i)
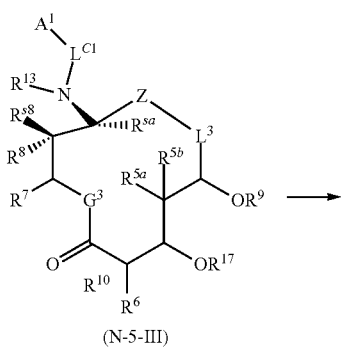
(N-5-III)
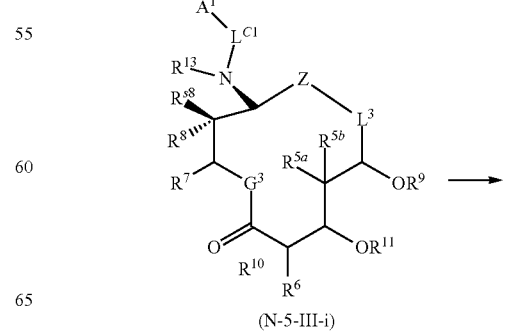
(N-5-III-i)

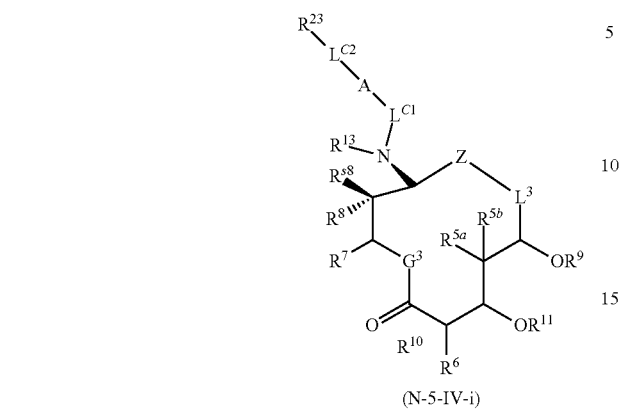

(N-5-IV-i)

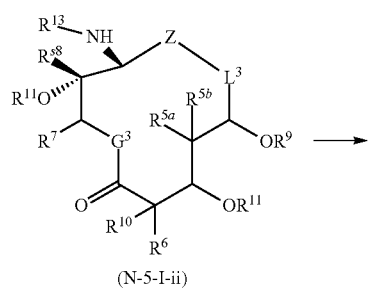

(N-5-I-ii)

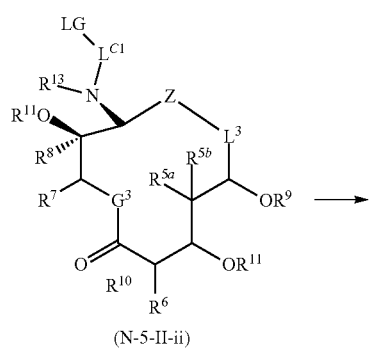

(N-5-II-ii)

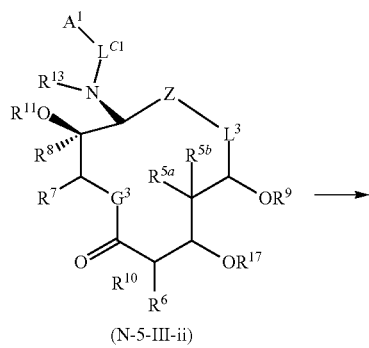

(N-5-III-ii)

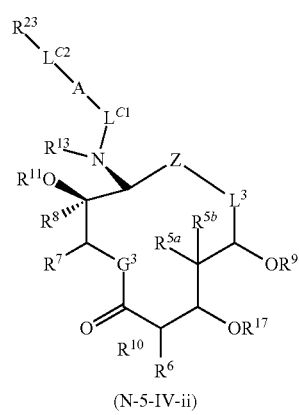

(N-5-IV-ii)

Alternatively, the group -$L^{C1}$-$A^1$ may be installed directly by reaction of the amine with a compound of formula LG-$L^{C1}$-$A^1$. Such reactions are also contemplated wherein $G^1$ is —OH.

Additionally, as depicted in Scheme 27, wherein $L^3$ is a group of formula ($L^3$-i), wherein $R^3$ is hydrogen (referred to as ($L^3$-ia)), installation of a group of formula ($L^{C1}$-i) by reaction of the alcohol with a compound of formula LG-$L^{C1}$-LG, followed by conversion of (e.g., by nucleophilic displacement or other synthetic manipulation) of the second leaving group with a group $A^1$ to provide a group of formula ($L^{C1}$-ii), followed by reaction of the group $A^1$ and with a compound of formula $A^2$-$L^{C2}$-$R^{23}$ to install a group of formula ($L^{C1}$-iii), is also contemplated herein.

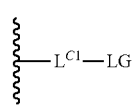

($L^{C1}$-i)

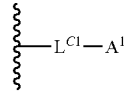

($L^{C1}$-ii)

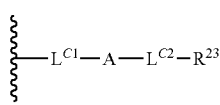

($L^{C1}$-iii)

Scheme 27.

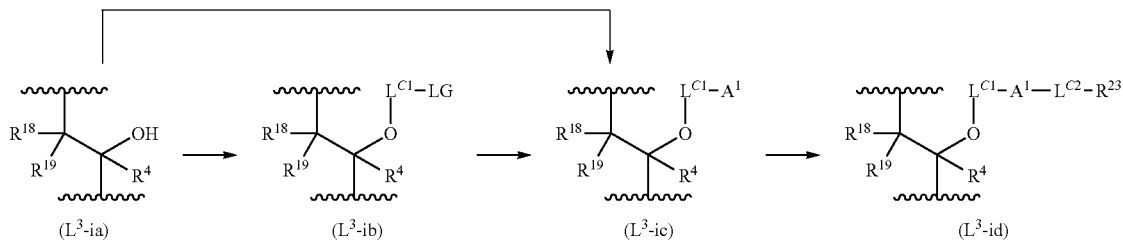

Alternatively, the group -L$^{C1}$-A$^1$ may be installed directly from (L$^3$-ia) to provide (L$^3$-ic) by reaction of the hydroxyl group with a compound of formula LG-L$^{C1}$-A$^1$.

Furthermore, there are many ways of adding a group of formula (L$^{C1}$-iii) which do not involve reaction of A$^1$ and A$^2$ to form A and thus A may be any group, e.g., for example, a cyclic moiety selected from the group consisting of optionally substituted carbocyclyl, optionally substituted heterocyclyl, optionally substituted aryl, and optionally substituted heteroaryl. For example, a group of formula (L$^{C1}$-iii) may be installed by reaction of the group —OR$^{12}$, —NR$^{13}$R$^{14}$, and/or —OR$^3$, wherein R$^{12}$, R$^{14}$, and/or R$^3$ are hydrogen, with a compound of formula (L$^{C1}$-vii), e.g., by nucleophilic displacement, to provide a group wherein R$^{12}$, R$^{14}$, and/or R$^3$ is of formula (L$^{C1}$-iii). See, e.g., Scheme 28.

group (L$^3$-iii) wherein one of R$^{20}$ and R$^{21}$ is halogen or hydroxyl or substituted hydroxyl, and one of R$^{20}$ and R$^{21}$ is hydrogen;

(v) X$_2$ addition to the double bond, wherein X is halogen, to provide a group (L$^3$-iii) wherein R$^{20}$ and R$^{21}$ are each independently halogen;

(vi) X$_2$/H$_2$O or X$_2$/alcohol addition to the double bond, wherein X is halogen, to provide a group (L$^3$-iii) wherein one of R$^{20}$ and R$^{21}$ is hydroxyl or substituted hydroxyl, and one of R$^{20}$ and R$^{21}$ is halogen; and (viii) oxidative hydroboration of the double bond to provide a group (L$^3$-iii) wherein one of R$^{20}$ and R$^{21}$ is hydroxyl or substituted hydroxyl, and one of R$^{20}$ and R$^{21}$ is hydrogen.

Scheme 28.

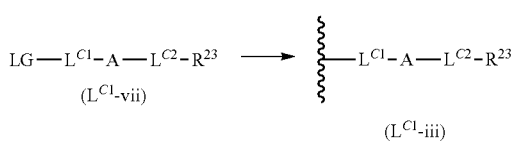

Scheme 29.

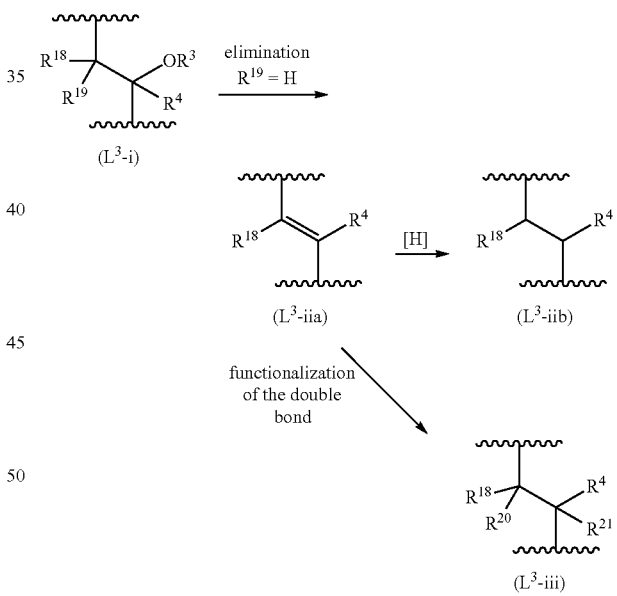

Furthermore, as depicted in Scheme 28, wherein L$^3$ is a group of formula (L$^3$-i), elimination of the group —OR$^3$ provides an alkenyl moiety, which may be reduced (e.g., by hydrogenation), or be further functionalized with groups R$^{20}$ and R$^{21}$, as depicted in Scheme 29. Functionalization of double bonds to provide groups R$^{20}$ and R$^{21}$ are known in the art. See, e.g., *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. Non-limiting examples of double bond functionalization include:

(i) reaction of the double bond with a cyclopropanting reagent to provide a group (L$^3$-iii) wherein R$^{20}$ and R$^{21}$ are joined to form an optionally substituted cyclopropyl ring;

(ii) reaction of the double bond with an epoxidizing reagent to provide a group (L$^3$-iii) wherein R$^{20}$ and R$^{21}$ are joined to form an oxiranyl ring;

(iii) reaction of the double bond with a dihydroxylation reagent (e.g., OsO$_4$), optionally followed by protection of the hydroxyl groups, to provide a group (L$^3$-iii) wherein R$^{20}$ and R$^{21}$ are each independently hydroxyl or substituted hydroxyl;

(iv) HX addition to the double bond, wherein X is a halogen or hydroxyl or substituted hydroxyl, to provide a For all of the transformations pertaining to functionalization of the pre-formed macrocycle, incorporation of these groups through such general transformations at steps prior to ring formation is contemplated herein. Such reordering of steps as is appropriate to accommodate particular intermediates or functional groups is understood by those skilled in the art.

Synthesizing Ketolides Via Wittig or Homer Emmons Reaction

As generally described herein, alternative methods of preparing the keto (oxo) product wherein Z is of formula:

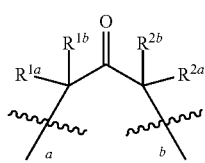

(z-i)

are further contemplated herein.

For example, the above recited Z linkage may be formed via Wittig or Horner Emmons reaction between an aldehyde and a ylide or phosphonate ester to form an α,β-unsaturated keto linked intermediate. See, e.g., Schemes 30 and 31. In certain embodiments of s Schemes 30 and 31, the α,β-unsaturated ketone is of the trans-configuration. In certain embodiments of s Schemes 30 and 31, the α,β-unsaturated ketone is of the cis-configuration.

The cyclic carbamate, installed prior to macrocyclization (see, e.g., Scheme 30) or after macrocylization (see, e.g., Scheme 31), may be formed via Michael addition of the amine $NH_2R^{14}$ to the α,β-unsaturated keto moiety, followed by reaction of the attached amino group —$NHR^{14}$ and vicinal hydroxyl group (i.e., $R^{11}$ is hydrogen) with reagent LG-C(=O)-LG, wherein each LG is a leaving group as defined herein (e.g., chloro), substituted hydroxyl (e.g., to provide a carbonate ester), substituted thiol, substituted amino (e.g., imidazolyl). In certain embodiments, the free hydroxyl group is first treated with reagent LG-C(=O)-LG, following which an amine of $NH_2R^{14}$ is added, leading to initial formation of an acyclic carbamate prior to conjugate addition of the intermediate —$NHR^{14}$ group to the unsaturated ketone.

Alternatively, the cyclic carbamate, installed prior to macrocyclization (see, e.g., Scheme 30) or after macrocylization (see, e.g., Scheme 31), may be formed via reaction of the free hydroxyl group (i.e., $R^{11}$ is hydrogen) with an isocyanate reagent O=C=N—$R^{14}$, followed by conjugate addition of the intermediate —$NHR^{14}$ group to the unsaturated ketone. In certain embodiments, the isocyanate reacts with the free hydroxyl group and —$NHR^{14}$ undergoes the conjugate addition reaction in a single step. In certain embodiments, the intermediate acyclic carbamate is isolated. In certain embodiments, base is added to the isolated acyclic carbamate to promote the conjugate addition reaction.

Scheme 30.

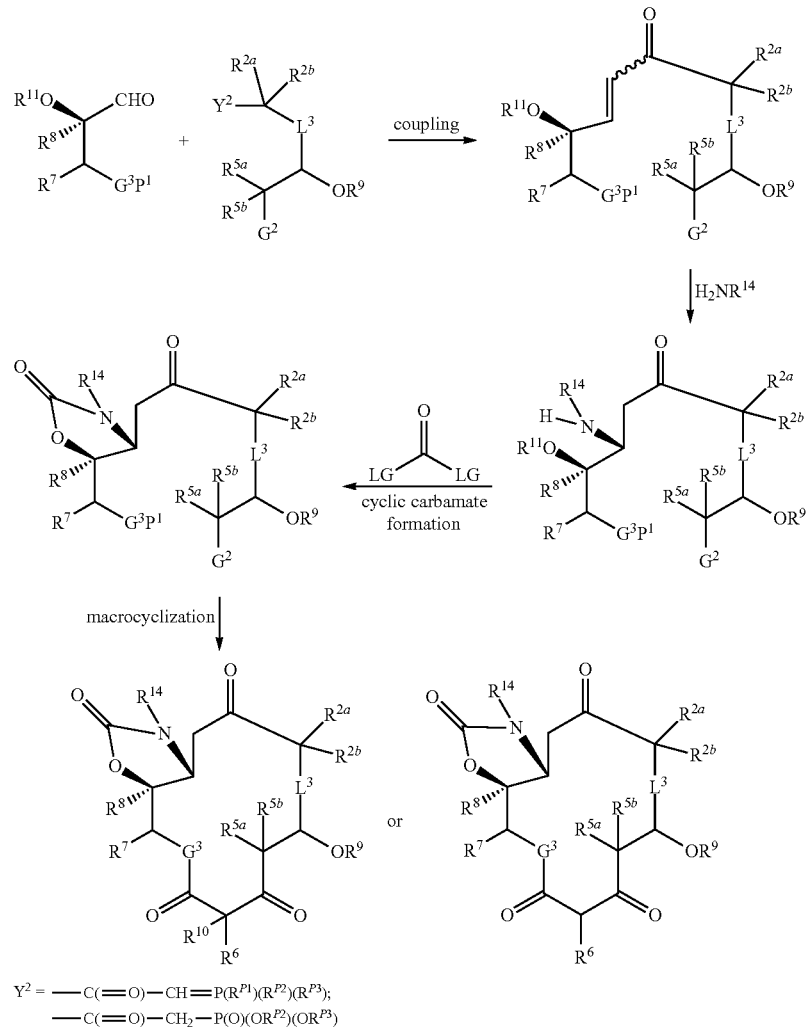

Scheme 31.

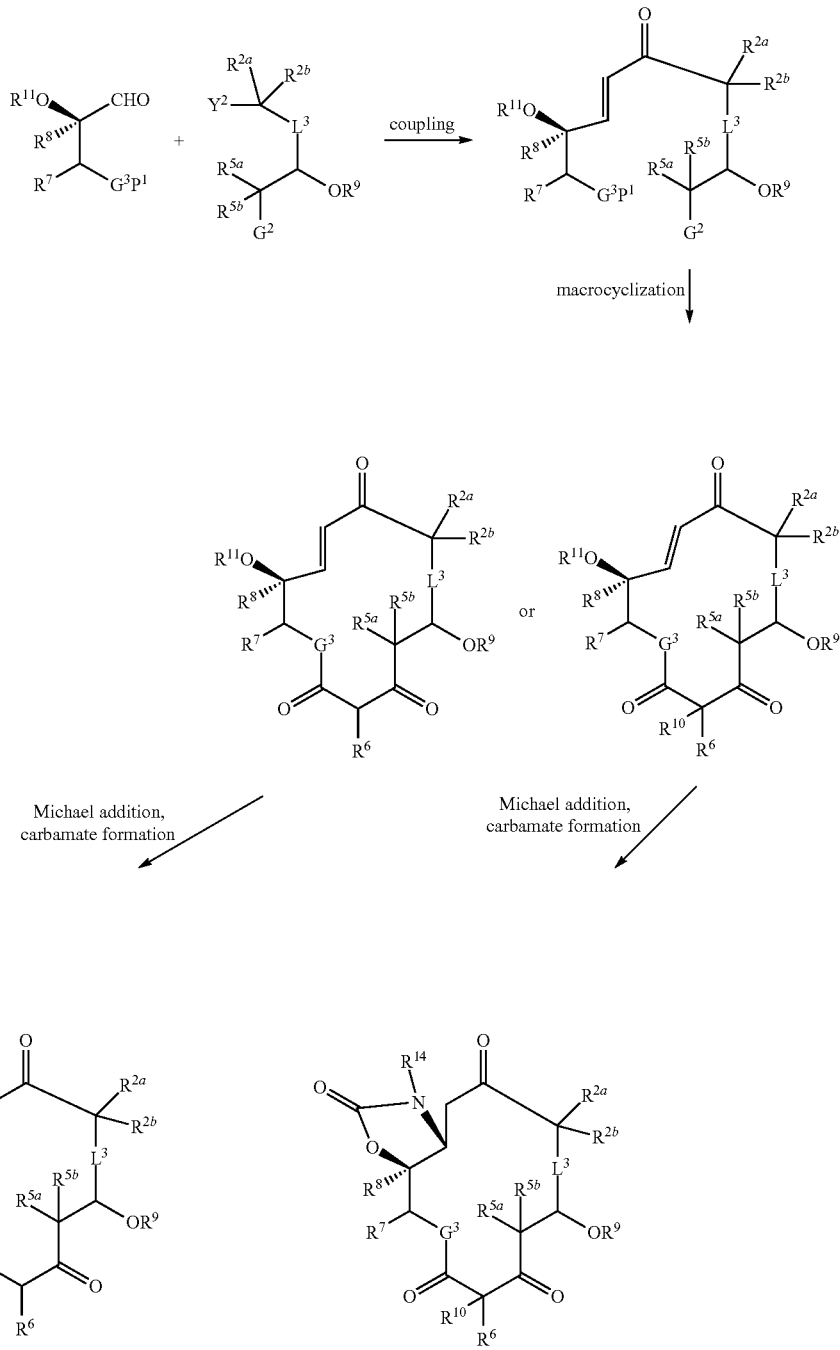

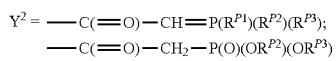
$Y^2 = -C(=O)-CH=P(R^{P1})(R^{P2})(R^{P3});$
$-C(=O)-CH_2-P(O)(OR^{P2})(OR^{P3})$ Scheme 32 depicts various synthetic modifications which are contemplated and further described in greater details elsewhere. For example, after formation of the cyclic carbamate, the carbon alpha to the ketone moiety so installed may be monosubstituted (e.g., wherein $R^{1a}$ is hydrogen and $R^{1b}$ is a non-hydrogen) or di-substituted (i.e., wherein both $R^{1a}$ and $R^{1b}$ are non-hydrogen groups). Synthetic modification of the C3 ketone by dihalogenation (e.g., wherein each of $R^{Y1}$ and $R^{Y2}$ is halogen (e.g., fluoro)), or by reduction to provide an alcohol wherein $R^{Y1}$ is $-OR^{17}$ and $R^{Y2}$ is hydrogen, followed by monohalogenation to provide a product wherein $R^{Y1}$ is halogen (e.g., fluoro) and $R^{Y2}$ is hydrogen is further contemplated.

Scheme 32.
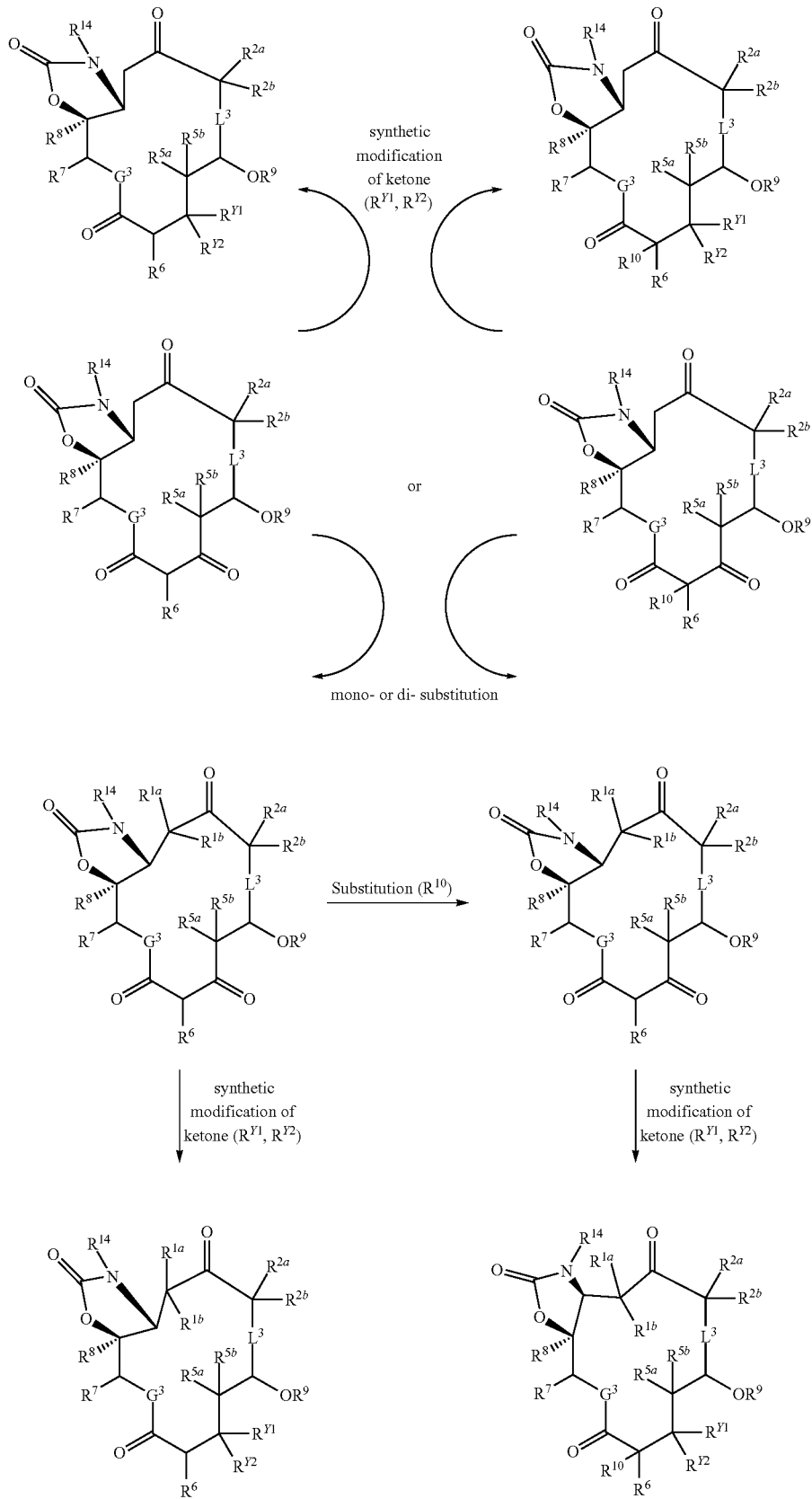

Scheme 33a depicts additional functionalization of ketolides prepared by the methods described herein via an enolate or trapped enolate, wherein PG is an oxygen protecting group as defined herein. In certain embodiments, the trapped enolate is trapped as a protected enol ether using a reagent of formula LG-PG wherein LG is leaving group and PG is protecting group as defined herein. In certain embodiments, either the protected enol ether or the enolate can be utilized to carry out an aldol condensation reaction with aldehydes of formula $R^{23}$—CHO. Alternatively, the protected enol ether can be contacted with iminium salts under suitable conditions to afford amino substituted products. Amines produced via this method can be eliminated to provide exocyclic alkenes.

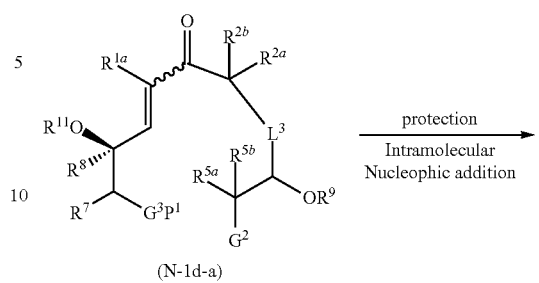

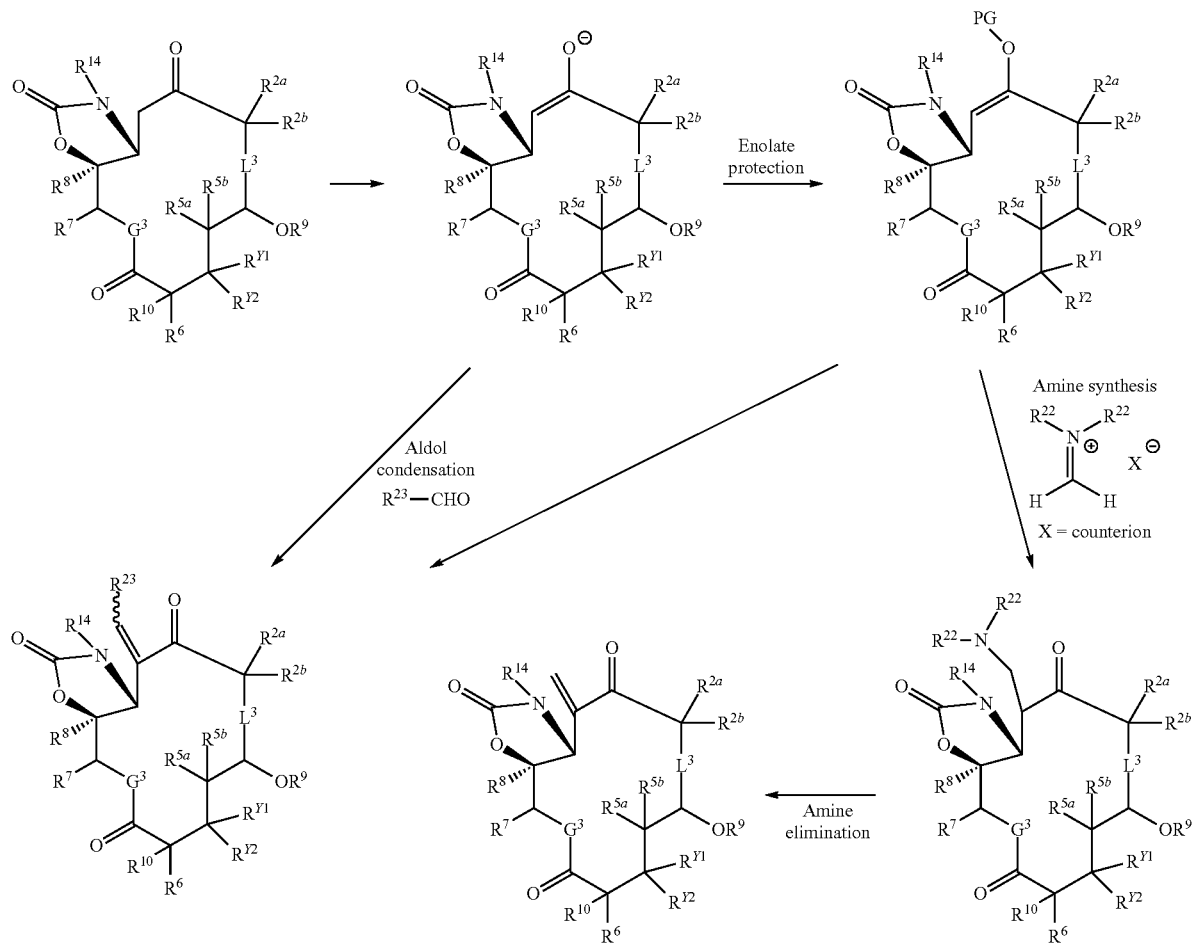

Scheme 33b depicts a scheme to synthesize compounds of Formula (N-1d). Scheme 33c depicts a scheme to synthesize macrolides from compounds of Formulae (N-1d) and (N-1d-a). As shown in Scheme 33b, macrocyclization can be performed after the formation of the cyclic carbamate of (N-1e) and subsequent elaboration at the C-10 position. Alternatively, as shown in Scheme 33c, formation of the cyclic carbamate and elaboration at C-10 can be performed after macrocyclization (i.e., after the macrocyclic ring has been formed).

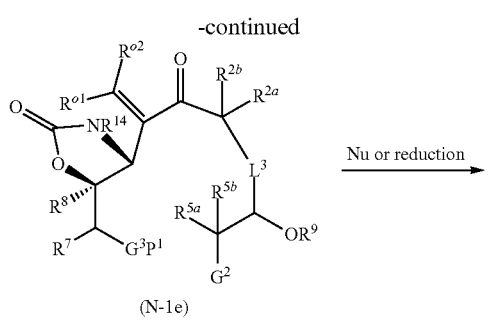

121

-continued

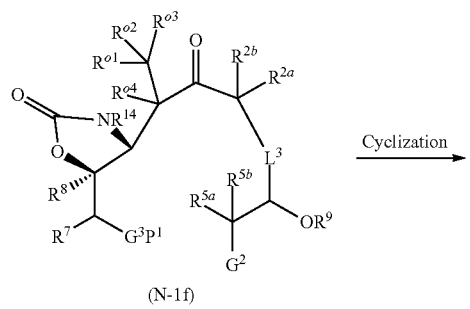

(N-1f)

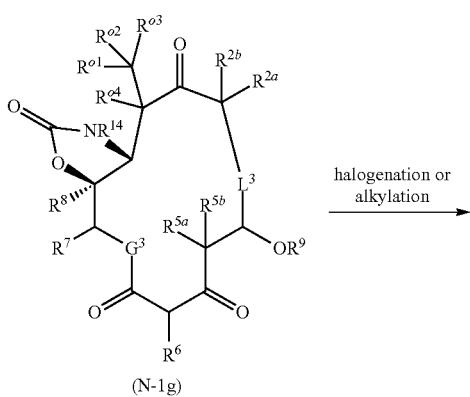

(N-1g)

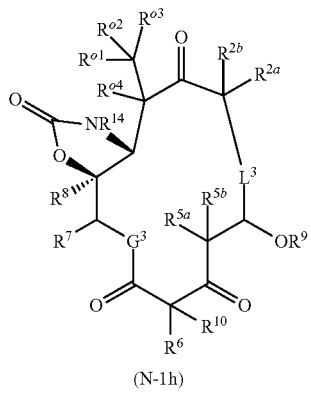

(N-1h)

Scheme 33c

Route 1B-a

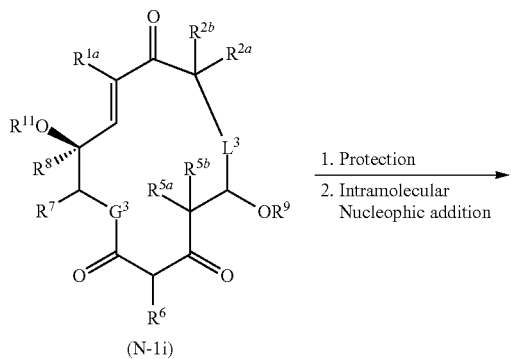

(N-1i)

122

-continued

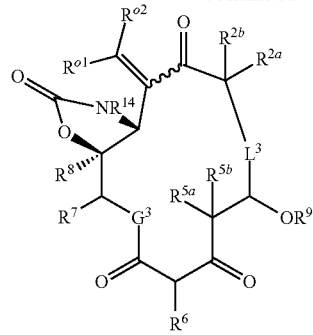

(N-1j)

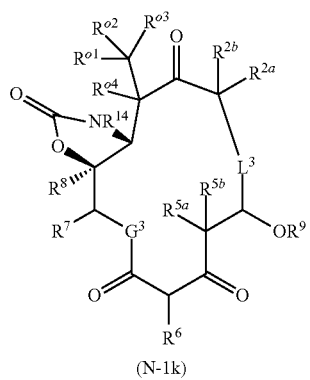

(N-1k)

Group $G^1$ and $R^{11}$

As generally defined herein, $G^1$ is hydrogen, —$OR^{12}$ or —$NR^{13}R^{14}$.

In certain embodiments, $G^1$ is hydrogen.

In certain embodiments, $G^1$ is —$OR^{12}$, then $R^{11}$ and $R^{12}$ are joined as a group of formula —C(=O)— to provide a cyclic carbonate.

In certain embodiments, $G^1$ is —$OR^{12}$ and $R^{11}$ and $R^{12}$ are not joined to form a cyclic carbonate. In that instance, in certain embodiments, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

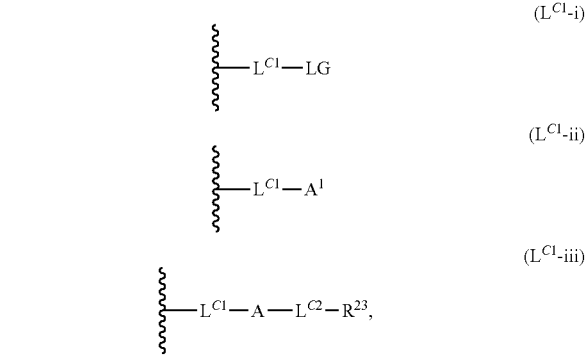

as defined herein.

In certain embodiments, wherein $R^{12}$ is not hydrogen, $R^{12}$ is optionally substituted with a non-hydrogen group of formula $R^{23}$ as defined herein.

In certain embodiments, $G^1$ is —$NR^{13}R^{14}$, and $R^{11}$ and $R^{13}$ are joined as a group of formula —C(=O)— to provide a cyclic carbamate.

In certain embodiments, $G^1$ is —$NR^{13}R^{14}$, and $R^{11}$ and $R^{13}$ are not joined to form a cyclic carbamate. In that instance, in certain embodiments, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, $R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

In certain embodiments, wherein $R^{13}$ is not hydrogen, $R^{13}$ is optionally substituted with a non-hydrogen group of formula $R^{23}$ as defined herein.

In certain embodiments, wherein $G^1$ is —$NR^{13}R^{14}$, $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)$R^{Z8}$, or —C(=O)O$R^{Z8}$, or a group of formula:

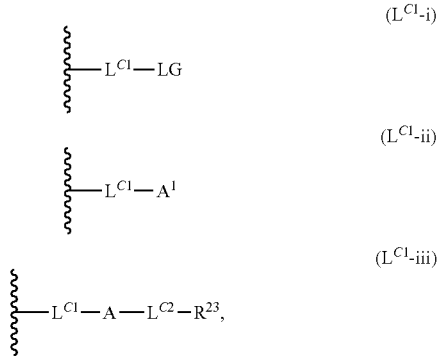

as defined herein.

In certain embodiments, wherein $R^{14}$ is not hydrogen, $R^{14}$ is optionally substituted with a non-hydrogen group of formula $R^{23}$ as defined herein.

In certain embodiments, wherein $G^1$ is —$NR^{13}R^{14}$, $R^{13}$ and $R^{14}$ are joined to form an optionally substituted heterocyclyl or optionally substituted heteroaryl. In certain embodiments, the heterocyclyl or heteroaryl ring system formed from the joining of $R^{13}$ and $R^{14}$ is optionally substituted with a non-hydrogen group of formula $R^{23}$ as defined herein.

Groups $R^{1a}$, $R^{1b}$, $R^{2a}$, and $R^{2b}$

As generally defined herein, each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or wherein $R^{1a}$ and $R^{1b}$ or $R^{2a}$ and $R^{2b}$ are taken together to form

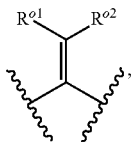

wherein each of $R^{o1}$ and $R^{o2}$ is independently hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl.

In certain embodiments, the carbon to which $R^{1a}$ and $R^{1b}$ is attached is a stereocenter of the (R)-configuration. In certain embodiments, the carbon to which $R^{1a}$ and $R^{1b}$ is attached is a stereocenter of the (S)-configuration In certain embodiments, at least one of $R^{1a}$ and $R^{1b}$ is hydrogen. In certain embodiments, both $R^{1a}$ and $R^{1b}$ are hydrogen.

In certain embodiments, at least one of $R^{1a}$ and $R^{1b}$ is halogen; e.g. —F, —Cl, —Br, or I. In certain embodiments, both $R^{1a}$ and $R^{1b}$ are halogen; e.g. —F, —Cl, —Br, or I.

In certain embodiments, at least one of $R^{1a}$ and $R^{1b}$ is carbonyl. In certain embodiments, at least one of $R^{1a}$ and $R^{1b}$ is a carboxylic acid. In certain embodiments, at least one of $R^{1a}$ and $R^{1b}$ is a ketone. In certain embodiments, at least one of $R^{1a}$ and $R^{1b}$ is an aldehyde (—CHO).

In certain embodiments, at least one instance of $R^{1a}$ and $R^{1b}$ is optionally substituted alkyl, e.g., optionally substituted $C_{1-4}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^{1a}$ and $R^{1b}$ is —$CH_3$. In certain embodiments, both instances of $R^{1a}$ and $R^{1b}$ are —$CH_3$. In certain embodiments, at least one instance of $R^{1a}$ and $R^{1b}$ is alkyl substituted with one or more halogen atoms, e.g., optionally substituted haloalkyl; e.g., —$CF_3$, —$CF_2CF_3$, or —$CF_2H$. In certain embodiments, at least one of $R^{1a}$ and $R^{1b}$ is —$CH_2CHO$.

In certain embodiments, at least one instance of $R^{1a}$ and $R^{1b}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^{1a}$ and $R^{1b}$ is vinyl, allyl, or prenyl.

In certain embodiments, at least one instance of $R^{1a}$ and $R^{1b}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, at least one instance of $R^{1a}$ and $R^{1b}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl. In certain embodiments, at least one instance of $R^{1a}$ and $R^{1b}$ is optionally substituted cyclopropyl. In certain embodiments, at least one instance of $R^{1a}$ and $R^{1b}$ is unsubstituted cyclopropyl. In certain embodiments, at least one instance of $R^{1a}$ and $R^{1b}$ is optionally substituted cyclobutyl. In certain embodiments, at least one instance of $R^{1a}$ and $R^{1b}$ is unsubstituted cyclobutyl. In certain embodiments, at least one instance of $R^{1a}$ and $R^{1b}$ is optionally substituted cyclopentyl. In certain embodiments, at least one instance of $R^{1a}$ and $R^{1b}$ is unsubstituted cyclopentyl. In certain embodiments, at least one instance of $R^{1a}$ and $R^{1b}$ is optionally substituted cyclohexyl. In certain embodiments, at least one instance of $R^{1a}$ and $R^{1b}$ is unsubstituted cyclohexyl.

In certain embodiments, at least one instance of $R^{1a}$ and $R^{1b}$ is optionally substituted heterocylyl, e.g., e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{1a}$ and $R^{1b}$ is optionally substituted aryl, e.g., optionally substituted phenyl.

In certain embodiments, at least one instance of $R^{1a}$ and $R^{1b}$ is optionally substituted heteroaryl, e.g., optionally substituted 5- to 6-membered heteroaryl.

In certain embodiments, $R^{1a}$ and $R^{1b}$ are taken together to form

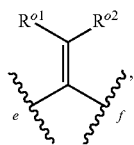

wherein e indicates point of attachment to the carbon linked to G1, and f indicates the point of attachment to the C=O or the carbon substituted by $OR^{no}$; $R^{o1}$ and $R^{o2}$ are as defined herein. In certain embodiments, each of $R^{o1}$ and $R^{o2}$ is independently hydrogen or optionally substituted alkyl. In certain embodiments, $R^{o1}$ and $R^{o2}$ are hydrogen. In certain embodiments, $R^{o1}$ is hydrogen and $R^{o2}$ is optionally substituted alkyl. In certain embodiments, $R^{o1}$ is hydrogen and $R^{o2}$ is optionally substituted $C_{1-6}$ alkyl. In certain embodiments, $R^{o1}$ is hydrogen and $R^{o2}$ is unsubstituted $C_{1-6}$ alkyl (e.g. methyl or ethyl). In certain embodiments, $R^{o1}$ is hydrogen and $R^{o2}$ is substituted $C_{1-6}$ alkyl (e.g. methyl or ethyl). In certain embodiments, $R^{o2}$ is hydrogen and $R^{o1}$ is optionally substituted alkyl. In certain embodiments, $R^{o2}$ is hydrogen and $R^{o1}$ is optionally substituted $C_{1-6}$ alkyl. In certain embodiments, $R^{o2}$ is hydrogen and $R^{o1}$ is unsubstituted $C_{1-6}$ alkyl (e.g. methyl or ethyl). In certain embodiments, $R^{o2}$ is hydrogen and $R^{o1}$ is substituted $C_{1-6}$ alkyl.

In certain embodiments, the moiety

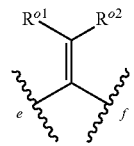

formed by $R^{1a}$ and $R^{1b}$ can be converted to the formula

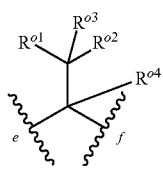

by a conjugated addition or reduction reaction, wherein $R^{o1}$-$R^{o4}$ are as defined herein.

In certain embodiments, $R^{1a}$ is optionally substituted alkyl. In certain embodiments, $R^{1a}$ is optionally substituted alkyl of the formula

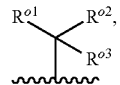

wherein $R^{o1}$-$R^{o3}$ are as defined herein. In certain embodiments, $R^{1a}$ is optionally substituted alkyl of the formula

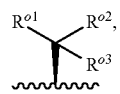

wherein $R^{o1}$-$R^{o3}$ are as defined herein. In certain embodiments, $R^{1a}$ is optionally substituted alkyl of the formula

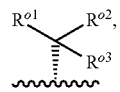

wherein $R^{o1}$-$R^{o3}$ are as defined herein. In certain embodiments, $R^{1b}$ is $R^{o4}$, wherein $R^{o4}$ is as defined herein.

As generally defined herein, $R^{o1}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{o1}$ is hydrogen. In certain embodiments, $R^{o1}$ is halogen (e.g. Br or I). In certain embodiments, $R^{o1}$ is optionally substituted alkyl. In certain embodiments, $R^{o1}$ is unsubstituted alkyl (e.g. methyl, ethyl, or n-propyl).

As generally defined herein, $R^{o2}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{o2}$ is hydrogen. In certain embodiments, $R^{o2}$ is halogen (e.g. Br or I). In certain embodiments, $R^{o2}$ is optionally substituted alkyl. In certain embodiments, $R^{o2}$ is unsubstituted alkyl (e.g. methyl, ethyl, or n-propyl).

As generally defined herein, $R^{o3}$ is independently hydrogen, halogen, optionally substituted alkyl, optionally substituted alkenyl, optionally substituted alkynyl, optionally substituted aryl, or optionally substituted heteroaryl, $-OR^{n1}$, $-SR^{n1}$, or $-N(R^{n1})_2$; and each instance of $R^{n1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen; or a sulfur protecting group when attached to a sulfur; or a nitrogen protecting group when attached to nitrogen. In certain embodiments, $R^{o3}$ is hydrogen. In certain embodiments, $R^{o3}$ is halogen (e.g. Br or I). In certain embodiments, $R^{o3}$ is optionally substituted alkyl. In certain embodiments, $R^{o1}$ is unsubstituted alkyl (e.g. methyl, ethyl, or n-propyl). In certain embodiments, $R^{o3}$ is $-OR^{n1}$, wherein $R^{n1}$ is as defined herein. In certain embodiments, $R^{o3}$ is —$OR^{n1}$, wherein $R^{n1}$ is hydrogen, optionally substituted alkyl, or an oxygen protecting group. In certain embodiments, $R^{o3}$ is —$SR^{n1}$, wherein $R^{n1}$ is hydrogen, optionally substituted alkyl, or an sulfur protecting group. In certain embodiments, $R^{o3}$ is —$N(R^{n1})_2$, wherein each instance of $R^{n1}$ is independently hydrogen, optionally substituted alkyl, or a nitrogen protecting group.

As generally defined herein, $R^{o4}$ is independently hydrogen, halogen, optionally substituted alkyl, optionally substituted alkenyl, optionally substituted alkynyl, optionally substituted aryl, or optionally substituted heteroaryl. In certain embodiments, $R^{o4}$ is hydrogen. In certain embodiments, $R^{o4}$ is halogen (e.g. Br or I). In certain embodiments, $R^{o4}$ is optionally substituted alkyl. In certain embodiments, $R^{o4}$ is unsubstituted alkyl (e.g. methyl, ethyl, or n-propyl).

In certain embodiments, $R^{o3}$ is hydrogen, halogen, or optionally substituted alkyl; and $R^{o4}$ is hydrogen. In certain embodiments, $R^{o3}$ and $R^{o4}$ are hydrogen. In certain embodiments, $R^{o3}$ is halogen or optionally substituted alkyl; and $R^{o4}$ is hydrogen. In certain embodiments, $R^{o3}$ is optionally substituted alkyl; and $R^{o4}$ is hydrogen. In certain embodiments, $R^{o3}$ is unsubstituted alkyl (e.g. methyl or ethyl); and $R^{o4}$ is hydrogen.

In certain embodiments, $R^{o3}$ is hydrogen, halogen, or optionally substituted alkyl; and $R^{o4}$ is optionally substituted alkyl. In certain embodiments, $R^{o3}$ is hydrogen and $R^{o4}$ is optionally substituted alkyl. In certain embodiments, $R^{o3}$ is halogen or optionally substituted alkyl; and $R^{o4}$ is optionally substituted alkyl. In certain embodiments, $R^{o3}$ is optionally substituted alkyl; and $R^{o4}$ is optionally substituted alkyl. In certain embodiments, $R^{o3}$ is unsubstituted alkyl (e.g. methyl or ethyl); and $R^{o4}$ is unsubstituted alkyl.

In certain embodiments, $R^{o1}$ is hydrogen or optionally substituted alkyl; $R^{o2}$ is hydrogen or optionally substituted alkyl; $R^{o3}$ is hydrogen, halogen, or optionally substituted alkyl; and $R^{o4}$ is hydrogen. In certain embodiments, $R^{o1}$, $R^{o2}$, $R^{o3}$ and $R^{o4}$ are hydrogen.

In certain embodiments, the carbon to which $R^{2a}$ and $R^{2b}$ is attached is a stereocenter of the (R)-configuration. In certain embodiments, the carbon to which $R^{2a}$ and $R^{2b}$ is attached is a stereocenter of the (S)-configuration.

In certain embodiments, at least one instance of $R^{2a}$ and $R^{2b}$ is hydrogen. In certain embodiments, both $R^{2a}$ and $R^{2b}$ are hydrogen.

In certain embodiments, at least one of $R^{2a}$ and $R^{2b}$ is halogen; e.g. —F, —Cl, —Br, or I. In certain embodiments, both $R^{2a}$ and $R^{2b}$ are halogen; e.g. —F, —Cl, —Br, or I.

In certain embodiments, at least one of $R^{2a}$ and $R^{2b}$ is carbonyl. In certain embodiments, at least one of $R^{2a}$ and $R^{2b}$ is a carboxylic acid. In certain embodiments, at least one of $R^{2a}$ and $R^{2b}$ is a ketone. In certain embodiments, at least one of $R^{2a}$ and $R^{2b}$ is an aldehyde (—CHO).

In certain embodiments, at least one instance of $R^{2a}$ and $R^{2b}$ is optionally substituted alkyl, e.g., optionally substituted $C_{1-6}$ alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^{2a}$ and $R^{2b}$ is —$CH_3$. In certain embodiments, both instances of $R^{2a}$ and $R^{2b}$ are —$CH_3$. In certain embodiments, at least one instance of $R^{2a}$ and $R^{2b}$ is alkyl optionally substituted with one or more halogen atoms, e.g., optionally substituted haloalkyl; e.g., —$CF_3$, —$CF_2CF_3$, or —$CF_2H$. In certain embodiments, at least one of $R^{2a}$ and $R^{2b}$ is —$CH_2CHO$.

In certain embodiments, at least one instance of $R^{2a}$ and $R^{2b}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^{2a}$ and $R^{2b}$ is vinyl, allyl, or prenyl.

In certain embodiments, at least one instance of $R^{2a}$ and $R^{2b}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, at least one instance of $R^{2a}$ and $R^{2b}$ is optionally substituted carbocyclyl, e.g., optionally substituted $C_{3-6}$carbocyclyl, optionally substituted $C_{3-4}$ carbocyclyl, optionally substituted $C_{4-5}$ carbocyclyl, or optionally substituted $C_{5-6}$ carbocyclyl.

In certain embodiments, at least one instance of $R^{2a}$ and $R^{2b}$ is optionally substituted heterocylyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{2a}$ and $R^{2b}$ is optionally substituted aryl, e.g., optionally substituted phenyl.

In certain embodiments, at least one instance of $R^{2a}$ and $R^{2b}$ is optionally substituted heteroaryl, e.g., optionally substituted 5- to 6-membered heteroaryl.

In certain embodiments, $R^{2a}$ and $R^{2b}$ are taken together to form

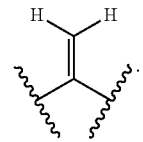

Group $L^3$ and Groups $R^3$, $R^4$, $R^{18}$, $R^{19}$, $R^{20}$, and $R^{21}$

As generally defined herein, $L^3$ is a group of the formula:

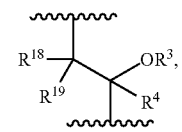 (L³-i)

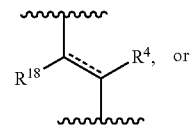 (L³-ii)

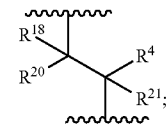 (L³-iii)

===== represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$C(=O)R^{Z8}$, —$C(=O)OR^{Z8}$, —$C(=O)N(R^{Z8})_2$, an oxygen protecting group, or a group of formula:

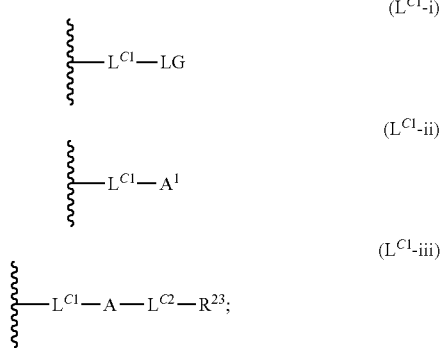

$R^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of $R^{18}$ and $R^{19}$ independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each instance of $R^{20}$ and $R^{21}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, carbonyl, or $R^{20}$ and $R^{21}$ are joined to form an optionally substituted cyclopropyl or an oxiranyl ring.

In certain embodiments, the carbon to which $R^3$ is attached is a stereocenter of the (R)-configuration. In certain embodiments, the carbon to which $R^3$ is attached is a stereocenter of the (S)-configuration.

In certain embodiments, $R^3$ is hydrogen.

In certain embodiments, $R^3$ is optionally substituted alkyl; e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or an optionally substituted $C_{5-6}$alkyl. In certain embodiments, $R^3$ is —$CH_3$. In certain embodiments, $R^3$ is —$CH_2CHO$. In certain embodiments, $R^3$ is —$CH_2N(R^{22})_2$ wherein each instance of $R^{22}$ is independently hydrogen or optionally substituted alkyl. In certain embodiments, $R^3$ is-$CH_2NH(R^{22})$. In certain embodiments, $R^3$ is —$CH_2NH_2$. In certain embodiments, $R^3$ is —$CH_2CH(OH)R^{24}$ wherein $R^{24}$ is hydrogen, optionally substituted alkyl, or optionally substituted aryl. In certain embodiments, $R^3$ is —$CH_2CH_2OH$. In certain embodiments, $R^3$ is —$CH_2CH_2R^{23}$ wherein $R^{23}$ is as defined herein.

In certain embodiments, $R^3$ is optionally substituted alkenyl; e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^3$ is vinyl, allyl, or prenyl. In certain embodiments, $R^3$ is optionally substituted allyl, e.g., substituted allyl, e.g.,

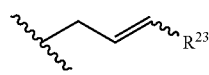

wherein $R^{23}$ is as defined herein, or unsubstituted allyl

In certain embodiments, $R^3$ is optionally substituted vinyl, e.g., substituted vinyl, e.g.,

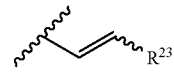

wherein $R^{23}$ is as defined herein, or unsubstituted vinyl

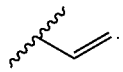

In certain embodiments, $R^3$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$ alkynyl, or optionally substituted $C_{5-6}$alkynyl.

In certain embodiments, $R^3$ is optionally substituted carbocyclyl; e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^3$ is optionally substituted aryl, e.g., optionally substituted phenyl.

In certain embodiments, $R^3$ is optionally substituted heteroaryl, e.g., optionally substituted 5- to 6-membered heteroaryl.

In certain embodiments, $R^3$ is —$C(=O)R^{Z8}$, —$C(=O)OR^{Z8}$, —$C(=O)N(R^{Z8})_2$, or an oxygen protecting group.

In certain embodiments, $R^3$ is or a group of formula:

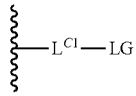

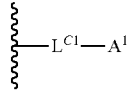

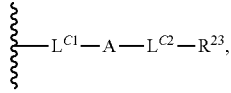

wherein $L^{C1}$, LG, $A^1$, A, $L^{C2}$, and $R^{23}$ are as defined herein.

In certain embodiments, the carbon to which $R^4$ is attached is a stereocenter of the (R)-configuration. In certain embodiments, the carbon to which $R^4$ is attached is a stereocenter of the (S)-configuration.

In certain embodiments, $R^4$ is hydrogen.

In certain embodiments, $R^4$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$ alkyl, or optionally substituted $C_{5-6}$alkyl. In certain embodiments, $R^4$ is —$CH_3$. In certain embodiments, $R^4$ is —$CH_2CHO$. In certain embodiments, $R^4$ is —$CH_2N(R^{22})_2$ wherein each instance of $R^{22}$ is independently hydrogen or optionally substituted alkyl. In certain embodiments, $R^4$ is-$CH_2NH$ ($R^{22}$). In certain embodiments, $R^4$ is —$CH_2NH_2$. In certain embodiments, $R^4$ is —$CH_2CH(OH)R^{24}$ wherein $R^{24}$ is hydrogen, optionally substituted alkyl, or optionally substituted aryl. In certain embodiments, $R^4$ is —$CH_2CH_2OH$. In certain embodiments, $R^4$ is —$CH_2CH_2R^{23}$ wherein $R^{23}$ is as defined herein.

In certain embodiments, $R^4$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^4$ is optionally substituted allyl, e.g., substituted allyl, e.g.,

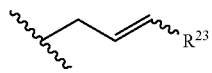

wherein $R^{23}$ is as defined herein, or unsubstituted allyl

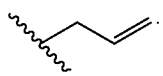 [SMILES: *CC=C]

In certain embodiments, $R^4$ is optionally substituted vinyl, e.g., substituted vinyl, e.g.,

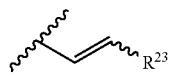

wherein $R^{23}$ is as defined herein, or unsubstituted vinyl

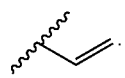

Various combinations of $R^4$ and $R^{21}$ are contemplated herein. For example, in certain embodiments, $R^4$ is optionally substituted $C_{1-3}$alkyl and $R^{21}$ is hydrogen. In certain embodiments, $R^3$ is —$CH_2CHO$, —$CH_2N(R^{22})_2$, —$CH_2CH(OH)R^{24}$, or —$CH_2CH_2R^{23}$ and $R^{21}$ is hydrogen. In certain embodiments, $R^4$ is optionally substituted $C_{2-3}$alkenyl, and $R^{21}$ is hydrogen. In certain embodiments, R is

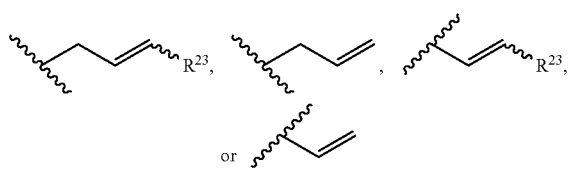

and $R^{21}$ is hydrogen.

In certain embodiments, $R^4$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$ alkynyl, or optionally substituted $C_{5-6}$ alkynyl.

In certain embodiments, $R^4$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^4$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^4$ is optionally substituted aryl, e.g., optionally substituted phenyl.

In certain embodiments, $R^4$ is optionally substituted heteroaryl, e.g., optionally substituted 5- to 6-membered heteroaryl.

In certain embodiments, each instance of $R^{18}$ and $R^{19}$ is independently hydrogen or optionally substituted alkyl, e.g., hydrogen or —$CH_3$. In certain embodiments, the carbon to which $R^{18}$ and $R^{19}$ are attached is a stereocenter in the (R) configuration. In certain embodiments, the carbon to which $R^{18}$ and $R^{19}$ are attached is a stereocenter in the (S) configuration.

In certain embodiments, each instance of $R^{20}$ and $R^{21}$ is independently hydrogen, hydroxyl, substituted hydroxyl, thiol, substituted thiol, amino, substituted amino, halogen, or $R^{20}$ and $R^{21}$ are joined to form an optionally substituted cyclopropyl or an oxiranyl ring. In certain embodiments, $R^{20}$ and $R^{21}$ are syn to each other. In certain embodiments, $R^{20}$ and $R^{21}$ are anti to each other.

In certain embodiments, $L^3$ is:

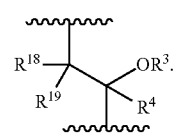

(L³-i)

In certain embodiments, $L^3$ is:

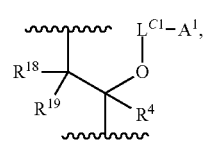

(L³-ic)

wherein $L^{C1}$ and $A^1$ are as defined herein.

In certain embodiments, $L^3$ is of the formula:

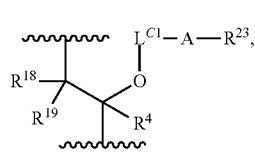

(L³-id)

wherein $L^{C1}$, A, $L^{C2}$, and $R^{23}$ are as defined herein.

Groups $R^{5a}$ and $R^{5b}$

As generally defined herein, each instance of $R^{5a}$ and $R^{5b}$ is independently hydrogen, halogen, silyl, optionally substituted alkyl, optionally substituted carbocyclyl, or optionally substituted heterocyclyl.

In certain embodiments, one instance of $R^{5a}$ and $R^{5b}$ is hydrogen, and the other of $R^{5a}$ and $R^{5b}$ is a non-hydrogen group. In certain embodiments, each instance of $R^{5a}$ and $R^{5b}$ is hydrogen. In certain embodiments, each instance of $R^{5a}$ and $R^{5b}$ is a non-hydrogen group, e.g., halogen, optionally substituted alkyl, optionally substituted carbocyclyl, or optionally substituted heterocyclyl.

In certain embodiments, the carbon to which $R^{5a}$ and $R^{5b}$ is attached is a stereocenter of the (R)-configuration. In certain embodiments, the carbon to which $R^{5a}$ and $R^{5b}$ is attached is a stereocenter of the (S)-configuration.

In certain embodiments, at least one instance of $R^{5a}$ and $R^{5b}$ is optionally substituted alkyl, e.g., optionally substituted $C_{1-6}$ alkyl, optionally substituted $C_{1-2}$alkyl, optionally substituted $C_{2-3}$alkyl optionally substituted $C_{3-4}$alkyl, optionally substituted $C_{4-5}$alkyl, or optionally substituted $C_{5-6}$alkyl. In certain embodiments, at least one instance of $R^{5a}$ and $R^{5b}$ is —$CH_3$. In certain embodiments, both instances of $R^{5a}$ and $R^{5b}$ are —$CH_3$.

In certain embodiments, at least one instance of $R^{5a}$ and $R^{5b}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, at least one instance of $R^{5a}$ and $R^{5b}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{5a}$ and $R^{5b}$ is halogen, e.g., bromo, iodo, chloro, or fluoro. In certain embodiments, at least one instance of $R^{5a}$ and $R^{5b}$ is fluoro. In certain embodiments, both instances of $R^{5a}$ and $R^{5b}$ are fluoro. In certain embodiments, one of $R^{5a}$ and $R^{5b}$ is hydrogen and the other of $R^{5a}$ and $R^{5b}$ is fluoro.

In certain embodiments, at least one instance of $R^{5a}$ and $R^{5b}$ is silyl.

Groups $R^6$ and $R^{10}$

As generally defined herein, $R^6$ and/or $R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen.

In certain embodiments, $R^6$ and/or $R^{10}$ is hydrogen. In certain embodiments, $R^6$ is hydrogen. In certain embodiments, $R^{10}$ is hydrogen. In certain embodiments, $R^6$ is hydrogen, and $R^{10}$ is hydrogen. In certain embodiments, both of $R^6$ and $R^{10}$ are non-hydrogen groups.

In certain embodiments, the carbon to which $R^6$ and $R^{10}$ is attached is a stereocenter of the (R)-configuration. In certain embodiments, the carbon to which $R^6$ and $R^{10}$ is attached is a stereocenter of the (S)-configuration.

In certain embodiments, at least one instance of $R^6$ and $R^{10}$ is optionally substituted alkyl; e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^6$ and $R^{10}$ is —$CH_3$. In certain embodiments, at least one instance of $R^6$ and $R^{10}$ is —$CH_3$. In certain embodiments, at least one instance of $R^6$ and $R^{10}$ is —$CH_2CN$. In certain embodiments, at least one instance of $R^6$ and $R^{10}$ is —$CH_2C(=O)OR^{32}$, wherein $R^{32}$ is hydrogen, optionally substituted alkyl, optionally substituted alkenyl, optionally substituted alkynyl, optionally substituted carbocycyl, optionally substituted heterocyclyl, optionally substituted aryl, optionally substituted heteroaryl. In certain embodiments, $R^{32}$ is optionally substituted alkyl, e.g. $C_{1-6}$ alkyl. In certain embodiments, $R^{32}$ is unsubstituted $C_{1-6}$ alkyl. In certain embodiments, $R^{32}$ is methyl, ethyl, or propyl. In certain embodiments, $R^{32}$ is substituted $C_{1-6}$ alkyl. In certain embodiments, $R^{32}$ is hydrogen.

In certain embodiments, at least one instance of $R^6$ and $R^{10}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^6$ and $R^{10}$ is substituted or unsubstituted allyl. In certain embodiments, at least one instance of $R^6$ and $R^{10}$ is substituted or unsubstituted vinyl. Such groups are contemplated after the macrocyclization step, converted, for example, from the enolate of the macrolide wherein $R^6$ and/or $R^{10}$ is hydrogen.

In certain embodiments, at least one instance of $R^6$ and $R^{10}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl. Such groups are contemplated after the macrocyclization step, converted, for example, from the enolate of the macrolide wherein $R^6$ and/or $R^{10}$ is hydrogen.

In certain embodiments, at least one instance of $R^6$ and $R^{10}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, at least one instance of $R^6$ and $R^{10}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^6$ and $R^{10}$ is optionally substituted aryl; e.g., optionally substituted phenyl.

In certain embodiments, at least one instance of $R^6$ and $R^{10}$ is optionally substituted aralkyl; e.g., optionally substituted benzyl.

In certain embodiments, at least one instance of $R^6$ and $R^{10}$ is optionally substituted heteroaryl, e.g., optionally substituted 5- to 6-membered heteroaryl.

In certain embodiments, at least one instance of $R^6$ and $R^{10}$ is optionally substituted heteroaralkyl; e.g., optionally substituted pyrazolylalkyl, imidazolylalkyl, thiazolylalkyl, oxazolylalkyl, pyridinylalkyl, pyrimidinylalkyl, or pyrazinylalkyl.

In certain embodiments, at least one instance of $R^6$ and $R^{10}$ is hydroxyl, substituted hydroxyl, thiol, substituted thiol, amino, or substituted amino. Such groups are contemplated after the macrocyclization step, converted, for example, from wherein $R^6$ and/or $R^{10}$ is a halogen.

In certain embodiments, at least one instance of $R^6$ and $R^{10}$ is carbonyl, e.g., acetyl.

In certain embodiments, at least one instance of $R^6$ and $R^{10}$ is silyl. In certain embodiments, $R^6$ is silyl prior to macrocyclization, but is removed after the macrolide is formed and replaced with, for example, hydrogen.

In certain embodiments, at least one instance of $R^6$ and $R^{10}$ is halogen, e.g., fluoro, bromo, chloro, or iodo.

Groups $R^7$ and $R^8$

As generally defined herein, $R^7$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^7$ is hydrogen. However, in certain embodiments, $R^7$ is a non-hydrogen group, and the carbon to which $R^7$ is attached is a stereocenter of the (R)-configuration. In certain embodiments, $R^7$ is a non-hydrogen group, and the carbon to which $R^7$ is attached is a stereocenter of the (S)-configuration.

In certain embodiments, $R^7$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$ alkyl, or optionally substituted $C_{5-6}$alkyl. In certain embodiments, $R^7$ is —$CH_3$ or —$CH_2CH_3$.

In certain embodiments, $R^7$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^7$ is vinyl, allyl, or prenyl.

In certain embodiments, $R^7$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$-alkynyl, or optionally substituted $C_{5-6}$ alkynyl.

In certain embodiments, $R^7$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^7$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^7$ is optionally substituted aryl; e.g., optionally substituted phenyl.

In certain embodiments, $R^7$ is optionally substituted heteroaryl, e.g., optionally substituted 5- to 6-membered heteroaryl.

As generally defined herein, $R^8$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^8$ is hydrogen.

In certain embodiments, $R^8$ is optionally substituted alkyl, e.g., optionally substituted $C_{1-6}$alkyl, optionally substituted $C_{1-2}$alkyl, optionally substituted $C_{2-3}$alkyl, optionally substituted $C_{3-4}$alkyl, optionally substituted $C_{4-5}$-alkyl, or optionally substituted $C_{5-6}$alkyl. In certain embodiments, $R^8$ is —$CH_3$ or —$CH_2CH_3$.

In certain embodiments, $R^8$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^8$ is vinyl, allyl, or prenyl.

In certain embodiments, $R^8$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$-alkynyl, or optionally substituted $C_{5-6}$ alkynyl.

In certain embodiments, $R^8$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^8$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^8$ is optionally substituted aryl, e.g., optionally substituted phenyl.

In certain embodiments, $R^8$ is optionally substituted heteroaryl, e.g., optionally substituted 5- to 6-membered heteroaryl.

Groups $R^9$ and $R^{17}$, $R^{Y1}$, $R^{Y2}$

As generally defined herein, $R^{Y1}$ is —$OR^{17}$ and $R^{Y2}$ is hydrogen, or $R^{Y1}$ is halogen and $R^{Y2}$ is hydrogen, or $R^{Y1}$ is halogen and $R^{Y2}$ is halogen, or $R^{Y1}$ and $R^{Y2}$ are joined to form an oxo (=O) group.

In certain embodiments, $R^{Y1}$ and $R^{Y2}$ are joined to form an oxo (=O) group.

In certain embodiments, R is —$OR^{17}$ and $R^{Y2}$ is hydrogen.

In certain embodiments, $R^{Y1}$ is halogen (e.g., fluoro) and $R^{Y2}$ is hydrogen.

In certain embodiments, $R^{Y1}$ is halogen (e.g., fluoro) and $R^{Y2}$ is halogen (e.g., fluoro).

As generally defined herein, $R^9$ and/or $R^{17}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$C(=O)R^{Z8}$, —$C(=O)OR^{Z8}$, —$C(=O)N(R^{Z8})_2$, an oxygen protecting group, or a carbohydrate, wherein each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocylyl or optionally substituted heteroaryl ring.

In certain embodiments, the carbon to which $R^9$ is attached is of the (R)-configuration. In certain embodiments, the carbon to which $R^9$ is attached is of the (S)-configuration.

In certain embodiments, the carbon to which $R^{17}$ is attached is of the (R)-configuration. In certain embodiments, the carbon to which $R^{17}$ is attached is of the (S)-configuration.

In certain embodiments, $R^9$ is hydrogen. In certain embodiments, $R^{17}$ is hydrogen.

In certain embodiments, $R^9$ and/or $R^{17}$ are each independently optionally substituted alkyl, e.g., optionally substituted $C_{1-6}$ alkyl, optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl, e.g., —$CH_3$.

In certain embodiments, $R^9$ is

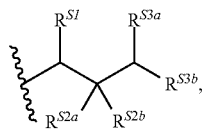

where $R^{S1}$, $R^{S2a}$, $R^{S2b}$, $R^{S3a}$, and $R^{S3b}$ are defined herein. In certain embodiments, $R^9$ is

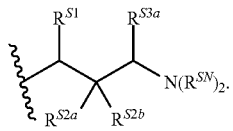

In certain embodiments, $R^9$ is

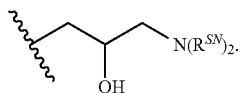

In certain embodiments, $R^9$ is

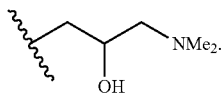

In certain embodiments, $R^9$ and/or $R^{17}$ are each independently optionally substituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^9$ and/or $R^{17}$ are each independently optionally substituted alkynyl, e.g., substituted or unsubstituted $C_{2-6}$ alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$ alkynyl.

In certain embodiments, $R^9$ and/or $R^{17}$ are each independently optionally substituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, $R^9$ and/or $R^{17}$ are each independently optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^9$ and/or $R^{17}$ are each independently optionally substituted aryl, e.g., optionally substituted phenyl.

In certain embodiments, $R^9$ and/or $R^{17}$ are each independently optionally substituted heteroaryl, e.g., optionally substituted 5- to 6-membered heteroaryl.

In certain embodiments, $R^9$ and/or $R^{17}$ are each independently —C(=O)$R^{Z8}$, —C(=O)O$R^{Z8}$, or —C(=O)N($R^{Z8}$)$_2$. For example, in certain embodiments, $R^{17}$ is —C(=O)$R^{Z8}$, wherein $R^{Z8}$ is optionally substituted aryl or optionally substituted heteroaryl. In certain embodiments, $R^{17}$ is —C(=O)$R^{Z8}$, wherein $R^{Z8}$ is optionally substituted aralkyl or optionally substituted heteroaralkyl.

In certain embodiments, $R^9$ and/or $R^{17}$ are each independently an oxygen protecting group.

In certain embodiments, $R^9$ and/or $R^{17}$ are each independently a carbohydrate.

In certain embodiments, $R^9$ and/or $R^{17}$ is a group of Formula (s-1), which encompasses carbohydrates, but also encompasses optionally substituted heterocylyl:

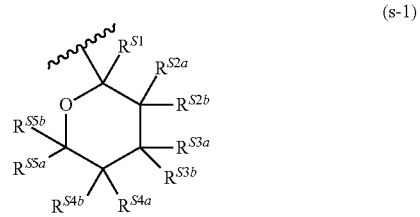

(s-1)

wherein:

each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, —OR$^{SO}$, —N($R^{SN}$)$_2$, or wherein $R^{S2a}$ or $R^{S2b}$ may be taken together with $R^{S3a}$ or $R^{S3b}$ to form an optionally substituted fused heterocyclic ring;

each instance of $R^{SO}$ is independently hydrogen, optionally substituted alkyl, optionally substituted alkenyl, optionally substituted heterocyclyl, or an oxygen protecting group; and each instance of $R^{SN}$ is independently hydrogen, optionally substituted alkyl, or a nitrogen protecting group; or optionally two $R^{SN}$ are taken with the intervening atoms to form a heterocyclic ring.

As generally defined herein, each instance of $R^{S1}$ is independently hydrogen, optionally substituted alkyl, —OR$^{SO}$, or —N($R^{SN}$)$_2$.

In certain embodiments, $R^{S1}$ is hydrogen.

In certain embodiments, $R^{S1}$ is optionally substituted alkyl. In certain embodiments, $R^{S1}$ is substituted $C_{1-6}$ alkyl. In certain embodiments, $R^{S1}$ is unsubstituted $C_{1-6}$ alkyl. In certain embodiments, $R^{S1}$ is methyl, ethyl, propyl, butyl, pentyl, or hexyl. In certain embodiments, $R^{S1}$ is isopropyl, isobutyl, or isoamyl. In certain embodiments, $R^{S1}$ is isobutyl. In certain embodiments, $R^{S1}$ is tert-butyl.

In certain embodiments, $R^{S1}$ is —OR$^{SO}$, wherein $R^{SO}$ is independently hydrogen, optionally substituted alkyl, optionally substituted alkenyl, optionally substituted heterocyclyl, or an oxygen protecting group. In certain embodiments, $R^{S1}$ is —OH. In certain embodiments, $R^{S1}$ is —OR$^{SO}$, wherein $R^{SO}$ is optionally substituted alkyl. In certain embodiments, $R^{S1}$ is —O— methyl, —O-ethyl, or —O-propyl. In certain embodiments, $R^{S1}$ is optionally substituted —O— alkyl-aryl. In certain embodiments, $R^{S1}$ is —O-Bz. In certain embodiments, $R^{S1}$ is optionally substituted —O-alkyl-heteroaryl. In certain embodiments, $R^{S1}$ is optionally substituted —O— alkenyl-aryl. In certain embodiments, $R^{S1}$ is optionally substituted —O-alkenyl-heteroaryl. In certain embodiments, $R^{S1}$ is —OR$^{SO}$, wherein $R^{SO}$ is

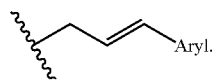

In certain embodiments, $R^{S1}$ is $—OR^{SO}$, wherein $R^{SO}$ is

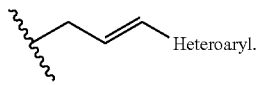

In certain embodiments, $R^{S1}$ is $—OR^{SO}$, wherein $R^{SO}$ is

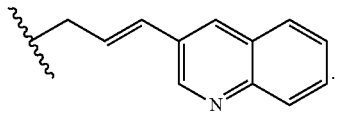 [SMILES: *C/C=C/c1cnc2ccccc2c1]

In certain embodiments, $R^{S1}$ is $—OR^{SO}$, wherein $R^{SO}$ is an oxygen protecting group. In certain embodiments, $R^{S1}$ is $—OR^{SO}$, wherein $R^{SO}$ is carbonyl. In certain embodiments, $R^{S1}$ is $—OR^{SO}$, wherein $R^{SO}$ is acetyl. In certain embodiments, $R^{S1}$ is $—OR^{SO}$, wherein $R^{SO}$ is optionally substituted heterocyclyl.

In certain embodiments, $R^{S1}$ is $—N(R^{SN})_2$. In some embodiments, $R^{S1}$ is $—N(R^{SN})_2$, wherein each $R^{SN}$ is the same. In some embodiments, $R^{S1}$ is $—N(R^{SN})_2$, wherein each $R^{SN}$ is different.

In certain embodiments, $R^{S1}$ is $—NH_2$.

In certain embodiments, $R^{S1}$ is $—NHR^{SN}$. In certain embodiments, $R^{S1}$ is $—NHR^{SN}$, wherein $R^{SN}$ is optionally substituted $C_{1-6}$ alkyl. In certain embodiments, $R^{S1}$ is $—NHR^{SN}$, wherein $R^{SN}$ is unsubstituted $C_{1-6}$ alkyl. In certain embodiments, $R^{S1}$ is $—NHR^{SN}$, wherein $R^{SN}$ is substituted $C_{1-6}$ alkyl. In certain embodiments, $R^{S1}$ is $—NH$-benzyl.

In certain embodiments, $R^{S1}$ is $—NHR^{SN}$, wherein $R^{SN}$ is a nitrogen protecting group. In certain embodiments, $R^{S1}$ is $—NHFmoc$. In certain embodiment, $R^{S1}$ is $—NHBoc$.

In certain embodiments, $R^{S1}$ is $—N(R^{SN})_2$, wherein each $R^{SN}$ is independently optionally substituted $C_{1-6}$ alkyl. In certain embodiments, $R^{S1}$ is $—N(R^{SN})_2$, wherein each $R^{SN}$ is independently unsubstituted $C_{1-6}$ alkyl. In certain embodiments, $R^{S1}$ is $—N(CH_3)R^{SN}$, wherein each $R^{SN}$ is independently optionally substituted $C_{1-6}$ alkyl. In certain embodiments, $R^{S1}$ is $—N(CH_3)R^{SN}$, wherein each $R^{SN}$ is independently unsubstituted $C_{1-6}$ alkyl. In certain embodiments, $R^{S1}$ is $—N(CH_2CH_3)R^{SN}$, wherein each $R^{SN}$ is independently optionally substituted $C_{1-6}$ alkyl. In certain embodiments, $R^{S1}$ is $—N(CH_2CH_3)R^{SN}$, wherein each $R^{SN}$ is independently unsubstituted $C_{1-6}$ alkyl. In certain embodiments, $R^{S1}$ is $—N(R^{SN})_2$, wherein each $R^{SN}$ is independently selected from the group consisting of methyl, ethyl, isopropyl, isobutyl, isoamyl, and benzyl.

In some embodiments, $R^{S1}$ is $—N(R^{SN})_2$, wherein two $R^{SN}$ groups are taken together with the intervening atoms to form an optionally substituted heterocyclic ring. For example, in certain embodiments, $R^{S1}$ is of the formula:

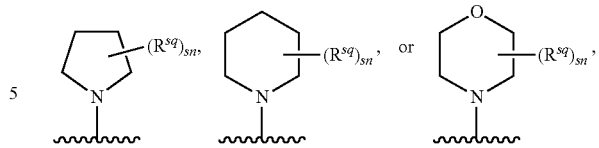

wherein $R^{sq}$ is as defined herein, and sn is 0, 1, 2, or 3.

As generally defined above, each instance of $R^{S2a}$ and $R^{S2b}$ is independently hydrogen, optionally substituted alkyl, $—OR^{SO}$, or $—N(R^{SN})_2$.

In certain embodiments, at least one instance of $R^{S2a}$ and $R^{S2b}$ is hydrogen.

In certain embodiments, at least one instance of $R^{S2a}$ and $R^{S2b}$ is optionally substituted alkyl. In certain embodiments, at least one instance of $R^{S2a}$ and $R^{S2b}$ is substituted $C_{1-6}$ alkyl. In certain embodiments, at least one instance of $R^{S2a}$ and $R^{S2b}$ is unsubstituted $C_{1-6}$ alkyl. In certain embodiments, at least one instance of $R^{S2a}$ and $R^{S2b}$ is methyl, ethyl, propyl, butyl, pentyl, or hexyl. In certain embodiments, at least one instance of $R^{S2a}$ and $R^{S2b}$ is isopropyl, isobutyl, or isoamyl. In certain embodiments, at least one instance of $R^{S2a}$ and $R^{S2b}$ is isobutyl. In certain embodiments, at least one instance of $R^{S2a}$ and $R^{S2b}$ is tert-butyl.

In certain embodiments, at least one instance of $R^{S2a}$ and $R^{S2b}$ is $—OR^{SO}$, wherein $R^{SO}$ is independently hydrogen, optionally substituted alkyl, optionally substituted alkenyl, optionally substituted heterocyclyl, or an oxygen protecting group. In certain embodiments, at least one instance of $R^{S2a}$ and $R^{S2b}$ is $—OH$. In certain embodiments, at least one instance of $R^{S2a}$ and $R^{S2b}$ is $—OR^{SO}$, wherein $R^{SO}$ is optionally substituted alkyl. In certain embodiments, at least one instance of $R^{S2a}$ and $R^{S2b}$ is $—O$-methyl, $—O$-ethyl, or $—O$-propyl. In certain embodiments, at least one instance of $R^{S2a}$ and $R^{S2b}$ is optionally substituted $—O$-alkyl-aryl. In certain embodiments, at least one instance of $R^{S2a}$ and $R^{S2b}$ is $—O$-Bz. In certain embodiments, at least one instance of $R^{S2a}$ and $R^{S2b}$ is $—O$-alkyl-heteroaryl. In certain embodiments, at least one instance of $R^{S2a}$ and $R^{S2b}$ is optionally substituted $—O$-alkenyl-aryl. In certain embodiments, at least one instance of $R^{S2a}$ and $R^{S2b}$ is optionally substituted $—O—$ alkenyl-heteroaryl. In certain embodiments, at least one instance of $R^{S2a}$ and $R^{S2b}$ is $—OR^{SO}$, wherein $R^{SO}$ is

wherein Aryl is an optionally substituted aryl group. In certain embodiments, at least one instance of $R^{S2a}$ and $R^{S2b}$ is $—OR^{SO}$, wherein $R^{SO}$ is

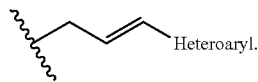

wherein Heteroaryl is an optionally substituted heteroaryl group. In certain embodiments, at least one instance of $R^{S2a}$ and $R^{S2b}$ is $—OR^{SO}$, wherein $R^{SO}$ is

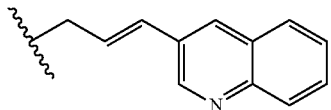

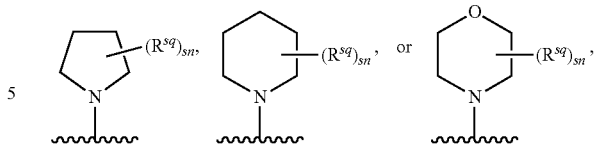

wherein $R^{sq}$ is as defined herein, and sn is 0, 1, 2, or 3.

As generally defined above, each instance of $R^{S3a}$ and $R^{S3b}$ is independently hydrogen, optionally substituted alkyl, —$OR^{SO}$, or —$N(R^{SN})_2$.

In certain embodiments, at least one instance of $R^{S3a}$ and $R^{S3b}$ is hydrogen.

In certain embodiments, at least one instance of $R^{S3a}$ and $R^{S3b}$ is optionally substituted alkyl. In certain embodiments, at least one instance of $R^{S3a}$ and $R^{S3b}$ is substituted $C_{1-6}$ alkyl. In certain embodiments, at least one instance of $R^{S3a}$ and $R^{S3b}$ is unsubstituted $C_{1-6}$ alkyl. In certain embodiments, at least one instance of $R^{S3a}$ and $R^{S3b}$ is methyl, ethyl, propyl, butyl, pentyl, or hexyl. In certain embodiments, at least one instance of $R^{S3a}$ and $R^{S3b}$ is isopropyl, isobutyl, or isoamyl. In certain embodiments, at least one instance of $R^{S3a}$ and $R^{S3b}$ is isobutyl. In certain embodiments, at least one instance of $R^{S3a}$ and $R^{S3b}$ is tert-butyl.

In certain embodiments, at least one instance of $R^{S3a}$ and $R^{S3b}$ is —$OR^{SO}$, wherein $R^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S3a}$ and $R^{S3b}$ is —OH. In certain embodiments, at least one instance of $R^{S3a}$ and $R^{S3b}$ is —$OR^{SO}$, wherein $R^{SO}$ is optionally substituted alkyl. In certain embodiments, at least one instance of $R^{S3a}$ and $R^{S3b}$ is —O-methyl, —O-ethyl, or —O-propyl. In certain embodiments, at least one instance of $R^{S3a}$ and $R^{S3b}$ is optionally substituted —O-alkyl-aryl. In certain embodiments, at least one instance of $R^{S3a}$ and $R^{S3b}$ —O-Bz. In certain embodiments, at least one instance of $R^{S3a}$ and $R^{S3b}$ is —O-alkyl-heteroaryl. In certain embodiments, at least one instance of $R^{S3a}$ and $R^{S3b}$ is optionally substituted —O-alkenyl-aryl. In certain embodiments, at least one instance of $R^{S3a}$ and $R^{S3b}$ is optionally substituted —O-alkenyl-heteroaryl. In certain embodiments, at least one instance of $R^{S3a}$ and $R^{S3b}$ is —$OR^{SO}$, wherein $R^{SO}$ is

wherein Aryl is an optionally substituted aryl group. In certain embodiments, at least one instance of $R^{S3a}$ and $R^{S3b}$ is —$OR^{SO}$, wherein $R^{SO}$ is

wherein Heteroaryl is an optionally substituted heteroaryl group. In certain embodiments, at least one instance of $R^{S3a}$ and $R^{S3b}$ is —$OR^{SO}$, wherein $R^{SO}$ is In certain embodiments, at least one instance of $R^{S2a}$ and $R^{S2b}$ is —$OR^{SO}$, wherein $R^{SO}$ is an oxygen protecting group. In certain embodiments, at least one instance of $R^{S2a}$ and $R^{S2b}$ is —$OR^{SO}$, wherein $R^{SO}$ is carbonyl. In certain embodiments, at least one instance of $R^{S2a}$ and $R^{S2b}$ is —$OR^{SO}$, wherein $R^{SO}$ is acetyl. In certain embodiments, at least one instance of $R^{S2a}$ and $R^{S2b}$ is —$OR^{SO}$, wherein $R^{SO}$ is optionally substituted heterocyclyl.

In certain embodiments, at least one instance of $R^{S2a}$ and $R^{S2b}$ is —$N(R^{SN})_2$. In some embodiments, at least one instance of $R^{S2a}$ and $R^{S2b}$ is —$N(R^{SN})_2$, wherein each $R^{SN}$ is the same. In some embodiments, at least one instance of $R^{S2a}$ and $R^{S2b}$ is —$N(R^{SN})_2$, wherein each $R^{SN}$ is different.

In certain embodiments, at least one instance of $R^{S2a}$ and $R^{S2b}$ is —$NH_2$.

In certain embodiments, at least one instance of $R^{S2a}$ and $R^{S2b}$ is —$NHR^{SN}$. In certain embodiments, at least one instance of $R^{S2a}$ and $R^{S2b}$ is —$NHR^{SN}$, wherein $R^{SN}$ is optionally substituted $C_{1-6}$ alkyl. In certain embodiments, at least one instance of $R^{S2a}$ and $R^{S2b}$ is —$NHR^{SN}$, wherein $R^{SN}$ is unsubstituted $C_{1-6}$ alkyl. In certain embodiment, at least one instance of $R^{S2a}$ and $R^{S2b}$ is —$NHR^{SN}$, wherein $R^{SN}$ is substituted $C_{1-6}$ alkyl. In certain embodiments, at least one instance of $R^{S2a}$ and $R^{S2b}$ is —NH-benzyl.

In certain embodiment, at least one instance of $R^{S2a}$ and $R^{S2b}$ is —$NHR^{SN}$, wherein $R^{SN}$ is a nitrogen protecting group. In certain embodiment, at least one instance of $R^{S2a}$ and $R^{S2b}$ is —NHFmoc. In certain embodiment, at least one instance of $R^{S2a}$ and $R^{S2b}$ is —NHBoc.

In certain embodiments, at least one instance of $R^{S2a}$ and $R^{S2b}$ is —$N(R^{SN})_2$, wherein each $R^{SN}$ is independently optionally substituted $C_{1-6}$ alkyl. In certain embodiments, at least one instance of $R^{S2a}$ and $R^{S2b}$ is —$N(R^{SN})_2$, wherein each $R^{SN}$ is independently unsubstituted $C_{1-6}$ alkyl. In certain embodiments, at least one instance of $R^{S2a}$ and $R^{S2b}$ is —$N(CH_3)R^{SN}$, wherein each $R^{SN}$ is independently optionally substituted $C_{1-6}$ alkyl. In certain embodiments, at least one instance of $R^{S2a}$ and $R^{S2b}$ is —$N(CH_3)R^{SN}$, wherein each $R^{SN}$ is independently unsubstituted $C_{1-6}$ alkyl. In certain embodiments, at least one instance of $R^{S2a}$ and $R^{S2b}$ is —$N(CH_2CH_3)R^{SN}$, wherein each $R^{SN}$ is independently optionally substituted $C_{1-6}$ alkyl. In certain embodiments, at least one instance of $R^{S2a}$ and $R^{S2b}$ is —$N(CH_2CH_3)R^{SN}$, wherein each $R^{SN}$ is independently unsubstituted $C_{1-6}$ alkyl. In certain embodiments, at least one instance of $R^{S2a}$ and $R^{S2b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S2a}$ and $R^{S2b}$ is —$N(R^{SN})_2$, wherein two $R^{SN}$ groups are taken together with the intervening atoms to form an optionally substituted heterocyclic ring. For example, in certain embodiments, at least one instance of $R^{S2a}$ and $R^{S2b}$ is of the formula:

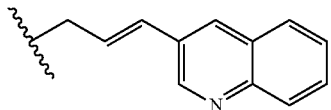

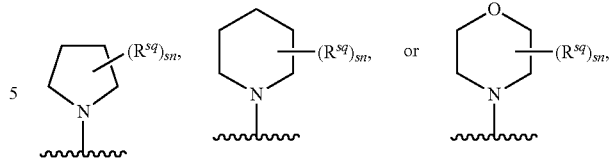

wherein $R^{sq}$ is as defined herein, and sn is 0, 1, 2, or 3.

In certain embodiments, at least one instance of $R^{S3a}$ and $R^{S3b}$ is —$OR^{SO}$, wherein $R^{SO}$ is an oxygen protecting group. In certain embodiments, at least one instance of $R^{S3a}$ and $R^{S3b}$ is —$OR^{SO}$, wherein $R^{SO}$ is carbonyl. In certain embodiments, at least one instance of $R^{S3a}$ and $R^{S3b}$ is —$OR^{SO}$, wherein $R^{SO}$ is acetyl. In certain embodiments, at least one instance of $R^{S3a}$ and $R^{S3b}$ is —$OR^{SO}$, wherein $R^{SO}$ is optionally substituted heterocyclyl.

In certain embodiments, at least one instance of $R^{S3a}$ and $R^{S3b}$ is —$N(R^{SN})_2$. In some embodiments, at least one instance of $R^{S3a}$ and $R^{S3b}$ is —$N(R^{SN})_2$, wherein each $R^{SN}$ is the same. In some embodiments, at least one instance of $R^{S3a}$ and $R^{S3b}$ is —$N(R^{SN})_2$, wherein each $R^{SN}$ is different.

In certain embodiments, at least one instance of $R^{S3a}$ and $R^{S3b}$ is —$NH_2$.

In certain embodiments, at least one instance of $R^{S3a}$ and $R^{S3b}$ is —$NHR^{SN}$. In certain embodiments, at least one instance of $R^{S3a}$ and $R^{S3b}$ is —$NHR^{SN}$, wherein $R^{SN}$ is optionally substituted $C_{1-6}$ alkyl. In certain embodiments, at least one instance of $R^{S3a}$ and $R^{S3b}$ is —$NHR^{SN}$, wherein $R^{SN}$ is unsubstituted $C_{1-6}$ alkyl. In certain embodiment, at least one instance of $R^{S3a}$ and $R^{S3b}$ is —$NHR^{SN}$, wherein $R^{SN}$ is substituted $C_{1-6}$ alkyl. In certain embodiments, at least one instance of $R^{S3a}$ and $R^{S3b}$ is —NH-benzyl.

In certain embodiment, at least one instance of $R^{S3a}$ and $R^{S3b}$ is —$NHR^{SN}$, wherein $R^{SN}$ is a nitrogen protecting group. In certain embodiment, at least one instance of $R^{S3a}$ and $R^{S3b}$ is —NHFmoc. In certain embodiment, at least one instance of $R^{S3a}$ and $R^{S3b}$ is —NHBoc.

In certain embodiments, at least one instance of $R^{S3a}$ and $R^{S3b}$ is —$N(R^{SN})_2$, wherein each $R^{SN}$ is independently optionally substituted $C_{1-6}$ alkyl. In certain embodiments, at least one instance of $R^{S3a}$ and $R^{S3b}$ is —$N(R^{SN})_2$, wherein each $R^{SN}$ is independently unsubstituted $C_{1-6}$ alkyl. In certain embodiments, at least one instance of $R^{S4a}$ and $R^{S4b}$ is —$N(CH_3)R^{SN}$, wherein each $R^{SN}$ is independently optionally substituted $C_{1-6}$ alkyl. In certain embodiments, at least one instance of $R^{S3a}$ and $R^{S3b}$ is —$N(CH_3)R^{SN}$, wherein each $R^{SN}$ is independently unsubstituted $C_{1-6}$ alkyl. In certain embodiments, at least one instance of $R^{S3a}$ and $R^{S3b}$ is —$N(CH_2CH_3)R^{SN}$, wherein each $R^{SN}$ is independently optionally substituted $C_{1-6}$ alkyl. In certain embodiments, at least one instance of $R^{S3a}$ and $R^{S3b}$ is —$N(CH_2CH_3)R^{SN}$, wherein each $R^{SN}$ is independently unsubstituted $C_{1-6}$ alkyl. In certain embodiments, at least one instance of $R^{S3a}$ and $R^{S3b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S3a}$ and $R^{S3b}$ is —$N(R^{SN})_2$, wherein two $R^{SN}$ groups are taken together with the intervening atoms to form an optionally substituted heterocyclic ring. For example, in certain embodiments, at least one instance of $R^{S3a}$ and $R^{S3b}$ is of the formula:

In certain embodiments, $R^{S2a}$ or $R^{S2b}$ is taken together with $R^{S3a}$ or $R^{S3b}$ to form an optionally substituted fused heterocyclic ring. In certain embodiments, $R^{S2a}$ is taken together with $R^{S3a}$ to form an optionally substituted fused heterocyclic ring. In certain embodiments, $R^{S2b}$ is taken together with $R^{S3b}$ to form an optionally substituted fused heterocyclic ring. In certain embodiments, $R^{S2a}$ is taken together with $R^{S3b}$ to form an optionally substituted fused heterocyclic ring. In certain embodiments, $R^{S2b}$ is taken together with $R^{S3a}$ to form an optionally substituted fused heterocyclic ring.

In certain embodiments, $R^{S2a}$ or $R^{S2b}$ is taken together with $R^{S3a}$ or $R^{S3b}$ to form an optionally substituted fused pyrrolidine. In certain embodiments, $R^{S2a}$ or $R^{S2b}$ is taken together with $R^{S3a}$ or $R^{S3b}$ to form an optionally substituted fused piperidine. In certain embodiments, $R^{S2a}$ or $R^{S2b}$ is taken together with $R^{S3a}$ or $R^{S3b}$ to form an optionally substituted fused piperidinone. In certain embodiments, $R^{S2a}$ or $R^{S2b}$ is taken together with $R^{S3a}$ or $R^{S3b}$ to form an optionally substituted fused piperazine. In certain embodiments, $R^{S2a}$ or $R^{S2b}$ is taken together with $R^{S3a}$ or $R^{S3b}$ to form an optionally substituted fused piperazinone. In certain embodiments, $R^{S2a}$ or $R^{S2b}$ is taken together with $R^{S3a}$ or $R^{S3b}$ to form an optionally substituted fused morpholine. In certain embodiments, $R^{S2a}$ or $R^{S2b}$ is taken together with $R^{S3a}$ or $R^{S3b}$ to form an optionally substituted fused morpholinone.

In certain embodiments, $R^{S2a}$ or $R^{S2b}$ is taken together with $R^{S3a}$ or $R^{S3b}$ to form an optionally substituted fused pyrrolidine; and $R^{SN}$ is methyl. In certain embodiments, $R^{S2a}$ or $R^{S2b}$ is taken together with $R^{S3a}$ or $R^{S3b}$ to form an optionally substituted fused piperidine; and $R^{SN}$ is methyl. In certain embodiments, $R^{S2a}$ or $R^{S2b}$ is taken together with $R^{S3a}$ or $R^{S3b}$ to form an optionally substituted fused piperidinone; and $R^{SN}$ is methyl. In certain embodiments, $R^{S2a}$ or $R^{S2b}$ is taken together with $R^{S3a}$ or $R^{S3b}$ to form an optionally substituted fused piperazine; and $R^{SN}$ is methyl. In certain embodiments, $R^{S2a}$ or $R^{S2b}$ is taken together with $R^{S3a}$ or $R^{S3b}$ to form an optionally substituted fused piperazinone; and $R^{SN}$ is methyl. In certain embodiments, $R^{S2a}$ or $R^{S2b}$ is taken together with $R^{S3a}$ or $R^{S3b}$ to form an optionally substituted fused morpholine; and $R^{SN}$ is methyl. In certain embodiments, $R^{S2a}$ or $R^{S2b}$ is taken together with $R^{S3a}$ or $R^{S3b}$ to form an optionally substituted fused morpholinone; and $R^{SN}$ is methyl.

In certain embodiments, $R^{S2a}$ is taken together with $R^{S3a}$ to form

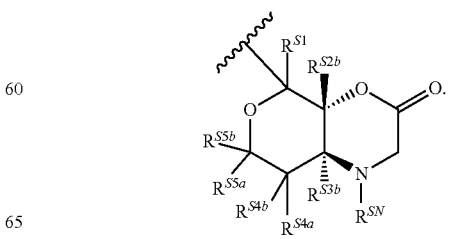

In certain embodiments, $R^{S2a}$ is taken together with $R^{S3a}$ to form

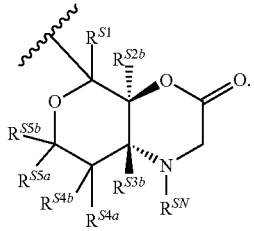

In certain embodiments, $R^{S2a}$ is taken together with $R^{S3a}$ to form

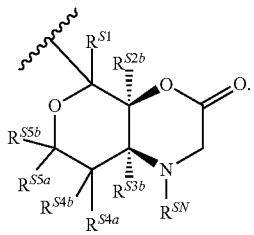

In certain embodiments, $R^{S2a}$ is taken together with $R^{S3a}$ to form

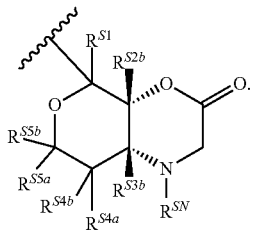

In certain embodiments, $R^{S2a}$ is taken together with $R^{S3a}$ to form

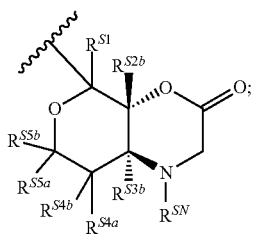

and $R^{SN}$ is methyl.

In certain embodiments, $R^{S2a}$ is taken together with $R^{S3a}$ to form

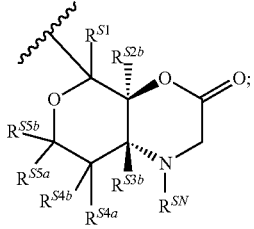

and $R^{SN}$ is methyl.

In certain embodiments, $R^{S2a}$ is taken together with $R^{S3a}$ to form

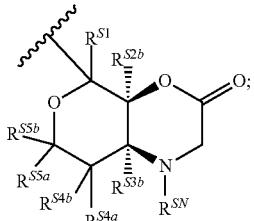

and $R^{SN}$ is methyl.

In certain embodiments, $R^{S2a}$ is taken together with $R^{S3a}$ to form

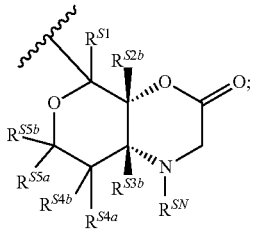

and $R^{SN}$ is methyl.

As generally defined above, each instance of $R^{S4a}$ and $R^{S4b}$ is independently hydrogen, optionally substituted alkyl, —$OR^{SO}$, or —$N(R^{SN})_2$.

In certain embodiments, at least one instance of $R^{S4a}$ and $R^{S4b}$ is hydrogen.

In certain embodiments, at least one instance of $R^{S4a}$ and $R^{S4b}$ is optionally substituted alkyl. In certain embodiments, at least one instance of $R^{S4a}$ and $R^{S4b}$ is substituted $C_{1-6}$ alkyl. In certain embodiments, at least one instance of $R^{S4a}$ and $R^{S4b}$ is unsubstituted $C_{1-6}$ alkyl. In certain embodiments, at least one instance of $R^{S4a}$ and $R^{S4b}$ is methyl, ethyl, propyl, butyl, pentyl, or hexyl. In certain embodiments, at least one instance of $R^{S4a}$ and $R^{S4b}$ is isopropyl, isobutyl, or isoamyl. In certain embodiments, at least one instance of $R^{S4a}$ and $R^{S4b}$ is isobutyl. In certain embodiments, at least one instance of $R^{S4a}$ and $R^{S4b}$ is tert-butyl.

In certain embodiments, at least one instance of $R^{S4a}$ and $R^{S4b}$ is —$OR^{SO}$, wherein $R^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S4a}$ and $R^{S4b}$ is —OH. In certain embodiments, at least one instance of $R^{S4a}$ and $R^{S4b}$ is —$OR^{SO}$, wherein $R^{SO}$ is optionally substituted alkyl. In certain embodiments, at least one instance of $R^{S4a}$ and $R^{S4b}$ is —O-methyl, —O-ethyl, or —O-propyl. In certain embodiments, at least one instance of $R^{S4a}$ and $R^{S4b}$ is optionally substituted —O-alkyl-aryl. In certain embodiments, at least one instance of $R^{S4a}$ and $R^{S4b}$ is —O-Bz. In certain embodiments, at least one instance of $R^{S4a}$ and $R^{S4b}$ is —$OR^{SO}$ wherein $R^{SO}$ is

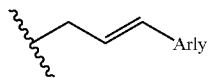

wherein Aryl is an optionally substituted aryl group. In certain embodiments, at least one instance of $R^{S4a}$ and $R^{S4b}$ is —$OR^{SO}$, wherein $R^{SO}$ is

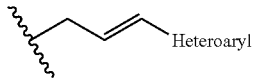

wherein Heteroaryl is an optionally substituted heteroaryl group. In certain embodiments, at least one instance of $R^{S4a}$ and $R^{S4b}$ is —$OR^{SO}$, wherein $R^{SO}$ is

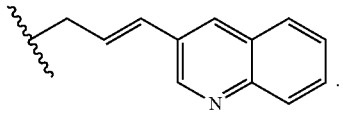 [SMILES: *C/C=C/c1cnc2ccccc2c1]

In certain embodiments, at least one instance of $R^{S4a}$ and $R^{S4b}$ is —$OR^{SO}$, wherein $R^{SO}$ is an oxygen protecting group. In certain embodiments, at least one instance of $R^{S4a}$ and $R^{S4b}$ is —$OR^{SO}$, wherein $R^{SO}$ is carbonyl. In certain embodiments, at least one instance of $R^{S4a}$ and $R^{S4b}$ is —$OR^{SO}$, wherein $R^{SO}$ is acetyl. In certain embodiments, at least one instance of $R^{S4a}$ and $R^{S4b}$ is —$OR^{SO}$, wherein $R^{SO}$ is optionally substituted heterocyclyl.

In certain embodiments, at least one instance of $R^{S4a}$ and $R^{S4b}$ is —$N(R^{SN})_2$. In some embodiments, at least one instance of $R^{S4a}$ and $R^{S4b}$ is —$N(R^{SN})_2$, wherein each $R^{SN}$ is the same. In some embodiments, at least one instance of $R^{S4a}$ and $R^{S4b}$ is —$N(R^{SN})_2$, wherein each $R^{SN}$ is different.

In certain embodiments, at least one instance of $R^{S4a}$ and $R^{S4b}$ is —$NH_2$.

In certain embodiments, at least one instance of $R^{S4a}$ and $R^{S4b}$ is —$NHR^{SN}$. In certain embodiments, at least one instance of $R^{S4a}$ and $R^{S4b}$ is —$NHR^{SN}$, wherein $R^{SN}$ is optionally substituted $C_{1-6}$ alkyl. In certain embodiments, at least one instance of $R^{S4a}$ and $R^{S4b}$ is —$NHR^{SN}$, wherein $R^{SN}$ is unsubstituted $C_{1-6}$ alkyl. In certain embodiment, at least one instance of $R^{S4a}$ and $R^{S4b}$ is —$NHR^{SN}$, wherein $R^{SN}$ is substituted $C_{1-6}$ alkyl. In certain embodiments, at least one instance of $R^{S4a}$ and $R^{S4b}$ is —NH-benzyl.

In certain embodiment, at least one instance of $R^{S4a}$ and $R^{S4b}$ is —$NHR^{SN}$, wherein $R^{SN}$ is a nitrogen protecting group. In certain embodiment, at least one instance of $R^{S4a}$ and $R^{S4b}$ is —NHFmoc. In certain embodiment, at least one instance of $R^{S4a}$ and $R^{S4b}$ is —NHBoc.

In certain embodiments, at least one instance of $R^{S4a}$ and $R^{S4b}$ is —$N(R^{SN})_2$, wherein each $R^{SN}$ is independently optionally substituted $C_{1-6}$ alkyl. In certain embodiments, at least one instance of $R^{S4a}$ and $R^{S4b}$ is —$N(R^{SN})_2$, wherein each $R^{SN}$ is independently unsubstituted $C_{1-6}$ alkyl. In certain embodiments, at least one instance of $R^{S4a}$ and $R^{S4b}$ is —$N(CH_3)R^{SN}$, wherein each $R^{SN}$ is independently optionally substituted $C_{1-6}$ alkyl. In certain embodiments, at least one instance of $R^{S4a}$ and $R^{S4b}$ is —$N(CH_3)R^{SN}$, wherein each $R^{SN}$ is independently unsubstituted $C_{1-6}$ alkyl. In certain embodiments, at least one instance of $R^{S4a}$ and $R^{S4b}$ is —$N(CH_2CH_3)R^{SN}$, wherein each $R^{SN}$ is independently optionally substituted $C_{1-6}$ alkyl. In certain embodiments, at least one instance of $R^{S4a}$ and $R^{S4b}$ is —$N(CH_2CH_3)R^{SN}$, wherein each $R^{SN}$ is independently unsubstituted $C_{1-6}$ alkyl. In certain embodiments, at least one instance of $R^{S4a}$ and $R^{S4b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S4a}$ and $R^{S4b}$ is —$N(R^{SN})_2$, wherein two $R^{SN}$ groups are taken together with the intervening atoms to form an optionally substituted heterocyclic ring. For example, in certain embodiments, at least one instance of $R^{S4a}$ and $R^{S4b}$ is of the formula:

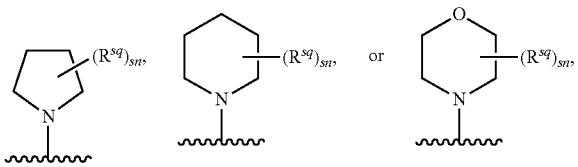

wherein $R^{sq}$ is as defined herein, and sn is 0, 1, 2, or 3.

As generally defined above, each instance of $R^{S5a}$ and $R^{S5b}$ is independently hydrogen, optionally substituted alkyl, —$OR^{SO}$, or —$N(R^{SN})_2$.

In certain embodiments, at least one instance of $R^{S5a}$ and $R^{S5b}$ is hydrogen.

In certain embodiments, at least one instance of $R^{S5a}$ and $R^{S5b}$ is optionally substituted alkyl. In certain embodiments, at least one instance of $R^{S5a}$ and $R^{S5b}$ is substituted $C_{1-6}$ alkyl. In certain embodiments, at least one instance of $R^{S5a}$ and $R^{S5b}$ is unsubstituted $C_{1-6}$ alkyl. In certain embodiments, at least one instance of $R^{S5a}$ and $R^{S5b}$ is methyl, ethyl, propyl, butyl, pentyl, or hexyl. In certain embodiments, at least one instance of $R^{S5a}$ and $R^{S5b}$ is isopropyl, isobutyl, or isoamyl. In certain embodiments, at least one instance of $R^{S5a}$ and $R^{S5b}$ is isobutyl. In certain embodiments, at least one instance of $R^{S5a}$ and $R^{S5b}$ is tert-butyl. In certain embodiments, at least one instance of $R^{S5a}$ and $R^{S5b}$ is alkoxyalkyl, e.g. —$CH_2OMe$, —$CH_2OEt$, or —$CH_2OBn$. In certain embodiments, at least one instance of $R^{S5a}$ and $R^{S5b}$ is —$CH_2OH$. In certain embodiments, at least one instance of $R^{S5a}$ and $R^{S5b}$ is —$CH_2OBz$. In certain embodiments, at least one instance of $R^{S5a}$ and $R^{S5b}$ is —$CH_2OPG$, wherein PG is an oxygen protecting group. In certain embodiments, at least one instance of $R^{S5a}$ and $R^{S5b}$ is aminoalkyl, e.g. —$CH_2NHMe$, —$CH_2NMe_2$, or —$CH_2NHBn$. In certain embodiments, at least one instance of $R^{S5a}$ and $R^{S5b}$ is —$CH_2NH_2$. In certain embodiments, at least one instance of $R^{S5a}$ and $R^{S5b}$ is —$CH_2NHPG$, wherein PG is an nitrogen protecting group.

In certain embodiments, at least one instance of $R^{S5a}$ and $R^{S5b}$ is —$OR^{SO}$, wherein $R^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S5a}$ and $R^{S5b}$ is —OH. In certain embodiments, at least one instance of $R^{S5a}$ and $R^{S5b}$ is —$OR^{SO}$, wherein $R^{SO}$ is optionally substituted alkyl. In certain embodiments, at least one instance of $R^{S5a}$ and $R^{S5b}$ is —O-methyl, —O-ethyl, or —O-propyl. In certain embodiments, at least one instance of $R^{S5a}$ and $R^{S5b}$ is optionally substituted —O-alkyl-aryl. In certain embodiments, at least one instance of $R^{S5a}$ and $R^{S5b}$ is —O-Bz. In certain embodiments, at least one instance of $R^{S5a}$ and $R^{S5b}$ is —$OR^{SO}$ wherein $R^{SO}$ is

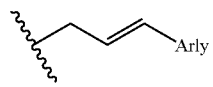

wherein Aryl is an optionally substituted aryl group. In certain embodiments, at least one instance of $R^{S5a}$ and $R^{S5b}$ is —$OR^{SO}$, wherein $R^{SO}$ is

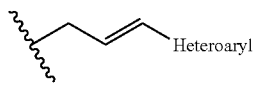

wherein Heteroaryl is an optionally substituted heteroaryl group. In certain embodiments, at least one instance of $R^{S5a}$ and $R^{S5b}$ is —$OR^{SO}$, wherein $R^{SO}$ is

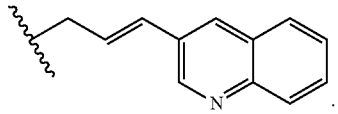 [SMILES: *C/C=C/c1cnc2ccccc2c1]

In certain embodiments, at least one instance of $R^{S5a}$ and $R^{S5b}$ is —$OR^{SO}$, wherein $R^{SO}$ is an oxygen protecting group. In certain embodiments, at least one instance of $R^{S5a}$ and $R^{S5b}$ is —$OR^{SO}$, wherein $R^{SO}$ is carbonyl. In certain embodiments, at least one instance of $R^{S5a}$ and $R^{S5b}$ is —$OR^{SO}$, wherein $R^{SO}$ is acetyl. In certain embodiments, at least one instance of $R^{S5a}$ and $R^{S5b}$ is —$OR^{SO}$, wherein $R^{SO}$ is optionally substituted heterocyclyl.

In certain embodiments, at least one instance of $R^{S5a}$ and $R^{S5b}$ is —$N(R^{SN})_2$. In some embodiments, at least one instance of $R^{S5a}$ and $R^{S5b}$ is —$N(R^{SN})_2$, wherein each $R^{SN}$ is the same. In some embodiments, at least one instance of $R^{S5a}$ and $R^{S5b}$ is —$N(R^{SN})_2$, wherein each $R^{SN}$ is different.

In certain embodiments, at least one instance of $R^{S5a}$ and $R^{S5b}$ is —$NH_2$.

In certain embodiments, at least one instance of $R^{S5a}$ and $R^{S5b}$ is —$NHR^{SN}$. In certain embodiments, at least one instance of $R^{S5a}$ and $R^{S5b}$ is —$NHR^{SN}$, wherein $R^{SN}$ is optionally substituted $C_{1-6}$ alkyl. In certain embodiments, at least one instance of $R^{S5a}$ and $R^{S5b}$ is —$NHR^{SN}$, wherein $R^{SN}$ is unsubstituted $C_{1-6}$ alkyl. In certain embodiment, at least one instance $R^{S5a}$ and $R^{S5b}$ is —$NHR^{SN}$, wherein $R^{SN}$ is substituted $C_{1-6}$ alkyl. In certain embodiments, at least one instance of $R^{S5a}$ and $R^{S5b}$ is —NH-benzyl.

In certain embodiment, at least one instance of $R^{S5a}$ and $R^{S5b}$ is —$NHR^{SN}$, wherein $R^{SN}$ is a nitrogen protecting group. In certain embodiment, at least one instance of $R^{S4a}$ and $R^{S4b}$ is —NHFmoc. In certain embodiment, at least one instance of $R^{S5a}$ and $R^{S5b}$ is —NHBoc.

In certain embodiments, at least one instance of $R^{S5a}$ and $R^{S5b}$ is —$N(R^{SN})_2$, wherein each $R^{SN}$ is independently optionally substituted $C_{1-6}$ alkyl. In certain embodiments, at least one instance of $R^{S5a}$ and $R^{S5b}$ is —$N(R^{SN})_2$, wherein each $R^{SN}$ is independently unsubstituted $C_{1-6}$ alkyl. In certain embodiments, at least one instance of $R^{S5a}$ and $R^{S5b}$ is —$N(CH_3)R^{SN}$, wherein each $R^{SN}$ is independently optionally substituted $C_{1-6}$ alkyl. In certain embodiments, at least one instance of $R^{S5a}$ and $R^{S5b}$ is —$N(CH_3)R^{SN}$, wherein each $R^{SN}$ is independently unsubstituted $C_{1-6}$ alkyl. In certain embodiments, at least one instance of $R^{S5a}$ and $R^{S5b}$ is —$N(CH_2CH_3)R^{SN}$, wherein each $R^{SN}$ is independently optionally substituted $C_{1-6}$ alkyl. In certain embodiments, at least one instance of $R^{S5a}$ and $R^{S5b}$ is —$N(CH_2CH_3)R^{SN}$, wherein each $R^{SN}$ is independently unsubstituted $C_{1-6}$ alkyl. In certain embodiments, at least one instance of $R^{S5a}$ and $R^{S5b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S5a}$ and $R^{S5b}$ is —$N(R^{SN})_2$, wherein two $R^{SN}$ groups are taken together with the intervening atoms to form an optionally substituted heterocyclic ring. For example, in certain embodiments, at least one instance of $R^{S5a}$ and $R^{S5b}$ is of the formula:

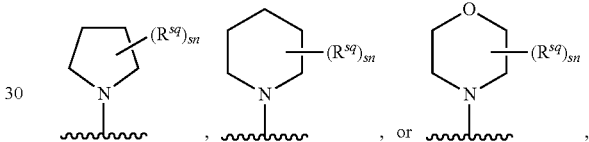

wherein $R^{sq}$ is as defined herein, and sn is 0, 1, 2, or 3.

As used herein, each instance $R^{sq}$ is independently halogen, optionally substituted alkyl, —$OR^{SO1}$, or —$N(R^{SN1})_2$, wherein $R^{SO1}$ is independently hydrogen, optionally substituted alkyl, or an oxygen protecting group; and $R^{SN1}$ is independently hydrogen, optionally substituted alkyl, or a nitrogen protecting group; or optionally two $R^{SN1}$ are taken together with the intervening atoms to form an optionally substituted heterocyclic ring.

As generally defined herein, each instance of $R^{SO}$ is independently hydrogen, optionally substituted alkyl, carbonyl, optionally substituted heterocyclyl, or an oxygen protecting group.

In certain embodiments, $R^{SO}$ is hydrogen. In certain embodiments, $R^{SO}$ is optionally substituted alkyl. In certain embodiments, $R^{SO}$ is optionally substituted $C_{1-6}$ alkyl. In certain embodiments, $R^{SO}$ is methyl, ethyl, or propyl. In certain embodiments, $R^{SO}$ is optionally substituted aralkyl, e.g., optionally substituted benzyl (Bn). In certain embodiments, $R^{SO}$ is optionally substituted heterocyclyl. In certain embodiments, $R^{SO}$ is carbonyl. In certain embodiments, $R^{SO}$ is —$C(=O)CH_3$ (acetyl, Ac). In certain embodiments, $R^{SO}$ is —$C(=O)Ph$ (benzoyl, Bz). In certain embodiments, $R^{SO}$ is

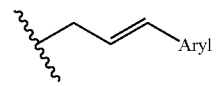

wherein Aryl is an optionally substituted aryl group. In certain embodiments, $R^{SO}$ is

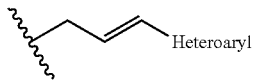

wherein Heteroaryl is an optionally substituted heteroaryl group. In certain embodiments, $R^{SO}$ is

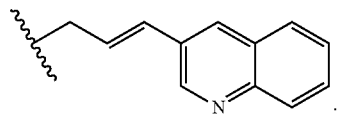 [SMILES: *C/C=C/c1cnc2ccccc2c1]

In certain embodiments, $R^{SO}$ is an oxygen protecting group.

As generally defined herein, each instance of $R^{SN}$ is independently hydrogen, optionally substituted alkyl, optionally substituted heterocyclyl, or a nitrogen protecting group; or optionally two $R^{SN}$ are taken together with the intervening atoms to form an optionally substituted heterocyclic ring. In certain embodiments, $R^{SN}$ is hydrogen. In certain embodiments, $R^{SN}$ is optionally substituted alkyl. In certain embodiments, $R^{SN}$ is optionally substituted $C_{1-6}$ alkyl. In certain embodiments, $R^{SN}$ is methyl, ethyl, or propyl. In certain embodiments, $R^{SN}$ is substituted aralkyl, e.g., optionally substituted benzyl (Bn). In certain embodiments, $R^{SN}$ is optionally substituted heterocyclyl. In certain embodiments, $R^{SN}$ is carbonyl. In certain embodiments, $R^{SN}$ is carbonyl. In certain embodiments, $R^{SN}$ is -C(=O)CH_3 (acetyl, Ac). In certain embodiments, $R^{SN}$ is —C(=O)Ph (benzoyl, Bz). In certain embodiments, $R^{SN}$ is a nitrogen protecting group.

In certain embodiments, $R^9$ and/or $R^{17}$ is of Formula (s-2):

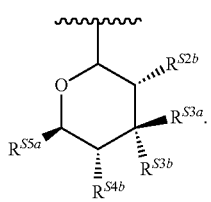

(s-2)

In certain embodiments, $R^9$ and/or $R^{17}$ is of Formula (s-2a):

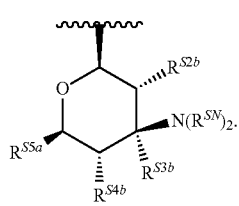

(s-2a)

In certain embodiments, $R^9$ and/or $R^{17}$ is of one of the following formulae:

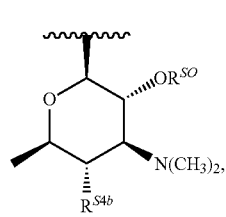

(s-2a-i)

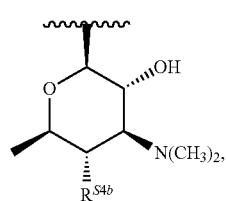

(s-2a-i-1)

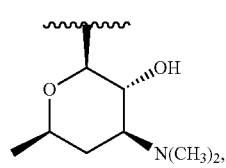

(s-2a-i-2)

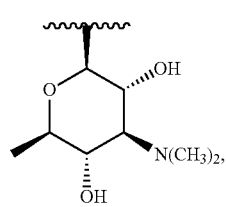

(s-2a-i-3)

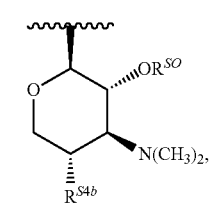

(s-2a-ii)

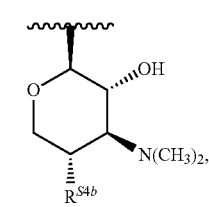

(s-2a-ii-1)

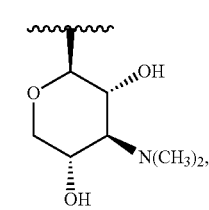

(s-2a-ii-2)

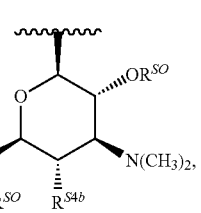

(s-2a-iii)

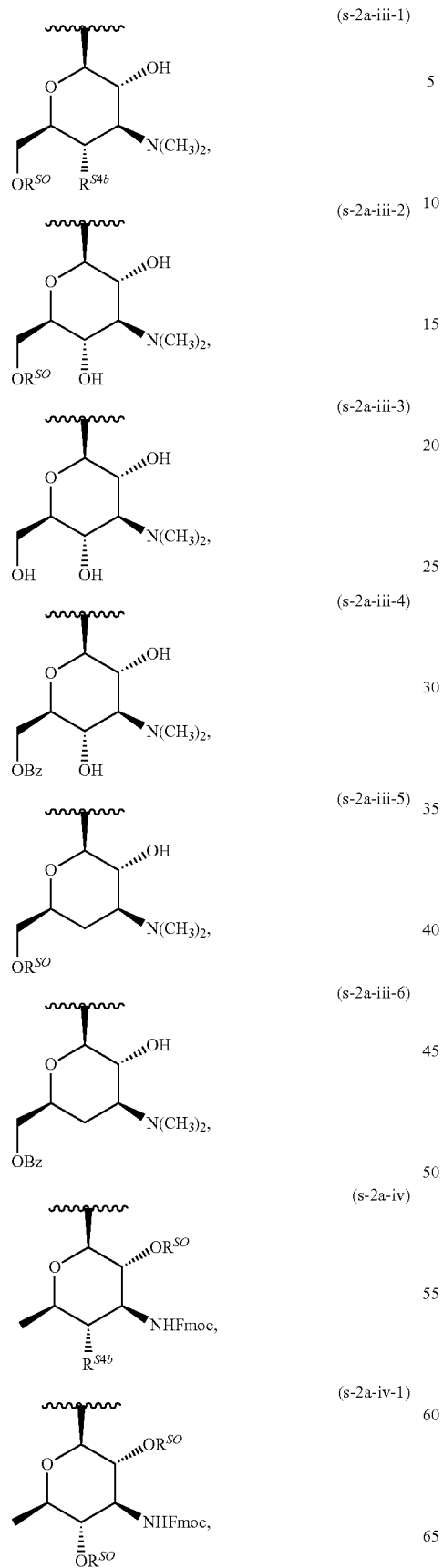
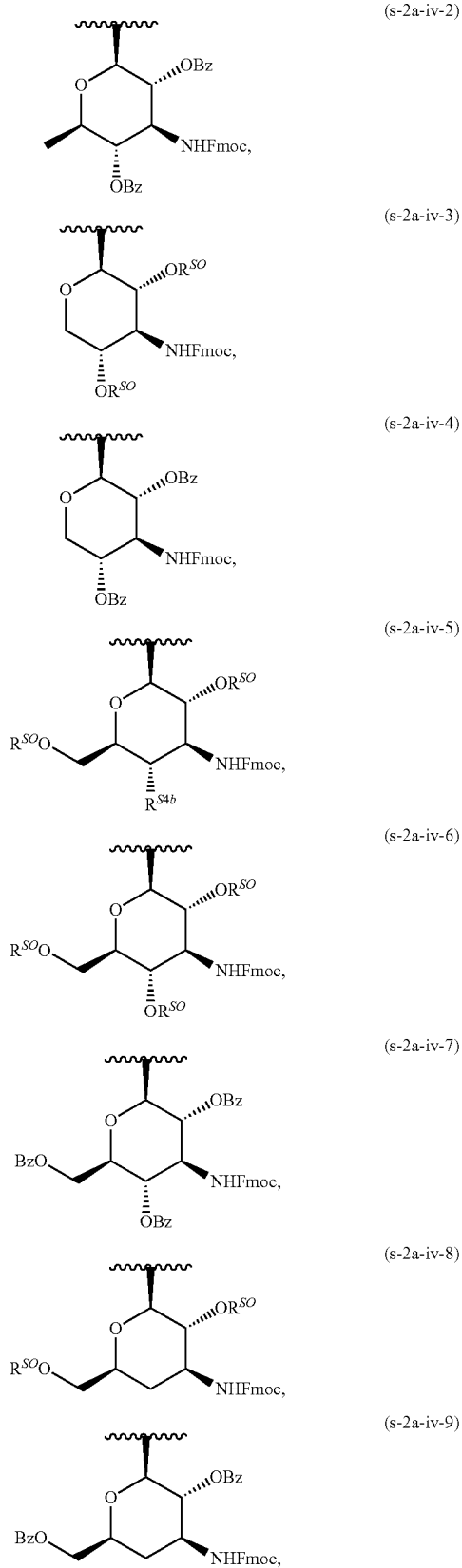

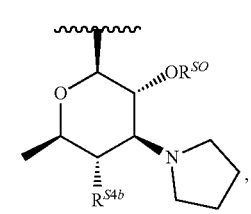 (s-2a-v)
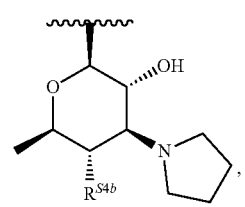 (s-2a-v-1)
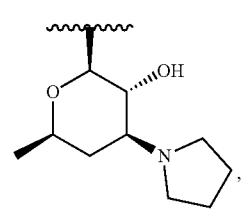 (s-2a-v-2)
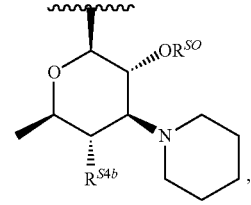 (s-2a-vi)
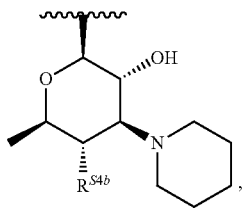 (s-2a-vi-1)
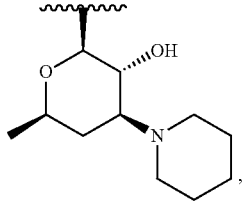 (s-2a-vi-2)
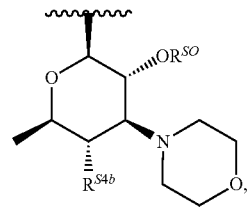 (s-2a-vii)
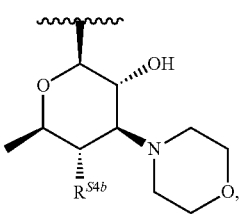 (s-2a-vii-1)
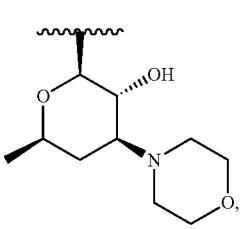 (s-2a-vii-2)
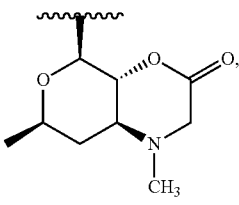 (s-2a-vii-3)
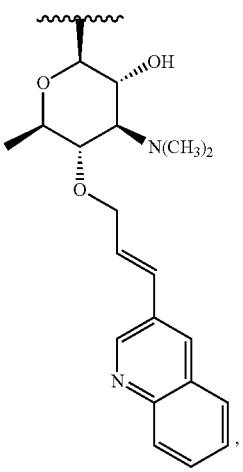 (s-2a-vii-4)
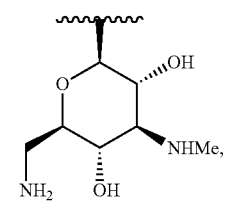 (s-2a-vii-5)
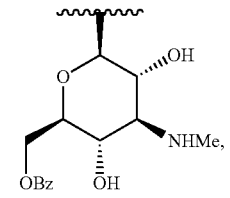 (s-2a-vii-5)

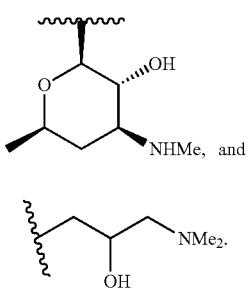
(s-2a-vii-5)
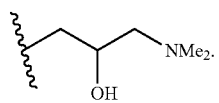
(s-2a-vii-5)
In certain embodiments, $R^9$ and/or $R^{17}$ is of Formula (s-2b):
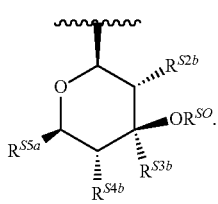
(s-2b)
In certain embodiments, R and/or R is of one of the following formulae:
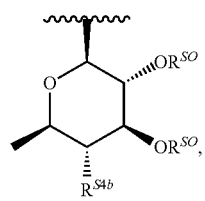
(s-2b-i)
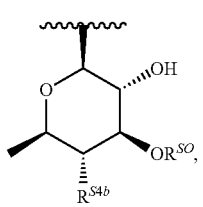
(s-2b-i-1)
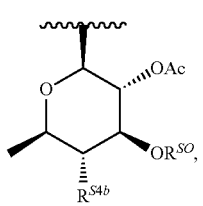
(s-2b-i-2)
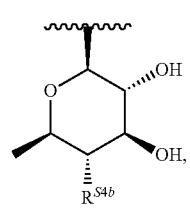
(s-2b-i-3)
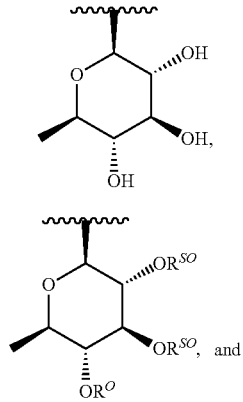
(s-2b-i-4)
(s-2b-i-5)
(s-2b-i-5)
In certain embodiments, $R^9$ and/or $R^{17}$ is of Formula (s-3):
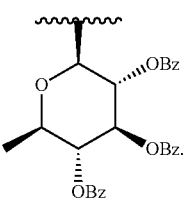
(s-3)
In certain embodiments, $R^9$ and/or $R^{17}$ is of Formula (s-3a):
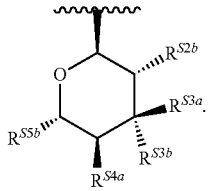
(s-3a)
In certain embodiments, $R^9$ and/or $R^{17}$ is one of the following formulae:
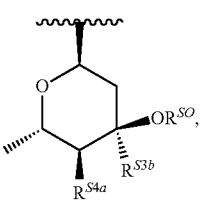
(s-3a-i)

-continued
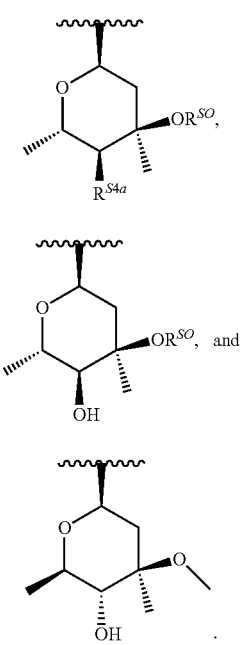
(s-3a-i-1)
(s-3a-i-2)
(s-3a-i-3)
In certain embodiments, R is an optionally substituted heterocycyl.
For example, in certain embodiments, $R^{SO}$ is of the formula:
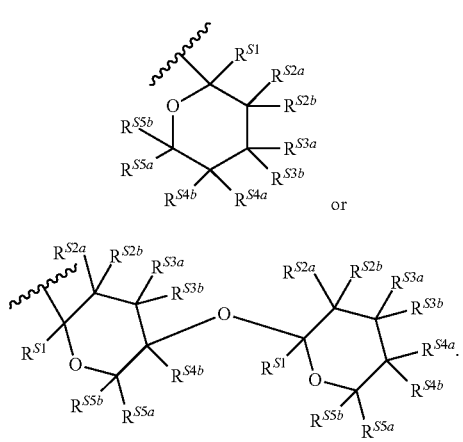
(s-4)
(s-5)
In certain embodiments, $R^{SO}$ is of the formula:
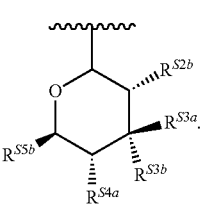
In certain embodiments, $R^{SO}$ is of the formula:
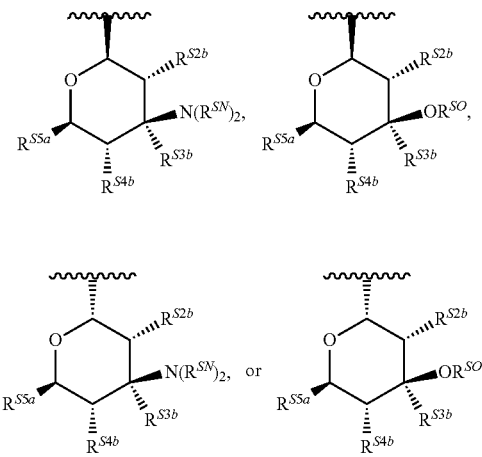
In certain embodiments, $R^{SO}$ is of the formula:
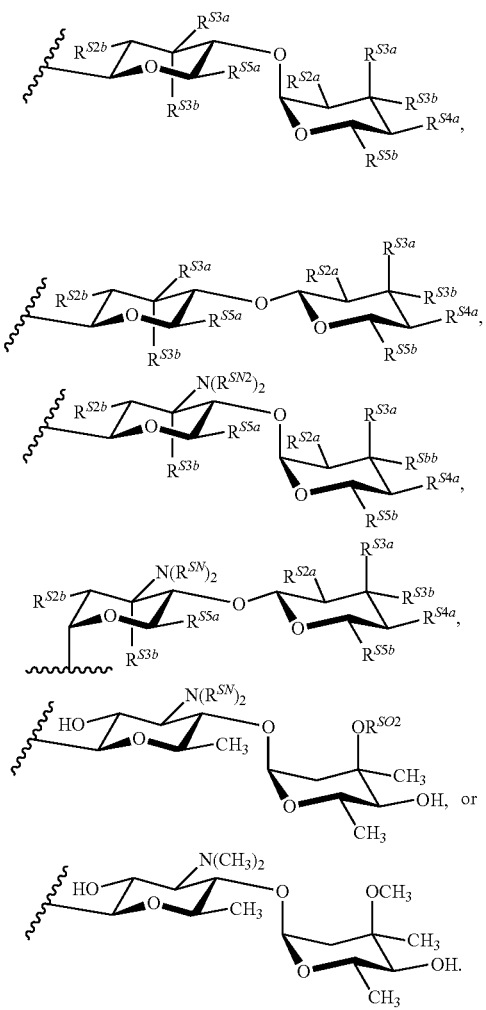

In certain embodiments, $R^9$ and/or $R^{17}$ is of the formula:

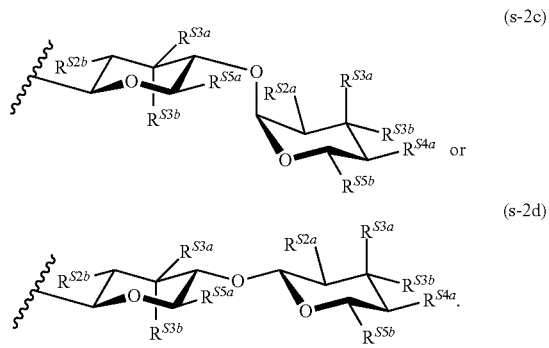

(s-2c)

(s-2d)

In certain embodiments, $R^9$ and/or $R^{17}$ is one of the following formulae:

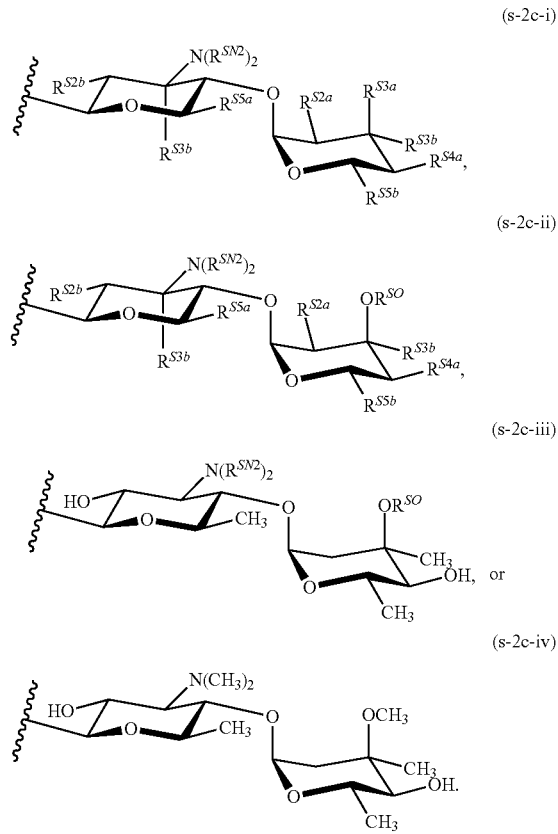

(s-2c-i)

(s-2c-ii)

(s-2c-iii)

(s-2c-iv)

Groups $A^1$, $A^2$, and A

As is generally understood from the above disclosure, in certain embodiments, $R^{12}$, $R^{14}$, and/or $R^3$ is a group of Formula ($L^{C1}$-i), wherein LG is a leaving group as defined herein. In certain embodiments, nucleophilic displacement of the leaving group provides a group of Formula ($L^{C1}$-ii). See Scheme A1. It is generally understood that $A^1$ is a group which is reactive with $A^2$ of a compound of Formula $A^2$-$L^{C2}$-$R^{23}$, and reaction between the two halves provides a group of Formula ($L^{C1}$-iii). See, Scheme A1. These reactions, from ($L^{C1}$-i) to ($L^{C1}$-ii), and ($L^{C1}$-ii) to ($L^{C1}$-iii), are envisioned to take place at any stage of the synthesis, for example, during construction of the eastern or western halves, after coupling of the eastern or western halves, or after the macrocyclization step.

Scheme A1.

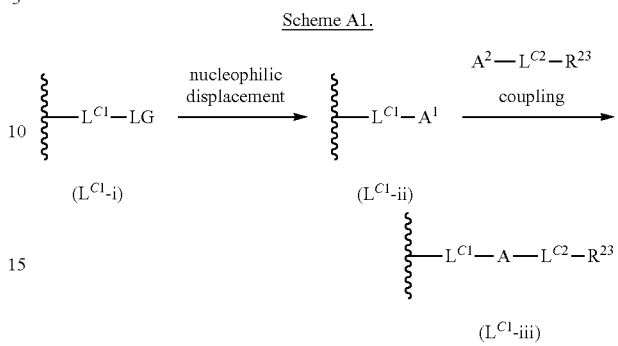

In certain embodiments, the coupling reaction from ($L^{C1}$-ii) to ($L^{C1}$-iii) comprises a reaction typically referred to as "click chemistry." Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition).

In general, for the group ($L^{C1}$-ii), $A^1$ should be complimentary and reactive with the group $A^2$ in order to form the group ($L^{C1}$-iii). For example, if the group $A^2$ of $A^2$-$L^{C2}$-$R^{23}$ is a nucleophilic group, the group $A^1$ must be a electrophilic group. Likewise, if the group $A^2$ of $A^2$-$L^{C2}$-$R^{23}$ is an electrophilic group, the group $A^1$ must be a nucleophilic group. While $A^1$ and $A^2$ are defined the same in the present invention, it is thus understood that such groups are paired complements.

As generally defined herein, $A^1$ and $A^2$ may be selected from the group consisting of a leaving group (LG), —SH, —OH, —NH$_2$, —NH—NH$_2$, —N$_3$, —O—NH$_2$, —C(=O)$R^{X1}$,

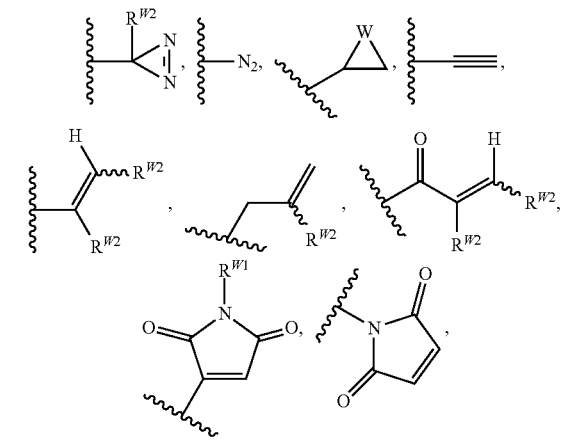

wherein:

$R^{X1}$ is hydrogen, a leaving group, or —$OR^{X2}$, wherein $R^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; an oxygen protecting group;

Leaving group (LG) is —Br, —I, —Cl, —O(C=O)$R^{LG}$, or —O(SO)$_2R^{LG}$, wherein $R^{LG}$ is optionally substituted alkyl, optionally substituted aryl, or optionally substituted heteroaryl;

W is O, S, or $NR^{W1}$;

$R^{W1}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl; or a nitrogen protecting group; and $R^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two $R^{W2}$ groups are joined to form a optionally substituted cyclic moiety.

In certain embodiments, $A^2$ is —SH. In certain embodiments, $A^1$ is —SH.

In certain embodiments, $A^2$ is —OH. In certain embodiments, $A^1$ is —OH.

In certain embodiments, $A^2$ is —$NH_2$. In certain embodiments, $A^1$ is —$NH_2$.

In certain embodiments, $A^2$ is —NH—$NH_2$. In certain embodiments, $A^1$ is —NH—$NH_2$.

In certain embodiments, $A^2$ is —O—$NH_2$. In certain embodiments, $A^1$ is —O—$NH_2$.

In certain embodiments, $A^2$ is —$N_3$. In certain embodiments, $A^1$ is —$N_3$.

In certain embodiments, $A^2$ is a leaving group, e.g., —Cl, —Br, or —I. In certain embodiments, $A^1$ is a leaving group, e.g., —Cl, —Br, or —I.

In certain embodiments, $A^2$ is —C(=O)$R^{X1}$, wherein $R^{X1}$ is hydrogen, i.e., to provide $A^2$ as an aldehyde —CHO. In certain embodiments, $A^1$ is —C(=O)$R^{X1}$, wherein $R^{X1}$ is hydrogen, i.e., to provide $A^1$ as an aldehyde —CHO.

In certain embodiments, $A^2$ is —C(=O)$R^{X1}$, wherein $R^{X1}$ is a leaving group (LG).

In certain embodiments, $A^1$ is —C(=O)$R^{X1}$, wherein $R^{X1}$ is a leaving group (LG).

In certain embodiments, $A^2$ is —C(=O)$R^{X1}$, wherein $R^{X1}$ is —$OR^{X2}$, and wherein $R^{X2}$ is hydrogen, i.e., to provide $A^2$ as a carboxylic acid —C(=O)OH.

In certain embodiments, $A^1$ is —C(=O)$R^{X1}$, wherein $R^{X1}$ is —$OR^{X2}$, and wherein $R^{X2}$ is hydrogen, i.e., to provide $A^1$ as a carboxylic acid —C(=O)OH.

In certain embodiments, $A^2$ is —C(=O)$R^{X1}$, wherein $R^{X1}$ is —$OR^{X2}$, and wherein $R^{X2}$ is a non-hydrogen group, i.e., to provide $A^2$ as an ester —C(=O)$OR^{X2}$.

In certain embodiments, $A^1$ is —C(=O)$R^{X1}$, wherein $R^{X1}$ is —$OR^X$, and wherein $R^{X2}$ is non-hydrogen group, i.e., to provide $A^1$ as an ester —C(=O)$OR^{X2}$.

In certain embodiments, $A^2$ is an oxiranyl, thiorenyl, or azirdinyl group of formula:

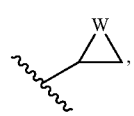

wherein W is O, S, or $NR^{W1}$. In certain embodiments, W is O. In certain embodiments, W is S. In certain embodiments, W is $NR^{W1}$.

In certain embodiments, $A^1$ is an oxiranyl, thiorenyl, or azirdinyl group of formula:

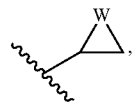

wherein W is O, S, or $NR^{W1}$. In certain embodiments, W is O. In certain embodiments, W is S. In certain embodiments, W is $NR^{W1}$.

In certain embodiments, $A^1$ or $A^2$ is ethynyl:

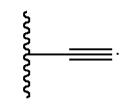

In certain embodiments, $A^1$ or $A^2$ is ethenyl or propenyl:

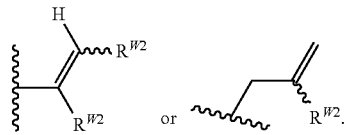

In certain embodiments, $A^1$ or $A^2$ is an α,β-unsaturated carbonyl:

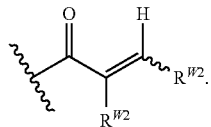

In certain embodiments, $A^1$ or $A^2$ is a maleimide group:

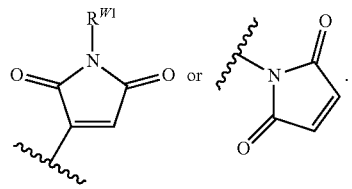

In certain embodiments, $A^1$ or $A^2$ is a group:

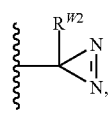

wherein $R^{W2}$ is alkyl, e.g., methyl.

In certain embodiments, A¹ or A² is a group:

Furthermore, as generally defined herein, A¹ or A² react together to form a group A, wherein A is a group of the formula:

—NH—, —NH—NH—, —NH—O—, —O—NH—, —S—, —O—,

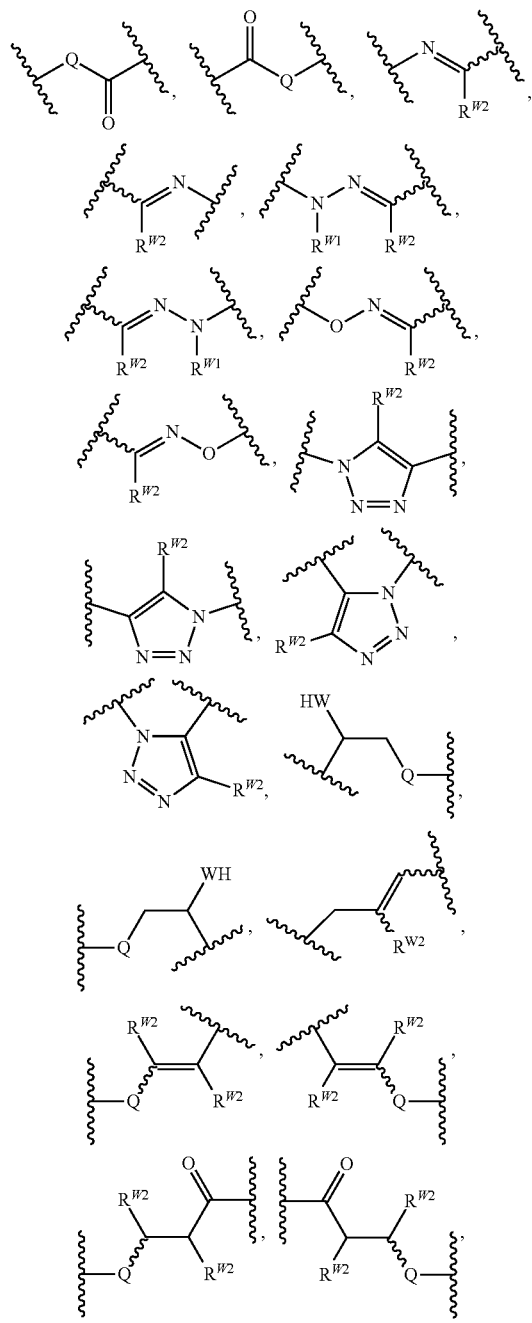

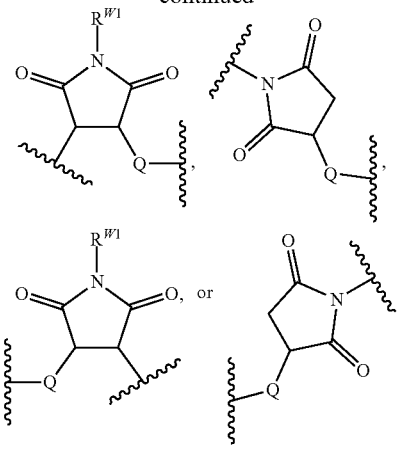

wherein:
Q is —NH—, —NH—NH—, —O—NH—, —NH—O—, —S—, or —O—;
W is O, S, or NR$^{W1}$;
R$^{W1}$ is Hydrogen, Optionally Substituted Alkyl; Optionally Substituted Alkenyl; optionally substituted alkynyl; optionally substituted carbocyclyl; optionally substituted heterocyclyl; optionally substituted aryl; optionally substituted heteroaryl; or a nitrogen protecting group; and
R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form an optionally substituted cyclic moiety.

In certain embodiments, A is —NH—.
In certain embodiments, A is —NH—NH—.
In certain embodiments, A is —S—.
In certain embodiments, A is —O—.
In certain embodiments, A is a disulfide group

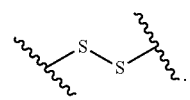 [SMILES: *SS*]

In certain embodiments, A is

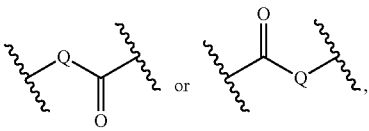

wherein Q is —NH—, —NH—NH—, —O—NH—, —NH—O—, —S—, —O—.

For example, in certain embodiments, wherein Q is —NH—, A is an amide group of the formula:

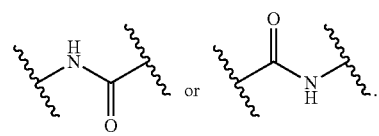 [SMILES: *NC(*)=O ; *NC(*)=O]

In certain embodiments, wherein Q is —NH—NH—, A is an amide hydrazide group of the formula:

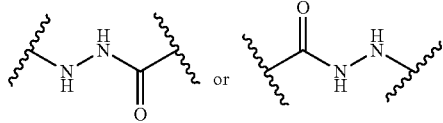

In certain embodiments, wherein Q is —S—, A is an thioester group of the formula:

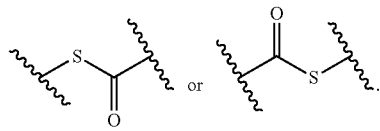 [SMILES: *SC(*)=O ; *SC(*)=O]

In certain embodiments, wherein Q is —O—, A is an ester group of the formula:

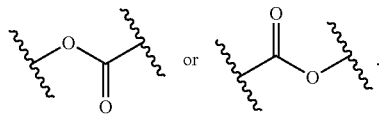 [SMILES: *OC(*)=O ; *OC(*)=O]

In certain embodiments, A is:

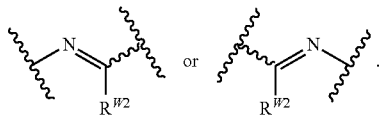

In certain embodiments, $R^{W2}$ is alkyl, e.g., methyl.

In certain embodiments, A is:

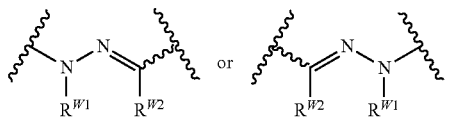

In certain embodiments, $R^{W2}$ is alkyl, e.g., methyl. In certain embodiments, $R^{W1}$ is hydrogen.

In certain embodiments, A is:

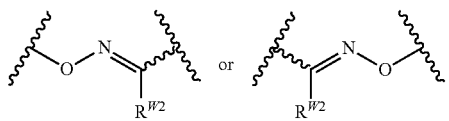

In certain embodiments, $R^{W2}$ is alkyl, e.g., methyl.

In certain embodiments, A is:

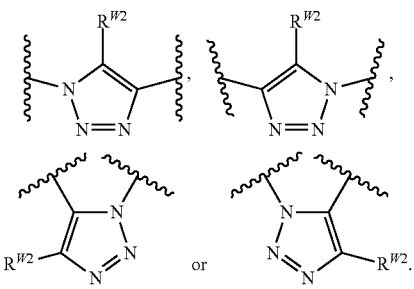

In certain embodiments, A is:

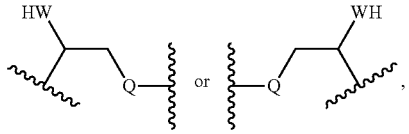

wherein W is O, S, or $NR^{W1}$, $R^{W1}$ is hydrogen, optionally substituted alkyl, or an amino protecting group; and Q is —NH—, —NH—NH—, —O—NH—, —NH—O—, —S—, or —O—. In certain embodiments, W is O. In certain embodiments, W is S. In certain embodiments, W is $NR^{W1}$. In certain embodiments, Q is —NH—. In certain embodiments, Q is —NH—NH—. In certain embodiments, Q is —S—. In certain embodiments, Q is —O—.

In certain embodiments, A is:

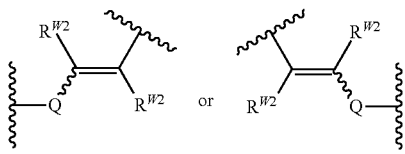

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

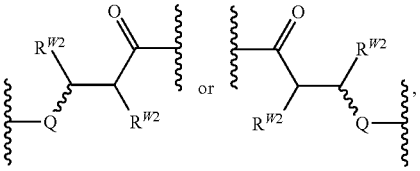

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

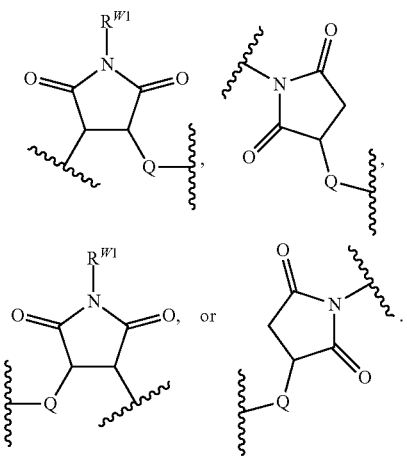

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, the method comprises coupling a group of formula ($L^{C1}$-ii) with a compound of formula $A^2$-$L^{C2}$-$R^{23}$, wherein one of $A^1$ and $A^2$ is —C(=O)$R^{X1}$, wherein $R^{X1}$ is a leaving group (LG) or —O$R^{X2}$, and the other of $A^1$ and $A^2$ is —SH, —OH, —NH$_2$, or —NH—NH$_2$ to provide a moiety A, wherein A is an amide, thioester, or ester group. See, for example, Scheme A2 and Table A1.

Scheme A2. Preparation via amide, thioester, and ester formation

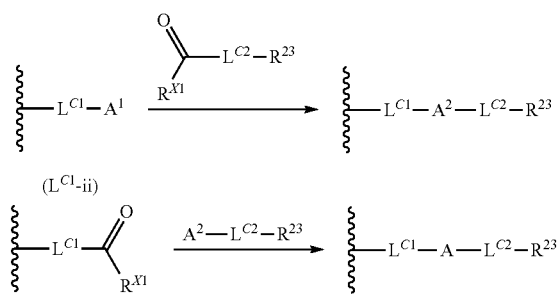

TABLE A1

| $R^{X1}$ | $A^1$ | $A^2$ | A<br>—C(=O)Q—, —QC(=O)— |
|---|---|---|---|
| LG or —O$R^{X2}$ | —SH | — | —C(=O)S— |
| | — | —SH | —SC(=O)— |
| | —OH | — | —C(=O)O— |
| | — | —OH | —OC(=O)— |
| | —NH$_2$ | — | —C(=O)NH— |
| | — | —NH$_2$ | —NHC(=O)— |
| | —NH—NH$_2$ | — | —C(=O)NHNH— |
| | — | —NH—NH$_2$ | —NHNHC(=O)— |

In certain embodiments, the method comprises coupling a group of formula ($L^{C1}$-ii) with compound of formula $A^2$-$L^{C2}$-$R^{23}$, wherein one of $L^1$ and $A^2$ is a leaving group (LG), and the other of $A^1$ and $A^2$ is —SH, —OH, —NH$_2$, or —NH—NH$_2$ to provide a group of formula ($L^{C1}$-iii) wherein A is, respectively, —S—, —O—, —NH—, or —NH—NH—. See, for example, Scheme A3 and Table A2.

Scheme A3. Nucleophilic displacement of a halide or other leaving group

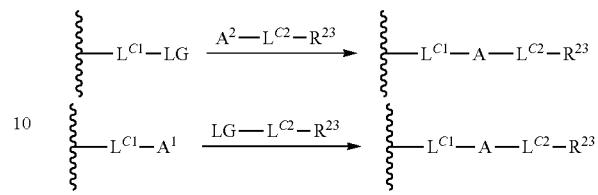

TABLE A2

| $A^1$ | $A^2$ | A |
|---|---|---|
| LG | —SH | —S— |
| | —OH | —O— |
| | —NH$_2$ | —NH— |
| | —NH—NH$_2$ | —NH—NH— |
| | —O—NH$_2$ | —O—NH— |
| —SH | LG | —S— |
| —OH | | —O— |
| —NH$_2$ | | —NH— |
| —NH—NH$_2$ | | —NH—NH— |
| —O—NH$_2$ | | —NH—O— |

In certain embodiments, the method comprises coupling a group of formula ($L^{C1}$-ii) with a compound of formula $A^2$-$L^{C2}$-$R^{23}$, wherein one of $A^1$ and $A^2$ is

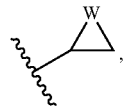

and the other of $A^1$ and $A^2$ is —SH, —OH, —NH$_2$, or —NH—NH$_2$ to provide a group of formula ($L^{C1}$-iii). See, for example, Scheme A4 and Table A3.

Scheme A4. Nucleophilic addition to strained ring systems

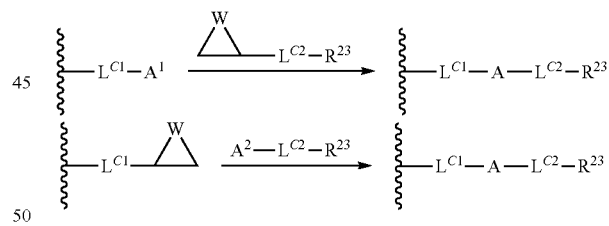

TABLE A3

| W | $A^2$ | $A^1$ | A |
|---|---|---|---|
| O, S, N$R^{W1}$ | —SH | — | HW<br>![structure]<br>S |
| | —OH | — | HW<br>![structure]<br>O |

TABLE A3-continued

| W | A² | A¹ | A |
|---|---|---|---|
| | —NH₂ | — | (structure) |
| | —NH—NH₂ | — | (structure) |
| | —O—NH₂ | — | (structure) |
| O, S, NR^{W1} | — | —SH | (structure) |
| — | — | —OH | (structure) |
| — | — | —NH₂ | (structure) |
| — | — | —NH—NH₂ | (structure) |
| — | — | —O—NH₂ | (structure) |

In certain embodiments, the method comprises coupling a group of formula ($L^{C1}$-ii) with a compound of formula $A^2$-$L^{C2}$-$R^{23}$, wherein one of $A^1$ and $A^2$ is

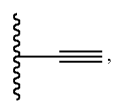

and the other of $A^1$ and $A^2$ is —N₃ to provide a group of formula ($L^{C1}$-iii). See, for example, Scheme A5 and Table A4.

Scheme A5. Azide-alkyne Huisgen cycloaddition

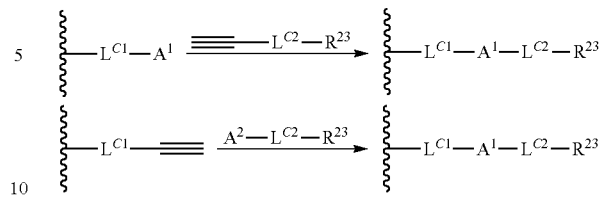

TABLE A4

| | | A | |
|---|---|---|---|
| A¹ | A² | 1,4-adduct | 1,5-adduct |
| — | —N₃ | (structure) | (structure) |
| —N₃ | — | (structure) | (structure) |

In certain embodiments, the method comprises coupling a group of formula ($L^{C1}$-ii) with a compound of formula $A^2$-$L^{C2}$-$R^{23}$, wherein one of A and $A^2$ is

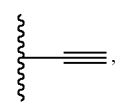

and the other of $A^1$ and $A^2$ is —SH to provide a group of formula ($L^{C1}$-iii). See, for example, Scheme A6 and Table A5.

Scheme A6. Thiol-yne addition

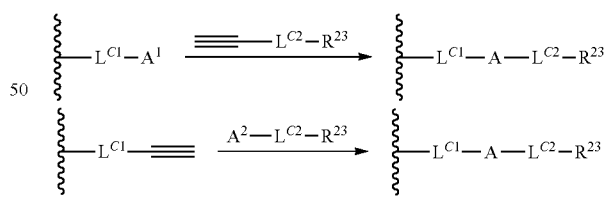

TABLE A5

| A¹ | A² | A |
|---|---|---|
| — | —SH | (structure) |

TABLE A5-continued

| $A^1$ | $A^2$ | A |
|---|---|---|
| —SH | — | 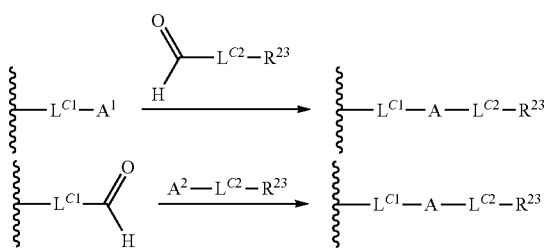 |

In certain embodiments, the method comprises coupling a group of formula ($L^{C1}$-ii) with a compound of formula $A^2$-$L^{C2}$-$R^{23}$ wherein one of $A^1$ and $A^2$ is an aldehyde —CHO or ketone, and the other of $A^1$ and $A^2$ is —NH$_2$, —NH—NH$_2$, or —O—NH$_2$ to provide a group of formula ($L^{C1}$-iii). See, for example, Scheme A7 and Table A6.

Scheme A7. Imine formation

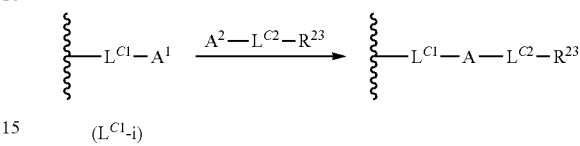

TABLE A6

| $A^1$ | $A^2$ | A |
|---|---|---|
| — | —NH$_2$ | ![N=structure with R^{W2}] |
| — | —NH—NH$_2$ | ![N-N=structure with R^{W2}, R^{W1}] |
| — | —O—NH$_2$ | ![N-O=structure with R^{W2}] |
| —NH$_2$ | — | ![N=structure with R^{W2}] |
| —NH—NH$_2$ | — | ![N-N structure with R^{W1}, R^{W2}] |
| —O—NH$_2$ | — | ![O-N=structure with R^{W2}] |

In certain embodiments, the method comprises coupling a group of formula ($L^{C1}$-ii) with a compound of formula $A^2$-$L^{C2}$-$R^{23}$, wherein one of $A^1$ and $A^2$ is an α,β-unsaturated carbonyl, and the other of $A^1$ and $A^2$ is —OH, —SH, —NH$_2$, —NHNH$_2$, or —O—NH$_2$ to provide a group of formula ($L^{C1}$-ii). See, for example, Scheme A8 and Table A7.

Scheme A8. Michael addition

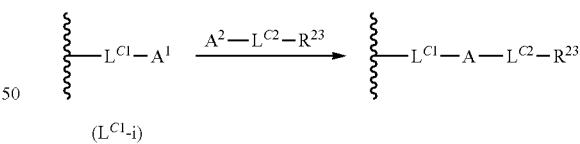

TABLE A7

| $A^1$ | $A_2$ | A |
|---|---|---|
| ![α,β-unsaturated ketone with R^{W2}] | —OH, —SH, —NH$_2$, —NHNH$_2$, —O—NH$_2$ | ![Michael adduct with R^{W2}, Q] |
| —OH, —SH, —NH$_2$, —NHNH$_2$, —O—NH$_2$ | ![α,β-unsaturated ketone with R^{W2}] | ![Michael adduct with R^{W2}, Q] |

In certain embodiments, the method comprises coupling a group of formula ($L^{C1}$-ii) with a compound of formula $A^2$-$L^{C2}$-$R^{23}$, wherein one of $A^1$ and $A^2$ is a maleimide group, and the other of $A^1$ and $A^2$ is —OH, —SH, —NH$_2$, —NHNH$_2$, or —O—NH$_2$ to provide a group of formula ($L^{C1}$-iii). See, for example, Scheme A9 and Table A8.

Scheme A9. Maleimide addition $$\{-L^{C1}-A^1 \xrightarrow{A^2-L^{C2}-R^{23}} \{-L^{C1}-A-L^{C2}-R^{23}$$

($L^{C1}$-i)

TABLE A8

| $A_1$ | $A_2$ | A |
|---|---|---|
| ![maleimide with R^{W1}] | —OH, —SH, —NH$_2$, —NHNH$_2$, —O—NH$_2$ | ![succinimide with R^{W1}, Q] |

TABLE A8-continued

| A₁ | A₂ | A |
|---|---|---|
| | —OH, —SH, —NH₂, —NHNH₂, —O—NH₂ | |
| —OH, —SH, —NH₂, —NHNH₂, —O—NH₂ | | |
| —OH, —SH, —NH₂, —NHNH₂, —O—NH₂ | | |

In certain embodiments, the method comprises coupling (e.g., palladium catalyzed coupling) of a group of formula ($L^{C1}$-ii) with a compound of formula $A^2$-$L^{C2}$-$R^{23}$, wherein one of $A^1$ and $A^2$ is an propenyl group, and one of $A^1$ and $A^2$ is a leaving group, to provide a group of formula ($L^{C1}$-iii) upon treatment with a palladium catalyst. See, for example, Table A9.

TABLE A9

| $A^1$ | $A^2$ | A |
|---|---|---|
| | LG | |
| LG | | |

In certain embodiments, the method comprises coupling a group of formula ($L^{C1}$-ii) with a compound of formula $A^2$-$L^{C2}$-$R^{23}$, wherein one of $A^1$ and $A^2$ is —SH to provide, upon treatment with an oxidant, a group of formula ($L^{C1}$-iii), wherein A is a disulfide bond. See, for example, Scheme A8.

Scheme A8. Disulfide formation

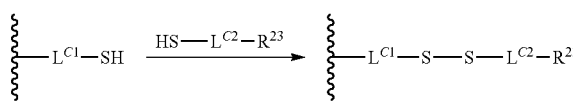

In certain preferred embodiments, $A^1$ is —N₃ and $A^2$ is

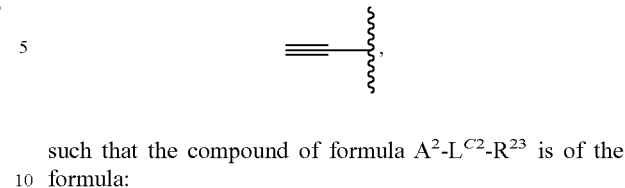

such that the compound of formula $A^2$-$L^{C2}$-$R^{23}$ is of the formula:

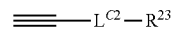

and $A^1$ and $A^2$-$L^{C2}$-$R^{23}$ react together to provide a group of formula:

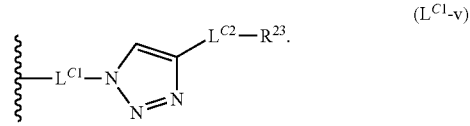

($L^{C1}$-v)

In certain preferred embodiments, $A^1$ is

and $A^2$ is a leaving group, and $A^1$ and $A^2$-$L^{C2}$-$R^{23}$ react together (e.g., via palladium catalysis) to provide a group of formula:

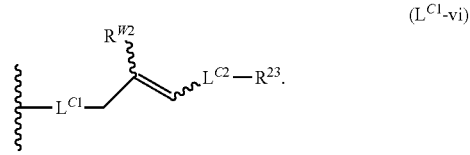

($L^{C1}$-vi)

Furthermore, as described herein, there are many ways of adding a group of formula ($L^{C1}$-iii) which do not involve reaction of $A^1$ and $A^2$ to form A. For example, a group of formula ($L^{C1}$-iii) may be installed by reaction of the group —$OR^{12}$, —$NR^{13}R^{14}$, and/or —$OR^3$, wherein $R^{12}$, $R^{14}$, and/or $R^3$ are hydrogen, with a compound of formula ($L^{C1}$-vii), e.g., by nucleophilic displacement, to provide a group wherein $R^{12}$, $R^{14}$, and/or $R^3$ is of formula ($L^{C1}$-iii). See, e.g., Scheme A9.

Scheme A9.

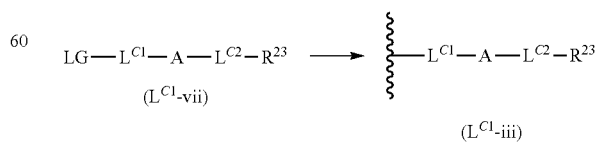

Thus, in certain embodiments, A may be any group as defined above, and further may be any cyclic moiety selected from the group consisting of optionally substituted carbocyclyl, optionally substituted heterocyclyl, optionally substituted aryl, and optionally substituted heteroaryl.

In certain embodiments, A is an optionally substituted heteroaryl, e.g., a 5- to 6-membered optionally substituted heteroaryl.

In certain embodiments, wherein A is a 5-membered optionally substituted heteroaryl, the group of formula ($L^{C1}$-iii) is of the formula ($L^{C1}$_v):

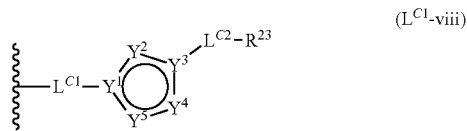

($L^{C1}$-viii)

wherein each instance of $Y^1$, $Y^2$, $Y^3$, $Y^4$, and $Y^5$ is independently $CR^Y$, O, S, N, or $NR^Y$, wherein $R^Y$ is hydrogen or optionally substituted alkyl.

In certain embodiments wherein A is a 5-membered heteroaryl, the group of formula ($L^{C1}$-iii) is selected from:

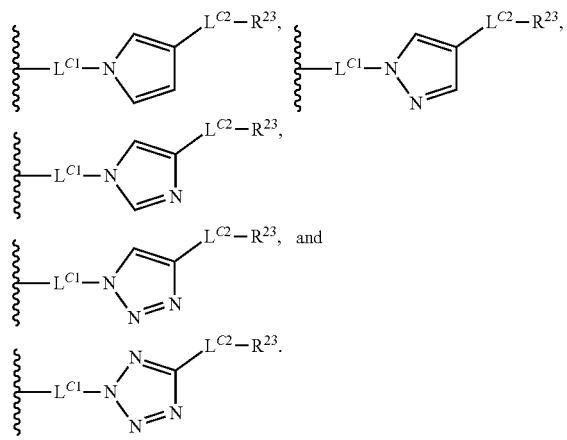

$L^{C1}$, $L^{C2}$ and Group $R^{23}$

As generally defined above, each instance of $L^{C1}$ and $L^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, optionally substituted carbocyclylene, optionally substituted heterocyclylene, and combinations thereof.

In certain embodiments, $L^{C1}$ is a bond. It is generally understood that if $L^{C1}$ is a bond, then the group -LG, -$A^1$, or -A-$L^{C2}$-$R^{23}$, as described herein, is directly attached to the parent moiety, e.g., the macrolide or intermediate compounds. Furthermore, in certain embodiments, $L^{C2}$ is a bond. It is generally understood that if $L^{C2}$ is a bond, then the group $R^{23}$ is directly attached to A, as described herein.

Alternatively, in certain embodiments, $L^{C1}$ is a linking group. In certain embodiments, $L^{C2}$ is a linking group.

In certain embodiments, $L^{C1}$ and $L^{C2}$ are each optionally and independently linking groups comprising at least one instance of optionally substituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene.

In certain embodiments, $L^{C1}$ and $L^{C2}$ are each optionally and independently an alkylene linking group of the formula —$(CH_2)_n$—, wherein n is 1, 2, 3, 4, 5, 6, 7, 8, 9, or 10.

In certain embodiments, $L^{C1}$ and $L^{C2}$ are each optionally and independently linking groups comprising at least one instance of substituted or unsubstituted alkenylene, e.g., substituted or unsubstituted $C_{2-6}$alkenylene, substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene.

In certain embodiments, $L^{C1}$ and $L^{C2}$ are each optionally and independently linking groups comprising substituted or unsubstituted alkenylene, wherein $L^{C1}$ and $L^{C2}$ are each optionally and independently linking groups comprising an allene moiety. In certain embodiments, $L^{C1}$ is a linking group comprising an allene moiety. In certain embodiments, $L^{C2}$ is a linking group comprising an allene moiety.

In certain embodiments, $L^{C1}$ and $L^{C2}$ are each optionally and independently linking groups comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene.

In certain embodiments, $L^{C1}$ and $L^{C2}$ are each optionally and independently linking groups comprising at least one instance of substituted or unsubstituted heteroalkylene, e.g., substituted or unsubstituted hetero$C_{1-6}$alkylene, substituted or unsubstituted hetero$C_{2-6}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene.

In certain embodiments, $L^{C1}$ and $L^{C2}$ are each optionally and independently linking groups comprising at least one instance of substituted or unsubstituted heteroalkenylene, e.g., substituted or unsubstituted hetero$C_{2-6}$alkenylene, substituted or unsubstituted hetero$C_{3-6}$alkenylene, substituted or unsubstituted hetero$C_{4-6}$alkenylene, substituted or unsubstituted hetero$C_{5-6}$alkenylene, substituted or unsubstituted hetero$C_{2-5}$alkenylene, substituted or unsubstituted hetero$C_{2-}$ 4alkenylene, substituted or unsubstituted heteroC$_{2-3}$alkenylene, substituted or unsubstituted heteroC$_2$alkenylene, substituted or unsubstituted heteroC$_3$alkenylene, substituted or unsubstituted heteroC$_4$alkenylene, substituted or unsubstituted heteroC$_5$alkenylene, or substituted or unsubstituted heteroC$_6$alkenylene.

In certain embodiments, L$^{C1}$ and L$^{C2}$ are each optionally and independently linking groups comprising at least one instance of substituted or unsubstituted heteroalkynylene, e.g., substituted or unsubstituted heteroC$_{2-6}$alkynylene, substituted or unsubstituted heteroC$_3$-6alkynylene, substituted or unsubstituted heteroC$_{4-6}$alkynylene, substituted or unsubstituted heteroC$_{5-6}$alkynylene, substituted or unsubstituted heteroC$_{2-5}$alkynylene, substituted or unsubstituted heteroC$_{2-4}$alkynylene, substituted or unsubstituted heteroC$_{2-3}$alkynylene, substituted or unsubstituted heteroC$_2$alkynylene, substituted or unsubstituted heteroC$_3$alkynylene, substituted or unsubstituted heteroC$_4$alkynylene, substituted or unsubstituted heteroC$_5$alkynylene, or substituted or unsubstituted heteroC$_6$alkynylene.

In certain embodiments, L$^{C1}$ and L$^{C2}$ are each optionally and independently linking groups comprising at least one instance of substituted or unsubstituted carbocyclylene, e.g., substituted or unsubstituted C$_{3-6}$carbocyclylene, substituted or unsubstituted C$_{4-6}$carbocyclylene, substituted or unsubstituted C$_{5-6}$carbocyclylene, substituted or unsubstituted C$_{3-5}$carbocyclylene, substituted or unsubstituted C$_{4-5}$carbocyclylene, or substituted or unsubstituted C$_{3-4}$carbocyclylene.

In certain embodiments, L$^{C1}$ and L$^{C2}$ are each optionally and independently linking groups comprising at least one instance of substituted or unsubstituted heterocyclylene, e.g., substituted or unsubstituted C$_{3-6}$heterocyclylene, substituted or unsubstituted C$_{4-6}$heterocyclylene, substituted or unsubstituted C$_{5-6}$heterocyclylene, substituted or unsubstituted C$_{3-5}$heterocyclylene, substituted or unsubstituted C$_{4-5}$heterocyclylene, or substituted or unsubstituted C$_{3-4}$heterocyclylene.

In certain embodiments, L$^{C1}$ and L$^{C2}$ are each optionally and independently linking groups of one of the following formulae:

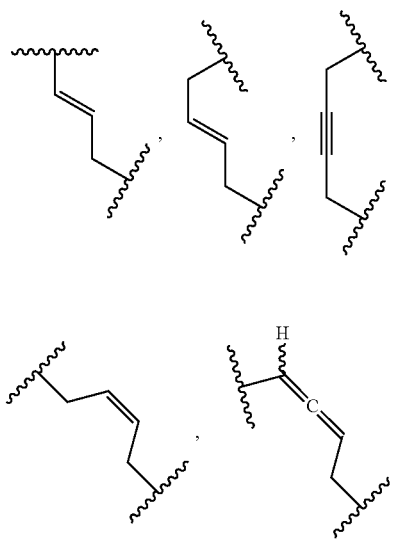

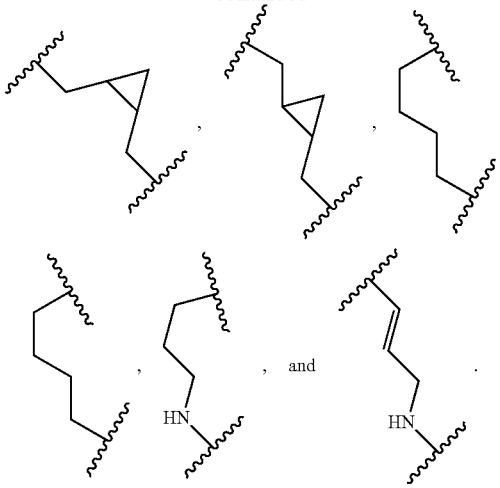

As demonstrated herein, macrolides which incorporate rigidifying motifs (e.g., unsaturated or cyclic motifs) into the L$^{C1}$ or L$^{C2}$ linker show improved potencies compared with solithromycin (See, e.g., Tables B1-B13). Therefore, in certain embodiments, one or both of L$^{C1}$ and L$^{C2}$ is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, and combinations thereof, provided the linker comprises a optionally substituted alkenylene, optionally substituted alkynylene, or optionally substituted carbocyclylene group therein, thereby rigidifying the linker moiety. In certain embodiments, L$^{C1}$ is a rigidified linker, as described herein, and L$^{C2}$ is a bond. In certain embodiments of L$^{C1}$ and/or L$^{C2}$, specific combinations contemplated herein include optionally substituted C$_{1-3}$alkyl-C$_{2-4}$alkenyl-C$_{1-3}$alkyl, optionally substituted C$_{1-3}$alkyl-C$_{2-4}$alkenyl-heteroC$_{1-3}$alkyl, optionally substituted heteroC$_{1-3}$alkyl-C$_{2-4}$alkenyl-C$_{1-3}$alkyl, optionally substituted heteroC$_{1-3}$alkyl-C$_{2-4}$alkenyl-heteroC$_{1-3}$alkyl, C$_{1-3}$alkyl-C$_{1-2}$alkynyl-C$_{1-3}$alkyl, and C$_{1-3}$alkyl-C$_{3-6}$carbocyclyl-C$_{1-3}$alkyl.

In certain embodiments, one or both of L$^{C1}$ and L$^{C2}$ is of one of the following formulae:

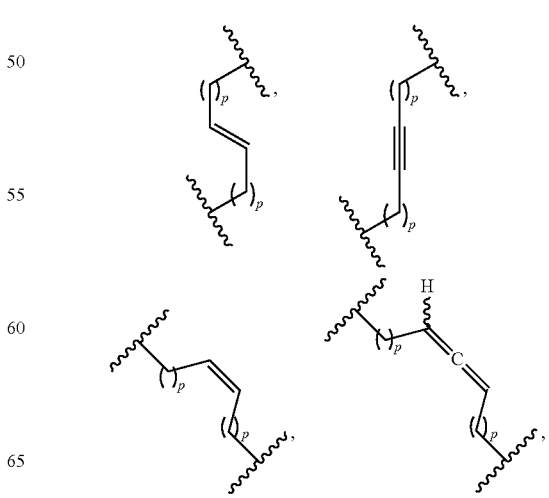

-continued

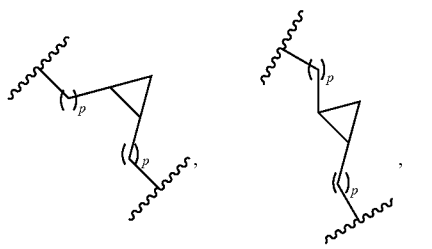

and

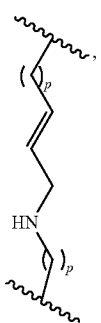

wherein each instance of p is independently 0, 1, or 2.

In certain embodiments of the present invention, each of $L^{C1}$ and $L^{C2}$ is independently selected from one of the following formulae:

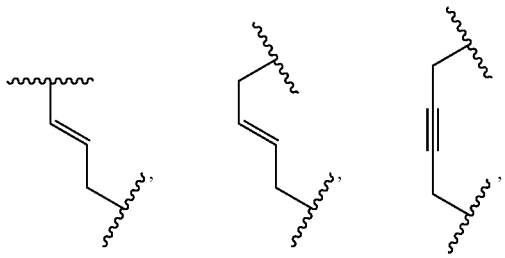

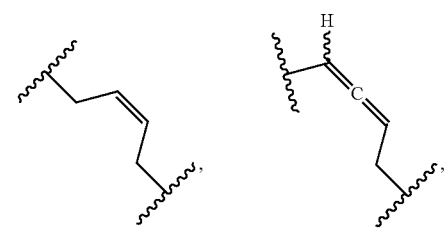

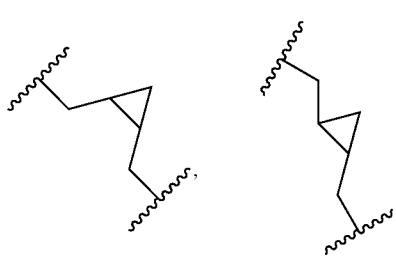

and

-continued

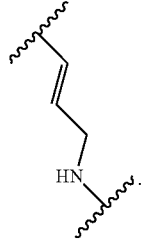

In certain embodiments, $L^{C1}$ is an optionally substituted alkylene, and $L^{C2}$ is a bond, e.g., $L^{C1}$ is an optionally substituted alkylene of the formula —(CH$_2$)$_n$—, wherein n is 1, 2, 3, 4, 5, 6, 7, 8, 9, or 10, and $L^{C2}$ is a bond in groups of formula ($L^{C1}$-v) or ($L^{C1}$-viii) as described herein.

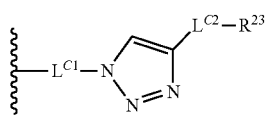 ($L^{C1}$-v)

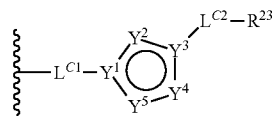 ($L^{C1}$-viii)

In other embodiments, both of $L^{C1}$ and $L^{C2}$ are bonds, e.g., both of $L^{C1}$ and $L^{C2}$ are bonds in the group of formula ($L^{C1}$-vi) as described herein.

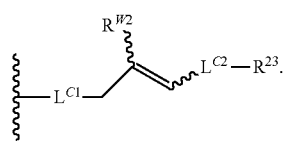 ($L^{C1}$-vi)

Furthermore, it is also generally understood that $R^{23}$ may be an acyclic moiety or a cyclic moiety selected from the group consisting of optionally substituted alkyl; optionally substituted alkenyl; optionally substituted alkynyl; optionally substituted carbocyclyl; optionally substituted heterocyclyl; optionally substituted aryl; and optionally substituted heteroaryl.

For example, in certain embodiments, $R^{23}$ is an acyclic moiety selected from the group consisting of optionally substituted alkyl; optionally substituted alkenyl; and optionally substituted alkynyl.

In certain embodiments, $R^{23}$ is optionally substituted alkyl, e.g., optionally substituted $C_{1-6}$alkyl, substituted or unsubstituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. Exemplary $R^{23}$ $C_{1-6}$ alkyl groups include, but are not limited to, optionally substituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, $R^{23}$ is optionally substituted alkenyl, e.g., optionally substituted $C_{2-6}$alkenyl, optionally substituted C$_{2-3}$alkenyl, optionally substituted C$_{3-4}$alkenyl, optionally substituted C$_{4-5}$ alkenyl, or optionally substituted C$_{5-6}$alkenyl.

In certain embodiments, R$^{23}$ is optionally substituted alkynyl, e.g., optionally substituted C$_{2-6}$alkynyl, optionally substituted C$_{2-3}$alkynyl, optionally substituted C$_{3-4}$alkynyl, optionally substituted C$_{4-5}$-alkynyl, or optionally substituted C$_{5-6}$alkynyl.

In certain embodiments, R$^{23}$ is a cyclic moiety selected from the group consisting of optionally substituted carbocyclyl; optionally substituted heterocyclyl; optionally substituted aryl; and optionally substituted heteroaryl.

In certain embodiments, R$^{23}$ is optionally substituted carbocyclyl, e.g., optionally substituted C$_{3-6}$carbocyclyl, optionally substituted C$_{3-4}$carbocyclyl, optionally substituted C$_{4-5}$ carbocyclyl, or optionally substituted C$_{5-6}$ carbocyclyl.

In certain embodiments, R$^{23}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, R$^{23}$ is optionally substituted aryl, e.g., optionally substituted monocyclic aryl, optionally substituted 5,6-fused bicyclic aryl, or optionally substituted 6,6-fused aryl. In certain embodiments, R$^{23}$ is optionally substituted phenyl. In certain embodiments, R$^{23}$ is optionally substituted napthyl.

In certain embodiments, R$^{23}$ is optionally substituted heteroaryl, e.g., optionally substituted monocyclic heteoaryl or optionally substituted bicyclic heteroaryl, e.g., optionally substituted 5-6 membered heteroaryl, optionally substituted 5,6 fused-bicyclic heteroaryl, or optionally substituted 6,6 fused-bicyclic heteroaryl.

Specific aryl and heteroaryl R$^{23}$ groups are further contemplated herein. For example, in certain embodiments, R$^{23}$ is an aryl or heteroaryl ring system of formula:

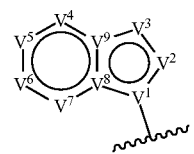 (e-1)

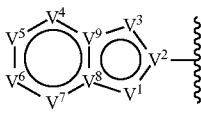 (e-2)

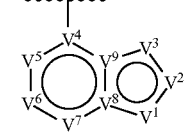 (e-3)

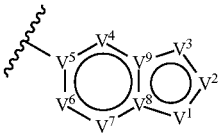 (e-4)

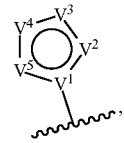 (e-5)

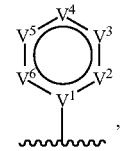 (e-6)

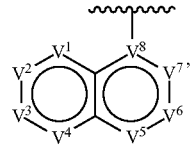 (e-7)

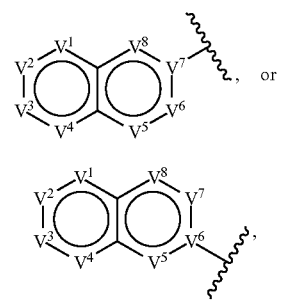 , or (e-8)

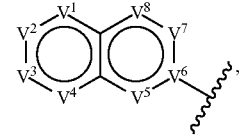 , (e-9)

wherein:
each instance of V$^1$, V$^2$, V$^3$, V$^4$, V$^5$, V$^6$, V$^7$, V$^8$, and V$^9$ may independently be O, S, N, NR$^{23N}$, C, or CR$^{23C}$, as valency permits;

R$^{23N}$ is independently hydrogen, optionally substituted alkyl, optionally substituted aryl, or a nitrogen protecting group; and R$^{23C}$ is hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, amino, substituted amino, thiol, substituted thiol, or carbonyl.

In certain embodiments, V$^1$ is O, S, N or NR$^{23N}$. In certain embodiments, V$^1$ is N or NR$^{23N}$. In certain embodiments, V$^1$ is O. In certain embodiments, V$^1$ is S.

In certain embodiments, V$^2$ is O, S, N or NR$^{23N}$. In certain embodiments, V$^2$ is N or NR$^{23N}$. In certain embodiments, V$^2$ is O. In certain embodiments, V$^2$ is S.

In certain embodiments, V$^3$ is O, S, N or NR$^{23N}$. In certain embodiments, V$^3$ is N or NR$^{23N}$. In certain embodiments, V$^3$ is O. In certain embodiments, V$^3$ is S.

In certain embodiments, V$^4$ is O, S, N or NR$^{23N}$. In certain embodiments, V$^4$ is N or NR$^{23N}$. In certain embodiments, V$^4$ is O. In certain embodiments, V$^4$ is S.

In certain embodiments, V$^5$ is O, S, N or NR$^{23N}$. In certain embodiments, V$^5$ is N or NR$^{23N}$. In certain embodiments, V$^5$ is O. In certain embodiments, V$^5$ is S.

In certain embodiments, V$^6$ is O, S, N or NR$^{23N}$. In certain embodiments, V$^6$ is N or NR$^{23N}$. In certain embodiments, V$^6$ is O. In certain embodiments, V$^6$ is S.

In certain embodiments, V$^7$ is O, S, N or NR$^{23N}$. In certain embodiments, V$^7$ is N or NR$^{23N}$. In certain embodiments, V$^7$ is O. In certain embodiments, V$^7$ is S.

In certain embodiments, $V^8$ is O, S, N or $NR^{23N}$. In certain embodiments, $V^8$ is N or $NR^{23N}$. In certain embodiments, $V^8$ is O. In certain embodiments, $V^8$ is S.

In certain embodiments, $V^9$ is O, S, N or $NR^{23N}$. In certain embodiments, $V^9$ is N or $NR^{23N}$. In certain embodiments, $V^9$ is O. In certain embodiments, $V^9$ is S.

In certain embodiments, only one of $V^1$, $V^2$, $V^3$, $V^4$, $V^5$, $V^6$, $V^7$, $V^8$, and $V^9$ is selected from the group consisting of N and $NR^{23N}$. In certain embodiments, only one of $V^1$, $V^2$, $V^3$, $V^4$, $V^5$, $V^6$, $V^7$, $V^8$, and $V^9$ is O. In certain embodiments, only one of $V^1$, $V^2$, $V^3$, $V^4$, $V^5$, $V^6$, $V^7$, $V^8$, and $V^9$ is S. In any of the above instances, in certain embodiments, the rest of $V^1$, $V^2$, $V^3$, $V^4$, $V^5$, $V^6$, $V^7$, $V^8$, and $V^9$ are independently C or $CR^{23C}$ as valency permits.

In certain embodiments, only two of $V^1$, $V^2$, $V^3$, $V^4$, $V^5$, $V^6$, $V^7$, $V^8$, and $V^9$ are each independently selected from the group consisting of N and $NR^{23N}$. In certain embodiments, only two of $V^1$, $V^2$, $V^3$, $V^4$, $V^5$, $V^6$, $V^7$, $V^8$, and $V^9$ are each independently selected from the group consisting of O, N and $NR^{23N}$. In certain embodiments, only two of $V^1$, $V^2$, $V^3$, $V^4$, $V^5$, $V^6$, $V^7$, $V^8$, and $V^9$ are each independently selected from the group consisting of S, N and $NR^{23N}$. In any of the above instances, in certain embodiments, the rest of $V^1$, $V^2$, $V^3$, $V^4$, $V^5$, $V^6$, $V^7$, $V^8$, and $V^9$ are independently C or $CR^{23C}$ as valency permits.

In certain embodiments, all $V^1$, $V^2$, $V^3$, $V^4$, $V^5$, $V^6$, $V^7$, $V^8$, and $V^9$ are independently C or $CR^{23C}$ as valency permits.

In certain embodiments, $R^{23C}$ is hydrogen, halogen, —CN, hydroxyl, substituted hydroxyl, amino, or substituted amino.

In certain embodiments, $R^{23N}$ is independently hydrogen or optionally substituted alkyl (e.g., —CH$_3$).

In certain embodiments, $R^{23}$ is selected from any one of the following aryl or heteroaryl ring systems:

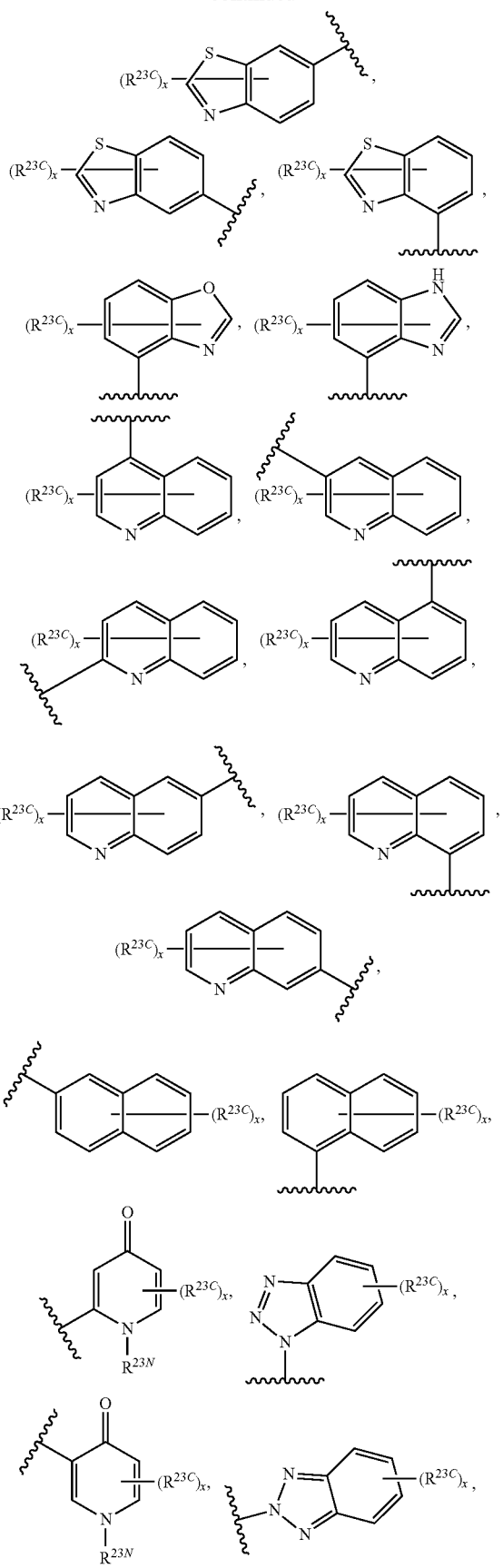

wherein $R^{23C}$ is as defined herein, and x is 0, 1, or 2.

In certain embodiments, $R^{23}$ is selected from any one of the following aryl or heteroaryl ring systems:

-continued

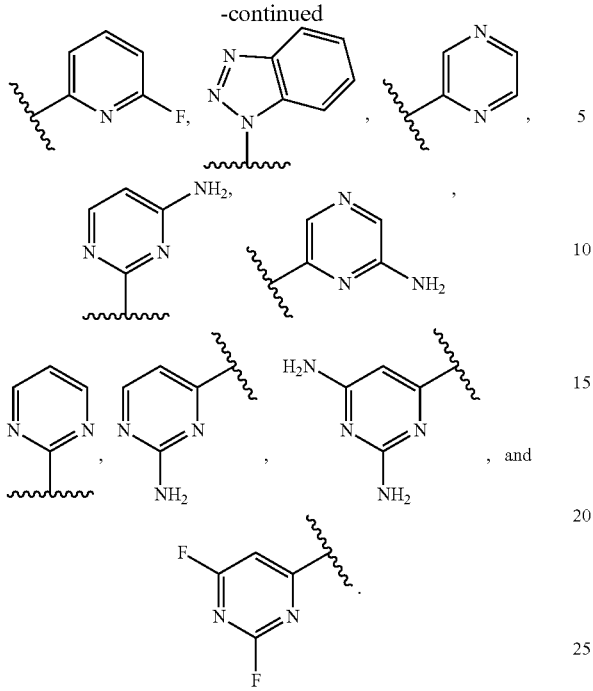

As described herein, ketolides comprising a heteroaryl $R^{23}$ group show improved potency over solithromycin and analogs thereof. Therefore, in certain embodiments, $R^{23}$ is of the formula:

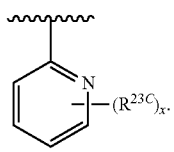

In specific embodiments, $R^{23}$ is of the formula:

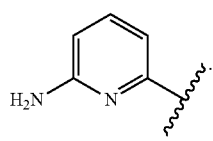

Further Embodiments of the Invention

Various combinations of the above described embodiments are further contemplated herein. For example, in certain embodiments, $G^1$ is —$NR^{13}NR^{14}$, to provide a compound or ketolide of formula:

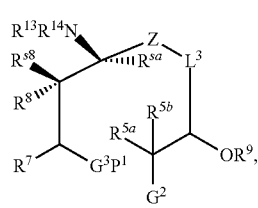
(N-1-A)

-continued

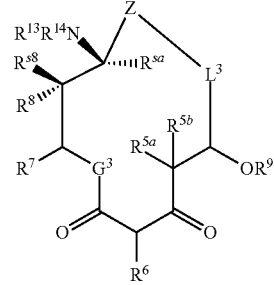
(N-2-A)

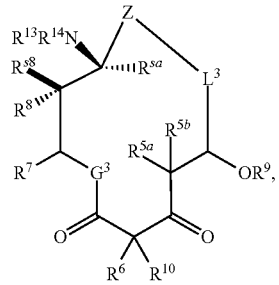
(N-3-A)

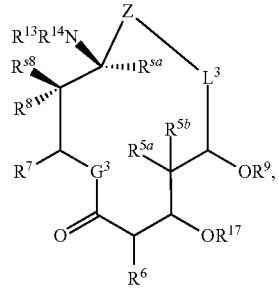
(N-4-A)

or a salt thereof.

In certain embodiments, $G^1$ is —$NR^{13}NR^{14}$, and $R^{13}$ and $R^{11}$ are joined to form a carbamate group to provide a compound or ketolide of formula:

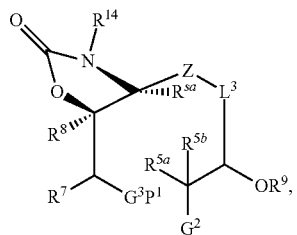
(N-1-B)

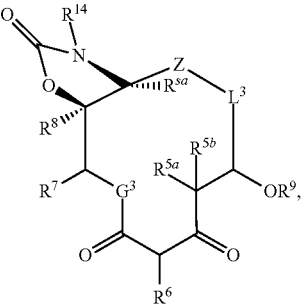
(N-2-B)

-continued
(N-3-B)
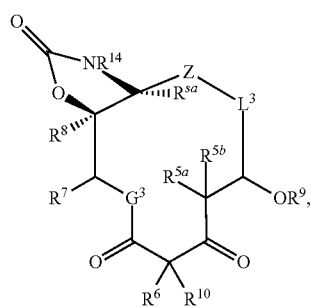
(N-4-B)
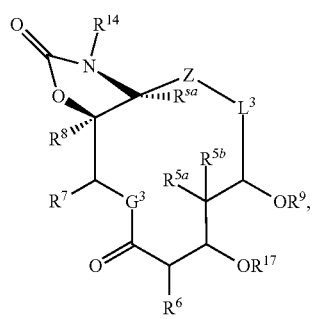
(N-5-B)
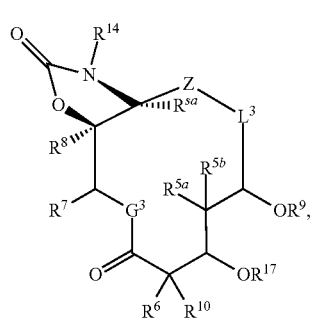
(N-6-B)
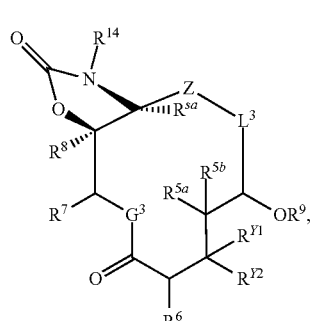
(N-7-B)
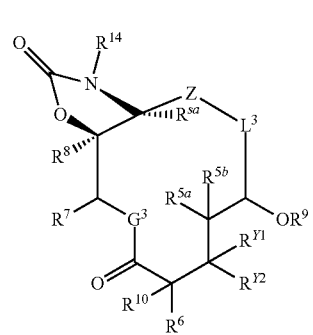
or a salt thereof.
In certain embodiments, $G^1$ is —$NR^{13}NR^{14}$, and $R^{13}$ and $R^{11}$ are joined to form a carbamate group to provide a compound or ketolide having the following stereochemistry:
(N-1-C)
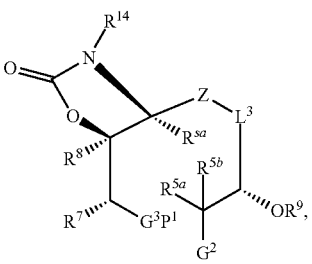
(N-2-C)
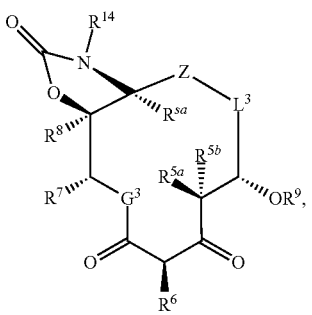
(N-2-C')
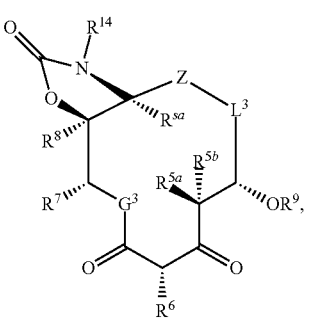
(N-4-C)
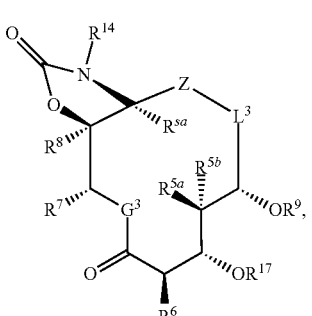
(N-4-C')
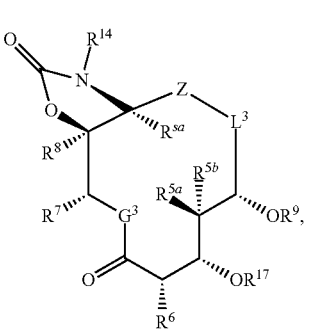

(N-3-C)
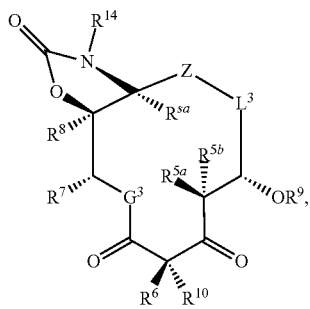

(N-3-C')
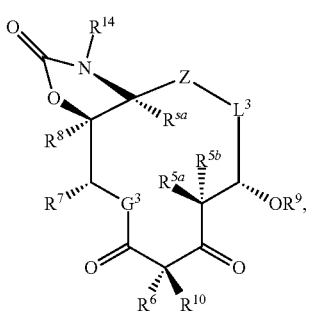

(N-5-C)
(N-5-C')
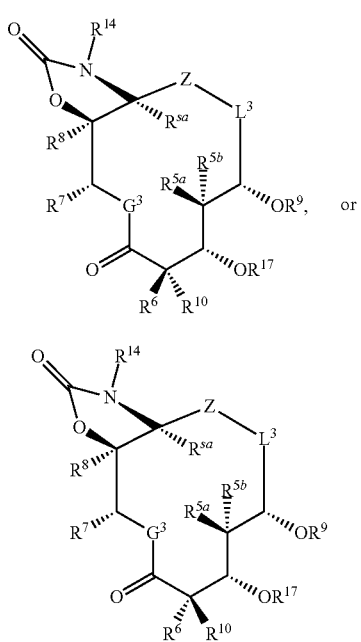

or salts thereof.

Various embodiments are further contemplated in combination with any formulae depicted herein, e.g., for example, any of the above depicted formulae (N-1-A) to (N-5-C').

For example, in certain embodiments of any of the above formulae, Z is of formula:

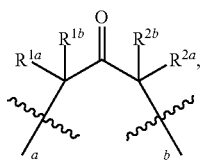
(z-i)

wherein $R^{1a}$ is —$CH_3$; $R^{1b}$ is hydrogen; $R^{2a}$ is —$CH_3$; and $R^{2b}$ is hydrogen; $R^7$ is —$CH_2CH_3$; $R^8$ is-$CH_3$; $G^3$, is —O—; $L^3$ is a group of formula

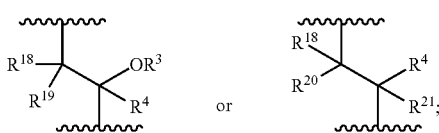

$R^{5a}$ is hydrogen; $R^{5b}$ is —$CH_3$; and $R^{18}$ is hydrogen. For example, in certain embodiments of any of the above formulae, Z is of formula:

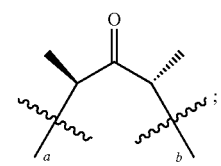 [SMILES: *[C@@H](C)C(=O)[C@@H](*)C]

$R^7$ is —$CH_2CH_3$; $R^8$ is —$CH_3$; $G^3$ is —O—; $L^3$ is a group of formula

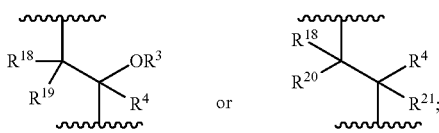

$R^{5a}$ is hydrogen; $R^{5b}$ is —$CH_3$; and $R^{18}$ is hydrogen. In certain embodiments of any of the above formulae, the $L^{C1}$ is a rigidified linker as described herein, e.g., selected from the group consisting of optionally substituted alkylene, optionally substituted alkenylene, optionally substituted alkynylene; optionally substituted heteroalkylene, optionally substituted heteroalkenylene, optionally substituted heteroalkynylene, optionally substituted carbocyclylene, optionally substituted heterocyclylene, and combinations thereof, provided the linker comprises a optionally substituted alkenylene, optionally substituted alkynylene, or optionally substituted carbocyclylene group therein, thereby rigidifying the linker moiety, and $L^{C2}$ is a bond. In certain embodiments of any of the above formulae, $R^{23}$ is of the formula:

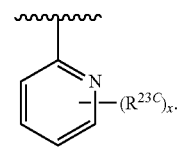

In specific embodiments, $R^{23}$ is of the formula:

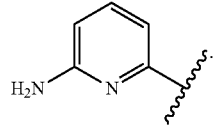

In certain embodiments of any of the above formulae, Z is of formula:

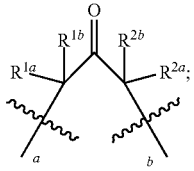 (z-i)

$R^{1a}$ is hydrogen; $R^{1b}$ is hydrogen; $R^{2a}$ is —CH$_3$; and $R^{2b}$ is hydrogen; $R^7$ is —CH$_2$CH$_3$; $R^8$ is —CH$_3$; $G^3$ is —O—; $L^3$ is a group of formula

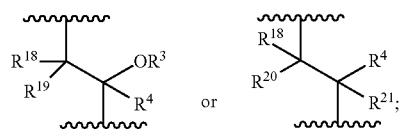

$R^{5a}$ is hydrogen; $R^{5b}$ is —CH$_3$; and $R^{18}$ is hydrogen. In certain embodiments of any of the above formulae, $L^{C1}$ is a rigidified linker as described herein; and $L^{C2}$ is a bond. In certain embodiments of any of the above formulae, $R^{23}$ is of the formula:

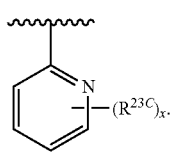

In specific embodiments, $R^{23}$ is of the formula:

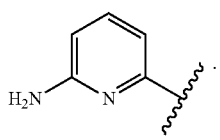

In certain embodiments of any of the above formulae, Z is of formula:

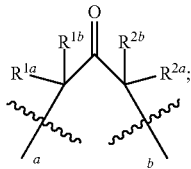 (z-i)

$R^{1a}$ and $R^{1b}$ are joined to form

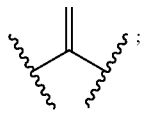 [SMILES: *C(*)=C];

$R^{2a}$ is —CH$_3$; and $R^{2b}$ is hydrogen; $R^7$ is —CH$_2$CH$_3$; $R^8$ is —CH$_3$; $G^3$ is —O—; $L^3$ is a group of formula

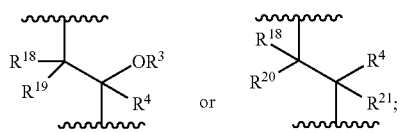

$R^{5a}$ is hydrogen; $R^{5b}$ is —CH$_3$; and $R^{18}$ is hydrogen. In certain embodiments of any of the above formulae, Z is of formula:

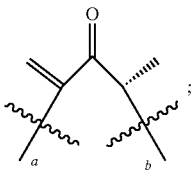 [SMILES: *C(=C)C(=O)[C@@H](*)C];

$R^7$ is —CH$_2$CH$_3$; $R^8$ is —CH$_3$; $G^3$ is —O—; $L^3$ is a group of formula

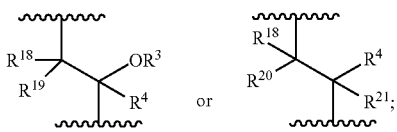

$R^{5a}$ is hydrogen; $R^{5b}$ is —CH$_3$; $R^{18}$ is hydrogen; $L^{C1}$ is a rigidified linker as described herein; and $L^{C2}$ is a bond. As described herein, in certain embodiments, $R^{23}$ is of the formula:

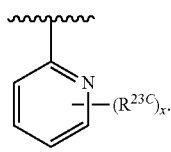

In specific embodiments, $R^{23}$ is of the formula:

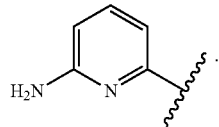

In certain embodiments of any of the above formulae, Z is of formula:

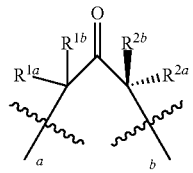

$R^{1a}$ is —$CH_3$; $R^{1b}$ and $R^{sa}$ are joined to form a bond; $R^{2a}$ is —$CH_3$; and $R^{2b}$ is hydrogen; $R^7$ is —$CH_2CH_3$; $R^8$ is —$CH_3$; $G^3$ is —O—; $L^3$ is a group of formula

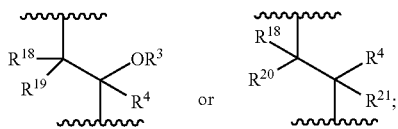

$R^{5a}$ is hydrogen; $R^{5b}$ is —$CH_3$; $R^{18}$ is hydrogen; $L^{C1}$ is a rigidified linker as described herein; and $L^{C2}$ is a bond.

In certain embodiments of any of the above formulae, Z is of formula:

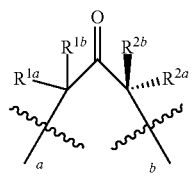

$R^{1a}$ is hydrogen; $R^{1b}$ and $R^{sa}$ are joined to form a bond; $R^{2a}$ is —$CH_3$; and $R^{2b}$ is hydrogen; $R^7$ is —$CH_2CH_3$; $R^8$ is —$CH_3$; $G^3$ is —O—; $L^3$ is a group of formula

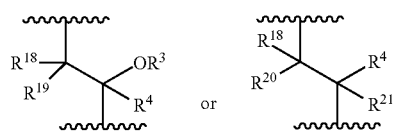

$R^{5a}$ is hydrogen; $R^{5b}$ is —$CH_3$; and $R^{18}$ is hydrogen. In certain embodiments of any of the above formulae, $L^{C1}$ is a rigidified linker as described herein; and $L^{C2}$ is a bond. In certain embodiments of any of the above formulae, $R^{23}$ is of the formula:

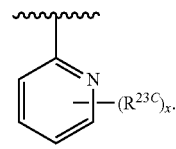

In specific embodiments, $R^{23}$ is of the formula:

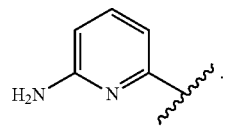

In certain aspects of the formulae depicted herein, e.g., for example, any of the above depicted formulae (N-1-A) to (N-5-C'), further specific combinations are contemplated, as provided below.

In certain embodiments, at least one of $R^{1a}$ and $R^{1b}$ is hydrogen. In certain embodiments, both $R^{1a}$ and $R^{1b}$ are hydrogen. In certain embodiments, neither $R^{1a}$ nor $R^{1b}$ are hydrogen. In certain embodiments, the carbon to which $R^{1a}$ and $R^{1b}$ is attached is a stereocenter of the (R)-configuration. In certain embodiments, the carbon to which $R^{1a}$ and $R^{1b}$ is attached is a stereocenter of the (S)-configuration. In certain embodiments, $R^{1a}$ is optionally substituted $C_{1-6}$alkyl; and $R^{1b}$ is hydrogen. In certain embodiments, $R^{1a}$ is optionally substituted $C_{1-2}$alkyl; and $R^{1b}$ is hydrogen. In certain embodiments, $R^{1a}$ is —$CH_3$; and $R^{1b}$ is hydrogen. In certain embodiments, both $R^{1a}$ and $R^{1b}$ are —$CH_3$. In certain embodiments, $R^{1a}$ is optionally substituted haloalkyl; and $R^{1b}$ is hydrogen. In certain embodiments, $R^{1a}$ is —$CF_3$; and $R^{1b}$ is hydrogen. In certain embodiments, $R^{1a}$ is —$CH_2CH_2OH$; and $R^{1b}$ is hydrogen. In certain embodiments, $R^{1a}$ is —$CH_2CH_2N(R^{22})_2$; and $R^{1b}$ is hydrogen. In certain embodiments, $R^{1a}$ is —$CH_2CH_2N(R^{22})_2$; $R^{22}$ is —$CH_3$; and $R^{1b}$ is hydrogen. In certain embodiments, $R^{1a}$ is —$CH_2CH_2NHR^{22}$; and $R^{1b}$ is hydrogen. In certain embodiments, $R^{1a}$ is —$CH_2CH_2NHR^{22}$; $R^{22}$ is —$CH_2C(=O)OH$; and $R^{1b}$ is hydrogen. In certain embodiments, $R^{1a}$ is —$CH_2CH_2NHR^{22}$; $R^{22}$ is

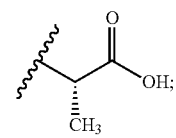

and $R^{1b}$ is hydrogen. In certain embodiments, $R^{1a}$ is —$CH_2CH_2NHR^{22}$; $R^{22}$ is

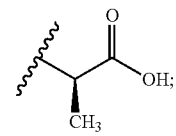 [SMILES: *[C@H](C)C(=O)O]

and $R^{1b}$ is hydrogen. In certain embodiments, $R^{1a}$ is optionally substituted aralkyl; and $R^{1b}$ bis hydrogen. In certain embodiments, $R^{1a}$ is optionally substituted benzyl; and $R^{1b}$ bis hydrogen. In certain embodiments, $R^{1a}$ is unsubstituted benzyl; and $R^{1b}$ is hydrogen. In certain embodiments, $R^{1a}$ is substituted benzyl; and $R^{1b}$ is hydrogen. In certain embodiments, $R^{1a}$ is monosubstituted benzyl; and $R^{1b}$ is hydrogen. In certain embodiments, $R^{1a}$ is benzyl substituted by one instance of halogen; and $R^{1b}$ is hydrogen. In certain embodiments, $R^{1a}$ is optionally substituted $C_{2-6}$alkenyl; and $R^{1b}$ is hydrogen. In certain embodiments, $R^{1a}$ is optionally substituted vinyl; and $R^{1b}$ is hydrogen. In certain embodiments, $R^{1a}$ is unsubstituted vinyl; and $R^{1b}$ is hydrogen. In certain embodiments, $R^{1a}$ is optionally substituted allyl; and $R^{1b}$ is hydrogen. In certain embodiments, $R^{1a}$ is unsubstituted allyl; and $R^{1b}$ is hydrogen. In certain embodiments $R^{1a}$ is optionally substituted carbocyclyl; and $R^{1b}$ is hydrogen. In certain embodiments, $R^{1a}$ is optionally substituted $C_{3-6}$carbocyclyl; and $R^{1b}$ is hydrogen. In certain embodiments, $R^{1a}$ is optionally substituted cyclopropyl; and $R^{1b}$ is hydrogen. In certain embodiments, $R^{1a}$ is unsubstituted cyclopropyl; and $R^{1b}$ is hydrogen.

In certain embodiments, at least one of $R^{2a}$ and $R^{2b}$ is hydrogen. In certain embodiments, both $R^{2a}$ and $R^{2b}$ are hydrogen. In certain embodiments, neither $R^{2a}$ nor $R^{2b}$ are hydrogen. In certain embodiments, $R^{2a}$ is optionally substituted $C_{1-4}$alkyl; and $R^{2b}$ is hydrogen. In certain embodiments, $R^{2a}$ is optionally substituted $C_{1-2}$alkyl; and $R^{2b}$ is hydrogen. In certain embodiments, $R^{2a}$ is —$CH_3$; and $R^{2b}$ is hydrogen. In certain embodiments, both $R^{2a}$ and $R^{2b}$ are —$CH_3$. In certain embodiments, $R^{2a}$ is optionally substituted haloalkyl; and $R^{2b}$ is hydrogen. In certain embodiments, $R^{2a}$ is —$CF_3$; and $R^{2b}$ is hydrogen. In certain embodiments, $R^{2a}$ is halogen; and $R^{2b}$ is hydrogen. In certain embodiments, $R^{2a}$ is —F; and $R^{2b}$ is hydrogen. In certain embodiments, $R^{2a}$ is halogen; and $R^{2b}$ is $C_{1-6}$alkyl. In certain embodiments, $R^{2a}$ is —F; and $R^{2b}$ is $C_{1-6}$ alkyl. In certain embodiments, $R^{2a}$ is halogen; and $R^{2b}$ is —$CH_3$. In certain embodiments, $R^{2a}$ is —F; and $R^{2b}$ is —$CH_3$.

In certain embodiments, the carbon to which $R^4$ is attached is a stereocenter of the (R)-configuration. In certain embodiments, the carbon to which $R^4$ is attached is a stereocenter of the (S)-configuration. In certain embodiments, $R^3$ is hydrogen; and $R^4$ is not hydrogen. In certain embodiments, neither $R^3$ nor $R^4$ are hydrogen. In certain embodiments, $R^3$ is hydrogen. In certain embodiments, $R^3$ is optionally substituted $C_{1-6}$alkyl. In certain embodiments, $R^3$ is optionally substituted $C_{1-2}$alkyl. In certain embodiments, $R^3$ is —$CH_3$. In certain embodiments, $R^3$ is optionally substituted $C_{2-6}$alkenyl. In certain embodiments, $R^3$ is optionally substituted allyl. In certain embodiments, $R^3$ is unsubstituted allyl. In certain embodiments, $R^3$ is allyl substituted with one optionally substituted heteroaryl ring. In certain embodiments, $R^3$ is allyl substituted with one optionally substituted quinoline ring. In certain embodiments, $R^3$ is hydrogen; and $R^4$ is —$CH_3$. In certain embodiments, $R^3$ is optionally substituted $C_{1-6}$alkyl; and $R^4$ is —$CH_3$. In certain embodiments, $R^3$ is optionally substituted $C_{1-2}$alkyl; and $R^4$ is —$CH_3$. In certain embodiments, $R^3$ is —$CH_3$; and $R^4$ is —$CH_3$. In certain embodiments, $R^3$ is optionally substituted $C_{2-6}$alkenyl; and $R^4$ is —$CH_3$. In certain embodiments, $R^3$ is optionally substituted allyl; and $R^4$ is —$CH_3$. In certain embodiments, $R^3$ is unsubstituted allyl; and $R^4$ is —$CH_3$. In certain embodiments, $R^3$ is allyl substituted with one optionally substituted heteroaryl ring; and $R^4$ is —$CH_3$. In certain embodiments, $R^3$ is allyl substituted with one optionally substituted quinoline ring; and $R^4$ is —$CH_3$. In certain embodiments, $R^4$ is optionally substituted $C_{1-6}$alkyl. In certain embodiments, $R^4$ is optionally substituted $C_{1-2}$alkyl. In certain embodiments, $R^4$ is —$CH_3$. In certain embodiments, $R^4$ is optionally substituted $C_{2-6}$alkenyl. In certain embodiments, $R^4$ is optionally substituted allyl. In certain embodiments, $R^4$ is unsubstituted allyl. In certain embodiments, $R^4$ is allyl substituted with one optionally substituted heteroaryl ring. In certain embodiments, $R^4$ is allyl substituted with one optionally substituted quinoline ring. In certain embodiments, $R^4$ is —$CH_2CH_2OH$. In certain embodiments, $R^4$ is —$CH_2CH_2N(R^{22})_2$. In certain embodiments, $R^4$ is —$CH_2CH_2N(R^{22})_2$; and $R^{22}$ is —$CH_3$. In certain embodiments, $R^4$ is —$CH_2CHO$. In certain embodiments, $R^4$ is optionally substituted $C_{1-6}$alkyl; and $R^3$ is —$CH_3$. In certain embodiments, $R^4$ is optionally substituted $C_{1-2}$alkyl; and $R^3$ is —$CH_3$. In certain embodiments, $R^4$ is optionally substituted $C_{2-6}$alkenyl; and $R^3$ is —$CH_3$. In certain embodiments, $R^4$ is optionally substituted allyl; and $R^3$ is —$CH_3$. In certain embodiments, $R^4$ is unsubstituted allyl; and $R^3$ is —$CH_3$. In certain embodiments, $R^4$ is allyl substituted with one optionally substituted heteroaryl ring; and $R^3$ is —$CH_3$. In certain embodiments, $R^4$ is allyl substituted with one optionally substituted quinoline ring; and $R^3$ is —$CH_3$. In certain embodiments, $R^4$ is —$CH_2CH_2OH$; and $R^3$ is —$CH_3$. In certain embodiments, $R^4$ is —$CH_2CH_2N(R^{22})_2$; and $R^3$ is —$CH_3$. In certain embodiments, $R^4$ is —$CH_2CH_2N(R^{22})_2$; $R^{22}$ is —$CH_3$; and $R^3$ is —$CH_3$. In certain embodiments, $R^4$ is —$CH_2CHO$; and $R^3$ is —$CH_3$. In certain embodiments, $R^4$ is optionally substituted $C_{1-6}$alkyl; and $R^3$ is hydrogen. In certain embodiments, $R^4$ is optionally substituted $C_{1-2}$alkyl; and $R^3$ is hydrogen. In certain embodiments, $R^4$ is optionally substituted $C_{2-6}$alkenyl; and $R^3$ is hydrogen. In certain embodiments, $R^4$ is optionally substituted allyl; and $R^3$ is hydrogen. In certain embodiments, $R^4$ is unsubstituted allyl; and $R^3$ is hydrogen. In certain embodiments, $R^4$ is allyl substituted with one optionally substituted heteroaryl ring; and $R^3$ is hydrogen. In certain embodiments, $R^4$ is allyl substituted with one optionally substituted quinoline ring; and $R^3$ is hydrogen. In certain embodiments, $R^4$ is —$CH_2CH_2OH$; and $R^3$ is hydrogen. In certain embodiments, $R^4$ is —$CH_2CH_2N(R^{22})_2$; and $R^3$ is hydrogen. In certain embodiments, $R^4$ is —$CH_2CH_2N(R^{22})_2$; $R^{22}$ is —$CH_3$; and $R^3$ is hydrogen. In certain embodiments, $R^4$ is —$CH_2CHO$; and $R^3$ is hydrogen. In certain embodiments, $R^4$ is optionally substituted $C_{1-6}$alkyl; and $R^{21}$ is hydrogen. In certain embodiments, $R^4$ is optionally substituted $C_{1-2}$alkyl; and $R^{21}$ is hydrogen. In certain embodiments, $R^4$ is optionally substituted $C_{2-6}$alkenyl; and $R^{21}$ is hydrogen. In certain embodiments, $R^4$ is optionally substituted allyl; and $R^{21}$ is hydrogen. In certain embodiments, $R^4$ is unsubstituted allyl; and $R^{21}$ is hydrogen. In certain embodiments, $R^4$ is allyl substituted with one optionally substituted heteroaryl ring; and $R^{21}$ is hydrogen. In certain embodiments, $R^4$ is allyl substituted with one optionally substituted quinoline ring; and $R^{21}$ is hydrogen. In certain embodiments, $R^4$ is —$CH_2CH_2OH$; and $R^{21}$ is hydrogen. In certain embodiments, $R^4$ is —$CH_2CH_2N(R^{22})_2$; and $R^{21}$ is hydrogen. In certain embodiments, $R^4$ is —$CH_2CH_2N(R^{22})_2$; $R^{22}$ is —$CH_3$; and $R^{21}$ is hydrogen. In certain embodiments, $R^4$ is —$CH_2CHO$; and $R^{21}$ is hydrogen.

In certain embodiments, $R^9$ is hydrogen. In certain embodiments, $R^9$ is not hydrogen. In certain embodiments, $R^9$ is an oxygen protecting group. In certain embodiments, $R^9$ is

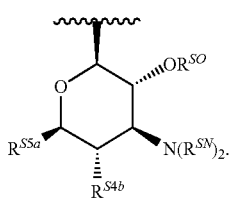

In certain embodiments, $R^{SO}$ is hydrogen. In certain embodiments, $R^{SO}$ is an oxygen protecting group. In certain embodiments, $R^9$ is methyl carbonate. In certain embodiments, at least one $R^{SN}$ is hydrogen. In certain embodiments, at least one $R^{SN}$ is $-CH_3$. In certain embodiments, one $R^{SN}$ is $-CH_3$; and the second $R^{SN}$ is hydrogen. In certain embodiments, both $R^{SN}$ groups are $-CH_3$. In certain embodiments, $R^{S4b}$ is hydrogen. In certain embodiments, $R^{S4b}$ is not hydrogen. In certain embodiments, $R^{S4b}$ is $-OR^{SO}$; and $R^{SO}$ is hydrogen. In certain embodiments, $R^{S4b}$ is $-OR^{SO}$; and $R^{SO}$ is an oxygen protecting group. In certain embodiments, $R^{S5a}$ is optionally substituted alkyl. In certain embodiments, $R^{S5a}$ is alkoxyalkyl. In certain embodiments, $R^{S5a}$ is $-CH_2OH$. In certain embodiments, $R^{S5a}$ is $-CH_2OBz$. In certain embodiments, $R^{S5a}$ is aminoalkyl. In certain embodiments, $R^{S5a}$ is $-CH_2NH_2$. In certain embodiments, $R^9$ is

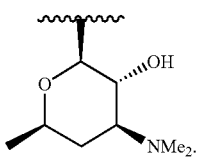

In certain embodiments, $R^9$ is

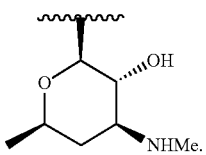 [SMILES: *[C@@H]1O[C@H](C)C[C@H](NC)[C@H]1O]

In certain embodiments, $R^9$ is

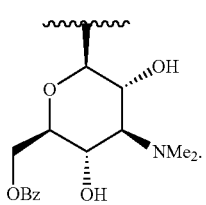

In certain embodiments, $R^9$ is

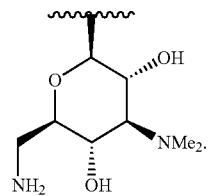

In certain embodiments, $R^9$ is

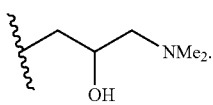 [SMILES: *CC(O)CN(C)C]

In certain embodiments, the carbon to which $R^{5a}$ and $R^{5b}$ is attached is a stereocenter of the (R)-configuration. In certain embodiments, the carbon to which $R^{5a}$ and $R^{5b}$ is attached is a stereocenter of the (S)-configuration. In certain embodiments, at least one of $R^{5a}$ and $R^{5b}$ is hydrogen. In certain embodiments, both $R^{5a}$ and $R^{5b}$ are hydrogen. In certain embodiments, neither $R^{5a}$ nor $R^{5b}$ are hydrogen. In certain embodiments, at least one instance of $R^{5a}$ and $R^{5b}$ is optionally substituted alkyl. In certain embodiments, at least one instance of $R^{5a}$ and $R^{5b}$ is optionally substituted $C_{1-4}$alkyl. In certain embodiments, at least one instance of $R^{5a}$ and $R^{5b}$ is optionally substituted $C_{1-2}$alkyl. In certain embodiments, at least one instance of $R^{5a}$ and $R^{5b}$ is unsubstituted $C_{1-2}$alkyl. In certain embodiments, at least one instance of $R^{5a}$ and $R^{5b}$ is $-CH_3$. In certain embodiments, $R^{5a}$ is optionally substituted alkyl; and $R^{5b}$ is hydrogen. In certain embodiments, $R^{5a}$ is optionally substituted $C_{1-6}$alkyl; and $R^{5b}$ is hydrogen. In certain embodiments, $R^{5a}$ is optionally substituted $C_{1-2}$alkyl; and $R^{5b}$ is hydrogen. In certain embodiments, $R^{5a}$ is unsubstituted $C_{1-2}$alkyl; and $R^{5b}$ is hydrogen. In certain embodiments, $R^{5a}$ is $-CH_3$; and $R^{5b}$ is hydrogen. In certain embodiments, both instances of $R^{5a}$ and $R^{5b}$ are $-CH_3$. In certain embodiments, neither $R^{5a}$ nor $R^{5b}$ is $-CH_3$.

In certain embodiments, $R^{17}$ is hydrogen. In certain embodiments, $R^{17}$ is not hydrogen. In certain embodiments, $R^{17}$ is an oxygen protecting group. In certain embodiments, $R^{17}$ is $-C(=O)R^{Z8}$.

In certain embodiments, the carbon to which $R^6$ and $R^{10}$ is attached is a stereocenter of the (R)-configuration. In certain embodiments, the carbon to which $R^6$ and $R^{10}$ is attached is a stereocenter of the (S)-configuration. In certain embodiments, at least one of $R^6$ and $R^{10}$ is hydrogen. In certain embodiments, both $R^6$ and $R^{10}$ are hydrogen. In certain embodiments, neither $R^6$ nor $R^{10}$ are hydrogen. In certain embodiments, at least one instance of $R^6$ and $R^{10}$ is optionally substituted alkyl. In certain embodiments, at least one instance of $R^6$ and $R^{10}$ is optionally substituted $C_{1-6}$alkyl. In certain embodiments, at least one instance of $R^6$ and $R^{10}$ is optionally substituted $C_{1-2}$alkyl. In certain embodiments, at least one instance of $R^6$ and $R^{10}$ is $-CH_3$. In certain embodiments, at least one instance of $R^6$ and $R^{10}$ is $-CH_2CN$. In certain embodiments, at least one instance of $R^6$ and $R^{10}$ is $-CH_2C(=O)OR^{32}$; and $R^{32}$ is optionally substituted alkyl or hydrogen. In certain embodiments, at least one instance of $R^6$ and $R^{10}$ is optionally substituted heteroarkyl. In certain embodiments, at least one instance of $R^6$ and $R^{10}$ is optionally substituted pyrazolylalkyl. In certain embodiments, at least one instance of $R^6$ and $R^{10}$ is imidazolylalkyl. In certain embodiments, at least one instance of $R^6$ and $R^{10}$ is thiazolylalkyl. In certain embodiments, at least one instance of $R^6$ and $R^{10}$ is oxazolylalkyl. In certain embodiments, at least one instance of $R^6$ and $R^{10}$ is pyridinylalkyl. In certain embodiments, at least one instance of $R^6$ and $R^{10}$ is pyrimidinylalkyl. In certain embodiments, at least one instance of $R^6$ and $R^{10}$ is pyrazinylalkyl. In certain embodiments, at least one instance of $R^6$ and $R^{10}$ is optionally substituted alkenyl. In certain embodiments, at least one instance of $R^6$ and $R^{10}$ is optionally substituted allyl. In certain embodiments, at least one instance of $R^6$ and $R^{10}$ is unsubstituted allyl. In certain embodiments, at least one instance of $R^6$ and $R^{10}$ is optionally substituted aralkyl. In certain embodiments, at least one instance of $R^6$ and $R^{10}$ is optionally substituted benzyl. In certain embodiments, at least one instance of $R^6$ and $R^{10}$ is unsubstituted benzyl. In certain embodiments, $R^6$ is optionally substituted alkyl; and $R^{10}$ is hydrogen. In certain embodiments, $R^6$ is optionally substituted $C_{1-2}$alkyl; and $R^{10}$ is hydrogen. In certain embodiments, $R^6$ is optionally substituted $C_{1-2}$alkyl; and $R^{10}$ is hydrogen. In certain embodiments, $R^6$ is —$CH_3$; and $R^{10}$ is hydrogen. In certain embodiments, $R^6$ is —$CH_2CN$; and $R^{10}$ is hydrogen. In certain embodiments, $R^6$ is —$CH_2C(=O)OR^{32}$; $R^{32}$ is optionally substituted alkyl or hydrogen; and $R^{10}$ is hydrogen. In certain embodiments, $R^6$ is optionally substituted heteroaralkyl; and $R^{10}$ is hydrogen. In certain embodiments, $R^6$ is optionally substituted pyrazolylalkyl; and $R^{10}$ is hydrogen. In certain embodiments, $R^6$ is imidazolylalkyl; and $R^{10}$ is hydrogen. In certain embodiments, $R^6$ is thiazolylalkyl; and $R^{10}$ is hydrogen. In certain embodiments, $R^6$ is oxazolylalkyl; and $R^{10}$ is hydrogen. In certain embodiments, $R^6$ is pyridinylalkyl; and $R^{10}$ is hydrogen. In certain embodiments, $R^6$ is pyrimidinylalkyl; and $R^{10}$ is hydrogen. In certain embodiments, $R^6$ is pyrazinylalkyl; and $R^{10}$ is hydrogen. In certain embodiments, $R^6$ is optionally substituted alkenyl; and $R^{10}$ is hydrogen. In certain embodiments, $R^6$ is optionally substituted allyl; and $R^{10}$ is hydrogen. In certain embodiments, $R^6$ is unsubstituted allyl; and $R^{10}$ is hydrogen. In certain embodiments, $R^6$ is optionally substituted aralkyl; and $R^{10}$ is hydrogen. In certain embodiments, $R^6$ is optionally substituted benzyl; and $R^{10}$ is hydrogen. In certain embodiments, $R^6$ is unsubstituted benzyl; and $R^{10}$ is hydrogen. In certain embodiments, at least one instance of $R^6$ and $R^{10}$ is halogen. In certain embodiments, at least one instance of $R^6$ and $R^{10}$ is fluorine. In certain embodiments, both $R^6$ and $R^{10}$ are halogen. In certain embodiments, both $R^6$ and $R^{10}$ are fluorine. In certain embodiments, $R^6$ is optionally substituted alkyl; and $R^{10}$ is halogen. In certain embodiments, $R^6$ is optionally substituted $C_{1-6}$alkyl; and $R^{10}$ is halogen. In certain embodiments, $R^6$ is optionally substituted $C_{1-2}$alkyl; and $R^{10}$ is halogen. In certain embodiments, $R^6$ is —$CH_3$; and $R^{10}$ is halogen. In certain embodiments, $R^6$ is optionally substituted alkyl; and $R^{10}$ is fluorine. In certain embodiments, $R^6$ is optionally substituted $C_{1-6}$alkyl; and $R^{10}$ is fluorine. In certain embodiments, $R^6$ is optionally substituted $C_{1-2}$alkyl; and $R^{10}$ is fluorine. In certain embodiments, $R^6$ is —$CH_3$; and $R^{10}$ is fluorine.

In certain embodiments, $R^{14}$ is hydrogen. In certain embodiments, $R^{14}$ is not hydrogen. In certain embodiments, $R^{14}$ is

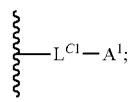

and $A^1$ is —$N_3$. In certain embodiments, $R^{14}$ is

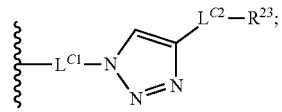

and $L^{C2}$ is a bond. In certain embodiments, $L^{C1}$ is a linking group comprising at least one instance of optionally substituted alkylene. In certain embodiments, $L^{C1}$ is a linking group comprising at least one instance of substituted or unsubstituted $C_{3-6}$-alkylene. In certain embodiments, $L^{C1}$ is an alkylene linking group of the formula —$(CH_2)_n$—, wherein n is 3, 4, or 5. In certain embodiments, $L^{C1}$ is a linking group comprising at least one instance of optionally substituted alkenylene. In certain embodiments, $L^{C1}$ is a linking group comprising at least one instance of substituted or unsubstituted $C_{3-6}$alkenylene. In certain embodiments, $L^{C1}$ is a linking group comprising at least one instance of optionally substituted alkynylene. In certain embodiments, $L^{C1}$ is a linking group comprising at least one instance of substituted or unsubstituted $C_{3-6}$alkynylene. In certain embodiments, $R^{23}$ is optionally substituted aryl. In certain embodiments, $R^{23}$ is optionally substituted phenyl. In certain embodiments, $R^{23}$ is optionally substituted 5-6 membered heteroaryl. In certain embodiments, $R^{23}$ is optionally substituted aniline. In certain embodiments, $R^{23}$ is optionally substituted pyridizine. In certain embodiments, $R^{23}$ is optionally substituted pyridine. In certain embodiments, $R^{23}$ is optionally substituted aminopyridine. In certain embodiments, $R^{23}$ is optionally substituted thiazole. In certain embodiments, $R^{23}$ is optionally substituted aminothiazole. In certain embodiments, $R^{23}$ is optionally substituted thiadiazole. In certain embodiments, $R^{23}$ is optionally substituted aminothiadiazole. In certain embodiments, $R^{23}$ is optionally substituted 5,6 fused-bicyclic heteroaryl. In certain embodiments, $R^{23}$ is optionally substituted benzothiazole.

In certain embodiments, known ketolides, such as the ketolides disclosed in FIG. 1, are specifically excluded. In certain embodiments, ketolides as disclosed in International Patent Application No. PCT/US2014/033025, filed Apr. 4, 2014, are specifically excluded. In certain embodiments, ketolides:

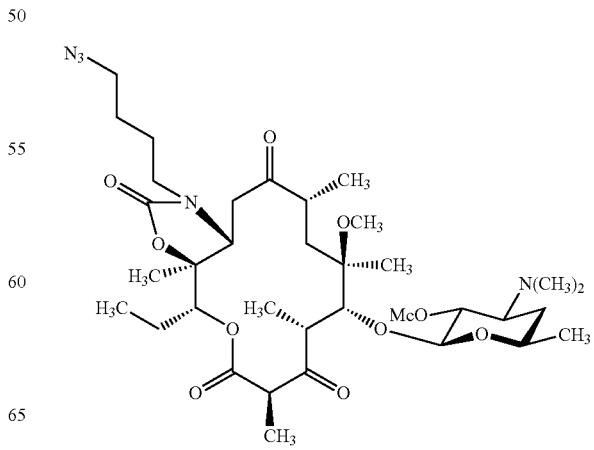

205
-continued
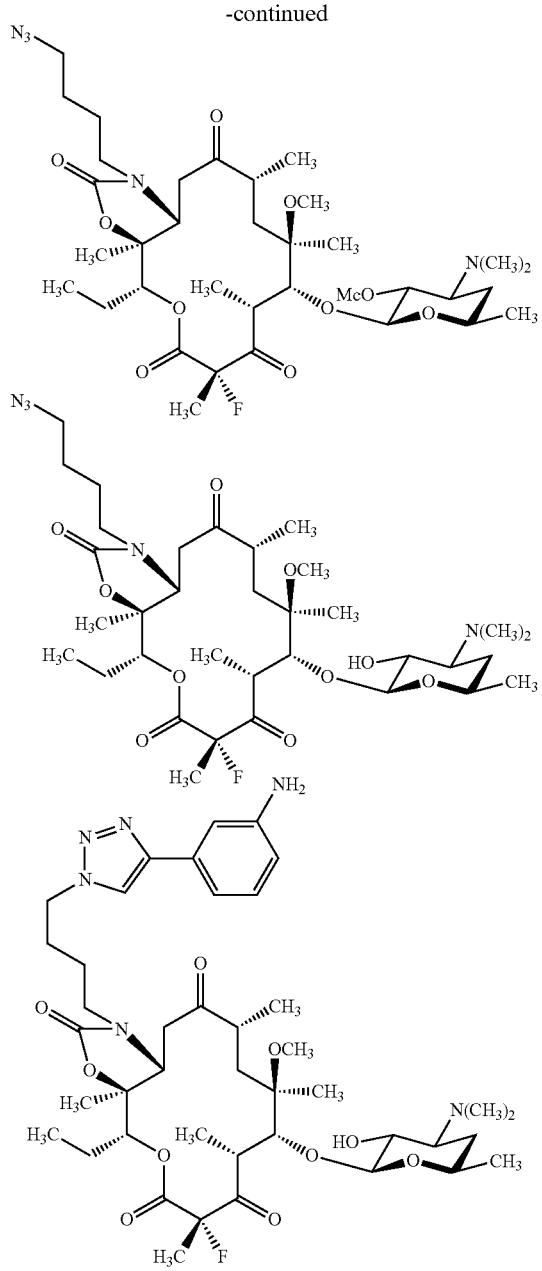
206
-continued
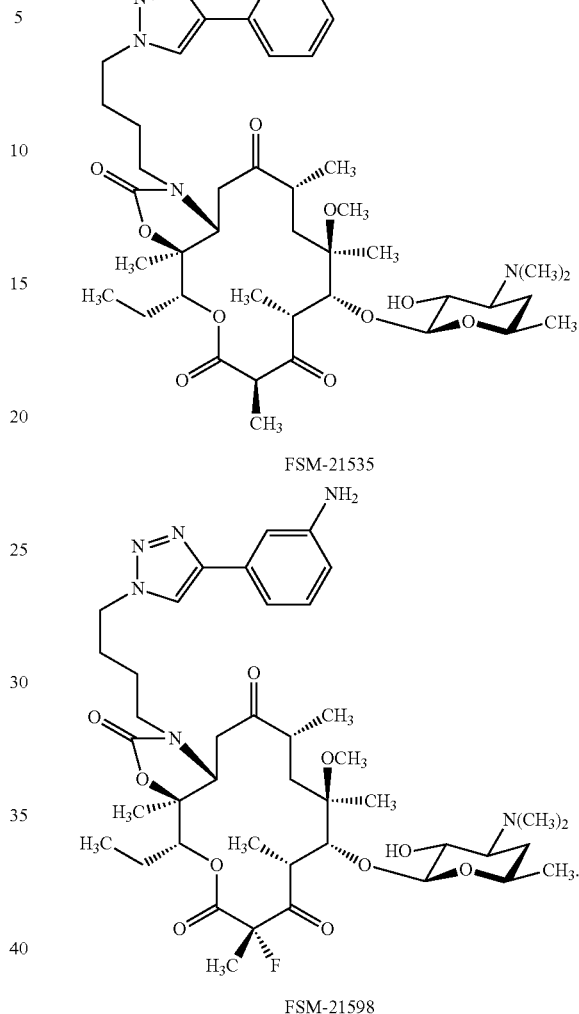
FSM-21535
FSM-21598
and salts thereof, are specifically excluded.
Exemplary novel ketolides of the present invention include, but are not limited to the compounds and salts thereof in Table 1.
TABLE 1
Exemplary Ketolides
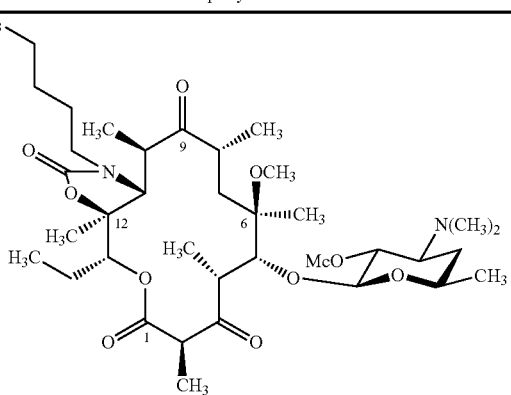

TABLE 1-continued
Exemplary Ketolides
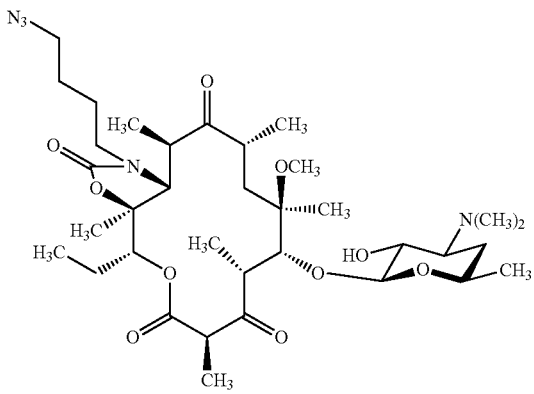
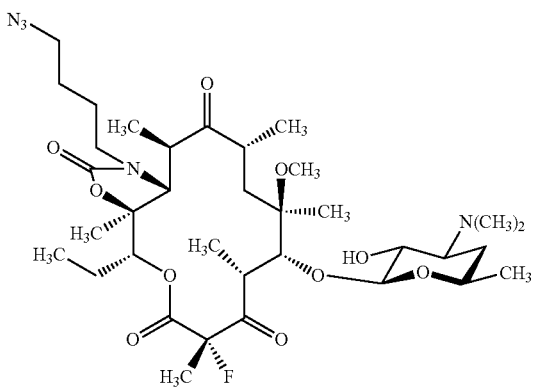
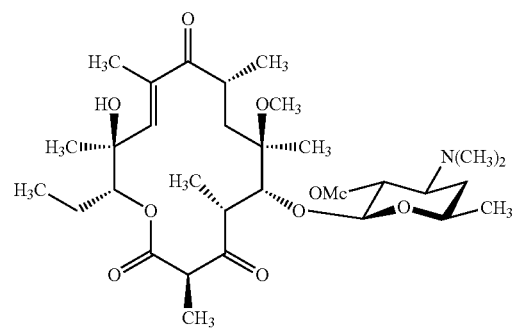
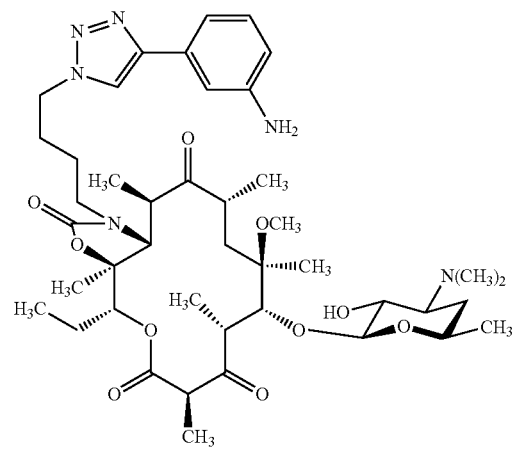

TABLE 1-continued
Exemplary Ketolides
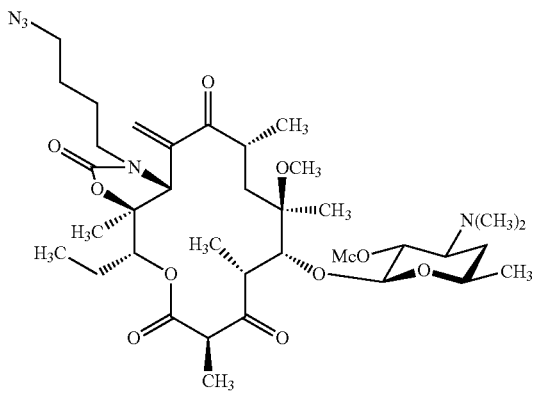
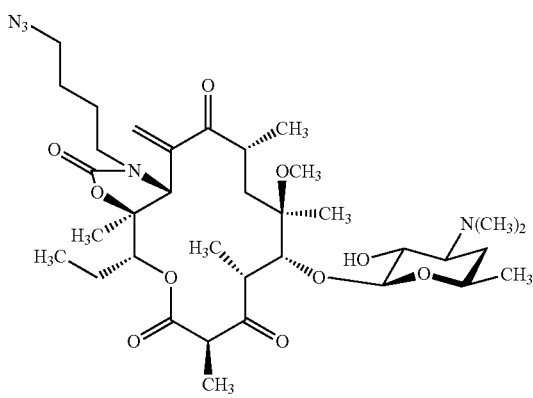
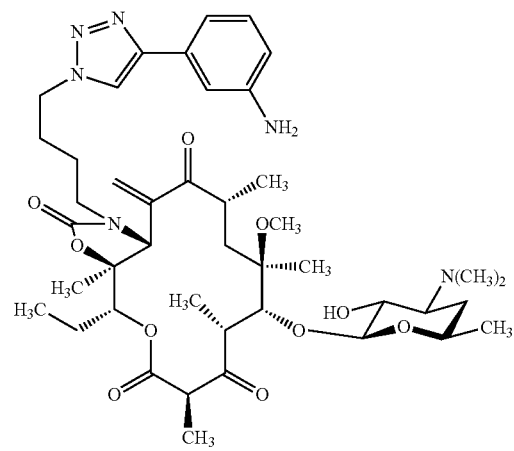
FSM-21828

TABLE 1-continued
Exemplary Ketolides
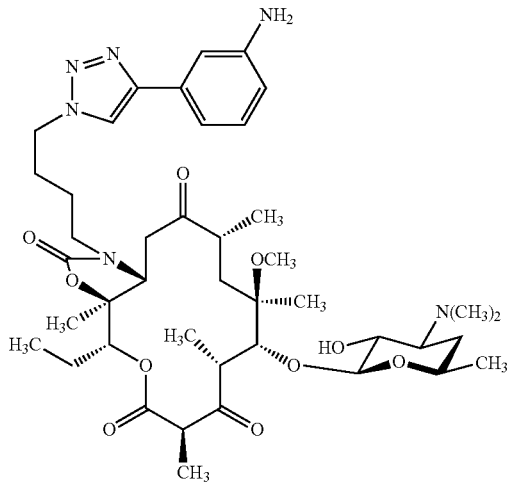
FSM-21535
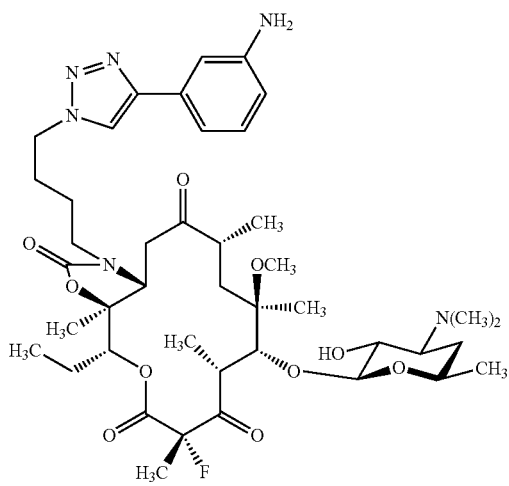
FSM-21598
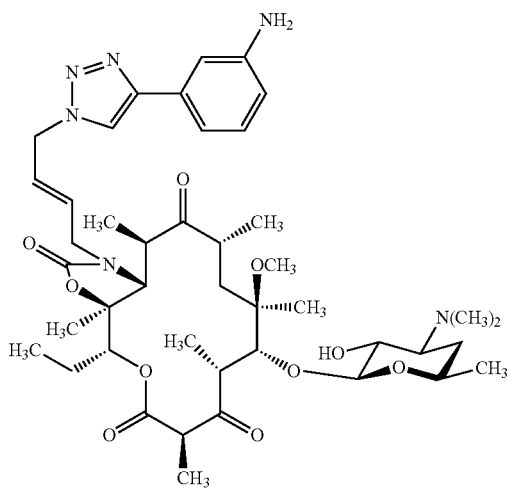
FSM-11561

TABLE 1-continued
Exemplary Ketolides
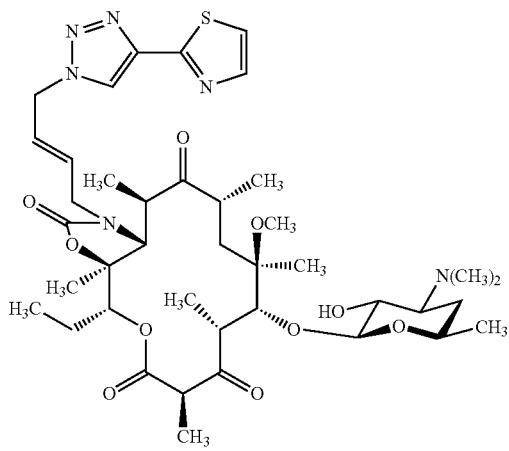
FSM-11559
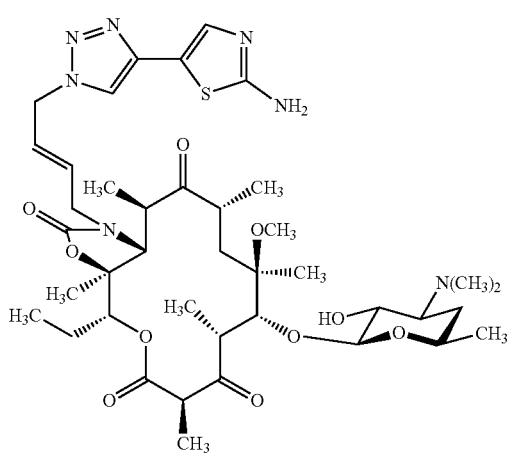
FSM-100237
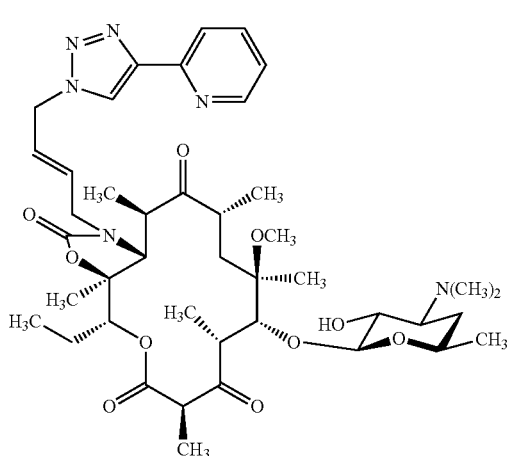
FSM-100341

TABLE 1-continued
Exemplary Ketolides
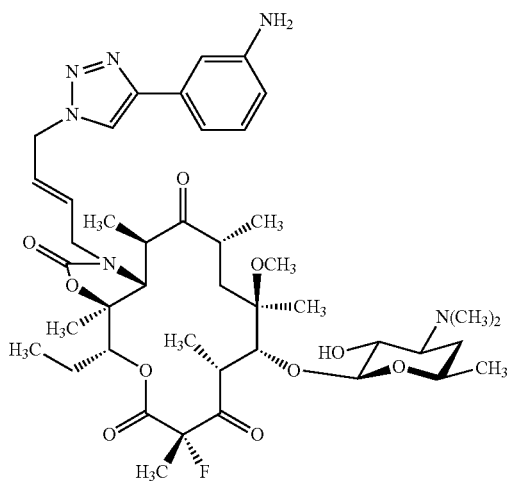
FSM-11563
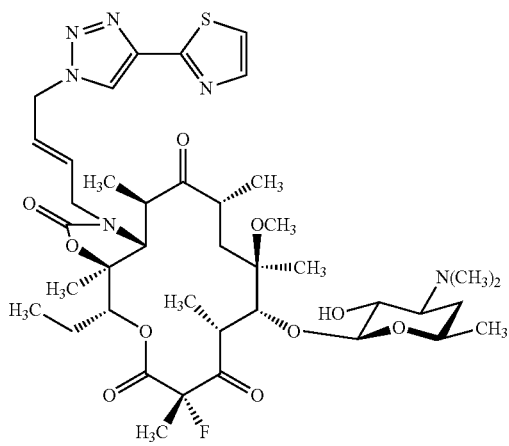
FSM-11562
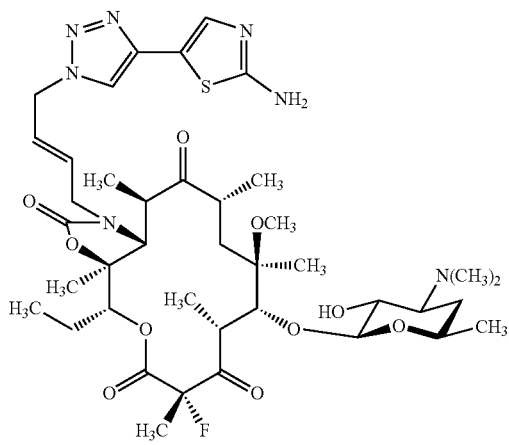
FSM-100240

TABLE 1-continued
Exemplary Ketolides
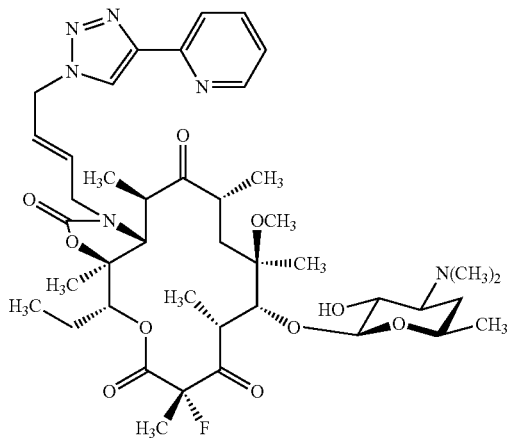
FSM-100383
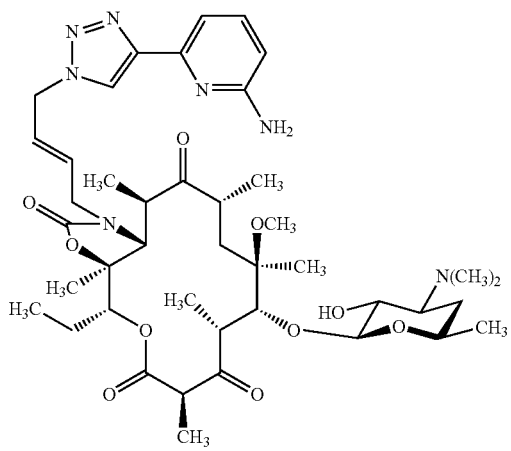
FSM-100364
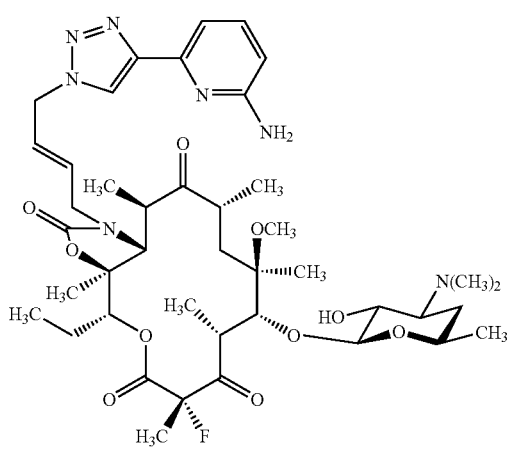
FSM-100407

TABLE 1-continued
Exemplary Ketolides
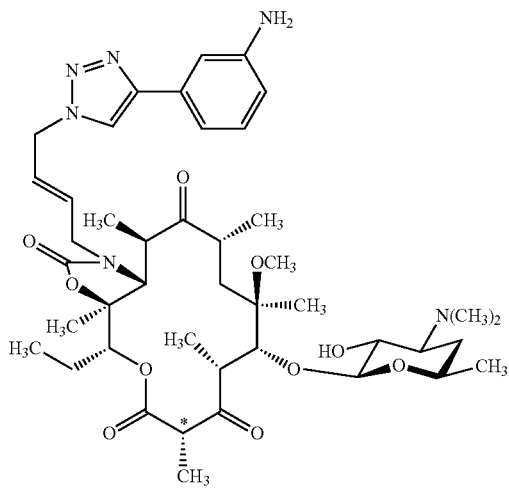
FSM-100432
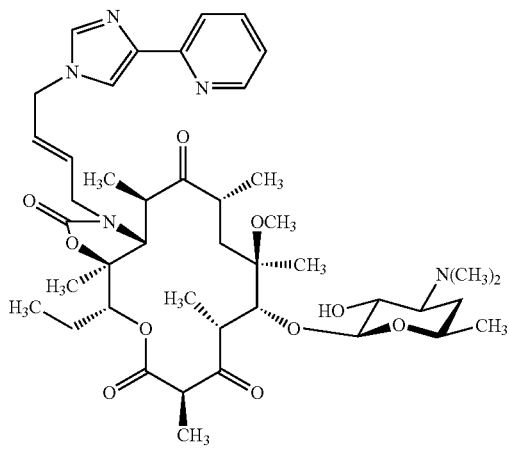
FSM-100421
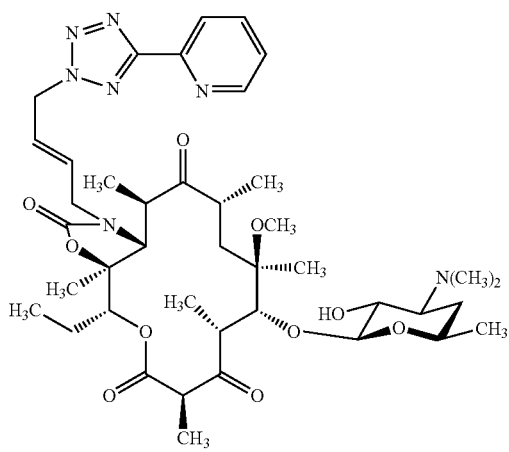
FSM-100371

TABLE 1-continued
Exemplary Ketolides
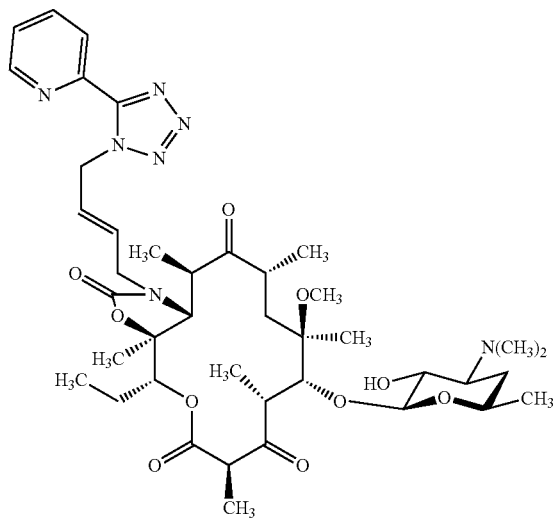
FSM-100376
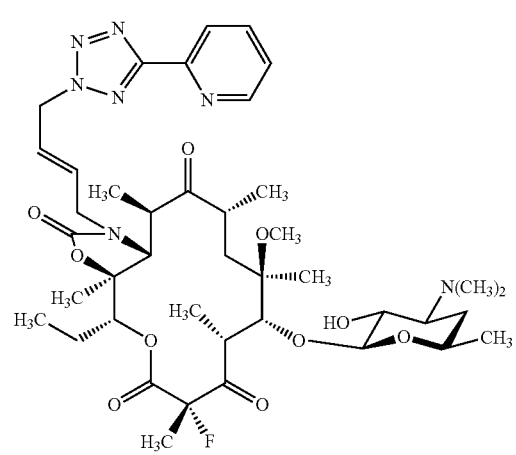
FSM-100389
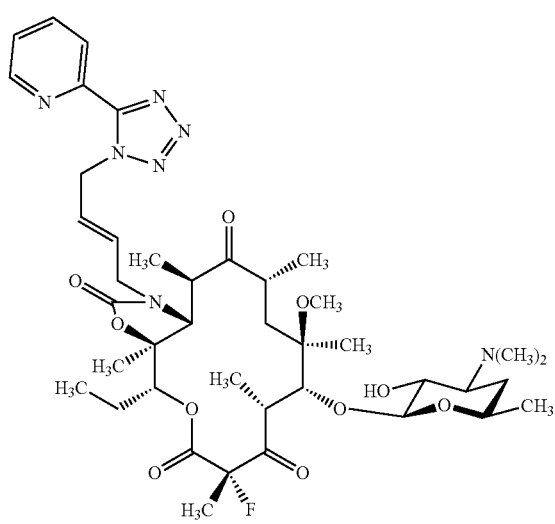
FSM-100386

TABLE 1-continued
Exemplary Ketolides
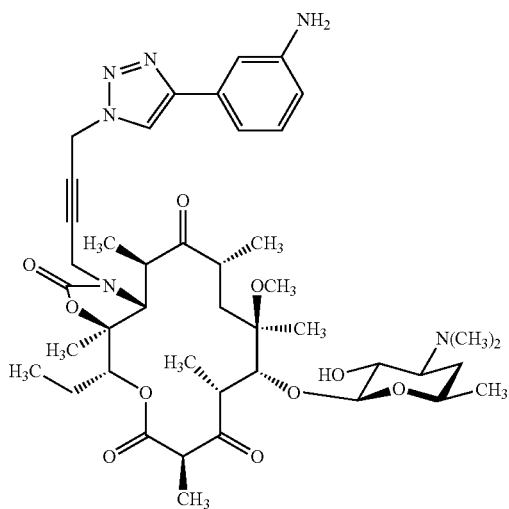
FSM-100239
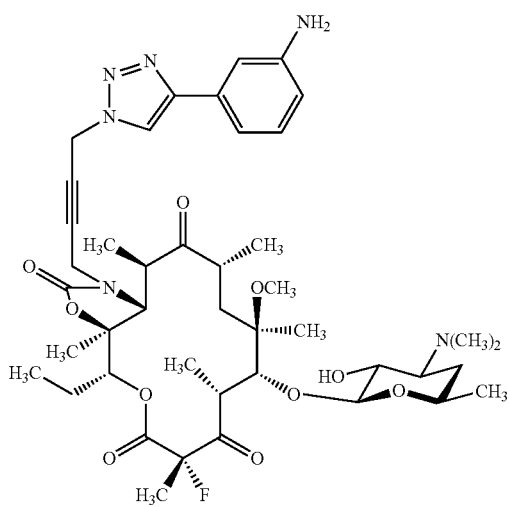
FSM-100426
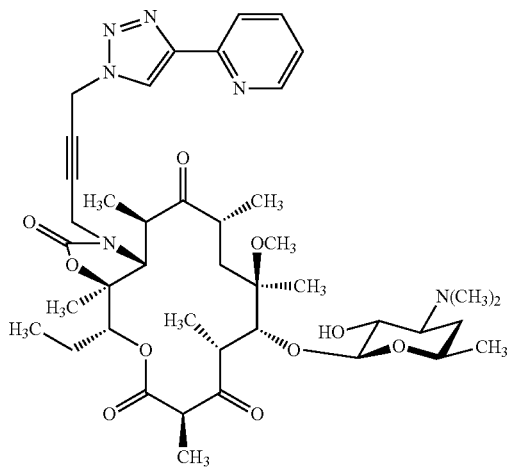
FSM-100479

TABLE 1-continued
Exemplary Ketolides
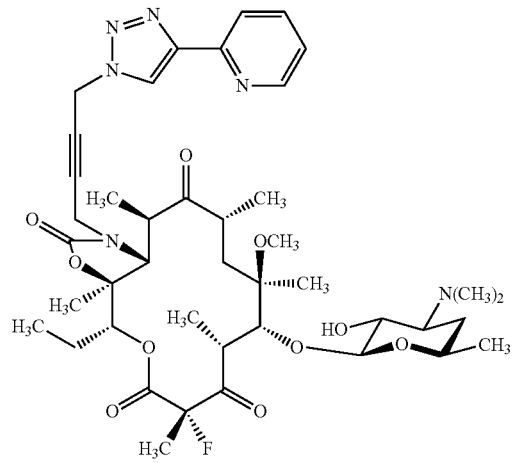
FSM-100490
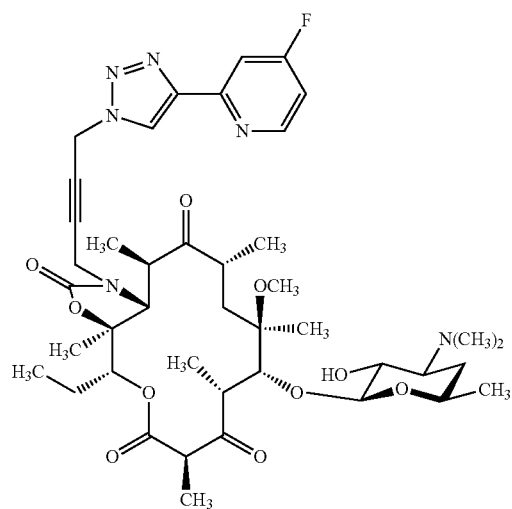
FSM-100566
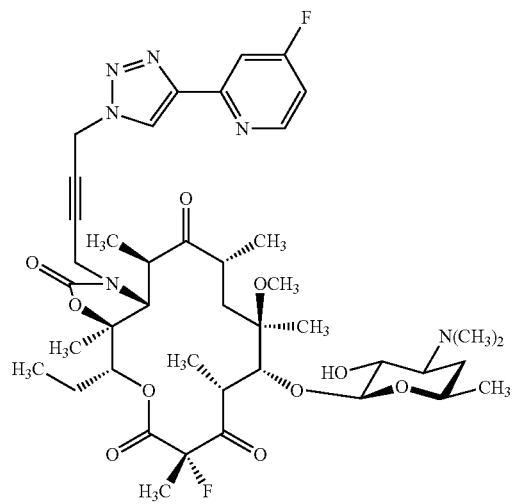
FSM-100563

TABLE 1-continued
Exemplary Ketolides
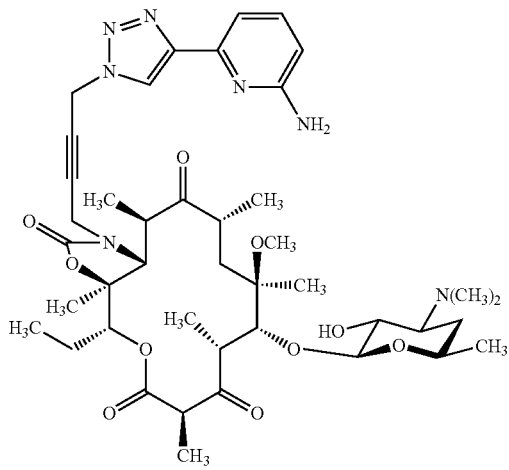
FSM-100551
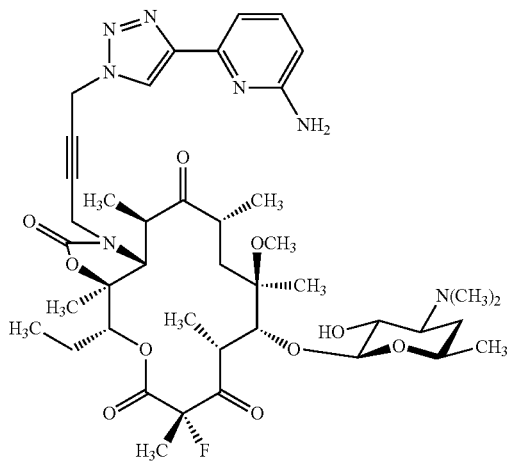
FSM-100573
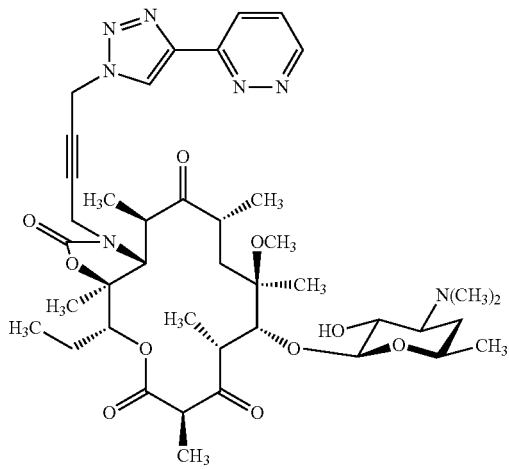
FSM-130216

TABLE 1-continued
Exemplary Ketolides
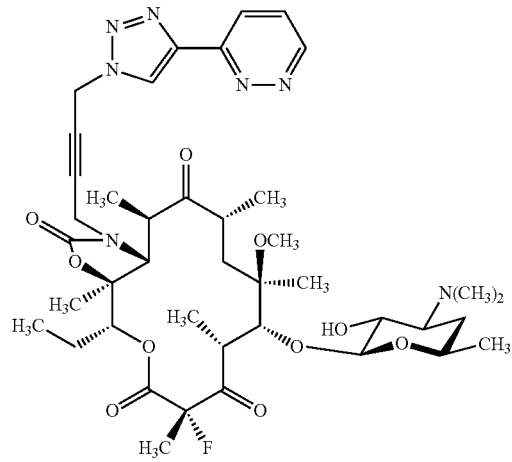
FSM-130217
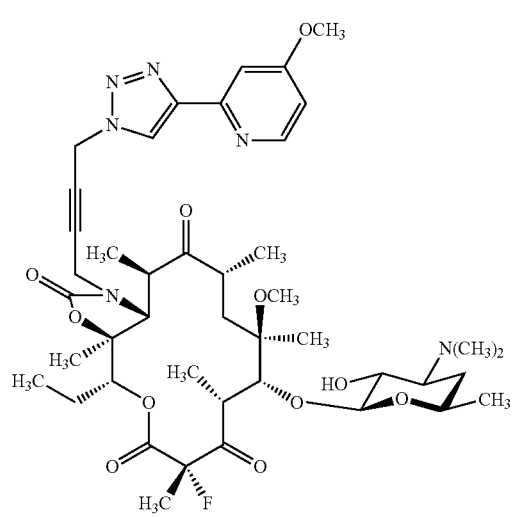
FSM-100576
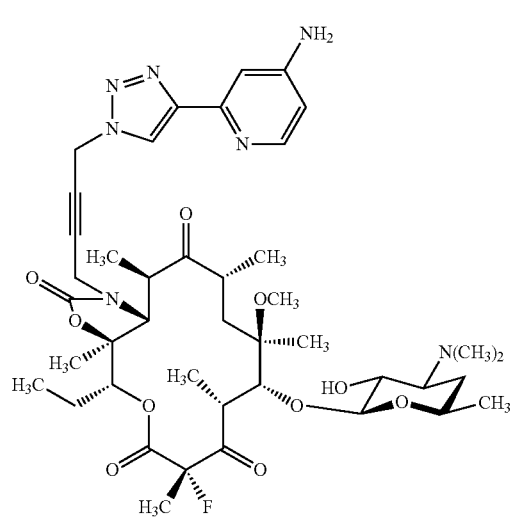
FSM-100593

TABLE 1-continued
Exemplary Ketolides
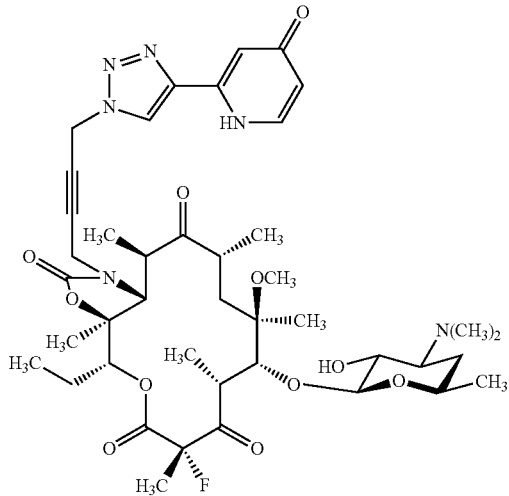
FSM-100597
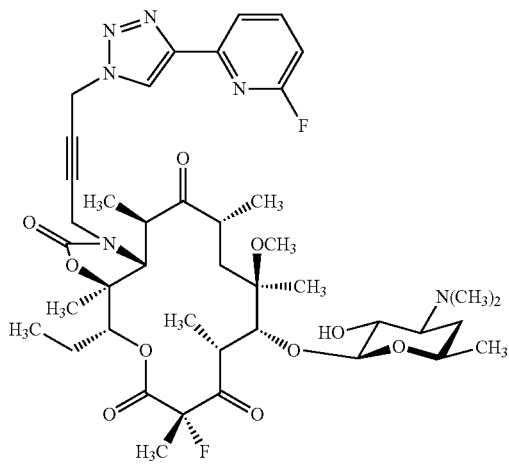
FSM-100627
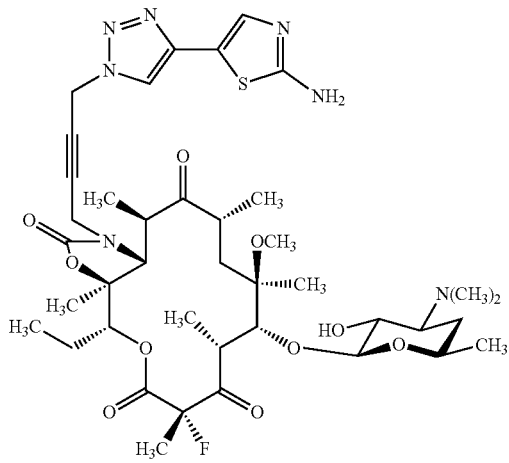
FSM-100633

TABLE 1-continued
Exemplary Ketolides
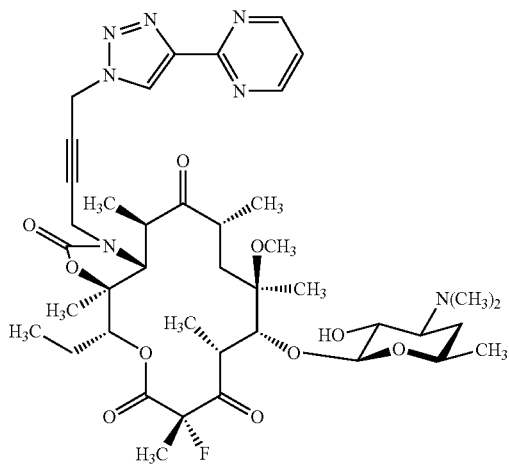
FSM-22741
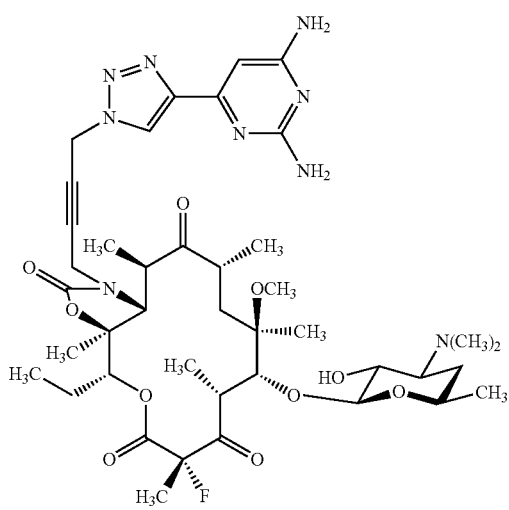
FSM-22742
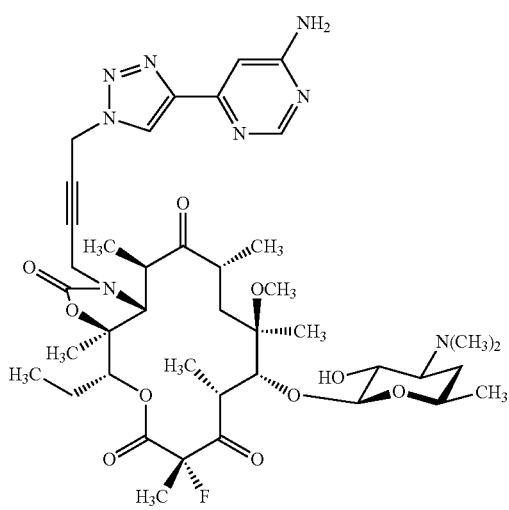
FSM-22745

TABLE 1-continued
Exemplary Ketolides
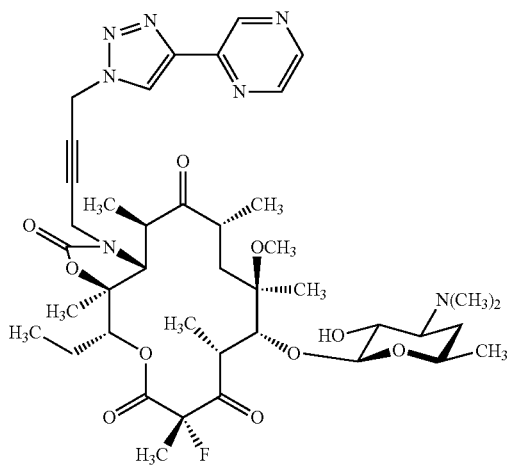
FSM-22746
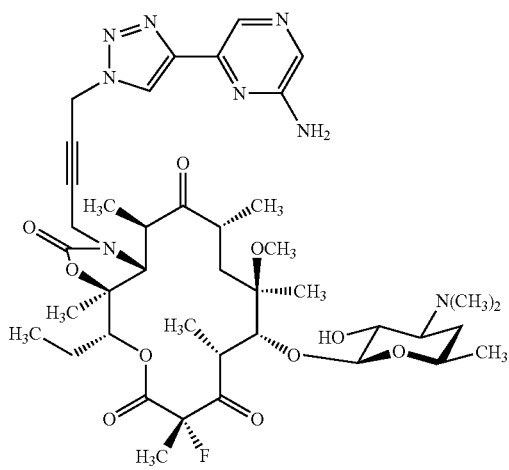
FSM-22747
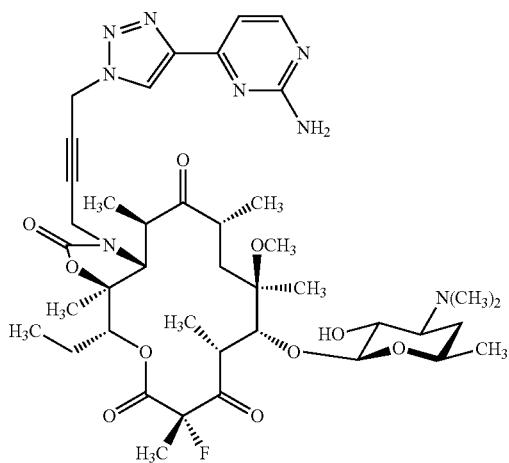
FSM-22748

TABLE 1-continued
Exemplary Ketolides
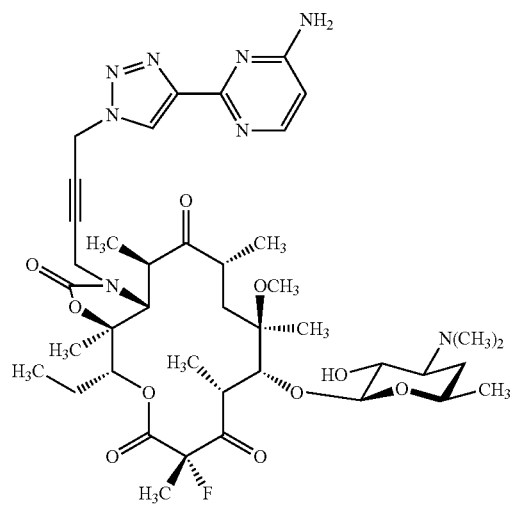
FSM-22749
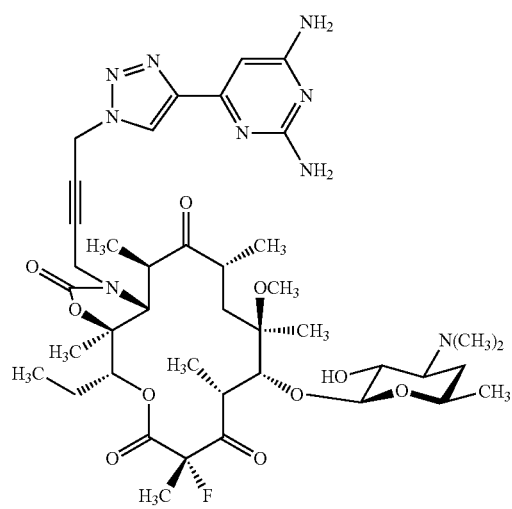
FSM-22750
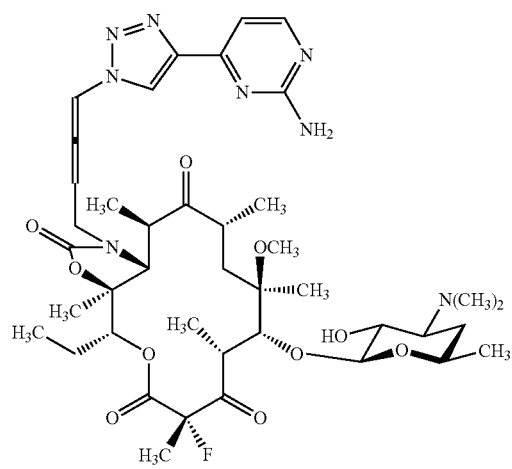
FSM-22737

TABLE 1-continued
Exemplary Ketolides
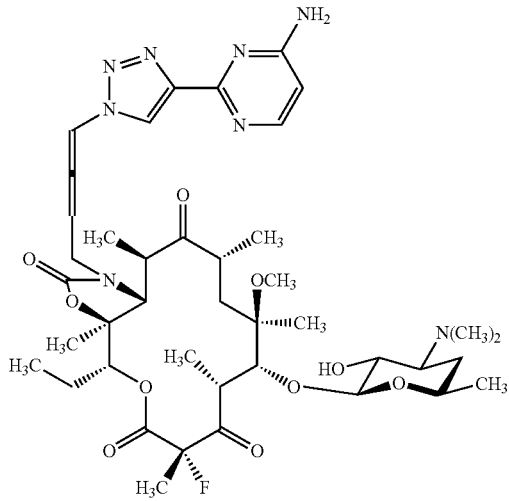
FSM-22738
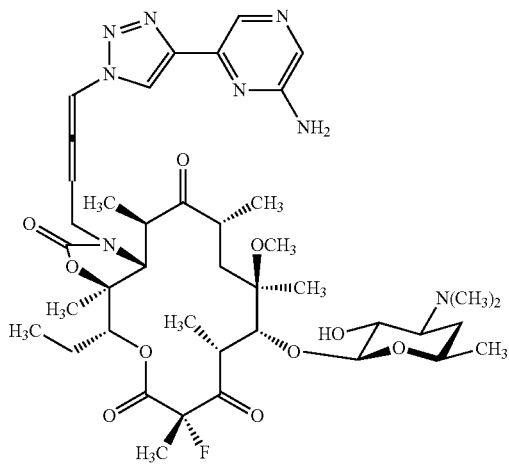
FSM-22739
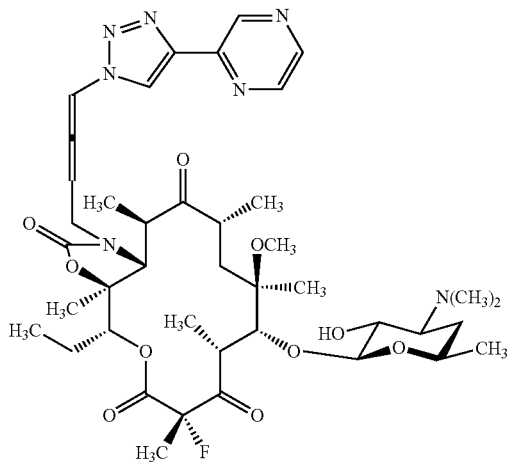
FSM-22740

TABLE 1-continued
Exemplary Ketolides
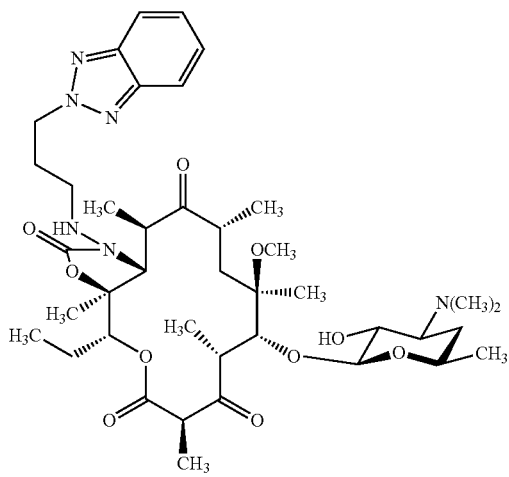
FSM-140132
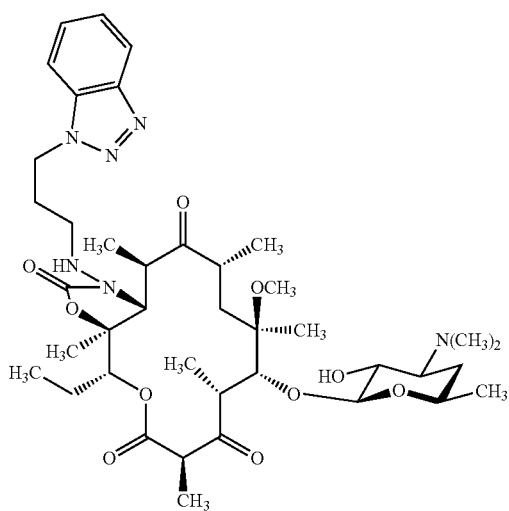
FSM-140133
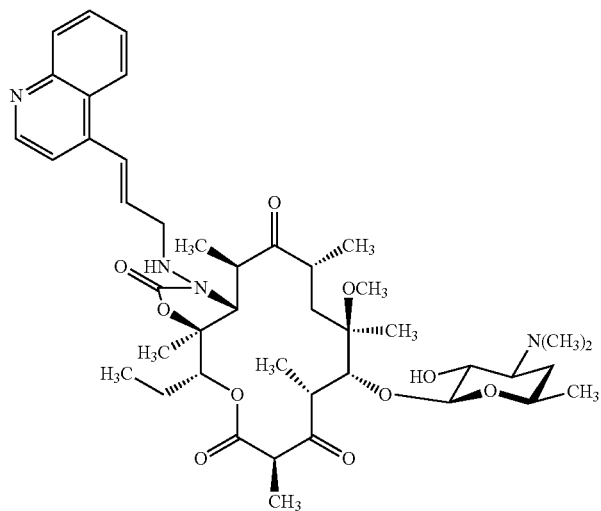
FSM-140135

TABLE 1-continued
Exemplary Ketolides
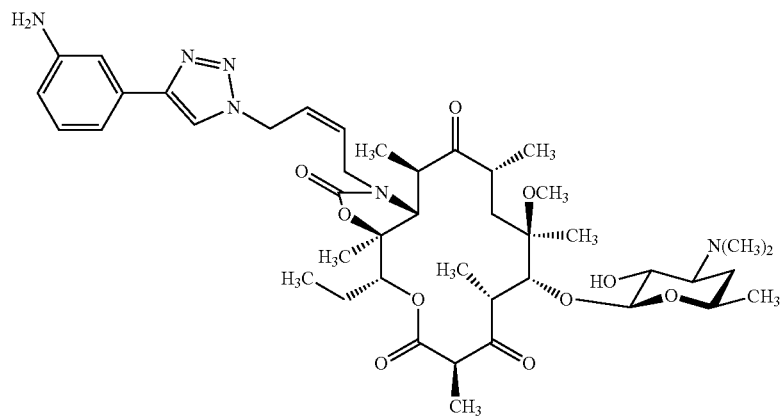
FSM-100423
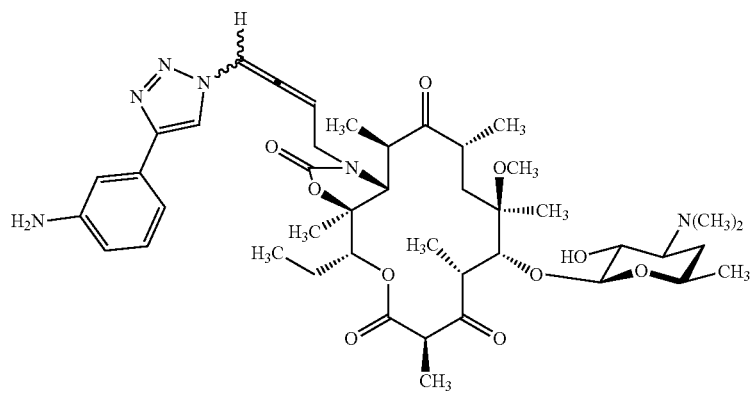
FSM-100427 Diastereomer 1
FSM-100433 Diastereomer 2
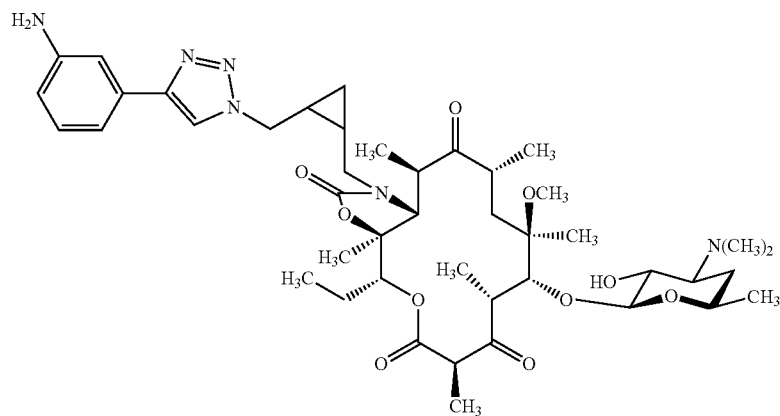
FSM-100429

TABLE 1-continued

Exemplary Ketolides

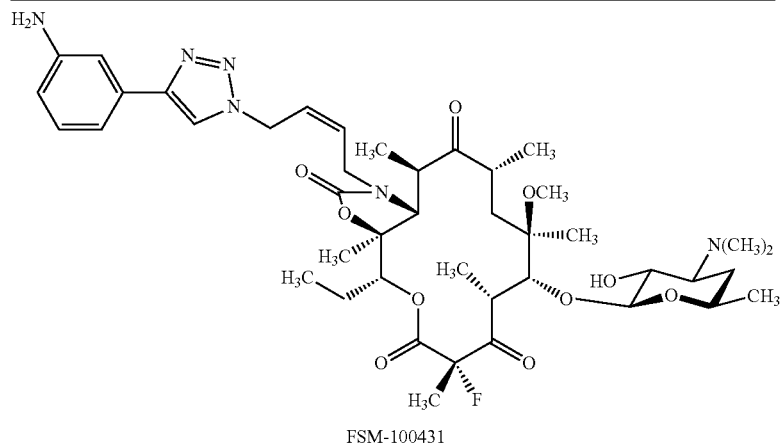

FSM-100431

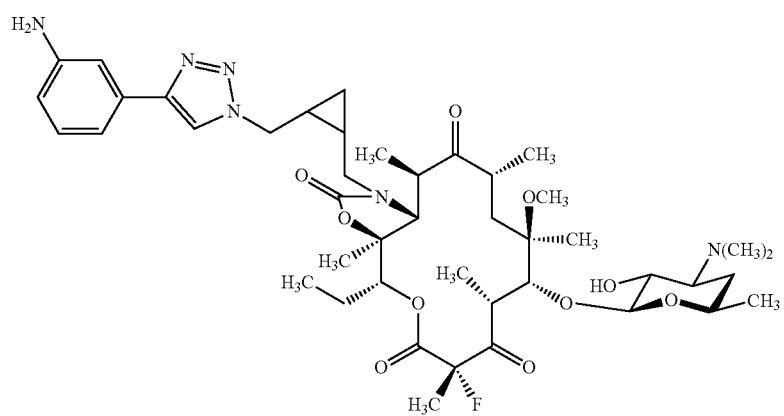

FSM-100439 Diastereomer 1
FSM-100441 Diastereomer 2

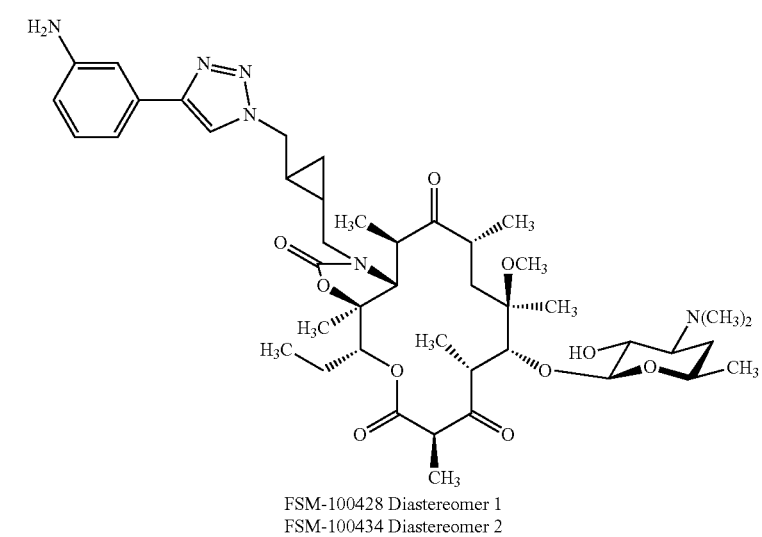

FSM-100428 Diastereomer 1
FSM-100434 Diastereomer 2

Pharmaceutical Compositions and Administration

The present invention provides pharmaceutical compositions comprising a ketolide as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the ketolide of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the ketolide of the present invention. The amount of the ketolide is generally equal to the dosage of the ketolide which would be administered to a subject and/or a convenient fraction of such a dosage such as, for example, one-half or one-third of such a dosage.

Relative amounts of the ketolide, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) ketolide.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the ketolides, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the ketolide.

Solid dosage forms for oral administration include capsules, tablets, pills, powders, and granules. In such solid dosage forms, the ketolide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the ketolide(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The ketolide can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the ketolide can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the ketolide(s) only, or preferentially, in a certain part of the intestinal tract, optionally, in a delayed manner. Examples of embedding compositions which can be used include polymeric substances and waxes.

Dosage forms for topical and/or transdermal administration of a ketolide of this invention may include ointments, pastes, creams, lotions, gels, powders, solutions, sprays, inhalants and/or patches. Generally, the ketolide is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an ketolide to the body. Such dosage forms can be prepared, for example, by dissolving and/or dispensing the ketolide in the proper medium. Alternatively or additionally, the rate can be controlled by either providing a rate controlling membrane and/or by dispersing the ketolide in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) ketolide, although the concentration of the ketolide can be as high as the solubility limit of the ketolide in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the ketolide and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the ketolide dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the ketolide may constitute 0.1 to 20% (w/w) of the composition. The propellant may further comprise additional ingredients such as a liquid non-ionic and/or solid anionic surfactant and/or a solid diluent (which may have a particle size of the same order as particles comprising the ketolide).

Pharmaceutical compositions of the invention formulated for pulmonary delivery may provide the ketolide in the form of droplets of a solution and/or suspension. Such formulations can be prepared, packaged, and/or sold as aqueous and/or dilute alcoholic solutions and/or suspensions, optionally sterile, comprising the ketolide, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the ketolide and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the ketolide, and may comprise one or more of the additional ingredients described herein. A pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) ketolide, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the ketolide. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the ketolide in an aqueous or oily liquid carrier. Such drops may further comprise buffering agents, salts, and/or one or more other of the additional ingredients described herein. Other opthalmically-administrable formulations which are useful include those which comprise the ketolide in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Ketolides provided herein are typically formulated in dosage unit form for ease of administration and uniformity of dosage. It will be understood, however, that the total daily amount of the ketolide will be decided by the attending physician within the scope of sound medical judgment. The specific therapeutically effective dose level for any particular subject will depend upon a variety of factors including the disease, disorder, or condition being treated and the severity of the disorder; the activity of the specific ketolide employed; the specific composition employed; the age, body weight, general health, sex and diet of the subject; the time of administration, route of administration, and rate of excretion of the specific ketolide employed; the duration of the treatment; drugs used in combination or coincidental with the specific ketolide employed; and like factors well known in the medical arts.

The ketolides and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

The exact amount of a ketolide required to achieve an effective amount will vary from subject to subject, depending, for example, on species, age, and general condition of a subject, severity of the side effects or disorder, identity of the particular ketolide(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a ketolide for administration one or more times a day to a 70 kg adult human may comprise about 0.1 mg to about 3000 mg, about 0.1 mg to about 2000 mg, about 0.1 mg to about 1000 mg, about 0.1 mg to about 100 mg, about 1 mg to about 100 mg, or about 10 mg to about 100 mg, of a ketolide per unit dosage form.

In certain embodiments, the ketolides of the present invention may be administered at dosage levels sufficient to deliver from about 0.001 mg/kg to about 100 mg/kg, from about 0.01 mg/kg to about 100 mg/kg, from about 0.1 mg/kg to about 100 mg/kg, from about 0.5 mg/kg to about 100 mg/kg, from about 10 mg/kg to about 100 mg/kg, from about 20 mg/kg to about 100 mg/kg, and from about 25 mg/kg to about 100 mg/kg, of subject body weight per day, one or more times a day, to obtain the desired therapeutic effect.

It will be also appreciated that a ketolide or composition, as described herein, can be administered in combination with one or more additional therapeutically active agents. The ketolide or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive ketolide with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In any of the above described methods, one or more additional therapeutic agents (also referred to as the "agent")

may be administered concurrently with, prior to, or subsequent to, administration of the ketolide of the present invention, as described herein. The agent may be added at the same time as the ketolide of the present invention (simultaneous administration), before or after administration of the ketolide of the present invention (sequential administration), or any combination thereof. For example, in certain embodiments, the agent is administered first, followed by simultaneous administration of the agent and the ketolide of the present invention. In certain embodiments, the ketolide of the present invention is administered first, followed by simultaneous administration of the agent and the ketolide of the present invention. In any of the above embodiments, either the agent or the ketolide of the present invention may be further administered alone after the simultaneous administration.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfoprisin (Syndercid™).

Also encompassed by the invention are kits (e.g., pharmaceutical packs). The kits provided may comprise an inventive pharmaceutical composition or ketolide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or ketolide. In some embodiments, the inventive pharmaceutical composition or ketolide provided in the container and the second container are combined to form one unit dosage form.

Method of Treatment

The present invention contemplates using ketolides of the present invention for the treatment of infectious diseases, for example, fungal, bacterial, viral, or parasitic infections, and for the treatment of inflammatory conditions. Ketolides are known to exhibit anti-bacterial activity as well as anti-parasitic activity. See, for example, Clark et al., *Bioorganic & Medicinal Chemistry* Letters (2000) 10:815-819 (anti-bacterial activity); and Lee et al., *J. Med. Chem.* (2011) 54:2792-2804 (anti-bacterial and anti-parasitic activity). Ketolides are also known to exhibit an anti-inflammatory effect. See, for example, Amsden, *Journal of Antimicrobial Chemotherapy* (2005) 55:10-21 (chronic pulmonary inflammatory syndromes).

Thus, as generally described herein, provided is a method of treating a infectious disease comprising administering an effective amount of a ketolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylatically effective amount. For example, in certain embodiments, the method prevents or reduces the likelihood of an infectious disease, e.g., in certain embodiments, the method comprises administering a ketolide of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In another aspect, provided is an in vitro method of inhibiting pathogenic growth comprising contacting an effective amount of the ketolide of the present invention with a pathogen (e.g., a bacteria, virus, fungus, or parasite) in a cell culture.

As used herein, "infectious disease" and "microbial infection" are used interchangeably, and refer to an infection with a pathogen, such as a fungus, bacteria, virus, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a ketolide of the present invention, or a pharmaceutically acceptable salt thereof, to a subject in need thereof.

In certain embodiments, the ketolide has a mean inhibitory concentration (MIC), with respect to a particular bacteria, of less than 50 µg/mL, less than 25 µg/mL, less than 20 µg/mL, less than 10 µg/mL, less than 5 µg/mL, or less than 1 µg/mL.

In certain embodiments, the bacteria is susceptible (e.g., responds to) or resistant to known commercial macrolides, such as azithromycin, clindamycin, telithromycin, erythromycin, spiramycin, and the like. See also FIG. 1 for a listing of known macrolides. In certain embodiments, the bacteria is resistant to a known macrolide. For example, in certain embodiments, the bacteria is erythromycin resistant (ER).

In certain embodiments, the bacterial infection is resistant to other antibiotics (e.g., non-macrolide) therapy. For example, in certain embodiments, the pathogen is vancomycin resistant (VR). In certain embodiments, the pathogen is a methicillin-resistant (MR), e.g., in certain embodiments, the bacterial infection is an methicillin-resistant *S. aureus* infection (a MRSA infection).

In certain embodiments, the bacteria has an efflux (e.g., mef, msr) genotype. In certain embodiments, the bacteria has a methylase (e.g., erm) genotype. In certain embodiments, the bacteria has a constitutive genotype. In certain embodiments, the bacteria has an inducible genotype.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a Gram positive bacteria.

In certain embodiments, the Gram positive bacteria is a bacteria of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus*, and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection. In certain embodiments, the *S. aureus* has an efflux (e.g., mef, msr) genotype. In certain embodiments, the *S. aureus* has a methylase (e.g., erm) genotype.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus *Strepococcus*, i.e., the bacterial infection is a *Strepococcus* infection. Exemplary Strepococcus bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans*, and *S. zooepidemicus*. In certain embodiments, the *Strepococcus* infection is an *S. pyogenes* infection. In certain embodiments, the *Strepococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacterial infection is an infection with a Gram negative bacteria.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii*, and *E. vulneris*. In certain embodiments, the *Escherichia* infection is an *E. coli* infection.

In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*. In certain embodiments, the *Escherichia* infection is an *H. influenzae* infection.

In certain embodiments, the infectious disease is an infection with a parasitic infection. Thus, in certain embodiments, provided is a method of treating a parasitic infection comprising administering an effective amount of a ketolide of the present invention, or a pharmaceutically acceptable salt thereof, to a subject in need thereof.

In certain embodiments, the ketolide has a $IC_{50}$ (uM) with respect to a particular parasite, of less than 50 uM, less than 25 uM, less than 20 uM, less than 10 uM, less than 5 uM, or less than 1 uM.

Exemplary parasites include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*), *Crytosporidium* spp., *Isospora* spp., *Balantidium* spp., *Loa Loa, Ascaris lumbricoides, Dirofilaria immitis*, and *Toxoplasma* ssp. (e.g. *T. gondii*).

As generally described herein, the present invention further a method of treating an inflammatory condition comprising administering an effective amount of a ketolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylatically effective amount. For example, in certain embodiments, the method prevents or reduces the likelihood of an inflammatory condition, e.g., in certain embodiments, the method comprises administering a ketolide of the present invention to a subject in need thereof in an amount sufficient to prevent or reduce the likelihood of an inflammatory condition. In certain embodiments, the subject is at risk to an inflammatory condition.

In another aspect, provided is an in vitro method of treating an inflammatory condition comprising contacting an effective amount of the ketolide of the present invention with an inflammatory cell culture.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), chronic pulmonary inflammatory syndromes (e.g., diffuse panbronchiolitis, cystic fibrosis, asthma, bronchiectasis, chronic obstructive pulmonary disease), arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), a gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo, and Wegener's granulomatosis.

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

EXAMPLES

These and other aspects of the present invention will be further appreciated upon consideration of the following Examples, which are intended to illustrate certain particular embodiments of the invention but are not intended to limit its scope, as defined by the claims. International Application No. PCT/US2014/033025 is incorporated herein by reference in its entirety.

Exemplary Eastern Half Synthetic Procedures

Example 1A. Preparation of Aldehyde and Phosphonate Eastern Halves

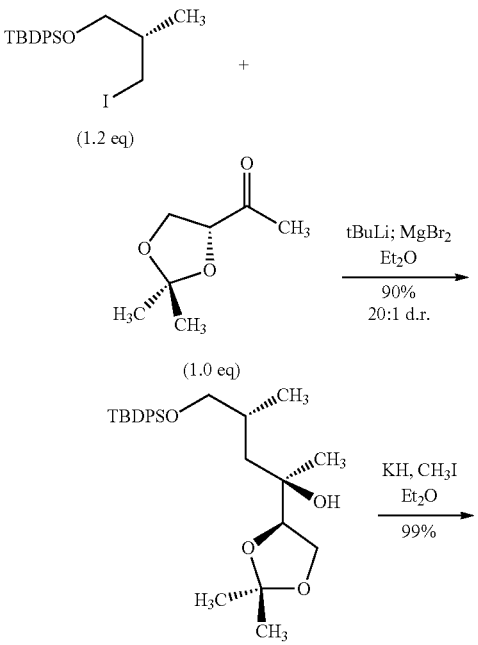

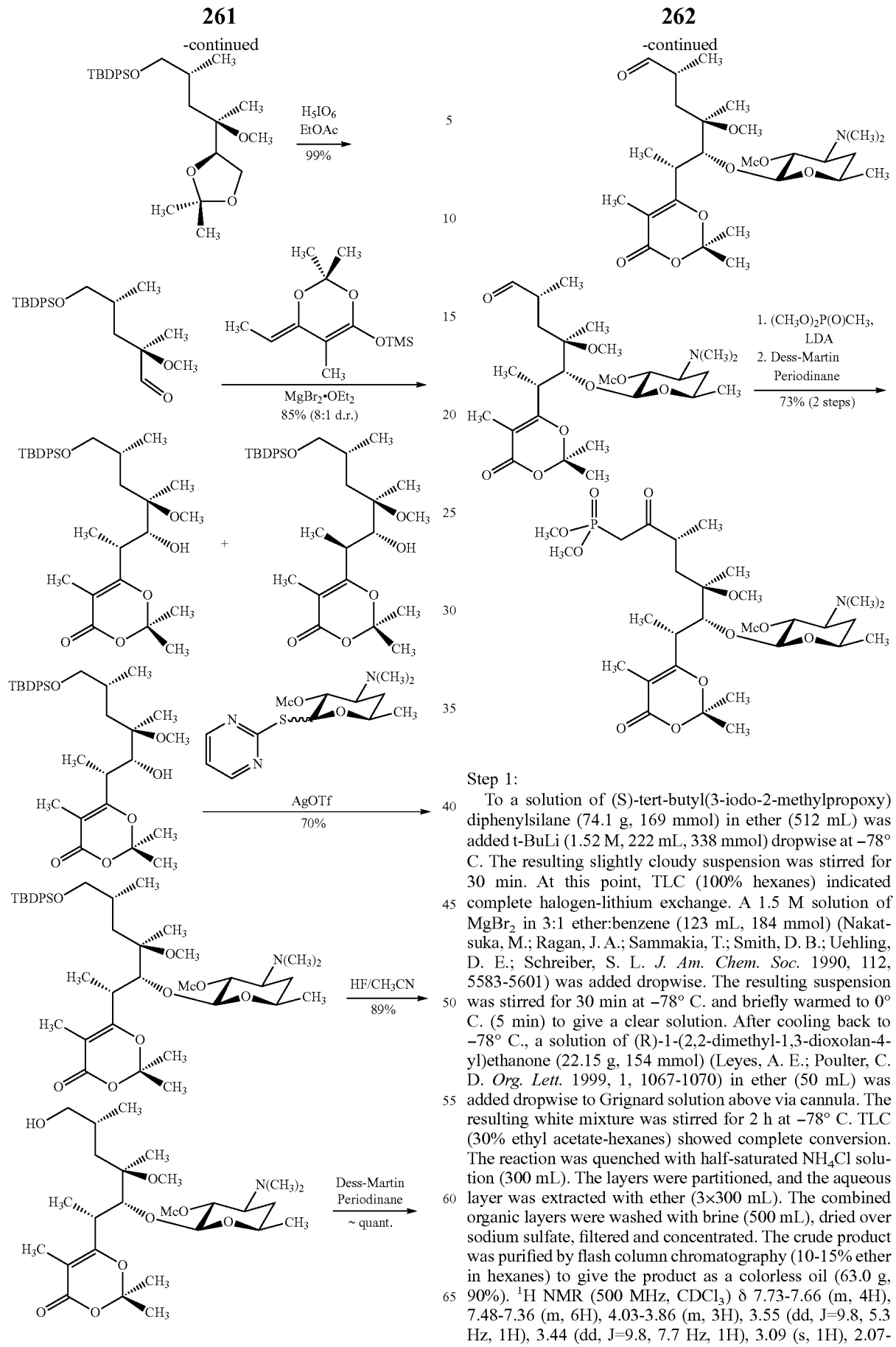

Step 1:

To a solution of (S)-tert-butyl(3-iodo-2-methylpropoxy)diphenylsilane (74.1 g, 169 mmol) in ether (512 mL) was added t-BuLi (1.52 M, 222 mL, 338 mmol) dropwise at −78° C. The resulting slightly cloudy suspension was stirred for 30 min. At this point, TLC (100% hexanes) indicated complete halogen-lithium exchange. A 1.5 M solution of $MgBr_2$ in 3:1 ether:benzene (123 mL, 184 mmol) (Nakatsuka, M.; Ragan, J. A.; Sammakia, T.; Smith, D. B.; Uehling, D. E.; Schreiber, S. L. *J. Am. Chem. Soc.* 1990, 112, 5583-5601) was added dropwise. The resulting suspension was stirred for 30 min at −78° C. and briefly warmed to 0° C. (5 min) to give a clear solution. After cooling back to −78° C., a solution of (R)-1-(2,2-dimethyl-1,3-dioxolan-4-yl)ethanone (22.15 g, 154 mmol) (Leyes, A. E.; Poulter, C. D. *Org. Lett.* 1999, 1, 1067-1070) in ether (50 mL) was added dropwise to Grignard solution above via cannula. The resulting white mixture was stirred for 2 h at −78° C. TLC (30% ethyl acetate-hexanes) showed complete conversion. The reaction was quenched with half-saturated $NH_4Cl$ solution (300 mL). The layers were partitioned, and the aqueous layer was extracted with ether (3×300 mL). The combined organic layers were washed with brine (500 mL), dried over sodium sulfate, filtered and concentrated. The crude product was purified by flash column chromatography (10-15% ether in hexanes) to give the product as a colorless oil (63.0 g, 90%). $^1$H NMR (500 MHz, $CDCl_3$) δ 7.73-7.66 (m, 4H), 7.48-7.36 (m, 6H), 4.03-3.86 (m, 3H), 3.55 (dd, J=9.8, 5.3 Hz, 1H), 3.44 (dd, J=9.8, 7.7 Hz, 1H), 3.09 (s, 1H), 2.07-

1.96 (m, 1H), 1.86 (dd, J=14.5, 6.3 Hz, 1H), 1.42 (s, 3H), 1.39 (s, 3H), 1.33 (dd, J=14.4, 4.5 Hz, 1H), 1.14 (s, 3H), 1.08 (s, 9H), 0.91 (d, J=6.9 Hz, 3H). $^{13}$C NMR (126 MHz, CDCl$_3$) δ 135.66, 135.61, 133.31, 133.27, 129.68, 127.68, 127.65, 109.17, 82.02, 71.46, 70.08, 65.12, 43.02, 30.83, 26.87, 26.36, 25.39, 22.49, 19.45, 19.16. FTIR (neat), cm$^{-1}$: 3450 (br), 2957(m), 1369 (s), 1211 (s), 1111 (s), 1066 (s), 823 (s), 738 (s), 702 (s); HRMS (ESI): Calcd for (C$_{27}$H$_{40}$O$_4$Si+H)$^+$: 457.2769; Found: 457.2775.

Step 2:

To a suspension of KH (35% dispersion in mineral oil, 6.67 g, 49.9 mmol) in ether (83 mL) was added an ether solution (83 mL) of (2R,4R)-5-((tert-butyldiphenylsilyl)oxy)-2-((R)-2,2-dimethyl-1,3-dioxolan-4-yl)-4-methylpentan-2-ol (19 g, 41.6 mmol) dropwise at 0° C. The transfer was quantitated with ether (2×5 mL). The resulting suspension was stirred for 1 h. Methyl iodide (freshly passed through basic alumina, 26.0 mL, 416 mmol) was added and the mixture was warmed to rt. After 2 h, TLC indicated complete reaction. The reaction mixture was slowly poured into 100 mL half-saturated NH$_4$Cl solution, and diluted with 100 mL ether. The layers were separated, and the aqueous layer was extracted with ether (2×50 mL). The combined organic layers were dried over MgSO$_4$, filtered and concentrated. The residue was purified by column chromatography (12% to 20% ether in hexanes) to give the product as a colorless oil. (19.5 g, 99%). $^1$H NMR (600 MHz, CDCl$_3$) δ 7.68-7.64 (m, 4H), 7.45-7.34 (m, 6H), 4.15 (t, J=7.2 Hz, 1H), 3.91 (dd, J=8.2, 6.9 Hz, 1H), 3.64 (t, J=7.9 Hz, 1H), 3.46 (dd, J=9.8, 6.2 Hz, 1H), 3.40 (dd, J=9.8, 6.5 Hz, 1H), 3.19 (s, 3H), 1.90-1.82 (m, 1H), 1.58 (dd, J=14.9, 4.0 Hz, 1H), 1.43 (s, 3H), 1.34 (s, 3H), 1.23 (dd, J=15.0, 7.8 Hz, 1H), 1.11 (s, 3H), 1.06 (d, J=2.8 Hz, 9H), 1.02 (d, J=6.7 Hz, 3H). $^{13}$C NMR (126 MHz, CDCl$_3$) δ 135.63, 135.59, 133.87, 129.56, 129.54, 127.59, 109.21, 80.14, 77.12, 69.60, 65.51, 49.92, 36.84, 31.28, 26.90, 26.23, 25.02, 19.26, 18.92, 18.50. FTIR (neat), cm$^{-1}$: 2957(m), 1471 (s), 1369 (s), 1211 (s), 1155 (s), 1107 (s), 1066 (s), 823 (s), 738 (s), 700 (s); HRMS (ESI): Calcd for (C$_{28}$H$_{43}$O$_4$Si+H)$^+$: 471.2925; Found: 471.2944.

Step 3:

tert-butyl(((2R,4R)-4-((R)-2,2-dimethyl-1,3-dioxolan-4-yl)-4-methoxy-2-methylpentyl)oxy)diphenylsilane (19.5 g, 41.4 mmol) was dissolved in ethyl acetate (138 mL), and then periodic acid (18.89 g, 83 mmol) was added in one portion. The mixture was vigorously stirred for 1 h. The reaction was diluted with hexanes (138 mL). The suspension was passed through a short pad of silica, eluting with 50% ethyl acetate/hexanes (300 mL). The filtrate was concentrated to give the product as a colorless oil (16.8 g, 99%). $^1$H NMR (500 MHz, CDCl$_3$) δ 9.52 (s, 1H), 7.67 (dd, J=7.9, 1.5 Hz, 4H), 7.47-7.35 (m, 6H), 3.48 (dd, J=9.9, 5.7 Hz, 1H), 3.41 (dd, J=9.8, 6.2 Hz, 1H), 3.24 (s, 3H), 1.90-1.77 (m, 2H), 1.42 (dd, J=14.1, 6.6 Hz, 1H), 1.22 (s, 3H), 1.07 (s, 9H), 0.97 (d, J=6.7 Hz, 3H).

$^{13}$C NMR (126 MHz, CDCl$_3$) δ 204.68, 135.62, 135.60, 133.80, 133.79, 129.55, 127.59, 82.41, 68.97, 51.51, 37.91, 31.31, 26.88, 19.28, 18.58, 17.69. FTIR (neat), cm$^{-1}$: 2958 (m), 1735 (s), 1427 (s), 1105 (s), 1080 (s), 823 (s), 738 (s), 700 (s); HRMS (ESI): Calcd for (C$_{24}$H$_{34}$O$_3$Si+H)$^+$: 399.2350; Found: 399.2360.

Step 4:

A solution of (2R, 4R)-5-((tert-butyldiphenylsilyl)oxy)-2-methoxy-2,4-dimethylpentanal (10.5 g, 26.3 mmol) in CH$_2$Cl$_2$ (105 mL) was cooled to −10° C. and treated with magnesium bromide diethyl etherate (20.41 g, 79 mmol). The mixture was stirred at this temperature for 10 min, and cooled to −78° C. (Z)-((4-ethylidene-2,2,5-trimethyl-4H-1,3-dioxin-6-yl)oxy)trimethylsilane (13.44 mL, 52.7 mmol) was added dropwise to the solution above. The mixture was stirred at −78° C. for 12 h, at which point TLC analysis (30% ethyl acetate/hexanes) indicated full conversion. The reaction was quenched by addition of ether (200 mL) and 1N HCl (100 mL). The layers were separated, and the aqueous layer was extracted with Et$_2$O (3×100 mL). The combined organic layers were washed with brine (2×100 mL) and dried over MgSO$_4$. The solution was filtered and concentrated in vacuo. Two columns were necessary to obtain pure syn diastereomer. The first column, eluting with 15:15:70 ether/ethyl acetate/hexanes gave product as an 8:1 diastereomeric mixture. The second column, eluting with 1-3% acetone in dichloromethane, gave the syn diastereomer (11.5 g, 77%), followed by anti diastereomer (1.2 g, 8%). Major isomer (syn): $^1$H NMR (500 MHz, CDCl$_3$) δ 7.73-7.62 (m, 4H), 7.48-7.34 (m, 6H), 3.72 (t, J=5.6 Hz, 1H), 3.47 (dd, J=9.8, 6.3 Hz, 1H), 3.43 (dd, J=9.8, 6.5 Hz, 1H), 2.96 (p, J=6.9 Hz, 1H), 2.42 (d, J=5.7 Hz, 1H), 1.85 (s, 3H), 1.83-1.77 (m, 1H), 1.74 (dd, J=14.3, 3.7 Hz, 1H), 1.66 (s, 3H), 1.65 (s, 3H), 1.33 (dd, J=14.2, 7.0 Hz, 1H), 1.21 (d, J=6.9 Hz, 3H), 1.11 (s, 3H), 1.07 (s, 9H), 1.00 (d, J=6.6 Hz, 3H). $^{13}$C NMR (126 MHz, CDCl$_3$) δ 168.22, 162.87, 135.59, 135.55, 133.76, 133.72, 129.60, 129.58, 127.61, 104.80, 99.04, 79.57, 73.86, 69.44, 49.08, 36.89, 35.98, 31.44, 26.87, 26.41, 23.62, 19.33, 19.26, 18.90, 14.14, 9.88. FTIR (neat), cm$^{-1}$: 3500 (br), 2931 (m), 1722 (s), 1637 (s), 1388 (s), 1356 (s), 1111 (s), 1072 (s), 702 (s), 613 (s); HRMS (ESI): Calcd for (C$_{33}$H$_{45}$O$_6$Si+H)$^+$: 569.3293; Found: 569.3304. Minor isomer (anti): $^1$H NMR (500 MHz, CDCl$_3$) δ 7.68 (d, J=6.5 Hz, 4H), 7.50-7.35 (m, 6H), 3.55-3.47 (m, 2H), 3.44 (dd, J=9.8, 6.6 Hz, 1H), 3.10 (s, 3H), 2.94-2.88 (m, 1H), 2.59 (d, J=7.5 Hz, 1H), 1.84 (s, 3H), 1.82-1.72 (m, 1H), 1.72-1.67 (m, 1H), 1.68 (s, 3H), 1.65 (s, 3H), 1.44 (dd, J=14.2, 7.1 Hz, 1H), 1.22 (d, J=7.0 Hz, 3H), 1.10 (s, 3H), 1.07 (s, 9H), 1.03 (d, J=6.7 Hz, 3H). $^{13}$C NMR (126 MHz, CDCl$_3$) δ 168.23, 162.88, 135.60, 135.57, 133.78, 133.74, 129.62, 129.59, 127.62, 104.82, 99.06, 79.58, 73.88, 69.45, 49.09, 36.90, 35.99, 31.46, 26.88, 26.43, 23.63, 19.34, 19.28, 18.91, 14.15, 9.89. FTIR (neat), cm$^{-1}$: 3483 (br), 2955 (m), 1720 (s), 1639 (s), 1466 (s), 1388 (s), 1359 (s), 1111 (s), 1074 (s), 702 (s), 615 (s); HRMS (ESI): Calcd for (C$_{33}$H$_{45}$O$_6$Si+H)$^+$: 569.3293; Found: 569.3292.

Step 5:

To a dry 200-mL flask was charged powdered dry 4 Å molecular sieves (10.0 g), toluene (41.8 mL) and CH$_2$Cl$_2$ (41.8 mL). In a separate flask, a mixture of 6-((2R,3R,4R,6R)-7-((tert-butyldiphenylsilyl)oxy)-3-hydroxy-4-methoxy-4,6-dimethylheptan-2-yl)-2,2,5-trimethyl-4H-1,3-dioxin-4-one (9.5 g, 16.70 mmol) and (2S,3R,4S,6R)-4-(dimethylamino)-6-methyl-2-(pyrimidin-2-ylthio)tetrahydro-2H-pyran-3-yl methyl carbonate (16.40 g, 50.1 mmol) (Velvadapu, V.; Andrade, R. B.; Carbohydr. Res. 2008, 343, 145-150) were azeotropically dried from benzene for 3 times. Then the residue was dissolved in CH$_2$Cl$_2$ (30 mL). This solution was added to the molecular sieves suspension above via cannula. The suspension was cooled to 0° C., and silver(I) trifluoromethanesulfonate (21.46 g, 84 mmol) was added in one portion. The mixture was stirred for 1 h at 0° C. At this point, TLC analysis (50% ethyl acetate in hexanes) indicated full consumption of starting material. The reaction was quenched with saturated aqueous NH$_4$Cl (10.0 mL), stirred for 5 min, and saturated aqueous NaHCO$_3$ (10 mL) was added. The mixture was filtered through a pad of Celite, rinsing with CH$_2$Cl$_2$ (100 mL), and the filtrate was washed with saturated aqueous NaHCO$_3$ (20 mL). The organic layer was dried over Na$_2$SO$_4$, filtered and concentrated. The crude product was purified by flash column chromatography (70% ethyl acetate in hexanes) to give the product as a white foam (9.0 g, 70%). $^1$H NMR (500 MHz, Benzene) δ 7.86-7.79 (m, 4H), 7.26-7.17 (m, 6H), 4.70 (dd, J=10.4, 7.5 Hz, 1H), 4.65 (d, J=7.5 Hz, 1H), 4.19 (t, J=8.0 Hz, 1H), 3.89 (dt, J=10.5, 5.3 Hz, 1H), 3.59 (dd, J=9.7, 7.5 Hz, 1H), 3.40 (s, 3H), 3.25-3.19 (m, 1H), 3.19-3.11 (m, 1H), 2.93 (s, 3H), 2.52 (td, J=12.1, 4.5 Hz, 1H), 2.09 (d, J=12.9 Hz, 6H), 2.03 (s, 3H), 1.85 (dd, J=14.3, 7.0 Hz, 1H), 1.62 (dt, J=18.6, 6.1 Hz, 1H), 1.45 (s, 3H), 1.34 (s, 3H), 1.28 (s, 3H), 1.22 (d, J=8.5 Hz, 3H), 1.20 (s, 9H), 1.18 (d, J=8.5 Hz, 3H), 1.06 (d, J=7.0 Hz, 3H). $^{13}$C NMR (126 MHz, CDCl$_3$) δ 167.94, 163.00, 155.17, 135.62, 134.26, 134.21, 129.38, 129.36, 127.47, 104.40, 99.83, 99.61, 79.02, 75.52, 69.16, 69.12, 63.11, 54.64, 49.40, 40.70, 36.40, 33.94, 31.12, 30.86, 26.87, 25.68, 24.38, 20.98, 20.20, 19.79, 19.34, 12.86, 9.77. FTIR (neat), cm$^{-1}$: 2935(m), 1755 (s), 1724 (s), 1641 (s), 1456 (s), 1377 (s), 1265 (s), 1106 (s), 1053 (s), 704 (s), 613 (s); HRMS (ESI): Calcd for (C$_{43}$H$_{65}$NO$_{10}$Si+H)$^+$: 784.4451; Found: 784.4467.

Step 6:

In a plastic vial, TBDPS-OCH$_3$-EH (9.0 g, 11.48 mmol) was dissolved in CH$_3$CN (57.4 mL), and hydrofluoric acid (48% aq, 9.90 mL, 574 mmol) was added with a plastic syringe. The mixture was then stirred at room temperature for 12 h, at which point TLC analysis (10% methanol in ethyl acetate) indicated full consumption of starting material. The reaction solution was slowly added to an Erlenmyer containing saturated aqueous NaHCO$_3$ solution (300 mL). After gas evolution subsided, the mixture was extracted with ether (3×100 mL). The organic layers were combined, and extracted with 1 N HCl (3×25 mL). The ether layer was discarded. The acid layers were combined, to which solid NaHCO$_3$ was slowly added to adjust pH to 8. This aqueous solution was extracted with CH$_2$Cl$_2$ (3×100 mL). The combined CH$_2$Cl$_2$ layers were dried over Na$_2$SO$_4$, filtered and concentrated to give the product as a white foam (5.58 g, 89%). $^1$H NMR (500 MHz, Benzene) δ 4.85 (dd, J=10.5, 7.7 Hz, 1H), 4.69 (d, J=7.6 Hz, 1H), 3.96 (d, J=2.9 Hz, 1H), 3.61 (ddd, J=11.3, 7.2, 4.4 Hz, 1H), 3.49-3.36 (m, 2H), 3.33 (s, 3H), 3.15-3.01 (m, 1H), 2.97 (t, J=6.4 Hz, 1H), 2.73 (s, 3H), 2.56 (td, J=12.0, 4.3 Hz, 1H), 2.11 (s, 6H), 1.87 (s, 3H), 1.86-1.81 (m, 1H), 1.74 (dd, J=14.5, 3.1 Hz, 1H), 1.57 (dd, J=14.4, 9.1 Hz, 1H), 1.41 (s, 3H), 1.38 (s, 3H), 1.32 (s, 3H), 1.26 (dd, J=12.8, 2.9 Hz, 1H), 1.16 (d, J=7.3 Hz, 3H), 1.11-1.04 (m, 1H), 1.02 (d, J=6.1 Hz, 3H), 0.88 (d, J=6.8 Hz, 3H). $^{13}$C NMR (126 MHz, CDCl$_3$) δ 167.34, 162.79, 155.25, 104.54, 99.84, 79.79, 76.37, 75.48, 69.27, 68.42, 63.05, 54.71, 49.56, 40.69, 38.69, 33.83, 31.07, 30.83, 25.89, 24.19, 20.99, 19.92, 19.86, 13.00, 9.89. FTIR (neat), cm$^{-1}$: 3437 (br), 2939 (m), 1753 (s), 1724 (s), 1641 (s), 1454 (s), 1379 (s), 1267 (s), 1109 (s), 1053 (s), 732 (s); HRMS (ESI): Calcd for (C$_{27}$H$_{47}$NO$_{10}$+H)$^+$: 546.3272; Found: 546.3280.

Step 7:

To a solution of the alcohol (2.1 g, 3.85 mmol) in CH$_2$Cl$_2$ (3.85 mL) was added Dess-Martin Periodinane (2.448 g, 5.77 mmol) and water (7.7 µL, 2 µL/mL CH$_2$Cl$_2$). The resulting milky suspension was stirred for 0.5 h at rt. The reaction was diluted with ether (50 mL), saturated aqueous Na$_2$S$_2$O$_3$ (20 mL), saturated aqueous NaHCO$_3$ (20 mL) and brine (20 mL). The resulting mixture was vigorously stirred for 30 min, and the layers were separated. The aqueous layer was extracted with ether (3×20 mL). The combined organic layers were washed with brine (10 mL), dried over MgSO$_4$, filtered and concentrated to give the product as a white foam (2.1 g, 100%). $^1$H NMR (500 MHz, CDCl$_3$) δ 9.36 (d, J=4.7 Hz, 1H), 4.62-4.51 (m, 2H), 3.86 (d, J=3.3 Hz, 1H), 3.78 (s, 3H), 3.51-3.40 (m, 1H), 3.37 (qd, J=7.3, 3.4 Hz, 1H), 2.97 (s, 3H), 2.81-2.69 (m, 1H), 2.47 (ddd, J=10.9, 7.7, 3.9 Hz, 1H), 2.31 (s, 6H), 1.86 (s, 3H), 1.81 (dd, J=14.0, 11.1 Hz, 1H), 1.77-1.73 (m, 1H), 1.68 (s, 3H), 1.66 (s, 3H), 1.58 (dd, J=14.1, 3.0 Hz, 1H), 1.43-1.30 (m, 1H), 1.26 (d, J=6.1 Hz, 3H), 1.25 (s, 3H), 1.07 (d, J=3.0 Hz, 3H), 1.06 (d, J=2.6 Hz, 3H). $^{13}$C NMR (126 MHz, Benzene) δ 202.57, 166.45, 161.71, 155.83, 104.17, 100.60, 100.46, 78.64, 78.26, 75.43, 69.23, 63.64, 54.18, 49.19, 42.02, 40.51, 37.52, 34.08, 30.22, 25.66, 24.02, 20.84, 20.33, 15.42, 13.14, 10.03. FTIR (neat), cm$^{-1}$: 2937 (m), 1753 (s), 1724 (s), 1643 (s), 1442 (s), 1377 (s), 1265 (s), 1109 (s), 1053 (s); HRMS (ESI): Calcd for (C$_{27}$H$_{45}$NO$_{10}$+H)$^+$: 544.3116; Found: 544.3139.

Step 8a: Phosphonate Preparation

Lithium diisopropylamide (1.0 M solution in THF, freshly prepared from diisopropylamine and nBuLi, 2.415 mL, 2.415 mmol) was charged into a flamed-dried flask. THF (6.9 mL) was added to supplement the volume to 9.3 mL, and the solution was cooled to −78° C. A solution of dimethyl methylphosphonate (0.262 mL, 2.415 mmol) in THF (1 mL) was added dropwise. The resulting solution was stirred at −78° C. for 15 min. A solution of the aldehyde (1.01 g, 1.858 mmol) in THF (9.3 mL) was added dropwise via cannula, and the reaction was stirred for 30 min at −78° C. At this point, TLC (10% methanol in ethyl acetate) indicated full consumption of the aldehyde. The reaction was quenched by addition of saturated aqueous NH$_4$Cl solution (10 mL) at −78° C. and diluted with ethyl acetate (10 mL). The mixture was warmed to rt, and the layers were separated. The aqueous layer was extracted with ethyl acetate (2×20 mL). The combined organic layers were washed with brine, dried over Na$_2$SO$_4$, and concentrated. The crude material was dissolved in CH$_2$Cl$_2$ (5 mL), and Dess-Martin Periodinane (1.18 g, 2.79 mmol) was added in one batch, followed by water (10 µL, 2 µL/mL CH$_2$Cl$_2$). The reaction was stirred at rt for 1 h. At this point, TLC (10% methanol in ethyl acetate) indicated complete conversion to a less polar compound. To the reaction mixture was added Et$_2$O (20 mL), saturated aqueous NaHCO$_3$ (10 mL) and saturated aqueous Na$_2$S$_2$O$_3$ (10 mL). The mixture was vigorously for 30 min. The layers were separated and the aqueous layer was extracted with Et$_2$O (2×20 mL). The combined organic layers were washed with brine, dried over MgSO$_4$ and concentrated. The crude product was purified by flash column chromatography (2-3% methanol in CH$_2$Cl$_2$+ 0.2% saturated NH$_4$OH) to give the product as a white foam (0.90 g, 73%). $^1$H NMR (600 MHz, CDCl$_3$) δ 4.57-4.46 (m, 2H), 3.84 (d, J=3.3 Hz, 1H), 3.76 (t, J=3.7 Hz, 3H), 3.74 (d, J=2.7 Hz, 3H), 3.74 (s, 3H), 3.42 (dtd, J=11.9, 5.9, 4.3 Hz, 1H), 3.30-3.21 (m, 1H), 3.16 (dd, J=22.0, 14.7 Hz, 1H), 3.04 (dd, J=21.0, 14.7 Hz, 1H), 2.94 (s, 3H), 2.84-2.76 (m, 1H), 2.76-2.66 (m, 1H), 2.27 (s, 6H), 1.92 (dd, J=14.1, 10.5 Hz, 1H), 1.78 (s, 3H), 1.77-1.69 (m, 1H), 1.64 (d, J=12.4 Hz, 3H), 1.62 (s, 3H), 1.47-1.40 (m, 1H), 1.38-1.28 (m, 1H), 1.23 (s, 3H), 1.23 (d, J=6.3 Hz, 3H), 1.08 (d, J=6.9 Hz, 3H), 1.02 (d, J=7.4 Hz, 3H). $^{13}$C NMR (126 MHz, CDCl$_3$) δ 205.81 (d, J=6.2 Hz), 167.20, 162.75, 155.17, 104.39, 99.91, 99.84, 78.41, 76.52, 75.40, 69.23, 62.97, 54.66, 52.75, 52.74, 49.47, 42.19, 42.17, 40.62, 40.37, 39.31, 33.92, 30.75, 25.79, 24.17, 20.92, 19.78, 18.43, 13.04, 9.64. FTIR (neat), cm$^{-1}$: 2937 (m), 1753 (s), 1716 (s), 1643 (s), 1456 (s), 1377 (s), 1265 (s), 1109 (s), 1053 (s), 731 (s); HRMS (ESI): Calcd for (C$_{30}$H$_{52}$NO$_{13}$P+H)$^+$: 666.3249; Found: 666.3266.

Step 8b: Alternative Phosphonate Preparation:

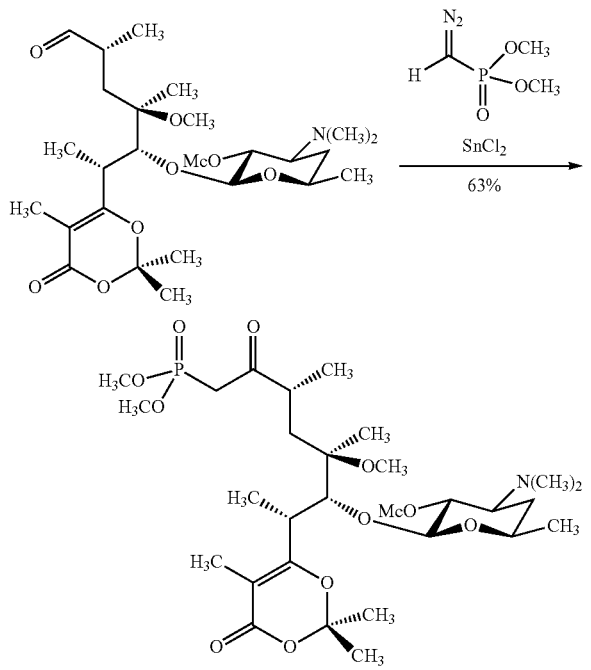

The aldehyde (100 mg, 0.184 mmol) was dissolved in CH$_2$Cl$_2$ (2.62 mL), and tin(II) chloride (6.98 mg, 0.037 mmol) was added. The solution was stirred at rt for 5 min, before dimethyl (diazomethyl)phosphonate (55.2 mg, 0.368 mmol) was added via syringe. The reaction was then warmed to 40° C. After 12 h, TLC (10% methanol in ethyl acetate) indicated full consumption of the aldehyde. The reaction was diluted with ethyl acetate (10 mL) and saturated aqueous NaHCO$_3$ (10 mL) and vigorously stirred. The layers were separated, and the aqueous layer was extracted with ethyl acetate (3×10 mL). The combined organic layers were dried over Na$_2$SO$_4$ and concentrated. The crude product was purified by flash column chromatography (2-3% methanol in CH$_2$Cl$_2$+0.2% saturated NH$_4$OH) to give the product as a white foam (75 mg, 63%).

Example 1B. Eastern Half without C2 Methyl Via β-Keto-t-Butyl Ester

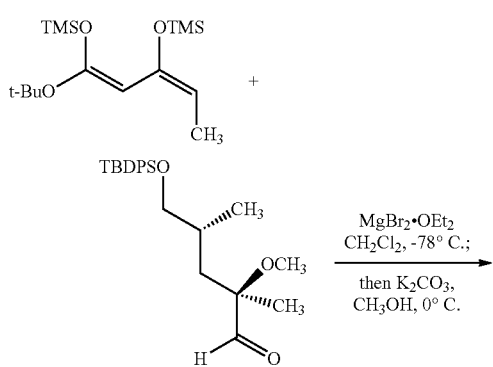

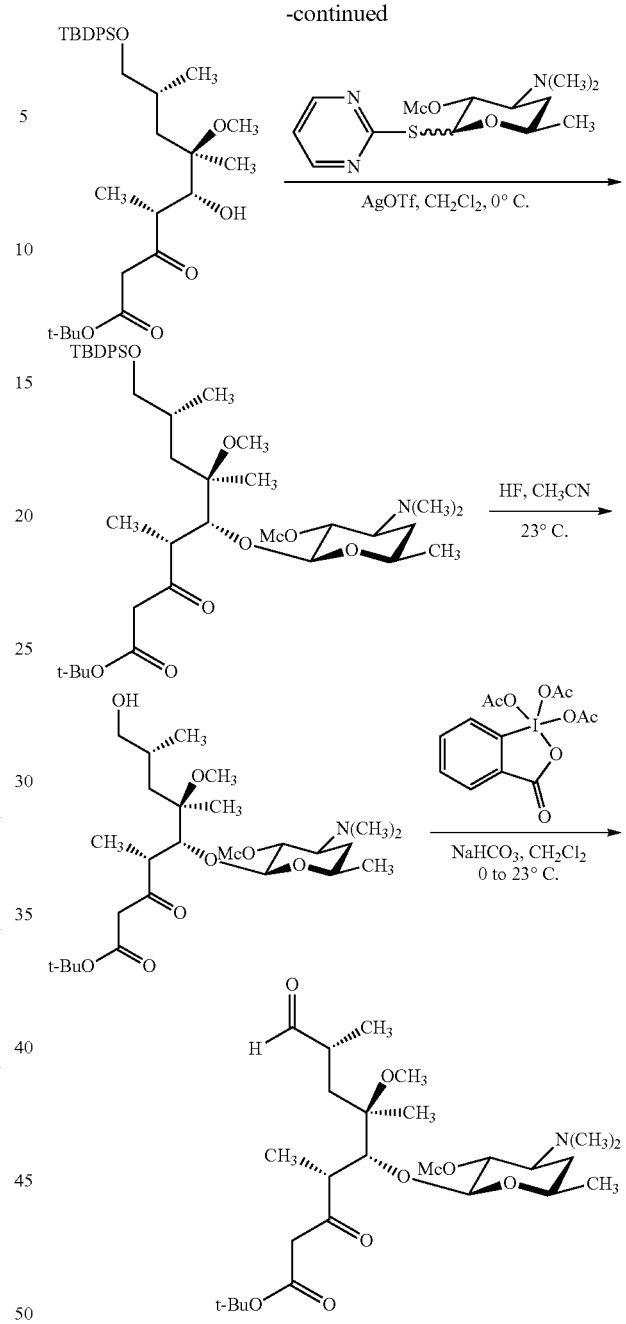

Step 1:

The aldehyde (575 mg, 1.443 mmol, 1 equiv) was dried by azeotropic distillation (benzene) and then dissolved in dichloromethane (11 mL). Magnesium bromide ethyl etherate (1.86 g, 7.21 mmol, 5.0 equiv) was added in one portion to this solution and the resulting mixture was cooled to −78° C. A solution of 1,3-bistrimethylsilyl dienol ether (1.37 g, 4.33 mmol, 3.0 equiv, for preparation see: Takai, K.; Nawate, Y.; Okabayashi, T.; Nakatsuji, H.; Iida, A.; Tanabe, Y. *Tetrahedron* 2009, 65, 5596-5607) in dichloromethane (1.5 mL) was added dropwise via syringe over 5 min to the aldehyde mixture at −78° C. The reaction mixture was stirred at this temperature for 3 h, then saturated aqueous ammonium chloride solution (12 mL) was added. The cooling bath was removed and the reaction flask was allowed to warm to 23° C. Water (40 mL) and dichloromethane (50 mL) were added and the phases were separated. The aqueous phase was extracted with dichloromethane (2×50 mL). The organic extracts were combined and the combined solution was dried over anhydrous sodium sulfate. The dried solution was filtered and the filtrate was concentrated. The crude aldol mixture was then dissolved in methanol (12 mL) and the resulting solution was cooled to 0° C. Potassium carbonate (20 mg, 0.1 equiv) was added in one portion to the crude product solution. After stirring at 0° C. for 6 min, aqueous potassium phosphate buffer solution (pH 7.0, 0.2 M, 25 mL) was added to the reaction solution. The cooling bath was removed and the reaction flask was allowed to warm to 23° C. Water (25 mL) and dichloromethane (60 mL) were added and the phases were separated. The aqueous phase was extracted with dichloromethane (2×60 mL). The organic extracts were combined and the combined solution was dried over anhydrous sodium sulfate. The dried solution was filtered and the filtrate was concentrated. The product was purified by flash-column chromatography (10% ethyl acetate-hexanes, grading to 12%), providing the aldol product in diastereomerically pure form (490 mg, 60%). A minor aldol diastereomer was isolated separately in diastereomerically pure form (97 mg, 12%). NB-clearly distinguishable peaks corresponding to the enol tautomer of aldol product (<10%) are reported with non-integer integrals. $^1$H NMR (500 MHz, CDCl$_3$) δ 7.67 (dd, 4H, J=7.8, 1.5 Hz), 7.42-7.36 (m, 6H), 4.96 (s, 0.07H), 3.86 (d, 1H, J=6.3 Hz), 3.53 (dd, 1H, J=9.8, 5.9 Hz), 3.41 (AB quartet, 2H), 3.40 (dd, 1H, J=9.8, 5.9 Hz), 3.12 (s, 0.21H), 3.00 (s, 3H), 2.86 (m, 1H), 2.24 (brs, 1H), 1.84-1.78 (m, 1H), 1.63 (dd, 1H, J=14.2, 4.9 Hz), 1.45 (s, 9H), 1.36 (dd, 1H, J=14.2, 6.3 Hz), 1.17 (d, 3H, J=7.3 Hz), 1.09 (s, 3H), 1.06 (s, 9H), 1.02 (d, 3H, J=6.3 Hz); $^{13}$C NMR (125 MHz, CDCl$_3$) δ 205.6, 166.6, 135.6, 135.6, 133.9, 129.5, 127.6, 81.5, 79.1, 75.1, 69.4, 49.9, 49.1, 47.0, 36.9, 31.5, 27.9, 26.9, 19.9, 19.2, 19.0, 12.9; FTIR (neat film), 3487 (w), 2932 (w), 1732 (m), 1707 (m), 1107 (s), 1071 (s), 700 (s) cm$^1$; HRMS-ESI (m/z): [M+Na]$^+$ calcd for C$_{33}$H$_{50}$O$_6$SiNa, 593.3269; found, 593.3278.

Step 2:

A mixture of the aldol product (1.55 g, 2.72 mmol, 1 equiv) and the 2-pyrimidinylthio glycoside (1.78 g, 5.43 mmol, 2.0 equiv) was dried by azeotropic distillation (benzene, 2×20 mL). The dried mixture was dissolved in dichloromethane (4.0 mL) and transferred via syringe to a flask containing a mixture of toluene (6.5 mL), dichloromethane (3.0 mL) and activated 4 Å molecular sieves (1.5 g). An additional portion of dichloromethane (1.0 mL) was used to ensure complete transfer into the reaction flask. The resulting mixture was stirred at 23° C. for 15 min, then was cooled to 0° C. Silver (I) trifluoromethanesulfonate (4.19 g, 16.3 mmol, 6.0 equiv) was added in one portion to the ice-cold, stirring reaction mixture. After stirring at 0° C. for 90 min, the reaction mixture was diluted with dichloromethane (10 mL) and then quenched by sequential dropwise addition of saturated aqueous ammonium chloride solution (1.5 mL) and saturated aqueous sodium bicarbonate solution (2.5 mL). The resulting mixture was allowed to warm to 23° C., then was filtered through a thick pad of Celite. The Celite pad was washed with dichloromethane (100 mL) and the resulting filtrate was concentrated, providing an orange-brown foam. The crude product was purified by flash-column chromatography (40% ethyl acetate-hexanes, grading to 70%), affording the glycosylated product ** as a white foam (1.09 g, 51%). $^1$H NMR (500 MHz, CDCl$_3$) δ 7.68 (d, 4H, J=6.3 Hz), 7.42-7.34 (m, 6H), 4.52 (dd, 1H, J=10.2, 7.8 Hz), 4.40 (d, 1H, J=7.8 Hz), 3.95 (d, 1H, J=7.8 Hz), 3.75 (s, 3H), 3.67 (dd, 1H, J=9.8, 4.4 Hz), 3.52-3.46 (m, 1H), 3.35-3.32 (m, 1H), 3.34 (AB quartet, 2H), 3.03-2.97 (m, 1H), 2.78 (s, 3H), 2.78-2.71 (m, 1H), 2.28 (s, 6H), 1.89-1.82 (m, 1H), 1.74 (brd, 1H), 1.43 (s, 9H), 1.35-1.30 (m, 2H), 1.26-1.23 (m, 1H), 1.22 (d, 3H, J=6.3 Hz), 1.14 (s, 3H), 1.12 (d, 3H, J=7.3 Hz), 1.06 (s, 9H), 1.04 (d, 3H, J=7.8 Hz); $^{13}$C NMR (125 MHz, CDCl$_3$) δ 204.6, 166.7, 155.1, 135.6, 134.2, 134.2, 129.4, 127.5, 101.2, 81.3, 80.8, 78.8, 75.5, 69.3, 69.0, 63.1, 54.7, 50.6, 49.4, 46.2, 40.7, 37.4, 31.4, 30.6, 28.0, 26.9, 20.9, 20.0, 19.6, 19.3, 13.7; FTIR (neat film), 2932 (w), 1755 (m), 1709 (w), 1263 (s), 1055 (s), 702 (s) cm$^{-1}$; HRMS-ESI (m/z): [M+H]$^+$ calcd for C$_{43}$H$_{68}$NO$_{10}$Si, 786.4607; found, 786.4619.

Step 3:

Concentrated aqueous hydrofluoric acid solution (48%, 2.00 mL, 50.9 mmol, 40 equiv) was added dropwise via syringe to a solution of the glycosylated product (1.00 g, 1.27 mmol, 1 equiv) in acetonitrile (12 mL) in a polypropylene reaction vessel at 23° C. The reaction solution was stirred vigorously at 23° C. for 15 h, then was added dropwise via plastic pipette to an ice-cold solution of saturated aqueous sodium bicarbonate (60 mL). The resulting mixture was extracted with ethyl acetate (3×60 mL). The organic extracts were combined and the combined solution was dried over anhydrous sodium sulfate. The dried solution was filtered and the filtrate was concentrated. The crude product was purified by flash column chromatography (65% ethyl acetate-hexanes, grading to 75%), affording the deprotection product as a white foam (435 mg, 62%). $^1$H NMR (500 MHz, CDCl$_3$) δ 4.52 (dd, 1H, J=10.7, 7.8 Hz), 4.42 (d, 1H, J=7.8 Hz), 4.09 (d, 1H, J=7.8 Hz), 3.76 (s, 3H), 3.57-3.48 (m, 2H), 3.43 (s, 2H), 3.29-3.23 (m, 2H), 3.10-3.05 (m, 1H), 2.98 (s, 3H), 2.75-2.70 (m, 1H), 2.26 (s, 6H), 1.85-1.80 (brm, 1H), 1.73 (dd, 1H, J=12.7, 2.4 Hz), 1.55-1.45 (m, 2H), 1.45 (s, 9H), 1.35-1.28 (m, 1H), 1.27 (s, 3H), 1.22 (d, 3H, J=5.9 Hz), 1.14 (d, 3H, J=7.3 Hz), 0.92 (d, 3H, J=6.8 Hz); $^{13}$C NMR (125 MHz, CDCl$_3$) δ 204.5, 166.5, 155.2, 101.2, 81.6, 79.7, 79.5, 75.5, 69.1, 68.2, 62.9, 54.7, 50.4, 49.7, 46.1, 40.6, 38.7, 31.1, 30.6, 27.9, 20.9, 20.0, 19.7, 13.8; FTIR (neat film), 2936 (w), 1751 (m), 1709 (m), 1263 (s), 1051 (s) cm$^{-1}$; HRMS-ESI (m/z): [M+H]$^+$ calcd for C$_{27}$H$_{50}$NO$_{10}$, 548.3429; found, 548.3435.

Step 4:

Sodium bicarbonate (557 mg, 6.63 mmol, 10 equiv) and Dess-Martin periodinane (618 mg, 1.46 mmol, 2.2 equiv) were added sequentially to a stirring solution of the alcohol (363 mg, 0.663 mmol, 1 equiv) in dichloromethane (10 mL) and water (20 µL) at 0° C. The resulting mixture was allowed to warm to 23° C. After stirring at this temperature for 1 h, the reaction mixture was diluted with diethyl ether (30 mL). Saturated aqueous sodium thiosulfate solution (15 mL), saturated aqueous sodium bicarbonate solution (7 mL) and saturated aqueous sodium chloride solution (7 ml) were added in sequence, and the resulting mixture was stirred vigorously for 10 min. The phases were then separated and the aqueous phase was extracted with diethyl ethyl (3×30 mL). The organic extracts were combined and the combined solution was washed sequentially with saturated aqueous sodium thiosulfate solution (2×20 mL) and saturated aqueous sodium chloride solution (20 mL). The resulting organic solution was then dried over anhydrous sodium sulfate. The dried solution was filtered and the filtrate was concentrated. The resulting yellow solid was used directly in the next step (reductive amination) without further purification (crude aldehyde >90% pure by $^1$H NMR analysis). $^1$H NMR (500 MHz, CDCl$_3$) δ 9.33 (d, 1H, J=4.9 Hz), 4.52 (dd, 1H, J=10.7, 7.8 Hz), 4.43 (d, 1H, J=7.8 Hz), 4.01 (d, 1H, J=8.8 Hz), 3.78 (s, 3H), 3.52-3.46 (m, 1H), 3.41 (AB quartet, 2H), 3.10-3.05 (m, 1H), 2.83 (s, 3H), 2.77-2.71 (m, 1H), 2.48-2.43 (m, 1H), 2.30-2.27 (m, 1H), 2.27 (s, 6H), 1.91 (dd, 1H, J=14.6, 11.2 Hz), 1.76-1.72 (m, 1H), 1.60 (dd, 1H, J=14.6, 3.4 Hz), 1.47 (s, 9H), 1.37-1.28 (m, 2H), 1.25 (s, 3H), 1.22 (d, 3H, J=5.9 Hz), 1.16 (d, 3H, J=7.3 Hz), 1.06 (d, 3H, J=6.8 Hz); $^{13}$C NMR (125 MHz, CDCl$_3$) δ 204.4, 204.1, 166.6, 155.2, 101.3, 81.5, 81.1, 78.3, 75.4, 69.1, 63.0, 54.7, 50.6, 49.5, 46.0, 41.9, 40.5, 38.0, 30.5, 27.9, 20.8, 19.9, 15.5, 13.8; FTIR (neat film), 2974 (w), 1753 (m), 1724 (m), 1711 (m), 1263 (s), 1053 (m) cm$^{-1}$; HRMS-ESI (m/z): [M+Na]$^+$ calcd for C$_{27}$H$_{47}$NNaO$_{10}$, 568.3092; found, 568.3094.

Example 1C. Synthesis of C6 Allyl Derivatives

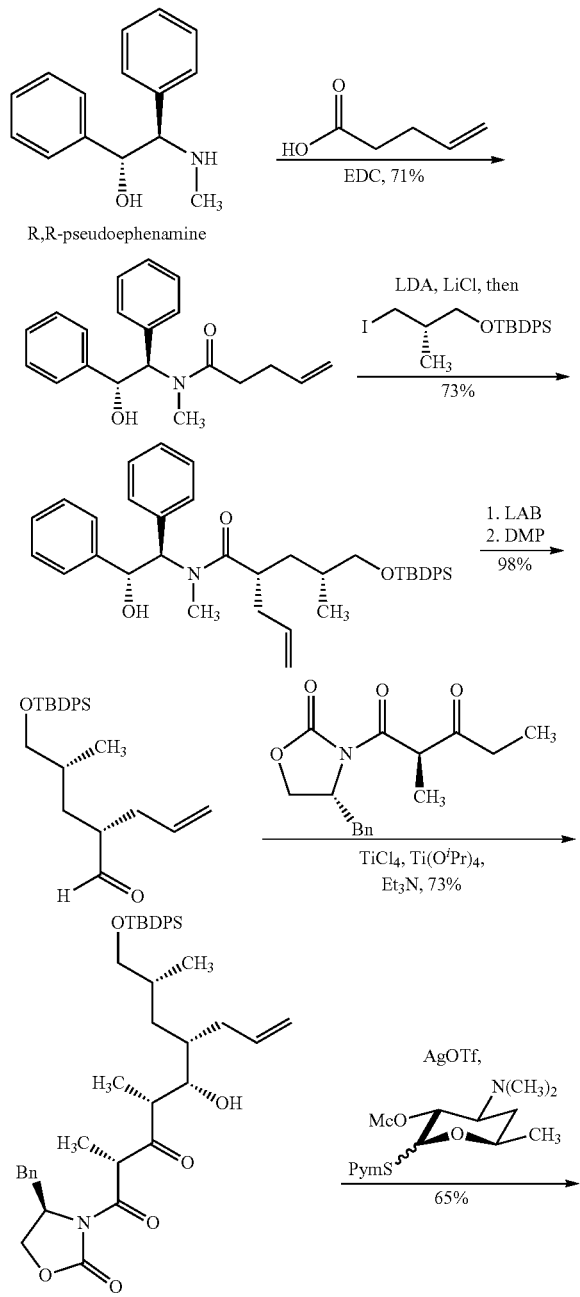

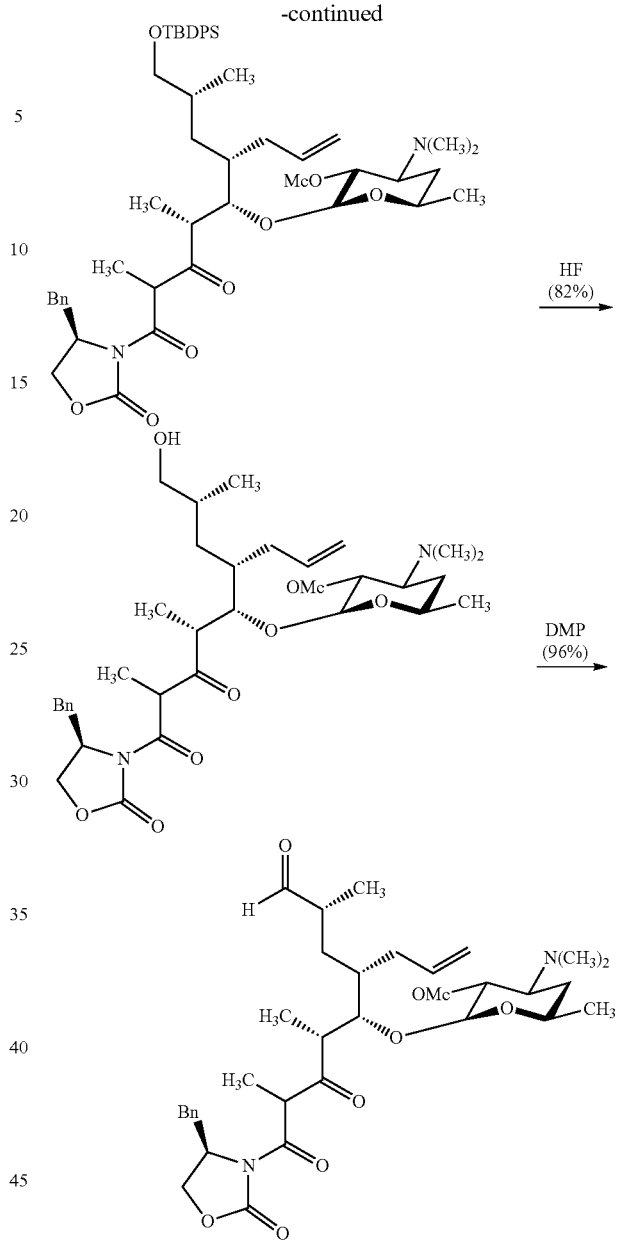

Step 1:

To a solution of Hunig's Base (10.48 ml, 60.0 mmol) in DMF (22 mL) cooled in an ice-water bath was added pent-4-enoic acid (2.041 ml, 20.00 mmol), HOBT (3.06 g, 20.00 mmol), and EDC (4.22 g, 22.00 mmol) sequentially. The solution was stirred at 0° C. for 5 minutes, and remains a light orange slurry throughout this time. (R,R)-pseudoephenamine (5 g, 22.00 mmol) (freshly crushed) was added in one portion, and the vessel was allowed to warm to 23° C. After 5 minutes, some product was visible by TLC (10% MeOH/DCM, +1% NH$_4$OH). After 20 minutes, the solution was completely homogeneous. After 1 h, conversion was >50%. At 19 h, progress had not changed. The mixture was diluted with water (200 mL) and extracted with ethyl acetate (3×75 mL). The organic layers were combined and the resulting light yellow solution was washed with water (2×100 mL), sat aq NaCl (1×75 mL), dried through a pad of sodium sulfate, and concentrated. The product was purified by flash chromatography (30% to 50% ethyl acetate to hexane) affording N-((1R,2R)-2-hydroxy-1,2-diphenylethyl)-N-methylpent-4-enamide (5.32 g, 17.19 mmol, 86% yield).

Step 2:

Lithium chloride (3.29 g, 78 mmol) was added to a 200-mL round-bottom flask equipped with a stir bar, and the whole was exposed to a gentle flame under vacuum (0.1 mmHg) for 2 minutes. The vessel and its contents were allowed to cool to 23° C., and THF (25 mL) and diisopropylamine (4.16 ml, 29.2 mmol) were added. The vessel was cooled to −78° C., and BuLi (12.06 ml, 28.6 mmol) was added dropwise. The solution was allowed to warm to 0° C., was stirred for 5 minutes at this temperature, and was re-cooled to −78° C. A solution of (R,R)-pseudoephenamine pent-4-enamide (4 g, 12.93 mmol) in tetrahydrofuran (20 mL+5 mL wash) was added dropwise via cannula, and the mixture was stirred for 30 min at −78° C., was allowed to warm to 23° C. and was stirred for 5 minutes at this temperature. A solution of (S)-tert-butyl(3-iodo-2-methylpropoxy)diphenylsilane (6.80 g, 15.51 mmol) in THF (10 mL) was added, and the transfer was quantitated with THF (2×2.5 mL). After 3 h, conversion was <50%. After 41 h, half-sat. aq. ammonium chloride (200 mL) was added, and the mixture was extracted with ethyl acetate (3×100 mL). The combined organic layers were washed with brine (100 mL), dried through a pad of sodium sulfate, and concentrated. The product was purified by column chromatography (20% to 25% ethyl acetate to hexanes) affording (S)-2-((R)-3-((tert-butyldiphenylsilyl)oxy)-2-methylpropyl)-N-((1R,2R)-2-hydroxy-1,2-diphenylethyl)-N-methylpent-4-enamide (5.86 g, 9.45 mmol, 73.1% yield).

Step 3:

BuLi (12.61 ml, 29.9 mmol) was added by syringe to a stirring solution of diisopropylamine (4.59 ml, 32.2 mmol) in THF (32 mL) at −78° C. The vessel was transferred to an ice-water bath and was allowed to warm to 0° C. Borane-ammonia complex (1.051 g, 30.6 mmol) was added as a single portion, and a vigorous evolution of gas was observed. The mixture was stirred for 3 minutes at 0° C., and was then allowed to warm to 23° C., and was stirred for 15 minutes at this temperature. The vessel was re-cooled to 0° C., and a solution of (S)-2-((R)-3-((tert-butyldiphenylsilyl)oxy)-2-methylpropyl)-N-((1R,2R)-2-hydroxy-1,2-diphenylethyl)-N-methylpent-4-enamide (4.75 g, 7.66 mmol) in THF (32 mL+5 mL wash) was added by cannula. The reaction vessel was then allowed to warm to 23° C. (11:50 AM). After 3 h, the starting material had been completely consumed. The vessel was cooled in an ice-water bath, and 3 M hydrochloric acid (90 mL) was added carefully with vigorous stirring. The mixture was stirred at 0-10° C. for 30 minutes, and was then extracted with ether (4×100 mL). The combined ether extracts were washed with 3 M HCl (100 mL), 2 M NaOH (100 mL), sat aq NaCl (100 mL). The washed organic solution was dried over sodium sulfate and filtered, and the filtrate was concentrated. The first acidic, aqueous layer was treated with 2 M NaOH (~200 mL) until pH 14, and the resulting suspension was extracted with dichloromethane (2×150 mL) to recover pseudoephenamine ((1R,2R)-2-(methylamino)-1,2-diphenylethanol (1.61 g, 7.08 mmol, 92% yield). The crude product was purified by column chromatography (25% ether to hexanes) affording (S)-2-((R)-3-((tert-butyldiphenylsilyl)oxy)-2-methylpropyl)pent-4-en-1-ol (2.99 g, 7.54 mmol, 98% yield).

To a solution of (S)-2-((R)-3-((tert-butyldiphenylsilyl)oxy)-2-methylpropyl)pent-4-en-1-ol (1 g, 2.52 mmol) in dichloromethane (25 mL, 0.1 M) was added water (0.045 ml, 2.52 mmol), and the mixture was stirred vigorously. The vessel was immersed in a 23° C. water bath, and DMP (2.139 g, 5.04 mmol) was added. After 10 minutes, sat. aq. sodium bicarbonate (15 mL) and sat. aq. sodium thiosulfate (15 mL) were added to the reaction mixture, and the resulting biphasic, cloudy solution was stirred rapidly until each layer was homogeneous (~30 minutes). The layers were separated, and the aqueous layer was extracted with dichloromethane (2×20 mL). The combined organic layers were filtered through sodium sulfate, and the filtrate was concentrated. The crude product was purified by column chromatography (5% ether to hexanes) affording the product (~850 mg).

Step 4:

Dichloromethane (3.5 mL, starting concentration of ketoimide 0.2 M, final concentration 0.1 M) was added to a flame-dried 25-mL round-bottom flask equipped with a magnetic stir bar. The vessel was cooled to 0° C., and TiCl$_4$ (535 µl, 0.535 mmol) (DCM solution) was added, followed by titanium (IV) tetraisopropoxide (52.1 µl, 0.178 mmol). The mixture was stirred for 15 minutes at this temperature, at which time a solution of (R)-1-((R)-4-benzyl-2-oxooxazolidin-3-yl)-2-methylpentane-1,3-dione (200 mg, 0.691 mmol) in DCM (1.2 mL+0.6 mL wash) was added. To the resulting yellow solution was added triethylamine (103 µl, 0.737 mmol), resulting in a dark red solution. Stirring was continued at 0° C. for 1 h, at which point the vessel was cooled in a dry ice/acetone bath to −78° C., and a solution of (S)-2-((R)-3-((tert-butyldiphenylsilyl)oxy)-2-methylpropyl)pent-4-enal (182 mg, 0.461 mmol) in DCM (1.2 mL+0.6 mL wash) was added dropwise. After 2 h, sat. aq. ammonium chloride was added (10 mL), and the mixture was allowed to warm to ambient temp with vigorous stirring. The layers were separated and the aqueous layer was extracted with DCM (2×10 mL). The organic layers were combined and the resulting solution was filtered through a pad of sodium sulfate, and the creamy filtrate was concentrated. The crude product was purified by column chromatography (33% to 40% ether to hexanes first column, DCM then 5% ether to DCM second column) affording the product (2R,4R,5S,6S)-1-((R)-4-benzyl-2-oxooxazolidin-3-yl)-6-((R)-3-((tert-butyldiphenylsilyl)oxy)-2-methylpropyl)-5-hydroxy-2,4-dimethylnon-8-ene-1,3-dione (229 mg, >10:1 dr, 0.335 mmol, 72.7% yield).

Step 5:

A solution of (2R,4R,5S,6S)-1-((R)-4-benzyl-2-oxooxazolidin-3-yl)-6-((R)-3-((tert-butyldiphenylsilyl)oxy)-2-methylpropyl)-5-hydroxy-2,4-dimethylnon-8-ene-1,3-dione (50 mg, 0.073 mmol) in benzene (2.5 mL) was added to a 10-mL round-bottom flask containing activated desosmaine (47.9 mg, 0.146 mmol), and the resulting solution was evaporated under reduced pressure. The residue was exposed to high vacuum (0.1 Torr) for 10 minutes, and the vessel was back-filled with argon, equipped with a stir bar and a septum. 4 Å molecular sieves were added, followed by toluene (244 µl) and CH$_2$Cl$_2$ (244 µl). The solution was cooled to 0° C., and silver(I) trifluoromethanesulfonate (65.7 mg, 0.256 mmol) was added as a single portion. The resulting suspension changes visibly from a grainy precipitate to a fine powdery precipitate within the first 5 minutes. After 1.5 h, dichloromethane (2 mL) was added, followed by sat. aq. NH$_4$Cl (2 mL). The layers were mixed vigorously for 5 minutes, and sat. aq. sodium bicarbonate (5 mL) was added, and the layers were mixed vigorously. The resulting emulsion was filtered through a sintered-glass funnel, and the resulting biphasic mixture was mixed vigorously and separated. The aqueous layer was extracted with dichloromethane (5 mL), and the organic phases were combined, and the resulting solution was dried through a pad of sodium sulfate. The filtrate was concentrated under reduced pressure. The crude product was purified by column chromatography (100% ethyl acetate) to afford the product (2S,3R, 4S,6R)-2-(((4S,5S,6R,8R)-9-((R)-4-benzyl-2-oxooxazolidin-3-yl)-4-((R)-3-((tert-butyldiphenylsilyl) oxy)-2-methylpropyl)-6,8-dimethyl-7,9-dioxonon-1-en-5-yl)oxy)-4-(dimethylamino)-6-methyltetrahydro-2H-pyran-3-yl methyl carbonate (43 mg, 0.048 mmol, 65.4% yield).

Step 6:

HF (80 µl, 2.224 mmol) (48% aqueous) was added to a solution of (2S,3R,4S,6R)-2-(((4S,5S,6R,8R)-9-((R)-4-benzyl-2-oxooxazolidin-3-yl)-4-((R)-3-((tert-butyldiphenylsilyl)oxy)-2-methylpropyl)-6,8-dimethyl-7,9-dioxonon-1-en-5-yl)oxy)-4-(dimethylamino)-6-methyltetrahydro-2H-pyran-3-yl methyl carbonate (40 mg, 0.044 mmol) in acetonitrile (445 µl) in a teflon tube at room temperature. After 20 h, the mixture was quenched carefully with sat. aq. sodium bicarbonate (3 mL), and was stirred vigorously until all bubbling ceased. The suspension was extracted with ether (3×2 mL). The organic layers were combined, and the resulting organic solution was extracted with 1 M HCl (2×1 mL). The acidic aqueous layer was basified with sat. aq. sodium bicarbonate (~5 mL), and the resulting suspension was extracted with dichloromethane (3×2 mL). The dichloromethane extracts were combined and the resulting clear, colorless solution was filtered through a pad of sodium sulfate. The filtrate was concentrated under reduced pressure to provide the product (2S,3R,4S,6R)-2-(((4S,5S,6R,8R)-9-((R)-4-benzyl-2-oxooxazolidin-3-yl)-4-((R)-3-hydroxy-2-methylpropyl)-6,8-dimethyl-7,9-dioxonon-1-en-5-yl)oxy)-4-(dimethylamino)-6-methyltetrahydro-2H-pyran-3-yl methyl carbonate as a colorless oil (24 mg, 0.036 mmol, 82% yield).

Step 7:

DMP (32.1 mg, 0.076 mmol) was added to a solution of (2S,3R,4S,6R)-2-(((4S,5S,6R,8R)-9-((R)-4-benzyl-2-oxooxazolidin-3-yl)-4-((R)-3-hydroxy-2-methylpropyl)-6,8-dimethyl-7,9-dioxonon-1-en-5-yl)oxy)-4-(dimethylamino)-6-methyltetrahydro-2H-pyran-3-yl methyl carbonate (25 mg, 0.038 mmol) in water-saturated dichloromethane (0.5 mL) in a 5-mL round-bottom flask that was immersed in a room-temperature water bath. After 15 minutes, LCMS indicated complete conversion to a peak of the desired mass. DCM (1 mL), sat aq sodium bicarbonate (1 mL), and sat sodium thiosulfate (1 mL) were added, and the solution was stirred vigorously for 10 minutes. The layers were separated, and the aqueous layer was extracted with dichloromethane (2×1 mL). The organic layers were combined and the resulting solution was filtered through a pad of sodium sulfate. The filtrate was concentrated to provide C6-allyl Evans Right Half aldehyde (24 mg, 0.036 mmol, 96% yield).

Example 1D. Synthesis of Eastern Half Building Blocks (Z)-((4-ethylidene-2,2,5-trimethyl-4H-1,3-dioxin-6-yl)oxy)trimethylsilane

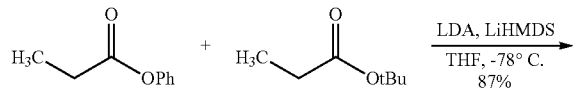

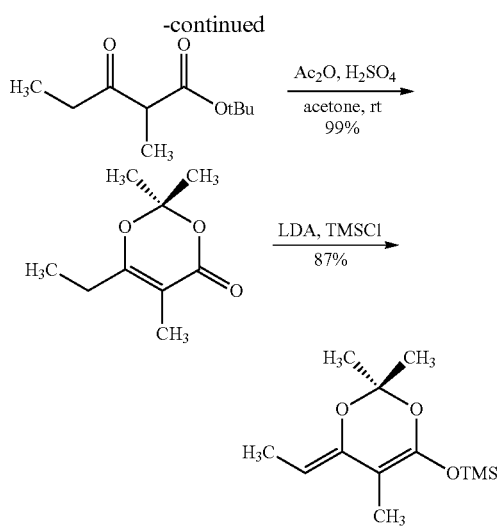

Step 1: Phenyl Propionate

Phenol (25 g, 266 mmol) and propionyl chloride (70 mL, 797 mmol) were added to a solution of trifluoromethanesulfonic acid (5.88 mL, 66.4 mmol) in acetonitrile (1 L) at 0° C. The resulting mixture was stirred at rt for 2 h. An ice water (1 L) and diethyl ether (500 mL) were added to the mixture. The organic layer was separated and the organic layer was washed with 1 M hydrogen chloride (1 L), saturated sodium bicarbonate aqueous solution (1 L), brine (1 L), dried over sodium sulfate and concentrated under reduced pressure. The residue was passed through a column of silica (n-pentane/diethyl ether, 10:1) to provide phenyl propionate (35.9 g, 90%) as a colorless oil. $^1$H NMR (CDCl$_3$, 600 MHz) δ=7.38 (t, 2H, J=7.8 Hz, CH of Ph), 7.22 (t, 1H, J=7.8 Hz, CH of Ph), 7.08 (d, 2H, J=7.8 Hz, CH of Ph), 2.60 (q, 2H, J=7.6 Hz, CH$_2$), 1.27 (t, 3H, J=7.6 Hz, CH$_3$).

Step 2: tert-Butyl 2-methyl-3-oxopentanoate

A 2.58 M solution of n-butyllithium in hexane (71.0 mL, 183 mmol) and a 2.41 M solution of n-butyllithium in hexane (33.2 mL, 80 mmol) was added dropwise to a solution of hexamethyldisilazane (58.4 mL, 275 mmol) in THF (160 mL) at 0° C. and the mixture was stirred at 0° C. for 45 min to prepare lithium hexamethyldisilazide (as a hexane and THF solution). A 2.42 M solution of n-butyllithium in hexane (69.0 mL, 167 mmol) and a 2.41 M solution of n-butyllithium in hexane (37.8 mL, 91 mmol) were added dropwise to a solution of diisopropylamine (36.3 mL, 258 mmol) in THF (160 mL) at −78° C. The resulting mixture was warmed to 0° C., stirred for 10 min and recooled to −78° C. A solution of tert-butyl propionate (32.5 g, 250 mmol) in THF (90 mL+35 mL×2 wash) was added to the above lithiumdiisopropylamide solution. The resulting mixture was stirred at −78° C. for 15 min. A freshly prepared solution of lithium hexamethyldisilazide in hexane and THF (323 mL, 30 mL×2 wash with THF) was added and then after 5 min a solution of phenyl propionate (39.4 g, 263 mmol) in THF (50 mL+25 mL×2 wash) was added to the reaction mixture at −78° C. The resulting mixture was stirred at −78° C. After 1 h, saturated ammonium chloride aqueous solution (150 mL) at −78° C. Diethyl ether (300 mL) and water (600 mL) were added to the mixture at rt. The organic layer was separated and washed with saturated sodium bicarbonate aqueous solution (2×300 mL), brine (300 mL) and dried over sodium sulfate. The aqueous layer was extracted with diethyl ether (2×300 mL). The combined organic layers were washed with a saturated NaHCO₃ aqueous solution (2×300 mL), brine (300 mL) and dried over sodium sulfate. The organic extracts were concentrated under reduced pressure. The residue was passed through a column of silica (n-pentane/diethyl ether, 40:1~2:1) to provide a mixture of phenyl propionate, tert-butyl 2-methyl-3-oxopentanoate and phenol. 1 M sodium hydroxide aqueous solution (500 mL) was added to a solution of the mixture in diethyl ether (250 mL) and the resulting solution was stirred at rt for 1.5 h. The organic layer was separated and washed with 1 M sodium hydroxide aqueous solution (250 mL), water (250 mL), brine (250 mL) and dried over sodium sulfate. The organic extract was concentrated under reduced pressure to provide tert-butyl 2-methyl-3-oxopentanoate (40.4 g, 87%) as a colorless oil. $^1$H NMR (CDCl₃, 600 MHz) δ=3.42 (q, 2H, J=7.3 Hz, CH₂ of Et), 2.64-2.46 (m, 1H, CH), 1.45 (s, 9H, (CH₃)₃), 1.29 (d, J=6.6 Hz, CH₃ of Me), 1.08 (t, 3H, J=7.3 Hz, CH₃ of Et).

Step 3: 6-Ethyl-2,2,5-trimethyl-4H-1,3-dioxin-4-one

Acetic anhydride (55.3 mL, 586 mmol) and sulfuric acid (10.4 mL, 195 mmol) were added to a mixture of tert-butyl 2-methyl-3-oxopentanoate (36.4 g, 195 mmol) and acetone (28.7 mL, 391 mmol) at 0° C. and the resulting mixture was stirred at rt for 5 h. The reaction mixture was diluted in diethyl ether (1 L) and saturated sodium bicarbonate aqueous solution (1.6 L). The mixture was stirred at rt for 2 h. The organic layer was separated and washed with saturated sodium bicarbonate aqueous solution (1 L×2), brine (1 L) and dried over sodium sulfate and concentrated under reduced pressure to provide 6-ethyl-2,2,5-trimethyl-4H-1,3-dioxin-4-one (32.8 g, 99%) as a colorless oil. The product was purified by distillation under reduced pressure (70° C., 520 mTorr). $^1$H NMR (CDCl₃, 600 MHz) δ=2.30 (q, 2H, J=7.6 Hz, CH₂ of Et), 1.82 (s, 3H, CH₃ of 5-Me), 1.65 (s, 6H, (CH₃)₂ of 2-Me), 1.12 (t, 3H, J=7.6 Hz, CH₃ of Et).

Step 4: (Z)-((4-ethylidene-2,2,5-trimethyl-4H-1,3-dioxin-6-yl)oxy)trimethylsilane To a solution of diisopropylamine (25.1 mL, 176 mmol) in THF (210 mL) at −78° C. was added nBuLi (76 mL, 2.32 M in hexanes, 176 mmol) dropwise. The resulting solution was warmed to 0° C. and stirred for 15 min. The solution was cooled to −78° C., and a solution of 6-ethyl-2,2,5-trimethyl-4H-1,3-dioxin-4-one in THF (50 mL+6 mL-rinse) was added dropwise via cannula. After stirring for 1 h at −78° C., freshly distilled TMSCl was added dropwise and the mixture was stirred for 3 h at −78° C. The mixture was warmed to r.t. and the solvent was removed under reduced pressure. The residue was diluted with dry pentane (100 mL) and filtered. The filtrate was concentrated. Crude material was purified by vacuum distillation. (~200 mTorr, 63-67° C.). $^1$H NMR (500 MHz, CDCl₃) δ 4.40 (q, J=6.9 Hz, 1H), 1.66 (d, J=6.9 Hz, 3H), 1.63 (s, 3H), 1.52 (s, 6H), 0.24 (s, 9H).

Example 1E. Synthesis of Eastern Half Building Blocks (S)-tert-Butyldiphenylsiloxy-3-iodo-2-methylpropane

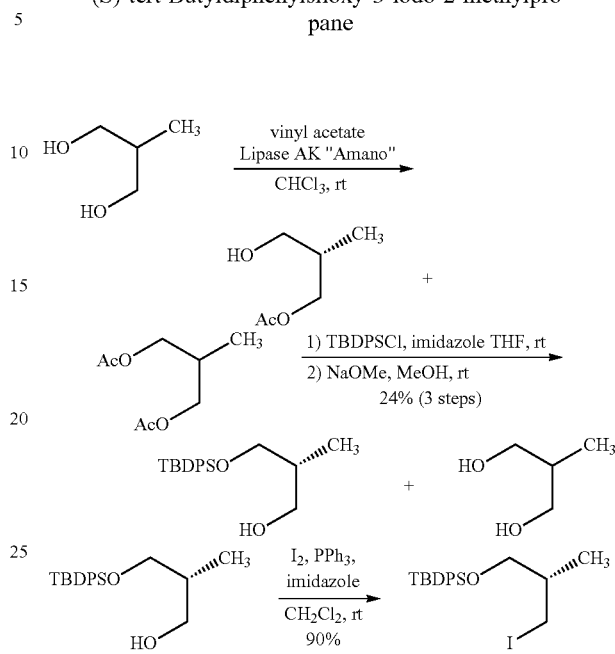

Step 1:
(R)-3-tert-Butyldiphenylsiloxy-2-methylpropan-1-ol

Vinyl acetate (286 mL, 3.11 mol) and lipase-AK "Amano" (17.1 g) were added to a solution of 2-methyl-1,3-propanediol (70 g, 777 mmol) in chloroform (1.5 L). The resulting mixture was stirred at rt for 20 h. The lipase was removed by filtration and washed with ethyl acetate. Then the filtrate was concentrated to provide a mixture of (S)-3-hydroxy-2-methylpropyl acetate (>99% ee) and 1,3-diacetoxy-2-methylpropane. The mixture was used in the next reaction step without separation. tert-Butyldiphenylsilylchloride (79 mL, 303 mmol) was added dropwise to a mixture of (S)-3-hydroxy-2-methylpropyl acetate and 1,3-diacetoxy-2-methylpropane (140 g, crude) and imidazole (41.3 g) in THF (620 mL). The resulting mixture was stirred at rt for 21 h. The reaction mixture was diluted with diethyl ether (1 L) and washed water (2×1 L) and brine. The organic layer was dried over sodium sulfate and concentrated under reduced pressure. A 25% solution of sodium methoxide in methanol (61 mL) was added to a solution of a mixture of (R)-3-tert-butyldiphenylsiloxy-2-methylpropyl acetate and 1,3-diacetoxy-2-methylpropane (194 mg, crude) in methanol (1 L) at 0° C. The resulting mixture was stirred at rt for 24 h. The reaction mixture was diluted with diethyl ether (1 L) and n-pentane (1 L), washed with saturated ammonium chloride aqueous solution (1 L), water (2×1 L) and brine (1 L). The organic layer was dried over sodium sulfate and concentrated under reduced pressure. The residue was passed through a column of silica (n-hexane/diethyl ether, 40:1~20:1~4:1) to provide (R)-3-tert-butyldiphenylsiloxy-2-methylpropan-1-ol (60.9 g) as a colorless oil. $^1$H NMR (CDCl₃, 400 MHz) δ=7.69-7.67 (m, 4H, CH of Ph), 7.46-7.38 (m, 6H, CH of Ph), 3.75-3.57 (m, 4H, CH₂OTBDPS, CH₂OH), 2.03-1.96 (m, 1H, CH₂CH(CH₃)CH₂), 1.06 (s, 9H, (CH₃)₃), 0.83 (d, 3H, J=10.8 Hz, CH₂CH(CH₃)CH₂)

Step 2: (S)-tert-Butyldiphenylsiloxy-3-iodo-2-methylpropane

Imidazole (12.4 g, 183 mmol, 2 equiv) and iodine (23.2 g, 91 mmol, 1 equiv) were added to a stirred solution of triphenylphosphine (24.0 g, 91 mmol, 1 equiv) in dichloromethane (180 mL). A solution of (R)-3-tert-butyldiphenylsiloxy-2-methylpropan-1-ol (30.0 g, 91 mmol) in dicholomethane (60 mL) was added to the reaction mixture at 0° C. The resulting mixture was stirred at rt for 5 h. A small amount of iodine was added to "titrate" triphenylphosphine, until the color of the reaction mixture is slightly yellow. The solvent was removed under reduced pressure. Siliga gel (75 g) and hexane (300 mL) were added to the residue. The suspension was stirred for 20 min to absorb triphenylphosphine oxide and salts on silica. Then the mixture was filtered through a short pad of silica (n-hexane/diethyl ether, 95:5) to provide (S)-tert-butyldiphenylsiloxy-3-iodo-2-methylpropane (35.9 g, 90%) as a colorless oil. $^1$H NMR (CDCl$_3$, 400 MHz) δ=7.69-7.65 (m, 4H, CH of Ph), 7.46-7.36 (m, 6H, CH of Ph), 3.61-3.31 (m, 4H, CH$_2$O, CH$_2$I), 1.78-1.68 (m, 1H, CH$_2$CH(CH$_3$)CH$_2$), 1.06 (s, 9H, (CH$_3$)$_3$), 0.96 (d, 3H, J=10.2 Hz, CH$_2$CH(CH$_3$)CH$_2$).

Exemplary Western Half Synthetic Procedures

Example 2A. Preparation of Western Half Building Blocks

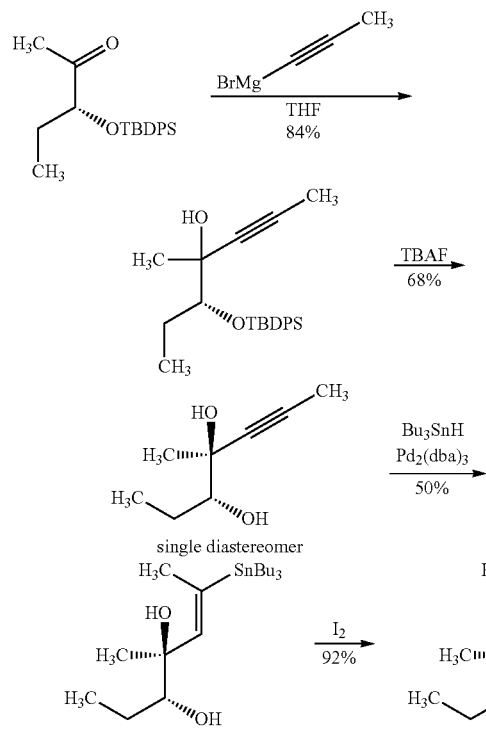

Step 1:

1-propynylmagnesium bromide (Sigma) (21.14 ml, 10.57 mmol) (0.5 M) was added dropwise over 6 minutes to a solution of (R)-3-((tert-butyldiphenylsilyl)oxy)pentan-2-one (2.4 g, 7.05 mmol) in Tetrahydrofuran (28.2 ml) at 0° C. Five minutes after the addition, TLC (eluted in 10% ether/hexanes) indicated ~30% conversion to a more polar spot. After 1 h, conversion was 60%. After 4 h, the mixture was poured into half-saturated aqueous NH4Cl (50 mL), and the layers were mixed vigorously and separated. The aqueous layer was extracted with hexanes (2×25 mL), and the combined organic layers were washed with water (50 mL) and brine (25 mL). The washed organic solution was gravity-filtered through a pad of sodium sulfate, and the filtrate was concentrated under reduced pressure. d.r.: 3:1. Column: 5% ether in hexanes. (5R)-5-((tert-butyldiphenylsilyl)oxy)-4-methylhept-2-yn-4-ol (2.25 g, 5.91 mmol, 84% yield) emerged as a 3:1 mixture of diastereomers, as a yellow oil.

Step 2:

TBAF (1971 µl, 1.971 mmol) was added dropwise to a solution of (5R)-5-((tert-butyldiphenylsilyl)oxy)-4-methylhept-2-yn-4-ol (500 mg, 1.314 mmol) in Tetrahydrofuran (6569 µl) at 0° C. The mixture was allowed to warm to 23° C. After 2 h, TLC (10% ether in hexanes) the mixture was concentrated under reduced pressure. The residue was purified with column chromatography (50% EtOAc in Hexanes). The purified product mixture was subjected to high vacuum for 5 minutes, at which point it began to crystallize. The vessel (200-mL round-bottom flask) was removed from high vacuum until crystallization was complete on the sides of the flask, and was re-exposed to high vacuum for 1 h. NMR at this point showed still >20% minor diastereomer left. The NMR sample was re-combined with the remaining crystals in the flask and the mixture was evaporated (from DCM/hexanes). The flask was equipped with a reflux condensor with cool water running through it, and exposed to high vacuum overnight. The product was very pure (minor diastereomer was almost undetectable, having evaporated overnight). No sublimation on the sides of the reflux condensor were observed. (3R,4S)-4-methylhept-5-yne-3,4-diol (127 mg, 0.893 mmol, 68.0% yield) was a white, crystalline solid. This matched the spectra from the following references: J. Org Chem. 2011, 76, 7516, and ACS Med. Chem. Lett. 2012, 3, 1013.

Steps 3 and 4:

These procedures were carried out identically to the following references: This matched the spectra from the following references: J. Org Chem. 2011, 76, 7516, and ACS Med. Chem. Lett. 2012, 3, 1013.

Example 2B. Preparation of Western Half Building Blocks

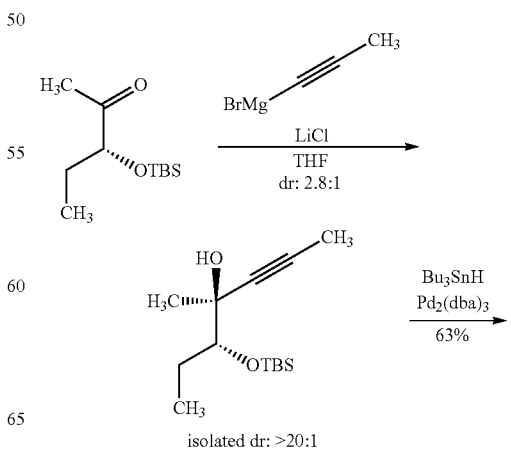

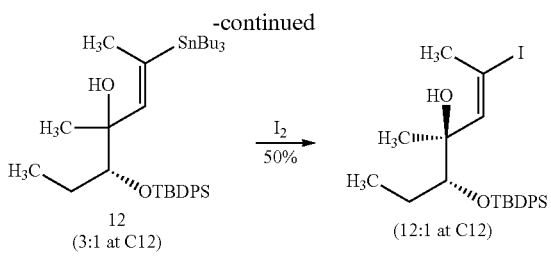

12
(3:1 at C12)

→ I₂, 50% →

(12:1 at C12)

Step 1:

1-propynylmagnesium bromide (Sigma) (12.02 ml, 6.01 mmol) (0.5 M in THF) was added dropwise over 6 minutes to a solution of (R)-3-((tert-butyldimethylsilyl)oxy)pentan-2-one (1 g, 4.62 mmol) in THF (9.24 ml) at −20° C. After 1 hour, TLC (25% ether/hexanes) indicated 90% conversion to a more polar spot. After 90 min, the starting material had been completely consumed. Half-sat aq NH4Cl (25 mL) was added, and the mixture was stirred vigorously for 5 minutes. The resulting biphasic solution was extracted with ether (2×25 mL), the organic layers were combined and washed with brine (10 mL), and the washed organic solution was gravity-filtered through a pad of sodium sulfate. The filtrate was concentrated. Crude dr: 2.8:1; Column: 4% ether in hexanes, once minor diast. is off, flush with 6% to remove rest of major. Second column: same conditions. The major diastereomer was isolated in 21:1 dr as a light yellow oil (614 mg, 2.394 mmol, 51.8% yield).

Step 2:

PdCl₂(PPh₃)₂ (1.844 mg, 2.63 µmol) was added to a solution of (5R)-5-((tert-butyldiphenylsilyl)oxy)-4-methyl-hept-2-yn-4-ol (50 mg, 0.131 mmol) (single diastereomer) in tetrahydrofuran (657 µl). tributylstannane (53.6 µl, 0.197 mmol) was added dropwise over 2 minutes. Visible gas elution occurred. After 2 minutes, TLC revealed very low conversion to a less polar spot (10% ether/hexanes). After 10 minutes, this had not changed. The solution had turned deep golden/brown. After 1 h, this had still not changed. Another portion of tributylstannane (53.6 µl, 0.197 mmol) was added, and TLC (2 min after addition) showed further (~20%?) conversion to the less polar spot. Another 3 equiv of Bu3SnH was added, resulting in more bubbling, and ~50% conversion after 5 minutes. The mixture was allowed to stir for 16 h, and the conversion did not change at all. Another 6 equiv of Bu3SnH was added over 30 min (portionwise, 6 portions), and TLC after 2 minutes indicated complete conversion to a less polar spot (which appeared to be two very close spots in several solvent systems. After 24 h, the THF was removed under a stream of argon, and the crude mixture was directly loaded onto a silica gel column and eluted with 20% DCM/hexanes to provide (5R,E)-5-((tert-butyldiphenylsilyl)oxy)-4-methyl-2-(tributylstannyl)hept-2-en-4-ol (56 mg, 0.083 mmol, 63.5% yield) as a yellow oil.

Step 3:

A solution of iodine (26.5 mg, 0.104 mmol) in dichloromethane (834 µl). To a solution of (5R,E)-5-((tert-butyl-diphenylsilyl)oxy)-4-methyl-2-(tributylstannyl)hept-2-en-4-ol (56 mg, 0.083 mmol) in Dichloromethane (834 µl) at 0° C. During the addition, the iodine color vanished until the end point, at which point the reaction was done. Sodium thiosulfate (sat aq, 3 mL) was added, and the mixture was stirred vigorously. The organic phase was separated, and the aqueous layer was further extracted with DCM (2×3 mL). The organic layers were filtered through a pad of sodium sulfate, and the filtrate was concentrated under reduced pressure. NMR revealed a pure mixture of two isomers (~3.5:1). Column: long silica gel column with 5% ether in hexanes. Some overlapping fractions, and products emerge fairly quickly. The major product that was isolated was 12:1 dr as a light yellow oil: (4S,5R,E)-5-((tert-butyldiphenylsilyl)oxy)-2-iodo-4-methylhept-2-en-4-ol (21 mg, 0.041 mmol, 49.5% yield).

Example 2C. Preparation of Western Half Building Blocks

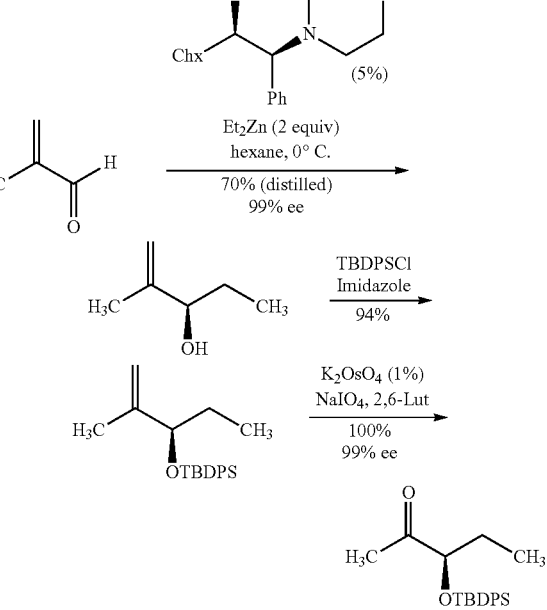

Step 1:

To a suspension of (1R,2S)-1-cyclohexyl-2-morpholino-2-phenylethanol (2.065 g, 7.13 mmol, prepared according to the procedure published by W. A. Nugent: *Org. Lett.* 2002, 4, 2133-2136) in n-hexane (100 mL) in a 1-L round-bottom flask under argon cooled with an ice water bath was added diethylzinc (285 ml, 285 mmol, Aldrich 1.0 M solution in hexanes) via cannula by applying a mild vacuum to the receiving flask. Large amounts of white smoke are present in the receiving flask during the transfer. The solution was allowed to stir for 30 minutes at this temperature, then methacrolein (11.81 ml, 143 mmol, freshly distilled prior to use to remove polymers and stabilizers) was added dropwise over 15 minutes, resulting in a pale-yellow, homogeneous solution. TLC (20% EA/H, compare to product, stain with KMnO4) five minutes after the addition showed only the desired product and catalyst-however, it should be noted that methacrolein boils at 69° C., and monitoring for its disappearance is very difficult. After 15 minutes, the color had faded and the solution was clear and colorless. After 3 hours, 2 M HCl was added carefully, and a white precipitate crashes out, but re-dissolves as the solution reaches pH 1 (~500 mL HCl). The biphasic mixture was transferred to a separatory funnel and the layers were separated. The aqueous layer was further extracted with diethyl ether (2×250 mL), and the combined organic layers were washed with brine (300 mL) dried over sodium sulfate, filtered, and the filtrate was concentrated under reduced pressure (~40 Torr) at 0° C. The resulting clear oil was transferred to a 100-mL round-bottom flask, and the transfer was quantitated with ether (2×5 mL). The solvent was distilled off at atmospheric pressure through a short-path distillation head using a 90° C. oil bath. The vessel was cooled and the pressure was reduced to 40 Torr. Once bubbling has stopped, the system was backfilled with air, the receiving flask was exchanged for a new one, and the pressure was once again reduced to 40 Torr. The receiving flask was immersed in a 0° C. ice bath, and the distillation was resumed using a 90° C. oil bath. The product distills as a clear liquid with a steady boiling point of 67° C. at ~40 Torr. Yield: 10.04 g (70%). The ee was not determined at this stage, but was measured for a later intermediate. The $^1$H-NMR and 13C-NMR data matched literature values: Paterson, I.; Perkins, M. V. Tetrahedron 1996, 52, 1811-1834; Cossy, J.; Bauer, D.; Bellosta, V. Tetrahedron 2002, 58, 5909-5922. The acidic aqueous layers from the extraction were combined and the resulting solution was basified with 2 M NaOH until the pH was 14, and a white solid precipitated. The resulting suspension was extracted with dichloromethane (3×100 mL). The organic layer was dried over sodium sulfate and concentrated. The residue was recrystallized from hexane to provide (1R,2S)-1-cyclohexyl-2-morpholino-2-phenylethanol (1.44 g, 4.98 mmol, 69.7% recovery).

Step 2:

To a solution of (R)-2-methylpent-1-en-3-ol (8 g, 80 mmol) in DMF (160 mL) was added imidazole (10.88 g, 160 mmol) followed by TBDPS-Cl (26.7 ml, 104 mmol) dropwise. The reaction solution was stirred at 23° C. for 18 hours, after which time TLC (20% EA/H) indicated that the starting material was consumed. The reaction solution was partitioned between hexanes (200 mL) and water (750 mL), and after vigorous mixing, the layers were separated. The aqueous layer was further extracted with hexanes (2×200 mL), and the combined organic layers were washed with water (2×300 mL). The washed solution was loaded onto a silica gel pad (4" diameter, 5" length) which was slurry-packed with hexanes. The pad was eluted in 500 mL fractions with hexanes (4000 mL total), and the fractions containing product (5-8) were combined and concentrated under reduced pressure, providing (R)-tert-butyl((2-methylpent-1-en-3-yl)oxy)diphenylsilane (25.33 g, 74.8 mmol, 94% yield) as a colorless oil. TLC (hexanes): $R_f$=0.24 (UV, KMnO$_4$), $^1$H NMR (500 MHz, CDCl$_3$), δ: 7.73-7.65 (m, 4H), 7.46-7.33 (m, 6H), 4.78-4.74 (m, 2H), 4.06 (dd, J=6.8, 5.6 Hz, 1H), 1.69 (s, 3H), 1.53-1.45 (m, 2H), 1.09 (s, 9H), 0.68 (t, J=7.5 Hz, 3H). $^{13}$C NMR (125 MHz, CDCl$_3$), δ: 146.0, 136.0, 135.9, 134.8, 134.2, 129.4, 129.4, 127.4, 127.3, 111.6, 78.4, 28.0, 27.0, 19.4, 17.2, 9.0. FTIR (neat), cm$^{-1}$: 2963, 2932, 1728, 1427, 1109, 1063, 714. HRMS could not be acquired due to poor ionization on ESI-TOF.

Step 3:

(R)-tert-butyl((2-methylpent-1-en-3-yl)oxy)diphenylsilane (13.65 g, 40.3 mmol) was suspended in THF (112 mL) and water (56 mL), resulting in a white slurry. 2,6-Lutidine (9.39 ml, 81 mmol) was added, followed by sodium periodate (34.5 g, 161 mmol) and potassium osmate dihydrate (0.149 g, 0.403 mmol), and the solution was vigorously stirred. After 26 h, the thick white slurry was diluted with water (400 mL) and extracted with hexanes (3×125 mL). The combined organic layers were washed with sodium thiosulfate (2×250 mL) and saturated copper sulfate (2×250 mL), and the washed solution was filtered through a pad of sodium sulfate. The filtrate was concentrated to provide (R)-3-((tert-butyldiphenylsilyl)oxy)pentan-2-one as a colorless oil (13.75 g, 100%). TLC (5% ether in hexanes): $R_f$=0.16 (UV, KMnO$_4$). $^1$H NMR (500 MHz, CDCl$_3$), δ: 7.67-7.60 (m, 4H), 7.48-7.41 (m, 2H), 7.41-7.34 (m, 4H), 4.09 (dd, J=6.5, 5.2 Hz, 1H), 2.08 (s, 3H), 1.71-1.52 (m, 2H), 1.13 (s, 9H), 0.82 (t, J=7.5 Hz, 3H). $^{13}$C NMR (125 MHz, CDCl$_3$), δ: 211.3, 135.8, 135.8, 133.5, 133.1, 129.9, 129.9, 127.7, 127.6, 80.2, 27.7, 27.00, 25.8, 19.3, 8.7. FTIR (neat), cm$^{-1}$: 2965, 2934, 2859, 1717, 1427, 1111, 1018, 713. HRMS (ESI): Calculated for $(C_{21}H_{28}O_2Si+Na)^+$: 363.1751; found: 363.1763.

The ee of the product was determined to be 99% by analysis on a chiral stationary phase OD-H column using pure hexanes as eluent with detection at 168-218 nm at a flow rate of 1.0 mL/min.

Example 2D. Preparation of Western Half Building Blocks

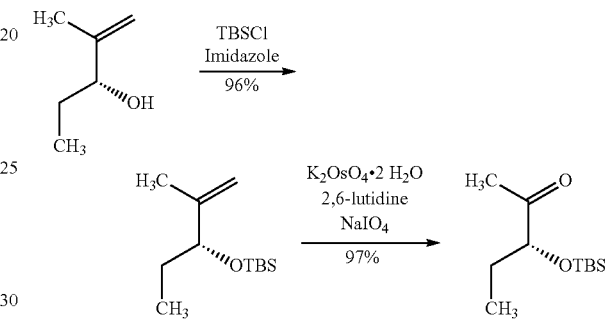

Step 1:

To a solution of (R)-2-methylpent-1-en-3-ol (3.4 g, 33.9 mmol) (pure from MLC-IV-050) in DMF (33 mL) was added imidazole (4.62 g, 67.9 mmol) followed by TBS-Cl (6.65 g, 44.1 mmol). The reaction solution was stirred at room temperature. After 24 h, the reaction solution was partitioned between hexanes (60 mL) and water (225 mL), and after vigorous mixing, the layers were separated. The aqueous layer was further extracted with hexanes (2×60 mL), and the combined organic layers were washed with water (2×90 mL), and loaded onto a silica gel pad (2" diameter, 9" length) which was slurry-packed with hexanes. The pad was eluted into 150 mL fractions with hexanes (1200 mL), and the fractions containing product were combined and concentrated under reduced pressure, providing (R)-tert-butyldimethyl((2-methylpent-1-en-3-yl)oxy)silane (7.00 g, 32.6 mmol, 96% yield) as a colorless liquid.

Step 2:

(R)-tert-butyldimethyl((2-methylpent-1-en-3-yl)oxy)silane (2.75 g, 12.83 mmol) was dissolved in THF:H$_2$O (42.8 ml) (2:1), resulting in a slurry. 2,6-lutidine (2.99 ml, 25.7 mmol) was added, followed by sodium periodate (10.97 g, 51.3 mmol) and potassium osmate dehydrate (0.095 g, 0.257 mmol), and the solution was vigorously stirred (9:45 AM). After 3 hours, the starting material was completely consumed as indicated by TLC (10% ether in hexanes). The thick white slurry was diluted with water (75 mL) and the resulting slurry was extracted with hexanes (2×50 mL). The combined organic layers were washed with sodium thiosulfate (2×100 mL, vigorous mixing) and saturated copper sulfate (2×50 mL). The washed organic solution was gravity-filtered through a pad of sodium sulfate, and the filtrate was concentrated (no high vacuum) to provide (R)-3-((tert-butyldimethylsilyl)oxy)pentan-2-one (2.7 g, 12.48 mmol, 97% yield) as a yellow oil.

Example 2E

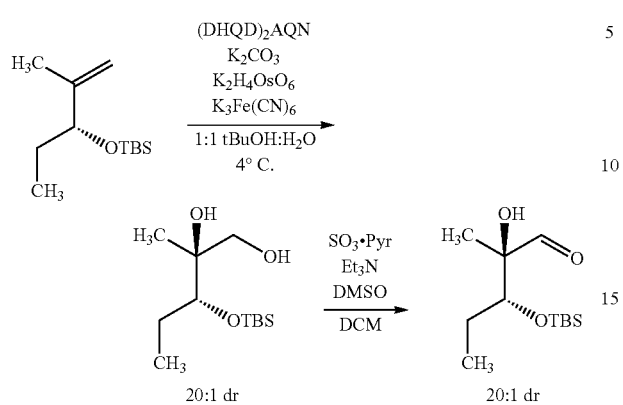

(DHQD)$_2$AQN (0.280 g, 0.326 mmol), K$_3$Fe(CN)$_6$ (32.2 g, 98 mmol), K$_2$CO$_3$ (13.54 g, 98 mmol), and Potassium Osmate Dihydrate (0.024 g, 0.065 mmol) were dissolved in 1:1 tBuOH:H$_2$O (330 mL) and was cooled to 0° C. with vigorous stirring. (R)-tert-butyldimethyl((2-methylpent-1-en-3-yl)oxy)silane (7 g, 32.6 mmol) was added neat via syringe. The mixture was stirred for 72 h at 4° C. Solid sodium sulfite was added and the mixture was stirred vigorously for 30 min. Then, ether (300 mL) and water (100 mL) were added and the layers were separated. The aqueous layer was further extracted with ether (2×150 mL) and the combined organics were washed with water and dried through a pad of sodium sulfate. The filtrate was concentrated under reduced pressure. The yellow residue was purified by flash chromatography (50% ether/hexanes). (2S, 3R)-3-((tert-butyldimethylsilyl)oxy)-2-methylpentane-1,2-diol was afforded as a 15:1-20:1 mixture of diastereomers in favor of the depicted one: 7.6 g, 94% yield.

To a solution of (2S,3R)-3-((tert-butyldimethylsilyl)oxy)-2-methylpentane-1,2-diol (1.2 g, 4.83 mmol) (16:1 ratio of isomers) in dichloromethane (20 mL) was added triethylamine (3.37 ml, 24.15 mmol) and DMSO (3.43 ml, 48.3 mmol). The mixture was cooled to 0° C., and SO$_3$•Pyridine (3.08 g, 19.32 mmol) was added as a solid. After 1.5 h at 0° C., conversion was about 50%, so the vessel was removed from the ice water bath. After 4 h total, the starting material was completely consumed. The mixture was diluted with ether (30 mL) and washed with water (2×30 mL), sat aq copper sulfate (20 mL), sat aq NaCl (20 mL), and was dried through a pad of sodium sulfate and concentrated (no high vacuum) to provide the aldehyde product in a yield of 1.10 g (92%) as a crude yellow oil.

Exemplary Coupling of Eastern and Western Halves

Example 3A. Synthesis of Solithromycin Via Horner-Emmons Coupling

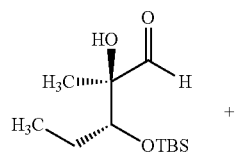

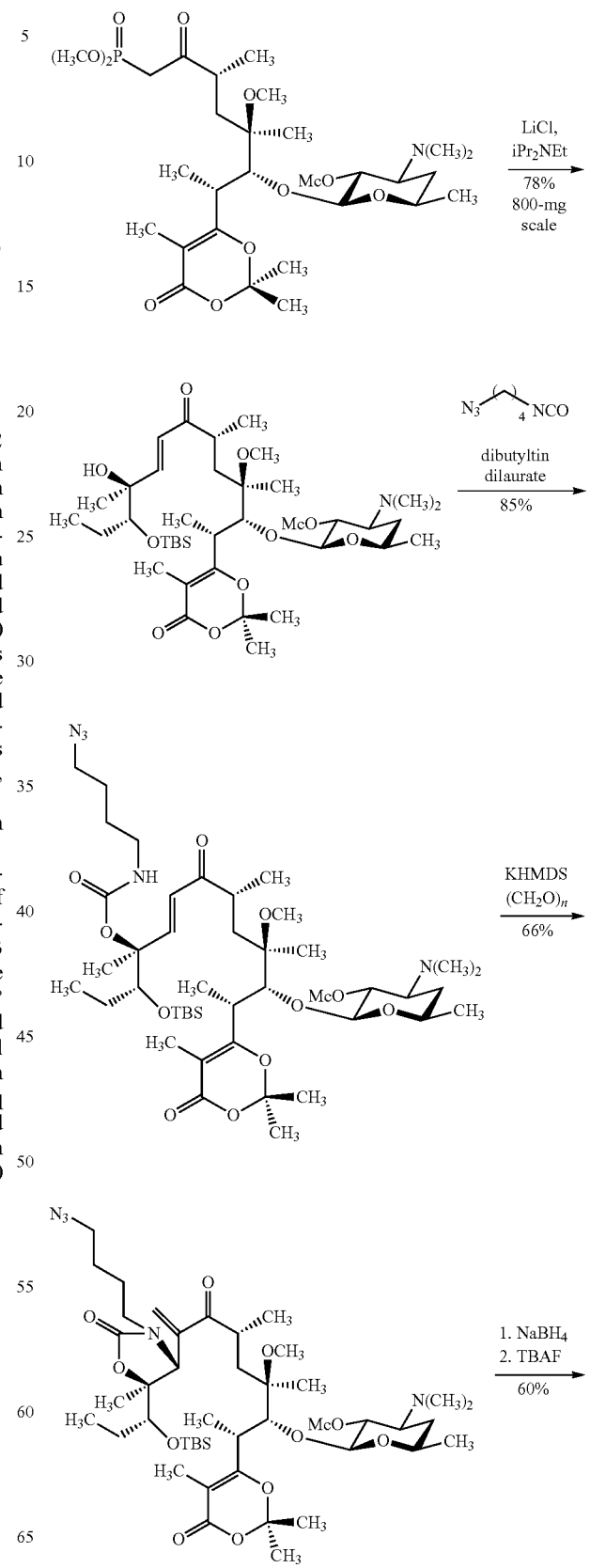

Step 1:

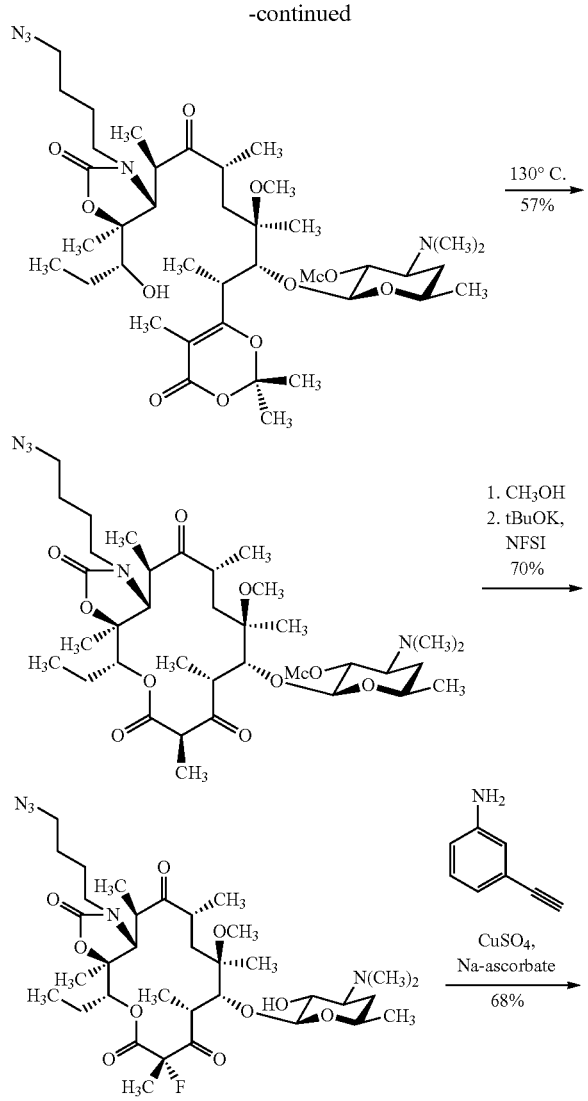

solithromycin, fully synthetic
17 steps

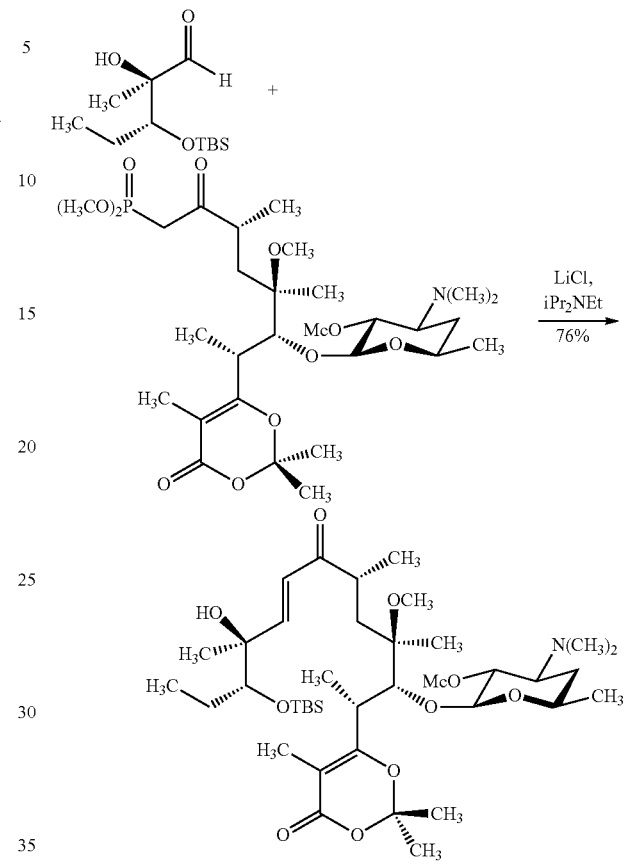

A 25-mL flask equipped with a stir bar was charged with anhydrous LiCl (0.153 g, 3.61 mmol). The vessel was heated with a gentle flame under vacuum (0.1 mmHg) for 2 min. The phosphonate (2.0 g, 3.00 mmol) was added as a solution in acetonitrile (15.02 mL), followed by diisopropylethylamine (0.630 mL, 3.61 mmol). The suspension was stirred at rt for 5 min. (2R,3R)-3-((tert-butyldimethylsilyl)oxy)-2-hydroxy-2-methylpentanal (0.740 g, 3.00 mmol) was added neat dropwise. The resulting suspension was then stirred at 30° C. After 12 h, TLC (10% methanol in ethyl acetate) indicated full consumption of the phosphonate. The reaction mixture was diluted with $CH_2Cl_2$ (30 mL), saturated aqueous $NaHCO_3$ (15 mL) and vigorously stirred. The layers were separated and the aqueous layer was extracted with $CH_2Cl_2$ (3×20 mL). The combined organic layers were dried over $Na_2SO_4$ and concentrated. The crude product was purified by flash column chromatography (2-3% methanol in $CH_2Cl_2$+0.2% saturated $NH_4OH$) to give the product as a white foam (1.80 g, 76%). $^1H$ NMR (500 MHz, $CDCl_3$) δ 6.82 (d, J=15.6 Hz, 1H), 6.46 (d, J=15.6 Hz, 1H), 4.63-4.48 (m, 2H), 3.82 (d, J=3.4 Hz, 1H), 3.78 (s, 3H), 3.52 (dd, J=5.8, 4.6 Hz, 1H), 3.48-3.40 (m, 1H), 3.38-3.30 (m, 1H), 2.93 (s, 3H), 2.80-2.71 (m, 1H), 2.59 (s, 1H), 2.31 (s, 6H), 2.12 (dd, J=14.1, 10.2 Hz, 1H), 1.82 (s, 3H), 1.80-1.74 (m, 1H), 1.66 (s, 3H), 1.65 (s, 3H), 1.64-1.57 (m, 1H), 1.49-1.41 (m, 2H), 1.41-1.31 (m, 1H), 1.27 (s, 3H), 1.25 (d, J=6.2 Hz, 4H), 1.21 (s, 3H), 1.07 (d, J=3.5 Hz, 3H), 1.06 (d, J=3.0 Hz, 3H), 0.92 (s, 9H), 0.90 (t, J=2.8 Hz, 3H), 0.10 (d, J=1.9 Hz, 6H). $^{13}C$ NMR (126 MHz, $CDCl_3$) δ 203.61, 167.58, 162.99, 155.24, 147.02, 125.97, 104.34, 99.94, 99.78, 79.32, 78.24, 77.40, 75.63, 75.49, 69.22, 63.04, 54.69, 49.40, 40.67, 39.82, 37.99, 34.12, 30.85, 26.16, 25.95, 25.89, 25.73, 24.32, 20.95, 20.09, 18.93, 18.20, 13.00, 10.75, 9.69, −3.88, −4.43. FTIR (neat), cm$^{-1}$: 3470(br), 2937 (m), 1751 (s), 1716(s), 1639 (s), 1267 (s), 1055 (s), 910 (s); HRMS (ESI): Calcd for $(C_{40}H_{71}NO_{12}Si+H)^+$: 786.4818; Found: 786.4824.

Step 2:

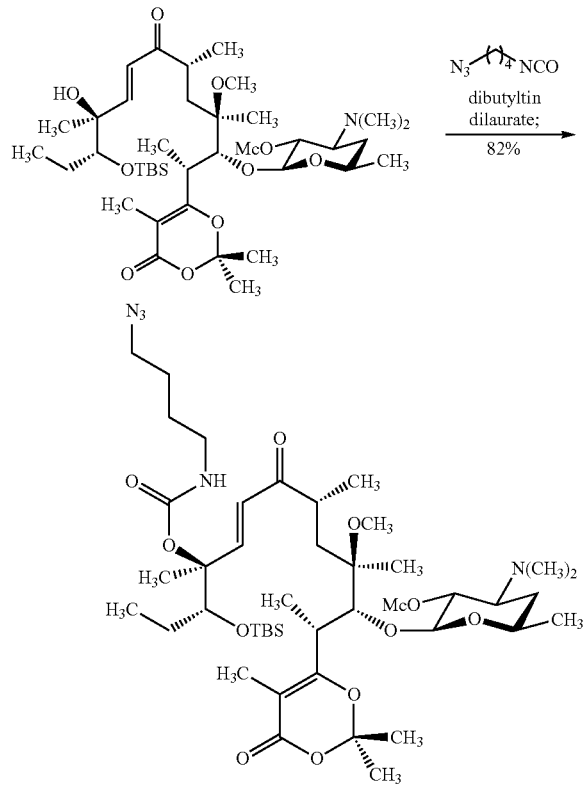

HWE Product (600 mg, 0.763 mmol) was dissolved in Dichloroethane (7633 μl). 1-azido-4-isocyanatobutane (105 μl, 0.840 mmol) was added, followed by dibutyltin dilaurate (455 μl, 0.763 mmol). The reaction was heated to reflux (80° C.). After 18 h, LC-MS indicated complete conversion. The reaction mixture was directly concentrated purified by column chromatography (10-25% Acetone in Hexanes+0.5% Et3N) to give the product as a white foam (580 mg, 82%). $^1$H NMR (500 MHz, cdcl$_3$) δ 6.95 (d, J=16.2 Hz, 1H), 6.19 (d, J=16.2 Hz, 1H), 4.78 (s, 1H), 4.59 (dt, J=13.9, 7.6 Hz, 2H), 3.98 (d, J=4.6 Hz, 1H), 3.85 (d, J=3.3 Hz, 1H), 3.80 (s, 3H), 3.47 (dd, J=10.1, 5.2 Hz, 1H), 3.42-3.24 (m, 3H), 3.17 (q, J=6.4 Hz, 1H), 3.05-2.98 (m, 1H), 2.95 (s, 3H), 2.81-2.70 (m, 1H), 2.32 (s, 6H), 2.20 (dd, J=14.1, 9.9 Hz, 1H), 1.83 (s, 3H), 1.81-1.73 (m, 1H), 1.67 (s, 3H), 1.67 (s, 3H), 1.65-1.58 (m, 5H), 1.57 (s, 3H), 1.46-1.32 (m, 4H), 1.27 (d, J=6.1 Hz, 3H), 1.23 (s, 3H), 1.09 (d, J=3.4 Hz, 3H), 1.08 (d, J=3.0 Hz, 3H), 0.98-0.92 (m, 1H), 0.91 (s, 9H), 0.09 (s, 6H). $^{13}$C NMR (126 MHz, cdcl$_3$) δ 203.4, 167.6, 163.0, 155.3, 154.8, 146.1, 128.0, 104.3, 99.9, 99.8, 84.3, 78.4, 78.2, 77.1, 75.5, 69.2, 63.0, 54.7, 51.0, 49.5, 40.7, 40.1, 38.3, 37.8, 34.1, 30.9, 27.3, 26.1, 26.0, 25.7, 25.5, 24.3, 20.9, 20.19, 20.14, 19.2, 13.0, 11.3, 9.70, −3.94. FTIR (neat), cm$^{-1}$: 3381(br), 2951 (s), 2096 (s), 1720 (s), 1267 (s), 1053 (s), 731 (s); HRMS (ESI): Calcd for $(C_{45}H_{79}N_5O_{13}Si+H)^+$: 926.5516; Found: 926.5533.

Step 3:

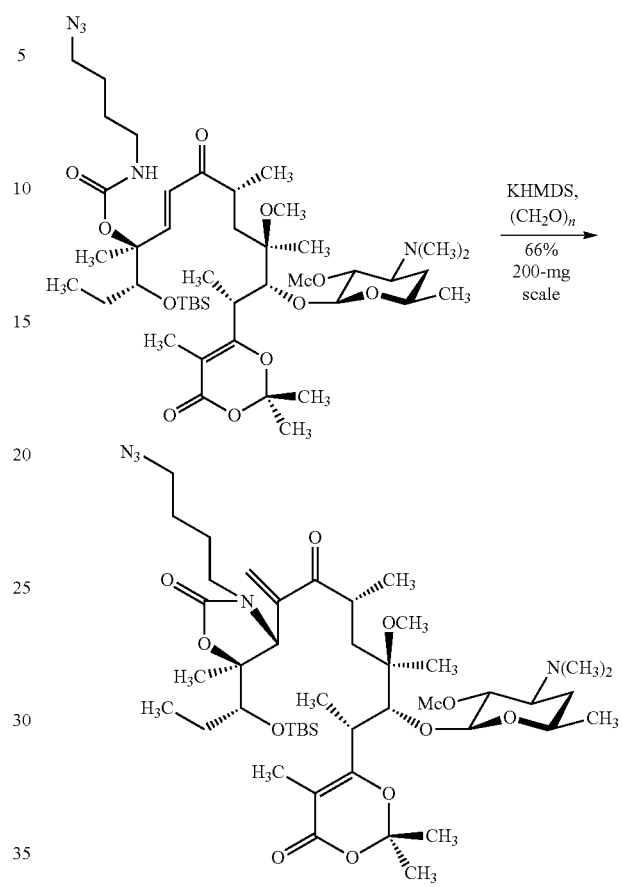

Paraformaldehyde (324 mg, 10.8 mmol, 50.0 equiv) was added to a solution of open carbamate (200 mg, 0.216 mmol, 1 equiv) in THF (1.0 mL) at 23° C. The suspension was cooled to −78° C. (dry ice-acetone bath). A solution of KHMDS in THF (0.50 M, 0.950 mL, 0.475 mmol, 2.20 equiv) was added dropwise via syringe at −78° C. over 10 min. The resulting solution was allowed to warm to 0° C. over 1 h and was held at that temperature for 1 h. Saturated aqueous sodium bicarbonate solution (10 mL) was added at 0° C. After warming to 23° C., the mixture was extracted with ether (3×10 mL). The combined ether layers were washed with brine and dried over magnesium sulfate. The dried solution was concentrated under reduced pressure and the residue was purified by flash column chromatography (10→25% acetone-hexanes+0.5% triethylamine) to afford the product as a white foam (134 mg, 66%).

$^1$H NMR (500 MHz, cdcl$_3$) δ 6.62 (br s, J=33.7 Hz, 1H), 5.84 (br s, J=31.9 Hz, 1H), 4.96 (br s, 1H), 4.62-4.52 (m, 2H), 3.84 (d, J=3.3 Hz, 1H), 3.79 (s, 3H), 3.68-3.60 (m, 1H), 3.59-3.38 (m, 3H), 3.38-3.23 (m, 3H), 2.92 (s, 3H), 2.82-2.73 (m, 1H), 2.73-2.61 (m, 1H), 2.31 (s, 6H), 1.80 (s, 3H), 1.79-1.75 (m, 1H), 1.66 (s, 3H), 1.66 (s, 3H), 1.62-1.47 (m, 7H), 1.47-1.29 (m, 2H), 1.25 (d, J=6.1 Hz, 3H), 1.20 (s, 3H), 1.09 (d, J=7.4 Hz, 3H), 1.06 (s, 2H), 1.05 (d, J=7.0 Hz, 3H), 1.00 (t, J=7.5 Hz, 3H), 0.93 (s, 10H), 0.13 (d, J=12.8 Hz, 6H).

$^{13}$C NMR (126 MHz, cdcl$_3$) δ 167.35, 162.78, 157.64, 155.31, 142.69, 104.42, 100.13, 99.79, 78.80, 78.27, 77.70, 75.46, 69.27, 63.00, 54.73, 51.12, 50.88, 49.53, 42.00, 40.65, 37.51, 34.83, 34.25, 30.85, 26.34, 26.07, 25.94, 25.48, 24.70, 24.14, 20.99, 20.27, 18.25, 13.04, 11.73, 9.62, −3.92, −4.23. Note: The carbon spectrum of this compound is complicated by severe line broadening. Only clearly discernible peaks are reported. FTIR (neat), cm$^{-1}$: 2937 (m), 2096 (s), 1749 (s), 1724 (s), 1267 (s), 1112 (s), 1053 (s), 729 (s). HRMS (ESI): Calcd for $(C_{46}H_{79}N_5O_{13}Si+H)^+$: 938.5516; Found: 938.5550.

Step 4:

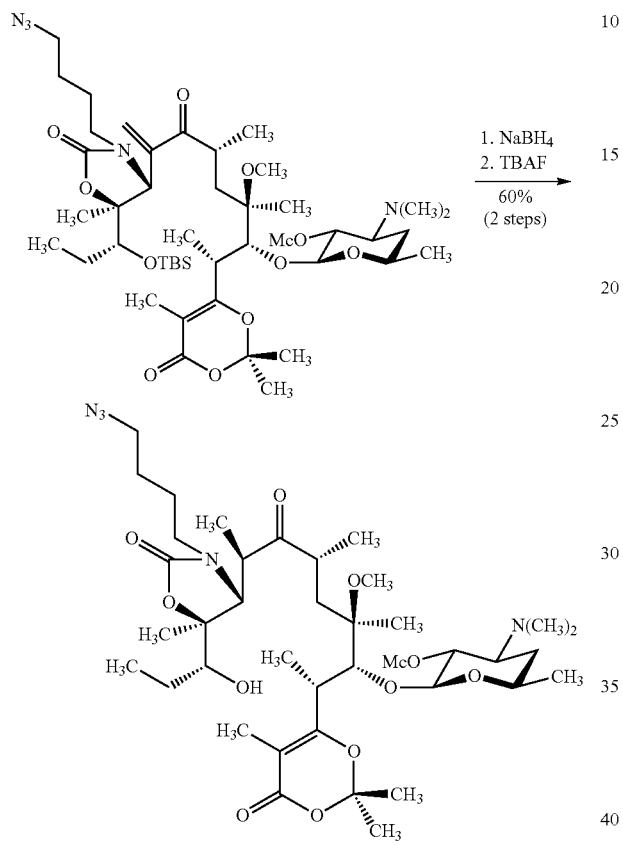

Sodium borohydride (2.2 mg, 0.059 mmol, 1.0 equiv) was added to a solution of open chain exomethylene (55 mg, 0.059 mmol, 1 equiv) in methanol (0.2 mL) at −15° C. After 30 min, the reaction mixture was allowed to warm to 23° C. and concentrated under reduced pressure. The residue was partitioned between ether (5 mL) and saturated aqueous sodium bicarbonate solution (5 mL). The aqueous layer was extracted with ether (2×5 mL). The combined ether layers were dried over magnesium sulfate and the dried solution was concentrated under reduced pressure. The residue was dissolved in THF (0.2 mL), and a solution of TBAF in THF (0.12 mL, 0.12 mmol, 2.0 equiv) was added at 23° C. After 1 h, the solution was concentrated under reduced pressure. The residue was purified by flash column chromatography (10→25% acetone-hexanes+0.5% triethylamine) to afford the product as a white foam (31 mg, 60%). $^1$H NMR (500 MHz, cdcl$_3$) δ 4.59-4.48 (m, 2H), 4.27 (s, 1H), 3.86 (d, J=3.1 Hz, 1H), 3.75 (s, 3H), 3.53-3.36 (m, 3H), 3.35-3.22 (m, 3H), 2.96-2.91 (m, 1H), 2.93 (s, 3H), 2.88-2.79 (m, 1H), 2.79-2.67 (m, 1H), 2.41 (br s, 1H), 2.28 (s, 6H), 2.10 (dd, J=14.2, 10.0 Hz, 1H), 1.78 (s, 3H), 1.77-1.73 (m, 1H), 1.70-1.66 (m, 2H), 1.65 (s, 3H), 1.64 (s, 3H), 1.62-1.51 (m, 6H), 1.41-1.37 (m, 1H), 1.34 (s, 3H), 1.24 (d, J=6.4 Hz, 3H), 1.23 (s, 3H), 1.10 (d, J=7.2 Hz, 3H), 1.08 (d, J=7.0 Hz, 3H), 1.05 (d, J=7.4 Hz, 3H), 1.02 (t, J=7.4 Hz, 3H). $^{13}$C NMR (126 MHz, CDCl$_3$) δ 215.21, 167.20, 162.72, 157.51, 155.27, 104.46, 99.94, 99.84, 83.34, 78.53, 77.80, 76.56, 75.44, 69.26, 62.93, 57.06, 54.69, 51.00, 49.41, 46.10, 42.10, 40.63, 38.51, 33.89, 30.84, 26.02, 25.90, 24.27, 24.16, 23.63, 20.95, 20.11, 15.67, 13.03, 10.85, 10.57, 9.68. FTIR (neat), cm$^{-1}$: 3462 (br), 2939 (m), 2098 (s), 1753 (s), 1724 (s), 1267 (s), 1112 (s), 1053 (s), 999 (s). HRMS (ESI): Calcd for $(C_{40}H_{67}N_5O_{13}+H)^+$: 826.4808; Found: 826.4820.

Step 5:

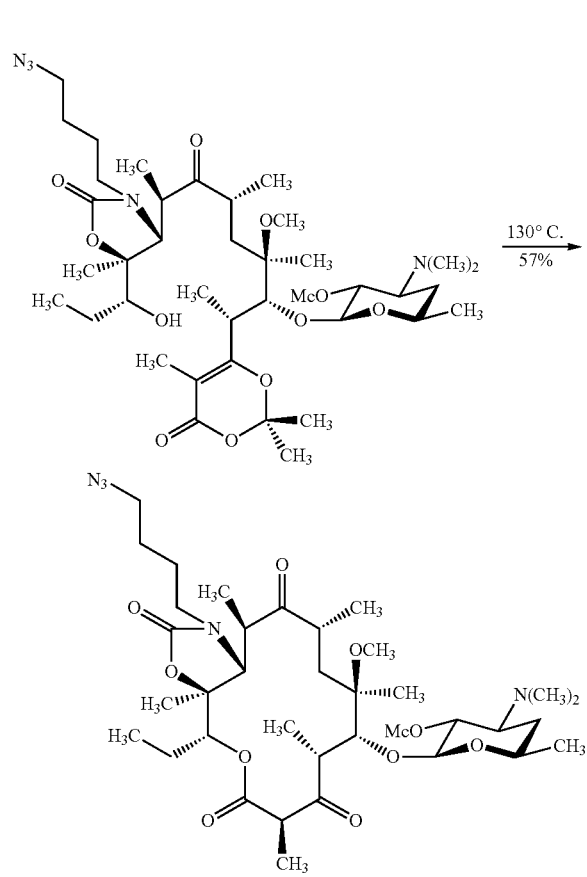

C10-methylmacrocyclization_precursor (31 mg, 0.038 mmol) was dissolved in chlorobenzene (38 mL) in a 50-mL flask. The flask was fitted with a dry reflux condensor. Dry argon was bubbled through the solution via a 19-gauge needle for 10 min. The flask was then immersed in an oil bath preheated to 150° C. to allow a gentle reflux of the reaction solution. After 16 h, the heating bath was removed and the solution was allowed to cool to 23° C. The cooled solution was concentrated under reduced pressure (rotary evaporation, 10 mmHg, 40° C. water bath) and the residue was purified by flash column chromatography (25% acetone-hexanes+0.5% triethylamine) to afford the product as a white foam (15 mg, 52%). $^1$H NMR (3:1 diastereomeric mixture at C2, major isomer is reported, 500 MHz, cdcl$_3$) $^1$H NMR (500 MHz, cdcl$_3$) δ 4.95 (dd, J=10.6, 2.4 Hz, 1H), 4.53 (dd, J=10.5, 7.6 Hz, 1H), 4.40 (d, J=7.6 Hz, 1H), 4.25 (d, J=8.1 Hz, 1H), 3.83 (q, J=6.5 Hz, 1H), 3.80 (s, 3H), 3.71-3.64 (m, 1H), 3.60 (s, 1H), 3.59-3.53 (m, 1H), 3.40-3.22 (m, 3H), 3.15-3.08 (m, 1H), 3.08-3.02 (m, 1H), 2.78-2.69 (m, 1H), 2.66 (s, 3H), 2.64-2.52 (m, 1H), 2.28 (s, 6H), 2.03-1.89 (m, 1H), 1.81-1.59 (m, 8H), 1.49 (s, 3H), 1.36 (d, J=6.8 Hz, 3H), 1.34 (s, 3H), 1.28-1.25 (m, 4H), 1.20-1.14 (m, 6H), 1.02 (d, J=7.0 Hz, 3H), 0.86 (t, J=7.4 Hz, 3H).

Note: peaks for the minor isomer are not clearly discernible. $^{13}$C NMR (3:1 diastereomeric mixture at C2, major isomer is reported, 126 MHz, cdcl$_3$) δ 215.98, 203.72, 169.53, 157.15, 155.19, 101.36, 82.10, 78.56, 78.11, 77.42, 75.55, 69.19, 63.27, 60.48, 54.78, 51.17, 50.96, 49.65, 46.99, 44.87, 42.95, 40.62, 39.12, 39.01, 30.23, 26.24, 24.34, 22.30, 20.95, 20.92, 19.69, 18.36, 15.49, 14.71, 13.94, 13.91, 10.39. FTIR (neat), cm$^{-1}$: 2941 (m), 2096 (s), 1753 (s), 1712 (s), 1267 (s), 1109 (s), 1055 (s), 999 (s). HRMS (ESI): Calcd for (C$_{37}$H$_{61}$N$_5$O$_{12}$+H)$^+$: 768.4389; Found: 768.4395.

Step 6:

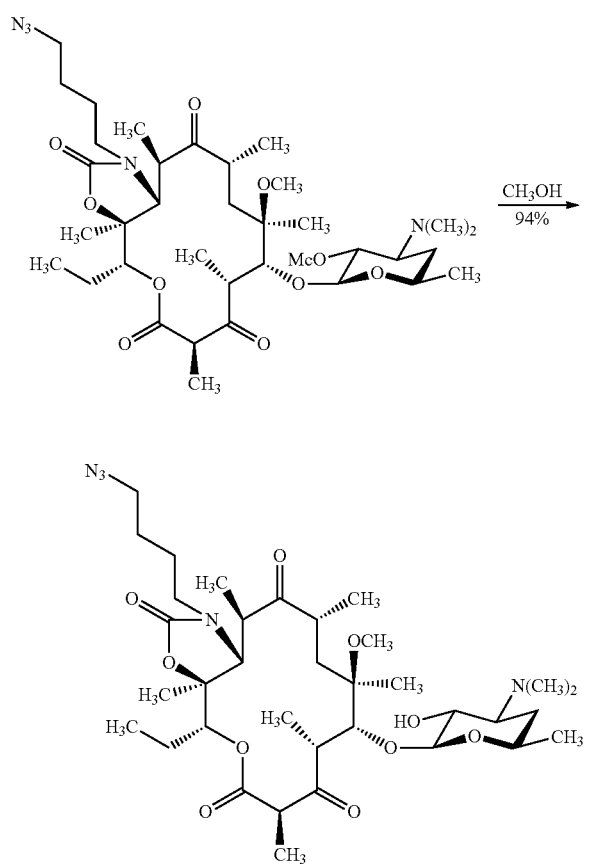

A solution of C10-methyl-macrocycle (15 mg, 0.020 mmol) in methanol (1 mL) was allowed to stand at 23° C. for 24 h. The solution was then concentrated to afford the product as a colorless film (13 mg, 94%). $^1$H NMR (500 MHz, cdcl$_3$) δ 4.94 (dd, J=10.6, 2.4 Hz, 1H), 4.29 (d, J=7.3 Hz, 1H), 4.25 (d, J=8.8 Hz, 1H), 3.85 (q, J=6.8 Hz, 1H), 3.73-3.65 (m, 1H), 3.65-3.59 (m, 1H), 3.58 (s, 1H), 3.57-3.48 (m, 1H), 3.38-3.23 (m, 2H), 3.19 (dd, J=10.2, 7.3 Hz, 1H), 3.15-3.11 (m, 1H), 3.11-3.04 (m, 1H), 2.67 (s, 3H), 2.65-2.57 (m, 1H), 2.45 (ddd, J=12.3, 10.4, 3.9 Hz, 1H), 2.27 (s, 6H), 2.00-1.88 (m, 1H), 1.83 (dd, J=14.5, 2.4 Hz, 1H), 1.78-1.51 (m, 7H), 1.47 (s, 3H), 1.37 (d, J=6.8 Hz, 3H), 1.36 (s, 3H), 1.31 (d, J=7.5 Hz, 3H), 1.25 (d, J=6.2 Hz, 3H), 1.24-1.21 (m, 1H), 1.17 (d, J=7.0 Hz, 3H), 1.01 (d, J=7.0 Hz, 3H), 0.86 (t, J=7.4 Hz, 3H). $^{13}$C NMR (151 MHz, CDCl3) δ 216.09, 203.76, 169.54, 157.17, 103.92, 82.11, 79.54, 78.14, 77.30, 70.33, 69.60, 65.85, 60.39, 51.21, 50.97, 49.75, 47.57, 44.90, 42.92, 40.20, 39.53, 39.01, 29.66, 28.14, 26.26, 24.32, 22.25, 21.16, 19.72, 18.36, 15.76, 14.63, 14.34, 13.88, 10.38. FTIR (neat), cm$^{-1}$: 3477 (br), 2937 (m), 2096 (s), 1753 (s), 1712 (s), 1456 (s), 1165 (s), 1109 (s), 1076 (s), 1051 (s), 991 (s). HRMS (ESI): Calcd for (C$_{35}$H$_{59}$N$_5$O$_{10}$+H)$^+$: 710.4335; Found: 710.4343.

Step 7:

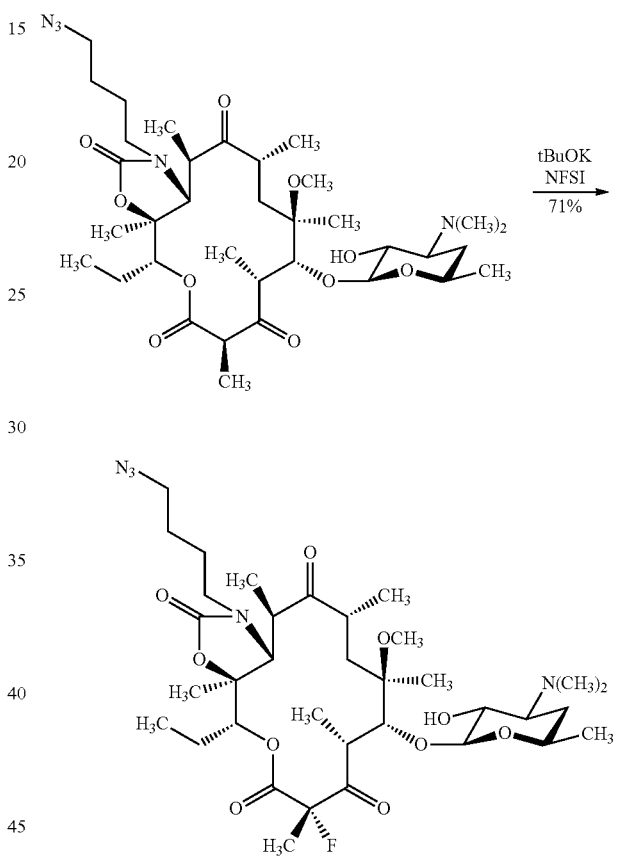

A solution of potassium tert-butoxide in THF (1.0 M, 18 μL, 18 μmol, 1.0 equiv) was added dropwise to a solution of C10-methylmacrocycle (13 mg, 18 μmol, 1 equiv) in THF (0.2 mL) at −78° C. The solution was stirred for 5 min, and a solution of N-fluorobenzenesulfonimide (5.8 mg, 18 μmol, 1.0 equiv) in THF (0.1 mL) was added dropwise via syringe at −78° C. The mixture was stirred at −78° C. for 1 h. Saturated aqueous sodium thiosulfate solution (0.5 mL) and saturated aqueous sodium bicarbonate solution (0.5 mL) were added at −78° C. The mixture was allowed to warm to 23° C., and was extracted with dichloromethane (3×1 mL). The combined organic layers were dried over sodium sulfate and the dried solution was concentrated under reduced pressure. The residue was purified by flash column chromatography (3% methanol-dichloromethane+0.3% saturated ammonium hydroxide solution) to afford the C2 fluorination product as a colorless film (9.4 mg, 71%). This product is an 8:1 mixture of C2 diastereomers.

Step 8:

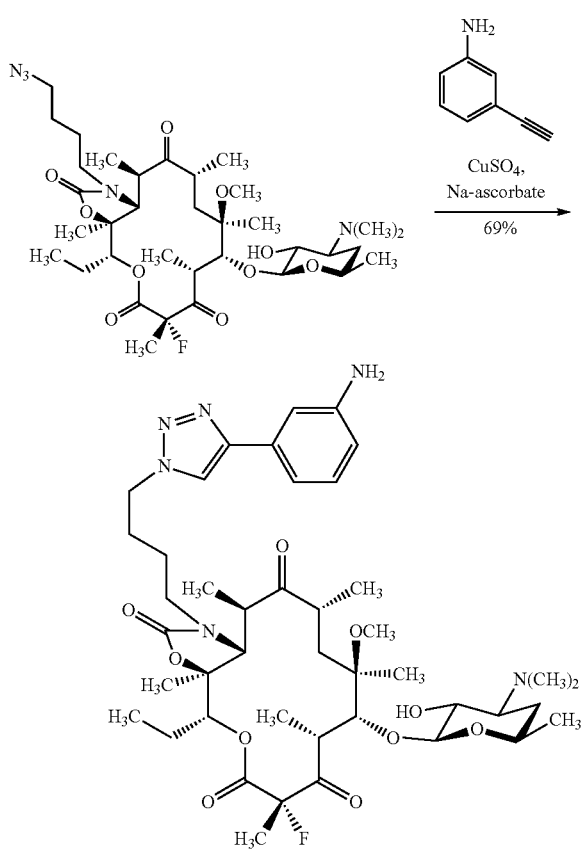

3-ethynylaniline (4.5 mg, 0.039 mmol, 3.0 equiv), an aqueous solution of sodium ascorbate (0.10 M, 26 µL, 2.6 µmol, 0.20 equiv) and an aqueous solution of copper(II) sulfate (0.10 M, 6.5 µL, 0.65 µmol, 0.050 equiv) were added sequentially to a stirred solution of C2-fluoromacrocycle (9.4 mg, 0.013 mmol, 1 equiv) 1:1 t-butanol:water (0.2 mL). After 16 h, the reaction mixture was partitioned between dichloromethane (1 mL) and saturated aqueous sodium bicarbonate solution (1 mL). The aqueous layer was extracted with dichloromethane (2×1 mL). The combined organic layers were dried over sodium sulfate and the dried solution was concentrated under reduced pressure. The residue was purified by preparatory thin layer chromatography (10% methanol-dichloromethane+1% saturated ammonium hydroxide solution) to afford solithromycin as a white solid (7.5 mg, 69%). $^1$H NMR (500 MHz, cdcl$_3$) δ 7.82 (s, 1H), 7.31-7.29 (m, 1H), 7.23-7.15 (m, 2H), 6.66 (dt, J=7.2, 2.1 Hz, 1H), 4.89 (dd, J=10.3, 2.0 Hz, 1H), 4.43 (td, J=7.1, 1.5 Hz, 2H), 4.32 (d, J=7.3 Hz, 1H), 4.08 (d, J=10.6 Hz, 1H), 3.82-3.73 (m, 1H), 3.68-3.60 (m, 1H), 3.60-3.49 (m, 2H), 3.45 (s, 1H), 3.20 (dd, J=10.2, 7.3 Hz, 1H), 3.13 (q, J=6.9 Hz, 1H), 2.69-2.59 (m, 1H), 2.57 (s, 3H), 2.51-2.42 (m, 1H), 2.29 (s, 6H), 2.05-1.93 (m, 3H), 1.90 (dd, J=14.5, 2.7 Hz, 1H), 1.79 (d, J=21.4 Hz, 3H), 1.75-1.60 (m, 4H), 1.55 (d, J=13.0 Hz, 1H), 1.52 (s, 3H), 1.36 (s, 3H), 1.32 (d, J=7.0 Hz, 3H), 1.28-1.24 (m, 1H), 1.26 (d, J=6.1 Hz, 3H), 1.20 (d, J=6.9 Hz, 3H), 1.02 (d, J=7.0 Hz, 3H), 0.89 (t, J=7.4 Hz, 3H). $^{13}$C NMR (126 MHz, cdcl$_3$) δ 216.52, 202.79 (d, J=28.0 Hz), 166.44 (d, J=22.9 Hz), 157.19, 147.82, 146.82, 131.72, 129.63, 119.66, 116.14, 114.71, 112.36, 104.24, 97.78 (d, J=206.2 Hz), 82.11, 80.72, 78.59, 78.54, 70.35, 69.64, 65.82, 61.05, 49.72, 49.22, 44.58, 42.77, 40.86, 40.22, 39.57, 39.20, 28.13, 27.59, 25.20 (d, J=22.4 Hz) 24.28, 22.14, 21.15, 19.76, 17.90, 15.04, 14.70, 13.76, 10.47. $^{19}$F NMR (471 MHz, cdcl$_3$) δ-163.24 (q, J=11.2 Hz). FTIR (neat), cm$^{-1}$: 3362 (br), 2976 (m), 1753 (s), 1460 (s), 1263 (s), 1078 (s), 1051 (s), 991 (s). HRMS (ESI): Calcd for $(C_{43}H_{65}FN_6O_{10}+H)^+$: 845.4819; Found: 845.4841.

Example 3B. Synthesis of Solithromycin Intermediate Via Hydromagnesiation

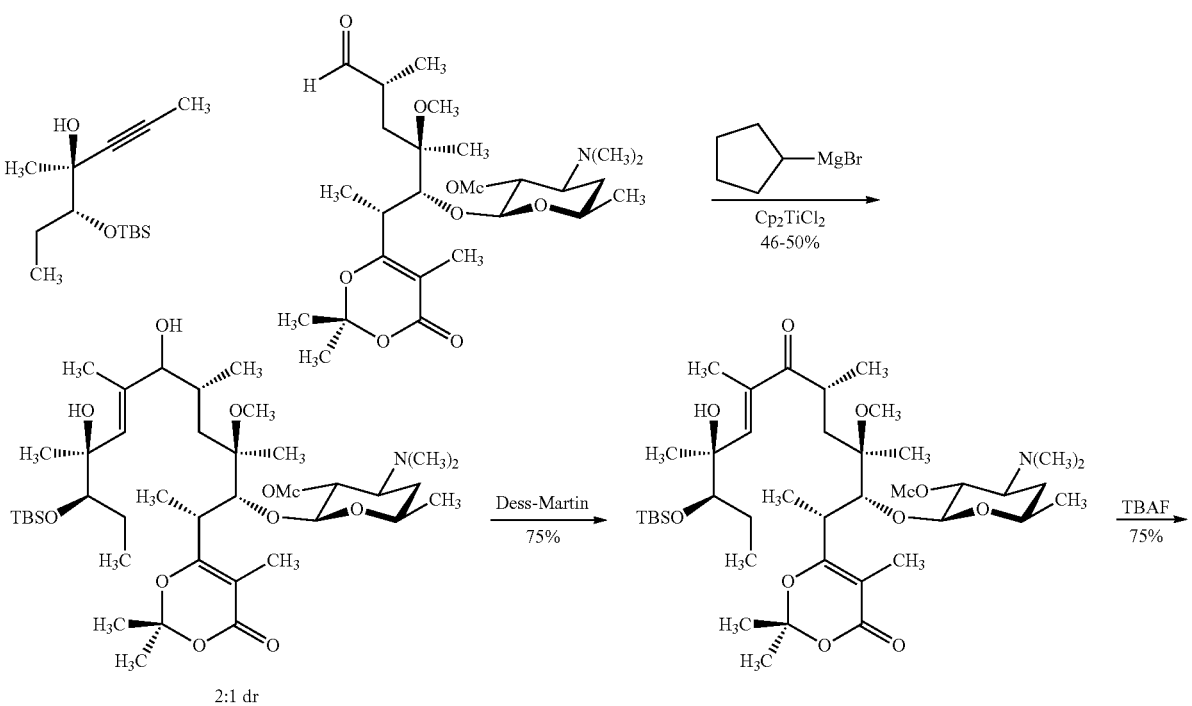

297 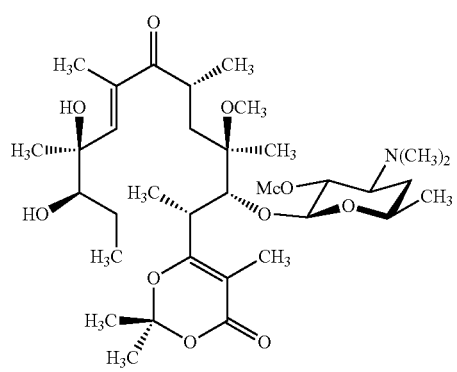 298 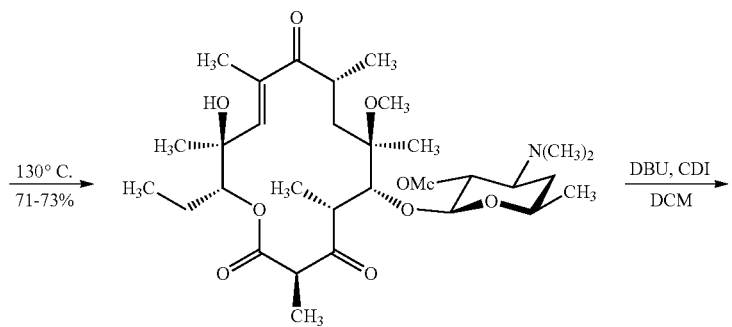
-continued
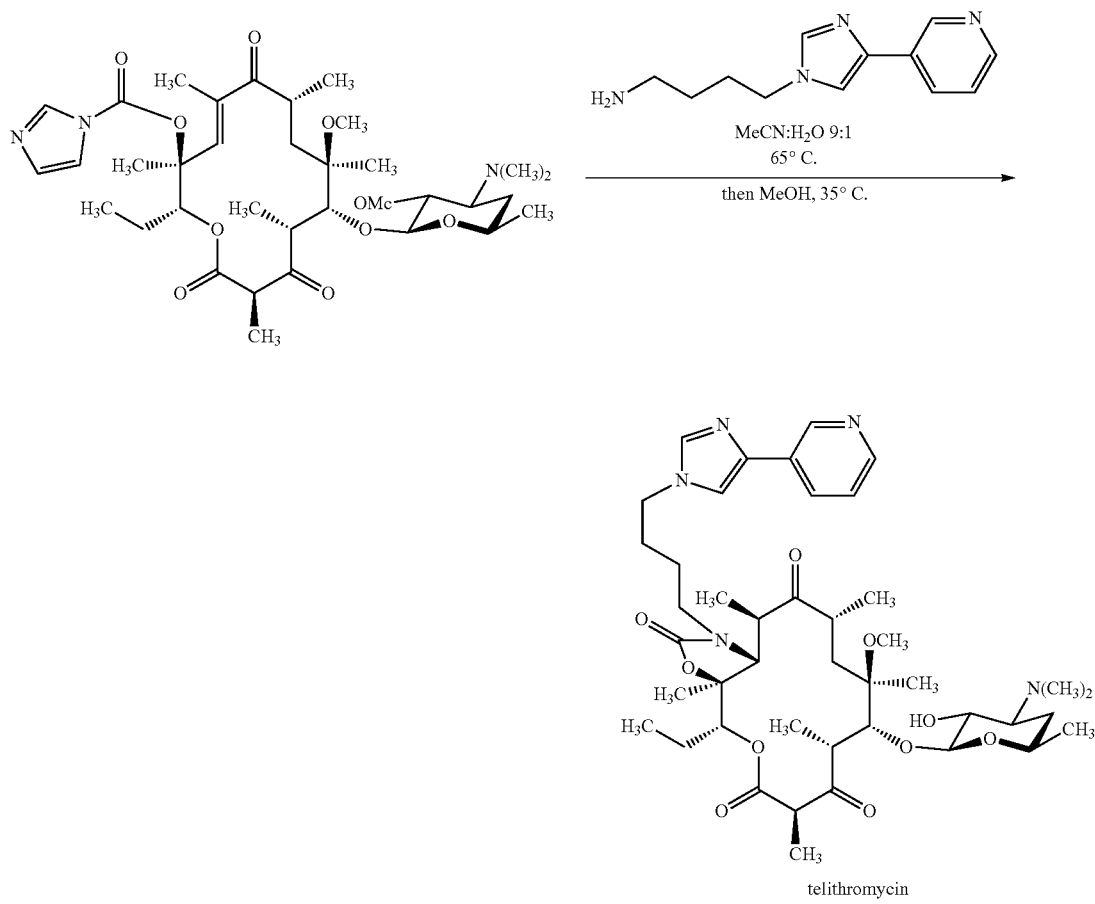
telithromycin
Step 1:
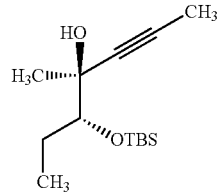
-continued
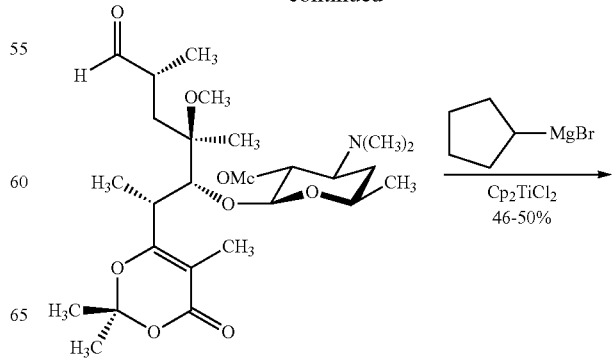

-continued

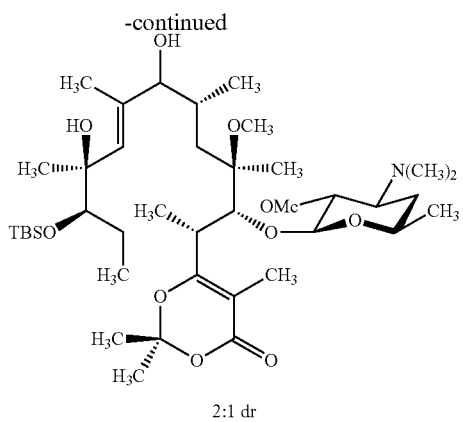

2:1 dr

A flame-dried, 5-mL flask was charged with Cp$_2$TiCl$_2$ (47.6 mg, 0.191 mmol). The vessel was evacuated and refilled with dry argon (this process was repeated three times), and was then equipped with a rubber septum and a positive pressure of argon through a needle. Ethyl ether (5790 μl) was added and the red suspension was cooled to 0° C. in an ice water bath. cyclopentylmagnesium bromide (2548 μl, 5.10 mmol) (2 M solution in ether) was added, and the purple/gray solution was stirred for 5 minutes at this temperature. A solution of (4S,5R)-5-((tert-butyldimethylsilyl)oxy)-4-methylhept-2-yn-4-ol (490 mg, 1.911 mmol) in ether (2 mL) was added dropwise (the transfer was quantitated with 2×0.5 mL ether). After 5 min, the mixture was allowed to warm to 23° C. After 2 h, the mixture was cooled to −20° C., and a solution of Right Half Aldehyde (630 mg, 1.158 mmol) in ether (2 mL) was added. The mixture was allowed to warm to 23° C., and THF (5 mL) was added, and most of the solids went into solution. TLC revealed high conversion to a less polar spot, with some "starting material" and some more polar contaminant. After 30 minutes at 23° C., sat aq NH$_4$Cl (20 mL) was added, and the layers were mixed vigorously and were separated. The aqueous layer was extracted with ethyl acetate (2×15 mL), and the organic layers were combined and washed with water (20 mL) and brine (20 mL). The washed organic solution was gravity-filtered through a pad of sodium sulfate and the filtrate was concentrated. The resulting residue was purified by column chromatography (15% to 20% acetone in hexanes+0.5% Et$_3$N). The byproducts were flushed off with 30% acetone/hexanes. The coupled allylic alcohol (425 mg, 0.530 mmol, 45.8% yield) emerged in >85% purity as a 2.5:1 mixture of diastereomers as yellow foam.

Step 2:

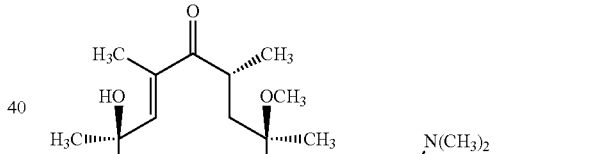

-continued

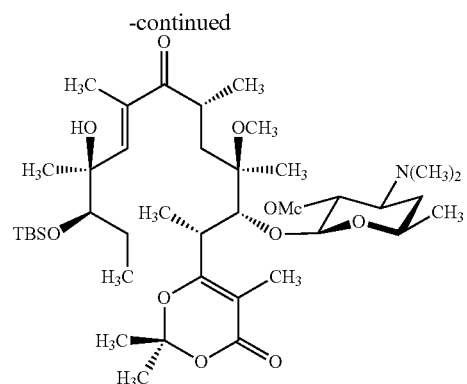

Dess-Martin Periodinane (439 mg, 1.035 mmol) (DMP) was added to a solution of coupled allylic diol (415 mg, 0.517 mmol) in squirt bottle DCM (5174 μl) at 23° C. Monitored by TLC (30% acetone/hexanes+0.5% Et3N). After 30 minutes added another portion of DMP (26 mg, 1.0 equiv). After another 15 minutes the TLC had not changed, so sat aq NaHCO$_3$ (3 mL), sat aq Na$_2$S$_2$O$_4$ (3 mL), and DCM (3 mL) were added. The layers were stirred vigorously until each layer was clear (~5 minutes). The organic layer was separated, and the aqueous layer was extracted with DCM (2×3 mL). The combined organic layers were filtered through a pad of sodium sulfate, and the filtrate was concentrated under reduced pressure. Silica gel chromatography (10% to 16% acetone/hexanes+0.5% Et$_3$N) provided the desired enone (310 mg, 0.387 mmol, 74.9% yield) as a white foam.

Step 3:

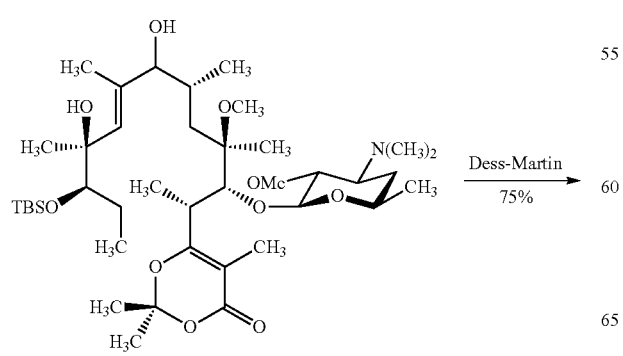

TBAF (750 μl, 0.750 mmol)(1.0 M solution in THF) was added to a solution of enone TBS ether (300 mg, 0.375 mmol) in THF (3750 μl) at 0° C. (11:40 AM). After 30 minutes, the starting material was no longer present by TLC (33% acetone in hexanes+0.5% Et₃N). The THF was evaporated under a stream of argon, and the crude residue was directly purified by silica gel chromatography (20% to 30% acetone/hexanes+0.5% Et3N). This effectively removed the impurities (less polar, all). The product emerged in high purity: enone diol (210 mg, 0.306 mmol, 82% yield)
Step 4:

LCMS indicated consumption starting material. The mixture was cooled to 23° C. and was concentrated under reduced pressure. By crude ¹H-NMR: 2:1 mixture of C2 epimers. Purification by silica gel chromatography (15% to 20% acetone/hexanes+0.5% Et3N) provided enone macrocycle (136 mg, 0.217 mmol, 70.8% yield) as a white foam. Post-column NMR: 16:1 ratio of C2 epimers, equilibrated on column.
Step 5:

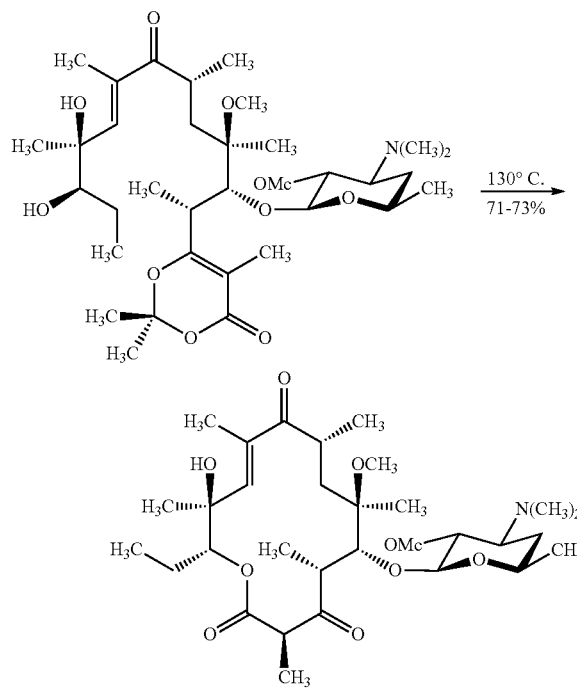

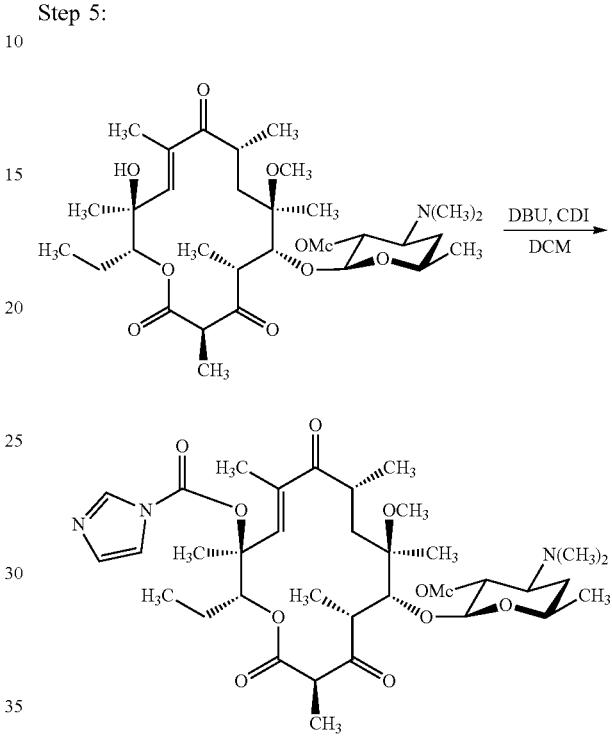

A stream of argon was passed through a solution of enone macrocycle precursor (210 mg, 0.306 mmol) and in chlorobenzene (300 mL) in a 50-mL round-bottom flask by means of a needle through a rubber septum while the vessel was exposed to sonication. After 10 minutes, the vessel was removed from sonication and was equipped with a straight-path reflux condensor. The system was evacuated and back-filled with argon (this process was repeated three times), and was then heated in a 150° C. oil bath. After 1 h, LCMS showed very low conversion to the desired mass (confirmed by TLC in 30% acetone in hexanes, +1% Et₃N). After 18 h, CDI (3.87 mg, 0.024 mmol) (solution in DCM) was added to a solution of macrocyclic enone (5 mg, 7.96 µmol) in DCM (0.3 mL) at −15° C. DBU (4.80 µl, 0.032 mmol) was added and the solution was allowed to stir at this temperature. After 90 min, sat aq NH₄Cl (1 mL) was added, and the mixture was stirred vigorously for 1 min and then extracted with DCM (2×1 mL). the organic layers were dried through a pad of sodium sulfate and the filtrate was concentrated to provide the acyl imidazole as a white foam, which was of sufficient purity to carry forward.
Step 6:

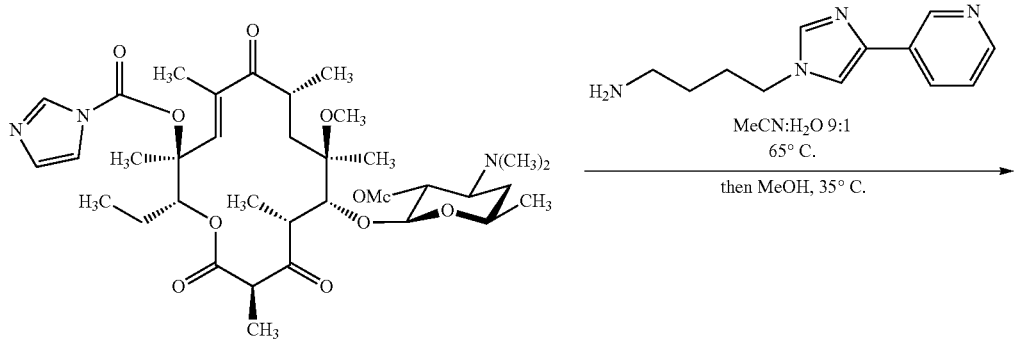

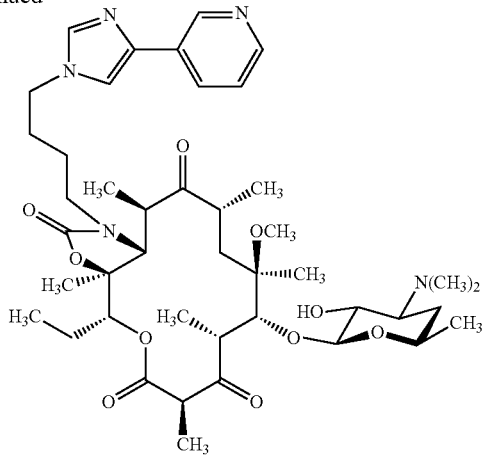
telithromycin 4-(4-(pyridin-3-yl)-1H-imidazol-1-yl)butan-1-amine (7.49 mg, 0.035 mmol) was added to a solution of Acyl Imidazole (5 mg, 6.93 µmol) in Acetonitrile:H2O (0.5 ml). The solution was heated to 65° C. for 36 h, and the mixture was concentrated. The residue was dissolved in methanol (0.5 mL) and the mixture was heated to 35° C. After 2 h, the mixture was allowed to cool to 23° C. and was concentrated. The crude residue was purified by column chromatography on silica gel (5% methanol in DCM, 0.5% NH₄OH) to provide telithromycin as a white foam. The product was confirmed to be telithromycin by H-NMR and LCMS matching spectra published by Bioorg. Med. Chem. 2006, 14, 5592.

Example 3C. Synthesis of C12-Desoxy Analogs by Hydromagnesiation

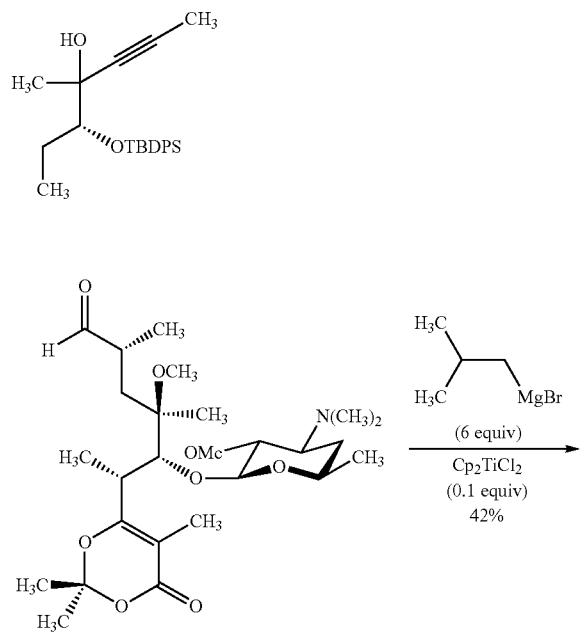

To a suspension of Cp₂TiCl₂ (3.27 mg, 0.013 mmol) in ethyl ether (525 µl) at 0° C. was added cyclopentyl magnesium chloride (394 µl, 0.788 mmol). The deep grey mixture was stirred for 5 min at this temperature, and a solution of (5R)-5-((tert-butyldiphenylsilyl)oxy)-4-methylhept-2-yn-4-ol (100 mg, 0.263 mmol) in ethyl ether (525 µl) was added. The mixture was allowed to warm to 23° C. (10:30 AM). After 2.5 h, conversion was >90% to a more polar spot that stains pink in anisaldehyde (15% ethyl ether/hexanes). The mixture was cooled to −78° C. (solid crashed out), and (2S,3R,4S,6R)-4-(dimethylamino)-2-(((2R,3R,4R,6R)-4-methoxy-4,6-dimethyl-7-oxo-2-(2,2,5-trimethyl-4-oxo-4H-1,3-dioxin-6-yl)heptan-3-yl)oxy)-6-methyltetrahydro-2H-pyran-3-yl methyl carbonate (71.4 mg, 0.131 mmol) was added as a solution in ether (0.3 mL+0.2 mL wash). An emulsion formed, which was warmed to 23° C. The emulsion did not get better, so THF (0.5 mL) was added, and helped a little. TLC showed high conversion to a more polar spot. After 1 h, the mixture was quenched by the addition of sat aq ammonium chloride (1 mL), and the layers were mixed vigorously and separated. The aqueous layer was extracted with ether (2×1 mL), and the combined organic layers were filtered through a pad of sodium sulfate. The filtrate was concentrated, and crude NMR indicated one major product from the eastern half. Column: 25% to 30% acetone in hexanes with +0.5% Et3N). The structure was confirmed by 1D and 2D NMR, along with HRMS as the C12-deoxygenated product (37 mg, 0.055 mmol, 41.9% yield).

Example 3D. Synthesis of Solithromycin Via Hydromagnesiation
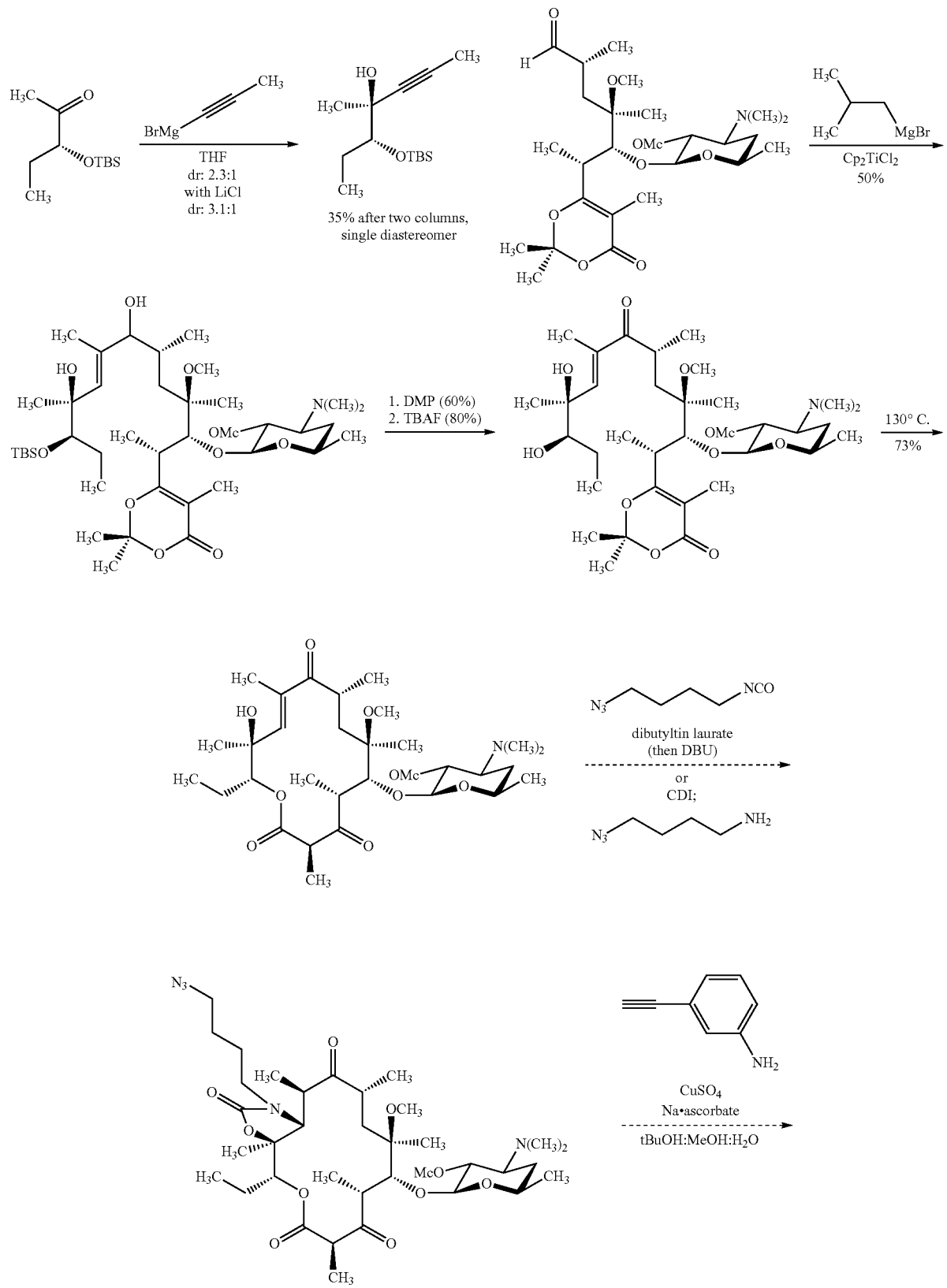

307
308
-continued
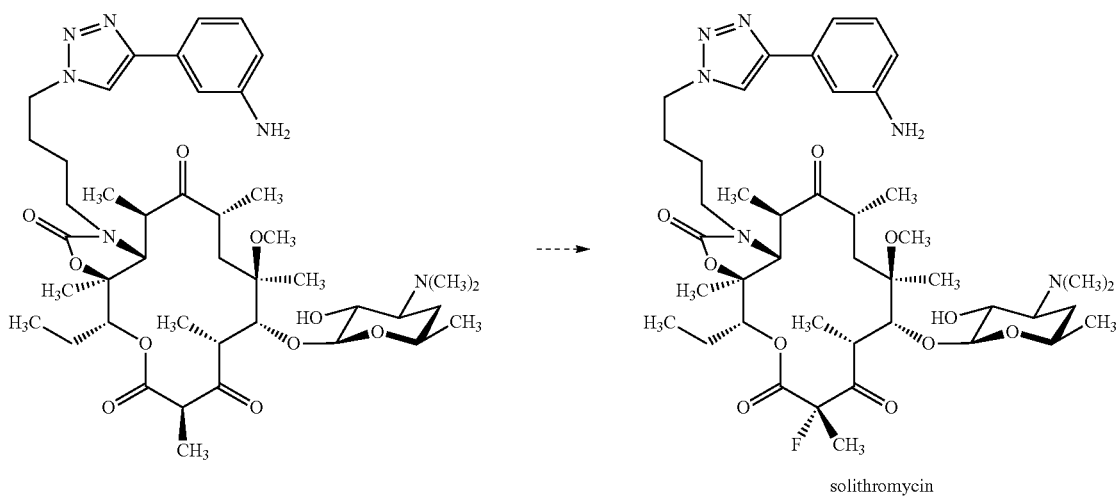
solithromycin
Example 3D-1. Synthesis of Solithromycin Via Hydromagnesiation (Alternative Route)
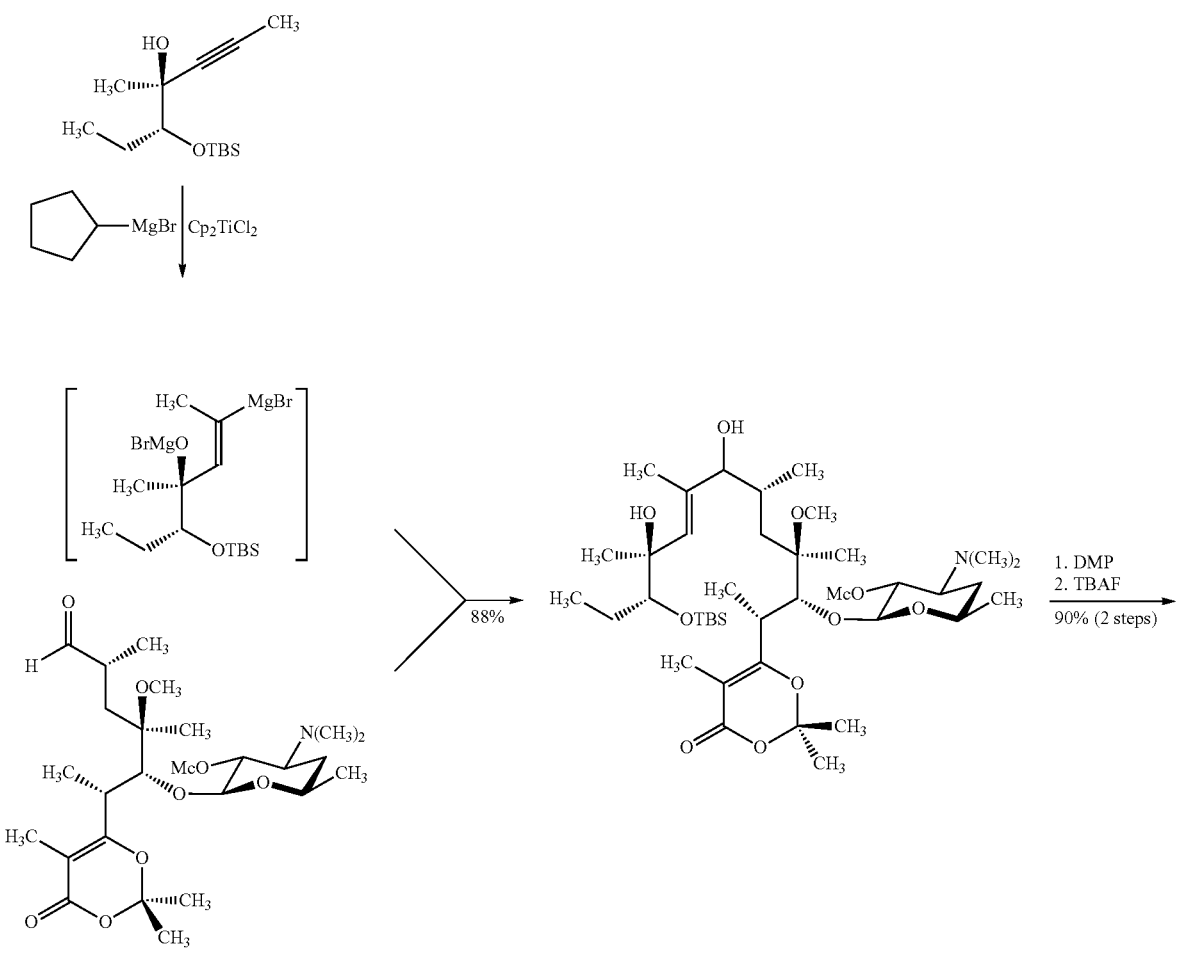

309 310
-continued
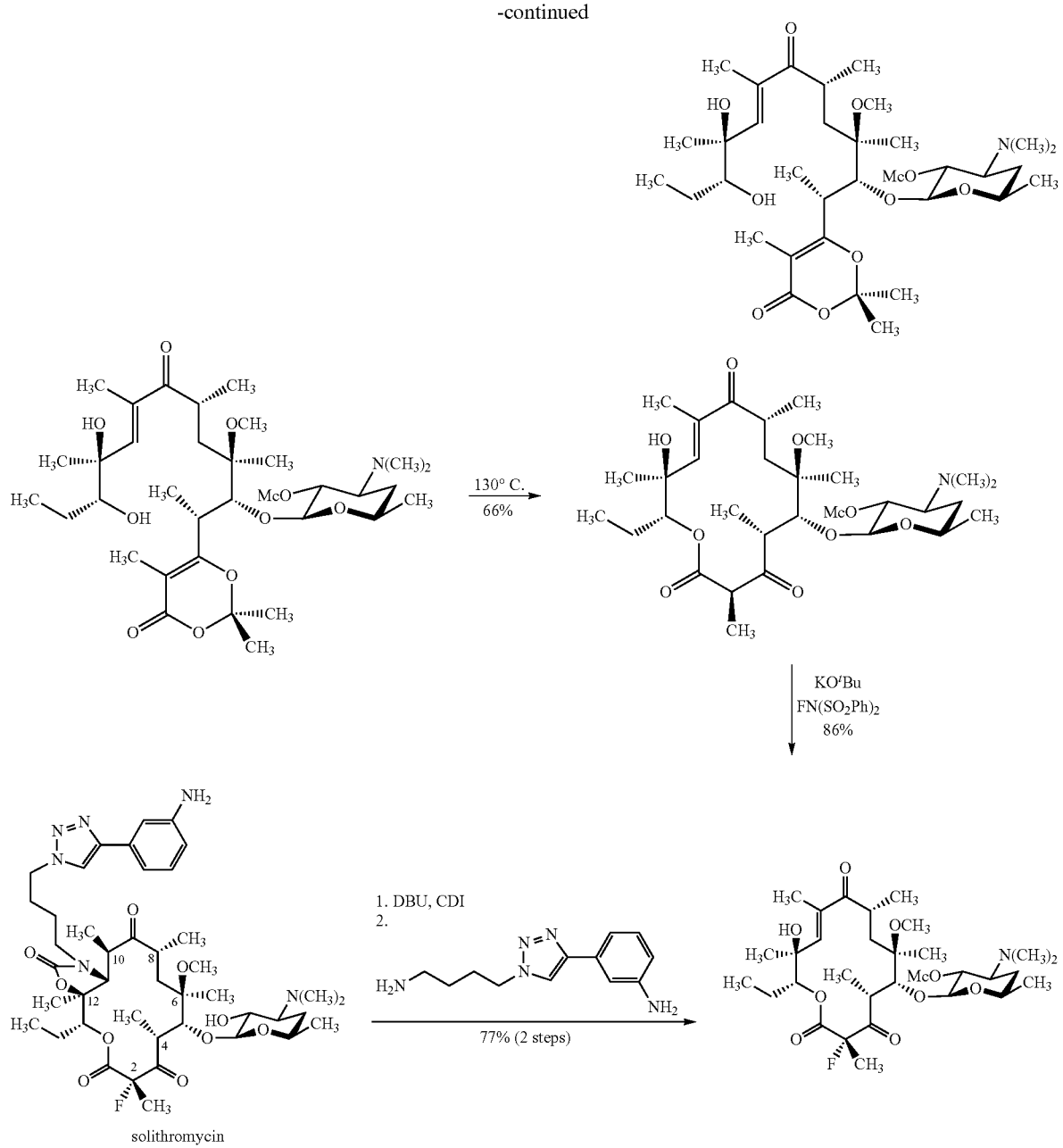
Step 1:
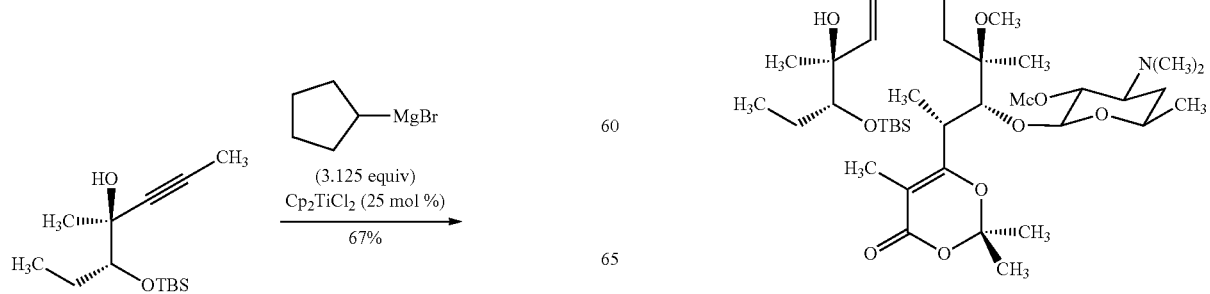

A flame-dried, 200-mL round-bottom flask was charged with ethyl ether (18.39 ml). The vessel was cooled to 0° C. in an ice-water bath and cyclopentylmagnesium bromide (2.0 M solution in ether, 8.62 ml, 17.24 mmol, 3.13 equiv) was added. Cp$_2$TiCl$_2$ (343 mg, 1.38 mmol, 0.25 equiv) was added in a single portion, and the black solution was stirred for 30 minutes at this temperature. A solution of (4S,5R)-5-((tert-butyldimethylsilyl)oxy)-4-methylhept-2-yn-4-ol (1.77 g, 6.90 mmol, 1.25 equiv) in ether (7.5 mL) was added dropwise over the course of 5 minutes. The transfer was quantitated with ether (2×1 mL). Stirring was continued at 4° C. for 20 h, after which time a green/gray solid had precipitated from the dark gray solution. Analysis by TLC analysis indicated complete consumption of the starting material and appearance of a less polar spot (85:15 hexanes:ether; visualization: UV and then anisaldehyde stain). The mixture was diluted with THF (18 mL), and the precipitate dissolved. A solution of right half aldehyde (3.00 g, 5.52 mmol, 1 equiv) in THF (7.0 mL) was added dropwise over 5 minutes. The transfer was quantitated with THF (2×1 mL). The mixture was stirred at 0° C. for 30 min, at which point TLC indicated complete consumption of starting material (eluent: 50:50:1 acetone:hexanes:triethylamine; visualization: UV and anisaldehyde). Saturated aqueous ammonium chloride (100 mL) was added in a single portion. The resulting biphasic mixture was allowed to warm to 23° C. and was rapidly stirred for 8 h. The mixture was filtered through a sintered glass funnel, and the filtrate was transferred to a 500-mL separatory funnel. The layers were separated, and the aqueous layer was extracted with ethyl ether (3×50 mL). The organic layers were combined and the resulting solution was washed with water (100 mL) and brine (100 mL). The washed organic solution was dried with sodium sulfate, filtered, and the filtrate was concentrated. The crude residue was purified by column chromatography on silica gel (20% acetone in hexanes as eluent). The overlapping fractions were re-purified in the same solvent system to provide the allylic alcohol as a 2:1 mixture if diastereomers as a white foam (2.95 g, 3.68 mmol, 67% yield). Spectrum indicates a 2:1 mixture of diastereomers; reported as seen. TLC (50:50:1 hexanes:acetone:triethylamine): R$_f$=0.65 (UV, anisaldehyde). $^1$H NMR (500 MHz, CDCl$_3$), δ: 5.47 (s, 1.0 H), 5.37 (s, 0.53 H), 4.63-4.55 (m, 3.41 H), 4.09 (br s, 0.98 H), 3.96 (d, J=2.8 Hz, 0.5 H), 3.89 (d, J=3.1 Hz, 0.97 H), 3.77 (s, 1.43 H), 3.77 (s, 2.65 H), 3.53-3.37 (m, 3.21 H), 3.16 (s, 1.43 H), 3.10 (s, 2.82 H), 3.01 (br s, 0.85 H), 2.79-2.72 (m, 2.65 H), 2.36 (s, 1.44 H), 2.31 (ap s, 8.89 H), 2.03-1.94 (m, 0.89 H), 1.86 (s, 1.51 H), 1.85 (s, 2.50 H), 2.32-2.30 (m, 5.79 H), 1.69-1.64 (m, 9.90 H), 1.57-1.49 (m, 3.72 H), 1.43-1.33 (m, 1.82 H), 1.32 (s, 3.25 H), 1.32 (s, 1.65 H), 1.29 (s, 2.55 H), 1.29-1.26 (m, 5.27 H), 1.05 (d, J=7.4 Hz, 3.62 H), 0.97-0.91 (m, 16.35 H), 0.81 (d, J=7.0 Hz, 1.36 H), 0.76 (d, J=6.8 Hz, 2.66 H). $^{13}$C NMR (125 MHz, CDCl$_3$), δ: 167.48, 167.10, 162.80, 162.70, 155.20, 137.53, 136.24, 131.05, 126.63, 104.50, 104.47, 100.03, 99.88, 99.79, 99.65, 85.74, 80.39, 80.32, 79.83, 79.73, 77.20, 76.50, 76.48, 76.10, 76.02, 75.66, 75.45, 75.42, 69.28, 69.22, 63.06, 63.00, 54.68, 49.86, 49.49, 40.66, 39.33, 36.08, 33.83, 31.87, 31.48, 30.84, 30.82, 27.39, 26.83, 26.04, 25.91, 25.89, 25.83, 25.80, 24.26, 24.13, 20.97, 20.71, 19.74, 19.18, 18.26, 15.50, 14.97, 12.98, 12.92, 11.46, 11.19, 9.87, 9.79, −3.71, −3.76, −4.22, −4.25. FTIR (neat), cm$^{−1}$: 3485, 2936, 2858, 2251, 1755, 1720, 1641, 1456, 1377, 1267. HRMS (ESI): Calculated for (C$_{41}$H$_{75}$NO$_{12}$Si+H)$^+$: 802.5131; found: 802.5149.

Step 2:

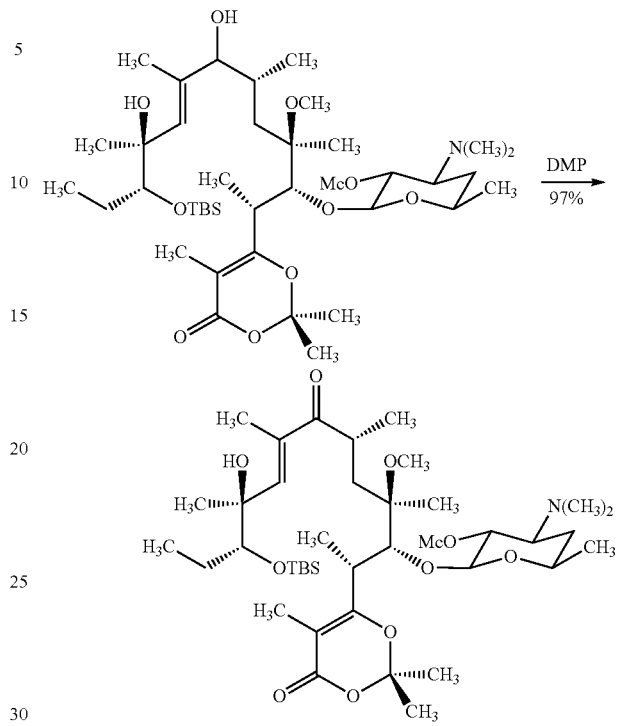

Dess-Martin periodinane (1.533 g, 3.62 mmol, 1.0 equiv) was added to a solution of Coupled Allylic Alcohol (2.9 g, 3.62 mmol, 1 equiv) in water-saturated DCM (36 ml) in a 200-mL round-bottom flask that was immersed in a 22° C. water bath. After 5 minutes, a second portion of Dess-Martin periodinane (1.533 g, 3.62 mmol, 1 equiv) was added. After 90 min, the mixture was diluted with 10% aqueous sodium biarbonate (50 mL) and ether (50 mL). The mixture was stirred vigorously for 3 min, at which time saturated aqueous sodium thiosulfate (50 mL) was added. The resulting cloudy mixture was stirred vigorously for 20 min, and the layers were separated. The aqueous layer was extracted with ether (3×50 mL). The organic layers were combined, and the resulting solution was washed with 1:1 10% aqueous sodium bicarb:saturated aqueous sodium thiosulfate (50 mL) and brine (50 mL). The washed organic solution was dried with sodium sulfate, and the dried solution was filtered. The filtrate was concentrated and the resulting residue was purified by chromatography on silica gel (short column, 160:40:1 hexanes:acetone:triethylamine as eluent) to provide the acyclic TBS protected enone (2.8 g, 3.50 mmol, 97% yield) as a white foam. TLC (50:50:1 acetone:hexanes:triethylamine): R$_f$=0.42 (UV, anisaldehyde). $^1$H NMR (500 MHz, CDCl$_3$), δ: 6.58 (s, 1H), 4.57 (dd, J=10.3, 7.6 Hz, 1H), 4.52 (d, J=7.6 Hz, 1H), 3.82 (d, J=3.2 Hz, 1H), 3.77 (s, 3H), 3.67 (dd, J=5.9, 4.1 Hz, 1H), 3.49-3.40 (m, 1H), 3.40-3.29 (m, 2H), 2.89 (s, 3H), 2.75 (ddd, J=12.3, 10.5, 4.4 Hz, 1H), 2.57 (s, 1H), 2.30 (s, 6H), 2.21 (dd, J=14.0, 10.1 Hz, 1H), 1.96 (s, 3H), 1.80 (s, 3H), 1.76 (ddd, J=13.0, 4.2, 1.6 Hz, 1H), 1.69-1.66 (m, 1H), 1.64 (s, 6H), 1.57-1.49 (m, 1H), 1.43-1.38 (m, 1H), 1.36 (s, 3H), 1.35-1.31 (m, 1H), 1.24 (d, J=6.1 Hz, 3H), 1.18 (s, 3H), 1.07 (d, J=7.4 Hz, 3H), 1.03 (d, J=6.9 Hz, 3H), 0.94 (t, J=7.1 Hz, 3H), 0.92 (s, 9H), 0.12 (t, J=4.1 Hz, 6H). $^{13}$C NMR (125 MHz, CDCl$_3$), δ: 206.81, 167.57, 162.98, 155.26, 141.13, 137.14, 104.33, 100.00, 99.98, 79.49, 78.28, 77.20, 77.09, 76.56, 75.50, 69.24, 63.02, 54.71, 49.45, 40.71, 38.95, 34.17, 34.11, 30.98, 26.32, 26.25, 25.96, 25.83, 24.28, 20.98, 20.28, 20.09, 18.22, 13.08, 10.90, 9.66, −3.77, −4.32. FTIR (neat), cm$^{-1}$: 3565 (br), 2935, 2858, 2251, 1755, 1720, 1641, 1454, 1377, 1267. HRMS (ESI): Calculated for $(C_{41}H_{73}NO_{12}Si+Na)^+$: 822.4794; found: 822.4776.

Step 3:

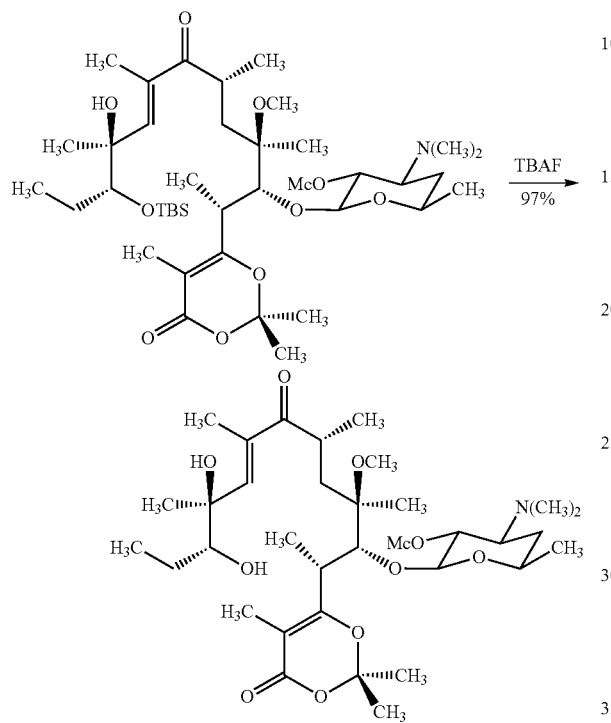

Tetrabutylammonium fluoride (1.0 M solution in THF, 4.20 ml, 4.20 mmol, 1.2 equiv) was added dropwise to a solution of TBS-protected enone (2.8 g, 3.50 mmol, 1 equiv) in THF (17.50 ml) at 0° C. The mixture was allowed to warm to 23° C., and was stirred at this temperature for 90 min, and then was concentrated. The resulting brown oil was purified by column chromatography on silica gel (25-30-40% acetone in hexanes with +0.5% triethylamine additive throughout) to provide the macrocycle precursor as a white foam (2.28 g, 3.32 mmol, 95% yield). TLC (50:50:1 acetone:hexanes:triethylamine): $R_f$=0.51 (UV, anisaldehyde). $^1$H NMR (500 MHz, CDCl$_3$), δ: 6.58 (d, J=1.1 Hz, 1H), 4.57 (dd, J=10.4, 7.6 Hz, 1H), 4.52 (d, J=7.6 Hz, 1H), 3.79 (d, J=3.3 Hz, 1H), 3.77 (s, 3H), 3.49 (dd, J=10.4, 2.1 Hz, 1H), 3.48-3.35 (m, 2H), 3.35-3.27 (m, 1H), 2.93 (s, 3H), 2.75 (ddd, J=12.2, 10.6, 4.3 Hz, 1H), 2.50 (s, 1H), 2.30 (s, 6H), 2.23 (dd, J=14.1, 10.0 Hz, 1H), 1.98 (d, J=1.0 Hz, 3H), 1.80 (s, 3H), 1.80-1.72 (m, 1H), 1.64 (s, 3H), 1.64 (s, 3H), 1.63-1.58 (m, 1H), 1.44 (s, 3H), 1.44-1.31 (m, 3H), 1.24 (d, J=6.1 Hz, 3H), 1.15 (s, 3H), 1.06 (d, J=7.4 Hz, 3H), 1.03 (d, J=7.1 Hz, 3H), 1.02 (t, J=7.2 Hz, 3H). $^{13}$C NMR (125 MHz, CDCl$_3$), δ: 206.87, 167.56, 163.03, 155.37, 141.01, 137.87, 104.36, 100.00, 99.94, 79.58, 78.21, 77.76, 77.20, 76.22, 75.56, 69.28, 63.03, 54.78, 49.41, 40.73, 38.51, 34.31, 34.21, 30.97, 25.84, 25.11, 24.85, 24.25, 20.96, 20.42, 20.02, 13.03, 12.97, 11.10, 9.66. FTIR (neat), cm$^{-1}$: 3487 (br), 2974, 2935, 2875, 2833, 2785, 2251, 1753, 1717, 1641.

HRMS (ESI): Calculated for $(C_{35}H_{59}NO_{12}+Na)^+$: 708.3929 found: 708.3907.

Step 4:

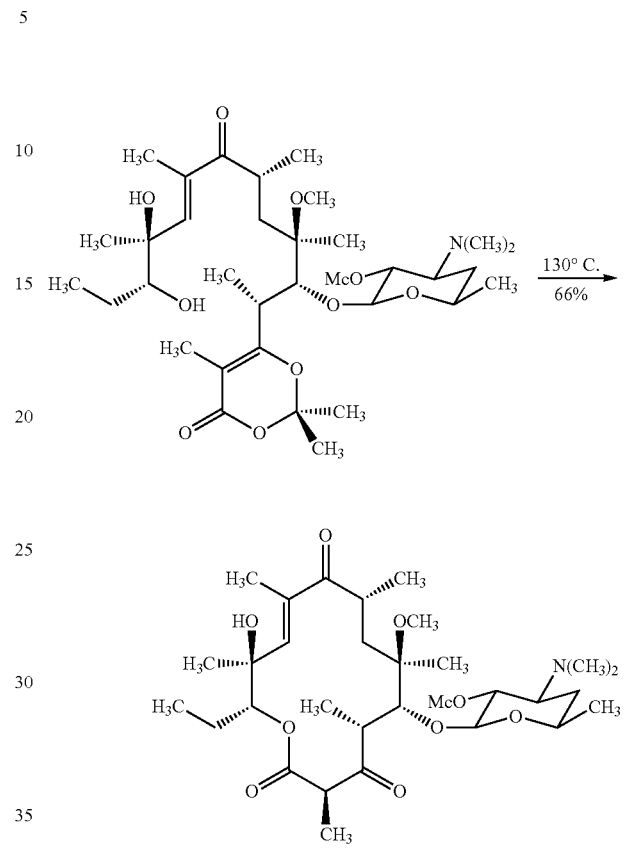

A solution of Macrocycle precursor (1.70 g, 2.48 mmol, 1 equiv) in chlorobenzene (4.0 mL) in a 5-L round-bottom flask was degassed by means of a stream of argon for 1 h. The vessel was equipped with a dry reflux condenser, and the system was evacuated to 1 Torr and refilled with argon (this process was repeated three times). The vessel and its contents were then heated by means of an oil bath. The solution was maintained at reflux for 16 h, after which time it was allowed to cool to 23° C. and was concentrated. The crude residue was purified by column chromatography (2% methanol in dichloromethane with +0.2% NH4OH). TLC (50:50:1 hexanes:acetone:triethylamine): Compound was a ~5:1 mixture of diastereomers (presumed to be C2 epimers based on equilibration in subsequent steps); spectral data is only reported for the major diastereomer. $R_f$=0.60 (UV, anisaldehyde). $^1$H NMR (500 MHz, CDCl$_3$), δ: 6.58 (s, 1H), 4.94 (dd, J=9.8, 2.9 Hz, 1H), 4.44 (dd, J=10.5, 7.6 Hz, 1H), 4.32 (d, J=7.6 Hz, 1H), 4.10 (d, J=8.6 Hz, 1H), 3.71 (s, 3H), 3.69 (t, J=6.9 Hz, 1H), 3.52-3.43 (m, 1H), 3.16-3.08 (m, 1H), 3.04-2.95 (m, 2H), 2.81 (s, 3H), 2.70-2.59 (m, 1H), 2.49 (s, 1H), 2.21 (s, 6H), 1.96 (d, J=1.1 Hz, 3H), 1.95-1.86 (m, 1H), 1.79 (dd, J=14.5, 6.1 Hz, 1H), 1.72-1.66 (m, 1H), 1.56-1.44 (m, 2H), 1.42 (s, 3H), 1.29 (d, J=6.9 Hz, 3H), 1.27 (s, 3H), 1.19 (d, J=6.1 Hz, 3H), 1.10 (d, J=6.7 Hz, 3H), 1.06 (d, J=7.4 Hz, 3H), 0.88 (t, J=7.4 Hz, 3H). FTIR (neat), cm$^{-1}$: 3493 (br), 2972, 2939, 2879, 2787, 2255, 1745, 1708, 1668, 1456, 1443, 1377, 1265. HRMS (ESI): Calculated for $(C_{32}H_{53}NO_{11}+H)^+$: 628.3691; found: 628.3713.

Step 5:

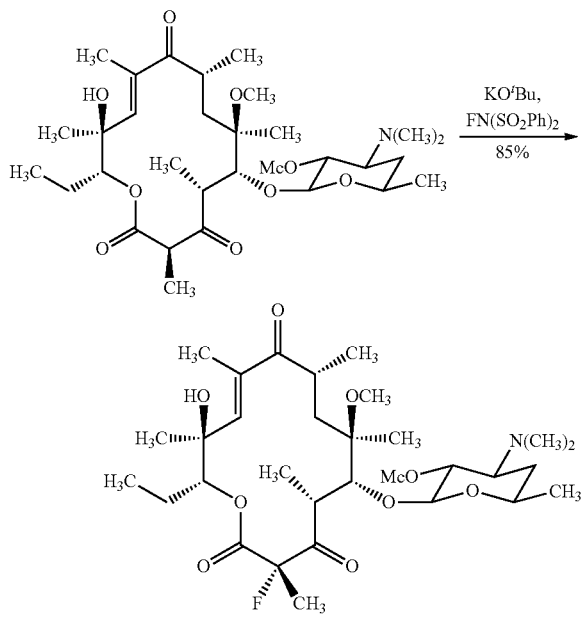

A solution of potassium tert-butoxide in THF (1.0 M, 89 μL, 0.089 mmol, 1.4 equiv) was added dropwise to a solution of Macrocyclic enone (40 mg, 0.064 mmol, 1 equiv) in THF (0.64 mL) at −78° C. The mixture was stirred at 78° C. for 5 minutes, and a solution of N-fluorobenzenesulfonimide (24 mg, 0.076 mmol, 1.2 equiv) in THF (100 mg/mL) was added. After 5 min, the solution was allowed to warm to 23° C. After 30 min, saturated aqueous sodium bicarbonate solution (1 mL), saturated aqueous sodium thiosulfate solution (1 mL) and dichloromethane (1 mL) were added sequentially, and the mixture was stirred rapidly for 1 min. The layers took 5 minutes to resolve, at which point they were separated. The aqueous layer was extracted with dichloromethane (2×1 mL). The organic layers were filtered through a pad of sodium sulfate, and the filtrate was concentrated. The residue was purified by column chromatography on silica gel (15-20% acetone in hexanes) to afford the fluoromacrocyclic enone as a white foam (35 mg, 85%). TLC (50:50:1 hexanes:acetone:triethylamine): $R_f$=0.65 (UV, anisaldehyde). $^1$H NMR (500 MHz, CDCl$_3$) δ: 6.50 (s, 1H), 5.00 (dd, J=9.4, 2.9 Hz, 1H), 4.51 (dd, J=10.3, 7.6 Hz, 1H), 4.41 (d, J=7.5 Hz, 1H), 4.01 (d, J=10.0 Hz, 1H), 3.81 (s, 3H), 3.57-3.42 (m, 2H), 3.04-2.94 (m, 1H), 2.77-2.68 (m, 1H), 2.66 (s, 3H), 2.27 (s, 6H), 2.11-1.99 (m, 2H), 1.97 (s, 3H), 1.85 (dd, J=14.0, 9.2 Hz, 1H), 1.76 (d, J=21.6 Hz, 3H), 1.71-1.56 (m, 2H), 1.51 (s, 3H), 1.41-1.30 (m, 2H), 1.28-1.21 (m, 9H), 1.16 (d, J=7.0 Hz, 3H), 0.97 (t, J=7.4 Hz, 3H). FTIR (neat), cm$^{-1}$: 3497 (br), 2974, 1753, 1654, 1442, 1263, 1053, 997. HRMS (ESI): Calculated for (C$_{32}$H$_{52}$FNO$_{11}$+Na)$^+$: 668.3417; found: 668.3407.

Step 6:

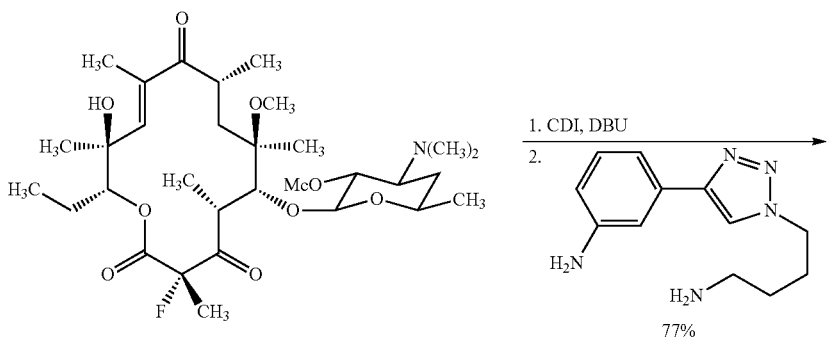

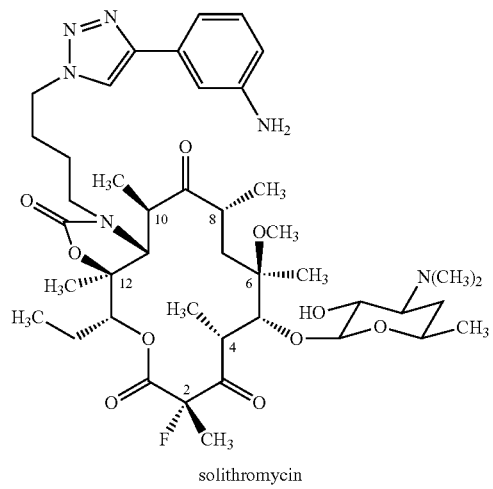

solithromycin

DBU (55 μL, 0.37 mmol, 3.0 equiv) was added to a solution of Fluoro Macrocyclic Enone (79 mg, 0.122 mmol, 1 equiv) in DCM (1.22 mL) at −10° C. (ice/acetone bath). A solution of carbonyl diimidazole (60 mg, 0.37 mmol, 3.0 equiv) in dichloromethane (0.23 mL) was added dropwise via syringe. After 30 min, TLC in 50:50:1 acetone:hexanes: triethylamine indicated complete conversion to a more polar spot. After 1.5 h total, saturated aqueous ammonium chloride solution (3 mL) was added. The mixture was extracted with ether (3×2 mL). The organic layers were combined and the resulting solution was washed with water (2 mL) and brine (2 mL). The dried organic solution was gravity-filtered through a pad of sodium sulfate. The filtrate was concentrated to provide the crude acyl imidazolide intermediate as a white foam. NMR analysis of the residue showed the desired product in high purity. The foam was dried under vacuum (0.1 mmHg) at 23° C. for 12 h. 3-(1-(4-aminobutyl)-1H-1,2,3-triazol-4-yl)aniline (84 mg, 0.37 mmol, 3.0 equiv), acetonitrile (0.30 mL) and DBU (18 μL, 0.12 mmol, 1.0 equiv) were added sequentially. The resulting solution was warmed to 45° C. In 2 h, TLC analysis (50% acetone-hexanes) indicated full consumption of starting material. The reaction mixture was allowed to cool to 23° C. Methanol (5 mL) was added, and the solution was allowed to stand at 23° C. After 24 h, the reaction solution was concentrated under reduced pressure. The residue was partitioned between water (5 mL) and dichloromethane (5 mL). The aqueous layer was separated and further extracted with dichloromethane (2×5 mL). The combined organic layers were dried over sodium sulfate and concentrated. The residue was purified by column chromatography (3% methanol-dichloromethane+0.3% saturated aqueous ammonium hydroxide) to provide solithromycin (79 mg, 77%) as a white powder. TLC (90:10:1 dichloromethane:methanol: saturated aqueous ammonium hydroxide): $R_f$=0.48 (UV, anisaldehyde). $^1$H NMR (500 MHz, CDCl$_3$) δ: 7.82 (s, 1H), 7.31-7.29 (m, 1H), 7.23-7.15 (m, 2H), 6.66 (dt, J=7.2, 2.1 Hz, 1H), 4.89 (dd, J=10.3, 2.0 Hz, 1H), 4.43 (td, J=7.1, 1.5 Hz, 2H), 4.32 (d, J=7.3 Hz, 1H), 4.08 (d, J=10.6 Hz, 1H), 3.82-3.73 (m, 1H), 3.68-3.60 (m, 1H), 3.60-3.49 (m, 2H), 3.45 (s, 1H), 3.20 (dd, J=10.2, 7.3 Hz, 1H), 3.13 (q, J=6.9 Hz, 1H), 2.69-2.59 (m, 1H), 2.57 (s, 3H), 2.51-2.42 (m, 1H), 2.29 (s, 6H), 2.05-1.93 (m, 3H), 1.90 (dd, J=14.5, 2.7 Hz, 1H), 1.79 (d, J=21.4 Hz, 3H), 1.75-1.60 (m, 4H), 1.55 (d, J=13.0 Hz, 1H), 1.52 (s, 3H), 1.36 (s, 3H), 1.32 (d, J=7.0 Hz, 3H), 1.28-1.24 (m, 1H), 1.26 (d, J=6.1 Hz, 3H), 1.20 (d, J=6.9 Hz, 3H), 1.02 (d, J=7.0 Hz, 3H), 0.89 (t, J=7.4 Hz, 3H). $^{13}$C NMR (125 MHz, CDCl$_3$) δ 216.52, 202.79 (d, J=28.0 Hz), 166.44 (d, J=22.9 Hz), 157.19, 147.82, 146.82, 131.72, 129.63, 119.66, 116.14, 114.71, 112.36, 104.24, 97.78 (d, J=206.2 Hz), 82.11, 80.72, 78.59, 78.54, 70.35, 69.64, 65.82, 61.05, 49.72, 49.22, 44.58, 42.77, 40.86, 40.22, 39.57, 39.20, 28.13, 27.59, 25.20 (d, J=22.4 Hz).

24.28, 22.14, 21.15, 19.76, 17.90, 15.04, 14.70, 13.76, 10.47. $^{19}$F NMR (471 MHz, CDCl$_3$) δ −163.24 (q, J=11.2 Hz). FTIR (neat), cm$^{-1}$: 3362 (br), 2976 (m), 1753 (s), 1460 (s), 1263 (s), 1078 (s), 1051 (s), 991 (s). HRMS (ESI): Calcd for $(C_{43}H_{65}FN_6O_{10}+H)^+$: 845.4819; Found: 845.4841.

Example 3E. Synthesis of Solithromycin Via Hydroacylation

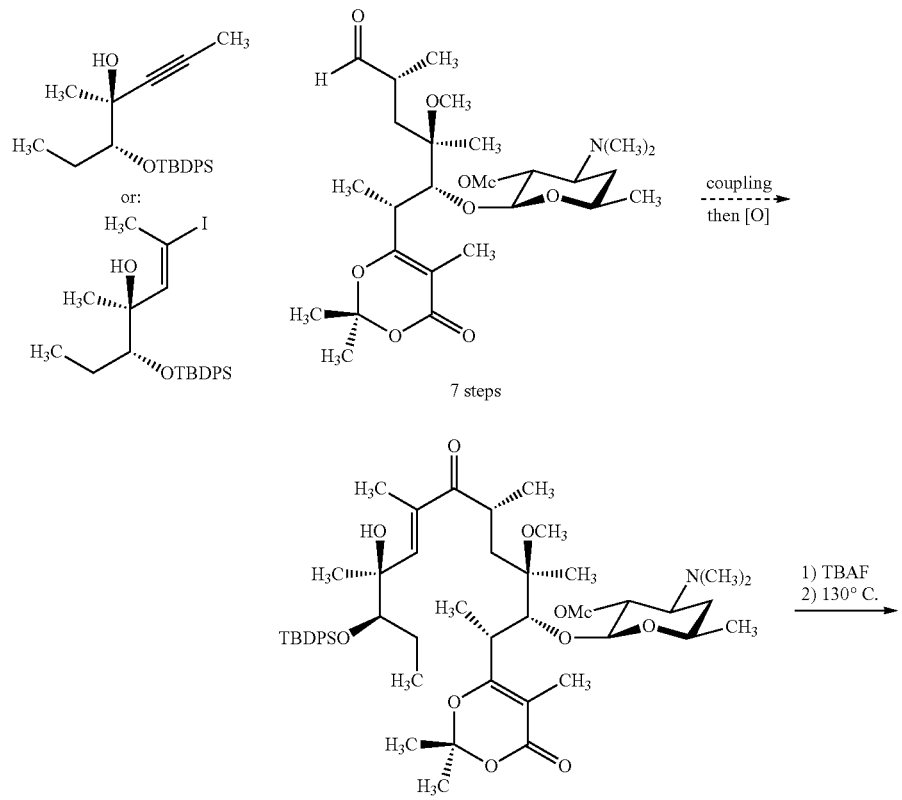

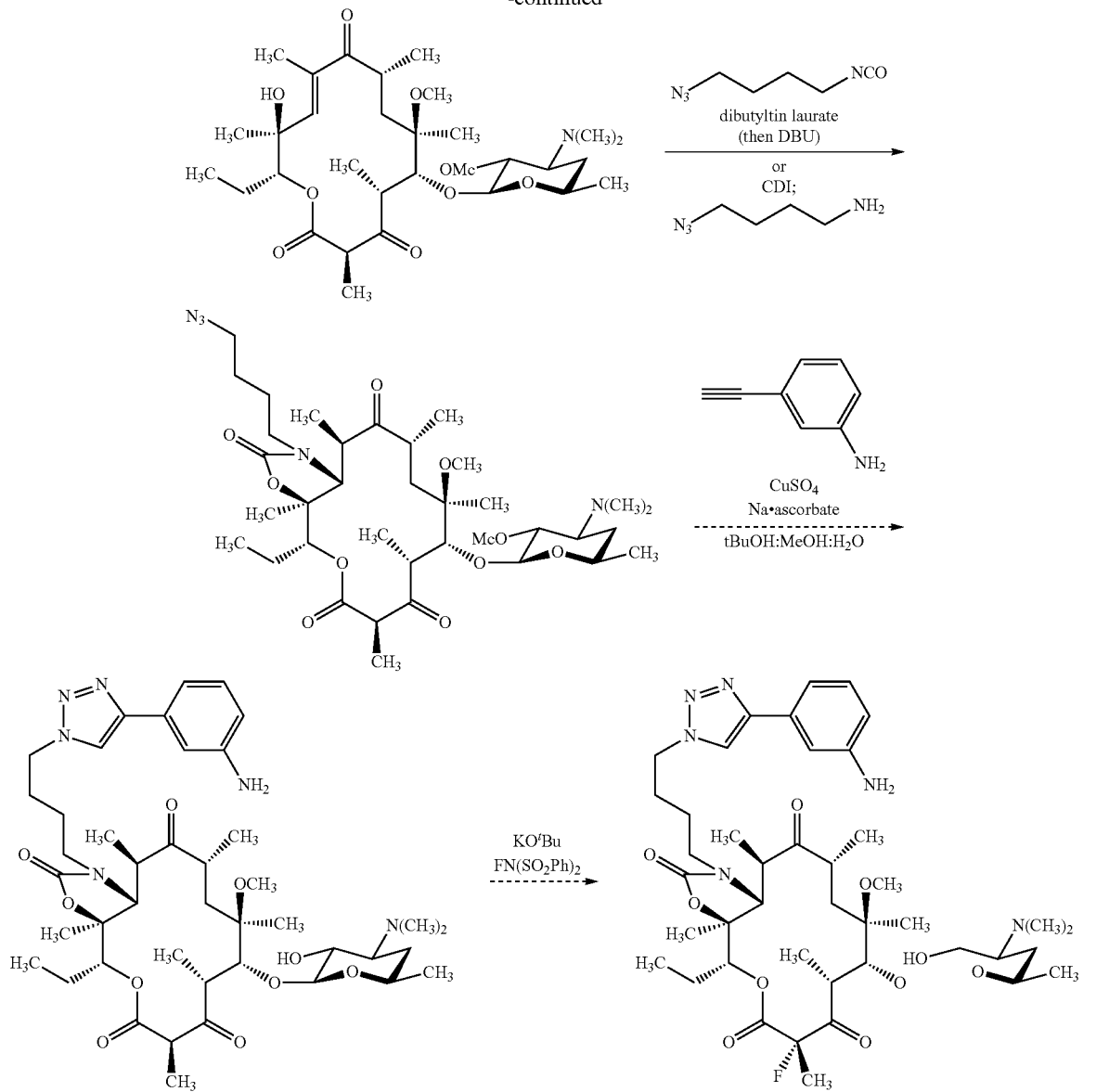
Example 3F. Synthesis of Exemplary 10-Desmethyl Ketolides
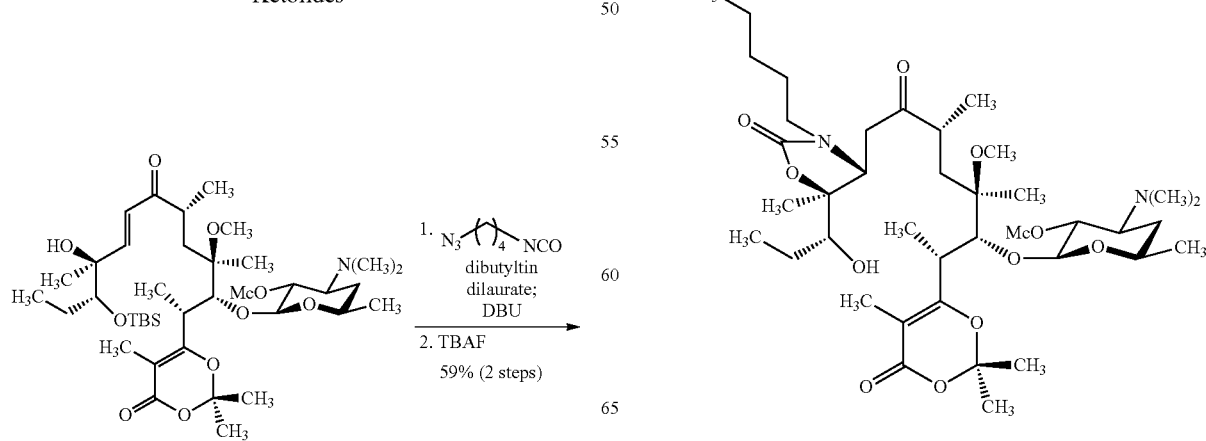

1-Azido-4-isocyanatobutane (176 mg, 1.26 mmol, 5.00 equiv) and dibutyltin dilaurate (150 μL, 0.252 mmol, 1.00 equiv) were added to a solution of HWE_Product (198 mg, 0.252 mmol, 1 equiv) in dichloromethane (2.5 mL) at 23° C. The solution was warmed to 80° C. and held at that temperature for 6 h, at which point LC-MS indicated full consumption of starting material. The solution was concentrated under reduced pressure and the residue was dissolved in DMF (2 mL). DBU (38.0 μL, 0.252 mmol, 1.00 equiv) was added at 23° C. After 1 h, the reaction mixture was partitioned between ether (10 mL) and water (5 mL). The aqueous layer was extracted with ether (2×5 mL). The combined ether layers were washed with saturated sodium chloride solution and dried over magnesium sulfate. The dried solution was concentrated under reduced pressure and the residue was dissolved in THF (2 mL). A solution of TBAF in THF (1.0 M, 0.378 mL, 0.378 mmol, 1.50 equiv) was added via syringe at 23° C. After 20 min, the reaction mixture was concentrated under reduced pressure and the residue was purified by flash column chromatography (2-3% methanol-dichloromethane+0.2→0.3% saturated aqueous ammonium hydroxide solution) to afford the product as a white foam (120 mg, 59%). $^1$H NMR (10:1 ratio of C11 epimers, major epimer is reported, 500 MHz, CDCl$_3$) δ 4.60-4.50 (m, 2H), 4.27 (t, J=5.9 Hz, 1H), 3.87 (d, J=3.5 Hz, 1H), 3.77 (s, 3H), 3.51 (d, J=10.5 Hz, 1H), 3.49-3.41 (m, 2H), 3.32 (t, J=6.5 Hz, 2H), 3.25 (qd, J=7.2, 3.4 Hz, 1H), 2.96 (s, 3H), 2.91-2.87 (m, 1H), 2.87-2.80 (m, 1H), 2.80-2.71 (m, 2H), 2.29 (s, 6H), 2.02 (dd, J=14.1, 10.7 Hz, 1H), 1.81 (s, 3H), 1.79-1.74 (m, 1H), 1.67 (d, J=6.3 Hz, 3H), 1.65 (s, 3H), 1.63-1.51 (m, 5H), 1.45 (dd, J=14.2, 1.9 Hz, 1H), 1.42-1.33 (m, 3H), 1.33-1.27 (m, 1H), 1.25 (d, J=6.0 Hz, 3H), 1.25 (s, 3H), 1.23 (s, 3H), 1.07 (d, J=7.0 Hz, 3H), 1.07 (d, J=7.4 Hz, 3H), 1.03 (t, J=7.4 Hz, 3H). $^{13}$C NMR (126 MHz, CDCl$_3$) δ 212.38, 167.16, 162.69, 156.89, 155.22, 104.51, 100.00, 99.58, 83.44, 78.67, 78.25, 75.41, 69.27, 62.94, 54.67, 54.45, 50.89, 49.62, 41.48, 41.29, 40.68, 40.61, 38.35, 34.02, 30.75, 25.94, 24.12, 23.99, 23.44, 20.92, 20.01, 19.06, 16.50, 13.08, 10.79, 9.72. FTIR (neat), cm$^{-1}$: 3443(br), 2939 (m), 2096 (s), 1747 (s), 1720 (s), 1641 (s), 1265 (s), 1053 (s), 731 (s); HRMS (ESI): Calcd for (C$_{39}$H$_{65}$N$_5$O$_{13}$+H)$^+$: 812.4652; Found: 812.4666.

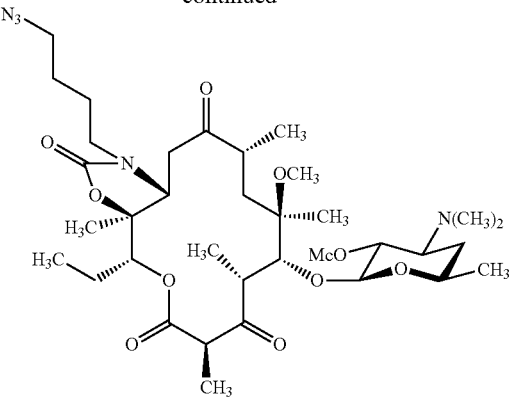

Cyclic carbamate (110 mg, 0.135 mmol) was dried by azeotropic distillation (benzene) and was dissolved in chlorobenzene (13.5 mL) in a 50-mL flask. The flask was fitted with a dry reflux condenser, and dry argon was bubbled through the solution via a 19-gauge needle for 10 min. The flask was then immersed in a 150-° C. oil bath to maintain a gentle reflux of the reaction solution. After 16 h, the reaction solution was cooled to 23° C. and concentrated under reduced pressure (rotary evaporation, 10 mmHg, 40° C. water bath). The residue was purified by flash column chromatography (2→3% methanol-dichloromethane+ 0.2→0.3% saturated aqueous ammonium hydroxide solution) to afford the product as a white foam (78 mg, 76%). $^1$H NMR (500 MHz, CDCl$_3$) δ 4.94 (dd, J=9.1, 3.1 Hz, 1H), 4.49 (dd, J=10.4, 7.6 Hz, 1H), 4.39 (d, J=7.3 Hz, 1H), 3.97 (d, J=10.1 Hz, 1H), 3.84-3.81 (m, 1H), 3.79 (s, 3H), 3.71 (q, J=7.1 Hz, 1H), 3.55-3.42 (m, 2H), 3.37-3.25 (m, 2H), 3.10-3.00 (m, 1H), 3.00-2.89 (m, 2H), 2.76-2.66 (m, 1H), 2.66-2.57 (m, 1H), 2.53 (s, 3H), 2.39 (dd, J=18.0, 9.3 Hz, 1H), 2.26 (s, 6H), 2.01-1.88 (m, 1H), 1.78-1.66 (m, 4H), 1.66-1.47 (m, 4H), 1.43 (d, J=6.8 Hz, 3H), 1.36 (s, 3H), 1.30 (s, 3H), 1.28-1.24 (m, 1H), 1.22 (d, J=5.7 Hz, 3H), 1.16 (d, J=7.0 Hz, 6H), 0.89 (t, J=7.4 Hz, 3H). $^{13}$C NMR (126 MHz, CDCl$_3$) δ 209.98, 203.32, 168.76, 156.80, 155.18, 101.78, 81.62, 81.09, 79.65, 78.57, 75.56, 69.18, 63.24, 59.95, 54.80, 51.52, 51.02, 49.70, 48.45, 43.69, 42.92, 40.72, 40.61, 36.60, 30.17, 26.09, 25.22, 23.52, 20.85, 19.15, 18.20, 18.00, 15.35, 14.83, 10.47. FTIR (neat), cm$^{-1}$: 2939 (m), 2096 (s), 1751 (s), 1712 (s), 1265 (s), 1053 (s), 993 (s), 731 (s); HRMS (ESI): Calcd for (C$_{36}$H$_{59}$N$_5$O$_{12}$+H)$^+$: 754.4233; Found: 754.4257.

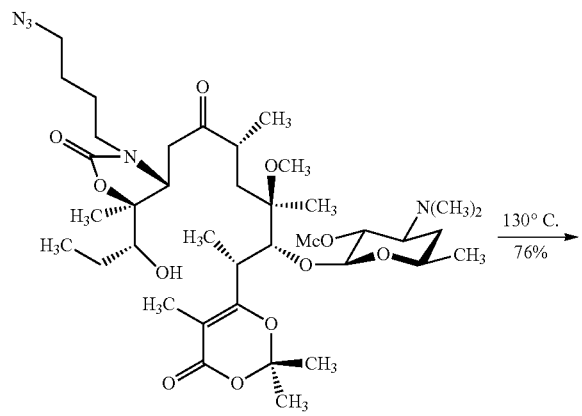

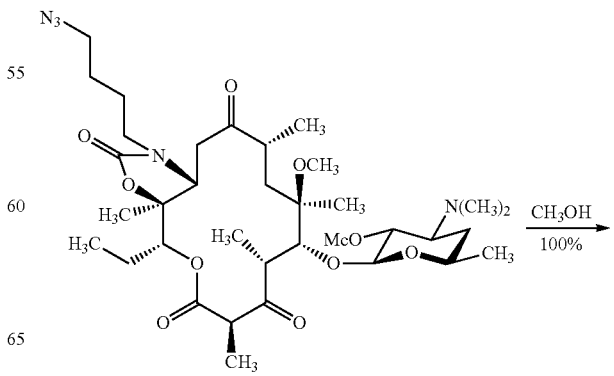

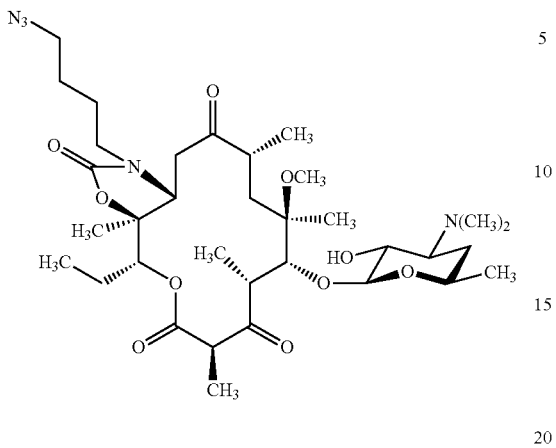

A solution of C10-desmethyl-macrocycle (29 mg, 0.038 mmol) in methanol (1 mL) was allowed to stand at 23° C. for 24 h. The solution was then concentrated under reduced pressure to afford the product as a white foam (27 mg, 100%). $^1$H NMR (8:1 diastereomeric mixture at C2, major isomer is reported, 500 MHz, cdcl$_3$) δ 4.96 (dd, J=9.1, 3.2 Hz, 1H), 4.31 (d, J=7.3 Hz, 1H), 4.00 (d, J=10.3 Hz, 1H), 3.86 (d, J=8.7 Hz, 1H), 3.74 (q, J=7.0 Hz, 1H), 3.61-3.38 (m, 3H), 3.38-3.24 (m, 2H), 3.17 (dd, J=10.2, 7.3 Hz, 1H), 3.11-2.95 (m, 2H), 2.68-2.59 (m, 1H), 2.56 (s, 3H), 2.49-2.43 (m, 1H), 2.40 (dd, J=18.2, 9.6 Hz, 1H), 2.27 (s, 6H), 2.03-1.91 (m, 1H), 1.87 (dd, J=14.4, 3.8 Hz, 1H), 1.84-1.70 (m, 2H), 1.70-1.64 (m, 1H), 1.64-1.50 (m, 4H), 1.45 (d, J=7.1 Hz, 3H), 1.38 (s, 3H), 1.34 (s, 3H), 1.32 (d, J=7.0 Hz, 3H), 1.23 (d, J=6.1 Hz, 3H), 1.22-1.20 (m, 1H), 1.16 (d, J=7.0 Hz, 3H), 0.91 (t, J=7.5 Hz, 3H). $^{13}$C NMR (126 MHz, CDCl$_3$) δ 209.97, 203.53, 168.77, 156.89, 104.29, 82.46, 81.11, 79.71, 78.58, 70.32, 69.60, 65.78, 59.99, 51.62, 51.05, 49.70, 48.74, 43.78, 42.96, 41.20, 40.19, 36.54, 28.09, 26.12, 25.23, 23.56, 21.11, 19.13, 18.22, 17.98, 15.34, 15.28, 10.48. FTIR (neat), cm$^{-1}$: 3444 (br), 2970 (m), 2096 (s), 1747 (s), 1712 (m), 1070 (s), 908 (s), 731 (s); HRMS (ESI): Calcd for (C$_{34}$H$_{57}$N$_5$O$_{10}$+H)$^+$: 696.4178; Found: 696.4194.

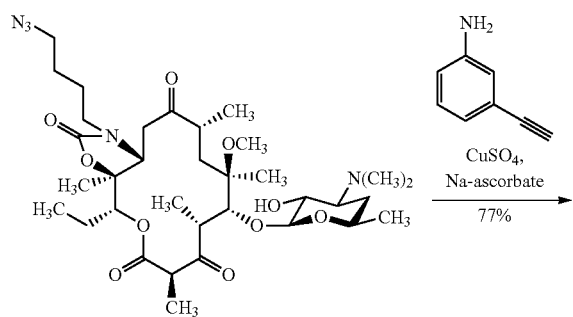

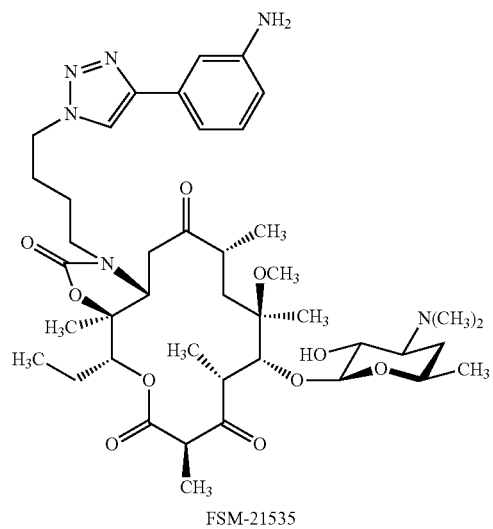

FSM-21535

3-ethynylaniline (13.6 mg, 0.116 mmol, 3.00 equiv), an aqueous solution of sodium ascorbate (0.10 M, 78 μL, 7.7 μmol, 0.20 equiv) and an aqueous solution of copper (II) sulfate (0.10 M, 19 μL, 1.9 μmol, 0.050 equiv) were added sequentially to a solution of C10-desmethyl-ketolide-2'OH (27 mg, 39 μmol) in 1:1 t-butanol:water (0.8 mL) at 23° C. After 16 h, the reaction mixture was partitioned between saturated aqueous sodium bicarbonate solution (1 mL) and dichloromethane (1 mL). The aqueous layer was separated and further extracted with dichloromethane (2×1 mL). The combined organic layers were dried over sodium sulfate and concentrated under reduced pressure. The residue was purified by flash column chromatography (2→3% methanol-dichloromethane+0.2→0.3% saturated aqueous ammonium hydroxide solution) to afford the product as a pale yellow solid (24.3 mg, 77%). TLC (10% methanol-dichloromethane+1% saturated aqueous ammonium hydroxide solution): R$_f$=0.60 (UV, p-anisaldehyde). $^1$H NMR (500 MHz, CDCl$_3$) δ 7.81 (s, 1H), 7.24-7.09 (m, 3H), 6.66 (d, J=6.2 Hz, 1H), 4.97 (d, J=9.0 Hz, 1H), 4.45 (t, J=6.7 Hz, 2H), 4.32 (d, J=7.2 Hz, 1H), 3.98 (d, J=10.3 Hz, 1H), 3.85 (d, J=9.3 Hz, 1H), 3.73 (q, J=6.9 Hz, 1H), 3.62-3.49 (m, 2H), 3.24-3.14 (m, 1H), 3.14-2.89 (m, 3H), 2.67-2.55 (m, 1H), 2.52 (s, 3H), 2.49-2.43 (m, 1H), 2.37 (dd, J=18.6, 9.2 Hz, 1H), 2.30 (s, 6H), 2.06-1.91 (m, 2H), 1.89-1.63 (m, 7H), 1.45 (d, J=7.0 Hz, 3H), 1.37 (s, 3H), 1.31 (s, 3H), 1.28 (d, J=10.9 Hz, 3H), 1.25 (d, J=5.6 Hz, 3H), 1.23-1.20 (m, 1H), 1.10 (d, J=6.8 Hz, 3H), 0.92 (t, J=7.4 Hz, 3H). $^{13}$C NMR (126 MHz, cdcl$_3$) δ 210.15, 203.51, 168.76, 157.01, 147.76, 146.83, 131.60, 129.64, 119.71, 115.99, 114.75, 112.20, 104.26, 82.48, 81.22, 79.69, 78.58, 70.30, 69.57, 65.75, 60.05, 51.61, 49.73, 49.65, 48.72, 43.74, 42.59, 41.20, 40.18, 36.45, 28.08, 27.45, 24.97, 23.57, 21.10, 19.07, 18.25, 17.98, 15.33, 15.29, 10.46. FTIR (neat), cm$^{-1}$: 3365 (br), 2939 (m), 1747 (s), 1708 (m), 1163 (s), 1074 (s), 1049 (s), 995 (s), 731 (s); HRMS (ESI): Calcd for (C$_{42}$H$_{64}$N$_6$O$_{10}$+H)$^+$: 813.4757; Found: 813.4764.

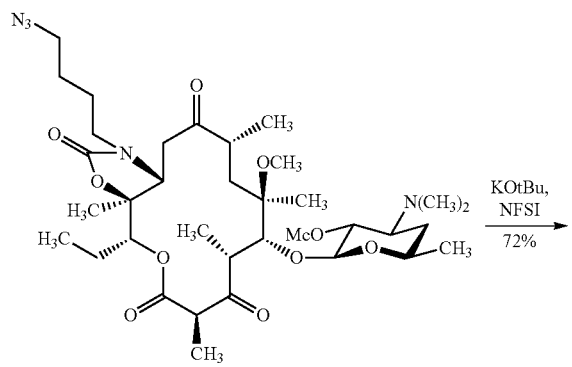

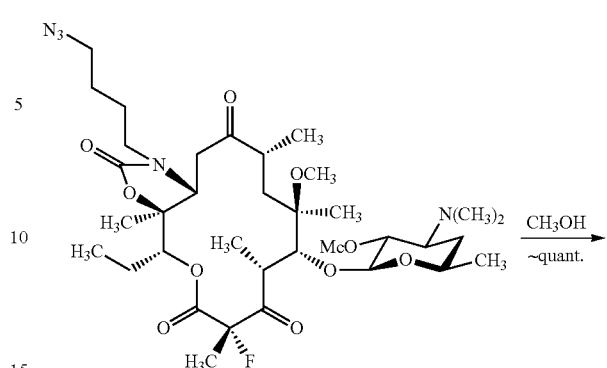

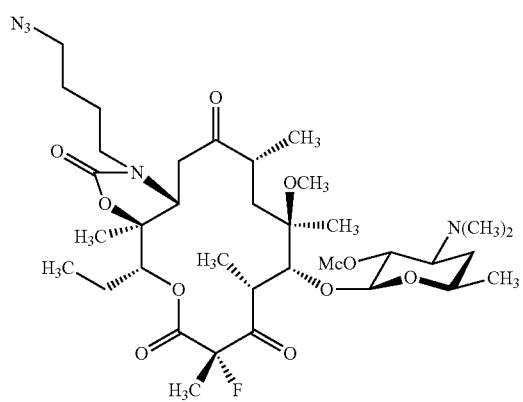

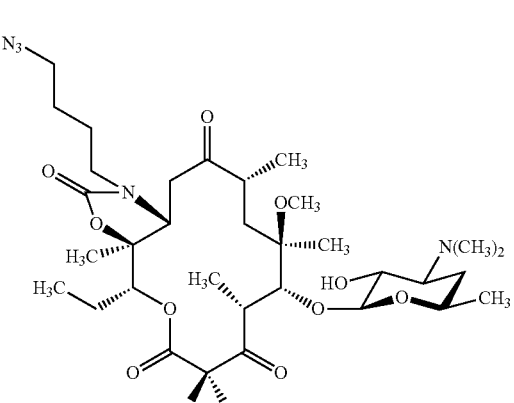

A solution of potassium tert-butoxide in THF (1.0 M, 0.044 mL, 0.044 mmol, 1.1 equiv) was added dropwise via syringe to a solution of C10-desmethylmarcrocycle (30 mg, 0.040 mmol, 1 equiv) in THF (0.5 mL) at −78° C. The resulting solution was stirred at −78° C. for 30 min and warmed to −20° C. After 5 min, the solution was cooled to −78° C., and a solution of N-fluorobenzenesulfonimide (13 mg, 0.040 mmol, 1.0 equiv) in THF (0.5 mL) was added via syringe. After 20 min, saturated aqueous sodium bicarbonate solution (1 mL) and ethyl acetate (5 mL) were added, and the mixture was allowed to warm to 23° C. The layers were separated, and the aqueous layer was extracted with ethyl acetate (2×5 mL). The combined organic layers were washed with saturated sodium chloride solution and dried over sodium sulfate. The dried solution was concentrated under reduced pressure and the residue was purified by flash column chromatography (2→3% methanol-dichloromethane+0.2→0.3% saturated aqueous ammonium hydroxide solution) to afford the product (22 mg, 72%) as a white foam. $^1$H NMR (500 MHz, cdcl$_3$) δ 4.94 (dd, J=8.2, 3.7 Hz, 1H), 4.50 (dd, J=10.5, 7.6 Hz, 1H), 4.42 (d, J=7.6 Hz, 1H), 3.85 (d, J=10.4 Hz, 1H), 3.81 (s, 3H), 3.83-3.79 (m, 1H), 3.62-3.57 (m, 1H), 3.55-3.37 (m, 2H), 3.36-3.24 (m, 2H), 3.06 (d, J=18.4 Hz, 1H), 2.76-2.67 (m, 2H), 2.65-2.56 (m, 1H), 2.43 (s, 3H), 2.42-2.33 (m, 1H), 2.26 (s, 6H), 2.06-1.90 (m, 2H), 1.75 (d, J=21.4 Hz, 3H), 1.70-1.48 (m, 7H), 1.38 (s, 3H), 1.28 (s, 3H), 1.27-1.24 (m, 1H), 1.22 (d, J=6.1 Hz, 3H), 1.18 (d, J=6.8 Hz, 6H), 0.95 (t, J=7.5 Hz, 3H). HRMS (ESI): Calcd for $(C_{36}H_{58}FN_5O_{12}+H)^+$: 772.4139; Found: 772.4155.

A solution of C10-desmethyl-C2-fluoro-macrocycle (8.0 mg, 10 μmol) in methanol (1 mL) was allowed to stand at 23° C. for 24 h. The solution was then concentrated under reduced pressure to afford the product as a white foam (7.4 mg, ~100%). $^1$H NMR (500 MHz, CDCl$_3$) δ 4.94 (dd, J=8.1, 3.8 Hz, 1H), 4.35 (d, J=7.3 Hz, 1H), 3.87 (d, J=9.9 Hz, 1H), 3.82 (d, J=9.7 Hz, 1H), 3.75-3.66 (m, 1H), 3.56-3.49 (m, 1H), 3.49-3.40 (m, 1H), 3.37-3.23 (m, 2H), 3.24-3.14 (m, 1H), 3.09 (d, J=18.8 Hz, 1H), 3.04 (dd, J=12.6, 4.1 Hz, 1H), 2.68-2.57 (m, 1H), 2.52-2.47 (m, 1H), 2.45 (s, 3H), 2.39 (dd, J=18.7, 9.9 Hz, 1H), 2.28 (s, 6H), 2.05-1.93 (m, 2H), 1.93-1.81 (m, 2H), 1.75 (d, J=21.4 Hz, 3H), 1.72-1.46 (m, 5H), 1.39 (s, 3H), 1.32 (d, J=7.0 Hz, 3H), 1.31 (s, 3H), 1.27-1.25 (m, 1H), 1.23 (d, J=6.1 Hz, 3H), 1.17 (d, J=6.9 Hz, 3H), 0.96 (t, J=7.6 Hz, 3H). HRMS (ESI): Calcd for $(C_{34}H_{56}FN_5O_{10}+H)^+$: 714.4084; Found: 714.4101.

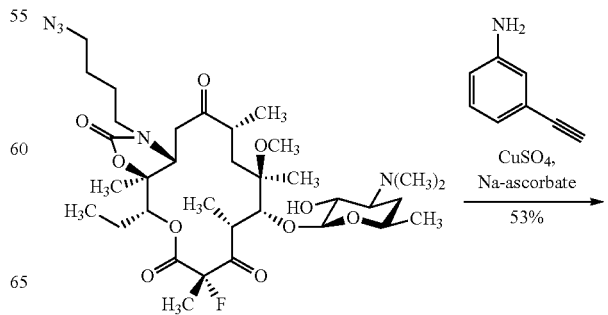

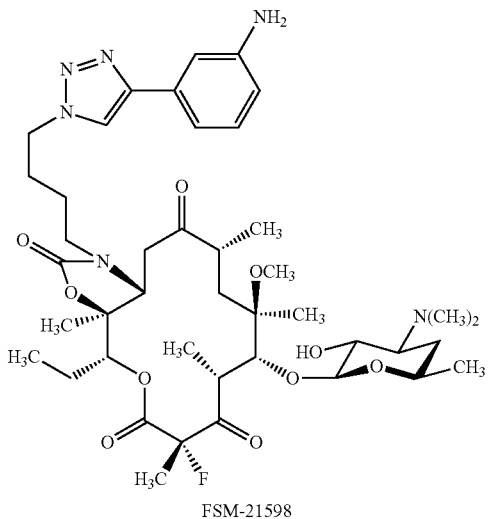

FSM-21598

3-ethynylaniline (3.5 mg, 0.030 mmol, 3.0 equiv), an aqueous solution of sodium ascorbate (0.1 M, 19 μL, 1.9 μmol, 0.20 equiv) and an aqueous solution of copper (II) sulfate (0.1 M, 4.9 μL, 0.49 μmol, 0.050 equiv) were added sequentially to a solution of C10-desmethyl-C2-fluoro-ketolide-2'OH (7.4 mg, 10 μmol) in 1:1 t-butanol:water (0.2 mL) at 23° C. After 16 h, the reaction mixture was partitioned between saturated aqueous sodium bicarbonate solution (1 mL) and dichloromethane (1 mL). The aqueous layer was separated and further extracted with dichloromethane (2×1 mL). The combined organic layers were dried over sodium sulfate and concentrated under reduced pressure. The residue was purified by flash column chromatography (2→3% methanol-dichloromethane+0.2→0.3% saturated aqueous ammonium hydroxide solution) to afford the product as a pale yellow solid (4.3 mg, 53%). $^1$H NMR (500 MHz, CDCl$_3$) δ 7.81 (s, 1H), 7.26-7.13 (m, 3H), 6.68-6.61 (m, 1H), 4.96 (dd, J=8.1, 3.8 Hz, 1H), 4.45 (dd, J=7.4, 6.2 Hz, 2H), 4.36 (d, J=7.3 Hz, 1H), 3.86 (d, J=9.8 Hz, 1H), 3.81 (d, J=9.7 Hz, 1H), 3.76-3.63 (m, 1H), 3.59-3.48 (m, 2H), 3.20 (dd, J=10.2, 7.3 Hz, 1H), 3.09 (d, J=18.7 Hz, 1H), 3.06-2.99 (m, 1H), 2.63-2.55 (m, 1H), 2.55-2.45 (m, 1H), 2.42 (s, 3H), 2.34 (dd, J=18.7, 9.9 Hz, 1H), 2.29 (s, 6H), 2.09-1.81 (m, 4H), 1.77 (d, J=21.4 Hz, 3H), 1.74-1.54 (m, 5H), 1.40 (s, 3H), 1.33 (d, J=6.8 Hz, 3H), 1.29 (s, 3H), 1.28-1.26 (m, 1H), 1.25 (d, J=6.1 Hz, 3H), 1.11 (d, J=6.9 Hz, 3H), 0.98 (t, J=7.5 Hz, 3H). $^{13}$C NMR (126 MHz, CDCl$_3$) δ 210.78, 202.42 (d, J=29.1 Hz), 165.28 (d, J=23.4 Hz), 157.08, 147.79, 146.83, 131.61, 129.66, 119.72, 116.03, 114.78, 112.21, 104.30, 96.39 (d, J=207.0 Hz), 83.06, 81.30, 81.18, 79.02, 70.29, 69.55, 65.81, 60.66, 49.75, 48.90, 43.63, 42.68, 40.64, 40.22, 39.20, 36.22, 28.24, 27.48, 25.96 (d, J=23.2 Hz), 25.04, 23.87, 21.12, 18.79, 17.87, 16.10, 15.25, 10.67. FTIR (neat), cm$^{-1}$: 3381 (br), 2974 (s), 2098 (s), 1753 (s), 1712 (s), 1267 (s), 1053 (s), 731 (s); HRMS (ESI): Calcd for (C$_{42}$H$_{63}$FN$_6$O$_{10}$+H)$^+$: 831.4662; Found: 831.4668.

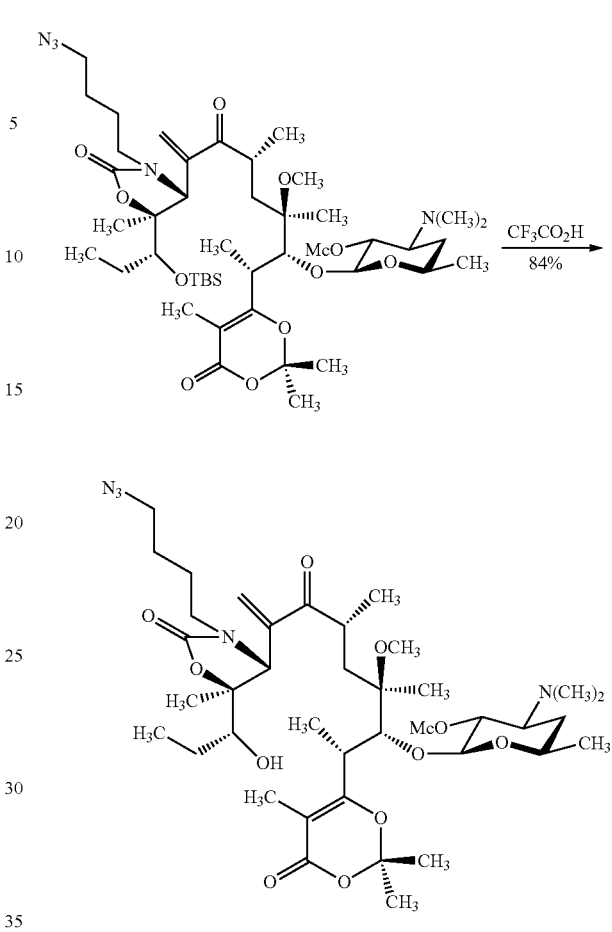

Trifluoroacetic acid (0.30 mL, 3.9 mmol, 56 equiv) was added to a solution of Open chain exomethylene (65 mg, 0.069 mmol, 1 equiv) in 9:1 dichloromethane:water (1.0 mL) at 0° C. The solution was allowed to warm to 23° C. and was stirred at that temperature for 20 h. Saturated aqueous sodium bicarbonate solution (10 mL) was added, and the mixture was extracted with dichloromethane (3×10 mL). The combined organic layers were dried over sodium sulfate and the dried solution was concentrated under reduced pressure. The residue was purified by flash column chromatography (2→3% methanol-dichloromethane+0.2→0.3% saturated aqueous ammonium hydroxide solution) to afford the product as a white foam (48 mg, 84%). $^1$H NMR (500 MHz, cdcl$_3$) δ 6.68 (br s, 1H), 5.91 (br s, 1H), 4.82 (br s, 1H), 4.60-4.49 (m, 2H), 3.84 (d, J=3.8 Hz, 1H), 3.80 (s, 3H), 3.62-3.41 (m, 4H), 3.38-3.23 (m, 3H), 2.91 (s, 3H), 2.77 (ddd, J=12.3, 10.2, 4.4 Hz, 1H), 2.74-2.64 (m, 1H), 2.32 (s, 6H), 1.82 (s, 3H), 1.81-1.74 (m, 2H), 1.67 (s, 3H), 1.66 (s, 3H), 1.70-1.52 (m, 6H), 1.45 (d, J=13.1 Hz, 1H), 1.35 (dd, J=23.8, 12.6 Hz, 1H), 1.26 (d, J=6.1 Hz, 3H), 1.21 (s, 3H), 1.13-1.04 (m, 12H).

$^{13}$C NMR (126 MHz, cdcl$_3$) δ 205.60, 167.23, 162.76, 157.55, 155.27, 141.72, 127.44, 104.41, 100.18, 99.71, 84.33, 78.89, 78.22, 77.57, 75.41, 69.24, 62.93, 58.17, 50.76, 49.63, 41.67, 40.60, 38.05, 34.58, 34.34, 30.82, 25.98, 25.94, 23.99, 23.97, 23.44, 20.95, 20.25, 17.48, 13.08, 10.91, 9.58. HRMS (ESI): Calcd for (C$_{40}$H$_{65}$N$_5$O$_{13}$+H)$^+$: 824.4652; Found: 824.4672.

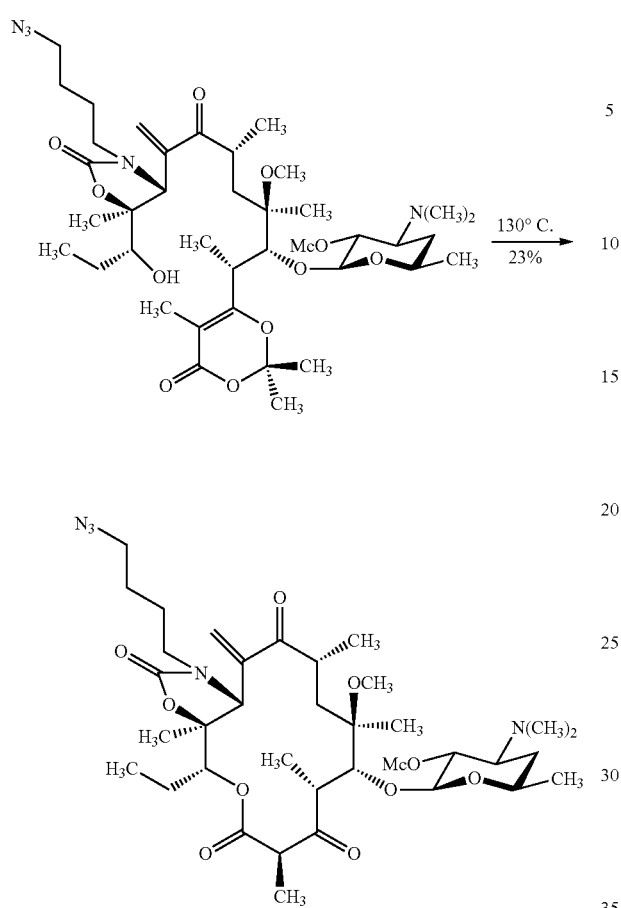

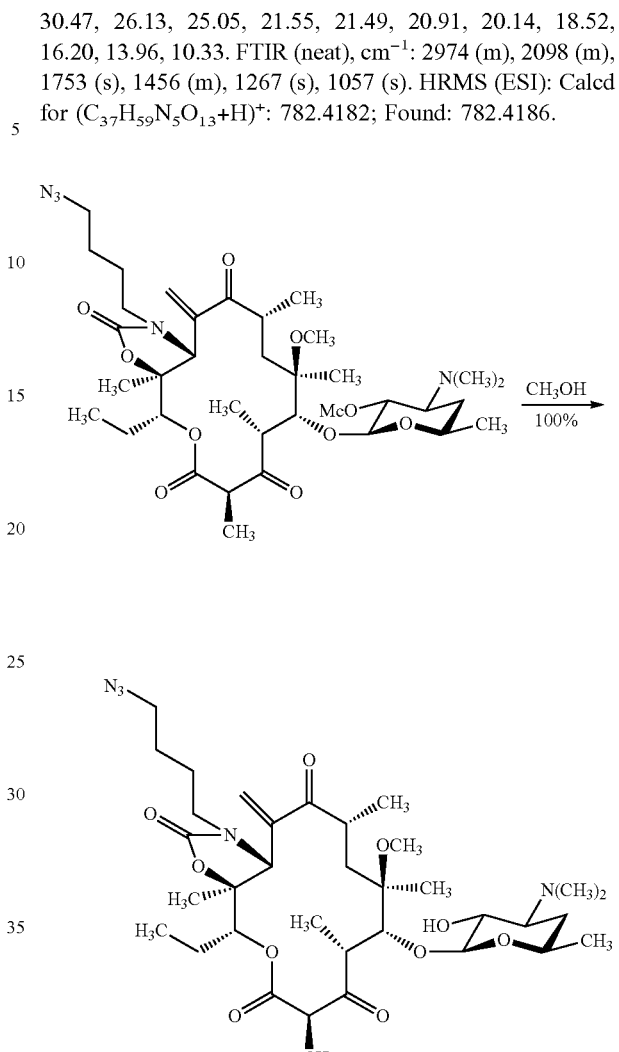

C10-methyl macrocyclization precursor (70 mg, 0.085 mmol) was dissolved in chlorobenzene (85 mL) in a 200-mL flask. The flask was fitted with a dry reflux condensor. Dry argon was bubbled through the solution via a 19-gauge needle for 10 min. The flask was then immersed in an oil bath preheated to 150° C. to allow a gentle reflux of the reaction solution. After 16 h, the heating bath was removed and the solution was allowed to cool to 23° C. The cooled solution was concentrated under reduced pressure (rotary evaporation, 10 mmHg, 40° C. water bath) and the residue was purified by flash column chromatography (2→3% methanol-dichloromethane+0.2→0.3% saturated aqueous ammonium hydroxide solution) to afford the product as a white foam (15 mg, 23%). $^1$H NMR (17:1 diastereomeric mixture at C2, major isomer is reported, 500 MHz, cdcl$_3$) δ 6.03 (s, 1H), 5.53 (s, 1H), 4.93 (dd, J=11.0, 1.9 Hz, 1H), 4.52 (dd, J=10.6, 7.5 Hz, 1H), 4.37 (d, J=7.5 Hz, 1H), 4.19 (d, J=8.8 Hz, 1H), 4.01 (q, J=7.0 Hz, 1H), 3.95 (s, 1H), 3.81 (s, 3H), 3.60-3.44 (m, 2H), 3.41-3.17 (m, 3H), 2.97-2.86 (m, 1H), 2.75 (s, 3H), 2.75-2.60 (m, 1H), 2.42-2.31 (m, 1H), 2.29 (s, 6H), 1.96-1.86 (m, 1H), 1.86-1.51 (m, 8H), 1.47 (d, J=7.1 Hz, 3H), 1.40 (s, 3H), 1.28 (s, 3H), 1.25 (d, J=6.1 Hz, 3H), 1.23-1.21 (m, 1H), 1.18 (d, J=6.9 Hz, 6H), 0.92 (t, J=7.3 Hz, 3H). $^{13}$C NMR (17:1 diastereomeric mixture at C2, major isomer is reported, 126 MHz, cdcl$_3$) δ 206.87, 205.57, 171.25, 156.81, 155.22, 145.01, 120.69, 101.66, 83.33, 77.79, 77.59, 75.65, 69.06, 63.26, 63.08, 54.83, 51.09, 50.81, 50.42, 49.04, 42.74, 41.46, 40.62, 38.97, 30.47, 26.13, 25.05, 21.55, 21.49, 20.91, 20.14, 18.52, 16.20, 13.96, 10.33. FTIR (neat), cm$^{-1}$: 2974 (m), 2098 (m), 1753 (s), 1456 (m), 1267 (s), 1057 (s). HRMS (ESI): Calcd for $(C_{37}H_{59}N_5O_{13}+H)^+$: 782.4182; Found: 782.4186.

A solution of Exomethylene-macrocycle (15 mg, 0.020 mmol) in methanol (1 mL) was allowed to stand at 23° C. for 24 h. The solution was then concentrated under reduced pressure to afford the product as a white foam (14 mg, 100%). $^1$H NMR (500 MHz, cdcl$_3$) δ 6.02 (s, 1H), 5.52 (s, 1H), 4.94 (dd, J=10.9, 1.7 Hz, 1H), 4.28 (d, J=7.3 Hz, 1H), 4.20 (d, J=9.0 Hz, 1H), 4.04 (q, J=7.0 Hz, 1H), 3.97 (s, 1H), 3.62-3.47 (m, 2H), 3.47-3.38 (m, 1H), 3.38-3.23 (m, 2H), 3.18 (dd, J=10.2, 7.3 Hz, 1H), 3.00-2.86 (m, 1H), 2.76 (s, 3H), 2.73-2.61 (m, 1H), 2.57-2.42 (m, 2H), 2.28 (s, 6H), 1.95-1.85 (m, 1H), 1.85-1.75 (m, 1H), 1.75-1.51 (m, 7H), 1.48 (d, J=7.1 Hz, 3H), 1.40 (s, 3H), 1.33 (d, J=7.5 Hz, 3H), 1.30 (s, 3H), 1.28-1.25 (m, 1H), 1.24 (d, J=6.1 Hz, 3H), 1.17 (d, J=6.9 Hz, 3H), 0.92 (t, J=7.4 Hz, 3H). $^{13}$C NMR (126 MHz, cdcl$_3$) δ 206.40, 205.92, 171.31, 156.84, 145.10, 120.54, 104.20, 83.34, 78.44, 77.82, 77.17, 70.43, 69.44, 65.73, 63.23, 51.03, 50.81, 50.47, 49.24, 42.75, 41.69, 40.22, 39.01, 30.30, 29.67, 28.29, 26.14, 25.01, 21.55, 21.47, 21.16, 20.15, 18.66, 16.25, 14.45, 10.32. FTIR (neat), cm$^{-1}$: 3454 (br), 2937 (m), 2098 (m), 1753 (s), 1458 (m), 1161 (s), 1053 (s). HRMS (ESI): Calcd for $(C_{35}H_{57}N_5O_{10}+H)^+$: 708.4178; Found: 708.4195.

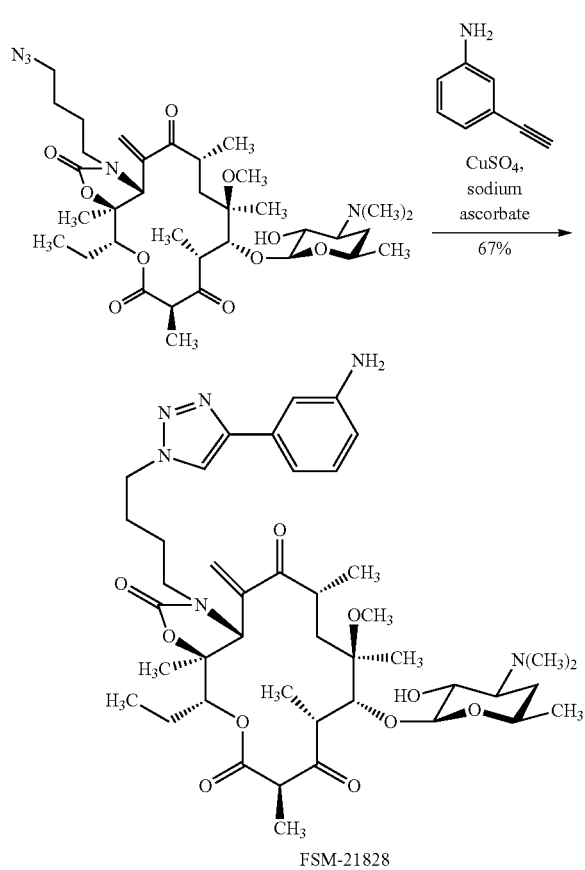

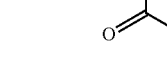

3-ethynylaniline (7.0 mg, 0.059 mmol, 3.0 equiv), an aqueous solution of sodium ascorbate (0.10 M, 40 μL, 4.0 μmol, 0.20 equiv) and an aqueous solution of copper(II) sulfate (0.10 M, 10 μL, 1.0 μmol, 0.050 equiv) were added sequentially to a stirred solution of C10-methylenemacrocycle (14 mg, 0.020 mmol, 1 equiv) 1:1 t-butanol:water (0.2 mL). After 16 h, the reaction mixture was partitioned between dichloromethane (1 mL) and saturated aqueous sodium bicarbonate solution (1 mL). The aqueous layer was extracted with dichloromethane (2×1 mL). The combined organic layers were dried over sodium sulfate and the dried solution was concentrated under reduced pressure. The residue was purified by preparatory thin layer chromatography (10% methanol-dichloromethane+1% saturated ammonium hydroxide solution) to afford FSM-21828 as a white solid (11 mg, 67%). $^1$H NMR (10:1 diastereomeric mixture at C2, major isomer is reported, 500 MHz, cdcl$_3$) δ 7.80 (s, 1H), 7.32-7.29 (m, 1H), 7.24-7.19 (m, 2H), 6.71-6.62 (m, 1H), 6.02 (s, 1H), 5.51 (s, 1H), 4.94 (dd, J=10.9, 1.7 Hz, 1H), 4.51-4.33 (m, 2H), 4.28 (d, J=7.3 Hz, 1H), 4.18 (d, J=9.0 Hz, 1H), 4.06 (q, J=7.1 Hz, 1H), 3.98 (s, 1H), 3.80 (br s, 2H), 3.60-3.48 (m, 2H), 3.48-3.37 (m, 1H), 3.18 (dd, J=10.2, 7.3 Hz, 1H), 3.00-2.86 (m, 1H), 2.74 (s, 3H), 2.74-2.68 (m, 1H), 2.55-2.41 (m, 2H), 2.28 (s, 6H), 2.03-1.56 (m, 9H), 1.49 (d, J=7.1 Hz, 3H), 1.41 (s, 3H), 1.33 (d, J=7.5 Hz, 3H), 1.28 (s, 3H), 1.27-1.25 (m, 1H), 1.23 (d, J=6.1 Hz, 3H), 1.16 (d, J=6.9 Hz, 3H), 0.92 (t, J=7.3 Hz, 3H). $^{13}$C NMR (10:1 diastereomeric mixture at C2, major isomer is reported, 126 MHz, cdcl$_3$) δ 206.32, 205.97, 171.49, 157.00, 147.84, 146.88, 144.85, 131.59, 129.67, 120.70, 119.78, 116.04, 114.76, 112.31, 104.26, 83.50, 78.46, 77.84, 70.43, 69.47, 65.75, 63.22, 51.13, 50.50, 49.54, 49.27, 42.19, 41.68, 40.23, 38.93, 28.27, 27.40, 24.88, 21.55, 21.48, 21.17, 20.13, 18.71, 16.25, 14.44, 10.38. FTIR (neat), cm$^{-1}$: 3360 (br), 2972 (m), 1753 (s), 1458 (m), 1109 (s), 1049 (s), 734 (s). HRMS (ESI): Calcd for $(C_{43}H_{64}N_6O_{10}+H)^+$: 825.4757; Found: 825.4764.

Potassium azodicarboxylate (2.3 mg, 0.012 mmol, 5.0 equiv) was added to a solution of FSM-21828 (2.0 mg, 2.4 μmol, 1 equiv) in methanol (0.1 mL) at 23° C. Acetic acid (0.6 μL, 10 μmol, 4.0 equiv) was added dropwise as a solution in methanol (0.1 mL) at 23° C. After 2 h, the reaction solution was concentrated under reduced pressure. The residue was purified by flash column chromatography (5% methanol-dichloromethane+0.5% saturated aqueous ammonium hydroxide solution) to afford the product as a colorless film (1.4 mg, 69%).

$^1$H NMR (500 MHz, cdcl$_3$) δ 7.80 (s, 1H), 7.22-7.12 (m, 3H), 6.67 (d, J=6.4 Hz, 1H), 5.36 (br s, 1H), 4.99 (dd, J=9.7, 2.8 Hz, 1H), 4.47 (t, J=7.1 Hz, 2H), 4.32-4.24 (m, 2H), 4.11 (s, 1H), 3.85 (q, J=6.7 Hz, 1H), 3.77 (br s, 2H), 3.70-3.48 (m, 3H), 3.29-3.21 (m, 1H), 3.18 (dd, J=10.1, 7.3 Hz, 1H), 3.14-2.98 (m, 2H), 2.94 (s, 3H), 2.82 (dt, J=10.7, 5.7 Hz, 1H), 2.66-2.55 (m, 1H), 2.50-2.41 (m, 1H), 2.28 (s, 6H), 2.08-1.90 (m, 1H), 1.77-1.49 (m, 8H), 1.47 (s, 3H), 1.46 (d, J=6.8 Hz, 3H), 1.37 (d, J=6.8 Hz, 3H), 1.34 (d, J=6.5 Hz, 3H), 1.32 (d, J=7.4 Hz, 3H), 1.30-1.28 (m, 1H), 1.27 (s, 3H), 0.91 (t, J=7.3 Hz, 3H). HRMS (ESI): Calcd for $(C_{43}H_{66}N_8O_9+H)^+$: 839.5026; Found: 839.5030.

Biological Screening

MIC data was collected for the novel macrolides that this platform has produced against over 21 unique strains of B.

subtilis, E. coli, S. aureus, S. pneumoniae, and H. influenzae, including several multidrug-resistant strains, with a special focus on macrolide resistant mechanisms (vide supra). Azithromycin (Azithro) and Solithromycin (Solithro) were included as a control macrolides in many cases. CLSI standard procedures for broth dilution MIC determination were used. Data for exemplary macrolides of the present invention are shown in Tables B1-13. Certain analogs show greater activity than azithromycin in all strains of bacteria, especially against S. aureus and S. pneumoniae with efflux (mef, msr) and methylase (erm) genotypes, which are the two most prevalent forms of resistance to macrolides in the United States and Europe (ermA/B=ribosomal methylation, mefA, msrA macrolide efflux). These genotypes can b constitutive or inducible.

In the future, all fully synthetic macrolides will be evaluated in a two-tier system, involving an initial in house screen against macrolide susceptible strains of S. aureus and S. pneumoniae. Macrolides found to possess threshold activity (MICs of 4 μg/mL or lower) against these bacterial strains will then be submitted for second-tier analysis against a full panel (16 strains, Gram-positive and Gram-negative organisms, including macrolide-resistant strains). After further rounds of optimization (synthesis, MIC determination), macrolides showing highly promising anti-microbial activity, especially against resistant strains, may be subject to further evaluation in rodent models of infection.

TABLE B1

| Species | Strain or Genotype | Azithro | Solithro | FSM-11561 | FSM-11563 | FSM-11559 | FSM-11562 |
|---|---|---|---|---|---|---|---|
| | | | Gram-positive | | | | |
| S. aureus | ATCC 29213 | 1 | 0.125 | 0.0625 | 0.0625 | 0.125 | 0.0625 |
| S. aureus | MRSA: USA300 | 32 | 1 | 0.5 | 0.125 | 4 | 1 |
| S. aureus | MRSA: USA100 | >32 | >32 | >32 | >32 | >32 | >32 |
| S. aureus | erm A genotype | >32 | >32 | >32 | >32 | >32 | >32 |
| S. aureus | USA600, GISA | >32 | >32 | >32 | >32 | >32 | >32 |
| S. pneumoniae | ATCC 49619 | <0.03125 | <0.03125 | ≤0.03125 | ≤0.03125 | ≤0.03125 | ≤0.03125 |
| S. pneumoniae | mef A genotype | 0.25 | <0.03125 | ≤0.03125 | ≤0.03125 | ≤0.03125 | ≤0.03125 |
| S. pneumoniae | mef A genotype | 4 | 0.125 | 0.0625 | ≤0.03125 | 0.125 | 0.0625 |
| S. pneumoniae | erm B + tet(M, O) genotype | <0.03125 | <0.03125 | ≤0.03125 | ≤0.03125 | ≤0.03125 | ≤0.03125 |
| S. pneumoniae | erm B + mef A genotype | >32 | 0.25 | 0.125 | ≤0.03125 | 1 | 0.25 |
| S. pyogenes | ATCC 19615 | <0.03125 | <0.03125 | ≤0.03125 | ≤0.03125 | ≤0.03125 | ≤0.03125 |
| S. pyogenes | Macrolide-resistant | 2 | 0.0625 | 0.0625 | ≤0.03125 | 0.125 | 0.125 |
| E. faecalis | ATCC 29212 | 4 | <0.03125 | ≤0.03125 | ≤0.03125 | ≤0.03125 | ≤0.03125 |
| E. faecalis | Vancomycin-resistant | >32 | 32 | 32 | 4 | >32 | >32 |
| | | | Gram-negative | | | | |
| E. coli | ATCC 25922 | 4 | 32 | 16 | 16 | >32 | 16 |
| E. coli | NDM-1 | >32 | >32 | >32 | >32 | >32 | >32 |
| E. coli | TEM-1 | 1 | 32 | 8 | 16 | 32 | 16 |
| E. coli | CTX-M-14 | >32 | >32 | >32 | >32 | >32 | >32 |
| A. baumannii | ATCC 19606 | 16 | 8 | 4 | 4 | 16 | 8 |
| A. baumannii | imipenem-resistant | 8 | 4 | 2 | 4 | 32 | 8 |
| A. baumannii | chromosomal class C | 32 | 8 | 4 | 2 | 16 | 8 |
| A. baumannii | IMP-4 | >32 | >32 | >32 | >32 | >32 | >32 |
| K. pneumoniae | ATCC 10031 | 4 | 8 | 2 | 4 | 4 | 4 |
| K. pneumoniae | KPC-2 | >32 | >32 | >32 | >32 | >32 | >32 |
| K. pneumoniae | TEM-10 | 8 | >32 | 32 | 32 | >32 | 32 |
| K. pneumoniae | SHV-12 | 16 | >32 | >32 | >32 | >32 | >32 |
| P. aeruginosa | ATCC 27853 | >32 | >32 | 32 | 32 | >32 | >32 |
| P. aeruginosa | HPA101-1477 | >32 | >32 | >32 | >32 | >32 | >32 |
| H. influenzae | Erythro >4, Azithro 1 | 0.125 | 2 | 2 | 4 | 4 | 2 |
| H. influenzae | ATCC49247 | 0.5 | 4 | 2 | 2 | 4 | 4 |

TABLE B2

| Species | Strain or Genotype | FSM-100364 | FSM-100407 | FSM-100239 | FSM-100240 | FSM-100341 | FSM-100383 |
|---|---|---|---|---|---|---|---|
| | | | Gram-positive | | | | |
| S. aureus | ATCC 29213 | <0.03125 | <0.03125 | ≤0.03125 | ≤0.03125 | <0.03125 | <0.03125 |
| S. aureus | MRSA: USA300 | 2 | 0.5 | 0.25 | 1 | 2 | 0.5 |
| S. aureus | MRSA: USA100 | >32 | >32 | >32 | >32 | >32 | >32 |
| S. aureus | erm A genotype | >32 | >32 | >32 | >32 | >32 | >32 |
| S. aureus | USA600, GISA | >32 | >32 | >32 | >32 | >32 | >32 |
| S. pneumoniae | ATCC 49619 | <0.03125 | <0.03125 | ≤0.03125 | ≤0.03125 | <0.03125 | <0.03125 |
| S. pneumoniae | mef A genotype | <0.03125 | <0.03125 | ≤0.03125 | ≤0.03125 | <0.03125 | <0.03125 |
| S. pneumoniae | mef A genotype | 0.25 | <0.03125 | <0.03125 | 0.25 | <0.03125 | <0.03125 |
| S. pneumoniae | erm B + tet(M, O) genotype | <0.03125 | <0.03125 | ≤0.03125 | ≤0.03125 | <0.03125 | <0.03125 |
| S. pneumoniae | erm B + mef A genotype | 0.125 | <0.03125 | 0.0625 | 0.125 | 0.25 | <0.03125 |

TABLE B2-continued

| Species | Strain or Genotype | FSM-100364 | FSM-100407 | FSM-100239 | FSM-100240 | FSM-100341 | FSM-100383 |
|---|---|---|---|---|---|---|---|
| S. pyogenes | ATCC 19615 | <0.03125 | <0.03125 | ≤0.03125 | ≤0.03125 | <0.03125 | <0.03125 |
| S. pyogenes | Macrolide-resistant | <0.03125 | <0.03125 | ≤0.03125 | 0.25 | <0.03125 | <0.03125 |
| E. faecalis | ATCC 29212 | <0.03125 | <0.03125 | ≤0.03125 | ≤0.03125 | <0.03125 | <0.03125 |
| E. faecalis | Vancomycin-resistant | >32 | 16 | 16 | 8 | >32 | >32 |
| Gram-negative | | | | | | | |
| E. coli | ATCC 25922 | 16 | 16 | 16 | >32 | >32 | 8 |
| E. coli | NDM-1 | >32 | >32 | >32 | >32 | >32 | 32 |
| E. coli | TEM-1 | >32 | >32 | 16 | 32 | 32 | 16 |
| E. coli | CTX-M-14 | >32 | >32 | >32 | >32 | >32 | >32 |
| A. baumannii | ATCC 19606 | 8 | 8 | 8 | 32 | 16 | 4 |
| A. baumannii | imipenem-resistant | 4 | 8 | 4 | 32 | 16 | 8 |
| A. baumannii | chromosomal class C | 8 | 8 | 2 | 16 | 32 | 8 |
| A. baumannii | IMP-4 | >32 | >32 | >32 | >32 | >32 | >32 |
| K. pneumoniae | ATCC 10031 | 8 | 4 | 4 | 4 | 8 | 2 |
| K. pneumoniae | KPC-2 | >32 | >32 | >32 | >32 | >32 | >32 |
| K. pneumoniae | TEM-10 | 32 | 32 | 32 | 32 | 32 | 16 |
| K. pneumoniae | SHV-12 | >32 | >32 | >32 | >32 | >32 | >32 |
| P. aeruginosa | ATCC 27853 | >32 | 32 | >32 | >32 | >32 | >32 |
| P. aeruginosa | HPA101-1477 | >32 | >32 | >32 | >32 | >32 | >32 |
| H. influenzae | Erythro >4, Azithro 1 | 0.5 | 1 | 1 | 1 | 1 | 0.5 |
| H. influenzae | ATCC49247 | 2 | 1 | 1 | 1 | 1 | 0.5 |

TABLE B3

| Species | Strain or Genotype | Azithro | Solithro | FSM-11561 | FSM-11563 | FSM-100371 | FSM-100389 | FSM-100376 | FSM-100386 | FSM-100421 |
|---|---|---|---|---|---|---|---|---|---|---|
| Gram-positive | | | | | | | | | | |
| S. aureus | ATCC 29213 | 1 | 0.125 | 0.0625 | 0.0625 | <0.03125 | <0.03125 | <0.03125 | <0.03125 | 0.0625 |
| S. aureus | MRSA: USA300 | 32 | 1 | 0.5 | 0.125 | 4 | 2 | 8 | 4 | 2 |
| S. aureus | MRSA: USA100 | >32 | >32 | >32 | >32 | >32 | >32 | >32 | >32 | >32 |
| S. aureus | erm A genotype | >32 | >32 | >32 | >32 | >32 | >32 | >32 | >32 | >32 |
| S. aureus | USA600, GISA | >32 | >32 | >32 | >32 | >32 | >32 | >32 | >32 | >32 |
| S. pneumoniae | ATCC 49619 | <0.03125 | <0.03125 | ≤0.03125 | ≤0.03125 | <0.03125 | <0.03125 | <0.03125 | <0.03125 | <0.03125 |
| S. pneumoniae | mef A genotype | 0.25 | <0.03125 | ≤0.03125 | ≤0.03125 | <0.03125 | <0.03125 | <0.03125 | <0.03125 | <0.03125 |
| S. pneumoniae | mef A genotype | 4 | 0.125 | 0.0625 | ≤0.03125 | 0.125 | <0.03125 | <0.03125 | 0.0625 | 0.0625 |
| S. pneumoniae | erm B + tet(M, O) genotype | <0.03125 | <0.03125 | ≤0.03125 | ≤0.03125 | <0.03125 | <0.03125 | <0.03125 | <0.03125 | <0.03125 |
| S. pneumoniae | erm B + mef A genotype | >32 | 0.25 | 0.125 | ≤0.03125 | 0.25 | 0.0625 | 0.25 | 0.25 | <0.03125 |
| S. pyogenes | ATCC 19615 | <0.03125 | <0.03125 | ≤0.03125 | ≤0.03125 | <0.03125 | <0.03125 | <0.03125 | <0.03125 | <0.03125 |
| S. pyogenes | Macrolide-resistant | 2 | 0.0625 | 0.0625 | ≤0.03125 | 0.0625 | <0.03125 | <0.03125 | 0.0625 | <0.03125 |
| E. faecalis | ATCC 29212 | 4 | <0.03125 | ≤0.03125 | ≤0.03125 | <0.03125 | <0.03125 | <0.03125 | <0.03125 | <0.03125 |
| E. faecalis | Vancomycin-resistant | >32 | 32 | 32 | 4 | >32 | >32 | >32 | >32 | 32 |
| Gram-negative | | | | | | | | | | |
| E. coli | ATCC 25922 | 4 | 32 | 16 | 16 | >32 | 32 | 8 | 16 | 32 |
| E. coli | NDM-1 | >32 | >32 | >32 | >32 | >32 | >32 | >32 | >32 | >32 |
| E. coli | TEM-1 | 1 | 32 | 8 | 16 | >32 | 32 | 16 | 16 | 32 |
| E. coli | CTX-M-14 | >32 | >32 | >32 | >32 | >32 | >32 | >32 | >32 | >32 |
| A. baumanni | ATCC 19606 | 16 | 8 | 4 | 4 | 16 | 16 | 16 | 32 | 16 |
| A. baumanni | imipenem-resistant | 8 | 4 | 2 | 4 | >32 | 16 | 32 | >32 | 16 |
| A. baumanni | chromosomal class C | 32 | 8 | 4 | 2 | 32 | 32 | 16 | 32 | 32 |
| A. baumanni | IMP-4 | >32 | >32 | >32 | >32 | >32 | >32 | >32 | >32 | >32 |
| K. pneumoniae | ATCC 10031 | 4 | 8 | 2 | 4 | 8 | 4 | 8 | 8 | 4 |
| K. pneumoniae | KPC-2 | >32 | >32 | >32 | >32 | >32 | >32 | >32 | >32 | >32 |

TABLE B3-continued

| Species | Strain or Genotype | Azithro | Solithro | FSM-11561 | FSM-11563 | FSM-100371 | FSM-100389 | FSM-100376 | FSM-100386 | FSM-100421 |
|---|---|---|---|---|---|---|---|---|---|---|
| K. pneumoniae | TEM-10 | 8 | >32 | 32 | 32 | >32 | >32 | 32 | >32 | 32 |
| K. pneumoniae | SHV-12 | 16 | >32 | >32 | >32 | >32 | >32 | >32 | >32 | >32 |
| P. aeruginosa | ATCC 27853 | >32 | >32 | 32 | 32 | >32 | >32 | 32 | >32 | >32 |
| P. aeruginosa | HPA101-1477 | >32 | >32 | >32 | >32 | >32 | >32 | >32 | >32 | >32 |
| H. influenzae | Erythro >4, Azithro 1 | 0.125 | 2 | 2 | 4 | 2 | 1 | 1 | 2 | 1 |
| H. influenzae | ATCC49247 | 0.5 | 4 | 2 | 2 | 2 | 1 | 1 | 4 | 2 |

TABLE B4

| Species | Strain or Genotype | Azithro | Solithro | FSM-100239 | FSM-100426 | FSM-100423 |
|---|---|---|---|---|---|---|
| | | Gram-positive | | | | |
| S. aureus | ATCC 29213 | 1 | 0.125 | ≤0.03125 | 0.0625 | 0.125 |
| S. aureus | MRSA: USA300 | 32 | 1 | 0.25 | 0.5 | >32 |
| S. aureus | MRSA: USA100 | >32 | >32 | >32 | >32 | >32 |
| S. aureus | erm A genotype | >32 | >32 | >32 | >32 | >32 |
| S. aureus | USA600, GISA | >32 | >32 | >32 | 32 | >32 |
| S. pneumoniae | ATCC 49619 | <0.03125 | <0.03125 | ≤0.03125 | <0.03125 | <0.03125 |
| S. pneumoniae | mef A genotype | 0.25 | <0.03125 | ≤0.03125 | <0.03125 | <0.03125 |
| S. pneumoniae | mef A genotype | 4 | 0.125 | ≤0.03125 | <0.03125 | <0.03125 |
| S. pneumoniae | erm B + tet(M,O) genotype | <0.03125 | <0.03125 | ≤0.03125 | <0.03125 | <0.03125 |
| S. pneumoniae | erm B + mef A genotype | >32 | 0.25 | 0.0625 | <0.03125 | 0.0625 |
| S. pyogenes | ATCC 19615 | <0.03125 | <0.03125 | ≤0.03125 | <0.03125 | <0.03125 |
| S. pyogenes | Macrolide-resistant | 2 | 0.0625 | ≤0.03125 | <0.03125 | <0.03125 |
| E. faecalis | ATCC 29212 | 4 | <0.03125 | ≤0.03125 | <0.03125 | <0.03125 |
| E. faecalis | Vancomycin-resistant | >32 | 32 | 16 | 8 | >32 |
| | | Gram-negative | | | | |
| E. coli | ATCC 25922 | 4 | 32 | 16 | 32 | >32 |
| E. coli | NDM-1 | >32 | >32 | >32 | >32 | >32 |
| E. coli | TEM-1 | 1 | 32 | 16 | 32 | >32 |
| E. coli | CTX-M-14 | >32 | >32 | >32 | >32 | >32 |
| A. baumannii | ATCC 19606 | 16 | 8 | 8 | 16 | 32 |
| A. baumannii | imipenem-resistant | 8 | 4 | 4 | 8 | 32 |
| A. baumannii | chromosomal class C | 32 | 8 | 2 | 32 | 32 |
| A. baumannii | IMP-4 | >32 | >32 | >32 | >32 | >32 |
| K. pneumoniae | ATCC 10031 | 4 | 8 | 4 | 8 | 16 |
| K. pneumoniae | KPC-2 | >32 | >32 | >32 | >32 | >32 |
| K. pneumoniae | TEM-10 | 8 | >32 | 32 | >32 | >32 |
| K. pneumoniae | SHV-12 | 16 | >32 | >32 | >32 | >32 |
| P. aeruginosa | ATCC 27853 | >32 | >32 | >32 | >32 | >32 |
| P. aeruginosa | HPA101-1477 | >32 | >32 | >32 | >32 | >32 |
| H. influenzae | Erythro >4, Azithro 1 | 0.125 | 2 | 1 | 4 | 4 |
| H. influenzae | ATCC49247 | 0.5 | 4 | 1 | 4 | 2 |

TABLE B5

| Species | Strain or Genotype | FSM-100431 | FSM-100427 | FSM-100433 | FSM-100429 | FSM-100428 | FSM-100434 |
|---|---|---|---|---|---|---|---|
| | | Gram-positive | | | | | |
| S. aureus | ATCC 29213 | 0.125 | <0.03125 | 0.5 | 0.125 | <0.03125 | 0.25 |
| S. aureus | MRSA: USA300 | >32 | 0.5 | >32 | >32 | 4 | >32 |
| S. aureus | MRSA: USA100 | >32 | >32 | >32 | >32 | >32 | >32 |
| S. aureus | erm A genotype | >32 | >32 | >32 | >32 | >32 | >32 |
| S. aureus | USA600, GISA | >32 | 32 | >32 | >32 | >32 | >32 |
| S. pneumoniae | ATCC 49619 | <0.03125 | <0.03125 | <0.03125 | <0.03125 | <0.03125 | <0.03125 |
| S. pneumoniae | mef A genotype | <0.03125 | <0.03125 | <0.03125 | <0.03125 | <0.03125 | <0.03125 |
| S. pneumoniae | mef A genotype | <0.03125 | <0.03125 | <0.03125 | 0.0625 | <0.03125 | 0.125 |
| S. pneumoniae | erm B + tet(M,O) genotype | <0.03125 | <0.03125 | <0.03125 | <0.03125 | <0.03125 | <0.03125 |
| S. pneumoniae | erm B + mef A genotype | 8 | <0.03125 | 2 | >32 | 0.0625 | 1 |

TABLE B5-continued

| Species | Strain or Genotype | FSM-100431 | FSM-100427 | FSM-100433 | FSM-100429 | FSM-100428 | FSM-100434 |
|---|---|---|---|---|---|---|---|
| S. pyogenes | ATCC 19615 | <0.03125 | <0.03125 | <0.03125 | <0.03125 | <0.03125 | <0.03125 |
| S. pyogenes | Macrolide-resistant | <0.03125 | <0.03125 | <0.03125 | <0.03125 | <0.03125 | <0.03125 |
| E. faecalis | ATCC 29212 | <0.03125 | <0.03125 | 0.0625 | <0.03125 | <0.03125 | <0.03125 |
| E. faecalis | Vancomycin-resistant | >32 | 8 | >32 | >32 | >32 | >32 |
| Gram-negative | | | | | | | |
| E. coli | ATCC 25922 | >32 | 32 | >32 | >32 | 32 | >32 |
| E. coli | NDM-1 | >32 | >32 | >32 | >32 | >32 | >32 |
| E. coli | TEM-1 | >32 | 32 | >32 | >32 | 32 | >32 |
| E. coli | CTX-M-14 | >32 | >32 | >32 | >32 | >32 | >32 |
| A. baumannii | ATCC 19606 | 16 | 16 | >32 | >32 | 16 | 16 |
| A. baumannii | imipenem-resistant | 16 | 8 | >32 | 32 | 16 | 16 |
| A. baumannii | chromosomal class C | 8 | 16 | >32 | 32 | 16 | 16 |
| A. baumannii | IMP-4 | >32 | >32 | >32 | >32 | >32 | >32 |
| K. pneumoniae | ATCC 10031 | 32 | 4 | >32 | 32 | 16 | 32 |
| K. pneumoniae | KPC-2 | >32 | >32 | >32 | >32 | >32 | >32 |
| K. pneumoniae | TEM-10 | >32 | 32 | >32 | >32 | 32 | >32 |
| K. pneumoniae | SHV-12 | >32 | >32 | >32 | >32 | >32 | >32 |
| P. aeruginosa | ATCC 27853 | >32 | >32 | >32 | >32 | >32 | >32 |
| P. aeruginosa | HPA101-1477 | >32 | >32 | >32 | >32 | >32 | >32 |
| H. influenzae | Erythro >4, Azithro 1 | >32 | 2 | >32 | >32 | 2 | >32 |
| H. influenzae | ATCC49247 | >32 | 2 | >32 | >32 | 4 | >32 |

TABLE B6

| Species | Strain or Genotype | Azithro | Solithro | FSM-21535 | FSM-21598 | FSM-21828 | FSM-100432 |
|---|---|---|---|---|---|---|---|
| Gram-positive | | | | | | | |
| S. aureus | ATCC 29213 | 1 | 0.125 | 16 | 32 | 4 | 1 |
| S. aureus | MRSA: USA300 | 32 | 1 | 32 | 32 | >32 | >32 |
| S. aureus | MRSA: USA100 | >32 | >32 | >32 | >32 | >32 | >32 |
| S. aureus | erm A genotype | >32 | >32 | >32 | >32 | >32 | >32 |
| S. aureus | USA600, GISA | >32 | >32 | >32 | >32 | >32 | >32 |
| S. pneumoniae | ATCC 49619 | <0.03125 | <0.03125 | ≤0.03125 | ≤0.03125 | ≤0.03125 | <0.03125 |
| S. pneumoniae | mef A genotype | 0.25 | <0.03125 | 0.0625 | ≤0.03125 | 0.0625 | 0.125 |
| S. pneumoniae | mef A genotype | 4 | 0.125 | 0.5 | 0.25 | 0.5 | 0.5 |
| S. pneumoniae | erm B + tet(M,O) genotype | <0.03125 | <0.03125 | ≤0.03125 | ≤0.03125 | ≤0.03125 | <0.03125 |
| S. pneumoniae | erm B + mef A genotype | >32 | 0.25 | 8 | 8 | 32 | 2 |
| S. pyogenes | ATCC 19615 | <0.03125 | <0.03125 | ≤0.03125 | ≤0.03125 | ≤0.03125 | <0.03125 |
| S. pyogenes | Macrolide-resistant | 2 | 0.0625 | 0.5 | 0.25 | 0.5 | 0.0625 |
| E. faecalis | ATCC 29212 | 4 | <0.03125 | ≤0.03125 | ≤0.03125 | 1 | 0.125 |
| E. faecalis | Vancomycin-resistant | >32 | 32 | >32 | >32 | >32 | >32 |
| Gram-negative | | | | | | | |
| E. coli | ATCC 25922 | 4 | 32 | >32 | >32 | >32 | >32 |
| E. coli | NDM-1 | >32 | >32 | >32 | >32 | >32 | >32 |
| E. coli | TEM-1 | 1 | 32 | >32 | >32 | >32 | >32 |
| E. coli | CTX-M-14 | >32 | >32 | >32 | >32 | >32 | >32 |
| A. baumannii | ATCC 19606 | 16 | 8 | >32 | >32 | >32 | >32 |
| A. baumannii | imipenem-resistant | 8 | 4 | >32 | >32 | >32 | >32 |
| A. baumannii | chromosomal class C | 32 | 8 | >32 | 32 | >32 | >32 |
| A. baumannii | IMP-4 | >32 | >32 | >32 | >32 | >32 | >32 |
| K. pneumoniae | ATCC 10031 | 4 | 8 | 4 | 8 | 16 | 32 |
| K. pneumoniae | KPC-2 | >32 | >32 | >32 | >32 | >32 | >32 |
| K. pneumoniae | TEM-10 | 8 | >32 | >32 | >32 | >32 | >32 |
| K. pneumoniae | SHV-12 | 16 | >32 | >32 | >32 | >32 | >32 |
| P. aeruginosa | ATCC 27853 | >32 | >32 | >32 | >32 | >32 | >32 |
| P. aeruginosa | HPA101-1477 | >32 | >32 | >32 | >32 | >32 | >32 |
| H. influenzae | Erythro >4, Azithro 1 | 0.125 | 2 | 8 | 8 | 16 | 8 |
| H. influenzae | ATCC49247 | 0.5 | 4 | 4 | 4 | 16 | 8 |

TABLE B7

| Species | Strain No. | Genotype | FSM-100563 | FSM-100566 | FSM-100551 | FSM-100573 |
|---|---|---|---|---|---|---|
| Gram-positive | | | | | | |
| S. aureus | MP-12 | ATCC29213 | 0.06 | 0.06 | 0.06 | 0.06 |
| S. aureus (MRSA) | MP-549 | USA300 | 0.125 | 0.125 | 0.125 | 0.06 |
| S. aureus (MRSA) | MP-618 UNT-096 | USA100 | 32 | >64 | >64 | 16 |
| S. aureus (MRSA) | MP-620 UNT-146 | ermA phenotype | 16 | >64 | >64 | 16 |
| S. aureus (MRSA) | MP-619 UNT-120 | GISA USA600 | 16 | 64 | 64 | 16 |
| S. pneumoniae | MP-21 | ATCC49619 | <0.03 | <0.03 | <0.03 | <0.03 |
| S. pneumoniae | MP-626 UNT-038 | mefA | <0.03 | <0.03 | <0.03 | <0.03 |
| S. pneumoniae | MP-627 UNT-039 | mefA | <0.03 | <0.03 | <0.03 | <0.03 |
| S. pyogenes | MP-19 | ATCC19615 | <0.03 | <0.03 | <0.03 | <0.03 |
| S. pyogenes | MP-625 UNT-014 | mac resistant | <0.03 | <0.03 | 0.06 | <0.03 |
| E. faecalis | MP-24 | ATCC29212 | <0.03 | <0.03 | <0.03 | <0.03 |
| E. faecalis | UNT-039 | van resistant | 2 | 8 | 4 | 1 |
| A. baumannii | MP-15 | ATCC19606 | 8 | 16 | 4 | 2 |
| K. pneumoniae | MP-14 | ATCC10031 | 8 | 8 | 8 | 2 |
| P. aeruginosa | MP-3 | ATCC27853 | 32 | 64 | 16 | 16 |
| E. coli | MP-4 | ATCC25922 | 16 | 32 | 8 | 8 |
| New Strains | | | | | | |
| E. coli | MP-9 | ATCC25922:tolC | 2 | 2 | 2 | 2 |
| P. aeruginosa | MP-7 | PAO1 | 64 | >64 | 32 | 32 |
| P. aeruginosa | MP-8 | PAO1:mex | 8 | 8 | 4 | 4 |
| S. aureus | MP-17 | ATCCBAA-977 | 0.06 | 0.06 | 0.06 | 0.06 |
| S. aureus (MRSA) | MP-513 | ST-228 cErm | 16 | >64 | >64 | 16 |
| E. coli | MP541 | clinical | 16 | 32 | 16 | 16 |
| E. coli | MP532 | clinical - cErm | >64 | >64 | >64 | 64 |
| K. pneumoniae | MP548 | clinical | 64 | 64 | 32 | 32 |
| K. pneumoniae | MP546 | clinical | >64 | >64 | >64 | 64 |
| A. baumannii | MP577 | clinical | 32 | 64 | 16 | 16 |
| A. baumannii | MP576 | clinical | >64 | >64 | >64 | 64 |

TABLE B8

| Species | Description | Strain No. | FSM-100576 | FSM-100593 | FSM-100597 | FSM-140132 |
|---|---|---|---|---|---|---|
| Gram-positive | | | | | | |
| S. aureus | ATCC29213 | MP-12 | 0.125 | 0.125 | 1 | 0.25 |
| S. aureus | BAA 977 iErm | MP-17 | 0.125 | 0.125 | 1 | 0.25 |
| S. aureus | Clinical- cErm | MP-513 | >32 | 64 | >64 | >64 |
| S. aureus | USA300 - msr(a) | MP-549 | 0.25 | 0.25 | 2 | 0.5 |
| Gram-negative | | | | | | |
| E. coli | ATCC25922 | MP-4 | 32 | 4 | 64 | 16 |
| E. coli | tolC | MP-9 | 2 | 0.5 | 4 | 2 |
| E. coli | Clinical | MP-541 | 32 | 8 | 32 | 32 |
| E. coli | clinical-cErmB | MP-532 | >32 | >64 | >64 | >64 |
| K. pneumoniae | ATCC 10031 | MP-14 | 4 | 1 | 8 | 4 |
| K. pneumoniae | Clinical | MP-548 | >32 | 16 | >64 | 64 |
| K. pneumoniae | Clinical - MDR | MP-546 | >32 | 32 | >64 | >64 |
| P. aeruginosa | ATCC27853 | MP-3 | >32 | 32 | >64 | >64 |
| P. aeruginosa | mex-oprM-deletion | MP-8 | 8 | 2 | 16 | 8 |
| P. aeruginosa | PAO1 | MP-7 | >32 | 32 | >64 | >64 |
| A. baumannii | ATCC 19606 | MP-15 | 16 | 8 | 64 | 32 |
| A. baumannii | Clinical - AZT low | MP-577 | >32 | 8 | >64 | 32 |
| A. baumannii | Clinical - MDR | MP-576 | >32 | >64 | >64 | >64 |

TABLE B9

| Species | Description | Strain No. | FSM-100627 | FSM-100633 | FSM-130216 | FSM-130217 | FSM-140133 |
|---|---|---|---|---|---|---|---|
| Gram-positive | | | | | | | |
| S. aureus | ATCC29213 | MP-12 | 0.06 | 0.125 | 0.25 | 0.25 | 0.25 |
| S. aureus | BAA 977 iErm | MP-17 | 0.06 | 0.125 | 0.25 | 0.25 | 0.25 |
| S. aureus | Clinical- cErm | MP-513 | 32 | 64 | >64 | >64 | >64 |
| S. aureus | USA300 - msr(a) | MP-549 | 0.125 | 0.125 | 0.5 | 0.25 | 0.5 |

TABLE B9-continued

| Species | Description | Strain No. | FSM-100627 | FSM-100633 | FSM-130216 | FSM-130217 | FSM-140133 |
|---|---|---|---|---|---|---|---|
| Gram-negative | | | | | | | |
| E. coli | ATCC25922 | MP-4 | 16 | 8 | 32 | 32 | 16 |
| E. coli | tolC | MP-9 | 1 | 1 | 4 | 4 | 4 |
| E. coli | Clinical | MP-541 | 8 | 8 | 64 | 32 | 16 |
| E. coli | clinical-cErmB | MP-532 | >64 | >64 | >64 | >64 | >64 |
| K. pneumoniae | ATCC 10031 | MP-14 | 2 | 2 | 4 | 8 | 4 |
| K. pneumoniae | Clinical | MP-548 | 32 | 32 | >64 | >64 | 64 |
| K. pneumoniae | Clinical - MDR | MP-546 | 64 | 64 | >64 | >64 | >64 |
| P. aeruginosa | ATCC27853 | MP-3 | 64 | 32 | >64 | >64 | 64 |
| P. aeruginosa | mex-oprM-deletion | MP-8 | 4 | 4 | 16 | 16 | 8 |
| P. aeruginosa | PAO1 | MP-7 | 64 | 32 | >64 | >64 | 64 |
| A. baumannii | ATCC 19606 | MP-15 | 8 | 4 | 16 | 16 | 8 |
| A. baumannii | Clinical - AZT low | MP-577 | 32 | 16 | 64 | 32 | 64 |
| A. baumannii | Clinical - MDR | P-576 | >64 | >64 | >64 | >64 | >64 |

TABLE B10

| Species | Description | Strain No. | FSM-140135 | FSM-22737 | FSM-22738 | FSM-22739 | FSM-22740 |
|---|---|---|---|---|---|---|---|
| Gram-positive | | | | | | | |
| S. aureus | ATCC29213 | MP-12 | 2 | 0.25 | 0.25 | 0.25 | 0.25 |
| S. aureus | BAA 977 iErm | MP-17 | 2 | 0.25 | 0.25 | 0.25 | 0.25 |
| S. aureus | Clinical- cErm | MP-513 | >64 | >64 | 32 | 64 | 64 |
| S. aureus | USA300 - msr(a) | MP-549 | 2 | 0.25 | 0.25 | 0.25 | 0.25 |
| Gram-negative | | | | | | | |
| E. coli | ATCC25922 | MP-4 | >64 | 16 | 8 | 16 | 16 |
| E. coli | tolC | MP-9 | 16 | 2 | 1 | 4 | 2 |
| E. coli | Clinical | MP-541 | >64 | 16 | 16 | 16 | 16 |
| E. coli | clinical-cErmB | MP-532 | >64 | >64 | >64 | >64 | >64 |
| K. pneumoniae | ATCC 10031 | MP-14 | 8 | 8 | 4 | 8 | 8 |
| K. pneumoniae | Clinical | MP-548 | >64 | 64 | 64 | 64 | >64 |
| K. pneumoniae | Clinical - MDR | MP-546 | >64 | >64 | >64 | >64 | >64 |
| P. aeruginosa | ATCC27853 | MP-3 | >64 | >64 | 64 | >64 | >64 |
| P. aeruginosa | mex-oprM-deletion | MP-8 | 32 | 16 | 8 | 16 | 16 |
| P. aeruginosa | PAO1 | MP-7 | >64 | >64 | 64 | >64 | >64 |
| A. baumannii | ATCC 19606 | MP-15 | >64 | 16 | 8 | 16 | 16 |
| A. baumannii | Clinical - AZT low | MP-577 | >64 | 32 | 32 | 32 | 64 |
| A. baumannii | Clinical - MDR | MP-576 | >64 | >64 | >64 | >64 | >64 |

TABLE B11

| Species | Description | Strain No. | FSM-22741 | FSM-22742 | FSM-22745 | FSM-22746 | FSM-22747 | FSM-22748 | FSM-22749 | FSM-22750 |
|---|---|---|---|---|---|---|---|---|---|---|
| Gram-positive | | | | | | | | | | |
| S. aureus | ATCC29213 | MP-12 | 0.125 | 0.5 | 0.5 | 0.25 | 0.25 | 0.25 | 2 | 4 |
| S. aureus | BAA 977 iErm | MP-17 | 0.125 | 1 | 1 | 0.25 | 0.25 | 0.25 | 2 | 8 |
| S. aureus | Clinical-cErm | MP-513 | >64 | >64 | >64 | >64 | >64 | >64 | >64 | >64 |
| S. aureus | USA300 - msr(a) | MP-549 | 0.25 | 1 | 1 | 0.5 | 0.5 | 0.25 | 2 | 8 |
| Gram-negative | | | | | | | | | | |
| E. coli | ATCC25922 | MP-4 | 16 | 16 | 32 | 32 | 32 | 16 | 64 | >64 |
| E. coli | tolC | MP-9 | 4 | 2 | 4 | 4 | 4 | 4 | 8 | >64 |
| E. coli | Clinical | MP-541 | 32 | 16 | 32 | 64 | 32 | 16 | 64 | >64 |
| E. coli | clinical-cErmB | MP-532 | >64 | >64 | >64 | >64 | >64 | >64 | >64 | >64 |
| K. pneumoniae | ATCC 10031 | MP-14 | 4 | 4 | 8 | 8 | 8 | 8 | 16 | >64 |
| K. pneumoniae | Clinical | MP-548 | 64 | 64 | >64 | >64 | >64 | 64 | >64 | >64 |
| K. pneumoniae | Clinical - MDR | MP-546 | >64 | >64 | >64 | >64 | >64 | >64 | >64 | >64 |
| P. aeruginosa | ATCC27853 | MP-3 | >64 | 64 | >64 | >64 | >64 | 64 | >64 | >64 |

TABLE B11-continued

| Species | Description | Strain No. | FSM-22741 | FSM-22742 | FSM-22745 | FSM-22746 | FSM-22747 | FSM-22748 | FSM-22749 | FSM-22750 |
|---|---|---|---|---|---|---|---|---|---|---|
| P. aeruginosa | mex-oprM-deletion | MP-8 | 8 | 8 | 16 | 16 | 16 | 16 | 16 | >64 |
| P. aeruginosa | PAO1 | MP-7 | >64 | 64 | >64 | >64 | >64 | 64 | >64 | >64 |
| A. baumannii | ATCC 19606 | MP-15 | 8 | 16 | 32 | 16 | 16 | 16 | 32 | >64 |
| A. baumannii | Clinical - AZT low | MP-577 | 32 | 32 | 64 | 64 | 32 | 32 | >64 | >64 |
| A. baumannii | Clinical - MDR | MP-576 | >64 | >64 | >64 | >64 | >64 | >64 | >64 | >64 |

Table B12 below shows MIC data for FSM-100426 compared with solithromycin. The data suggests that incorporating a rigidified linker between the cyclic carbamate and the triazole (i.e., the alkynylene linker moiety of FSM-10042) can provide a more potent analog. The rigid alkynyl linker of FSM-10042 corresponds to the linking group $L^{C1}$ as described herein.

TABLE B12

| | Species | Strain or Genotype | Solithro | FSM-100426 |
|---|---|---|---|---|
| Gram-positive | S. aureus | ATCC 29213 | 0.125 | 0.0625 |
| | S. aureus | MRSA: USA300 | 1 | 0.5 |
| | S. aureus | MRSA: USA100 | >32 | >32 |
| | S. aureus | erm A genotype | >32 | >32 |
| | S. aureus | USA600, GISA | >32 | 32 |
| | S. pneumoniae | ATCC 49619 | <0.03125 | <0.03125 |
| | S. pneumoniae | mef A genotype | <0.03125 | <0.03125 |
| | S. pneumoniae | mef A genotype | 0.125 | <0.03125 |
| | S. pneumoniae | erm B + tet(M, O) genotype | <0.03125 | <0.03125 |
| | S. pneumoniae | erm B + mef A genotype | 0.25 | <0.03125 |
| | S. pyogenes | ATCC 19615 | <0.03125 | <0.03125 |
| | S. pyogenes | Macrolide-resistant | 0.0625 | <0.03125 |
| | E. faecalis | ATCC 29212 | <0.03125 | <0.03125 |
| | E. faecalis | Vancomycin-resistant | 32 | 8 |
| Gram-negative | E. coli | ATCC 25922 | 32 | 32 |
| | E. coli | NDM-1 | >32 | >32 |
| | E. coli | TEM-1 | 32 | >32 |
| | E. coli | CTX-M-14 | >32 | >32 |
| | A. baumannii | ATCC 19606 | 8 | 16 |
| | A. baumannii | imipenem-resistant | 4 | 8 |
| | A. baumannii | chromosomal class C | 8 | 32 |
| | A. baumannii | IMP-4 | >32 | >32 |
| | K. pneumoniae | ATCC 10031 | 8 | 8 |
| | K. pneumoniae | KPC-2 | >32 | >32 |
| | K. pneumoniae | TEM-10 | >32 | >32 |
| | K. pneumoniae | SHV-12 | >32 | >32 |
| | P. aeruginosa | ATCC 27853 | >32 | >32 |
| | P. aeruginosa | HPA101-1477 | >32 | >32 |
| | H. influenzae | Erythro >4, Azithro 1 | 2 | 4 |
| | H. influenzae | ATCC49247 | 4 | 4 |

Table B13 below shows MIC data for FSM-100573 compared with solithromycin. The data suggests that incorporating a rigidified linker between the cyclic carbamate and the triazole (linking group $L^{C1}$ as defined herein), in addition to a heteroaryl triazole substituent (group $R^{23}$ as defined herein), provides an even more potent analog.

TABLE B13

| | Species | Strain No. | Solithro | FSM-100573 |
|---|---|---|---|---|
| Gram-positive | S. aureus | MP-12 | 0.125 | 0.06 |
| | S. aureus (MRSA) | MP-549 | 0.125 | 0.06 |
| | S. aureus (MRSA) | MP-618 UNT-096 | >32 | 16 |
| | S. aureus (MRSA) | MP-620 UNT-146 | >32 | 16 |
| | S. aureus (MRSA) | MP-619 UNT-120 | >32 | 16 |
| | S. pneumoniae | MP-21 | <0.015 | <0.03 |
| | S. pneumoniae | MP-626 UNT-038 | <0.015 | <0.03 |
| | S. pneumoniae | MP-627 UNT-039 | <0.015 | <0.03 |
| | S. pneumoniae | | | |
| | S. pneumoniae | | | |
| | S. pyogenes | MP-19 | <0.015 | <0.03 |
| | S. pyogenes | MP-625 UNT-014 | 0.03 | <0.03 |
| | E. faecalis | MP-24 | 0.03 | <0.03 |
| | E. faecalis | UNT-039 | 8 | 1 |

TABLE B13-continued

| | Species | Strain No. | Solithro | FSM-100573 |
|---|---|---|---|---|
| Gram-negative | H. influenzae | | | |
| | H. influenzae | | | |
| | A. baumannii | MP-15 | 8 | 2 |
| | K. pneumoniae | MP-14 | 4 | 2 |
| | P. aeruginosa | MP-3 | >32 | 16 |
| | E. coli | MP-4 | 16 | 8 |
| New Strains | E. coli | MP-9 | 4 | 2 |
| | P. aeruginosa | MP-7 | >32 | 32 |
| | P. aeruginosa | MP-8 | 8 | 4 |
| | S. aureus | MP-17 | 0.125 | 0.06 |
| | S. aureus (MRSA) | MP-513 | >32 | 16 |
| | E. coli | MP541 | 16 | 16 |
| | E. coli | MP532 | >32 | 64 |
| | K. pneumoniae | MP548 | 32 | 32 |
| | K. pneumoniae | MP546 | >32 | 64 |
| | A. baumannii | MP577 | 32 | 16 |
| | A. baumannii | MP576 | >32 | 64 |

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating an infectious disease or an inflammatory condition comprising administering an effective amount of a compound of formula:

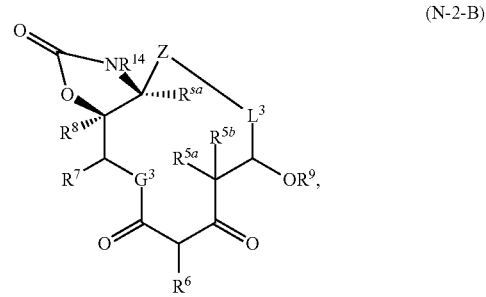

(N-2-B)

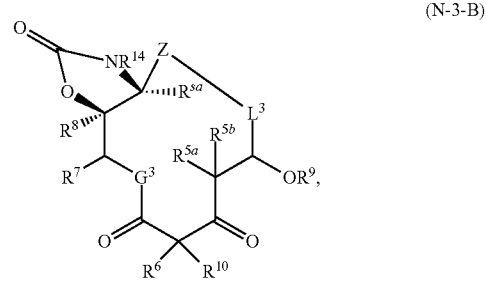

(N-3-B)

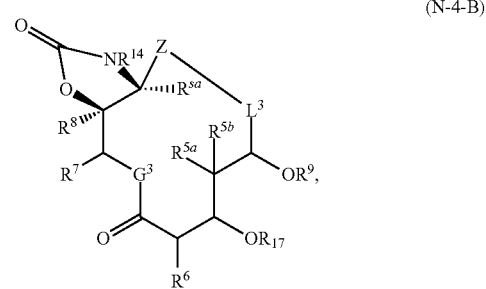

(N-4-B)

-continued

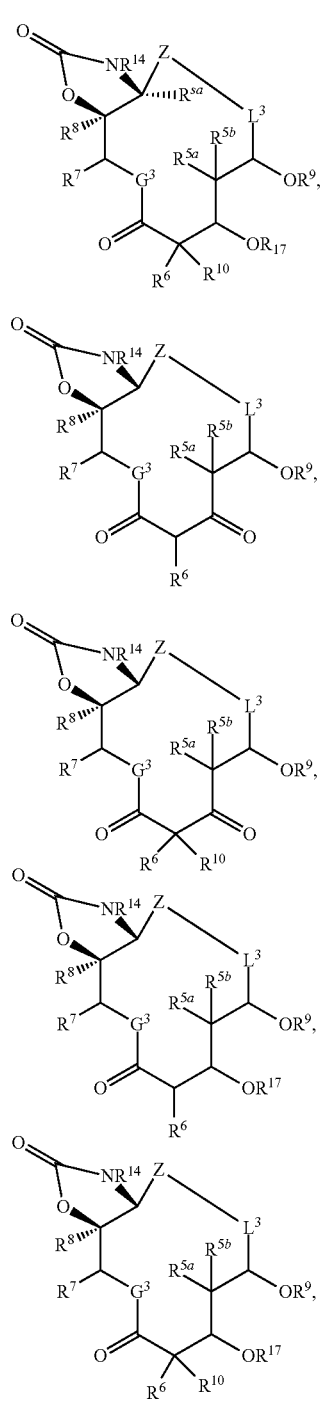

(N-5-B)

(N-2-B1)

(N-3-B1)

(N-4-B1)

(N-5-B1)

or a pharmaceutically acceptable salt thereof; wherein:

Z is of the formula

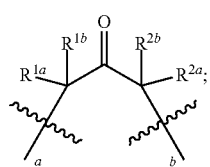 (z-i)

each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocylyl, optionally substituted aryl, or optionally substituted heteroaryl, or wherein $R^{1a}$ and $R^{1b}$ or $R^{2a}$ and $R^{2b}$ are taken together to form

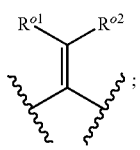

a indicates the point of attachment to the carbon substituted by —$NR^{14}$—;
b indicates the point of attachment to $L^3$;
each of $R^{o1}$ and $R^{o2}$ is independently hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;
$R^{sa}$ is hydrogen, halogen, carbonyl, optionally substituted alkyl, optionally substituted alkenyl, optionally substituted alkynyl, optionally substituted carbocyclyl, optionally substituted heterocylyl, optionally substituted aryl, or optionally substituted heteroaryl;
$L^3$ is a group of formula:

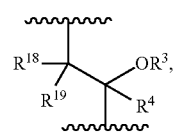 ($L^3$-i)

($L^3$-ii)

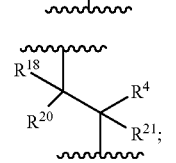 ($L^3$-iii)

====== represents a single or double bond;
$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, or an oxygen protecting group
$R^4$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^{18}$ and $R^{19}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{20}$ and $R^{21}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, or carbonyl, or $R^{20}$ and $R^{21}$ are joined to form an optionally substituted cyclopropyl or an oxiranyl ring;

each instance of $R^{5a}$ and $R^{5b}$ is independently hydrogen, halogen, silyl, optionally substituted alkyl, optionally substituted carbocyclyl, or optionally substituted heterocyclyl;

$R^6$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ and $R^{17}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a carbohydrate;

$R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, carbonyl, silyl, or halogen;

$G^3$ is —O—, —S—, or —N($R^{G1}$)—, wherein $R^{G1}$ is hydrogen, optionally substituted alkyl, or a nitrogen protecting group;

$R^{14}$ is a group of formula:

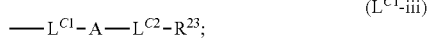

($L^{C1}$-iii)

$L^{C1}$ is a linking group selected from the group consisting of optionally substituted alkenylene, optionally substituted alkynylene, and optionally substituted carbocyclylene;

$L^{C2}$ is a bond;

A is optionally substituted carbocyclene, optionally substituted imidazolene, optionally substituted tetrazolene,

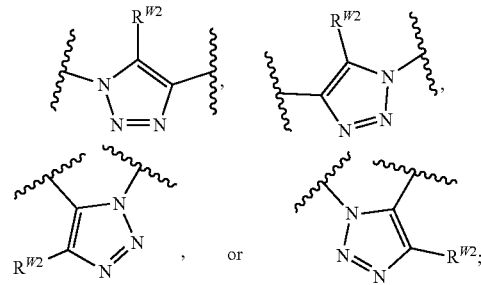

$R^{W2}$ is hydrogen, optionally substituted alkyl; optionally substituted alkenyl; optionally substituted alkynyl; optionally substituted carbocyclyl; optionally substituted heterocyclyl; optionally substituted aryl; or optionally substituted heteroaryl;

$R^{23}$ is optionally substituted aryl; or optionally substituted heteroaryl; and each instance of $R^{Z8}$ is independently hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl, or two $R^{Z8}$ groups are joined to form an optionally substituted heterocylyl or optionally substituted heteroaryl ring;

to a subject in need thereof.

2. The method of claim 1, wherein the compound is of Formula:

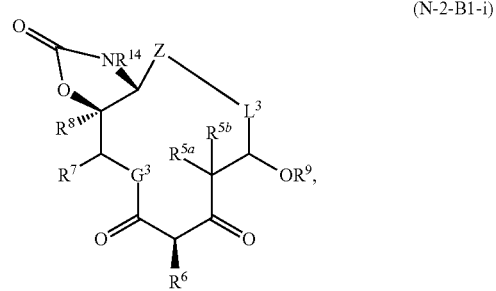

(N-2-B1-i)

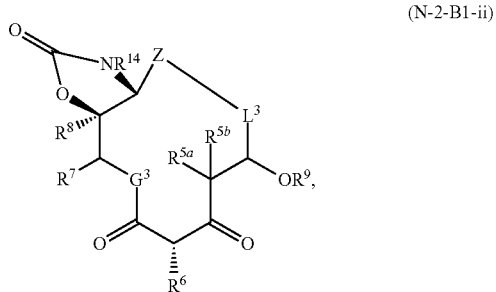

(N-2-B1-ii)

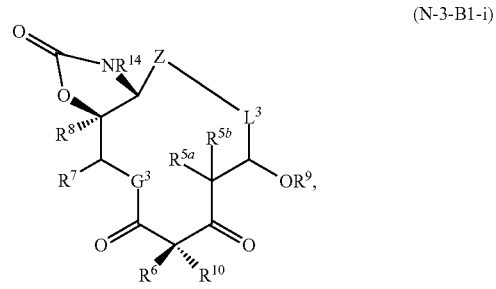

(N-3-B1-i)

(N-3-B1-ii)
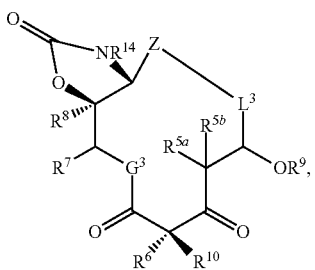

(N-4-B1-i)
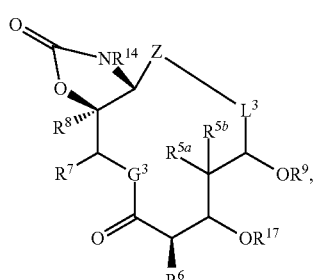

(N-4-B1-ii)
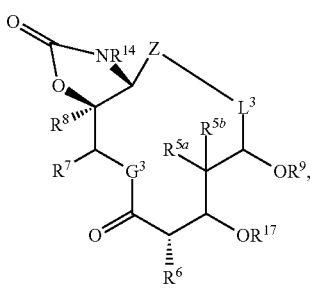

(N-5-B1-i)
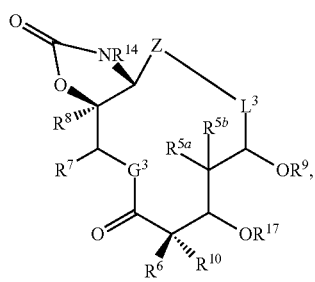

(N-5-B1-ii)
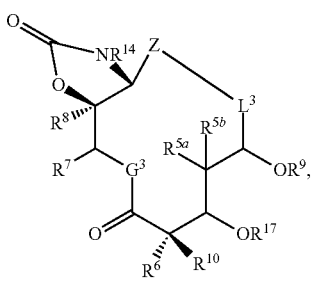

or a pharmaceutically acceptable salt thereof.

3. The method of claim 1, wherein $L^3$ is a group of formula:

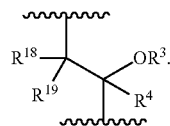
(L³-i)

4. The method of claim 1, wherein $R^4$ is hydrogen, optionally substituted $C_{1-6}$ alkyl, or optionally substituted $C_{2-6}$ alkenyl.

5. The method of claim 1, wherein $R^9$ is a group of formula:

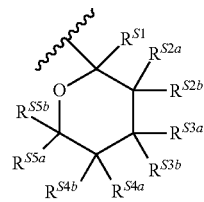
(S-1)

wherein:
each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, —$OR^{SO}$, or —$N(R^{SN})_2$, or wherein $R^{S2a}$ or $R^{S2b}$ may be taken together with $R^{S3a}$ or $R^{S3b}$ to form an optionally substituted fused heterocyclic ring;
each instance of $R^{SO}$ is independently hydrogen, optionally substituted alkyl, optionally substituted alkenyl, optionally substituted heterocyclyl, or an oxygen protecting group; and
each instance of $R^{SN}$ is independently hydrogen, optionally substituted alkyl, or a nitrogen protecting group; or optionally two $R^{SN}$ are taken with the intervening atoms to form a heterocyclic ring.

6. The method of claim 1, wherein A is:

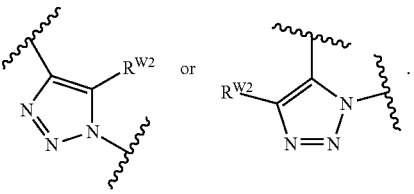

7. The method of claim 1, wherein $R^{23}$ is of formula:

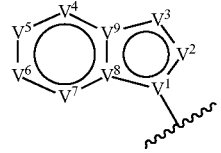
(e-1)

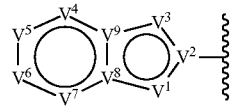
(e-2)

-continued

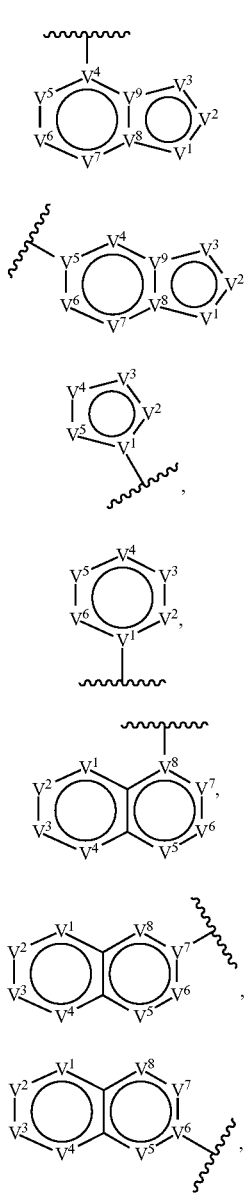

wherein:
  each instance of $V^1$, $V^2$, $V^3$, $V^4$, $V^5$, $V^6$, $V^7$, $V^8$, and $V^9$ may independently be O, S, N, $NR^{23N}$, C, or $CR^{23C}$, as valency permits;
  $R^{23N}$ is independently hydrogen, optionally substituted alkyl, optionally substituted aryl, or a nitrogen protecting group; and
  $R^{23C}$ is hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, amino, substituted amino, thiol, substituted thiol, or carbonyl.

8. The method of claim 7, wherein $R^{23}$ is of formula:

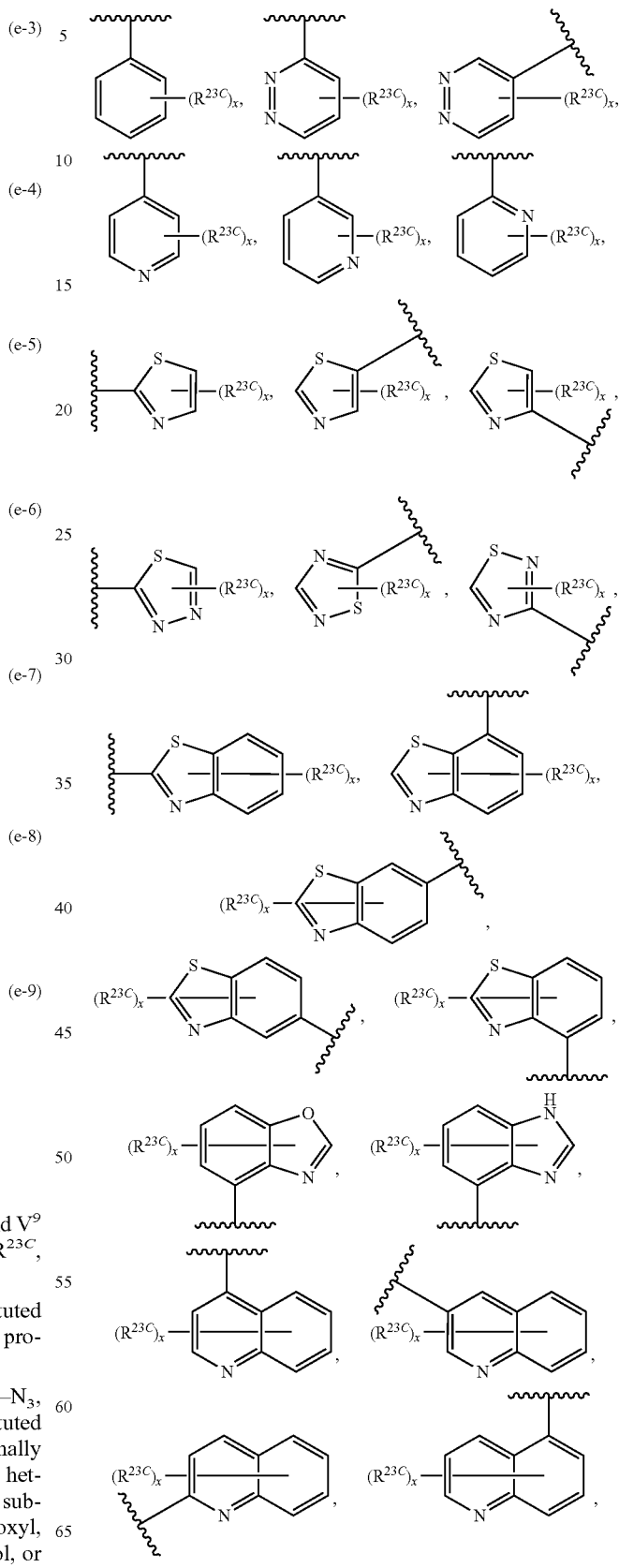

-continued
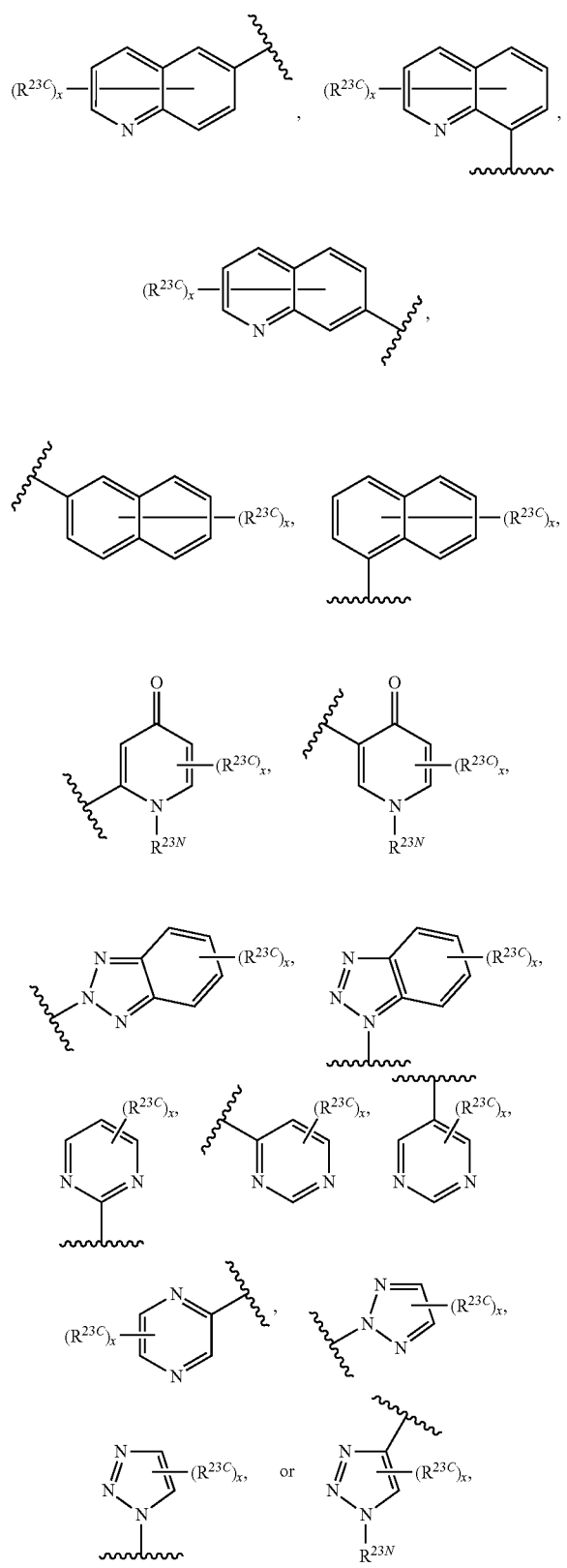
wherein x is 0, 1, or 2.
9. The method of claim 1, wherein the compound is of the formula:
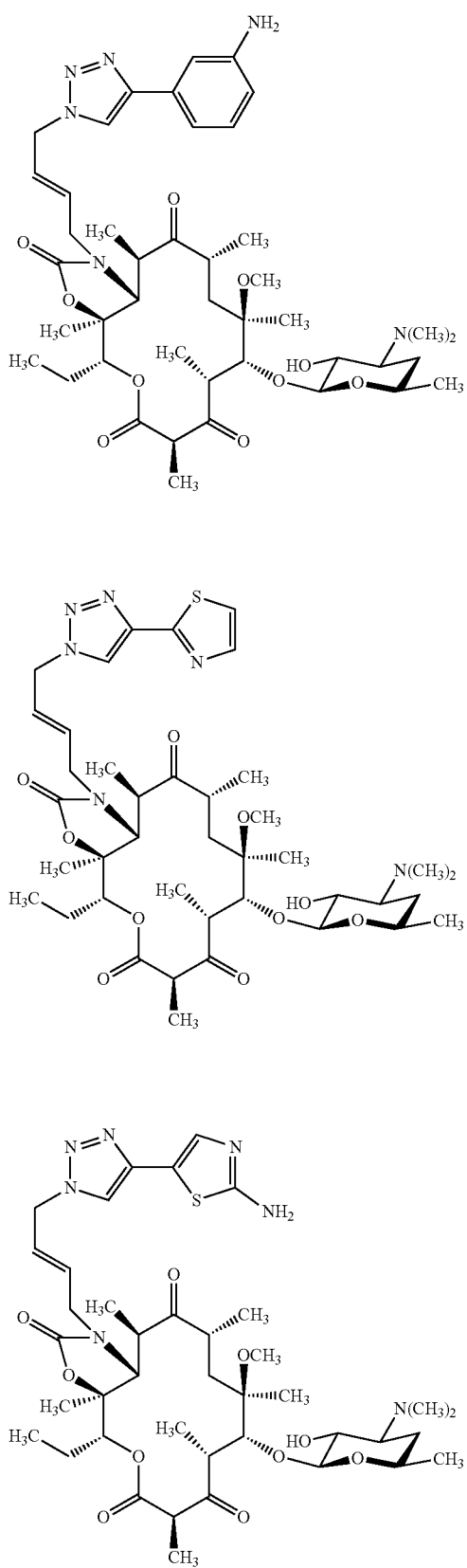

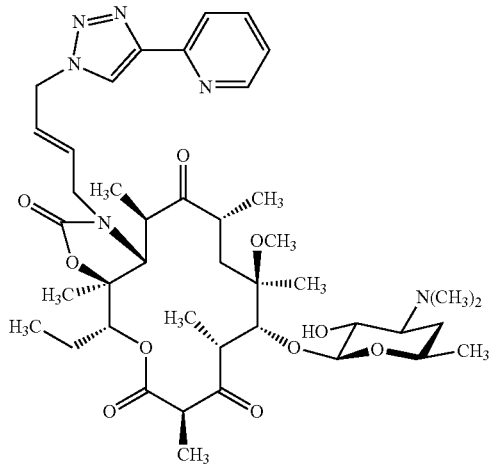
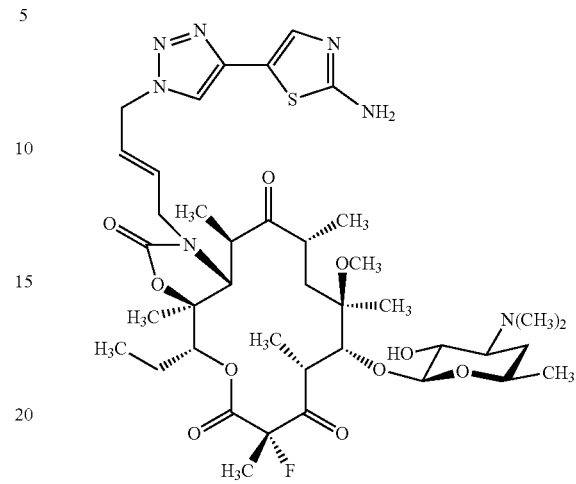
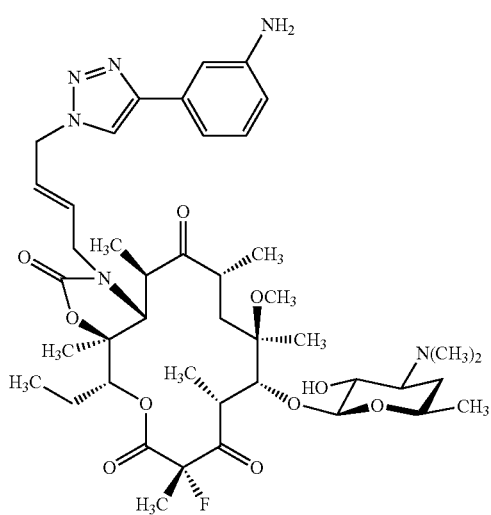
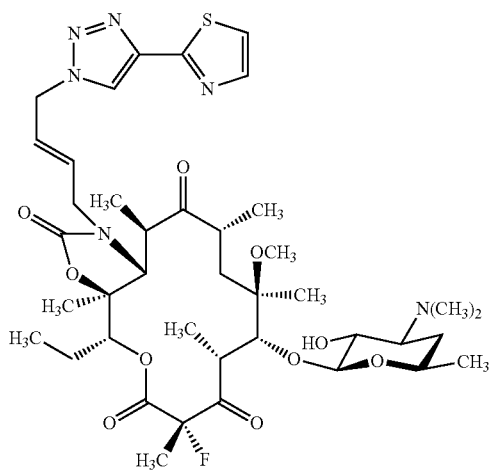
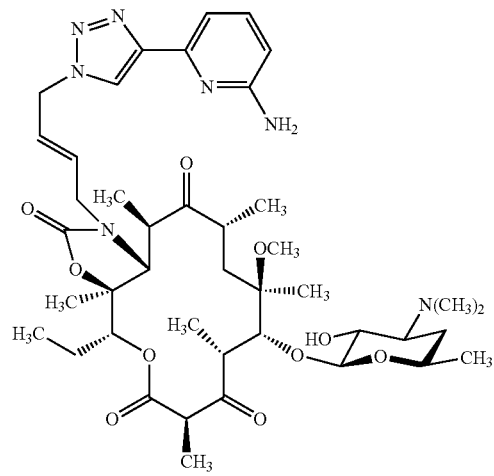

361
-continued
362
-continued
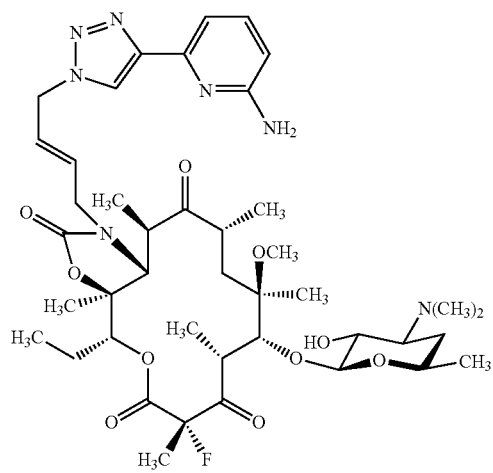
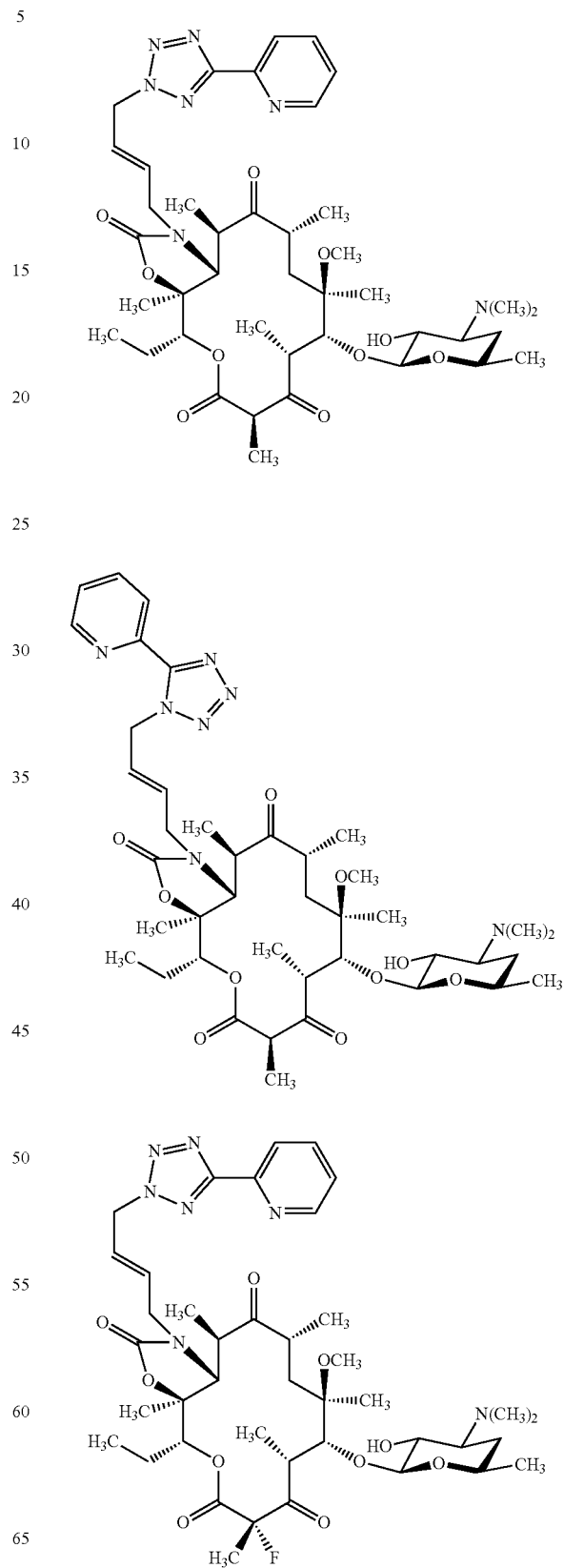

363
-continued
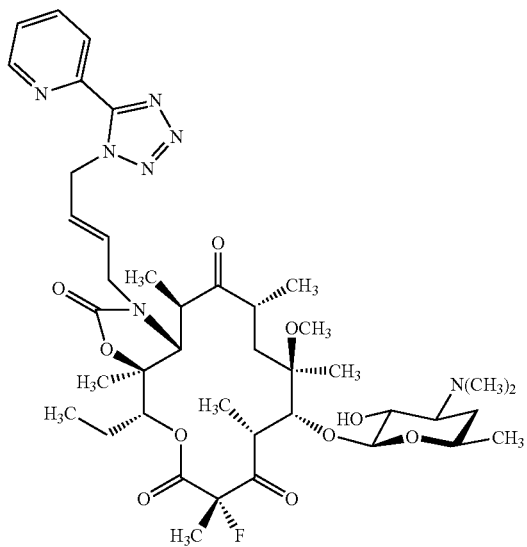
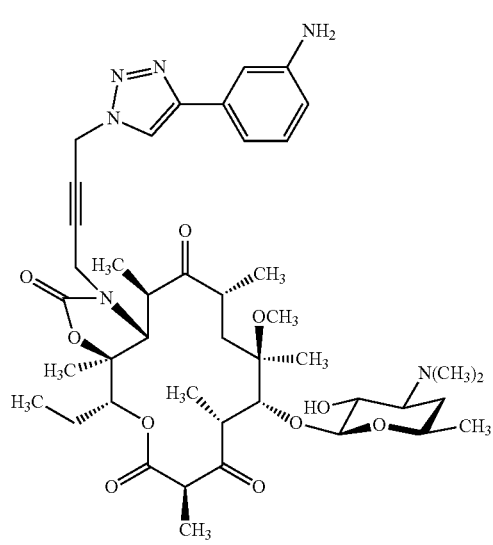
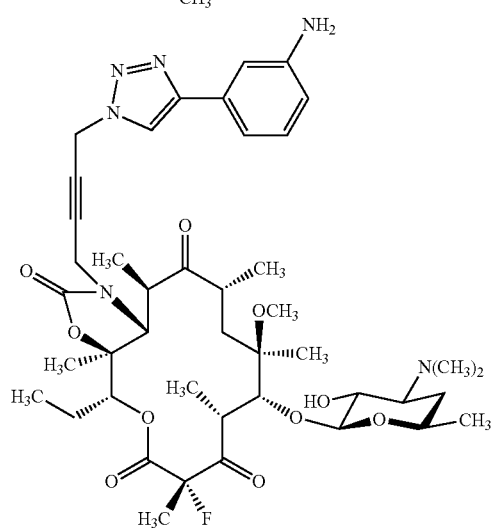
364
-continued
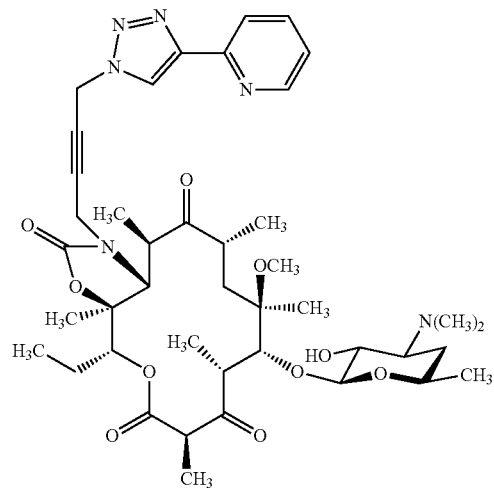
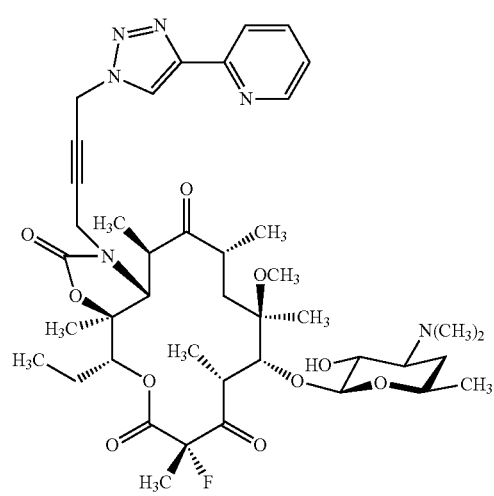
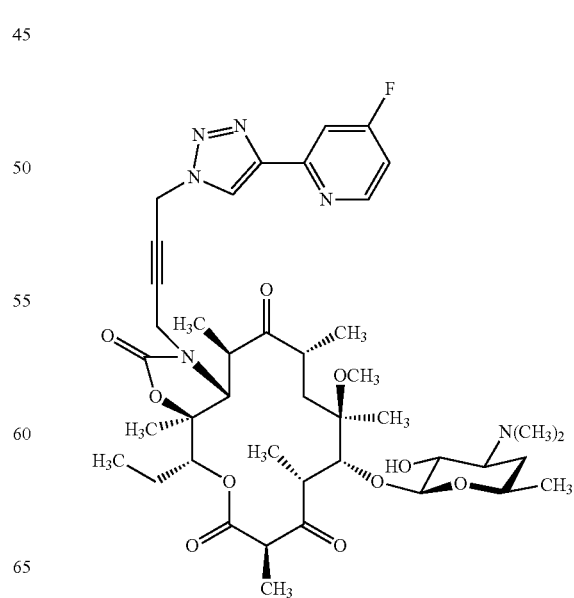

365
-continued
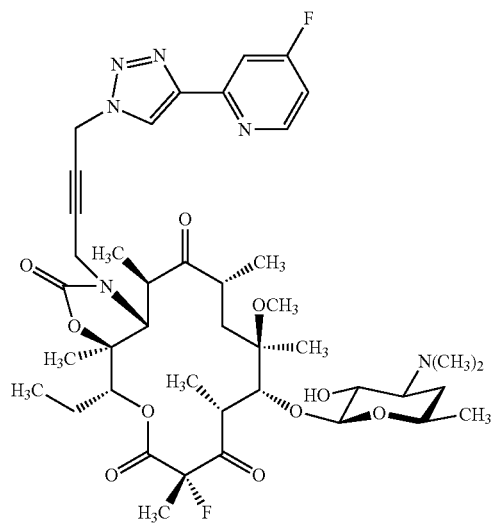
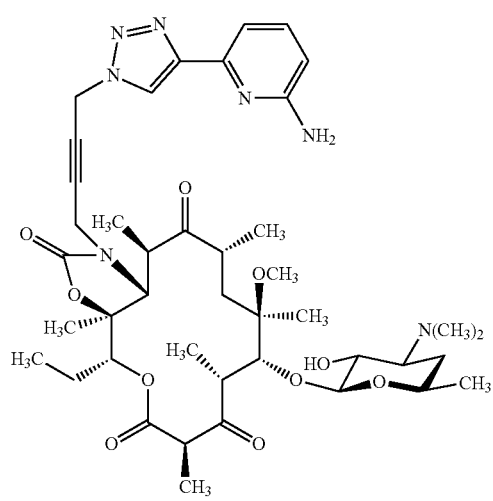
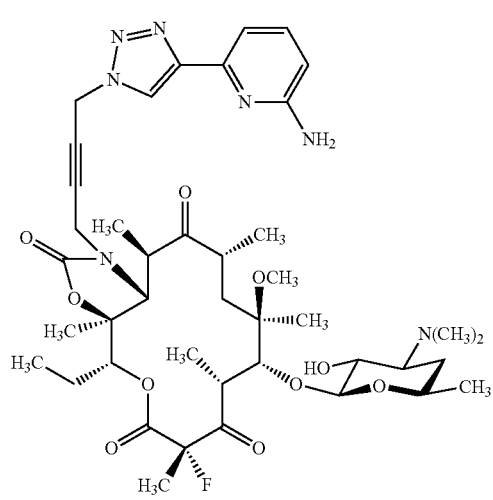
366
-continued
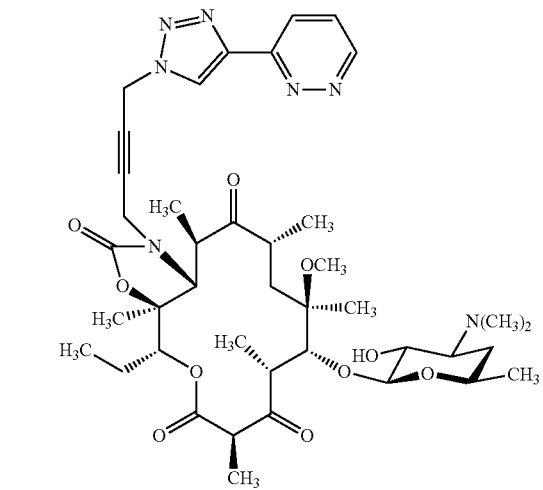
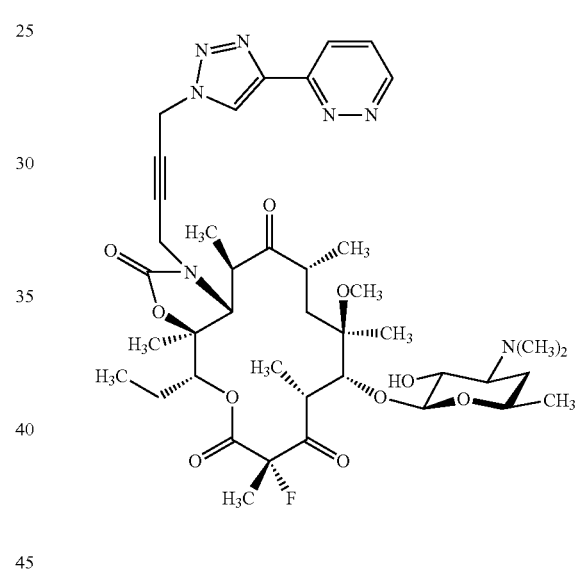
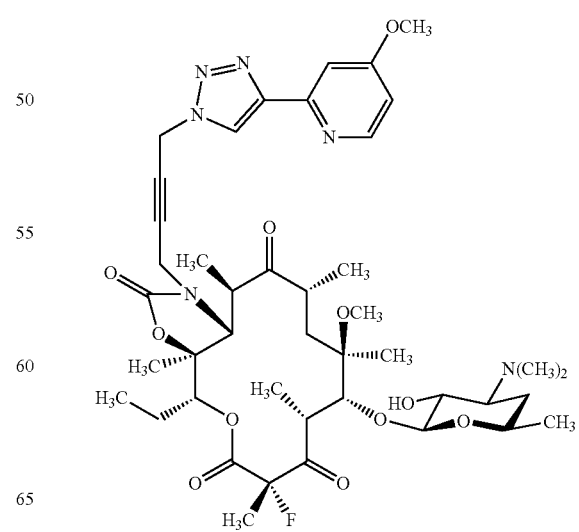

367
-continued
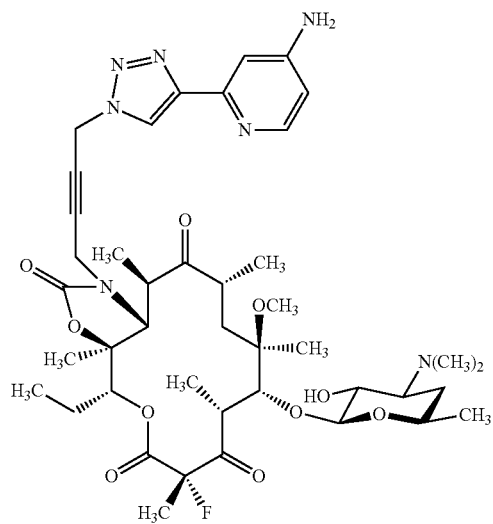
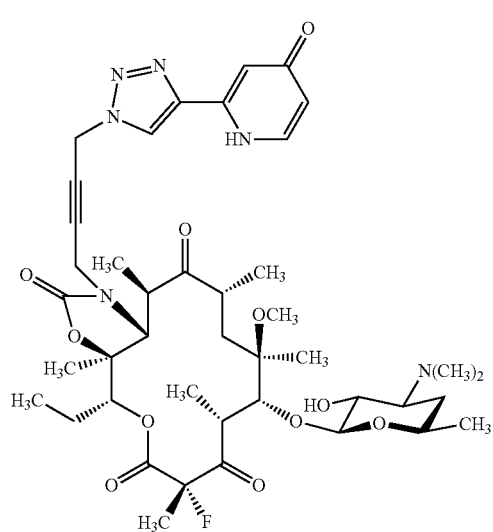
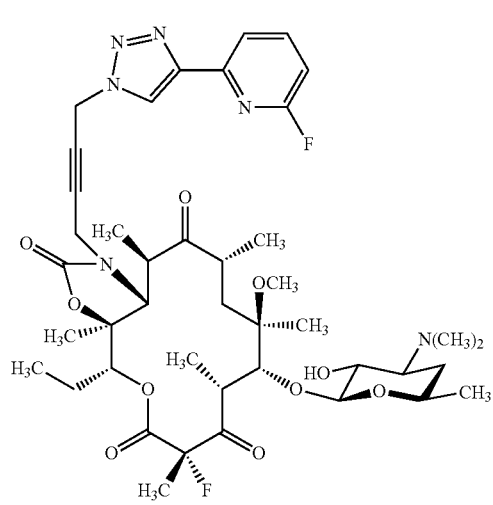
368
-continued
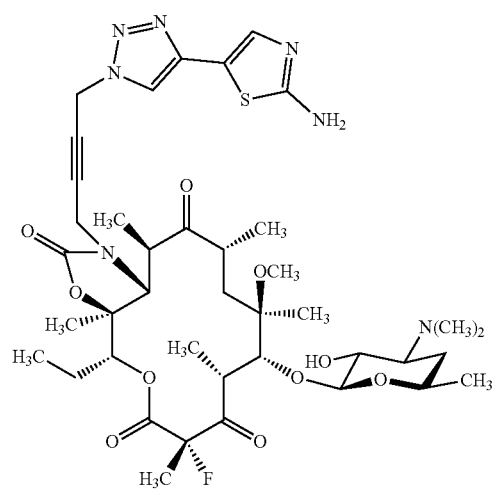
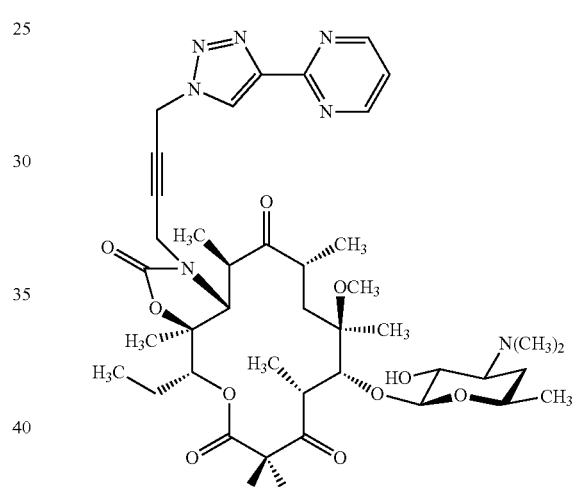
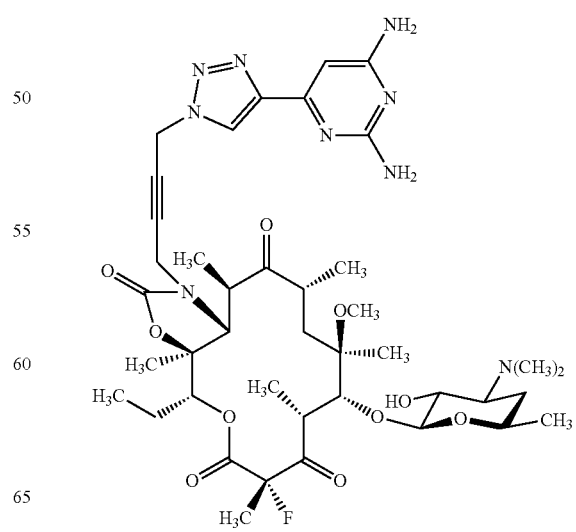

369
-continued
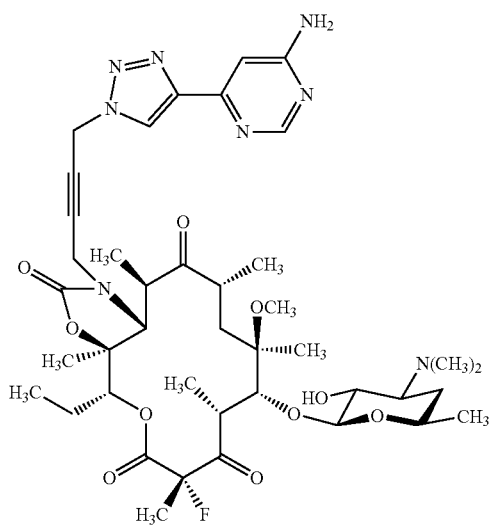
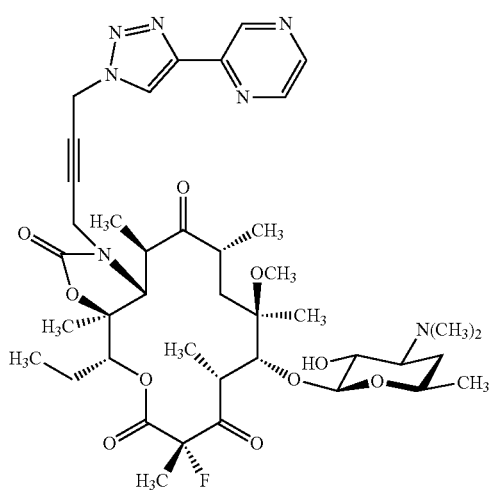
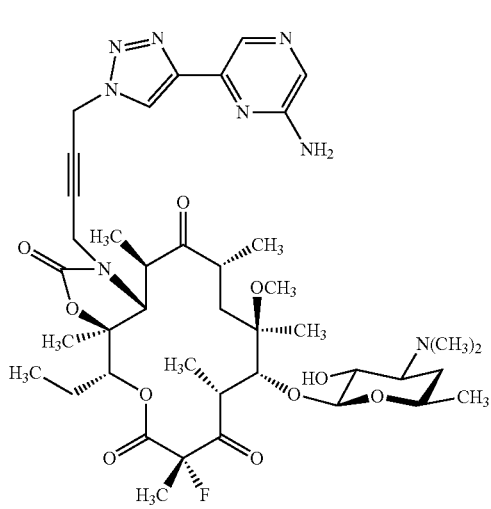
370
-continued
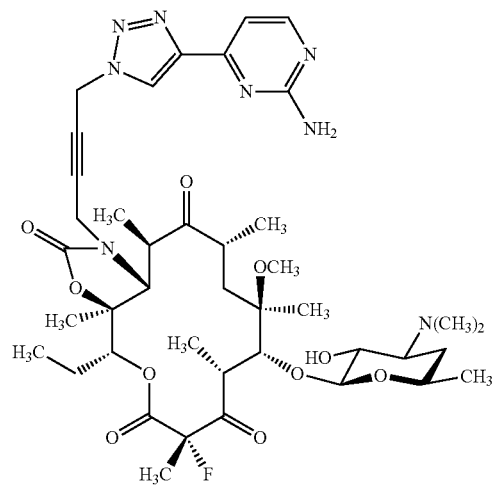
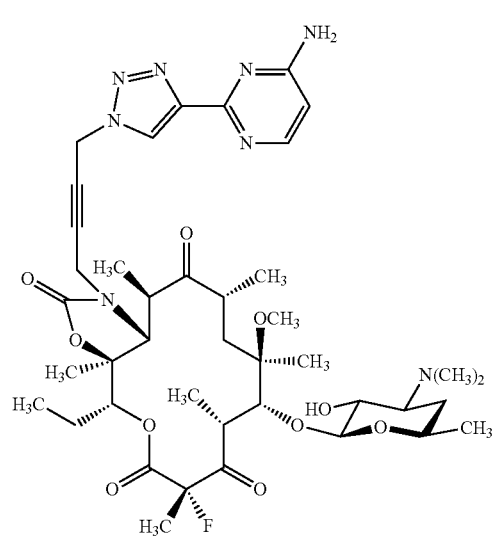
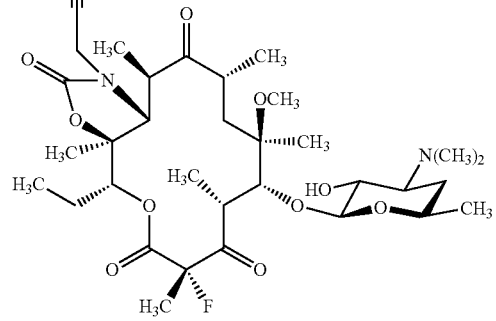

371
-continued
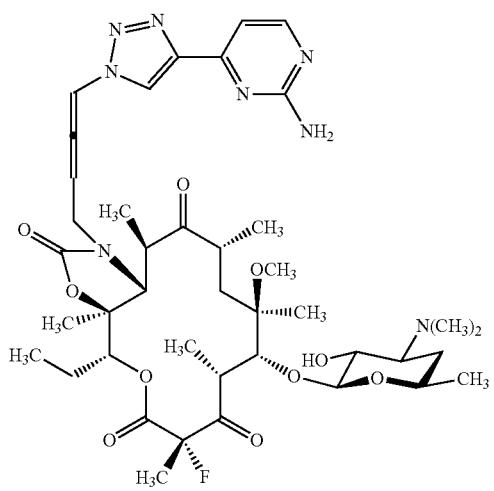
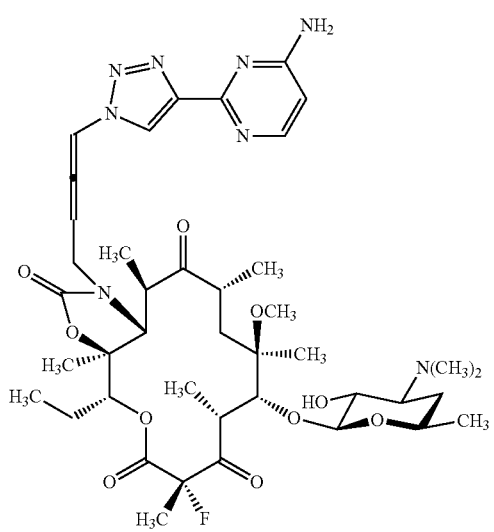
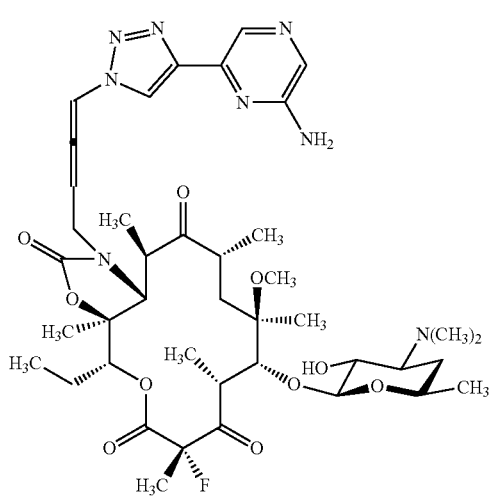
372
-continued
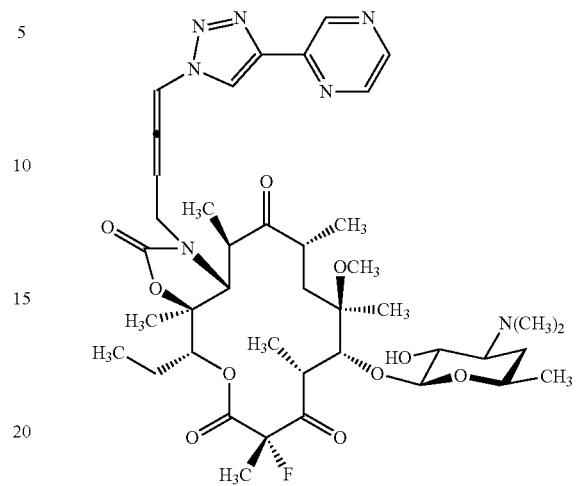
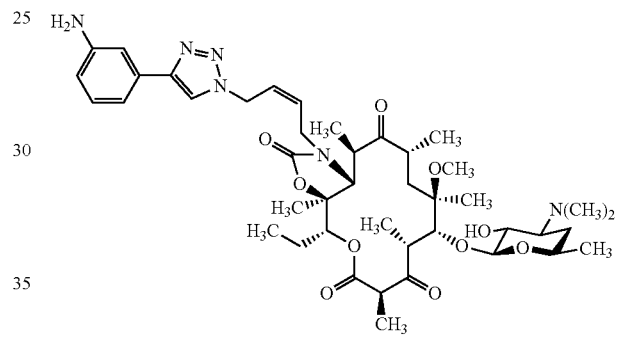
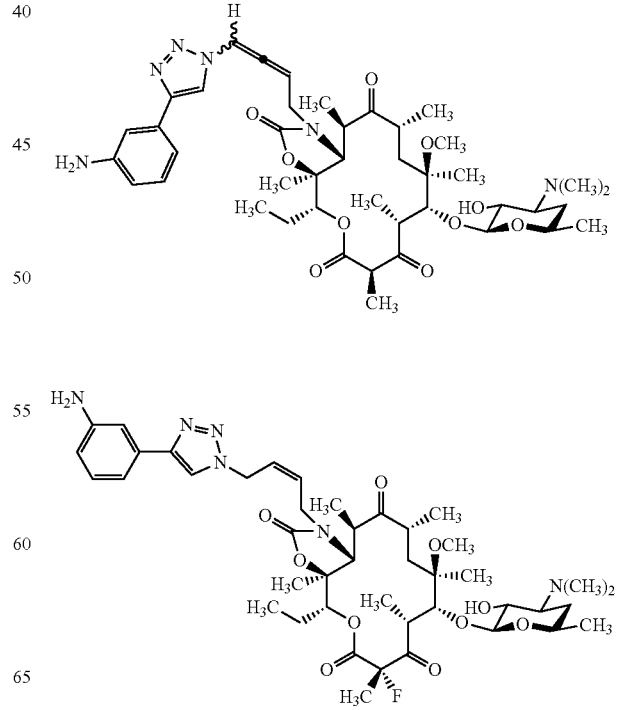

-continued

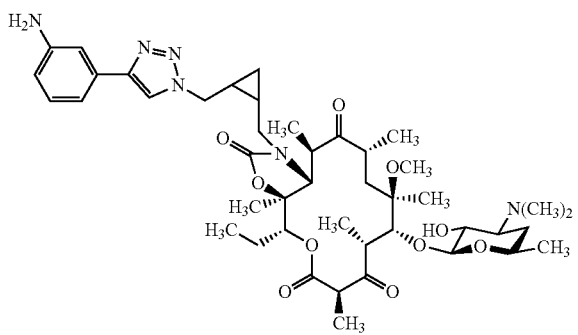

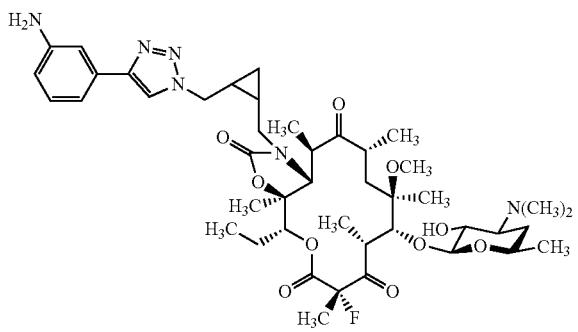

or

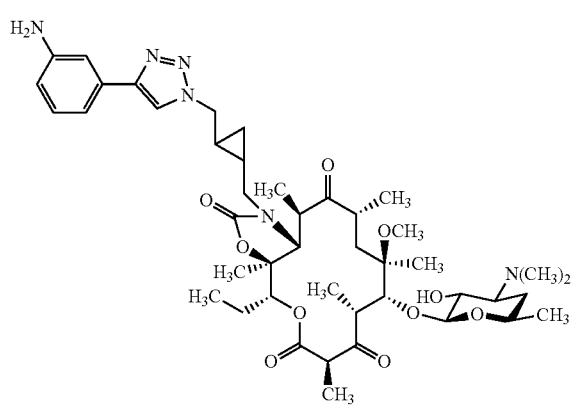

or pharmaceutically acceptable salt thereof.

10. The method of claim 1, wherein the infectious disease is a bacterial infection.

11. The method of claim 10, wherein the bacterial infection is an infection with a Gram positive bacteria.

12. The method of claim 10, wherein the bacterial infection is an infection with a Gram negative bacteria.

13. The method of claim 10, wherein the bacterial infection is a *Staphylococcus* infection, a *Bacillus* infection, a *Streptococcus* infection, an *Escherichia* infection, or a *Haemophilus* infection.

14. The method of claim 10, wherein the infectious disease is a parasitic infection.

15. The method of claim 1, wherein each of $L^{C1}$ is

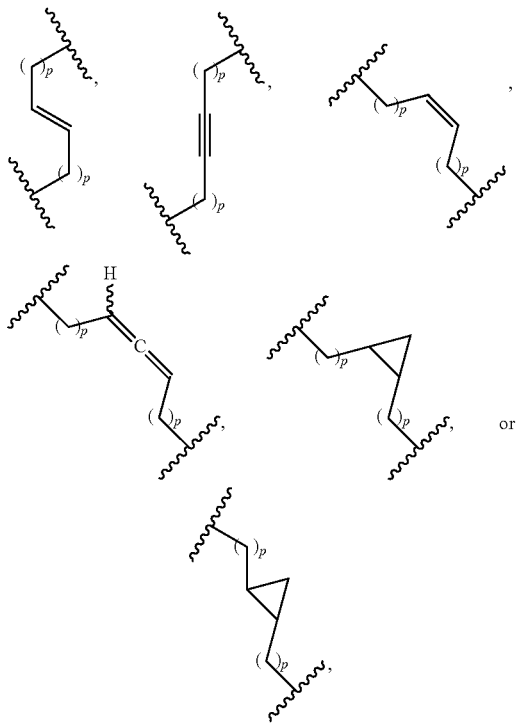

wherein each instance of p is 0, 1, or 2.

16. The method of claim 1, wherein $L^{C1}$ is

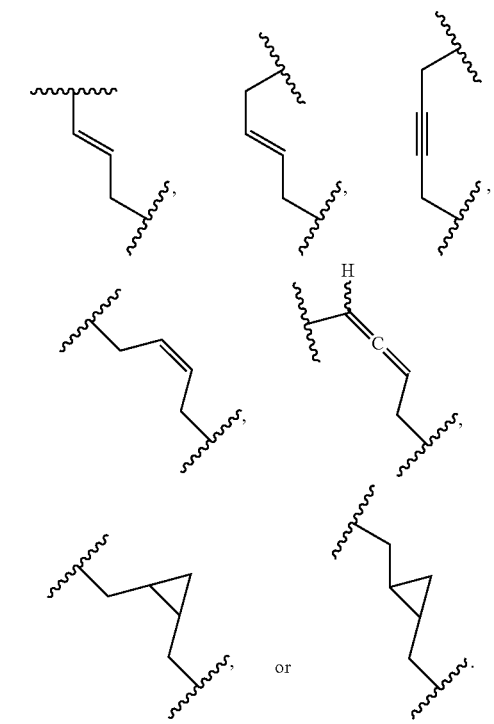

17. The method of claim 1, wherein $R^6$ is —$CH_3$; and $R^{10}$ is fluorine.

18. The method of claim 1, wherein $R^7$ is —$CH_2CH_3$; and $R^8$ is —$CH_3$.

19. The method of claim 1, wherein $R^9$ is a group of formula:
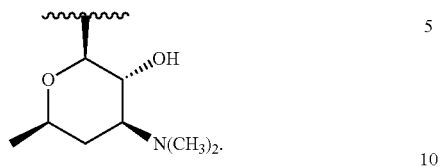
20. The method of claim 1, wherein the inflammatory condition is a chronic pulmonary inflammatory syndrome.
21. The method of claim 1, wherein the method is treating an infectious disease.
22. The method of claim 1, wherein the method is treating an inflammatory condition.
* * * * *

UNITED STATES PATENT AND TRADEMARK OFFICE
CERTIFICATE OF CORRECTION

PATENT NO. : 11,466,046 B2
APPLICATION NO. : 16/843259
DATED : October 11, 2022
INVENTOR(S) : Andrew G. Myers et al.

Page 1 of 2

It is certified that error appears in the above-identified patent and that said Letters Patent is hereby corrected as shown below:

In the Claims

In Claim 1, at Column 348, Lines 55-67, formula (N-4-B): " 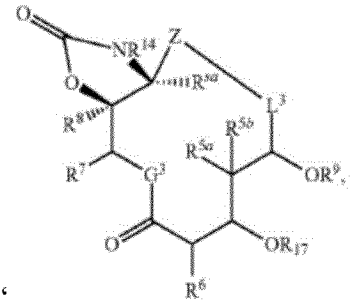 "

Should be replaced with the formula: -- 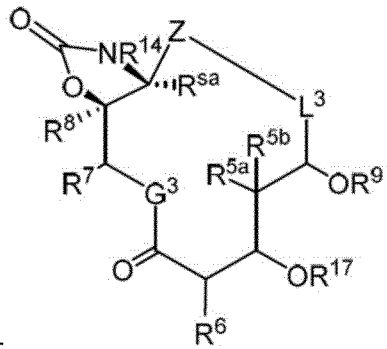 --.

Signed and Sealed this
Seventeenth Day of January, 2023

Katherine Kelly Vidal
*Director of the United States Patent and Trademark Office*

CERTIFICATE OF CORRECTION (continued)
U.S. Pat. No. 11,466,046 B2

In Claim 1, at Column 349, Lines 1-12, formula (N-5-B): " 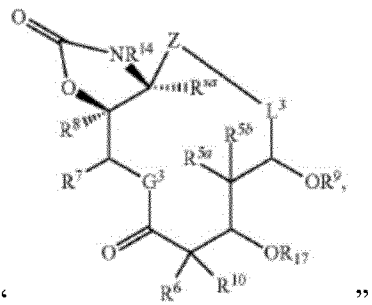 "

Should be replaced with the formula: -- 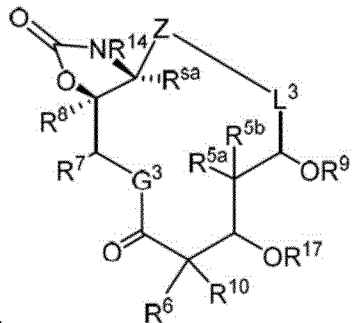 --.

In Claim 1, at Column 350, Lines 54-60, the text: "$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, -C(=O)$R^{Z8}$, -C(=O)O$R^{Z8}$, -C(=O)N($R^{Z8}$)$_2$, or an oxygen protecting group"

Should be replaced with: -- $R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, -C(=O)$R^{Z8}$, -C(=O)O$R^{Z8}$, -C(=O)N($R^{Z8}$)$_2$, or an oxygen protecting group; --.